US011723934B2

(12) United States Patent
Honda et al.

(10) Patent No.: US 11,723,934 B2
(45) Date of Patent: Aug. 15, 2023

(54) COMPOSITIONS AND METHODS FOR THE INDUCTION OF CD8+ T-CELLS

(71) Applicant: Keio University, Tokyo (JP)

(72) Inventors: Kenya Honda, Tokyo (JP); Takeshi Tanoue, Tokyo (JP); Yutaka Kawakami, Tokyo (JP); Koji Atarashi, Tokyo (JP); Satoru Morita, Tokyo (JP); Ashwin Nicholas Skelly, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 16/968,263

(22) PCT Filed: Feb. 8, 2019

(86) PCT No.: PCT/JP2019/004703
§ 371 (c)(1),
(2) Date: Aug. 7, 2020

(87) PCT Pub. No.: WO2019/156234
PCT Pub. Date: Aug. 15, 2019

(65) Prior Publication Data

US 2022/0133813 A1 May 5, 2022

Related U.S. Application Data

(60) Provisional application No. 62/795,506, filed on Jan. 22, 2019, provisional application No. 62/756,029, filed on Nov. 5, 2018, provisional application No. 62/737,318, filed on Sep. 27, 2018, provisional application No. 62/673,436, filed on May 18, 2018, provisional application No. 62/628,501, filed on Feb. 9, 2018.

(51) Int. Cl.

| | |
|---|---|
| ***A61K 35/741*** | (2015.01) |
| ***A61P 31/04*** | (2006.01) |
| ***A61P 35/00*** | (2006.01) |
| ***A61K 39/395*** | (2006.01) |
| ***C07K 16/28*** | (2006.01) |
| *A61K 35/00* | (2006.01) |

(52) U.S. Cl.
CPC ........ *A61K 35/741* (2013.01); *A61K 39/3955* (2013.01); *A61P 31/04* (2018.01); *A61P 35/00* (2018.01); *C07K 16/2818* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 3,249,504 | A * | 5/1966 | Cappel | C12M 23/08 435/392 |
| 9,533,014 | B2 * | 1/2017 | Henn | A23P 10/30 |
| 10,576,136 | B2 | 3/2020 | Honda et al. | |
| 10,695,412 | B2 | 6/2020 | Honda et al. | |
| 11,167,018 | B2 | 11/2021 | Honda et al. | |
| 2008/0193373 | A1 | 8/2008 | Stritzker et al. | |
| 2009/0217401 | A1 | 8/2009 | Korman et al. | |
| 2013/0017199 | A1 | 1/2013 | Langermann | |
| 2019/0343944 | A1 | 11/2019 | Honda et al. | |
| 2019/0381111 | A1 | 12/2019 | Honda et al. | |
| 2020/0093871 | A1 | 3/2020 | Honda et al. | |
| 2020/0254079 | A1 | 8/2020 | Honda et al. | |

FOREIGN PATENT DOCUMENTS

| | | | |
|---|---|---|---|
| BR | 112015018625-4 | A2 | 9/2017 |
| BR | 112016011830-8 | A2 | 9/2017 |
| BR | 112017025813-7 | A2 | 8/2018 |
| EP | 3012270 | A1 | 4/2016 |
| RU | 2546251 | C2 | 4/2015 |
| WO | WO 2004/000042 | A2 | 12/2003 |
| WO | WO 2010/132440 | A2 | 11/2010 |
| WO | WO 2011/058535 | A1 | 5/2011 |
| WO | WO 2013/080561 | A1 | 6/2013 |
| WO | WO 2014/121298 | A2 | 8/2014 |
| WO | WO 2014/121302 | A2 | 8/2014 |
| WO | WO 2015/069770 | A1 | 5/2015 |
| WO | WO 2015/077794 | A1 | 5/2015 |
| WO | WO 2015/156419 | A1 | 10/2015 |
| WO | WO 2016/063263 | A2 | 4/2016 |
| WO | WO 2016/196605 | A1 | 12/2016 |
| WO | WO 2018/117263 | A1 | 6/2018 |

OTHER PUBLICATIONS

Kim et al., Towards a taxonomic coherence between average nucleotide identity and 16S rRNA gene sequence similarity for species demarcation of prokaryotes. Int J Syst Evol Microbiol. Feb. 2014;64(Pt2):346-351. doi: 10.1099/ijs.0.059774-0.
Genbank accession No. AB247141. Hasegawa et al. Jan. 19, 2006.
Genbank accession No. AB249652. Tamura et al. Oct. 17, 2012.
Genbank accession No. AB261128. Sakamoto et al. Nov. 9, 2012.
Genbank accession No. AB331897. Morotomi et al. Aug. 19, 2009.
Genbank accession No. AB470343. Sakamoto et al. Nov. 9, 2012.
Genbank accession No. AB490801. Watanabe et al. Aug. 6, 2010.
Genbank accession No. AB595134. Sakamoto et al. Nov. 9, 2012.
Genbank accession No. AF139525. Gregg et al. Jun. 2, 1999.
Genbank accession No. AY608696. Song et al. Dec. 2, 2005.
Genbank accession No. CP011531. Russell et al. May 3, 2016.

(Continued)

*Primary Examiner* — Oluwatosin A Ogunbiyi
(74) *Attorney, Agent, or Firm* — Wolf, Greenfield & Sacks, P.C.

(57) ABSTRACT

Provided herein are compositions and methods for the induction and/or proliferation of CD8+ T-cells. The disclosure also provides methods of treatment of diseases that can be treated by the induction and/or proliferation of CD8+ T-cells.

17 Claims, 133 Drawing Sheets

Specification includes a Sequence Listing.

(56) References Cited

OTHER PUBLICATIONS

Genbank accession No. CR626927. Cerdano-Tarraga et al. Feb. 6, 2015.
Genbank accession No. HE974920. Sjoberg et al. Jul. 1, 2013.
Genbank accession No. KR822463. Asao et al. Oct. 27, 2016.
Genbank accession No. LN998073. Ndongo et al. Feb. 6, 2016.
Genbank accession No. NR_112933. Sakamoto et al. Feb. 3, 2015.
Genbank accession No. NR_112935. Sakamoto et al. Feb. 3, 2015.
Genbank accession No. NR_112945. Sakamoto et al. Feb. 3, 2015.
Genbank accession No. NR_113076. Sakamoto et al. Feb. 3, 2015.
Genbank accession No. NZ_ACWB00000000. Apr. 17, 2017.
Genbank accession No. NZ_ACWW00000000. Jun. 19, 2017.
Genbank accession No. NZ CAEG00000000. Apr. 8, 2017.
Pitt et al., Fine-Tuning Cancer Immunotherapy: Optimizing the Gut Microbiome. Cancer Res. Aug. 15, 2016;76(16):4602-7. doi: 10.1158/0008-5472.CAN-16-0448. Epub Jul. 29, 2016.
Tanoue et al., A defined commensal consortium elicits CD8 T cells and anti-cancer immunity. Nature. 2019;565(7741):600-605. doi:10.1038/s41586-019-0878-z.
PCT/JP2017/046232, Apr. 3, 2018, International Search Report and Written Opinion.
PCT/JP2017/046232, Jul. 4, 2019, International Preliminary Report on Patentability.
PCT/JP2019/004703, May 7, 2019, International Search Report and Written Opinion.
EP 17884311.6, Oct. 14, 2020, Partial Supplementary European Search Report.
PCT/JP2019/004703, Aug. 20, 2020, International Preliminary Report on Patentability.
Li et al., Gut microbes in correlation with mood: case study in a closed experimental human life support system. Neurogastroenterol Motil. Aug. 2016;28(8):1233-40. doi: 10.1111/nmo.12822. Epub Mar. 29, 2016.
Perez-Cano et al., In vitro immunomodulatory activity of *Lactobacillus fermentum* CECT5716 and *Lactobacillus salivarius* CECT5713: two probiotic strains isolated from human breast milk. Immunobiology. Dec. 2010;215(12):996-1004. doi: 10.1016/j.imbio.2010.01.004. Epub Feb. 6, 2010.
Sivan et al., Commensal *Bifidobacterium* promotes antitumor immunity and facilitates anti-PD-L1 efficacy. Science. Nov. 27, 2015;350(6264):1084-9. doi: 10.1126/science.aac4255. Epub Nov. 5, 2015.
Smelt et al., Probiotics can generate FoxP3 T-cell responses in the small intestine and simultaneously inducing CD4 and CD8 T cell activation in the large intestine. PLoS One. Jul. 4, 2013;8(7):e68952. doi: 10.1371/journal.pone.0068952.
Third Party Observations for Application No. BR 112019013125-6, mailed Feb. 1, 2021. 11 pages.
Vetizou et al., Anticancer immunotherapy by CTLA-4 blockade relies on the gut microbiota. Science. Nov. 27, 2015;350(6264):1079-84. doi: 10.1126/science.aad1329. Epub Nov. 5, 2015.
Yarza et al., Update of the All-Species Living Tree Project based on 16S and 23S rRNA sequence analyses. Syst Appl Microbiol. Oct. 2010;33(6):291-9. doi: 10.1016/j.syapm.2010.08.001.

* cited by examiner

IFNγ⁺ CD8 T cells are highly abundant in the intestine

IFNγ⁺ CD8 T cells are present in various organs. This population usually constitutes 15% among CD8 T cells in lymphoid and non-lymphoid organs. In contrast, the frequency is much higher in the intestinal LP. They are TCRα/β+, CD8α/β+, so-called conventional CD8 T cells.

Microbiota-mediated accumulation of IFNγ$^+$ CD8 T cells

The frequency was markedly decreased in the colon and the SI of GF mice. Therefore, the gut microbiota plays a critical role in the accumulation of IFNγ$^+$ CD8$^+$ T cells in the intestine.

Induction of IFNγ$^+$ CD8 T cells by healthy human fecal samples

Stool samples were obtained from six healthy volunteers.
The samples were orally inoculated into GF mice housed in separate gnotobiotic isolators.
After 3 weeks, colonic IFNγ$^+$ CD8 T cells were examined.

Fig. 15

Isolated 26 strains

| ID | S_ab score | Isolated 26 strains | # |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2C9 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Alistipes timonensis | 8 |
| 2F11 | 0.989 | Parabacteroides johnsonii | 7 |
| 2A6 | 0.966 | Paraprevotella xylaniphila | 6 |
| 2B1 | 1 | Subdoligranulum variabile | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

Fig. 16

Selected 21 strains

| ID | S_ab score | | # |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2G9 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Alistipes timonensis | 8 |
| 2F11 | 0.989 | Parabacteroides johnsonii | 7 |
| 2A6 | 0.966 | Paraprevotella xylaniphila | 6 |
| 2B1 | 1 | Subdoligranulum variabile | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

To investigate whether the isolated and selected 21 strains have the ability to induce IFN$\gamma^+$ CD8 T cells, Induction of colonic IFNγ$^{+}$ CD8 T cells by the 21 strains

Fig. 20

Selected 11 strains

| | | | |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2G9 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Alistipes timonensis | 8 |
| 2F11 | 0.989 | Parabacteroides johnsonii | 7 |
| 2A6 | 0.966 | Paraprevotella xylaniphila | 6 |
| 2B1 | 1 | Subdoligranulum variabile | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

Fig. 22

The other 10 strains which were excluded from the 21 strains

| | | | |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2G8 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Alistipes timonensis | 8 |
| 2F11 | 0.989 | Parabacteroides johnsonii | 7 |
| 2A6 | 0.966 | Paraprevotella xylaniphila | 6 |
| 2B1 | 1 | Subdoligranulum variabile | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

The 11 strains induce IFNγ⁺ CD8 T through activation of Batf3-dependend and Irf4-depedent DC subsets.

Fig. 29

7 Bacteroides strains vs 4 non-Bacteroides strains

| | | | |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2G9 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Alistipes timonensis | 8 |
| 2F11 | 0.989 | Parabacteroides johnsonii | 7 |
| 2A6 | 0.966 | Paraprevotella xylaniphila | 6 |
| 2B1 | 1 | Subdoligranulum variabile | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

Most of the 11 strains were rare, low-abundance components of the healthy human microbiota.

**11-mix prevented intestinal pathology in *L. monocytogenes* infected mice.**

Fig. 36

Oral administration with 11-mix enhanced αPD1 Ab therapy

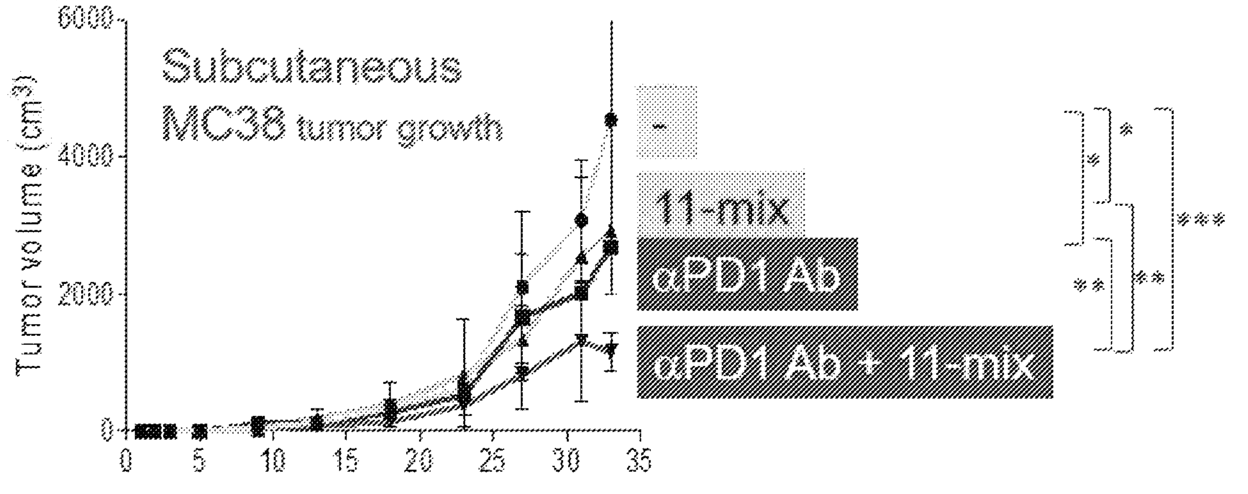

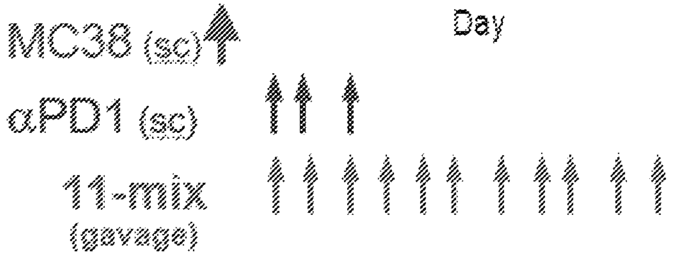

To test whether supplementation with 11-mix could be effective as a therapy for tumor, MC38 were SC injected and mice were then treated with αPD1 Ab, 11-mix, or the combination of αPD1Ab and 11-mix. (Result) Treatment with 11-mix alone resulted in significantly slower tumor growth, to the same degree as treatment with αPD1 Ab. Combination treatment significantly enhanced tumor control.

% IFNγ+ of CD8 T
GF
GF+21mix
GF+Treg 17mix

% IFNγ+ of CD8 T
GF
GF+11mix
GF+10mix

% GrB+ IFNγ+ of CD8 T
GF
GF+11mix
GF+10mix $T_H1$
% IFNγ+ of CD4+ T
$T_H17$
% IL17+ of CD4+ T
GF
GF+11mix
GF+Kp2H7
GF+ $T_H17$ 20mix Histological score
SPF
GF+11mix % IFNγ+ of CD8 T
GF
GF+4mix
GF+7mix
GF+11mix % IFNγ CD8 T
GF
+HK 11mix
+11mix
ns
mucus layer
11 strains (EUB)
MUC2 DAPI
% IFNγ of CD8 T
GF+11mix
SI
Caecum
Colon
cIEL
MLN
iLN
Liver
Lung
Spleen
PBL
Relative expression
Cxcl9
Cxcl10
% Ki67+ of CD8 T
%CD103+ of IFNγ CD8 T
weeks after 11-mix inoculation
B6
IQI
BALB/c +11mix
% initial body weight
115
110
105
100
95
90
85
80
0
1
2
3
4
5
Days post Lm gavage SIINFEKL pep. stim.
IFNγ⁺ CD8 T cell number
6000
4000
2000
0
Cont
+11mix
*

Liver
Spleen
Lm CFU (x10³)
10
7.5
5
2.5
0
60
40
20
*

CD8 T cell number (x10⁴) / g tumor

% IFNγ+ of CD8 T
% GrB of IFNγ+CD8 T

PD1+ICOS+IFNγ+ CD8 T cell number (x10⁴) / g tumour p15E pep. stim.
IFNγ+ CD8 T cell number (x10³) / g tumour MHCII+CD11c+ DC number (x10⁵) / g tumour H-2Kᵇ MFI
αPD-1
+11mix IFNγ+CD8 T
Cell number (x10³)
SPF (CLEA)
GF
Colon
SI Colon
% IFNγ+ in CD8 T
GF
GF+SPF fee (CLEA)

Colon
SPF (CLEA) +
AVMN

Colon
CLEA
Charles
SLC
SPF
0W
2W
6W
Charles co-housed with CLEA

Fig. 53

| | Strain | Sequence | Length (bp) | Top hit species/strain | Database | % identity | Match length / % coverage | # contigs |
|---|---|---|---|---|---|---|---|---|
| * | [illegible] | 16S rRNA | 1438 | *Clostridium innocuum*; 6071432009; HM008265 | RDP | 99.9 | 1433 | - |
| * | [illegible] | 16S rRNA | 1433 | *Ruminococcaceae bacterium* GD1; LN828944 | RDP | 99.5 | 1425 | - |
| * | [illegible] | 16S rRNA | 1428 | *Clostridium lavalense*; CCRI-9929; EF564278 | RDP | 99.4 | 1420 | - |
| * | [illegible] | 16S rRNA | 1439 | *Hungatella hathewayi* (T); type strain: DSM 13479; AJ311620 | RDP | 99.8 | 1421 | - |
| * | [illegible] | 16S rRNA | 915 | *Clostridium* sp. AT5; LN881614 | RDP | 94.5 | 898 | - |
| + | [illegible] | 16S rRNA | 1408 | *Clostridium* sp. AUH-JLC39; KC823278 | RDP | 96.2 | 1362 | - |
| | | | | *Candidatus Stoquefichus* sp. SB1; LN880736 | RDP | 94.1 | 1328 | - |
| | | Genome | 2849874 | Candidatus Stoquefichus sp. SB1 | GenomeDB | 88.1 | 18.2 | 153 |
| + | [illegible] | 16S rRNA | 1413 | *Parabacteroides goldsteinii*; JCM13446; 14; EU136697 | RDP | 99.8 | 1410 | - |
| | | Genome | 6647681 | Parabacteroides goldsteinii | GenomeDB | 98.8 | 76.6 | 77 |
| + | [illegible] | 16S rRNA | 1145 | *Bacteroides thetaiotaomicron*; JCM 5827; AB510710 | RDP | 99.8 | 1144 | - |
| | | Genome | 6611050 | Bacteroides thetaiotaomicron | GenomeDB | 98.7 | 81.4 | 74 |
| + | [illegible] | 16S rRNA | 1406 | *Bacteroides salyersiae*; JCM 12988; AB510707 | RDP | 99.7 | 1402 | - |
| | | Genome | 5831422 | Bacteroides salyersiae | GenomeDB | 99.4 | 90.3 | 36 |
| + | [illegible] | 16S rRNA | 1408 | *Bacteroides cellulosilyticus*; WH2; CP012801 | RDP | 99.8 | 1400 | - |
| | | Genome | 7326077 | Bacteroides cellulosilyticus CAG:158 | GenomeDB | 98.8 | 89.5 | 147 |
| + | [illegible] | 16S rRNA | 1417 | *Bacteroides fragilis* (T); CR626927 | RDP | 99.9 | 1415 | - |
| | | Genome | 5447734 | Bacteroides fragilis | GenomeDB | 99.2 | 82.8 | 93 |
| + | [illegible] | 16S rRNA | 1420 | *Bacteroides eggerthii*; JCM 12986; AB510700 | RDP | 99.7 | 1416 | - |
| | | Genome | 4223171 | Bacteroides eggerthii | GenomeDB | 99.3 | 76.2 | 40 |
| + | [illegible] | 16S rRNA | 938 | *Anaerostipes caccae*; L2; AB243986 | RDP | 99.5 | 933 | - |
| | | Genome | 3502298 | Clostridia bacterium UC5.1_2E1 | GenomeDB | 99.1 | 85.8 | 58 |
| + | [illegible] | 16S rRNA | 1407 | *Bacteroides uniformis*; mat-281; AB215083 | RDP | 99.9 | 1406 | - |
| | | Genome | 4646113 | Bacteroides sp. D20 | GenomeDB | 97.1 | 74.8 | 82 |
| + | [illegible] | 16S rRNA | 1415 | *Bacteroides clarus*; JCM 16067; AB547636 | RDP | 99.8 | 1409 | - |
| | | Genome | 4053993 | Bacteroides clarus CAG:160 | GenomeDB | 99.5 | 94 | 90 |
| – | [illegible] | 16S rRNA | 1413 | *Parabacteroides distasonis* ATCC 8503; CP000140 | RDP | 99.3 | 1403 | - |
| | | Genome | 5139199 | Parabacteroides sp. CAG:2 | GenomeDB | 99.4 | 95.4 | 79 |
| – | [illegible] | 16S rRNA | 1416 | *Parabacteroides gordonii* (T); JCM 15724; MS-1; AB470343 | RDP | 97.4 | 1379 | - |
| | | Genome | 6696681 | Parabacteroides sp. HGS0025 | GenomeDB | 90 | 50 | 133 |
| – | [illegible] | 16S rRNA | 1414 | *Alistipes senegalensis* JC50; JF824804 | RDP | 99.5 | 1407 | - |
| | | Genome | 3832744 | Alistipes senegalensis | GenomeDB | 98.7 | 72.2 | 57 |
| – | [illegible] | 16S rRNA | 1419 | *Parabacteroides johnsonii* (T); JCM 13406; M-165; AB261128 | RDP | 99.9 | 1417 | - |
| | | Genome | 4747421 | Parabacteroides johnsonii | GenomeDB | 99.8 | 90.8 | 88 |
| – | [illegible] | 16S rRNA | 1418 | *Paraprevotella xylaniphila*; JCM 14860; AB547652 | RDP | 99.2 | 1407 | - |
| | | Genome | 4058006 | Paraprevotella xylaniphila | GenomeDB | 98.9 | 92.1 | 57 |
| – | [illegible] | 16S rRNA | 1443 | *Bacteroides dorei*; HS1_L_1_B_010; CP007619 | RDP | 99.7 | 1438 | - |
| | | Genome | 5551051 | Bacteroides dorei | GenomeDB | 99.3 | 79.8 | 147 |
| – | [illegible] | 16S rRNA | 1420 | *Bacteroides* sp. AR20; AF139524 | RDP | 99.7 | 1418 | - |
| | | | | *Bacteroides uniformis*; JCM 5828; AB510711 | RDP | 99.7 | 1418 | - |
| | | Genome | 5125648 | Bacteroides sp. D20 | GenomeDB | 98.5 | 81 | 55 |
| # | [illegible] | 16S rRNA | 1419 | *Eubacterium limosum*; JCM 6421; AB595134 | RDP | 99.9 | 1418 | - |
| | | Genome | 4781937 | Eubacterium limosum | GenomeDB | 95 | 81 | 114 |
| # | [illegible] | 16S rRNA | 1410 | *Clostridiales bacterium* canine oral taxon 085; OC079; JN713248 | RDP | 99.8 | 1407 | - |
| | | | | *Ruminococcaceae bacterium* cv2; LN827534 | RDP | 99.8 | 1407 | - |
| | | Genome | 4359677 | Ruminococcaceae bacterium cv2 | GenomeDB | 99.2 | 73.6 | 186 |
| # | [illegible] | 16S rRNA | 1440 | *Phascolarctobacterium faecium*; X72867 | RDP | 98.8 | 1437 | - |
| | | Genome | 2828852 | Phascolarctobacterium sp. CAG:207 | GenomeDB | 99.2 | 87 | 28 |
| # | [illegible] | 16S rRNA | 1392 | *Fusobacterium varium*; JCM 3722; AB538132 | RDP | 99.8 | 1385 | - |
| | | Genome | 2741484 | Fusobacterium ulcerans | GenomeDB | 93.2 | 78.6 | 136 |

* 5 strains detected in +Chlo 35 mice
\+ 10 strains
– 7 strains
\# 4 strains 7 strains + 4 strains: 11 strains
10 strains + 11 strains: 21 strains
5 strains + 21 strains: 26 strains % IFNγ+ of CD8 T
WT
Ifnγ-/-
MyD88-/- Trif-/-
Il18-/-
Il1r1-/-
Batf3+/+
Batf3-/-
Xcr1+/+ ; DTA
Xcr1cre/+ ; DTA
Irf4fl/fl
Irf4ΔDC
Notch2fl/fl
Notch2ΔDC
GF
GF+11mix
ns
*
**
***

Histological score
GF
GF+10mix
GF+11mix

GF
GF+10mix
GF+11mix
% initial body weight
Days post Lm-WT gavage

Histological score
GF+11mix
GF+11mix +αCD8

GF+11mix
GF+11mix+αCD8
% initial body weight
Days post Lm-WT gavage

SPF
SPF+11mix
SPF+11mix+αCD8
Histological score
ns

% initial body weight
***
Days post Lm-InlA$^m$ gavage

Colon
MLNs
SPF+11mix+αCD8
SPF+11mix
p=0.135
**
*
Lm CFU / mg organ
Days post Lm-InlA$^m$ gavage SPF(n=10)
SPF+αPD-1(n=8)
SPF+10mix(n=10)
SPF+10mix+αPD-1(n=10)
SPF+11mix(n=8)
SPF+11mix +αPD-1(n=9)
Tumour volume (x10³ mm³)
Days post MC38 injection % IFNγ+ of CD8 T
αPD-1
SPF
SPF+11mix
SPF+10mix SPF+11mix+αPD-1 TILs
% IFNγ+ of CD8 T
Medium
+p15E pep.
+11 st. lysate
+PMA+Iono.

% GrB of IFNγ+CD8 T
αPD-1
SPF
SPF +11mix

GF
GF+11mix (4 weeks)
GF+11mix (6 months)

Histological score
20
15
10
5
0
ns
GF
GF+11mix (4w)
GF+11mix (6m)

%IFN-γ+ of CD8 T
80
60
40
20
0
GF
GF+11mix (4w)
GF+11mix (6m)

Fig. 71

| Strain | Length (bp) of sequenced 16S rRNA / total contig | Number of contigs | Mean of sequence depth (x) | Top hit species or strain in RDP (BLAST with 16S rRNA) / in NCBI genome database (BLAST with ribosomal proteins) | Genome size (bp) | Similarity (%) |
|---|---|---|---|---|---|---|
| [illegible] | 1,438 | - | - | *Clostridium innocuum*; 507145/2009 | - | 99.9 |
| | Not sequenced | - | - | - | - | |
| [illegible] | 1,433 | - | - | *Ruminococcaceae bacterium* GD1 | - | 99.5 |
| | Not sequenced | - | - | - | - | |
| [illegible] | 1,428 | - | - | *Clostridium lavalense*; CCRI-9929 | - | 99.4 |
| | Not sequenced | - | - | - | - | |
| [illegible] | 1,438 | - | - | *Hungatella hathewayi* (T); type strain: DSM 13479 | - | 99.6 |
| | Not sequenced | - | - | - | - | |
| [illegible] | 916 | - | - | *Clostridium sp.* AT5 | - | 94.5 |
| | Not sequenced | - | - | - | - | |
| [illegible] | 1,408 | - | - | *Clostridium sp.* AUH-JLC39 | - | 99.2 |
| | | | | *Candidatus Stoquefichus sp.* SB1 | | 94.1 |
| | 2,849,574 | 153 | 151.7 | (*Massiliomicrobiota timonensis* strain An13) | 2,784,379 | 98.9 |
| [illegible] | 1,413 | - | - | *Parabacteroides goldsteinii*; JCM13446 | - | 99.8 |
| | 6,947,881 | 77 | 39.88 | *Parabacteroides goldsteinii* DSM 19448 | 6,463,122 | 99.8 |
| [illegible] | 1,145 | - | - | *Bacteroides thetaiotaomicron*; JCM 5827 | - | 99.9 |
| | 6,811,002 | 74 | 47.73 | *Bacteroides thetaiotaomicron* VPI-5482 | 6,260,361 | 99.8 |
| [illegible] | 1,406 | - | - | *Bacteroides salyersiae*; JCM 12988 | - | 99.7 |
| | 5,831,422 | 38 | 53.2 | *Bacteroides salyersiae* WAL 10018 | 5,309,980 | 99.9 |
| [illegible] | 1,406 | - | - | *Bacteroides cellulosilyticus*; WH2 | - | 99.6 |
| | 7,328,877 | 147 | 19.28 | *Bacteroides cellulosilyticus* strain WH2 | 7,084,828 | 99.8 |
| [illegible] | 1,417 | - | - | *Bacteroides fragilis* (T); CR626927 | - | 99.9 |
| | 5,447,734 | 93 | 65.09 | *Bacteroides fragilis* YCH46 | 5,277,274 | 99.9 |
| [illegible] | 1,429 | - | - | *Bacteroides eggerthii*; JCM 12986 | - | 99.7 |
| | 4,223,171 | 40 | 80.62 | (*Bacteroides stercoris* ATCC 43183) | 4,009,229 | 98.8 |
| [illegible] | 938 | - | - | *Anaerostipes caccae*; L2 | - | 99.5 |
| | 3,502,298 | 56 | 82.34 | *Anaerostipes caccae* DSM 14662 | 3,606,836 | 99.6 |
| [illegible] | 1,407 | - | - | *Bacteroides uniformis*; mas-281 | - | 99.9 |
| | 4,945,113 | 83 | 56.21 | *Bacteroides uniformis* ATCC 8492 | 4,717,497 | 98.8 |
| [illegible] | 1,418 | - | - | *Bacteroides clarus*; JCM 16067 | - | 99.8 |
| | 4,253,993 | 60 | 109 | (*Bacteroides stercoris* ATCC 43183) | 4,009,229 | 97.1 |
| [illegible] | 1,413 | - | - | *Parabacteroides distasonis* ATCC 8503 | - | 99.3 |
| | 5,139,199 | 79 | 80.15 | *Parabacteroides distasonis* ATCC 8503 | 4,811,379 | 99.9 |
| [illegible] | 1,416 | - | - | *Parabacteroides gordonii* (T); JCM 15724 | - | 97.4 |
| | 6,859,881 | 133 | 49.43 | *Parabacteroides goldsteinii* DSM 19448 | 6,463,122 | 96 |
| [illegible] | 1,414 | - | - | *Alistipes senegalensis* JC50 | - | 99.5 |
| | 3,632,744 | 57 | 64.31 | *Alistipes senegalensis* | 3,985,199 | 99.2 |
| [illegible] | 1,419 | - | - | *Parabacteroides johnsonii* (T); JCM 13406 | - | 99.9 |
| | 4,747,421 | 86 | 71.13 | *Parabacteroides johnsonii* | 4,613,562 | 99.6 |
| [illegible] | 1,418 | - | - | *Paraprevotella xylaniphila*; JCM 14860 | - | 99.2 |
| | 4,058,006 | 67 | 76.22 | *Paraprevotella xylaniphila* YIT 11841 | 3,789,431 | 99.8 |
| [illegible] | 1,443 | - | - | *Bacteroides dorei*; HS1_L_1_B_010 | - | 99.7 |
| | 5,561,051 | 147 | 69.78 | (*Bacteroides vulgatus* ATCC 8482) | 5,163,189 | 98.7 |
| [illegible] | 1,420 | - | - | *Bacteroides sp.* AR20 | - | 99.7 |
| | | | | *Bacteroides uniformis*; JCM 5828 | | 99.7 |
| | 5,125,848 | 55 | 130.9 | *Bacteroides uniformis* ATCC 8492 | 4,717,497 | 99.8 |
| [illegible] | 1,418 | - | - | *Eubacterium limosum*; JCM 6421 | - | 99.9 |
| | 4,761,937 | 114 | 51.47 | *Eubacterium limosum* strain ATCC 8486 | 4,422,837 | 99.8 |
| [illegible] | 1,410 | - | - | *Clostridiales bacterium* canine oral taxon 085; OC079 | - | 99.8 |
| | | | | *Ruminococcaceae bacterium* cv2 | | 99.8 |
| | 4,359,877 | 166 | 57.04 | (*Ruthenibacterium lactatiformans* strain 585-1) | 4,111,078 | 99.8 |
| [illegible] | 1,440 | - | - | *Phascolarctobacterium faecium*; X72867 | - | 99.8 |
| | 2,529,602 | 38 | 126.6 | (*Phascolarctobacterium succinatutens* YIT 12067) | 2,121,567 | 86.1 |
| [illegible] | 1,392 | - | - | *Fusobacterium varium*; JCM 3722 | - | 99.6 |
| | | | | *Fusobacterium ulcerans* (T); NCTC 12111T | | 99.5 |
| | 3,741,464 | 126 | 119.7 | *Fusobacterium ulcerans* ATCC 49185 | 3,483,404 | 99.2 |

11 strains (bracket beside the last 11 strains)

5 strains detected in GF+Chlo B5 mice
10 strains
7 strains
4 strains
11 strains (7 strains + 4 strains)
21 strains (10 strains + 11 strains)
26 strains (all)

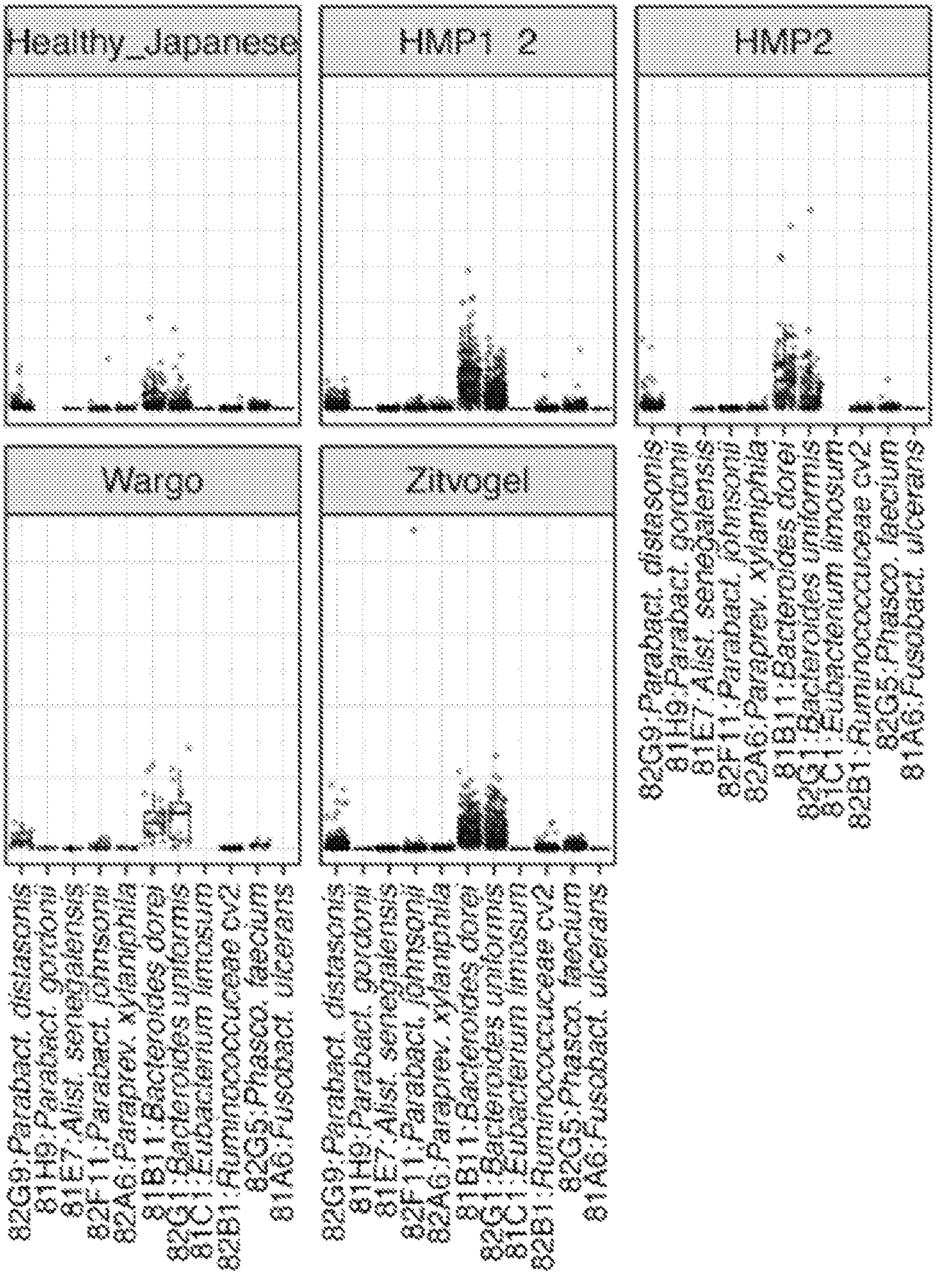
Fig. 82, continued

COMPOSITIONS AND METHODS FOR THE INDUCTION OF CD8+ T-CELLS

RELATED APPLICATIONS

This application is a national stage filing under 35 U.S.C. § 371 of international application number PCT/JP2019/004703, filed Feb. 8, 2019, which claims the benefit under 35 U.S.C. § 119(e) of U.S. provisional application No. 62/628,501, filed Feb. 9, 2018; U.S. provisional application No. 62/673,436, filed May IS, 2018; U.S. provisional application No. 62/737,318, filed Sep. 27, 2018; U.S. provisional application No. 62/756,029, filed Nov. 5, 2018; and U S. provisional application No. 62/795,506, filed Jan. 22, 2019, each of which is incorporated herein by inference in its entirety.

TECHNICAL FIELD

The disclosure relates to compositions and methods for the induction and/or proliferation of CD8+ T cells. The disclosure also provides methods of treatment of diseases that can be treated by the induction and/or proliferation of CD8+ T cells.

BACKGROUND

Animals, including humans, harbor a multitude of microbes (collectively referred to as the microbiota) in anatomical locations including the mouth, esophagus, stomach, small intestine, large intestine, caecum, vagina, skin, nasal cavities, ear, and lungs. The human microbiota is responsible for a multitude of critical processes, including the development of the immune system, metabolism of carbohydrates, proteins and xenobiotics, formation and regeneration of the epithelium, fat storage, production of hormones, production of vitamins, and protection from pathogen infections, among others (See e.g., LeBlanc et al. Curr. Opin. Biotechnol. (2013) 24(2):160-168; Hooper et al. Science (2012) 336(6086):1268-1273; Hughes et al. Am. J. Gastroenterol. (2013) 108(7):1066-1074). Modification of the human microbiota, which can be caused by a number of factors such as antibiotic use, excessive hygiene, diet generic background or combinations of the above, has been associated with a number of unwanted effects including the occurrence of infectious diseases (e.g., *C. difficile* infections), inflammatory, autoimmune and allergic diseases (e.g., ulcerative colitis, Crohn's disease. Type I diabetes, food allergies, asthma, rheumatoid arthritis) and metabolic diseases (e.g., Type II diabetes, metabolic syndrome, obesity, malnutrition), and cancer, among others. For instance, modifications of the microbiota can lead to a loss of tolerance against harmless food antigens or commensal bacterial antigens, subsequent excessive inflammatory responses, metabolic dysregulation, and damage to the intestinal tissue, which compromises its ability to serve as a barrier between the gut lumen and the systemic circulation.

Manipulation of the immune response is of great importance in the treatment of cancer and in vaccination. Cancer therapies that target the immune system have attained improvement in survival rates. However, a large percentage of patients do not respond to cancer immunotherapies. Similarly, large population subsets (e.g., the elderly) cannot mount strong immune responses to vaccines.

Approaches for countering the harmful effects of microbiota modifications on health are limited, despite the role that such modifications play in promoting human pathology. Interventions known to modulate the microbiota include antibiotics, prebiotics, probiotics and fecal transplants, each of which has limitations and potential adverse effects. Additional approaches to counter the detrimental effects of microbiome modification on human health are clearly needed. Furthermore, approaches for promoting stronger immune responses to cancer and to vaccines are also needed.

SUMMARY OF INVENTION

The disclosure relates to compositions of bacterial strains and methods for the induction and/or proliferation of CD8+ T-cells by administering these compositions. The disclosure also provides compositions and methods for the treatment of diseases that can be treated by the induction and/or proliferation of CD8+ T-cells. Diseases that can be treated by the induction and/or proliferation of CD8+ T-cells include infectious diseases and cancers.

While microbial-based compositions for inducing proliferation or accumulation of regulatory T-cells (WO2011/152566), and composition for inducing Th17 cells (WO2015/156419) were previously reported, as disclosed herein, compositions of human-derived bacterial strains are provided which activate the immune system through the induction of interferon gamma producing CD8+ T cells (also referred to herein as IFN+CD8+ T cells, CD8+ IFN+T cells, CD8+ T cells or CD8 positive T-cells). IFN+CD8+ T-cells play important roles in the immune system, in particular the surveillance of infections (e.g., viral infections) and cancer cell development. The compositions provided herein can therefore be used in, for instance, the treatment of infectious diseases and cancer immunotherapy.

Aspects of the present disclosure provide compositions comprising a purified bacterial mixture comprising two or more bacterial strains of species selected from *Fusobacterium ulcerans* and *Eubacterium limosum*, or *Bacteroides dorei* and *Bacteroides uniformis*. In some embodiments of the compositions provided herein, the purified bacterial mixture comprises at least 3, at least 4, at least 5, at least 6, at least 7, at least 8, at least 9, at least 10, or at least 11 bacterial strains.

In some embodiments of the compositions provided herein, the purified bacterial mixture comprises *Fusobacterium ulcerans* and *Eubacterium limosum* and further comprises one or more bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis.*

In some embodiments of the compositions provided herein, the purified bacterial mixture comprises *Bacteroides dorei* and *Bacteroides uniformis* and further comprises one or more bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum.*

In some embodiments of the compositions provided herein, the purified bacterial mixture comprises *Fusobacterium ulcerans, Eubacterium limosum, Bacteroides dorei, Bacteroides uniformis, Parabacteroides gordonii, Paraprevotella xylaniphila, Alistipes* sp., *Parabacteroides johnsonii*, and *Parabacteroides distasonis.*

In some embodiments of the compositions provided herein, the purified bacterial mixture comprises *Fusobacte-*

*rium ulcerans, Eubacterium limosum, Phascolarctobacterium faecium, Subdoligranulum* sp. *Bacteroides dorei, Bacteroides uniformis, Alistipes* sp., *Parabacteroides johnsonii*, and *Parabacteroides distasonis.*

In some embodiments of the compositions provided herein, the purified bacterial mixture comprises *Fusobacterium ulcerans, Eubacterium limosum, Phascolarctobacterium faecium, Subdoligranulum* sp., *Bacteroides dorei, Bacteroides uniformis, Parabacteroides gordonii*, and *Paraprevotella xylaniphila.*

In some embodiments of the compositions provided herein, the purified bacterial mixture comprises *Subdoligranulum* sp., *Phascolarctobacterium faecium, Bacteroides dorei, Bacteroides uniformis, Parabacteroides gordonii, Paraprevotella xylaniphila, Alistipes* sp., *Parabacteroides johnsonii*, and *Parabacteroides distasonis.*

In some embodiments of the compositions provided herein, the purified bacterial mixture comprises *Fusobacterium ulcerans, Eubacterium limosum, Subdoligranulum* sp., *Phascolarctobacterium faecium, Parabacteroides gordonii, Paraprevotella xylianiphila, Alistipes* sp., *Parabacteroides johnsonii*, and *Parabacteroides distasonis.*

In some embodiments of the compositions provided herein, the purified bacterial mixture does not comprise any one or more bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii*, and *Parabacteroides distasonis.*

Aspects of the present disclosure provide compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterium limosum*, and *Parabacteroides distasonis.*

Aspects of the present disclosure provide compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterium limosum*, and *Parabacteroides distasonis.*

Aspects of the present disclosure provide compositions comprising a purified bacterial mixture comprising one or more bacterial strains of species selected from the group consisting of *Parabacteroides distasonis, Parabacteroides gordonii, Alistipes* sp., *Parabacteroides johnsonii, Paraprevotella xylaniphila, Bacteroides dorei*, and *Bacteroides uniformis.*

Aspects of the present disclosure provide compositions comprising a purified bacterial mixture comprising one or mote bacterial strains of species selected from the group consisting of *Eubacterium limosum, Subdoligranulum* sp. *Phascolarctobacterium faecium*, and *Fusobacterium ulcerans.*

In some embodiments of the compositions provided herein, the bacterial strain of specks *Fusobacterium ulcerans* is found in less than 10% of microbiota of healthy human subjects.

In some embodiments of the compositions provided herein, the bacterial strain of species *Fusobacterium ulcerans* is found in less than 1% of microbiota of healthy human subjects.

In some embodiments of the compositions provided herein, the bacterial strain of species *Eubacterium limosum* is found in less than 10% of microbiota of healthy human subjects.

In some embodiments of the compositions provided herein, the bacterial strain of species *Eubacterium limosum* is found in less than 1% of microbiota of healthy human subjects.

Aspects of the present disclosure provide compositions comprising a purified bacterial mixture comprising two or more bacterial strains comprising 16S rDNA sequences of at least 95% homology to SEQ ID NO:2 and SEQ ID NO:10, or SEQ ID NO:3 and SEQ ID NO:4. In some embodiments of the compositions provided herein, the purified bacterial mixture comprises at least 2, at least 3, at least 4, at least 5, at least 6, at least 7, at least 8, at least 9, at least 10, or at least 11 bacterial strains.

Aspects of the present disclosure provide compositions comprising a purified bacterial mixture comprising two or more bacterial strains comprising 16S rDNA sequences of at least 95% sequence identity to SEQ ID NO:2 and SEQ ID NO:10, or SEQ ID NO:3 and SEQ ID NO:4. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In some embodiments of the compositions provided herein, the purified bacterial mixture comprises bacterial strains comprising 16S rDNA sequences of at least 95% homology to SEQ ID NO:2 and SEQ ID NO:10, and further comprises one or more bacterial strains comprising 16S rDNA sequences of at least 95% homology to 16S rDNA sequences selected from the group consisting of SEQ ID NO:1, SEQ ID NO:3, SEQ ID NO 4, SEQ ID NO:5, SEQ ID NO:6, SEQ ID NO:7, SEQ ID NO:8, SEQ ID NO:9, and SEQ ID NO:11.

In some embodiments of the compositions provided herein, the purified bacterial mixture comprises bacterial strains comprising 16S rDNA sequences of at least 95% sequence identity to SEQ ID NO:2 and SEQ ID NO:10, and further comprises one or more bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions provided herein, the purified bacterial mixture comprises bacterial strains comprising 16S rDNA sequences of at least 95% homology to SEQ ID NO:3 and SEQ ID NO:4, and further comprises one or more bacterial strains comprising 16S rDNA sequences of at least 95% homology to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

In some embodiments of the compositions provided herein, the purified bacterial mixture comprises bacterial strains comprising 16S rDNA sequences of at least 95% sequence identity to SEQ ID NO 3 and SEQ ID NO:4, and further comprises one or more bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

In some embodiments of the compositions provided herein, the purified bacterial mixture comprises bacterial strains comprising 16S rDNA sequences of at least 95% homology to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions provided herein, the purified bacterial mixture comprises bacterial strains comprising 16S rDNA sequences of at least 95% sequence identity to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions provided herein, the purified bacterial mixture comprises bacterial strains comprising 16S rDNA sequences of at least 95% homology to SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

In some embodiments of the compositions provided herein, the purified bacterial mixture comprises bacterial strains comprising 16S rDNA sequences of at least 95% sequence identity to SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

In some embodiments of the compositions provided herein, the purified bacterial mixture comprises bacterial strains comprising 16S rDNA sequences of at least 95% homology to SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11.

In some embodiments of the compositions provided herein, the purified bacterial mixture comprises bacterial strains composing 16S rDNA sequences of at least 95% sequence identity to SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11.

In some embodiments of the compositions provided herein, the purified bacterial mixture comprises bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11.

In some embodiments of the compositions provided herein, the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11.

In some embodiments of the compositions provided herein, the purified bacterial mixture comprises bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:9, and SEQ ID NO:10.

In some embodiments of the compositions provided herein, the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:9, and SEQ ID NO:10.

Aspects of the present disclosure provide compositions comprising a purified bacterial mixture comprising one or more bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

Aspects of the present disclosure provide compositions comprising a purified bacterial mixture comprising one or mere bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In some embodiments, the purified bacterial mixture comprises bacterial strains comprising 16S rDNA sequences of at least 95% sequence identity to SEQ ID NQ:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In some embodiments, the purified bacterial mixture comprises bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In some embodiments, the purified bacterial mixture comprises bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11.

In some embodiments, the purified bacterial mixture comprises bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, and SEQ ID NO:11.

In some embodiments, the purified bacterial mixture comprises bacterial strains comprising 16S rDNA sequences of at least 95% sequence identity to SEQ ID NO:1, SEQ ID NO:2, SEQ ID NO:5, and SEQ ID NO:10.

In some embodiments, the purified bacterial mixture comprises bacterial strains comprising 16S rDNA sequences of at least 95% homology to SEQ ID NO:1, SEQ ID NO:2, SEQ ID NO:5, and SEQ ID NO:10.

In some embodiments of the compositions provided herein, the one or more bacterial strain comprises 16S rDNA sequences of at least 96%, at least 97%, at least 98%, or at least 99% homology to the SEQ ID NOs.

In some embodiments of the compositions provided herein, the one or more bacterial strain comprises 16S rDNA sequences of at least 96%, at least 97%, as least 98%, or at least 99% sequence identity to the SEQ ID NOs.

In some embodiments of the compositions provided herein, the purified bacterial mixture does not comprise one or more bacterial strains comprising 16S rDNA sequences of at least 95% sequence identity to 16S rDNA sequences selected from the group consisting of SEQ ID NO:1, SEQ ID NO:5, SEQ ID NO:6, SEQ ID NO:7, SEQ ID NO:8, SEQ ID NO:9, and SEQ ID NO:11.

In some embodiments of the compositions provided herein, the purified bacterial mixture does not comprise one or more bacterial strains comprising 16S rDNA sequences of at least 95% homology to 16S rDNA sequences selected from the group consisting of SEQ ID NO:1, SEQ ID NO:5, SEQ ID NO:6, SEQ ID NO:7, SEQ ID NO:8, SEQ ID NO:9, and SEQ ID NO:11.

Aspects of the present disclosure provide compositions comprising a purified bacterial mixture comprising two or more bacterial strains comprising 16S rDNA sequences of at least 95% homology or sequence identity to the sequences of the following NCBI accession numbers: KR822463 and NR113248, or CP011531 and NR_12945. In some embodiments of the compositions provided herein, the purified bacterial mixture comprises at least 3, at least 4, at least 5, at least 6, at least 7, at least 8, at least 9, at least 10, or at least 11 bacterial strains.

In some embodiments of the compositions provided herein, the purified bacterial mixture comprises bacterial strains comprising 16S rDNA sequences of at least 95% homology or sequence identity to the sequences of NCBI accession numbers KR822463 and NR113248, and further comprising one or more bacterial strains comprising 16S rDNA sequences of at least 95% homology to the sequences of the following NCBI accession numbers: CP011531, NR_112945, LN998073, KM098109, NR_113078, NR_041464, LT223566, NR_112835, and NR041342.

In some embodiments of the compositions provided herein, the purified bacterial mixture comprises bacterial strains comprising 16S rDNA sequences of at least 95% homology or sequence identity to the sequences of NCBI accession numbers CR011531 and NR_112945, and further comprising one or more bacterial strains comprising 16S rDNA sequences of at least 95% homology to the sequences of the following NCBI accession numbers: KR822463, NR113248, LN998073, KM098109, NR_113078, NR_041464, LT223566, NR_112835, and NR041342.

In some embodiments of the compositions provided herein, the purified bacterial mixture comprises bacterial strains comprising 16S rDNA sequences of at least 95% homology or sequence identity to the sequences of the following NCBI accession numbers: CP011531, NR_112945, LN998073, KM098109, NR_113078, NR_043464, LT223566, NR_112835, and NR041342.

In some embodiments of the compositions provided herein, the purified bacterial mixture comprises bacterial strains comprising 16S rDNA sequences of at least 95% homology or sequence identity to the sequences of the following NCBI accession numbers: KR822463, NR113248, LN998073, KM098109, NR_113078, NR_041464, LT223566, NR_112835, and NR041342.

In some embodiments of the compositions provided herein, the two or more bacterial strains comprises 16S rDNA sequences with at least 96%, at least 97%, at least 98%, or at least 99% homology or sequence identity to the sequences of the NCBI accession numbers.

In some embodiments of the compositions provided herein, the purified bacterial mixture does not comprise one or more bacterial strains comprising 16S rDNA sequences of at least 95% homology or sequence identity to the sequences of the following NCBI accession numbers: LN998073, KM098109, NR_113078, NR_041464, LT223506, NR_112835, and NR041342.

In some embodiments of the compositions provided herein, at least 50% of the bacterial strains belong to the order of Bacteriodaies. In some embodiments of the compositions provided herein, one or more of the bacterial strains belong to the order of Bacteriodales and one or more of the bacterial strains belong to the order of Clostridiales. In some embodiments of the compositions provided herein, at least 25% of the bacterial strains belong to the family of Bacteroidaceae. In some embodiments of the compositions provided herein, one or more of the bacterial strains belongs to the genes Bacteroides. In some embodiments of the compositions provided herein, the composition does not include bacterial strains that belong to the order of Bacteriodales.

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former. In some embodiments of the compositions provided herein, the composition composes only obligate anaerobic bacterial strains. In some embodiments of the compositions provided herein, one or more of the bacterial strains does not have an antibiotic resistance gene. In some embodiments of the compositions provided herein, the antibiotic resistance gene renders the bacterial strain resistant to vancomycin. In some embodiments of the compositions provided herein, the bacterial strains are human-derived bacteria.. In some embodiments of the compositions provided herein, the bacterial strains are derived from more than one human donor. In some embodiments of the compositions provided herein, the composition induces proliferation and/or accumulation of CD8+ T-cells. In some embodiments of the compositions provided herein, the composition activates CD8+ IFN-gamma producing T-cells through Irf4-dependent and/or Batf3-dependent dendritic cells.

In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

In one aspect, the disclosure provides a food product comprising any of the compositions provided herein and a nutrient.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor. In some embodiments of the compositions provided herein, the immune checkpoint inhibitor is a CTLA-4 inhibitor. In some embodiments of the compositions provided herein, the composition further comprises one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28 antibody, OX-40 antibody, 4-1BB antibody, CD40 antibody, ICOS/CD278, CD26-type molecule, CD27/TNFRSF7, CD30/TNFRSF8, or GITR/CD357.

In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen.

In some embodiments of the compositions provided herein, the composition further comprises one or more anti-inflammatory agents. In some embodiments of the compositions provided herein, the anti-inflammatory agent is an NSAID.

In some embodiments of the compositions provided herein, administration of the composition to a subject results in the induction of proliferation and/or accumulation of CD8+ T-cells in the intestine of the subject. In some embodiments of the compositions provided herein, the CD8+ T-cells are IFN-gamma producing CD8+ T-cells. In some embodiments of the compositions provided herein, the induction of CD8+ T-cells is dependent on CD103+ dendritic cells. In some embodiments of the compositions provided herein, administration of the composition to a subject results in an increase in IFN-gamma production in the intestine of a subject. In some embodiments of the compositions provided herein, administration of the composition to a subject results in activation of CD8+ IFN-gamma producing T-cells through Irf4-dependent and/or Batf3-dependent dendritic cells. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial stratus of the administered composition in the intestine of the subject. In some embodiments of the compositions provided herein, administration of the composition to a subject results in an increase in the number of the bacterial strains of the administered composition engrafted in the intestine of the subject. In some embodiments of the compositions provided herein, administration of the composition to a subject results in an increase in the amount of bacteria of the bacterial strains of the administered composition in the intestine of the subject. In some embodiments of the compositions provided herein, administration of the composition to a subject results in an increase in the amount of bacteria of the bacterial strains of the administered composition engrafted in the intestine of the subject.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition. In some embodiments of the methods provided herein, the administration of the composition to the subject results in an increase of IFN-gamma production in the intestine of the subject when compared to the IFN-gamma production in the intestine of the subject before the administration of the composition. In some embodiments of the methods provided herein, the IFN-gamma is produced in the intestine by CD8+ IFN-gamma producing T-cells. In some embodiments of the methods provided herein, the CD8+ IFN-gamma producing T-cells are activated through Irf4-dependent and/or Batf3-dependent dendritic cells. In some embodiments of the methods provided herein, the administration of the composition to the subject results in an increase of IFN-gamma production in the intestine of the subject by at least 10%, at least 20%, at least 30%, at least 40%, at least 50%, at least 100%, or at least 200% when compared to the IFN-gamma production in the intestine of the subject before the administration of the composition. In some embodiments of the methods provided herein, the administration results in systemic induction of CD8+ T cells. In some embodiments of the methods provided herein, the administration results in a long-term induction of CD8+ T cells.

In some embodiments of the methods provided herein, an antibiotic is administered prior to the administration of any one of the compositions. In some embodiments of the methods provided herein, wherein the antibiotic is vancomycin.

In some embodiments of the methods provided herein, the subject has cancer. In some embodiments of the methods provided herein, the cancer is carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent. In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the cancer immunotherapy agent is a PD-1 inhibitor and a CTLA-4 inhibitor. In some embodiments of the methods provided herein, the administration does not induce an adverse event. In some embodiments of the methods provided herein, the administration does not induce a checkpoint inhibitor associated adverse event. In some embodiments of the methods provided herein, the administration does not induce colitis.

In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28 antibody, OX-40 antibody, 4-1BB antibody, CD40 antibody, ICOS/CD278, CD28-type molecule, CD27/TNFRSF7, CD30/TNFRSF8, or GITR/CD357.

In some embodiments of the methods provided herein, the method further includes administering one or more vaccines. In some embodiments of the methods provided herein, the vaccine is a dendritic cell vaccine.

In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus.

In some embodiments of the methods provided herein, five subject has an autoimmune disease or an allergic disease.

In some embodiments of the methods provided herein, the composition further includes one or more anti-inflammatory agents. In some embodiments of the methods provided heroin, the anti-inflammatory is an NSAID.

In some embodiments of the methods provided herein, the composition mas be administered as one dose or more than one dose.

In some embodiments of the compositions provided herein, the composition activates the immune system.

In one aspect, the disclosure provides a method for activating the immune system, the method comprising administration of one or more of the compositions provided herein.

In one aspect, the disclosure provides a method for activating CD8+ IFN-gamma-producing T-cells, the method comprising administration of one or more of the compositions provided herein to a subject. In some embodiments, the CD8+ IFN-gamma producing T-cells are activated through Irf4-dependent and/or Batf3-dependent dendritic cells.

In one aspect, the disclosure provides a method for inducing the proliferation and/or accumulation of CD8+ T cells in the intestine, comprising administering to a subject any one or more of the compositions provided herein, wherein the administering results in the induction of proliferation and/or accumulation of CD8+ T cells in the intestine of the subject. In some embodiments, the CD8+ IFN-gamma producing T-cells are activated through Irf4-dependent and/or Batf3-dependent dendritic cells.

In one aspect, the disclosure provides a method for treating, assisting in treatment, and/or preventing cancer or viral infection, comprising administering to a subject any one or more of the compositions provided herein, wherein the administering treats, assists in treatment, and/or prevents cancer or viral infection.

In one aspect, the disclosure provides a vaccine composition containing antigen derived from constituents and/or metabolites of bacterial species of any one of the compositions provided herein.

In one aspect, the disclosure provides a method for inducing an immune response in a subject, comprising administering to the subject any of the vaccines provided herein, wherein the administering results in the induction of an immune response of the subject.

In some embodiments of the methods provided herein, the one or more bacterial strains of the administered composition was not previously present in the intestine of the subject. In some embodiments of the methods provided herein, administration of the composition to a subject results in the engraftment of one or more bacterial strains of the administered composition in the intestine of the subject. In some embodiments of the methods provided herein, the one or more bacterial strains of the administered composition was not previously engrafted in the intestine of the subject. In some embodiments of the methods provided herein, administration of the composition to a subject results in an increase in the number of the bacterial strains of the administered composition in the intestine of the subject. In some embodiments of the methods provided herein, administration of the composition to a subject results in an increase in the number of the bacterial strains of the administered composition engrafted in the intestine of the subject. In some embodiments of the methods provided herein, administration of the composition to a subject results in an increase in the amount of bacteria of the bacterial strains of the administered composition in the intestine of the subject. In some embodiments of the methods provided herein, administration of the composition to a subject results in an increase in the amount of bacteria of the bacterial strains of the administered composition engrafted in the intestine of the subject.

In some embodiments of the methods provided herein, the induction of CD8 T cells does not result in inflammation in the subject.

In one aspect, the disclosure provides a method comprising evaluating if a subject has one or more CD8 T cell inducing bacterial strains in its microbiome, wherein if the subject does not have detectable levels of the one or more CD8 T cell inducing bacterial strains, any of the compositions of the preceding claims is administered to the subject.

In one aspect, the disclosure provides a method comprising, evaluating if a subject has one or more CD8 T cell inducing bacterial strains in its microbiome at a level sufficient to induce a CD8 T cell response, wherein if the subject does not have one or more CD8 T cell inducing bacterial strains at a level sufficient to induce a CD8 T cell response, any of the compositions of the preceding claims is administered to the subject.

In some embodiments of the methods provided herein, the method does not include a step of administering an antibiotic. In some embodiments of the methods provided herein, the subject is not administered an antibiotic.

In some embodiments, the compositions provided herein further comprise one or more metabolites selected from the group consisting of mevalonate, dimethylglycine, hypoxanthine, IMP, 2-deoxy-glucose 6P, TMP, 6PG, Rib5P, Ru5P, Xu5p, GDP, GlcNAc 6P, UMP, GMO, CDP, Pyridoine B6, Opthalomic acid, Ctp, GTP, ATP, F6P, 5-methyltetrahydrofolic acid, adenylosuccinate, G6P, 3-hydroxyanthranalinic acid, glycerol 3P, sedoheptulose 7P, 2-keto-4-methylthiobutyrate, dUMP, histamine, valeric acid, 3PG+2 PG, G1P, thymidine, CMP, dopamine, phosphoenolpuryvate, HPO4, iso-butyrate, allotoin, acatylcarnitine, and thymine; and a pharmaceutically acceptable carrier.

In some embodiments, the compositions provided herein further comprise one or more metabolites selected from the group consisting of mevalonate, dimethylglycine, hypoxanthine, IMP, 2-deoxy-glucose 6P, TMP, 6PG, Rib5P, Ru5P, Xu5p, GDP, GlcNAc 6P, UMP, GMO, and CDP, and a pharmaceutically acceptable carrier.

In some embodiments, the compositions provided herein further comprise one or more metabolites selected from the group consisting of mevalonate and dimethylglycine, and a pharmaceutically acceptable carrier. In some embodiments, the compositions provided herein further comprise mevalonate and a pharmaceutically acceptable carrier. In some embodiments, the compositions provided herein further comprise dimethylglycine and a pharmaceutically acceptable carrier. In some embodiments, the compositions provided herein further comprise mevalonate, dimethylglycine, and a pharmaceutically acceptable carrier.

Any of the compositions provided herein may further comprise one or more anticancer agents. In some embodiments, the anticancer agent is a chemotherapy agent. In some embodiments, the anticancer agent is a cancer immunotherapy agent. In some embodiments, the cancer immunotherapy agent is an immune checkpoint inhibitor. In some embodiments, the immune checkpoint inhibitor is a PD-1 inhibitor, PD-L-1 inhibitor, or CTLA-4 inhibitor. In some embodiments, the immune checkpoint inhibitor is a PD-1 inhibitor. In some embodiments, the immune checkpoint inhibitor is a CTLA-4 inhibitor.

Any of the compositions provided herein may further comprise one or more metabolites selected from the group consisting of mevalonate, dimethylglycine, hypoxanthine, IMP, 2-deoxy-glucose 6P, TMP, 6PG, Rib5P, Ru5P, Xu5p, GDP, GlcNAc 6P, UMP, GMO, CDP, Pyridoine B6, Opthalomic acid, Ctp, GTP, ATP, F6P, 5-methyltetrahydrofolic acid, adenylosuccinate, G6P, 3-hydroxyanthranalinic acid, glycerol 3P, sedoheptulose 7P, 2-keto-4-methylthiobutyrate, dUMP, histamine, valeric acid, 3PG+2 PG, G1P, thymidine, CMP, dopamine, phosphoenolpuryvate, HPO4, iso-butyrate, allotoin, acetylcarnitine, and thymine. In some embodiments, the compositions provided herein further comprise one or more metabolites selected from the group consisting of mevalonate, dimethylglycine, hypoxanthine, IMP, 2-deoxy-glucose 6P, TMP, 6PG, Rib5P, Ru5P, Xu5p, GDP, GlcNAc 6P, UMP, GMO, and CDP. In some embodiments, the compositions provided herein further comprise one or more metabolites selected from the group consisting of mevalonate and dimethylglycine. In some embodiments, the compositions provided herein further comprise mevalonate. In some embodiments, the compositions provided herein further comprise dimethylglycine. In some embodiments, the compositions provided herein further comprise mevalonate and dimethylglycine.

In one aspect, the present disclosure provides a method of treating a disease in a subject comprising administering any of the compositions described herein to a subject in an effective amount to treat a disease. In some embodiments of the methods described herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject prior to the administration of the composition.

In some embodiments, administration of any of the compositions provided herein to the subject results in an increase of IFNγ production in the intestine of the subject compared to the IFNγ production in the intestine of the subject prior to the administration of the composition. In some embodiments, the IFNγ produced in the intestine is by CD8+ IFNγ producing T-cells. In some embodiments, the CD8+ IFNγ producing T-cells are activated through Irf4-dependent and/or Batf3-dependent dendritic cells. In some embodiments, administration of any of the compositions provided herein to a subject results in an increase of IFNγ production in the intestine of the subject by at least 10%, at least 20%, at least 30%, at least 40%, at least 50%, at least 100%, or at least 200% as compared to the proliferation and/or accumulation of CD8+ T-cells in the intestine of the subject prior to the administration of the composition.

In some embodiments of the methods described herein, the subject has cancer. In some embodiments, the cancer is carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney canter, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments, the cancer is prostate cancer, bladder cancer, non-small cell lung cancer, urothelial carcinoma, melanoma, or renal cell carcinoma.

In some embodiments of the methods described herein of the methods described herein, the infectious disease is a bacterial infection, a vital infection, a parasitic infection, or a fungal infection. In some embodiments, the infectious disease is a viral infection. In some embodiments, the viral infection is HIV.

In some embodiments of the methods described herein, the subject has an autoimmune disease or an allergic disease.

In some embodiments, the PD-1 inhibitor is nivolumab. In some embodiments, the PD-1 inhibitor is pembrolizumab. In some embodiments, the PD-1 inhibitor is pidiluzimab.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. The figures are illustrative only and are not required for enablement of the disclosure. For purposes of clarity, not every component may be labeled in every drawing. In the drawings:

FIG. 15 shows the species of the 26 isolated bacterial strains.

FIG. 16 shows the 21 isolated bacterial strains selected for further analysis, indicated in a box. Five of the 26 isolated bacterial strains were excluded due to a negative correlation with induction of IFN-positive CD8 T cells.

FIG. 20 shows the 11 isolated bacterial strains selected for further analysis, indicated in a box. The selected 11 isolated bacterial strains were found to be positively correlated with induction of IFN positive CD8 T cells.

FIG. 22 shows the other 10 isolated bacterial strains of the set of 21 isolated bacterial strains (FIG. 16) that were excluded from further analysis, indicated by the upper box.

FIG. 29 shows the 11 isolated bacterial strains selected for further analysis, indicated in a box. The 4 strains indicated with arrows are non-Bacteroides strains, whereas the other 7 strains are Bacteroides strains.

FIG. 36 shows data from the experiments with the MC38 tumor model described in Example 4. Mice were administered anti-PD1 antibody ("+α-PD1 Ab") on the indicated days. Mice were gavaged with the mixture of 11 isolated bacterial strains ("11-mix") on the indicated days. Tumor volume was measured. *, , and * indicate increasing amounts of statistical significance.

FIGS. 43A and 43B show the percentage of IFN+ cells among CD3+TCR+CD8 T cells in the indicated organs (iLN, inguinal lymph node; SI, small intestine) of SPF mice (FIG. 43A) and in the colon and small intestine lamina propria of SPF and GF mice (FIG. 43B). FIG. 43C shows the percentages of CD103+ and GzB+ cells among the colonic IFN+CD8 T cell populations of SPF and GF mice. FIG. 43D shows the percentage of colonic CD8 T cells that are IFN+ from GF mice orally inoculated with faecal samples from one of six (A-F) healthy human donors. The arrow indicates mouse B5, which was chosen for further analysis. FIG. 43E shows the percentage of CD8 T cells that are IFN+ from GF mice inoculated with the caecal contents from mouse B5, in the absence of antibiotics or the presence of the indicated antibiotics in the drinking water (B5+ the indicated antibiotic), or from GF mice inoculated with chloroform-treated caecal contents from mouse B5 ("Chlo B5"). The arrows indicate mouse B5-Amp2 and mouse B5-Amp3, which were chosen for further analysis. FIG. 43F shows the caecal microbiota composition of each mouse as determined by 16S rRNA gene sequencing. OTUs that positively correlated with the frequency of IFN+CD8 T cells are indicated with a "#"; OTUs that were detected in +Chlo B5 mice are indicated with a "+"; and OTUs that did not significantly correlate with the frequency of IFN+CD8 T cells are indicated with a "–". OTUs corresponding to the 26 isolated strains are indicated with a ">>". FIG. 43G shows a list of the 26 strains isolated from mice B5-Amp2 and B5-Amp3. The closest species/strain to each of the isolated strains and the % similarity to the RDP database are indicated. FIGS. 43H-43M show the percentages of IFN+CD8 T (FIGS. 43H, 43I, and 43M), GrB+IFN+CD8 T (FIG. 43J), TH1 cells (FIG. 43K, left panel), and TH17 cells (FIG. 43K, right panel) from GF mice inoculated with the indicated mixture of bacterial strains. FIG. 43L shows the histology score tor colons from the indicated mice 4-weeks post-colonization. SPF mice from CLEA were analyzed in FIGS. 43A-43C. In FIGS. 43A-43E and 43H-43M, each circle represents an individual animal, and the height of the bars indicates the mean. Data are representative of at least two independent experiments. Error bars. s.d. *P<0.001; P<0.01; *P<0.05; ns, not significant.

FIG. 44A shows the percentage of IFN+CD8 T cells in the colon of GF mice orally administered the mixture of 11 bacterial strains, either live or heat-killed ("HK"). FIG. 44B shows fluorescence in situ hybridization (FISH) staining with DAP1 (blue), EUB338 FISH probe (green), and Mucin 2 (MUC2, red) of the proximal colon of GP+11-mix mice. Scale bar, 25 m. FIG. 44C shows the percentage of IFN+CD8 T cells in the indicated organs of GF mice (light gray columns) or GF mice inoculated with the 11-mix (GF+11mix) 1-week post-colonization (dark gray columns) (cIEL, colonic intraepithelial lymphocyte; MLN, mesenteric lymph node; iLN, inguinal lymph node; PBL, peripheral blood lymphocyte). FIG. 44D shows expression of chemokine transcripts (Cxcl9 and Cxcl10) normalized to -actin in colonic epithelial cells (ECs), as quantified by qPCR. FIG. 44E shows the percentages of Ki67+ cells (left panel) and IFN+ cells (middle panel) among the CD8 T cell population and CD103+ cells (right panel) among the IFN+CD8 T cell population in GF mice that were inoculated with the mixture of the 11 bacterial strains at the indicated time points. FIG. 44F shows the percentage of IFN+ cells among colonic lamina propria CD8 T cells from mice of the indicated genetic background, colonized with the mixture of 11 bacterial strains (GF+11mix) or without (GF). FIG. 44G shows the frequencies of V gene usage among IFN+CD8 T cells (left panel) and IFN−CD8 T cells (right panel) from GF mice and GF mice inoculated with the mixture of 11 bacterial strains (GF+11-mix). FIGS. 44H-44J show the percentage of IFN+ cells among colonic lamina propria CD8 T cells from the indicated GF mice or GF mice colonized with the mixture of 11 bacterial strains (GF+11mix). FIG. 44K shows H-2Kb expression by the indicated subset of dendritic cells from GF mice and GF trace colonized with the mixture of 11 bacterial strains (GF+11-mix) at 1-week post-colonization). In FIGS. 44A and 44C-44J, each circle represents an individual animal, and the height of each bar indicates the mean. The means are connected with a line in FIG. 44E. Data are representative of at least two independent experiments. Error bars, s.d. *P<0.001; P<0.01; *P<0.05; ns, not significant.

FIG. 45A shows the experimental design. C57BL/6 SPF mice obtained from SLC mice (IFN+ CD8+ T low mice, see FIG. 47E) were treated with AVMN (ampicillia, vancomycin, metronidazole, neomycin), then reconstituted with SPF faecal microbiota (SPFfae) by oral gavage. In the group that received the mixture of 11 bacterial strains (+11mix), the initial administration of the 11-mix was done simultaneously with SPFfae, followed by repeated oral gavage with the 11-mix at the indicated time points. Then, the mice were infected orally (FIGS. 45D-45G) or intraperitoneally (FIG. 45H) with Lm (FIGS. 45D-45F and 45H) or Lm-OVA (FIG. 45G). FIG. 45B shows the percentage of IFN+ cells among colonic lamina propria CD8+ T cells in control mice and mice colonized with the mixture of 11 bacterial strains (+11mix) prior to Lm infection on day 0. FIG. 45C shows expression of the indicated genes normalized to -actin in colonic epithelial cells in control mice (Cont) and mice colonized with the mixture of 11 bacterial strains (+11mix) prior to Lm infection on day 0. FIG. 45D shows Lm CFU in faeces of control mice (Cont) and mice colonized with the mixture of 11 bacterial strains (+11mix) following the Lm gavage. FIG. 45E shows photomicrographs of haematoxylin and eosin stained samples (scale bar, 50 m) and a histology score of the colon of control mice infected with Lm (Cont+Lm; Cont) or mice colonized with the 11 mix and infected with Lm (+11 mix+Lm; +11mix). FIG. 45F shows the percent weight change following Lm gavage during the course of Lm infection of control mice (Cont) or mice colonized with the mixture of 11 bacterial strains (+11mix). FIG. 45G shows the number of SIINFEKL-specific colonic IFN+CD8+ T cells induced after Lm-OVA infection of control mice (Cont) or mice colonized with the mixture of 11 bacterial strains (+11mix), as enumerated by FACS on day 7 post-infection. FIG. 45H shows Lm CFU in livers and spleens of control mice (Cont) or mice colonized with the mixture of 11 bacterial strains on day 3 post-intraperitoneal infection with Lm. In FIGS. 45B-45H, each circle represents an individual animal. In FIGS. 45B, 45C, 45E, 45G, and 45H, the height of the bars indicates the mean. Data are representative of at least two independent experiments. Error bars, s.d. **P<0.01; *P<0.05.

FIG. 46A shows the experimental design. SPF mice obtained from SLC were subjected to treatment with AVMN (ampicillin, vancomycin, metronidazole, neomycin) (from day -7 to day 2) followed by subcutaneous implantation of MC38 adenocarcinoma cells (FIGS. 46B-46I) or BRAFV600EPTEN-/-melanoma cells (FIG. 46J) on day 0. The mice were reconstituted with SPF faecal microbiota (SPFfae) on day 3. The groups that received the mixture of 11 bacterial strains, the initial oral administration of the 11-mix was done simultaneously with the SPFfae on day 3, followed by repeated dosing of the 11-mix alone 2 or 3 times per week until the end of the experiment. The anti-PD1 antibody (PD1 mAb) (FIGS. 46B-46H and 46J) or anti-CTLA4 antibody (CTLA4 mAb) (FIG. 46I) was injected intraperitoneally every third day between days 3 and 9. FIGS. 46B, 46I, and 46J show representative tumour growth data of MC38 adenocarcinoma (FIGS. 46B and 46I) and BRAFV600EPTBN−/− melanoma (FIG. 46J). FIGS. 46C-46H show the number or percentage of tumour-infiltrating CD8+ T cells (FIG. 46C), IFN+CD8+ and GrB+IFN+CD8+ T cells (FIG. 46D), PD-1+ ICOS+IFN+CD8+ T cells (FIG. 46E), p15E-specific IFN+ CD8+ T cells (FIG. 46F), MHC class II+CD11c+DCs (FIG. 46G), and mean fluorescence intensity of H-2Kb on DCs (FIG. 46H), as determined by flow cytometry. Each circle in FIGS. 46C-46H represents an individual animal, and the height of the bars indicates the mean. The symbols in FIGS. 46B, 46I, and 46J represent the means. Data are representative of at least two independent experiments. Error bars, s.d. *P<0.001; P<0.01; *P<0.05; ns, not significant.

FIG. 47A shows representative flow cytometry plots showing expression of CD8+, IFN, TCR, CD8, CD44, GrB, T-bet, CD103, and ICOS by colonic lamina propria CD3+CD8+ or CD3+ TCR+CD8+ T cells from SPF mice obtained from CLEA. FIG. 47B shows the number of IFN+CD3+TCR+CD8 T cells in the colonic or small intestinal lamina propria cells of GF and SPF mice. FIG. 47C shows data from GF mice (7 weeks old) that were orally inoculated with the faecal microbiome from SPF CLEA mice (SPFfae). After 4 weeks, the percentage of IFN+ cells among CD8 T cells was analyzed. FIG. 47D shows the percentage of IFN+ cells among CD8 T cells in the colonic lamina propria of CLEA SPF mice treated with/without AVMN (ampicillin, vancomycin, metronidazole, neomycin) via the drinking water for 4 weeks (from 8 to 12 weeks old). FIG. 47E shows the percentage of IFN+ cells among colonic CD8 T cells in the colonic lamina propria of SPF C57BL/6 mice (10 weeks old) reared at the indicated institute or vendor (left panel). SPF C57BL/6 mice (8 weeks old) obtained from Charles River were co-housed with C57BL/6 mice from CLEA for 2 or 6 weeks. The percentage of IFN+ cells among colonic CD8 T cells in the colonic lamina propria of co-housed Charles River mice are shown (FIG. 47E, right panel). Each circle represents an individual animal (n=3-5), and the height of the bars indicates the mean. Data are representative of at least two independent experiments. Error bars, s.d. ***P<0.001; *P<0.05.

FIGS. 49A and 40B show induction of IFN+CD8+ T cells by healthy human gut microbiota from various donors. FIG. 49A shows representative flow cytometry plots showing expression of IFN and CD8 by colonic (top panels) or small intestine (SI; bottom panels) LP CD3+TCR+ T cells from GF mice orally inoculated with faecal samples from the indicated healthy human donors (donors A to F). The bar graph summarizes the frequency of IFN+ cells among the CD3+TCR+CD8+ parent T cell population in the small intestine lamina propria.

FIG. 51A shows representative flow cytometry plots showing expression of IFN, CD8, CD103, ICOS, KLRG1, GrB, T-bet, CD44, Foxp3, and IL17A by colonic lamina propria CD3+TCR+ or CD3+TCR+CD8+ T cells from GF mice and GF mice colonized with the mixture of 11 bacterial strains (GF +11-mix). FIG. 51B shows percentages of IFN+ cells among the CD3+TCR+CD4 T cells (TH1 cells) (left panel), IFN+ cells among CD3+TCR+CD4-negative T cells (mostly CD8 T cells) (middle panel), and IL-17A+ cells among the CD3+TCR+CD4 T cells (TH17 cells) (right panel) in the colonic lamina propria of the indicated mice. Each circle represents an individual animal, and the height of the bars indicates the mean. Data are representative of at least two independent experiments. Error bars, s.d. *P<0.001; P<0.01.

FIG. 52A shows expression of the indicated genes (I16 and Lcn2) in colonic epithelial cells of GF, GF colonized with the mixture of 11 bacterial strains (GF+11-mix) (4 week post-colonization), and SPF mice, as determined by qPCR. Each symbol represents an individual animal, and the height of the burs indicates the mean. FIG. 52B shows representative photographs of the colons of GF, GF+11-mix, and SPF mice. FIG. 52C shows haemotoxylin and eosin stained photomicrographs of colons from SPF mice and GF mice colonized with the mixture of 11 bacterial strains (GF+11-mix). Scale bar, 50 m. Data are representative of at least two independent experiments. Error bars, s.d. as, not significant.

FIG. 53 presents a table showing 16S rRNA gene and genome sequencing analysis of the 26 strains. Bacterial DNA was isolated from each of the 26 strains. The 16S rRNA gene sequences were determined by PCR and Sanger sequencing. Genome sequencing was conducted for the 21 strains using Illumina MiSeqR sequencer. The 16S rRNA and gene encoding 42 ribosomal proteins predicted from the assembled draft genome of each strain were compared to the RDP database and the NCBI genome database (Refseq genome representative), respectively, to find the closest reference species or strain. The top hit organisms with the 16S rRNA sequence and ribosomal proteins of each strain (more than 37 ribosomal proteins hit) are listed in the table, whereas bacteria with less similarity (less than 34 proteins hit) are shown with parentheses. The percent similarity refers to the average sequence similarity of the hit ribosomal protein genes. The percent similarity of each ribosomal protein gene was calculated between the isolated strain and the closest reference bacteria using a global-local alignment search program (GLSEARCH).

FIG. 55A shows data related to the luminal contents from the indicated anatomical positions of the gut and faecal samples from three GF mice colonized with the mixture of 11 bacterial strains 3-4 weeks post-colonization. The relative abundance of DNA from each of the 11 strains was determined by qPCR (top panel ). For each anatomical location, the strains are, from left to right, 81A6, 81B11, 81C1, 81E7, 81H9, 82A6, 82B1, 82F11, 82G1, 82G5, and 82G9 (top panel). The percentage of IFN+CD8 T cells in the small intestine lamina propria, caecum, and colonic lamina propria of GF mice (left columns) and GF mice colonized with the mixture of 11 bacterial strains (right columns, GF+11-mix) is shown in the bottom panel. FIG. 55B shows the relative expression of the indicated genes in colonic epithelial cells of GF mice and GF mice colonized with the 11-mix (GF+11-mix) 1-week post-colonization, as determined by qPCR. Each circle represents an individual animal (n=3-4), and the height of the bars indicates the mean. Error bars, s.d. *P<0.001; P<0.01; P<0.05.

FIG. 56A shows the experimental design. SPF mice obtained from SLC were either left untreated or treated with AVMN (ampicillin, vancomycin, metronidazole, neomycin), and then reconstituted with SPF faecal microbiota ("SPFfae"). For the groups that received the mixture of 11 bacterial strains, the initial oral administration was simultaneous with SPFfac. The single gavage group ("single") did not receive any further administration of the 11-mix, while the groups that received repeated gavage ("rep."), received the 11-mix orally every 3-4 days. FIG. 56B shows the percentage of colonic IFN+CD8 T cells on day 28, as analyzed by FACS. Each circle represents an individual animal (n=4-7), and the height of the bars indicates the mean. Error bars, s.d. *P<0.001; P<0.01.

FIG. 57A shows a photograph of representative MC38 tumours on day 27 from mice having received the indicated treatments. FIG. 57B shows haematoxylin and eosin staining and a histology score of the colons on day 27 (no treatment "–", +αPD1 mAb, +11mix, and +11mix+αPD1 mAb) and day 44 (αCTLA4 mAb and +11mix+αCTLA4 mAb). For comparison, the histology score of the colon of SPF 1110−/−mice (colitis prone mice) is shown. Scale bar, 50 μm. Each symbol represents an individual animal (n=4-8), and the height of the bars indicates the mean. Error bars, s.d.

FIG. 58A shows the median abundance across all marker regions plotted against marker genes coverage. Points with high abundance at low coverage, e.g. <75%, indicate limited marker region resolution and likely represent other strains of a species. FIG. 58B shows data related to detection of strains. A strain was deemed detected if at least 95% of the 1 kbp regions in the marker region was detected. Among the 11 strains, 5 strains were detected in 15 out of 3039 microbiome samples evaluated.

FIG. 60A shows the abundance of the strain specific marker regions in the faecal microbiome of six healthy Japanese volunteers (Donors A to F), as performed in FIGS. 58A and 58B. A strain was deemed detected if at least 95% of the 1 kbp regions in the marker region were detected. Two strains were detected in the same from donor B. FIG. 60B shows the abundance at species level, which was calculated as in FIG. 59. The mapped read counts were normalized to reads per kilobase per million (RPKM).

FIGS. 61A and 61B show the percentage of IFNγ+ cells among CD3+TCRβ+CD8 T cells in the indicated organs (iLN, inguinal lymph nodes) of SPF mice (FIG. 61A) and in the colonic and small intestine lamina propria (SI LP) of SPF and GF mice (FIG. 61B). FIG. 61C shows the percentage of colonic CD8 T cells that were IFNγ+ from GF mice orally inoculated with one of six (A-F) healthy human faecal samples. Arrow indicates mouse B5, which was selected for follow-up analysis. FIG. 61D shows the percentage of CD8 T cells that are IFNγ+ from GF mice inoculated with caecal contents from mouse B5 and treated with or without the indicated antibiotics via the drinking water (B5+Abx), or from GF mice inoculated with chloroform-treated caecal contents from mouse B5 (Chlo B5). The arrow indicates mice B5-Amp2 and B5-Amp3, which were selected for further analysis. FIG. 61E shows the composition of the caecal microbiota of each mouse as determined by 16S rRNA gene sequencing. OTUs positively correlated with frequency of IFNγ+CD8 T cells, those detected in Chlo B5 mice, and those not significantly correlated are marked OTUs corresponding to the 26 isolated strains are also marked. FIG. 61F is a list of the 26 strains isolated from mice B5-Amp2 and B5-Amp3. The closest species/strain and percent similarity in the RDP database are indicated. FIGS. 61G, 61H, and 61J show the percentage of CD8 T ceils that were IFNγ+ from GF mice inoculated with the indicated mixture of bacterial strains. FIG. 61I shows the percentage of CD8 T cells that were IFNγ+ (left panel) and percentage of IFNγ+CD8 T ceils that were CD103+ (right panel) in GF mice at the various time points following inoculation. Each circle in FIGS. 61A-61D and 61G-61J represents an individual animal. The height of each bar, and horizontal line at each time point in FIG. 61I, indicates the mean. Error bars, s.d. *P<0.001; P<0.01; *P<0.05; ns, not significant.

FIG. 62A shows the percentage of colonic lamina propria (LP) CD8 T cells that were IFNγ+ from GF mice that were orally administered the mixture of 11 bacterial strains live or heat-killed (HK) ("+11-mix"). FIG. 62B shows fluorescence in situ hybridization (FISH) staining with DAPI, EUB338 FISH probe, and mucin 2 (MUC2) of the proximal colon from GF mice that were administered the 11 bacterial strains. The dashed line outlines the mucus layer. Scale bar, 25 μm. FIG. 62C shows the expression of chemokine transcripts Cxcl9 and Cxcl10 normalized to β-actin in colonic epithelial cells (ECs) (day 7 post-colonization with the mixture of 11 bacterial strains), as quantified by qPCR. FIGS. 62D, 62H, 62I, and 62K show the percentage of IFNγ+ cells among colonic LP CD8 T cells from the indicated mice colonized with or without the mixture of 11 bacterial strains (+11mix) for 1 week (FIG. 62D) or 4 weeks (FIGS. 62H, 62I, and 62K). FIG. 62E shows the percentage of Ki67 cells among the IFNγ+CD8 T cell population in GF mice were colonized with the mixture of 11 bacterial strains (+11-mix) for 1 week. FIG. 62F shows the frequencies of Vβ gene usage among IFNγ+CD8 T cells (left panel) and IFNγ−CD8 T cells (right panel) from the colon of GF mice or GF mice that were colonized with the mixture of 11 bacterial strains (+11-mix), as determined by flow cytometry, 2-way ANOVA interaction p-values: 0.0001 (IFNγ+ subset), 0.31 (IFNγ− subset). FIG. 62G shows the percentage of IFNγ+ cells among the CD8 T cell population after the indicated ex vivo stimulation: lysate from the mixture of 11 bacterial strains ("+11 st. lysate"), lysate from the mixture of 10 bacterial strains ("+10 st. lysate"), PMA+ ionomycin. FIG. 62J shows H2-Kb expression by the indicated subset of DC cells (CD11b−CD103+, CD11b+ CD103+) from GF mice or GF mice that were colonized with the mixture of 11 bacterial strains (+11-mix) (1 week post-colonization). FIG. 62L shows the percentage of CD8 T cells that were IFNγ+ in the indicated organs of GF mice 1 week following colonization with the mixture of 11 bacterial strains (cIEL, colonic intraepithelial lymphocytes; MLN, mesenteric lymph nodes; PBL, peripheral blood lymphocytes). Each circle represents an individual mouse (FIGS. 62A, 62C, 62D, 62E, 62H, 62I, 62K, 62K) or a pool of mice (FIGS. 62F and 62G, n=3-5) and the height of each bar indicates the mean. Error bars, s.d. *P<0.001; P<0.01; *P<0.05; ns, nor significant.

FIGS. 63A and 63C show the colon histology score on day 3 or 5, respectively, and FIGS. 63B and 63D show the percent weight change over the course of Listeria monocytogenes infection. FIGS. 63E-63J show C57BL/6 SPF mice were treated with AVMN, then reconstituted with SPF faecal microbiota (SPFfae) by oral gavage. As shown in the experimental design in FIG. 78D, the group that was colonized with the mixture of 11 bacterial strains (+11mix) received the initial administration of the mixture simultaneously with SPFfae, followed by repetitive oral gavage of the 11-mix alone thereafter. Then, the mice were orally (FIGS. 63E-63H, and FIG. 63J) or intraperitoneally (FIG. 63I) infected with Lm-InlA$^{m}$ (FIGS. 63E-63G and FIG. 63J), Listeria monocytogenes (Lm) Lm-OVA (FIG. 63H) or Lm-WT (FIG. 63I). FIGS. 63E and 63F show the colon histology score anti percent weight change at various time points following Lm-InlA$^{m}$ gavage. FIGS. 63G, 63I, and 63J show colony forming units (CFU) of Lm in the indicated tissues over the course of the experiment (FIG. 63G), on day 3 (FIG. 63I), or on day 5 (FIG. 63J) post-infection. FIG. 63H shows the number of SIINFEKL (SEQ ID NO:71)-specific colonic IFNγ+CD8 T cells induced after Lm-OVA infection, as enumerated by flow cytometry on day 7 post-infection. For depletion of CD8 T cells, anti-CD8α mAb was administered intraperitoneally 1 day before the administration of 11-mix, and every 3 to 4 days thereafter. For each graph, each circle represents an individual animal. The mean of each group is represented by the lines in the line graphs and by the height of each bar in the bar graphs, pep. stim., peptide stimulation. Error bars, s.d. *P<0.001; P<0.01; *P<0.05; ns, not significant.

FIGS. 64A and 64C show representative MC38 tumour growth data (tumour volume). FIG. 64B shows the percentage of IFNγ+ among CD8 T cells isolated from the tumours. FIGS. 64D-64K show C57BL/6 SPF mice were subjected to treatment with AVMN (from day −7 to day 2) and subcutaneous implantation of MC38 adenocarcinoma cells (FIGS. 64D-64J) or BRAF$^{V600E}$PTEN−/− melanoma cells (FIG. 64K) on day 0. The mice were reconstituted with SPFfae on day 3. For the groups of mice that were colonized with the mixture of 11 bacterial strains or mixture of 10 bacterial strains, the initial oral administration of the mixtures was done simultaneously with SPFfae on day 3, followed by repetitive dosing of the mixtures alone, 2 or 3 times per week until the end of the experiment. As shown in the experimental design in FIG. 80A, the anti-PD-1 mAb (αPD-1) (FIGS. 64D-64I, FIG. 64K) or anti-CTLA-4 mAb (αCTLA-4) (FIG. 64J) was injected intraperitoneally every third day between days 3 and 9. FIGS. 64D, 64J, 64K show representative tumour growth data of MC38 tumours (tumour volume) (FIGS. 64D and 64J) and $BRAF^{V600E}$PTEN−/− tumours (FIG. 64K) (tumour volume). FIG. 64E shows the percentage of tumour-infiltrating IFNγ+CD8 cells. FIG. 64G shows the percentage of GrB+IFNγ+CD8 T cells. FIG. 64H shows the number of MHC class II+CD11+DCs per gram tumour. FIG. 64I shows the mean fluorescence intensity (MFI) of H2-Kb on DCs, as determined by flow cytometry. FIG. 64F shows the percentage of IFNγ+ cells among the CD8+ TIL cell population from MC38 tumours in SPF mice colonized with the mixture of 11 bacterial strains and administered the PD-1 mAb (+11-mix+PD-1) following ex vivo stimulation with the indicated antigens: p15E peptide (p15E pep), lysate from the 11 strains (+11 st lysate), +PMA and ionomycin (+PMA+iono). Each circle in FIGS. 64B, 64E-64I represents an individual mouse, and the height of each bar indicates the mean. Each circle in FIGS. 64A, 64C, 64D, 64J, 64K represents the mean of a group of mice, and the number of mice for each group are shown in the parentheses. The asterisks show significance of the +11-mix+PD-1 mAb, +11-mix, and +11-mix+CTLA-4 mAb groups. Dotted brackets in a denote comparison with the GF+10-mix group. Error bars, s.d. *P<0.001; P<0.01; *P<0.05, ns, not significant.

FIGS. 65A and 65B show representative flow cytometry plots and histograms showing the expression of CD8α, IFNγ, CD8β, CD44, T-bet, ICOS, CD103, KLRG1, and GrB by colonic LP CD3+TCRβ+ or CD3+TCRβ+CD8α+ T cells isolated from SPF mice obtained from CLEA. FIG. 65C shows the number of IFNγ+CD8 T cells in the colonic or small intestinal lamina propria (SI IP) of GF and SPF mice. FIG. 65D shows the percentage of IFNγ+ cells among CD8 T cells in the colonic lamina propria (LP) of CLEA SPF mice (between 8 and 12 weeks old) that received AVMN or no antibiotics via the drinking water for 4 weeks. FIG. 65E shows the percentage of IFNγ+ cells among CD8 T cells in the colonic LP of SPF C57BL/6 mice from CLEA (between 8-12 weeks old) treated with or without AVMN via the drinking water for 4 weeks. FIG. 65F shows the percentage of IFNγ+ cells among CD8 T cells in the colonic LP of SPF C57BL/6 mice (10 weeks old), reared at the indicated institute or vendor (left panel). SPF C57BL/6 mice (8 weeks old) obtained front Charles River Laboratories ("Charles") were cohoused with C57BL/6 mice from CLEA for 0, 2, or 6 weeks, and percentage of IFNγ+ cells among colonic LP CD8 T cells was analyzed (right panel). Each circle represents an individual mouse, and the height of each bar indicates the mean. Error bars, s.d. ***P<0.001; *P<0.05.

FIG. 67A shows representative flow cytometry plots showing expression of IFNγ and CD8α by colonic or SI LP CD3+TCRβ+ T cells from GF mice orally inoculated with faecal samples from healthy human donors (from donors A to F). FIG. 67B shows a bar graph summarizing the frequency of IFNγ+ cells among the CD8 T cell population in the SI LP. Note that the induction was more pronounced in the colon than in the SI (FIG. 67A), potentially due to preferential colonic colonization. Each circle represents an individual mouse, and the height of each bar indicates the mean. Error bars, s.d. *P<0.001; P<0.01; *P<0.05.

FIG. 69A shows the percentage of IFNγ+ cells among colonic LP CD8 T cells from mice of the indicated genetic background, colonized with or without the mixture of 11 bacterial strains. FIGS. 69B and 69C show representative flow cytometry plots and histograms showing the expression of CD8a, IFNγ, CD103, PD-1, CD44, Tbet, ICOS, KLRG1, and GrB by colonic LP CD3+TCRβ+CD8+IFNγ+ cell (FIG. 69B) or CD3+TCRβ+CD8α+ cells from GF mice and GF mice colonized with the mixture of 11 bacterial strains 4 week post-colonization. FIG. 69D shows the percentages of IFNγ+ cells among CD3+TCRβ+CD4− T cells (representing primarily CD8 T cells) (left panel), IFN+ of CD4+ T cells ($T_H1$ cells) (middle panel), and IL-17A+ of CD4+ T cells ($T_H17$) (right panel) in the colonic LP of the indicated mice. Each circle represents an individual animal, and the height of each bar indicates the mean. Error bars, s.d. *P<0.001; P<0.01; *P<0.05.

FIG. 70A shows expression of the indicated pro-inflammatory genes (I16 (left panel) and Lcn2 (right panel)) in colonic ECs from GF mice and GF mice colonized with the mixture of 11 bacterial strains (4 weeks post-colonization), and SPF mice, as determined by qPCR. FIG. 70B shows representative photographs of the caecums and colons from GF mice, GF mice colonized with the mixture of 11 bacterial strains (4 weeks post-colonization), and SPF mice. FIG. 70C shows representative photomicrographs of haematoxylin and eosin-stained colon sections from GF mice and GF mice colonized with the mixture of 11 bacterial strains 4 weeks or 6 months following colonization (scale bar, 50 μm). FIG. 70D shows the histology score for colons from GF mice and GF mice colonized with the mixture of 11 bacterial strains 4 weeks ("4 w") or 6 months ("6 m") following colonization. FIG. 70E shows the percentage of IFNγ+ cells among CD8 T cells in the colonic LP GF mice and GF mice colonized with the mixture of 11 bacterial strains 4 weeks ("4 w") or 6 months ("6 m") following colonization. Each circle represents an individual animal and the height of each bar indicates the mean. Error bars, s.d. ***P<0.001; ns, not significant.

FIG. 71 shows results from 16S rRNA gene and genome sequencing analysis of the 26 isolated strains. DNA was extracted from each of the 26 strains and 16S rRNA gene sequences were determined via PCR and Sanger sequencing. Genome sequencing was conducted for 21 strains using an Illumina MiSeq sequencer. To identify the closest reference species or strain, 16S rRNA and genes encoding 42 ribosomal proteins predicted from the assembled draft genome of each strain were compared to the RDP and NCBI genome databases (Refseq genome representative), respectively. Top-hit strains were defined as those with the highest 16S rRNA sequence similarity or those with the highest ribosomal gene sequence similarity for the maximum percentage of the 42 queried genes (strains for which this is <37/42 are listed in parentheses). Percent similarity refers to average sequence similarity between ribosomal genes of the isolated strain and those of the top-hit reference strain.

FIG. 73A shows the relative expression of the indicated genes in colonic ECs of GF mice and GF mice colonized with the mixture of 11 bacterial strains 1 week post-colonization, as determined by qPCR. Each circle represents an individual animal, and the height of each bar indicates the mean. FIG. 73B shows the luminal contents from the indicated anatomical positions of die gastrointestinal tract as well as faecal samples collected from three GF mice colonized with the mixture of 11 bacterial strains 3-4 weeks post-colonization. The relative abundance of DNA of each of the 11 strains was determined by qPCR (top panel). The percentage of IFNγ+ CD8 T cells in the SI LP, caecum, and colonic LP of GF mice and GF mice colonized with the mixture of 11 bacterial strains was enumerated by flow cytometry (bottom panel). FIG. 73C shows MLN and caecal contents collected from GF mice colonized with the mixture of 11 bacterial strains 1 week post-colonization. The relative abundance of DNA from each of the 11 strains was determined by qPCR. Each circle represents an individual animal, and the height of each bar indicates the mean, n.d., not detected. Error bars, s.d. *P<0.001; P<0.01; *P<0.05.

FIGS. 74A and 748 show characterization of IFNγ+CD8 T cells induced in the iLNs following colonization with the mixture of 11 bacterial strains. FIG. 74A shows representative flow cytometry histograms showing expression of IFNγ, CD103, PD-1, CD44, ICOS, and KLRG1 by iLN or colonic LP CD3+TCRβ+CD8α+ or CD3+TCRβ+CD8α+IFNγ+ cells from GF mice or GF mice colonized with the mixture of 11 bacterial strains. Note that the expression patterns of these surface markers by iLN IFNγ+CD8 T cells were similar between GF and GF mice colonized with the mixture of 11 bacterial strains. FIG. 74B, bottom row, shows the frequencies of Vβ gene usage among IFNγ+CD8 T cells (left panel) and IFNγ−CD8 T cells (right panel) from the colons or iLNs of GF mice colonized with the mixture of 11 bacterial strains. For each gene, the left column corresponds to the column and the right column corresponds to rite iLN of GF mice colonized with the mixture of 11 bacterial strains. Each circle represents an individual mouse (for iLN data) or a pool of mice (n=5, for colon data), and the height of each bar indicates the mean. Error bars, s.d. *P<0.05.

FIG. 75A, left panel, shows a Principal Component Analysis (PCA) plot of the water-soluble caecal metabolome from GF mice, SPF mice, and mice colonized with a mixture of 4 bacterial strains, 7 bacterial strains, 11 bacterial strains (left panel). FIG. 75A, right panel, shows a PCA plot of the water-soluble caecal metabolome from GF mice and mice colonized with a mixture of 10 bacterial strains for 1 week (10 Mix (1 w)), 10 bacterial strains for 4 weeks ( 0 Mix (4 w)), 11 bacterial strains for 1 week (11 Mix (1 w)), and 11 bacterial strains for 4 weeks (11 Mix (4 w)). FIGS. 75B-75D show heatmaps depicting differentially elevated metabolites in the caecum (FIGS. 75B and 75C) or serum (FIG. 75D) of GF mice, GF mice colonized with a mixture of 11 bacterial strains for 1 week or 4 weeks, and GF mice colonized with a mixture of 10 bacterial strains for 1 week or 4 weeks. Raw metabolomic data were screened for metabolites specifically elevated in GF mice colonized with the mixture of 11 bacterial strains only (FIGS. 75B and 75C) or in GF mice colonized with the mixture of 11 bacterial strains and GF mice colonized with the mixture of 4 bacterial strains only (FIG. 75B) with at least 4-fold enrichment as compared to GF controls and at least 2-fold enrichment compared to the other gnotobiotic groups, with a cutoff p-value of 0.05. Overlapping metabolites between the two datasets were selected (highlighted), and their levels in the serum were queried (FIG. 75D). Candidate effector molecules for the local and systemic effects observed in GF+11-mix mice were identified by considering the metabolomic data in light of the phenotypic immunomodulatory data, and are indicated with asterisks (FIGS. 75B-75D). Heatmap shading represent the z-score normalized Area/ISTD values for each metabolite (red and blue indicate high and low abundance, respectively). Caecal contents were isolated 4 weeks post-gavage unless otherwise noted (1 w, 1 week; 4 w, 4 weeks). Rib5P, ribose-5-phosphate; Ru5P, ribulose-5-phosphate; Xu5P, xylulose-5-phosphate; GlcNAc 6P, N-acetyl-D-glucosamine 6-phosphate; GlcNAc 1P, N-acetyl-D-glucosamine 1-phosphate; 3PG, 3-phospho-D-glycerate; 2PG, 2-phospho-D-glycerate.

FIG. 76A shows the experimental design. SPF mice were either left untreated or treated with AVMN (ampicillin, vancomycin, metronidazole, neomycin), and then reconstituted with SPF faecal microbiota (SPFfae). For the administration of the mixture of 11 bacterial strains, the initial oral administration was done simultaneously with SPFfae, followed by repetitive oral gavage of the mixture of 11 bacterial strains alone at the indicated time points. The single gavage group ("single") did not receive any further administration of the mixture of 11 bacterial strains, while the repetitive gavage group ("rep.") received the mixture of 11 bacterial strains orally every 3-4 days. The group that received SPFfae without the mixture of 11 bacterial strains and the single gavage group received PBS orally every 3-4 days. FIG. 76B shows the percentage of colonic IFNγ+CD8 T cells on day 28 as determined by flow cytometry. FIG. 76C shows SPF snice that were treated with AVMN, then reconstituted with SPFfae by oral gavage. In the group of mice that received the mixture of 11 bacterial strains (+11mix) were administered the initial mixture of 11 bacterial strains simultaneously with SPFfae, followed by repetitive oral gavage of the mixture of 11 bacterial strains alone at the indicated time points. The percentage of IFNγ+ cells of the colonic LP CD8 T cells was determined, and expression of the indicated genes normalized to β-actin in colonic ECs was quantified. Each circle represents an individual animal and the height of each bar indicates the mean. Error bars, s.d. *P<0.001; P<0.01; *P<0.05.

FIG. 78A shows a schematic of the experimental design for experiments using GF mice. C57BL/6 GF mice were colonized with the mixture of 11 bacterial strains, a mixture of 10 bacterial strains, or were left uncolonized as a control. Then, the mice were orally infected with wild-type Lm ("Lm-WT"). FIG. 78B shows colony forming units (CFU) of Lm in the colon on day 3 post-infection. FIG. 78C shows representative micrographs of haematoxylin and eosin (H&E) stained tissue sections from day 3 post infection of GF mice infected with Lm-WT, GF mice colonized with the mixture of 10 bacterial strains and infected with Lm-WT, GF mice colonized with the mixture of 11 bacterial strains and infected with Lm-WT, and GF mice colonized with the mixture of 11 bacterial strains infected with Lm-WT and treated with an anti-CD8 mAb (scale bar, 50 μm). FIG. 78D shows a schematic of the experimental design for experiments using SPF mice. C57BL/6 SPF mice were treated with AVMN, then reconstituted with SPFfae by oral gavage. The group of mice that received the mixture of 11 bacterial strains were administered the initial mixture of 11 bacterial strains simultaneously with SPFfae, followed by repetitive oral gavage of the mixture of 11 bacterial strains alone at the indicated time points. Then, the mice were orally infected with Lm-InlA$^{m}$ (FIG. 78E) or Lm-WT (FIGS. 78F-78I). FIG. 78E shows representative micrographs of haematoxylin and eosin (H&E) stained tissue sections from day 5 post infection of SPF mice infected with Lm-InlA$^{m}$; SPF mice colonized with the mixture of 11 bacterial strains and infected with Lm-InlA$^{m}$; and SPF mice colonized with the mixture of 11 bacterial strains, treated with an anti-CD8 mAb and infected with Lm-InlA$^{m}$. FIG. 78F shows representative micrographs of haematoxylin and eosin (H&E) stained tissue sections from day 5 post infection of SPF mice infected with Lm-WT and SPF mice colonized with the mixture of 11 bacterial strain and infected with Lm-WT. Scale bar, 50 μm. FIG. 78G shows colonic histology score at the indicated time points after Lm-WT infection of SPF mice or SPF mice colonized with the mixture of 11 bacterial strains. For each time point, the left column corresponds SPF mice, and the right column corresponds to SPF mice colonized with the mixture of 11 bacterial strains. FIGS. 78H and 78I show percent weight change over the course of Lm-WT infection. In FIG. 78I, to deplete CD8 T cells, an anti-CD8 mAb (αCD8) was administered intraperitoneally 1 day prior to administration of the mixture of 11 bacterial strains and every 3 to 4 days thereafter. Each circle represents an individual animal. The mean of each group is represented by the lines in the line graphs, and by the height of each bar in the bar graphs. Error bars, s.d. **P<0.01; *P<0.05.

FIG. 79A shows a schematic of the experimental design for experiments with GF mice. C57BL/6 GF mice were colonized with a mixture of 11 bacterial strains or 10 bacterial strains, or left uncolonized, and were subjected to subcutaneous ("sc") implantation of MC38 adenocarcinoma cells ("tumour") on day 0. An anti-PD-1 mAb (αPD-1) was injected intraperitoneally every third day between days 3 and 9. FIG. 79B shows representative flow cytometry histograms showing expression of IFNγ, CD103, PD-1, CD44, ICOS, and KLRG1 by TIL or colonic LP CD3+ TCRβ+CD8α+ cells or CD3+TCRβ+CD8α+IFNγ+ cells from the indicated mice. FIG. 79C, left panel, shows the frequencies of Vβ gene usage among IFNγ+CD8 TILs from GF mice that received the anti-PD-1 mAb (left column for each gene) or GF that were colonized with the mixture of 11 bacterial strains and received the anti-PD-1 mAb (right column for each gene). For each gene, the left column FIG. 79C, right panel, shows the frequencies of Vβ gene usage among IFNγ+CD8 T cells from the colons of GF mice that were colonized with the mixture of 11 bacterial strains (left column for each gene) and GF mice that were colonized with the mixture of 11 bacterial strains and received the anti-PD-1 mAb. Each circle represents an individual mouse (for TIL data) or a pool of mice (n=5, for colon data), and the height of each bar indicates the mean. Error bars, s.d. **P<0.01; *P<0.05.

FIG. 80A shows a schematic of the experimental design for experiments with SPF mice. SPF mice were subjected to treatment with AVMN (from day −7 to day 2) and then subcutaneous implantation of MC38 adenocarcinoma cells on day 0. The mice were reconstituted with SPFfae on day 3. For the groups that received the mixture of 11 bacterial strains or 10 bacterial strains, the initial oral administration of the mixture was done simultaneously with SPFfae on day 3, followed by repetitive dosing of the mixture of 11 or 10 bacterial strains alone 2 or 3 times per week until the end of the experiment. The anti-PD-1 mAb or anti-CTLA-4 mAb was injected intraperitoneally every third day between days 3 and 9. FIG. 80B shows a representative photograph of excised MC38 tumours from mice of the indicated groups on day 23 (scale bar, 10 mm). FIG. 80C shows representative microphotographs of haematoxylin and eosin stained tissue sections, along with a graph showing the histology score, of the colon on day 27 (SPF, SPF+αPD-1 mAb, SPF+11mix, and SPF+11mix+αPD-1 mAb groups) and on day 44 (SPF+αCTLA-4 mAb, and SPF+11mix+αCTLA-4 mAb groups) (scale bar, 50 μm). For comparison, the colonic histology score of SPF 1110−/− (colitis-prone) mice is shown. Each circle represents an individual animal, and the height of each bar indicates the mean.

FIG. 81A shows plots of the detection and abundance of the strain-specific marker regions of the indicated strains. Median abundance across all marker regions was plotted against maker gene coverage. Points with high abundance at low coverage, e.g. <75%, indicate limited marker region resolution and likely represent other strains of a species. FIG. 81B shows among the 11 strains, 4 were detected in 16 out of 3327 microbiome samples evaluated. A strain was deemed detected if at least 95% of 1 kbp regions in the marker region were detected.

FIG. 83A shows the abundance of the strain-specific marker regions in the faecal microbiome of the six healthy Japanese volunteers (Donors A to F), as shown in FIG. 81. A strain was deemed detected if at least 95% of the 1 kbp regions in the marker region were detected. At this sequencing depth, three strains were detected in the Donor B sample, and one in the Donor A sample. FIG. 83B shows the abundance at the species-level, calculated as in FIG. 82. The mapped read counts were normalized to RPKM.

FIG. 84A shows the percentage of IFNγ+ cells among the CD8 T cell population in colons from GF mice colonized with the mixture of 11 bacterial strains (left panel) or MC38 tumours isolated from GF mice colonized with the mixture of 11 bacterial strains and treated with the anti-PD-1 mAb, after ex vivo stimulation with the indicated antigens (right panel). FIG. 84B shows Principal Component Analysis (PCA) plots of TCR Vβ usage by the IFNγ+ and IFNγ− CD8 T cell subsets isolated from the indicated tissues of GF mice (left panel) or GF mice colonized with the mixture of 11 bacterial strains (right panel). For TILs data, IFNγ+ and IFNγ− CD8 T cells were isolated from GF mice±11mix+MC38+PD-1 mAb. Two-way ANOVA interaction p-values comparing two populations at a time were as follows: GF group: 0.006 (CLP IFNγ+ vs. iLN IFNγ+), 0.50 (CLP IFNγ+ vs. TIL IFNγ+), 0.20 (iLN IFNγ+ vs. TIL IFNγ+), <0.0001 (CLP IFNγ− vs. iLN IFNγ−), <0.0001 (CLP IFNγ− vs. TIL IFNγ−), 0.0024 (iLN IFNγ− vs. TIL IFNγ−), GF+11-mix group: <0.0001 (CLP IFNγ+ vs. iLN IFNγ+), <0.0001 (CLP IFNγ+ vs. TIL IFNγ+), 0.0001 (iLN IFNγ+ vs. TIL IFNγ+), +0.0001 (CLP IFNγ− vs. iLN IFNγ−), <0.0001 (CLP IFNγ− vs. TIL IFNγ−), 0.0099 (iLN IFNγ− vs. TIL IFNγ−). Each circle represents an individual mouse (for iLN and TIL data) or a pool of mice (n=3, for colon data), and the height of each bar indicates the mean. Error bars, s.d. *P<0001; P<0.01; ns, not significant.

FIG. 86A shows a schematic of the experimental design for experiments with C57BL/6 germ free (GF) mice. On day 0, GF mice were colonized with a faecal microbiota sample from human donor C ("GF+C") or left uncolonized ("GF"). For the groups that received the 11-mix of bacterial strains or the 10-mix of bacterial strains, the initial oral administration of the mixture of bacterial strains was performed simultaneously with the donor C faecal sample on day 0, followed by repeated dosing of the 11-mix or 10-mix alone 2 or 3 times per week until the end of the experiment. FIG. 86B shows the relative abundance of each of the 11 strains as assessed by quantifying DNA from each strain by qPCR. Faeces were collected at 0, 3, 7, 14, and 20 days post inoculation. Colonization with each of the 11 strains was confirmed. FIG. 86C shows the percentage of IFNα+CD8 T cells in the colonic lamina propria (colon) and inguinal lymph nodes (iLN) at day 21 post inoculation as quantified by flow cytometry. Data presented show the mean and standard error of the mean (FIG. 86B) or standard deviation (FIG. 86C). *P<0.001; P<0.01; *P<0.05; one-way ANOVA with Tukey's test.

DESCRIPTION OF EMBODIMENTS

Detailed Description

Figure 1:
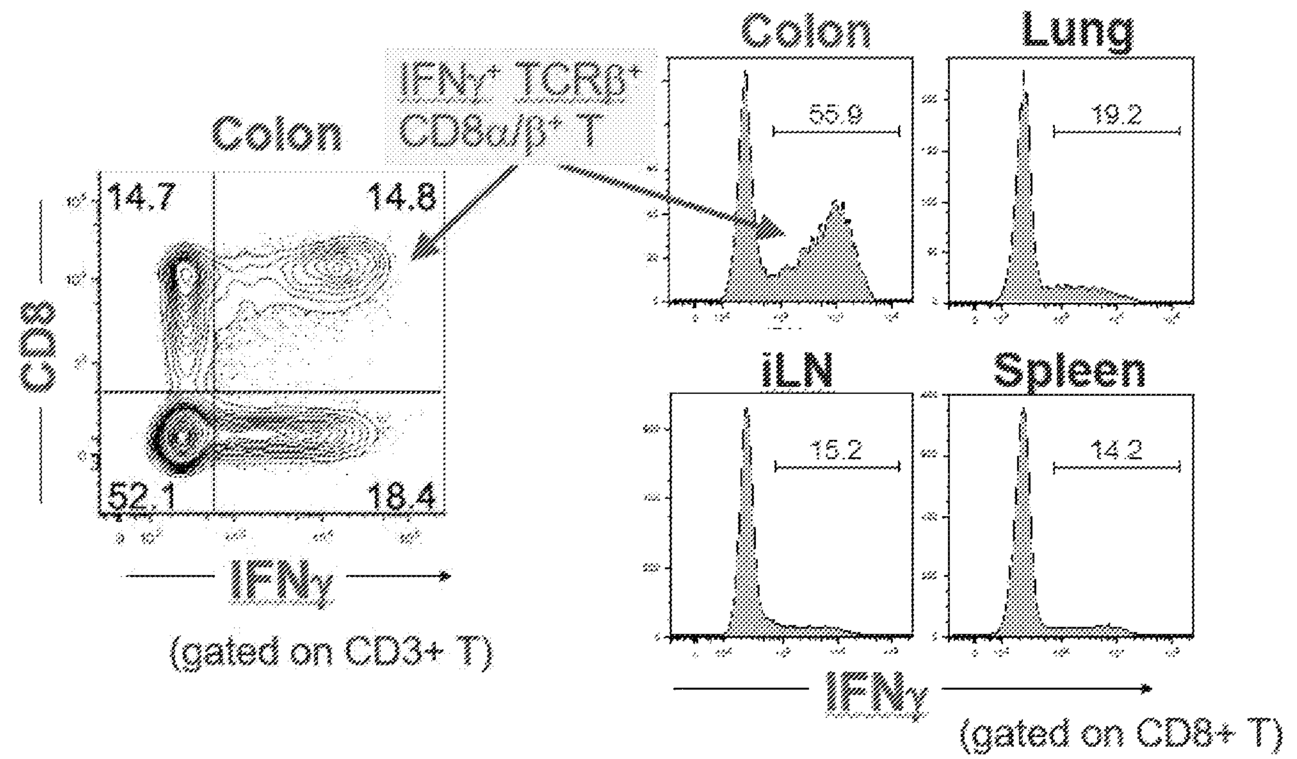
FIG. 1 presents flow cytometry analysis showing lymphocytes that were isolated from the color, lung, lymph nodes, and spleen of mice. IFN-gamma expressing CD8 T cells were found to be present in various organs.

Provided herein are compositions and methods for the induction and/or proliferation of CD8+ T-cells, and methods for the treatment of diseases and conditions that can be treated through the induction and/or proliferation of CD8+ T-cells, including infectious diseases and cancers.

In one aspect, the disclosure provides compositions comprising one or more bacterial strains with unique biological properties. In one aspect, the compositions of the bacterial strains disclosed herein, also referred to as bacterial compositions, can induce the proliferation and/or accumulation of CD8+ T-cells. In one aspect, the compositions of the bacterial strains disclosed herein can induce the proliferation and/or accumulation of CD8+ T-cells.

In one aspect, the bacteria of the compositions disclosed herein can be identified by their 16S rRNA (or 16S rDNA) nucleic acid sequence. In general, bacteria are classified as belonging to a specific species and/or genus based on their 16S rRNA nucleic acid sequence. Bacteria, such as bacteria derived from the microbiome, may also be classified info phylogenetic clusters with other closely related strains and species. (See e.g., Rajilic-Stojanovic, M., and de Vos, W. M. (2014). The first 1000 cultured species of the human gastrointestinal microbiota. FEMS Microbiol Rev 38, 996-1047). Methods for determining the identity of specific bacterial species based on their 16S rRNA (or 16S rDNA)

nucleic acid sequence are well known in the art (See e.g., Jumpstart Consortium Human Microbiome Project Data Generation Working, G. (2012). Evaluation of 16S rDNA-based community profiling for human microbiome research. PLoS One 7, e39315).

Aspects of the present disclosure provide compositions comprising purified bacterial mixtures as described in PCT Publication No. WO 2018/117263, which is incorporated herein by reference in its entirety. In one aspect, the present disclosure provides compositions comprising a purified bacterial mixture comprising one or more bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises al least 3, at least 4, at least 5, at least 6, at least 7, at least 8, at least 9, at least 10, or at least 11 bacterial strains.

In some embodiments, the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In some embodiments, the purified bacterial mixture comprises bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11. In some embodiments, the purified bacterial mixture comprises bacterial strains comprising 16S rDNA sequences of at least 95% sequence identity to SEQ ID NO:1, SEQ ID NO:2, SEQ ID NO:5, and SEQ ID NO:10.

In some embodiments, the purified bacterial mixture consists of bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO: 11. In some embodiments, the purified bacterial mixture consists of bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11. In some embodiments, the purified bacterial mixture consists of bacterial strains comprising 16S rDNA sequences of at least 95% sequence identity to SEQ ID NO:1, SEQ ID NO:2, SEQ ID NO:5, and SEQ ID NO:10.

In some embodiments, the purified bacterial mixture consists essentially of bacterial strains comprising 16S rDNA sequences of at least 95% sequence identity of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In some embodiments, the purified bacterial mixture consists essentially of bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11. In some embodiments, the purified bacterial mixture consists essentially of bacterial strains comprising 16S rDNA sequences of at least 95% sequence identity to SEQ ID NO:1, SEQ ID NO:2, SEQ ID NO:5, and SEQ ID NO:10.

In one aspect, the present disclosure provides compositions comprising a purified bacterial mixture comprising two or more bacterial strains comprising 16S rDNA sequences of at least 95% sequence identity to SEQ ID NQ:2 and SEQ ID NO:10, or SEQ ID NO:3 and SEQ ID NO:4. In some embodiments of the compositions provided herein, the purified bacterial mixture comprises at least 3, at least 4, at least 5, at least 6, at least 7, at least 8, at least 9, at least 10, or at least 11 bacterial strains.

In some embodiments of the compositions described herein, the purified bacterial mixture comprises bacterial strains comprising 16S rDNA sequences of at least 95% sequence identity to SEQ ID NO:2 and SEQ ID NO:10. In some embodiments of the compositions described herein, the composition further comprises one or more (e.g., 1, 2, 3, 4, 5 or more) bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises two bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises three bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises four bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises five bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions described herein, the composition further comprises six bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises seven bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises eight bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the composition further comprises nine bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions described herein, the purified bacterial mixture comprises bacterial strains comprising 16S rDNA sequences of at least 95% sequence identity to SEQ ID NO:3 and SEQ ID NO:4. In some embodiments of the compositions described herein, the composition further comprises one or more (e.g., 1, 2, 3, 4, 5 or more) bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises two bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises three bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises four bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises five bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises six bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises seven bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO: 11. In some embodiments of the compositions described herein, the composition further comprises eight bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the composition further comprises nine bacterial strains comprising 16S rDNA sequences of at least 95% sequence identity to 16S rDNA sequences selected from the group consisting of SEQ ID NO:1, SEQ ID NO:2, SEQ ID NO:3, SEQ ID NO:6, SEQ ID NO:7, SEQ ID NO 8, SEQ ID NO:9, SEQ ID NO:10, and SEQ ID NO:11.

In some embodiments of the compositions described herein, the purified bacterial mixture comprises bacterial strains comprising 16S rDNA sequences of at least 95% sequence identity to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the purified bacterial mixture consists of bacterial strains comprising 16S rDNA sequences of at least 95% sequence identity to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions described herein, the purified bacterial mixture comprises bacterial strains comprising 16S rDNA sequences of at least 97% sequence identity to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11. In some embodiments of the compositions described herein, the purified bacterial mixture consists of bacterial strains comprising 16S rDNA sequences of at least 97% sequence identity to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11.

In some embodiments of the compositions described herein, the purified bacterial mixture comprises bacterial strains comprising 16S rDNA sequences of at least 95% sequence identity to SEQ ID NO:1, SEQ ID NO:2, SEQ ID NO:5, SEQ TD NO:6, SEQ ID NO:7, SEQ ID NO:8, SEQ ID NO:9, SEQ ID NO:10, and SEQ ID NO:11. In some embodiments of the compositions described herein, the purified bacterial mixture consists of bacterial strains comprising 16S rDNA sequences of at least 95% sequence identity to SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

In some embodiments of the compositions described herein, the purified bacterial mixture comprises bacterial strains comprising 16S rDNA sequences of at least 97% sequence identify to SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11. In some embodiments of the compositions described herein, the purified bacterial mixture consists of bacterial strains comprising 16S rDNA sequences of at least 97 sequence identity to SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

In some embodiments of the compositions described herein, the purified bacterial mixture comprises bacterial strains comprising 16S rDNA sequences of at least 95% sequence identity to SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11. In some embodiments of the compositions described herein, the purified bacterial mixture consists of bacterial strains comprising 16S rDNA sequences of at least 95% sequence identity to SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11.

In some embodiments of the compositions described herein, the purified bacterial mixture comprises bacterial strains comprising 16S rDNA sequences of at least 97% sequence identity to SEQ ID NO:2, SEQ ID NO:3, SEQ ID NO:4, SEQ ID NQ:6, SEQ ID NO:7, SEQ ID NO:8, SEQ ID NO:9, SEQ ID NO:10, and SEQ ID NO:11. In some embodiments of the compositions described herein, the purified bacterial mixture consists of bacterial strains comprising 16S rDNA sequences of at least 97% sequence identity to SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11.

In some embodiments of the compositions described herein, the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11. In some embodiments of the compositions described herein, the purified bacterial mixture consists of bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11.

In some embodiments of the compositions described herein, the purified bacterial mixture comprises bacterial strains comprising 16S rDNA sequences of at least 97% sequence identity to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11. In some embodiments of the compositions described herein, the purified bacterial mixture consists of bacterial strains comprising 16S rDNA sequences of at least 97% sequence identity to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11.

In some embodiments of the compositions described herein, the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:9, and SEQ ID NO:10. In some embodiments of the compositions described herein, the purified bacterial mixture consists of bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:9, and SEQ ID NO:10.

In some embodiments of the compositions described herein, the purified bacterial mixture comprises bacterial strains comprising 16S rDNA sequences of at least 97% sequence identity to SEQ ID NO:1, SEQ ID NO:2, SEQ ID NO:3, SEQ ID NO:4, SEQ ID NO:5, SEQ ID NO:6, SEQ ID NO:9, and SEQ ID NO:10. In some embodiments of the compositions described herein, the purified bacterial mixture consists of bacterial strains comprising 16S rDNA sequences of at least 97% sequence identity to SEQ ID NO:1, SEQ ID NO:2, SEQ ID NO:3, SEQ ID NO:4, SEQ ID NO:5, SEQ ID NO:6, SEQ ID NO:9, and SEQ ID NO:10.

In any of the compositions described herein, the purified bacterial mixture does not comprises one or more bacterial strains comprising 16S rDNA sequences of at least 95% sequence identity to 16S rDNA sequences selected from the group consisting of SEQ ID NO:1, SEQ ID NO:5, SEQ ID NO:6, SEQ ID NO:7, SEQ ID NO:8, SEQ ID NO:9, and SEQ ID NO:11. In some embodiments, the purified bacterial mixture does not comprise a bacterial strain comprising a 16S rDNA sequence of at least 95% sequence identity to a 16S rDNA provided by SEQ ID NO:1. In some embodiments, the purified bacterial mixture does not comprise a bacterial strain comprising a 16S rDNA sequence of at least 95% sequence identity to a 16S rDNA provided by SEQ ID NO:2. In some embodiments, the purified bacterial mixture does not comprise a bacterial strain comprising a 16S rDNA sequence of at least 95% sequence identity to a 16S rDNA provided by SEQ ID NO:3. In some embodiments, the purified bacterial mixture does not comprise a bacterial strain comprising a 16S rDNA sequence of at least 95% sequence identity to a 16S rDNA provided by SEQ ID NO:4. In some embodiments, the purified bacterial mixture does not comprise a bacterial strain comprising a 16S rDNA sequence of at least 95% sequence identify to a 16S rDNA provided by SEQ ID NO:5. In some embodiments, the purified bacterial mixture does not comprise a bacterial strain comprising a 16S rDNA sequence of at least 95% sequence identity to a 16S rDNA provided by SEQ ID NO:6. In some embodiments, the purified bacterial mixture does not comprise a bacterial strain comprising a 16S rDNA sequence of at least 95% sequence identity to a 16S rDNA provided by SEQ ID NO:7. In some embodiments, the purified bacterial mixture does not comprise a bacterial strain comprising a 16S rDNA sequence of at least 95% sequence identity to a 16S rDNA provided by SEQ ID NO:8. In some embodiments, the purified bacterial mixture does not comprise a bacterial strain comprising a 16S rDNA sequence of at least 95% sequence identity to a 16S rDNA provided by SEQ ID NO:9. In some embodiments, the purified bacterial mixture does not comprise a bacterial strain comprising a 16S rDNA sequence of at least 95% sequence identity to a 16S rDNA provided by SEQ ID NO:10. In some embodiments, the purified bacterial mixture does not comprise a bacterial strain comprising a 16S rDNA sequence of at least 95% sequence identity to a 16S rDNA provided by SEQ ID NO:11.

In some embodiments of any of the compositions described herein, the purified bacterial mixture does not comprises one or more bacterial strains comprising 16S rDNA sequences of at least 97% sequence identity to 16S rDNA sequences selected from the group consisting of SEQ ID NO:1, SEQ ID NO:5, SEQ ID NO:6, SEQ ID NO:7, SEQ ID NO 8, SEQ ID NO:9, and SEQ ID NO:11. In some embodiments, the purified bacterial mixture does not comprise a bacterial strain comprising a 16S rDNA sequence of at least 97% sequence identity to a 16S rDNA provided by SEQ ID NO:1. In some embodiments, the purified bacterial mixture does not comprise a bacterial strain comprising a 16S rDNA sequence of at least 97% sequence identity to a 16S rDNA provided by SEQ ID NO:2. In some embodiments, the purified bacterial mixture does not comprise a bacterial strain comprising a 16S rDNA sequence of at least 97% sequence identity to a 16S rDNA provided by SEQ ID NO:3. In some embodiments, the purified bacterial mixture does not comprise a bacterial strain comprising a 16S rDNA sequence of at least 97% sequence identity to a 16S rDNA provided by SEQ ID NO:4. In some embodiments, the purified bacterial mixture does not comprise a bacterial strain comprising a 16S rDNA sequence of at least 97% sequence identity to a 16S rDNA provided by SEQ ID NO:5. In some embodiments, the purified bacterial mixture does not comprise a bacterial strain comprising a 16S rDNA sequence of at least 97% sequence identity to a 16S rDNA provided by SEQ ID NO:6. In some embodiments, the purified bacterial mixture does not comprise a bacterial strain comprising a 16S rDNA sequence of at least 97% sequence identity to a 16S rDNA provided by SEQ ID NO:7. In some embodiments, the purified bacterial mixture does not comprise a bacterial strain comprising a 16S rDNA sequence of at least 97% sequence identity to a 16S rDNA provided by SEQ ID NO:8. In some embodiments, the purified bacterial mixture does not comprise a bacterial strain comprising a 16S rDNA sequence of at least 97% sequence identity to a 16S rDNA provided by SEQ ID NO:9.

In some embodiments, the purified bacterial mixture does not comprise a bacterial strain comprising a 16S rDNA sequence of at least 97% sequence identity to a 16S rDNA provided by SEQ ID NO:10. In some embodiments, the purified bacterial mixture does not comprise a bacterial strain comprising a 16S rDNA sequence of at least 97% sequence identity to a 16S rDNA provided by SEQ ID NO:11.

In some embodiments of the compositions described herein, the purified bacterial mixture consists of bacterial strains comprising 16S rDNA sequences of at least 97% sequence identity to SEQ ID NO:2, SEQ ID NO:3, SEQ ID NO:4, and SEQ ID NO: 10. In some embodiments of the compositions described herein, the purified bacterial mixture essentially consists of bacterial strains comprising 16S rDNA sequences of at least 97% sequence identity to SEQ ID NO:2, SEQ ID NO:3, SEQ ID NO:4, and SEQ ID NO:10.

It should be appreciated that for all compositions provided herein, in some embodiments, the bacterial strains are purified. Thus, for example the disclosure provides a purified bacterial mixture comprising two or more bacterial strains comprising 16S rDNA sequences of at least 95% sequence identity to SEQ ID NO:2 and SEQ ID NO:10, or SEQ ID NO:3 and SEQ ID NO:4. In some embodiments, the composition comprises a purified bacterial mixture comprises at least 2, at least 3, at least 4, at least 5, at least 6, at least 7, at least 8, at least 9, at least 10, or at least 11 bacterial strains. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides a purified bacterial mixture comprising two or more bacterial strains comprising 16S rDNA sequences of at least 97% sequence identity to SEQ ID NO:2 and SEQ ID NO:10, or SEQ ID NO:3 and SEQ ID NO:4. In some embodiments, the composition comprises a purified bacterial mixture comprises at least 2, at least 3, at least 4, at least 5, at least 6, at least 7, at least 8, at least 9, at least 10, or at least 11 bacterial strains. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides bacterial strains with 16S rDNA sequences that have homology to a nucleic acid sequence of any one of the sequences of the bacterial strains or species described herein. In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

In one aspect, the disclosure provides bacterial strains with 16S rDNA sequences that have sequence identity to a nucleic acid sequence of any one of the sequences of the bacterial strains or species described herein. In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% sequence identity relative to any of the strains or bacterial species described herein over a specified region or over the entire sequence. Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipinan. Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group, Madison, Wis.), or by manual alignment, and visual inspection (see, e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altsehul et al., Nuc. Acids Res. 25:3389-3402, 1977; and Altschul et al., J. Mol. Biol. 215:403-410, 1990, respectively.

In one aspect, the disclosure provides compositions comprising multiple purified bacterial strains. In one aspect, the 16S rDNA sequences of purified bacterial strains of the compositions were compared to 16S rDNA sequences of known bacterial species/strains in a bacterial genome database to identity the closest known related bacterial species to the bacterial strains disclosed herein (See e.g., Table 1). It should be appreciated that multiple bacterial strains of the compositions disclosed herein may have the same closest related bacterial species.

In one aspect, the present disclosure provides compositions comprising bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the compositions described herein comprise at least 3, at least 4, at least 5, at least 6, at least 7, at least 8, at least 9, at least 10, or at least 11 bacterial strains.

In some embodiments, the composition comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In some embodiments, the composition comprises bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11. In some embodiments, the composition comprises bacterial strains comprising 16S rDNA sequences of at least 95% sequence identity to SEQ ID NO:1, SEQ ID NO:2, SEQ ID NO:5, and SEQ ID NO:10.

In some embodiments, the composition consists of bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In some embodiments, the composition consists of bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11. In some embodiments, the composition consists of bacterial strains comprising 16S rDNA sequences of at least 95% sequence identity to SEQ ID NO:1, SEQ ID NO:2, SEQ ID NO:5, and SEQ ID NO:10.

In some embodiments, the composition consists essentially of bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In some embodiments, the composition consists essentially of bacterial strains comprising 16S rDNA sequences of at least 95% sequence identity to SEQ ID NO:3, SEQ ID NO:4, SEQ ID NO:6, SEQ ID NO:7, SEQ ID NO:8, SEQ ID NO:9, and SEQ ID NO:11. In some embodiments, the composition consists essentially of bacterial strains comprising 16S rDNA sequences of at least 95% sequence identity to SEQ ID NO:1, SEQ ID NO:2, SEQ ID NO:5, and SEQ ID NO:10.

In one aspect, the disclosure provides compositions comprising two or more bacterial strains comprising 16S rDNA sequences of at least 95% sequence identity to SEQ ID NO:2 and SEQ ID NO:10, or SEQ ID NO:3 and SEQ ID NO:4. In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, or at least 11 bacterial strains (e.g., purified bacterial strains).

In one aspect, the disclosure provides bacterial strains and combinations of bacterial strains that are homologous or have a high percent of homology with bacterial strains comprising 16S rDNA sequences provided by SEQ ID NOs:1-11. As discussed previously, in some embodiments, the bacterial strains are purified. The bacterial strains disclosed herein that have a 16S rDNA sequence with a nucleic acid sequence provided by SEQ ID NOs:1-11 have a high percent of homology (e.g., greater than 90%) or sequence identity, with 16S rDNA sequences of bacterial strains that have been described in various databases (See e.g., the National Center for Biotechnology Information). Table 1 provides the closest known species by homology when the 16S rDNA sequences comprising SEQ ID NOs:1-11 are compared to 16S rDNA sequences of bacterial species available in public databases.

By way of example, the bacterial strain comprising a 16S rDNA sequence with SEQ ID NO:1 disclosed herein has the highest homology with a bacterial strain of the species *Phascolarctobacterium faecium* as defined by NCBI Accession #LN998073 (having 16S rDNA sequence SEQ ID NO:27). While the bacterial strain with SEQ ID NO:1 has homology with other published bacterial strains as well, the highest homology is with a bacterial strain of the species *Phascolarctobacterium faecium* as defined by NCBI Accession #LN998073. It should be appreciated that multiple bacterial strains disclosed herein may have the highest homology with the same species.

It should further be appreciated that the bacterial strains disclosed herein that have a 16S rDNA sequence with a nucleic acid sequence selected from the group consisting of SEQ ID NOs:1-11, are also homologous to other strains based on their whole genome sequence, or subset of their whole genome sequence.

Thus, it should be appreciated that, in one aspect, the disclosure also provides compositions and methods comprising bacterial species with close homology to the bacterial strains that have a 16S rDNA sequence with a nucleic acid sequence selected from the group consisting of SEQ ID NOs:1-11.

The disclosure also encompasses compositions comprising bacterial strains that are close in homology to and/or fall within the species *Subdoligranulum* sp., *Phascolarctobacterium faecium, Bacteroides dorei, Parabacteroides gordonii, Alistipes* sp., *Parabacteroides distasonis, Fusobacterium ulcerans, Bacteroides uniformis, Paraprevotella xylaniphila, Parabacteroides johnsonii*, and *Eubacterium limosum.*

Aspects of the present disclosure provide compositions comprising purified bacterial mixtures as described in PCT Publication No. WO 2018/117263, which is incorporated herein by reference in its entirety. Aspects of the present disclosure provide compositions comprising a purified bacterial mixture comprising two or more bacterial strains of species selected from *Subdoligranulum* sp., *Phascolarctobacterium faecium, Bacteroides dorei, Parabacteroides gordonii, Alistipes* sp., *Parabacteroides distasonis, Fusobacterium ulcerans, Bacteroides uniformis, Paraprevotella xylaniphila, Parabacteroides johnsonii*, and *Eubacterium limosum*. In some embodiments of the compositions described herein, wherein the purified bacterial mixture comprises at least 3, at least 4, at least 5, at least 6, at least 7, at least 8, at least 9, at least 10, or at least 11 bacterial strains.

In some embodiments, the composition comprises a purified bacterial mixture comprising *Phascolarctobacterium faecium, Fusobacterium ulcerans, Bacteroides dorei, Bacteroides unifomis, Subdoligranulum* sp., *Paraprevotella xylaniphila, Parabacteroides johnsonii, Alistipes* sp., *Parabacteroides gordonii, Eubacterium limosum, and Parabacteroides distasonis*. In some embodiments, the composition comprises a purified bacterial mixture comprising *Parabacteroides distasonis, Parabacteroides gordonii, Alistipes* sp., *Parabacteroides johnsonii, Paraprevotella xylaniphila, Bacteroides dorei*, and *Bacteroides uniformis*. In some embodiments, the composition comprises a purified bacterial mixture comprising *Eubacterium limosum, Subdoligranulum* sp., *Phascolarctobacterium faecium*, and *Fusobacterium ulcerans*.

As described herein, in some embodiments, the compositions comprise effector bacterial strains. As described herein, in some embodiments, the compositions comprise supporter bacterial strains. In some embodiments, the compositions comprise effector bacterial strains and supporter bacterial strains. In some embodiments, the composition comprises one or more effector bacterial strains selected from the group consisting of *Eubacterium limosum, Subdoligranulum* sp., *Phascolarctobacterium faecium*, and *Fusobacterium ulcerans*. In some embodiments, the composition comprises the effector bacterial strains *Eubacterium limosum, Subdoligranulum* sp., *Phascolarctobacterium faecium*, and *Fusobacterium ulcerans*. In some embodiments, the composition comprises one or more supporter bacterial strains selected from the group consisting of *Parabacteroides distasonis, Parabacteroides gordonii, Alistipes* sp., *Parabacteroides johnsonii, Paraprevotella xylaniphila, Bacteroides dorei*, and *Bacteroides uniformis*. In some embodiments, the composition comprises the supporter bacterial strains *Parabacteroides distasonis, Parabacteroides gordonii, Alistipes* sp., *Parabacteroides johnsonii, Paraprevotella xylaniphila, Bacteroides dorei*, and *Bacteroides uniformis*. In some embodiments, the composition comprises one or more effector bacterial strains selected from the group consisting of *Eubacterium limosum, Subdoligranulum* sp., *Phascolarctobacterium faecium*, and *Fusobacterium ulcerans*, and one or more supporter bacterial strains selected from the group consisting of *Parabacteroides distasonis, Parabacteroides gordonii, Alistipes* sp., *Parabacteroides johnsonii, Paraprevotella xylaniphila, Bacteroides dorei*, and *Bacteroides uniformis*. In some embodiments, the composition comprises the effector bacterial strains *Eubacterium limosum, Subdoligranulum* sp., *Phascolarctobacterium faecium*, and *Fusobacterium ulcerans*, and the supporter bacterial strains *Parabacteroides distasonis, Parabacteroides gordonii, Alistipes* sp., *Parabacteroides johnsonii, Paraprevotella xylaniphila, Bacteroides dorei*, and *Bacteroides uniformis*.

In some embodiments, the composition comprises a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterium limosum*, and *Parabacteroides distasonis*. In some embodiments, the composition comprises a purified bacterial mixture consisting of *Parabacteroides distasonis, Parabacteroides gordonii, Alistipes* sp., *Parabacteroides johnsonii, Paraprevotella xylaniphila, Bacteroides dorei*, and *Bacteroides uniformis*. In some embodiments, the composition comprises a purified bacterial mixture consisting of *Eubacterium limosum, Subdoligranulum* sp., *Phascolarctobacterium faecium*, and *Fusobacterium ulcerans*.

In some embodiments, the composition comprises a purified bacterial mixture consisting essentially of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubaclerium limosum*, and *Parabacteroides distasonis*. In some embodiments, the composition comprises a purified bacterial mixture consisting essentially of *Parabacteroides distasonis, Parabacteroides gordonii, Alistipes* sp., *Parabacteroides johnsonii, Paraprevotella xylaniphila, Bacteroides dorei*, and *Bacteroides uniformis*. In some embodiments, the composition comprises a purified bacterial mixture consisting essentially of *Eubacterium limosum, Subdoligranulum* sp., *Phascolarctobacterium faecium*, and *Fusobacterium ulcerans*.

Aspects of the present disclosure provide compositions comprising a purified bacterial mixture comprising two or more bacterial strains of species selected from *Fusobacterium ulcerans* and *Eubacterium limosum*, or *Bacteroides dorei* and *Bacteroides uniformis*. In some embodiments of the compositions described herein, the compositions comprise a purified bacterial mixture comprising *Fusobacterium ulcerans* and *Eubacterium limosum*. In some embodiments of the compositions described herein, the compositions comprise a purified bacterial mixture comprising *Bacteroides dorei* and *Bacteroides uniformis*. In some embodiments of the compositions described herein, wherein the purified bacterial mixture comprises at least 3, at least 4, at least 5, at least 6, at least 7, at least 8, at least 9, at least 10, or at least 11 bacterial strains.

In some embodiments of the compositions described herein, the purified bacterial mixture comprises *Fusobacterium ulcerans* and *Eubacterium limosum*. In some embodiments, the purified bacterial mixture further comprises one or more (e.g., 1, 2, 3, 4, 5 or more) bacterial strains of species selected from the group consisting of *Phascolarctobacterium faecium, Subdoligranulum* sp., *Parabacteroides gordonii, Paraprevotella xylaniphila, Alistipes sp., Parabacteroides johnsonii, Parabacteroides distasonis, Bacteroides dorei*, and *Bacteroides uniformis*. In some embodiments of the compositions described herein, the purified bacterial mixture further comprises two bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*. In some embodiments of the compositions described herein, the purified bacterial mixture further comprises three bacterial strains of species selected from the group consisting of *Phascolarctobacterium faecium, Subdoligranulum* sp., *Parabacteroides gordonii, Paraprevotella xylaniphila, Alistipes* sp., *Parabacte-* roides johnsonii, Parabacteroides distasonis, Bacteroides dorei, and Bacteroides uniformis. In some embodiments of the compositions described herein, the purified bacterial mixture further comprises four bacterial strains of species selected from the group consisting of *Phascolarctobacterium faecium, Subdoligrarnulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*. In some embodiments of the compositions described herein, the purified bacterial mixture further comprises five bacterial strains of specks selectee from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*. In some embodiments, the purified bacterial mixture further comprises six bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*. In some embodiments of the compositions described herein, the purified bacterial mixture further comprises seven bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*. In some embodiments of the compositions described herein, the purified bacterial mixture further comprises eight bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*. In some embodiments of the compositions described herein, the purified bacterial mixture further comprises nine bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Bacteroides dorei*, and *Bacteroides uniformis*.

In some embodiments of the compositions described herein, the purified bacterial mixture comprises *Bacteroides dorei* and *Bacteroides uniformis*. In some embodiments of the compositions described herein, the purified bacterial mixture further comprises one or more (e.g., 1, 2, 3, 4, 5 or more) bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises two bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises three bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises four bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises five bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises six bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises seven bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises eight bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*. In some embodiments of the compositions described herein, the purified bacterial mixture further comprises nine bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum*.

In some embodiments of the compositions described herein, the purified bacterial mixture comprises *Fusobacterium ulcerans, Eubacterium limosum, Bacteroides dorei, Bacteroides uniformis, Parabacteroides gordonii, Paraprevotella xylaniphila, Alistipes* sp., *Parabacteroides johnsonii*, and *Parabacteroides distasonis*. In some embodiments of the compositions described herein, the purified bacterial mixture consists of *Fusobacterium ulcerans, Eubacterium limosum, Bacteroides dorei, Bacteroides uniformis, Parabacteroides gordonii, Paraprevotella xylaniphila, Alistipes* sp., *Parabacteroides johnsonii*, and *Parabacteroides distasonis*.

In some embodiments of the compositions described herein, the purified bacterial mixture comprises *Fusobacterium ulcerans, Eubacterium limosum, Phascolarctobacterium faecium, Subdoligranulum* sp., *Bacteroides dorei, Bacteroides uniformis, Alistipes* sp., *Parabacteroides johnsonii*, and *Parabacteroides distasonis*. In some embodiments of the compositions described herein, the purified bacterial mixture consists of *Fusobacterium ulcerans, Eubacterium limosum, Phascolarctobacterium faecium, Subdoligranulum* sp., *Bacteroides dorei, Bacteroides uniformis, Alistipes* sp., *Parabacteroides johnsonii*, and *Parabacteroides distasonis*.

In some embodiments of the compositions described herein, the purified bacterial mixture comprises *Fusobacterium ulcerans, Eubacterium limosum, Phascolarctobacterium faecium, Subdoligranulum* sp., *Bacteroides dorei, Bacteroides uniformis, Parabacteroides gondonii*, and *Paraprevotella xylaniphila*. In some embodiments of the compositions described herein, the purified bacterial mixture consists of *Fusobacterium ulcerans, Eubacterium limosum, Phascolarctobacterium faecium, Subdoligranulum* sp., *Bacteroides dorei, Bacteroides uniformis, Parabacteroides gordonii*, and *Paraprevotella xylaniphila*.

In some embodiments of the compositions described herein, the purified bacterial mixture comprises *Subdoligranulum* sp., *Phascolarctobacterium faecium, Bacteroides dorei, Bacteroides uniformis, Parabacteroides gordonii, Paraprevotella xylaniphila, Alistipes* sp., *Parabacteroides johnsonii*, and *Parabacteroides distasonis*. In some embodiments of the compositions described herein, the purified bacterial mixture consists of *Subdoligranulum* sp., *Phascolarctobacterium faecium, Bacteroides dorei, Bacteroides uniformis, Parabacteroides gordonii, Paraprevotella xylaniphila, Alistipes* sp., *Parabacteroides johnsonii*, and *Parabacteroides distasonis*.

In some embodiments of the compositions described herein, the purified bacterial mixture comprises *Fusobacterium ulcerans, Eubacterium limosum, Subdoligratiulum* sp., *Phascolarctobacterium faecium, Parabacteroides gordonii, Paraprevotella xylaniphila, Alistipes* sp., *Parabacteroides johnsonii*, and *Parabacteroides distasonis*. In some embodiments of the compositions described herein, the purified bacterial mixture consists of *Fusobacterium ulcerans, Eubacterium limosum, Subdoligranulum* sp., *Phascolarctobacterium faecium, Parabacteroides gordonii, Paraprevotella xylaniphila, Alistipes* sp., *Parabacteroides johnsonii*, and *Parabacteroides distasonis*.

In some embodiments of any of the compositions described herein, the purified bacterial mixture does not comprise any one or more bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans, Eubacterium limosum, Bacteroides dorei*, and *Bacteroides uniformis*. In some embodiments, the purified bacterial mixture does not comprise *Phascolaretobacterium faecium*. In some embodiments, the purified bacterial mixture does not comprise *Subdoligranulum* sp. In some embodiments, the purified bacterial mixture does not comprise *Parabacteroides gordonii*. In some embodiments, the purified bacterial mixture does not comprise *Paraprevotella xylaniphila*. In some embodiments, the purified bacterial mixture does not comprise *Alistipes* sp. In some embodiments, the purified bacterial mixture does not comprise *Parabacteroides johnsonii*. In some embodiments, the purified bacterial mixture does not comprise *Parabacteroides distasonis*. In some embodiments, the purified bacterial mixture does not comprise *Fusobacterium ulcerans*. In some embodiments, the purified bacterial mixture does not comprise *Eubacterium limosum*. In some embodiments, the purified bacterial mixture does not comprise *Bacteroides dorei*. In some embodiments, the purified bacterial mixture does not comprise *Bacteroides uniformis*.

In some embodiments of the compositions described herein, the purified bacterial mixture comprises *Fusobacterium ulcerans, Eubacterium limosum, Bacteroides dorei* and *Bacteroides uniformis*.

In some embodiments of the compositions described herein, the purified bacterial mixture consists of *Fusobacterium ulcerans, Eubacterium limosum, Bacteroides dorei* and *Bacteroides uniformis*.

In some embodiments of the compositions described herein, the purified bacterial mixture essentially consists of *Fusobacterium ulcerans, Eubacterium limosum, Bacteroides dorei* and *Bacteroides uniformis*.

In some embodiments of the compositions provided herein, at least 50% of the bacterial strains belong to the order of Bacteriodales. In some embodiments of the compositions provided herein, at least 50% of the bacterial strains belong to the genus Bacteroides or Parabacteroides. In some embodiments of the compositions provided herein, one or more strains belongs to the genus Bacteroides and one or more strains belongs to the genus Parabacteroides. In some embodiments of the compositions provided herein, at least 25% of the bacterial strains belong to the family of Bacteroidaceae. In some embodiments of the compositions provided herein, one or more of the bacterial strains belongs to the genus Bacteroides. In some embodiments of the compositions provided herein, one or more of the bacterial strains belongs to the genus Parabacteroides.

In some embodiments of the compositions provided herein, the composition does not include bacterial strains that belong to the order of Bacteriodales.

In some embodiments of the compositions provided herein, one or more of the bacterial strains belong to the order of Bacteriodales and one or more of the bacterial strains belong to the order of Clostridiales. In some embodiments of the compositions provided herein, at least 50% of the bacterial strains belong to the order of Bacteriodales and one or more of the bacterial strains belong to the order of Clostridiales. In some embodiments of the compositions provided herein, at least 75% of the bacterial strains belong to the order of Bacteriodales and one or more of the bacterial strains belong to the order of Clostridiales. In some embodiments of the compositions provided herein, at least 90% of the bacterial strains belong to the order of Bacteriodales and one or more of the bacterial strains belong to the order of Clostridiales.

In some embodiments, the compositions provided herein do not include *E. coli*. In some embodiments, the compositions provided herein do not include Bifidobacterium. In some embodiments, the compositions provided herein do not include Bacillus. In some embodiments, the compositions provided herein do not include Enterococcus. In some embodiments, the compositions provided herein do not include Barnesiella. In some embodiments, the compositions provided herein do not include *B. fragilis*. In some embodiments, the compositions provided herein do not include *B. thetaiotaomicron*. In some embodiments, the compositions provided herein do not include Akkermansia. In some embodiments, the compositions provided herein do not include Proteobacteria. In some embodiments, the compositions provided herein do not include Burkholderia. In some embodiments, the compositions provided herein do not include clostridium species belonging to Cluster IV. In some embodiments, the compositions provided herein do not include Faecalibacterium. In some embodiments, the compositions provided herein do not include Clostridium species belonging to Cluster XIVa. In some embodiments, the compositions do not comprise fungi, such as Monilla species.

In one aspect, the disclosure provides purified fractions of human stool sample that can induce CD8 T cells.

In some embodiments of the compositions provided herein, one or more of the bacterial strains are human-derived bacteria. In some embodiments of the compositions provided herein, all of the bacterial strains are human-derived bacteria. In some embodiments of the compositions provided herein, the bacterial strains are derived from more than one human donor.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments of the compositions provided herein, the composition includes one or more anaerobic bacteria. In some embodiments of the compositions provided herein, the composition includes only anaerobic bacteria. In some embodiments of the compositions provided herein, the composition includes one or more facultative anaerobic bacteria. In some embodiments of the compositions provided herein, the composition includes only facultative anaerobic bacteria. In some embodiments of the compositions provided herein, the composition includes one or more obligate anaerobic bacteria. In some embodiments of the compositions provided herein, the composition includes only obligate anaerobic bacteria.

In some embodiments of the compositions provided herein, one or more of the bacterial strains does not have an antibiotic resistance gene. In some embodiments of the compositions provided herein, the bacterial strains do not have an antibiotic resistance gene that renders the bacterial strain resistant to vancomycin.

In some embodiments of the compositions provided herein, the compositions do not include bacterial strains that are resistant to one or more antibiotics. It should be appreciated that it may be desirable to have a mechanism to remove the bacterial compositions provided herein from the body after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. (An "antibiotic that is efficacious in a human" as used herein is an antibiotic that has been used to successfully treat bacterial infections in a human).

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former.

In some embodiments, the compositions described herein comprise spore forming and non-spore forming bacterial strains. In some embodiments, the compositions described herein comprise spore-forming bacterial strains. In some embodiments, the compositions described herein comprise only spore-forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (as discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

It is envisioned that the bacterial strains of the compositions provided herein are alive and will be alive when they reach the target area (e.g., the intestines). Bacterial spores are considered to be alive in this regard. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In one aspect, the bacterial strains of the compositions provided herein are alive. In some embodiments, one or more of the bacterial strains of the compositions provided herein is alive. In some embodiments, all of the bacterial strains of the compositions provided herein are alive. Without being limiting to a specific mechanism, in some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells. In some embodiments, if one or more of the bacterial strains is not alive, the combination of the bacterial strains may no longer be able to generate sufficient metabolites and/or cellular signals that stimulate the induction of proliferation and/or accumulation of CD8+ T-cells. In some embodiments, the mere presentation of non-viable bacteria and/or bacterial fragments as antigens is not sufficient to induce the proliferation and/or accumulation of CD8+ T-cells.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected. As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In one aspect, the disclosure provides bacterial strains and mixtures of bacterial strains with unique biological properties. In some embodiments of the compositions provided herein, the composition induces proliferation and/or accumulation of CD8+ T-cells. In some embodiments, the bacterial strains of the compositions provided herein can induce proliferation and/or accumulation of CD8+ T-cells, because of the synergy between the bacterial strains. Thus, without being limiting to a specific mechanism, in some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells. The bacterial compositions may do so, for instance through the use of nutrients in the intestinal tract (e.g., the colon or the cecum), and/or metabolic interactions that result in metabolites and/or cellular signals that stimulate the induction of proliferation and/or accumulation of CD8+ T-cells. In addition, without being limiting to a specific mechanism, in some embodiments, the combination of the bacterial strains of the compositions provided herein act synergistically in the induction of proliferation and/or accumulation of CD8+ T-cells because the combination of the strains is superior in engrafting specific niches in the intestinal tract (e.g., the colon or the cecum) that will result in the induction of proliferation and/or accumulation of CD8+ T-cells (e.g., by providing a favorable microenvironment). In some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells, and the combination is well suited to engraft in specific niches that result in localization of the metabolites and/or cellular signals to a target for the induction of proliferation and/or accumulation of CD8+ T-cells. Any of the compositions described herein that induces CD8+ T-cells, or bacterial strain that induces CD8+ T-cells, may be referred to as a CD8-inducing composition or CD8-inducing bacterial strain, respectively.

In some embodiments, the purified bacterial mixture comprises one or more bacterial strain that is of low abundance in a population of subjects. In some embodiments, the purified bacterial mixture comprises one or more bacterial strain that is detected in less than 5% (e.g., 5%, 4%, 3%, 2%, 1%, or less) of the population of subjects. Methods of assessing the abundance of one or more bacterial strains in a subject (or a sample thereof, e.g., a fecal sample) will be evident to one of ordinary skill in the art. See, e.g., Example 8.

Methods

In one aspect, the disclosure provides methods and compositions for colonizing mucus layers. In some embodiments, the disclosure provides methods and compositions for colonizing mucus layers of the intestine. In some embodiments, the disclosure provides methods and compositions for colonizing mucus layers of the colon and the caecum. In some embodiments, the disclosure provides compositions that colonize the mucus layer and induce the proliferation and/or accumulation of CD8+ T-cells. Without being limited to a specific mechanism, it is thought that the ability of the bacterial strains of the compositions to colonize the mucus layer, allows for the induction of proliferation and/or accumulation of CD8+ T-cells. By colonizing the mucus layer, the bacterial strains can secrete metabolites in sufficient quantity and proximity to epithelial cells and/or cells of the immune system, that will induce proliferation and/or accumulation of CD8+ T-cells. In some embodiments, the bacterial strains of the compositions provided herein colonize the mucus layer but do not infiltrate the epithelial layer.

In one aspect, the disclosure provides methods and compositions for systemically inducing the proliferation and/or accumulation of CD8+ T-cells. As provided herein, the compositions when administered to the intestine (e.g., colon or ceacum) induce the proliferation and/or accumulation of CD8+ T-cells in many tissues, including lymph nodes lung and spleen. Thus, surprisingly, the combinations provided herein allow for the induction of proliferation and/or accumulation of CD8+ T-cells in many tissues. Without being limited to a specific mechanism it is thought that the bacterial strains of the compositions provide signaling events that result in the proliferation and/or accumulation of CD8+ T-cells in many tissues, predominantly in the caecum and the colon, but also in the additional tissues, such as lymph nodes lung and spleen.

In one aspect, the disclosure provides methods and compositions for providing a long-term induction of the proliferation and/or accumulation of CD8+ T-cells. In some embodiments, the CD8+ T-cells are interferon-gamma (IFN-gamma) expressing CD8+ T-cells. In some embodiments, the IFNgamma+CD8+ T-cells express the alphabets T cell receptor (TCR), CD8alpha/beta, CD44 and T-bet. In some embodiments, the IFNgamma+CD8+ T-cells. In some embodiments, the IFNgamma+CD8+ T-cells were primarily activated or memory cells that differentiated from conventional CD8+ T cells.

In one aspect, the disclosure provides methods and compositions for providing a long-term induction of the proliferation and/or accumulation of CD8+ T-cells. In some embodiments, the induction is present one months, two months, three months, four months, five months, six months or more after the administration of the composition. In some embodiments, the disclosure provides methods and compositions that allow for persistent level of CD8+ T-cells. In some embodiments, the disclosure provides methods and compositions that allow for persistent level of IFNgamma+CD8+ T-cells. In some embodiments, the disclosure provides methods and compositions that allow for persistent level of CD103+IFNgamma+CD8+ T-cells. In some embodiments, the persistent level of CD8+ T-cells and/or CD103+IFNgamma+CD8+ T-cells is achieved by a single administration of the compositions of the disclosure. In some embodiments, the persistent level of CD8+ T-cells, IFNgamma+CD8+ T-cells, and/or CD103+IFNgamma+CD8+ T-cells is achieved by multiple administrations of the compositions of the disclosure.

In one aspect, the disclosure provides methods and compositions for upregulating the expression of chemokines that can induce proliferation and/or accumulation of CD8+ T-cells. In some embodiments, the disclosure provides methods and compositions for upregulating the expression of chemokines CXCL9 and CXCL10. In some embodiments, the disclosure provides methods and compositions for upregulating the expression of chemokines CxCl9 and CxCl10 in epithelial cells. Without being limited to a specific mechanism the activation of CxCl9 and CxCl10 may be one of the mechanisms through which the bacterial strains of the compositions of the disclosure induce proliferation and/or accumulation of CD8+ T-cells.

In some embodiments, the proliferation and/or accumulation of IFNγ+CD8 T cells is facilitated by colonic recruitment. In some embodiments, the proliferation and/or accumulation of IFNγ+CD8 T cells is facilitated by cellular expansion. In some embodiments, the proliferation and/or accumulation of IFNγ+CD8 T cells is facilitated by bacterial antigen-mediated differentiation. In some embodiments, the proliferation and/or accumulation of IFNγ+CD8 T cells is facilitated by colonic recruitment and cellular expansion. In some embodiments, the proliferation and/or accumulation of IFNγ+CD8 T cells is facilitated by cellular expansion and bacterial antigen-mediated differentiation. In some embodiments, the proliferation and/or accumulation of IFNγ+CD8 T cells is facilitated by colonic recruitment and bacterial antigen mediated differentiation. In some embodiments, the proliferation and/or accumulation of IFNγ+CD8 T cells is facilitated by due to the cumulative effects of colonic recruitment, cellular expansion, and bacterial antigen-mediated differentiation.

In one aspect, the disclosure provides methods and compositions for inducing changes in the T-cell repertoire (e.g., the induction of CD8+ T-cells). In some embodiments, the disclosure provides methods and compositions for expanding Vbeta6 and Vbeta8. In some embodiments, the disclosure provides methods and compositions for reducing Vbeta5. In some embodiments, the disclosure provides methods and compositions for expanding Vbeta6 and Vbeta8, while reducing Vbeta5.

In one aspect, the disclosure provides methods and compositions for induction of accumulation and proliferation of CD11b−CD103+ and CD11b+CD103+ dendritic cells. In some embodiments, the disclosure provides methods and compositions for induction of CD11b−CD103+ and CD11b+CD103+ dendritic cells that have MHC class I presentation. In some embodiments, the MHC calls I presentation are MHC class Ia molecules.

In one aspect, the disclosure provides methods and compositions for the induction of accumulation and proliferation of CD11b−CD103+ dendritic cells. In some embodiments, the disclosure provides methods and compositions for induction of CD11b−CD103+ dendritic cells that have MHC class I presentation. In some embodiments, the MHC calls I presentation are MHC class Ia molecules.

In one aspect, the disclosure provides methods and compositions for the induction of accumulation and proliferation of CD11b−CD103+ dendritic cells. In some embodiments, the disclosure provides methods and compositions for induction of CD11b−CD103+ dendritic cells that have MHC class I presentation. In some embodiments, the MHC calls I presentation are MHC class Ia molecules.

In some embodiments, the disclosure provides methods and compositions for induction of CD8+ T cells that is independent of the H2-M3 pathway.

In some embodiments, the disclosure provides methods and compositions for induction of CD8+ T cells that is independent of the pathways prevalent in skin cells.

In one aspect, the disclosure provides methods and compositions for induction of the proliferation and/or accumulation of CD11+ dendritic cells. In some embodiments, the disclosure provides methods and compositions for induction of the proliferation and/or accumulation of CD11+ dendritic cells with heightened MHC class I expression. In some embodiments, the MHC calls I presentation are MHC class Ia molecules.

In one aspect, the disclosure provides methods and compositions for the treatment of infections by a pathogenic agent. In some embodiments, the disclosure provides methods and compositions for the treatment of infection by a pathogenic agent through the induction of proliferation and/or accumulation of CD8+ T-cells. In some embodiments, the disclosure provides methods and compositions for the treatment of infection by a pathogenic agent through the induction of antimicrobial genes. In some embodiments, the disclosure provides methods and compositions for the treatment of infection by a pathogenic agent through the induction of proliferation and/or accumulation of CD8+ T-cells, and the induction of antimicrobial genes. In some embodiments, the infection by a pathogenic agent is an intracellular infection.

In one aspect, the disclosure provides methods and compositions for induction of antimicrobial genes. In some embodiments, the disclosure provides methods and compositions for induction of antimicrobial genes in epithelial cells. In some embodiments, the disclosure provides methods and compositions for induction of antimicrobial genes in colonic epithelial cells. Antibiotic genes that can be induced according to the methods and compositions of the disclosure include genes that control the expression of guanylate-binding proteins, interferon-induced proteins, Cxcl10 and autophagy-related lrgml. Without being limited to a specific mechanism it is thought that the expression of such antimicrobial genes results in the release of antimicrobial compounds that can target an infection by a pathogenic agent (e.g., an intracellular infection). It should further be appreciated that the targeting of an infection by a pathogenic agent can be potentiated through both the release of antimicrobial compounds and the induction of accumulation and/or proliferation of CD8+ T-cells at the same time.

In one aspect, the disclosure provides methods and compositions for the systemic treatment of infections by a pathogenic agent. As provided herein, administration of the compositions provided herein to the intestine allows for the treatment of infection by a pathogenic agent in organs other than the intestine. For instance, as provided herein, administration of the compositions provided herein to the intestine allows for the treatment of an intracellular infection in the liver and spleen. In some embodiments, the disclosure provides methods and compositions for the systemic treatment of infection by a pathogenic agent through the induction of proliferation and/or accumulation of CD8+ T-cells. In some embodiments, the disclosure provides methods and compositions for the systemic treatment of infection by a pathogenic agent through the induction of antimicrobial genes. In some embodiments, the disclosure provides methods and compositions for the systemic treatment of infection by a pathogenic agent through the induction of proliferation and/or accumulation of CD8+ T-cells, and the induction of antimicrobial genes.

In one aspect, the disclosure provides methods and compositions for inducing the proliferation and/or accumulation of tumor infiltrating CD8+ T-cells. In some embodiments, the disclosure provides methods and compositions for inducing the proliferation and/or accumulation of PD1+ and ICOS+CD8+ T-cells. In some embodiments, the disclosure provides methods and compositions for inducing the proliferation and/or accumulation of PD1+ and ICOS+ tumor infiltrating CD8+ T-cells. In some embodiments, the disclosure provides methods and compositions for inducing the proliferation and/or accumulation of tumor infiltrating IFN-gamma+CD8+ T-cells. In some embodiments, the disclosure provides methods and compositions for inducing the proliferation and/or accumulation of PD1+ICOS+IFNgamma+ CD8+ T-cells. In some embodiments, the disclosure provides methods and compositions for inducing the proliferation and/or accumulation of PD1+, ICOS+, IFN-gamma+ tumor infiltrating CD8+ T-cells.

In some embodiments, the compositions provided herein comprise one or more antigens derived from the one or more bacterial strains provided herein. While not being limited to a specific mechanism, in one embodiment, the one or more antigens induce or support the induction of the proliferation and/or accumulation of CD8+ T-cells. It should be appreciated that any one of the antigen-based compositions provided herein, in some embodiments, also include one or more anticancer agents (e.g., a PD-1 inhibitor or a CTLA-4 inhibitor). The methods disclosed herein in some embodiments include the one or more antigen comprising compositions.

In some embodiments, the methods described herein involve evaluating whether a subject has one or more bacterial strains (e.g., one or more bacterial strains of any of the compositions described herein) in the microbiome of the subject. In some embodiments, the methods described herein involve evaluating whether a subject has one or more bacterial strain (e.g., one or more bacterial strain of any of the compositions described herein) present in the microbiome of the subject at a level sufficient to induce a desired immune response (e.g., induce CD8+ T-cells). Methods of evaluating the presence of one or more bacterial strains and/or the level of the one or more bacterial strain in the microbiome of the subject will be evident to one of ordinary skill in the art and include, without limitation, sequencing, transcriptional analysis, and culturing methods. In some embodiments, if the subject does not have detectable levels of the one or more bacterial strains, the subject may be administered any of the compositions described herein. In some embodiments, if the subject does not have one or more bacterial strains present in the microbiome at a level sufficient to induce a desired immune response (e.g., induce CD8+ T-cells), the subject may be administered any of the compositions described herein.

Metabolites

In one aspect, the disclosure provides compositions and methods comprising metabolites produced by the bacterial strains and combinations of bacterial strains disclosed herein. It should be appreciated that the bacterial strains and combinations thereof of the compositions disclosed herein produce one or more metabolites. While not being limited to a specific mechanism, in one embodiment, the one or more metabolites induce or support the induction of the proliferation and/or accumulation of CD8+ T-cells. In some embodiments, the one or more metabolites that induce or support the induction of the proliferation and/or accumulation of CD8+ T-cells are metabolites that are observed in the sera.

In one aspect, the disclosure provides a composition comprising one or more metabolites selected from the group consisting of mevalonate, dimethylglycine, hypoxanthine, IMP, 2-deoxy-glucose 6P, TMP, 6PG, Rib5P, Ru5P, Xu5p, GDP, GlcNAc 6P, UMP, GMO, CDP, Pyridoine B6, Opthalomic acid, Ctp, GTP, ATP, F6P, 5-methyltetrahydrofolic acid, adenylosuccinate, G6P, 3-hydroxyanthranalinic acid, glycerol 3P, sedoheptulose 7P, 2-keto-4-methylthiobutyrate, dUMP, histamine, valeric acid, 3PG+2 PG, G1P, thymidine, CMP, dopamine, phosphoenolpuryvate, HPO4, iso-butyrate, allotoin, acetylcamitine, and thymine. In some embodiments, the composition comprises one or more metabolites selected from the group consisting of mevalonate, dimethylglycine, hypoxanthine, IMP, 2-deoxy-glucose 6P, TMO, 6PG, Rib5P, Ru5P, Xu5p, GDP, GlcNAc 6P, UMP, GMO, and CDP. In some embodiments, the composition comprises one or more metabolites selected from the group consisting of mevalonate and dimethylglycine. In some embodiments, the composition comprises mevalonate. Mevalonate is also referred to as mevalonic acid or the carboxylate anion of mevalonic acid. In some embodiments, the composition comprises dimethylglycine. In some embodiments, the composition comprises dimethylglycine and mevalonate. In some embodiments, the composition comprises mevalonate and a pharmaceutically acceptable carrier. In some embodiments, the composition comprises dimethylglycine and a pharmaceutically acceptable carrier. In some embodiments, the composition comprising the one or more metabolites comprise a pharmaceutically acceptable carrier. In some embodiments, the composition comprises dimethylglycine and mevalonate and a pharmaceutically acceptable carrier.

In should be appreciated that in some embodiments, the compositions comprising the one or more metabolites further comprise one or more anticancer agents. In some embodiments of the compositions provided herein, the anticancer agent is a chemotherapy agent. In some embodiments of the compositions provided herein, the anticancer agent is a cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor, PD-L-1 inhibitor, CTLA-4 inhibitor, IDO1 inhibitor, LAG3 inhibitor, or TIM3 inhibitor. In some embodiments of the compositions provided herein, the immune checkpoint inhibitor is a PD-1 inhibitor. In some embodiments, the PD-1 inhibitor is nivolumab. In some embodiments, the PD-1 inhibitor is pembrolizumab. In some embodiments, the PD-1 inhibitor is pidiluzimab. In some embodiments of the compositions provided herein, the immune checkpoint inhibitor is a PD-L-1 inhibitor. In some embodiments, the PD-L-1 inhibitor is atezolizumab. In some embodiments, the PD-L-1 inhibitor is avelumab. In some embodiments, the PD-L-1 inhibitor is durvalumab. In some embodiments of the methods provided herein, the immune checkpoint inhibitor is a CTLA-4 inhibitor. In some embodiments, the CTLA-4 inhibitor is an anti-CTLA-4 antibody. Examples of anti-CTLA-4 antibodies include, without limitation, ipilimumab, tremelimumab (CP-675,206), 9H10, 4F10, and 9D9. In some embodiments, the CTLA-4 inhibitor is ipilimumab. In some embodiments, the CTLA-4 inhibitor is tremelimumab.

It should further be appreciated that multiple anticancer agents (e.g., immune checkpoint inhibitors) may be included in the compositions and methods disclosed herein. For instance, in a non-limiting example, the compositions and methods disclosed include both a PD-1 inhibitor and a CTLA-4 inhibitor.

In one aspect, the compositions comprising the one or more metabolites further comprise one or more bacterial strains or combinations of bacterial strains disclosed herein.

In one aspect, the compositions comprising the one or more metabolites and one or more bacterial strains or combinations of bacterial strains disclosed herein, further comprise ore or more anticancer agents.

It should be appreciated that in some embodiments, the compositions used in any one of the methods disclosed herein, including any one of the treatment methods, include compositions comprising the one or more metabolites.

It should be appreciated that in some embodiments, the compositions used in any one of the methods disclosed herein, including any one of the treatment methods, include compositions comprising the one or more metabolites and the one or more bacterial strains.

It should be appreciated that in some embodiments, the compositions used in any one of the methods disclosed herein, including any one of the treatment methods, include compositions comprising the one or more metabolites and the one or more anticancer agents (e.g., a PD-1 inhibitor or a CTLA-4 inhibitor).

It should be appreciated that in some embodiments, the compositions used in any one of the methods disclosed herein, including any one of the treatment methods, include compositions comprising the one or more metabolites, the one or more bacterial strains and the one or more anticancer agents (e.g., a PD-1 inhibitor or a CTLA-4 inhibitor).

In one aspect, the disclosure provides compositions and methods comprising bacterial strains that produce one or more of the metabolites provided herein. Thus, in one aspect, the disclosure provides a composition comprising one or more bacterial strains that produce metabolites selected from the group consisting of mevalonate, dimethylglycine, hypoxanthine, IMP, 2-deoxy-glucose 6P, TMP, 6PG, Rib5P, Ru5P, Xu5p, GDP, GlcNAc 6P, UMP, GMO, CDP, Pyridoine B6, Opthalomic acid, Ctp, GTP, ATP, F6P, 5-methyltetrahydrofolic acid, adenylosuccinate, G6P, 3-hydroxyanthranalinic acid, glycerol 3P, sedoheptulose 7P, 2-keto-4-methylthiobutyrate, dUMP, histamine, valeric acid, 3PG+2 PG, G1P, thymidine, CMP, dopamine, phosphoenolpuryvate, HPO4, iso-butyrate, allotoin, aceylcarnitine, and thymine. It should be appreciated that a single bacterial strain may produce multiple of the recited metabolites. It should also be appreciated that multiple bacterial strains may be needed in combination to produce one or more of the metabolites. In some embodiments, the composition comprises one or more bacterial strains that produce metabolites selected from the group consisting of mevalonate, dimethylglycine, hypoxanthine, IMP, 2-deoxy-glucose 6P, TMO, 6PG, Rib5P, Ru5P, Xu5p, GDP, GlcNAc 6P, UMP, GMO, and CDP. In some embodiments, the composition comprises one or more bacterial strains that produce metabolites selected from the group consisting of mevalonate and dimethylglycine. In some embodiments, the composition comprises one or more bacterial strains that produce mevalonate. Many bacterial strains comprise the mevalonate pathway and have the ability to produce mevalonate (See e.g., Mizorki, *Arch Biochem Biophys.* 2001 Jan. 15;505(2):131-143).

It should further be appreciated that, in some embodiments, the compositions comprise bacterial strains in which a mevalonate pathway has been introduced (See e.g., Yang et al. Microb Cell Fact. 2016; 15:14.). In some embodiments, the composition comprises one or more bacterial strains that produce dimethylglycine. Bacterial strains that produce dimethylglycine are known in the art and include e.g., *Eubacterium limosum* (See e.g., Muller et al. Applied and Environmental Microbiology, 1981, 439-445). The disclosure also includes, in some embodiments, bacterial strains in which a dimethylglycine pathway has been introduced. In some embodiments, the composition comprises one or more bacterial strains that produce dimethylglycine and mevalonate. In some embodiments, the composition comprises one or more bacterial strains that produce mevalonate and a pharmaceutically acceptable carrier. In some embodiments, the composition comprises one or more bacterial strains that produce dimethylglycine and a pharmaceutically acceptable carrier. In some embodiments, the composition comprising one or more bacterial strains that produce the one or more metabolites comprise a pharmaceutically acceptable carrier. In some embodiments, the composition comprises one or more bacterial strains that produce dimethylglycine and mevalonate and a pharmaceutically acceptable carrier.

It should further be appreciated that in some embodiments, in any of the compositions and methods provided herein, the bacterial strains that produce one or more metabolites may combined with bacterial strains that induce proliferation and/or accumulation of CD8+ T cells.

PD-1 Inhibitors

Programmed death protein 1 (PD-1) is a surface protein on activated T cells which is an immune-checkpoint protein which is responsible for preventing the immune system from attacking the body's own tissues. Without wishing to be bound by any particular mechanism, it is generally thought that when PD-1 binds either of its ligands, programmed cell death 1 ligand 1/2 (PD-L1 or PD-L2), the T cell becomes inactivated, thus inhibiting the immune checkpoint blockade. Many tumor cells express PD-L1, and inhibition of the interaction between PD-1 and PD-L1 can enhance T-cell response in vitro and mediate preclinical antitumor activity.

PD-1 is an immune checkpoint that guards against autoimmunity through two mechanisms. First, PD-1 promotes apoptosis of antigen-specific T-cells in lymph nodes. Second, PD-1 reduces apoptosis in anti-inflammatory, regulatory T cells. PD-L1 is highly expressed in several cancers and monoclonal antibodies targeting PD-1 that boost the immune system are known in the art.

Examples of PD-1I inhibitors include, without limitation, nivolumab (OPDIVO®, Bristol Myers Squibb and Ono Pharmaceutical), pembrolizumab (KEYTRUDA®, Merck), and pidilizumab (CT-011, Curetech). In some embodiments, the PD-1 inhibitor is a PD-L1 inhibitor. In some embodiments, the PD-L1 inhibitor is atezolizumab (TECENTRIQ®, Genentech and Roche), avelumab (BAVENCIO®, Merck KGaA, Pfizer, and Eli Lilly), durvalumab (IMFINZI®, MedImmune and AstraZeneca), MPDL3230A (RG7446, Roche), MEDI4736 (AstraZeneca), or MSB0010718C (Merck Serono).

Nivolumab is a human IgG4 monoclonal antibody which inhibits the binding of PD-1 and its ligands PD-L1 and PD-L2. A detailed description of the properties and mechanism of action of nivolumab can be found in, for example, in PCT Publication No. WO 2013/173223, the contents of which are incorporated herein in their entirety. Briefly, nivolumab is a checkpoint inhibitor which blocks PD-1 ligand (PD-L1) binding to PD-1. Nivolumab is thought to bind primarily to the surface-exposed N-loop in PD-1 with high affinity and inhibit the interaction with both PD-L1 and PD-L2, thereby stimulating regulatory T cells against antigen-specific T cell proliferation. Nivolumab has been approved in the United States for the treatment of melanoma, squamous lung cancer, Hodgkin's Lymphoma, head and neck cancer, urothelial carcinoma, colorectal cancer, hepatocellular carcinoma, and metastatic non-small cell lung cancer.

In some embodiments, a PD-1 inhibitor is pembrolizumab (KEYTRUDA®). A detailed description of the properties and mechanism of action of pembrolizumab can be found in U.S. Pat. Nos. 8,354.509 and 8,900,587, the contents of which are incorporated herein in their entirety. Briefly, pembrolizumab binds and inhibits the activity of PD-1 on T cells, allowing the immune system to recognize and destroy cancer cells. Pembrolizumab is a humanized IgG4 immunoglobulin monoclonal antibody which binds primarily to the surface-exposed CD loop in PD-1 with high affinity and inhibits interaction with its ligands PD-L1 and PD-L2. Pembrolizumab has been approved in the United States for the treatment of metastatic melanoma, non-small cell lung cancer, head and neck cancer, Hodkgin's Lymphoma, urothelial carcinoma, gastric cancer, and cervical cancer.

Anti-PD1 antibodies such as nivolumab and pembrolizumab may also be useful in treatment of chronic viral infection, such as HIV.

Treatment of Diseases

Cancer

In one aspect, the disclosure includes compositions and methods for the treatment of diseases in a subject. In some embodiments of the methods provided herein, the subject has cancer. In one aspect, the cancers that can be treated according to the compositions and methods provided herein, include without limitation, carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiment of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent.

In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the cancer immunotherapy agent is a cancer vaccine that acts to increase the response of a subject's immune system to cancer cells. For example, cancer vaccines include cancer antigen(s) that act to induce or stimulate an immune response against cells bearing the cancer antigen(s). The immune response induced or stimulated can include an antibody (humoral) immune response and/or a T-cell (cell-mediated) immune response. CD8+ T-cells can differentiate into cytotoxic T-cells that kill target cells bearing the antigen recognized by CD8+ T-cells. Induction of CD8+ T-cells can, therefore, enhance the immune response to cancer antigens provided in a cancer vaccine.

In some embodiments of the methods provided herein, the cancer immunotherapy agent is a CAR-T therapeutic. CAR-T cells include T-cells taken from a patient that are genetically engineered to produce chimeric antigen receptors (CARs) on their surface. The CARs are engineered to recognize a specific antigen on cancer cells. After the CAR-T cells are infused into the patient, they recognize and kill cancer cells that express the specific antigen on their surfaces. Induction of CD8+ T-cells is useful to provide cells for conversion into CAR-T cells.

In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28 antibody, OX-40 antibody, 4-1BB antibody, CD40 antibody, ICOS/CD278, CD28-type molecule, CD27/TNFRSF7, CD30/TNFRSF8, or GITR/CD357.

In some embodiments of the methods provided herein, the method further includes administering one or more vaccines. In some embodiments of the methods provided herein, the vaccine is a dendritic cell vaccine.

In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor, PD-L-1 inhibitor, CTLA-4 inhibitor, IDOI inhibitor, LAG3 inhibitor or TIM3 inhibitor. In some embodiments of the compositions provided herein, the immune checkpoint inhibitor is a PD-1 inhibitor. In some embodiments, the PD-1 inhibitor is nivoilmab. In some embodiments, the PD-1 inhibitor is pembrolizumab. In some embodiments, the PD-1 inhibitor is pidiluzimab. In some embodiments of the compositions provided herein, the immune checkpoint inhibitor is a PD-L-1 inhibitor. In some embodiments, the PD-L-1 inhibitor is atezolizumab. In some embodiments, the PD-L-1 inhibitor is avelumab. In some embodiments, the PD-L-1 inhibitor is durvalumab. In some embodiments of the methods provided herein, the immune checkpoint inhibitor is a CTLA-4 inhibitor. In some embodiments, the CTLA-4 inhibitor is an anti-CTLA-4 antibody. Examples of anti-CTLA-4 antibodies include, without limitation, ipilimumab, tremelimumab (CP-675,206), 9H10, 4F10, and 9D9. In some embodiments, the CTLA-4 inhibitor is ipilimumab. In some embodiments, the CTLA-4 inhibitor is tremelimumab. It should further be appreciated that multiple anticancer agents (e.g., immune checkpoint inhibitors) may be included in the compositions and methods disclosed herein. For instance, in a non-limiting example, the compositions and methods disclosed include both a PD-1 inhibitor and a CTLA-4 inhibitor.

In one aspect, the disclosure provides a composition comprising a purified bacterial mixture comprising two or more bacterial strains of species selected from *Fusobacterium ulcerans* and *Eubacterium limosum*, or *Bacteroides dorei* and *Bacteroides uniformis* and a PD-1 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides a composition comprising a purified bacterial mixture comprising two or more bacterial strains of species selected from *Fusobacterium ulcerans* and *Eubacterium limosum*, or *Bacteroides dorei* and *Bacteroides uniformis* and a PD-L-1 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides a composition comprising a purified bacterial mixture comprising two or more bacterial strains of species selected from *Fusobacterium ulcerans* and *Eubacterium limosum*, or *Bacteroides dorei* and *Bacteroides uniformis* and a CTLA-4 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity to SEQ ID NO:2 and SEQ ID NO:10, or SEQ ID NO:3 and SEQ ID NO:4, and a PD-1 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity to SEQ ID NO:2 and SEQ ID NO:10, or SEQ ID NO:3 and SEQ ID NO:4, and a PD-L-1 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 95% sequence identity to SEQ ID NO:2 and SEQ ID NO:10, or SEQ ID NO:3 and SEQ ID NO:4, and a CTLA-4 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity to SEQ ID NO:2 and SEQ ID NO:10, or SEQ ID NO:3 and SEQ ID NO:4, and a PD-1 inhibitor. In some embodiments, the purified bacterial mixture comprises at least 3, at least 4, at least 5, at least 6, at least 7, at least 8, at least 9, at least 10, or at least 11 bacterial strains.

In one aspect, die disclosure provides compositions comprising a purified bacterial mixture comprising two or more bacterial strains comprising 16S rDNA sequences of at least 97% sequence identity to SEQ ID NO:2 and SEQ ID NO:10, or SEQ ID NO:3 and SEQ ID NO:4, and a PD-L-1 inhibitor. In some embodiments, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity to SEQ ID NO:2 and SEQ ID NO:10, or SEQ ID NO:3 and SEQ ID NO:4, and a CTLA-4 inhibitor. In some embodiments, the purified bacterial mixture comprises at least 3, at least 4, at least 5, at least 6, at least 7, at least 8, at least 9, at least 10, or at least 11 bacterial strains.

In some embodiments of the compositions provided herein, the composition further includes one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28 antibody, OX-40 antibody, 4-1BB antibody, CD40 antibody, ICOS/CD278, CD28-type molecule, CD27/TNFRSF7, CD30/TNFRSF8, or GITR/CD357.

In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T cell receptors or chimeric antigen receptors.

Infectious Disease

In one aspect, the disclosure includes compositions and methods for the treatment of diseases in a subject. In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus.

In some embodiments, the compositions provided herein can be used as a pharmaceutical composition for preventing or treating (reducing, partially or completely the adverse effects of) an infectious disease, such as a bacterial infection, a viral infection, a parasitic infection, and a fungal infection.

In some embodiments, the methods provided herein increase the protection of a subject against infectious disease. In some embodiments, the methods provide herein reduce the likelihood that a subject will acquire an infectious disease. In some embodiments, the methods provide herein reduce the likelihood that a subject will acquire an infectious disease upon exposure to an infectious agent. In some embodiments, administering the compositions of the disclosure will result in activation of the immune system (e.g., by the induction of proliferation and/or accumulation of the immune system, thereby reducing the likelihood that an infectious agent can take residence and multiple in the subject, or in the cells of the subject.

Bacterial infections that can be treated according to the methods provided herein include, but are not limited to *P. aeruginosa, E. coli, C. tetani, N. gonorrhoeas, C. botulinum, Klebsiella* sp., *Serratia* sp., *Pseudomonas* sp., *P. cepacia, Acinetobacter* sp., *S. epidermis, E. faecalis, S. pneumonias, S. aureus; S. mutans, Haemophilus* sp., *Neisseria* Sp., *N. meningitides, Bacteroides* sp., *Citrobacter* sp., *Branhamella* sp., *Salmonella* sp., *Shigella* sp., *S. pyogenes, Proteus* sp., *Clostridium* sp., *Erysipelothrix* sp., *Listeria* sp., *Pasteurella multocida, Streptobacillus* sp., *Spirillum* sp., *Fusospirocheta* sp., *Treponema pallidum, Borrdia* sp., *Actinomycetes, Mycoplasma* sp., *Chlamydia* sp., *Rickettsia* sp., *Spirochaeta, Borellia burgdorferi, Legionella* sp., *Mycobacteria* sp., *Urcaplasma* sp, *Streptomyces* sp., *Trichomoras* sp., *P. mirabilis; Vibrio cholera*, enterotoxigenic *Escherichia coli, Clostridium difficile, Salmonella typhi, C. diphtheria, Mycobacterium leprae, Mycobacterium lepromatosi*. Bacterial infections caused by drug resistant bacteria that can be treated according to the methods provided herein include, but are not limited to *Clostridium perfringens; Clostridium botulinum; Clostridium tributrycum; Clostridium sporogenes; Escherichia coli; Pseudomonas aeruginosa*, such as Multidrug Resistant *Pseudomonas aeruginosa*; Vancomycin Resistant *Enterococci* (VRE); Carbapenem Resistant Enterobacteriaceae (CRE); *Neisseria gonorrheae*; Acinetobacter, Multidrug Resistant Acinetobacter; Campylobacter; Multidrug-resistant Campylobacter; Candida, Fluconazole-Resistant Candida, Extended spectrum beta-lactamase (ESBL) producing Enterobacteriaceae; Salmonella, Salmonella Typhimurium, Drug resistant non-typhoid *Salmonella* spp.; Drug resistant Salmonella Typhi; Drug resistant Shigella; *Staphylococcus aureus*, such as Methicillin Resistant *S. aureus* or vancomycin resistant *S. aureus*; Drug resistant *Streptococcus pneumoniae*; Drug resistant Tuberculosis; Erythromycin Resistant Group A Streptococcus; Clindamycin resistant Group B Streptococcus, and any combinations thereof. In some embodiments, the bacterial infection is an intracellular bacterial infection. In some embodiments, the bacterial infection is an infection by Listeria monocytogenes.

Viral infections that can be treated according to the methods provided herein include, but are not limited to, picomaviridae, caliciviridae, togaviridae, flaviviridae, coronaviridae, rhabdoviridae, filoviridae, paramyxoviridae, orthomyxoviridae, bunyaviridae, arenaviridae, reoviridae, retroviridae, hepadnaviridae, parvoviridae, papovaviridae, adenoviridae, herpesviridae, poxviridae, rotavirus, parainfluenza virus, influenza virus A and B, hepatitis virus, syphilis, HIV, rabies virus, Epstein-Barr virus, and herpes simplex virus.

Viral infections that can be treated according to the methods provided herein include, but are not limited to *Plasmodium falciparum, P. vivax, P. ovale, P. malaria, Toxoplasma gondii, Lrishmania mexicana, L. tropica, L. major, L. aethiopica, L. donovani, Trypanosoma crozi, T. brucei, Schistosoma mansoni, S. haematobium, S. japonium, Trichinella spiralis, Wuchereria bancrofti, Brugia malayli, Entamoeba histolytica, Enterobius vermiculoarus, Taenia solium, T. saginata, Trichomonas vaginatis, T. hominis, T. tenax; Giardia lamblia, Cryptosporidium parvum, Pneumocytis carinii, Babesia bovis, B. divergens, B. microti, Isopore belli, Lhominis, Dientamoeba jragiles, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latum, Echinococcus granulosus, E. multilocularis, Paragonimus westermani, P. caliensis, Chlonorchis sinensis, Opisthorchis felineas, G. viverini, Fasciola hepatica, Sarcoptes scabiei, Pediculus humanus, Phthirius pubis*, and *Dermatobia hominis.*

Fungal infections that can be treated according to the methods provided herein include, but are net limited to *Cryptococcus neoformans, Blastomyces denmatitidis, Aiellomyces dermatitidis, Histoplasfria capsulatum, Coccidioides immitis, Candida* species, including *C. albicans, C. tropicalis, C. parapsilosis, C. guilliermondii* and *C. krusei, Aspergillus* species, including *A. fumigates, A. flavus, A. niger, Rhizopus* species, *Rhizomucor* species, *Cunninghammella* species, *Apophyscmyces* species, including *A. sakse-*

*naea, A. mucor* and *A. absidia, Sporothrix schenckii, Paracoecidioides brasiliensis, Pseudallescheria boydii, Torulopsis glabrata*; and *Dermatophytes* species.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen. In some embodiments, the bacterial compositions are administered as an adjuvant in combination with antigenic material. The antigenic material can include one or more portions of the protein coat, protein core, or functional proteins and peptides of a pathogen, or a full pathogen (live, killed, inactivated, or attenuated), or may comprise one or a plurality of cancer epitopes or cancer antigens. The antigenic material can be co-administered, administered before. or after the bacterial composition. The bacterial composition may also be administered with existing mucosal vaccines such as influenza vaccines, (e.g., FluMist from MedImmune or NASOVAC from Serum Institute of India), rotavirus vaccines (e.g. RotaTeq from Merck or Rotarix from GlaxoSmithKline), typhoid vaccines (e.g., Vivotif from Crucell, Ty21A), cholera vaccines (e.g., Orochol from Crucell, Shanchol from Shantha Biotechnics), traveller's diarrhea vaccines (e.g., Dukoral from Valneva), and with antigens of live attenuated influenza A virus H1 strain, live attenuated Influenza A virus H3 strain, Influenza B virus, live attenuated H1N1 influenza virus (swine flu), live attenuated rotavirus, mono- and multi-valent poliovirus, live attenuated *Salmonella typhi*, live recombinant Vibrio cholerae lacking cholera toxin subunit A, whole killed Vibrio cholerae 01 classical and El Tor biotypes with or without cholera toxin subunit B, cancer antigens, cancer epitopes, and combinations thereof.

Autoimmune Disease or Allergic Disease

In one aspect, the disclosure includes compositions and methods for the treatment of diseases in a subject. In some embodiments of the methods provided herein, the subject has an autoimmune disease or an allergic disease.

The compositions and methods of the current disclosure can be used for preventing or treating autoimmune disease and allergic disease. Autoimmune disease that can be treated include, but are not limited to, inflammatory bowel disease, systemic lupus erythematosus, rheumatoid arthritis, multiple sclerosis, or Hashimoto's disease. Allergic diseases that can be treated include, but are not limited to, food allergy, pollenosis, or asthma.

Additional examples of autoimmune and allergic disease that can be treated according to the methods and compositions provided herein include, without limitation, rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, *Yersinia* and *Salmonella* associated arthropathy, spondyloarthropathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulin dependent diabetes mellitus, sympathetic ophthalmia, pulmonary hypertension secondary to connective tissue disease, Goodpasture's syndrome, pulmonary manifestation of polyarteritis nodosa, acute rheumatoid fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, eosinophilic gastroenteritis, and diarrhea.

In some embodiments of the methods and compositions provided herein, the composition further comprises one or more anti-inflammatory agents. In some embodiment of the methods and compositions provided herein, the anti-inflammatory agent is a non-steroidal anti-inflammatory drug (NSAID). Exemplary NSAIDs include, but are not limited to, aspirin, ibuprofen, naproxen, celecoxib, rofecoxib, diclofenae, diflunisal, etodolac, fenoprofen, flurbiprofen, ketoprofen, ketorolac, mefenamic acid, meloxicam, nabumetone, oxaprozin, piroxicam, sulindac, tolmetin and combinations thereof. In some embodiments, the NSAID is an immune selective anti-inflammatory derivative (ImSAID).

Treatment of Disease

In one aspect, the disclosure provides compositions and methods of treatment for disease in a subject. In one aspect, and without being limiting, the compositions disclosed herein can treat disease because their administration results in the induction of proliferation and/or accumulation of CD8+ T-cells. In some embodiments, the disclosure provides compositions and methods of treatment for disease in a subject for diseases that can be treated by the induction of proliferation and/or accumulation of CD8+ T-cells. In some embodiments, the diseases that can be treated by the induction of proliferation and/or accumulation of CD8+ T-cell is cancer, an infectious disease, an autoimmune disease or allergic disease.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition. In some embodiments of the methods provided herein, the administration of the composition to the subject results in an increase of IFN-gamma production in the intestine of the subject when compared to the IFN-gamma production in the intestine of the subject before the administration of the composition. In some embodiments of the methods provided herein, the administration of the composition to the subject results in an increase of IFN-gamma production in the intestine of the subject by at least 10%, at least 20%, at least 30%, at least 40%, at least 50%, at least 100%, or at least 200% when compared to the IFN-gamma production in the intestine of the subject before the administration of the composition.

In one aspect, the disclosure provides methods of treating a disease in a subject comprising administering any one of the compositions provided herein to the subject in an effective amount to treat the disease, wherein the treatment minimizes adverse events. In some embodiments, the disclosure provides methods of treating a disease in a subject comprising administering any one of the compositions provided herein to the subject in an effective amount to treat the disease, wherein the treatment minimizes undesired inflammatory events. In some embodiments, the disclosure provides methods of treating a disease in a subject comprising the induction of proliferation and/or accumulation of CD8+ T-cells wherein the treatment minimizes adverse events. In some embodiments, the disclosure provides methods of treating a disease in a subject comprising the induction of proliferation and/or accumulation of CD8+ T-cells, wherein the treatment minimizes undesired inflammation. In some embodiments, the disclosure provides methods of treating a disease in a subject comprising the induction of proliferation and/or accumulation of CD8+ T-cells, wherein the treatment minimizes undesired inflammation in the intestine. In some embodiments, the disclosure provides methods of treating cancer in a subject comprising the induction of proliferation and/or accumulation of CD8+ T-cells, wherein the treatment minimizes undesired inflammation in the intestine. In some embodiments, the disclosure provides methods of treating cancer in a subject comprising the induction of proliferation and/or accumulation of CD8+ T-cells, wherein the treatment minimizes the development of colitis or other inflammatory bowel diseases. In some embodiments, the disclosure provides methods of treating cancer in a subject comprising the administration of one or more of the bacterial compositions provided herein and one or more immune checkpoint inhibitors, wherein the treatment minimizes the development of colitis or other inflammatory bowel diseases.

As shown herein, the compositions of the disclosure when administered in combination with immune checkpoint inhibitors increase the efficacy of the immune checkpoint inhibitor while simultaneously minimizing adverse events associated with immune checkpoint inhibitor therapy. Thus, in some embodiments, the disclosure provides methods and compositions that minimize adverse events that are caused by administration of an anticancer therapy (e.g., a checkpoint inhibitor). The term "adverse event" may be used interchangeably with the term "side effect" or toxicity" and refers to any undesired effect that is caused by administration of the anticancer therapy. An adverse event is considered to be caused by the anticancer therapy if the adverse event occurs subsequent to the initiation of the anticancer therapy. In general, the adverse event may be directly or indirectly caused by the anticancer therapy. In some embodiments, the adverse event is used as an indicator that the anticancer therapy is effective.

Examples of adverse events that may be caused by anticancer therapy include, without limitation, undesired immune responses, colitis, inflammation, dermatological toxicity, diarrhea, nausea, fatigue, hepatotoxicity, hypophysitis, eosinophilia, and autoimmune thyroid disease. Additional adverse events caused by the anticancer therapy will be evident to one of skill in the art.

Adverse events associated with checkpoint inhibitor therapy are summarized for instance in Postow et al., Up to Date June 2017, Toxicities associated with checkpoint inhibitor immunotherapy, authors Postow M and Wolchok J, editors Atkins M and Ross M., Yang et al., Recognizing and managing toxicities in cancer immunotherapy, Tumor Biology March (2017): 1-13; and Linardou et al., Toxicity management of immunotherapy for patients with metastatic melanoma", Ann Transl. Med (2016) 4 (14) 22, which are all incorporate herein by reference in their entirety.

In some embodiments, the adverse event is immune-check point inhibitor induced colitis (See e.g., Pricux-Clotz et al., Target Oncology 2017, 12, 301-308).

Any of the compositions described herein may be administered to a subject in a therapeutically effective amount or a dose of a therapeutically effective amount to treat or prevent a disease (e.g., cancer or infectious disease). The terms "treat" or "treatment" refer to reducing or alleviating one or more of the symptoms associated with a disease (e.g., cancer or infectious disease). The terms "prevent" or "prevention" encompass prophylactic administration and may reduce the incidence or likelihood of the occurrence of the disease (e.g., cancer or infectious disease). For instance, in some embodiments, administration of the compositions provided herein result in a healthy microbiome that induces proliferation and/or accumulation of CD8+ T-cells thereby protecting a subject against cancer and/or infectious disease.

As used herein, a "therapeutically effective amount" of composition, such as a pharmaceutical composition, is any amount that results in a desired response or outcome in a subject, such as those described herein, including but not limited to prevention of infection, an immune response or an enhanced immune response and/or augmentation of cancer treatment. It should be appreciated that the term effective amount may be expressed in number of bacteria or CFUs to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to treat the disease, e.g., enhance survival of the subject, suppress an infection and/or treat the cancer.

Any of the methods described herein may be for the treatment of cancer in a subject. As used herein, methods of treating cancer involve relieving or alleviating at least one symptom associated with the cancer, or slowing or reversing the cancer progression. A method of treating cancer may, for example, eliminate or reduce a subject's tumor burden, reduce the number or replication of cancer cells, and/or prevent, delay or inhibit metastasis.

Also provided herein are methods for the treatment or prevention of an infectious disease in a subject. As used herein, methods of treating an infectious disease may involve relieving or alleviating at least one symptom associated with infection, or slowing or reversing the progression of the infection. A method of treating an infectious disease may, for example, eliminate or reduce the load of an infectious organism (e.g., bacteria, virus, fungus, or parasite), or inhibit or reduce one or more symptoms of the infection. As also used herein, the terms "prevent," "prevention," and "preventing," include the administration of a composition to a subject to reduce, or delay the onset of the manifestation of clinical or subclinical symptoms, complications, pathologies or biochemical indicia of the infection, or to reduce or inhibit the spread/transmission of the infectious organism (e.g., bacteria, virus, fungus, or parasite).

Aspects of the present disclosure are related to methods for treating a disease or condition in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject.

The compositions and methods described herein may be utilized in conjunction with other types of therapy (i.e., combination treatment), such as additional therapeutic agents. Examples of additional combination therapies include, without limitation, surgery, radiation, gene therapy, and administration of additional therapeutic agents, such as chemotherapeutics, antibiotics, antivirals, anti-fungals, anti-parasitics, immunomodulatory agents, anti-inflammatory agents. In general, combination therapies can be administered simultaneously or sequentially (in any order) with the compositions and methods described herein. In some embodiments, any of the compositions described herein is administered simultaneously with one or more additional therapeutic agents, for example in a single dose or in multiple doses that are administered at substantially the same time.

In some embodiments, the compositions described herein are administered to a subject concomitantly with one or more additional therapeutic agents. In some embodiments, the compositions described herein are administered to a subject followed by administration of one or more additional therapeutic agent. In some embodiments, any of the compositions described herein is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the one or more additional therapeutic agent. Alternatively, in some embodiments, one or more therapeutic agent administered to a subject followed by administration of any of the compositions described herein. In some embodiments, one or more therapeutic agent is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of any the compositions described herein.

Additional Methods

Also within the scope of the present disclosure are methods of assessing whether one or more bacterial strains of any of the compositions described herein are present in the intestine of a subject. In some embodiments, if fewer than a threshold number of bacterial strains are detected in the intestine of the subject, any of the compositions described herein are administered to the subject to increase the number of the bacterial strains in the intestine of the subject. In some embodiments, the method further comprises identifying the subject as a candidate for a treatment of the disease based on the number of bacterial strains detected in the intestine.

Measuring the levels of the biomarker sets may also be useful in the evaluation and treatment of a disease.

In general, the bacterial population of the intestine (e.g., presence or absence of one or wore bacterial strains) may be determined by assessing a sample obtained from the subject, such as a fecal sample.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFN-gamma production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the engrafted number of the bacterial strains of the administered composition in the intestine of the subject. In some embodiments of the compositions provided herein, administration of the composition to a subject results in an increase in the abundance of total bacteria of the bacterial strains of the administered composition in the intestine of the subject. In some embodiments of the compositions provided herein, administration of the composition to a subject results in an increase in the engrafted total bacterial strains of the administered composition in the intestine of the subject.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject.

In some embodiments of the methods provided herein, the subject is undergoing, or will be undergoing, cancer treatment.

In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment.

In some embodiments of the methods provided herein, the cancer treatment is cancer immunotherapy treatment.

In one aspect, the disclosure provides a method for reducing the risk of a viral infection in a subject, wherein the method includes determining if one or more bacterial species of any of the compositions provided herein are present in the intestine of a subject wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject.

In one aspect, the disclosure provides a method for reducing the risk of a bacterial infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a bacterial infection in the subject. In some embodiments, the bacterial infection is an intracellular bacterial infection.

In some embodiments of the methods provided herein, determining the presence of one or more of the bacterial species is done by sequencing fecal matter of the subject.

Pharmaceutical Compositions

In one aspect, the disclosure provides pharmaceutical compositions comprising the bacterial strains and combinations of bacterial strains provided herein. In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. No. 3,261,761; U.S. Pat. No. 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake. In some embodiments, one or more of the bacterial strains of the compositions, including pharmaceutical compositions and food products, has been spray-dried. In some embodiments, a subset of the bacterial strains is spray-dried. The process of spray-drying refers to production of dry powder from a liquid comprising bacterial compositions. (See, e.g., Ledet et al., Spray-Drying of Pharmaceuticals in "Lyophilized Biologics and Vaccines" pages 273-294, Springer). In general, the process involves rapidly drying the bacterial compositions with a hot gas. A bacterial strain may be combined with a pharmaceutical excipient prior to combining it with the other bacterial strains or multiple spray-dried bacterial strains may be combined while in spray-dried form and the mixture of bacterial strains, once combined may be subsequently be combined with a pharmaceutical excipient.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coaling that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, AAPS PharmSciTech (2016) 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., Int J Pharm (2015) 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure charge caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in foe gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or foe colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions disclosed herein, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times. In some embodiments, the subject is treated with antibiotics prior to administration of one or more doses of the composition. In some embodiments, the subject is treated with antibiotics prior to composition is administered orally to the subject once, twice, 3 times, 4 times, 5 times, 6 times, 7 times, 8 times, 9 times, or at least 10 times.

In some embodiments, the subject may be administered one or more doses of an antibiotic prior to or concurrently with the CD8 T cell inducing bacterial compositions provided herein. Antibiotics may be administered for a variety of reasons. For instance, antibiotics may be administered to remove bacterial species from the colon and/or intestine prior to administration of the CD8 T cell inducing bacterial compositions provided herein. In some embodiments, antibiotics are administered to increase the ability of the bacterial strains of the CD8 T cell inducing bacterial compositions to engraft in the colon and/or intestine. It should be appreciated that, in some embodiments, it is desirable to remove bacterial species from the microbiome that induce immune responses that are undesired in cancer treatment. In some embodiments, antibiotics are administered to decrease the number of Treg inducing bacterial species present in the microbiome. It should be appreciated that bacterial species that belong to clostridium clusters IV and/or XIVa can induce Treg cells (See e.g., Atarahi et al. Nature 500, 232 (2013)). In some embodiments, antibiotics are administered to decrease the number of bacterial species of clostridium clusters IV and/or XIVa present in the microbiome. In some embodiments, antibiotics that have an antibiotic spectrum directed to bacterial species of clostridium clusters IV and/or XIVa are administered. In some embodiments, the antibiotic is vancomycin. Antibiotics may also be administered to suppress unwanted infections in the case of anticancer therapy. In some instances, antibiotics may be administered as a treatment method for an infectious disease. In some instances, antibiotics may be administered together with the CD8 T cell inducing bacterial compositions as a treatment method for an infectious disease. Examples of antibiotics that can be administered include, without limitation, kanamycin, gentamicin, colistin, metronidazole, vancomycin, clindamycin, fidaxomicin, and cefoperazone. In some embodiments, the antibiotic is vancomycin.

In some embodiments, the subject is administered a single dose of an antibiotic prior to the administration of the CD8 T cell inducing bacterial compositions. In some embodiments, the subject is administered multiple doses of an antibiotic prior to the administration of the CD8 T cell inducing bacterial compositions. In some embodiments, the subject is administered at least 2, 3, 4, 5 or more doses of an antibiotic prior to the administration of the CD8 T cell inducing bacterial compositions. In some embodiments, the subject is administered a dose of an antibiotic at substantially the same time as the administration of the CD8 T cell inducing bacterial compositions. Examples of antibiotics that can be administered include, without limitation, kanamycin, gentamicin, colistin, metronidazole, vancomycin, clindamycin, fidaxomicin, and cefoperazone.

In some embodiments, the disclosure provides compositions comprising an antibiotic and an anticancer agent (e.g., an immune checkpoint inhibitor). In some embodiments, the disclosure provides compositions comprising vancomycin and an anticancer agent (e.g., an immune checkpoint inhibitor). In some embodiments, the disclosure provides compositions comprising an antibiotic and CD8 T cell inducing bacterial compositions. In some embodiments, the disclosure provides compositions comprising vancomycin and CD8 T cell inducing bacterial compositions. In some embodiments, the disclosure provides compositions comprising an antibiotic, an anticancer agent (e.g., an immune checkpoint inhibitor) and CD8 T cell inducing bacterial compositions. In some embodiments, the disclosure provides compositions comprising vancomycin, an anticancer agent (e.g., an immune checkpoint inhibitor) and CD8 T cell inducing bacterial compositions.

In some embodiments, in any one of the methods provided herein an antibiotic is administered together with an anticancer agent (e.g., an immune checkpoint inhibitor). In some embodiments, in any one of the methods provided herein vancomycin is administered together with an anticancer agent (e.g., an immune checkpoint inhibitor). In some embodiments, in any ore of the methods provided herein an antibiotic is administered together with CD8 T cell inducing bacterial compositions. In some embodiments, in any one of the methods provided herein vancomycin is administered together with CD8 T cell inducing bacterial compositions. In some embodiments, in any one of the methods provided herein an antibiotic is administered together with an anticancer agent (e.g., an immune checkpoint inhibitor) and CD8 T cell inducing bacterial compositions. In some embodiments, in any one of the methods provided herein vancomycin is administered together with an anticancer agent (e.g., an immune checkpoint inhibitor) and CD8 T cell inducing bacterial compositions.

In some embodiments in any one the methods provided herein, a subject is evaluated for the presence of CD8 T cell inducing bacterial strains in the microbiome. In some embodiments if the subject does not have, or only has a low level of CD8 T cell inducing bacterial strains in the microbiome, any one of the compositions provided herein may be administered. In some embodiments, if a person does not have, or only has a low level of CD8 T cell inducing bacterial strains in its microbiome any one of the compositions provided herein may be administered, without the administration of an antibiotic.

In some embodiments in any one the methods provided herein, a subject is evaluated for the presence of CD8 T cells. In some embodiments if the subject does not have, or only has a low level of CD8 T cells, any one of the compositions provided herein may be administered. In some embodiments, if a person does not have, or only has a low level of CD8 T cells any one of the compositions provided herein may be administered, without the administration of an antibiotic.

In some embodiments, the subject is treated with antibiotics prior to administration of one or more doses of the composition. In some embodiments, the composition is administered in combination with additional commensal bacteria. In some embodiments, the subject is treated with antibiotics prior to administration of one or more doses of the composition in combination with additional commensal bacteria.

In some embodiments, the disclosure provides methods of treatment comprising administering one or more of the compositions provided herein and evaluating if the bacterial strains colonized in the intestine. In some embodiments, the disclosure provides methods of treatment comprising administering one or more of the compositions provided herein, evaluating if the bacterial strains colonized in the intestine, wherein if one or more of the bacterial strains did not colonize in the intestine, additional administrations of one or more of the compositions provided herein are performed. In some embodiments, evaluating if the bacterial strains colonized in the intestine of a subject is done by whole genome sequencing and/or qPCR of fecal matter of the subject. In some embodiments, the methods further comprise one or more nucleic acid sequences that allow for the detection of the bacterial strains. In some embodiments, the nucleic acid sequences are primers for qPCR. In some embodiments, the primers include one or more sequences selected from SEQ ID NOs:16-26, and 38-48.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and 10$^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and 10$^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria per dosage amount.

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and 10$^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and 10$^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-2}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined per dosage amount.

In one aspect, the disclosure provides a food product comprising any of the compositions provided herein and a nutrient. Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein. In some embodiments, the subject is treated with an amount of antibiotics sufficient to allow for the grafting of the one or more strains of the bacterial compositions provided herein.

In some embodiments, the subject may be administered one or more doses of an antibiotic prior to or concurrently with a bacterial composition. Antibiotics may be administered for a variety of reasons. For instance, antibiotics may be administered to remove bacterial species from the colon and/or intestine prior to administration of the bacterial compositions provided herein. Antibiotics may also be administered to suppress unwanted infections in the case of cancer treatment. In some instances, antibiotics may be administered as a treatment method for an infectious disease.

In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

Diagnostics and Prognostic Methods

Also described herein are diagnostic methods (e.g., companion diagnostics) for use in determining whether a subject should receive a treatment, such as a composition as described herein and/or any of the immune checkpoint inhibitors described herein. Such methods can be used for diagnosing a disease, monitoring the progress of a disease, assessing the efficacy of a treatment for the disease, and/or identifying patients suitable for a particular treatment.

Accordingly, the methods described herein are based on the level of a marker in a sample (e.g., a biological sample containing lymphocytes) obtained from a subject. In some embodiments, the methods involve analyzing the presence and/or level of a marker in one or more samples from a subject.

In some embodiments, the level of the marker in a sample obtained from a subject can then be compared with a reference sample or a control sample to determine a value indicating the amount of the marker in the sample. In some embodiments, a value for a marker is obtained by comparing the level of a marker in a sample to the level of another marker (e.g., an internal control or internal standard) in the sample. The value of the marker can be compared to a reference value to determine whether the subject has or is at risk for the disease. In some embodiments, the level of the marker is compared to a predetermined threshold for the marker, a deviation from which may indicate the subject has a disease. In some embodiments, if the level or value of the marker is higher than a reference level or value, the subject can be identified as having or at risk for a disease, as described herein. In some embodiments, if the level or value of the marker is lower than a reference level or value, the subject can be identified as having or at risk for a disease, as described herein.

In some embodiments, the level of the marker in a sample from a subject is compared to the level of the marker in another sample obtained from the same subject, for example, a sample obtained from the subject at a different time. In some embodiments, the level of the marker in a sample from a subject is compared to the level of the marker in a sample obtained from the subject at an earlier time, such as prior to administration of any of the compositions described herein. In some embodiments, the level of the marker in a sample from a subject is compared to the level of the marker in a sample obtained from the subject at a later time, such as after administration of any of the compositions described herein.

In some embodiments, if the level or value of the marker is higher in a sample as compared to the level or value of the marker in a sample from the subject obtained prior to administration of a composition described herein, the subject is administered an immune checkpoint inhibitor and a composition described herein. In some embodiments, if the level or value of the marker is higher in a sample as compared to the level or value of the marker in a sample from the subject obtained prior to administration of a composition described herein, the subject continues a therapy involving administration of an immune checkpoint inhibitor and a composition described herein. In some embodiments, the level or value of the marker in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, if the level or value of the marker is not increased (e.g., equal to or lower) in a sample as compared to the level or value of the marker in a sample from the subject obtained prior to administration of a composition described herein, administration of an immune checkpoint inhibitor and a composition described herein is discontinued. In some embodiments, if the level or value of the marker is not increased (e.g., equal to or lower) in a sample as compared to the level or value of the marker in a sample from the subject obtained prior to administration of a composition described herein, the administration of an immune checkpoint inhibitor and a composition described herein is reanalyzed after administration of a composition as described herein. In some embodiments, the level or value of the marker in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, the level of the marker is determined by analyzing the expression of the marker (e.g., protein or nucleic acid level) and/or the cell type in which the marker is expressed. Any method known the art may be used to analyze the expression of the marker and/or cell type in which the marker is expressed.

In some embodiments, the disclosure provides methods and compositions that allow for the detection and/or quantification of one or more bacterial strains of the compositions. In some embodiments, the disclosure provides methods and compositions that allow for the detection and/or quantification of one or more bacterial strains of the compositions in fecal matter. In some embodiments, the disclosure further comprises one or more nucleic acid sequences that allow for the detection of the bacterial strains. In some embodiments, the nucleic acid sequences are primers four qPCR. In some embodiments, the primers include one or more sequences selected from SEQ ID NOs:16-26, and 38-48.

Also provided herein are methods based on the level or degree of IFN production in a sample (e.g., a biological sample containing splenocytes) obtained from a subject. In some embodiments, the methods involve analyzing the presence and/or level of IFN production in one or more samples from a subject.

In some embodiments, the level of IFN production in a sample obtained from a subject can then be compared with a reference sample or a control sample to determine a value indicating the amount of the IFN production in the sample. In some embodiments, a value for IFN production is obtained by comparing the level of IFN production in a sample to the level of another molecule (e.g., an internal control or internal standard) in the sample. The value of IFN production can be compared to a reference value to determine whether the subject has or is at risk for the disease. In some embodiments, the level of IFN production is compared to a predetermined threshold for IFN production, a deviation from which may indicate the subject has a disease. In some embodiments, if the level or value of IFN production is higher than a reference level or value, the subject can be identified as having or at risk for a disease, as described herein. In some embodiments, if the level or value of IFN production is lower than a reference level or value, tire subject can be identified as having or at risk for a disease, as described herein.

In some embodiments, the level of IFN production in a sample from a subject is compared to the level of IFN production in another sample obtained from the same subject, for example, a sample obtained from the subject at a different time. In some embodiments, the level of IFN production in a sample from a subject is compared to the level of IFN production in a sample obtained from the subject at an earlier time, such as prior to administration of any of the compositions described herein. In some embodiments, the level of IFN production in a sample from a subject is compared to the level of IFN production in a sample obtained from the subject at a later time, such as after administration of any of the compositions described herein.

In some embodiments, if the level or value of IFN production is higher in a sample as compared to the level or value of IFN production in a sample from the subject obtained prior to administration of a composition described herein, the subject is administered an immune checkpoint inhibitor and a composition described herein. In some embodiments, if the level or value of IFN production is higher in a sample as compared to the level or value of IFN production in a sample from the subject obtained prior to administration of a composition described herein, the subject continues a therapy involving administration of an immune checkpoint inhibitor and a composition described herein. In some embodiments, the level or value of IFN production in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFN production in a sample prior to administration of a composition as described herein.

In some embodiments, if the level or value of IFN production is not increased (e.g., equal to or lower) in a sample as compared to the level or value of IFN production in a sample from the subject obtained prior to administration of a composition described herein, administration of an immune checkpoint inhibitor and a composition described herein is discontinued. In some embodiments, if the level or value of IFN production is not increased (e.g., equal to or lower) in a sample as compared to the level or value of IFN production in a sample from the subject obtained prior to administration of a composition described herein, the administration of an immune checkpoint inhibitor and a composition described herein is reanalyzed after administration of a composition as described herein. In some embodiments, the level or value of IFN production in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 150%, 140%, 150%, 160%, 170%, 180%, 190%, or at least 200% as compared the level of value of IFN production in a sample prior to administration of a composition as described herein.

In some embodiments, the level of IFN production is determined by analyzing the expression of IFN (e.g., protein or nucleic acid level) and/or the cell type by which IFN is produced. Any method known the art may be used to analyze the expression of IFN and/or identify the cell type that produces IFN.

The control level can also be a predetermined level or threshold. Such a predetermined level can represent the level of the marker or IFN production in a population of subjects that do not have or are not at risk for the target disease. It can also represent the level of the marker or IFN production in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the metabolite in a control population.

As used herein, “an elevated level” or “an increased level” means that the level of the marker or IFN production is higher than a reference value or the level in another sample, such as a sample obtained from the subject prior to administration of any of the compositions described herein. An elevated level of a marker or IFN production includes a level of the marker or IFN production that is, for example, 1%, 5%, 10%, 20%, 30%, 40%, 50%, 60%, 70%, 80%, 90%, 100%, 150%, 200%, 300%, 400%, 500% or more above a reference value or above the level in another sample from the subject. In some embodiments, the level of the marker or IFN production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more, higher than the level in a reference sample or the level in another sample from the subject.

As used herein, “a decreased level” means that the level of the marker or IFN production is lower than a reference value or the level in another sample, such as a sample obtained from the subject prior to administration of any of the compositions described herein. A decreased level of the marker or IFN production includes a level of the marker or IFN production that is, for example, 1%, 5%, 10%, 20%, 30%, 40%, 50%, 60%, 70%, 80%, 90%, 100%, 150%, 200%, 300%, 400%, 500% or more lower than a reference value or the level in another sample from the subject. In some embodiments, the level of the marker or IFN production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more lower than the level of the marker or IFN production in a reference sample or the level in another sample from the subject.

A subject identified in the methods described herein may be subject to a suitable treatment, such as treatment with a combination of an immune checkpoint inhibitor and any of the composition, as described herein.

The assay methods and kits described herein also can be applied for evaluation of the efficacy of a treatment for a disease, such as those described herein, given the correlation between the level of the marker or IFN production and such diseases. For examples, multiple biological samples can be collected from a subject to whom a treatment is performed either before and after the treatment or during the course of the treatment. The levels of a marker or IFN production may be indicative as to whether the treatment is effective.

If the subject is identified as not responsive to the treatment, a higher dose and/or frequency of dosage of the composition and/or immune checkpoint inhibitors are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a marker or IFN production can also be relied on to identify a disease may be treatable, for example by administering the compositions described herein.

Screening Methods

Provided herein are methods for screening bacteria or physiologically active substances derived from bacteria to identify bacteria or physiologically active substances thereof that produce a desired response. For example, in some embodiments, the screening methods are used to identify bacteria or physiologically active substances derived from bacteria that induce activation of CD8+ IFN-producing T cells. In some embodiments, the screening methods are used to identify bacteria or physiologically active substances derived from bacteria that induce activation of CD8+IFN-producing T cells. In some embodiments, the screening methods are used to identify bacteria or physiologically active substances derived from bacteria as an immunostimulatory agent.

Also provided herein are methods for screening test substances to identify substances that induce activation induce or exacerbate a disease caused by CD8+IFN-producing T cells.

In general, the screening methods may be performed in vitro (e.g., using cells) or in vivo (e.g., using non-human animal models). In some embodiments, the methods involve contacting a population of cells (e.g., intestinal epithelial cells, peripheral blood mononuclear cells) with a test substance (e.g., bacteria or physiologically active substances thereof) and assessing a response. In some embodiments, the response is the number and/or activity of a desired cell population (e.g., CD8+IFN T cells).

In some embodiments, the methods involve inoculating a non-human animal model with a test substance (e.g., bacteria or physiologically active substances thereof) and assessing a response. In some embodiments, the non-human animal model ingests the test substance. In some embodiments, the response is the number and/or activity of a desired cell population (e.g., CD8+IFN T cells). In some embodiments, the response is an improvement of a disease or symptom thereof, or induction/exacerbation of a disease or symptom thereof.

In some embodiments, the bacteria and/or the physiologically active substances derived from bacteria identified in any of the screening methods described herein may be administered to a subject, for example for the treatment of a disease.

In one aspect, the disclosure provides a rationally-designed consortium of human gut commensal microorganisms that induces CD8 T cells and modulates host anti-cancer immunity. Clinical data suggests the gut microbiome influences a response to checkpoint inhibitor therapy, however the precise identity and mode of action of commensals associated with a clinical response has not been elucidated. Provided herein is the generation of a consortium of human gut-derived commensal microorganisms capable of inducing CD8 T cells and augmenting anti-cancer immunity. The microbiota of healthy humans was used to inoculate germ-free mice and assess the level of CD8 T cell induction. Human-derived commensals were isolated from inoculated mice exhibiting high levels of CD8 T cell induction and sequenced. Consortia consisting of isolated human commensals were tested for the ability to induce CD8 T cells in germ-free (GF) and specific-pathogen free (SPF) mice. A minimal consortium capable of inducing CD8 T cells was administered with checkpoint inhibitor antibodies to tumor-bearing mice to assess anti-cancer activity and the level of accumulation of tumor infiltrating lymphocytes. Interferon-gamma producing CD8 T are abundant in the intestines of SPF but not germ-free mice. A consortium of 11 strains (the "11-mix," also referred to as "VE800") of human-derived commensals which robustly induces CD8 T cells in germ-free mice was identified. Administration of the 11-mix promotes activation of intestinal dendritic cells and stimulation of interferon-gamma producing CD8 T cells is dependent on the transcription factor BATF3. Comparative gene pathway analysis revealed several of the strains of the 11-mix are related to strains associated with favorable clinical response in metastatic melanoma patients treated with immunotherapy. Administration of the "11-mix" cocktail with anti-CTLA4 enhanced anti-tumor activity and survival in the MC38 tumor model. The 11-mix" cocktail also enhanced the anti-tumor activity of anti-PD1 in the MC38 and B-raf Pten melanoma tumor models. The "11-mix" cocktail alone was sufficient to enhance the level of tumor-infiltrating CD8 T cells in the MC38 model to a level comparable to anti-PD1 alone, however the combination of the "11-mix" cocktail and anti-PD1 antibody promoted the highest level of tumor infiltrating CD8 T cells in the MC38 model as well as in the more aggressive B-raf Pten model. The "11-mix" cocktail administration promoted enhanced accumulation of interferon-gamma producing CD8 T cells in the spleens of tumor-bearing mice indicating the consortium promotes systemic cellular immune cell activation. A rationally-designed consortium of human gut-derived commensals induced CD8 T cells in vivo and potentiated anti-cancer immunity when administered with checkpoint inhibitors. Given the consortium can be produced via cGMP manufacturing and administered orally on a repeated basis, the "11-mix" cocktail constitutes a safe agent for alteration of the microbiome of cancer patients to enhance anti-cancer immunity.

Kits

The present disclosure also provides kits for use in evaluating the immune system activation, for example based on the degree or level of IFN production in splenocytes, involving administering to a subject any of the compositions as described herein. In some embodiments, a sample may be obtained from the subject prior to, during, and/or after administration of any of the compositions described herein.

In some embodiments, the kit contains one or more molecules for detecting and/or measuring the amount of IFN production in a sample. In some embodiments, the molecule that detects or measures the amount of IFN production can comprise one or more binding agents that specifically bind to IFN. In some embodiments, the binding agent is an antibody that specifically binds to IFN. In some embodiments, the binding agent is part of a reporter system, such as a receptor on a cell that binds to the IFN and induces expression of a gene encoding a reporter molecule. In some embodiments, the kit also contains a standard or control sample to which the amount of IFN in the sample(s) obtained from the subject may be compared.

In some embodiments, the kit may be for carrying out any of the companion diagnostic methods described herein.

In some embodiments, the kit contains one or more molecules for detecting and/or measuring the amount or presence of any one of the bacterial species described herein, or component thereof. In some embodiments, the molecule that detects or measures the amount of a bacterial strain can comprise one or more binding agents that specifically bind to the bacterial strain. In some embodiments, the binding agent specifically binds to a feature of one or more bacterial species that identifies the bacterial species. In some embodiments, the binding agent is a nucleic acid that specifically binds to a nucleic acid sequence of one or more of the bacterial species described herein, such as a specific 16S rRNA sequence. In some embodiments, the kit also contains a standard or control sample to which the sample(s) obtained from the subject may be compared.

The present disclosure also provides kits for use in determining a treatment method, for example, a tumor therapy, involving analyzing the expression of a marker (e.g., CD44, CD8, IFN, GzmB, gp70 MC38 peptide (KSPWFTTL (SEQ ID NO:53))-specific T TCR, or an antigen-derived ligand-specific TCR), prior to, during, and/or after administration of any of the compositions described herein. Also provided herein are kits comprising companion diagnostics for tumor therapy with an immune checkpoint inhibitor (e.g., a PD-1 inhibitor).

In some embodiments, the kit includes one or more components for analyzing or monitoring expression levels of a marker, such as CD44, CD8, IFN, GzmB, or a tumor antigen-derived ligand-specific TCR. In some embodiments, the marker is analyzed by detecting the presence of the marker, by measuring the level (amount) of the marker, and/or a specific cell type on which the marker is presented. In some embodiments, the molecule that detects or measures the amount of the marker can comprise one or more binding agents that specifically bind to the marker. In some embodiments, the binding agent is an antibody that specifically binds to the marker. In some embodiments, the binding agent is an MHC multimer that specifically binds to the marker.

In some embodiments, the marker is analyzed by detecting the presence of a nucleic acid encoding the marker, by measuring the level (amount) of a nucleic acid encoding the marker, and/or a specific cell type in which the nucleic acid encoding the marker is expressed. In some embodiments, the kit includes one or more reagents for the isolation of nucleic acids (e.g., RNA) from a sample obtained from subject.

In some embodiments, the kits further comprise a detection agent (e.g., an antibody binding to the binding agent ) for detecting binding of the agent to the target (e.g., IFN, bacterial species) in the sample. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In some embodiments, the kits further comprise one or more nucleic acid sequences that allow for the detection of the bacterial strains. In some embodiments, the nucleic acid sequences are primers for qPCR. In some embodiments, the primers include one or more sequences selected from SEQ ID NOs: 16-26, and 38-48.

In some embodiments, the kit may further include one or more therapeutics and/or compositions for administering to the subject. For example, in some embodiments, the kit may include one or more immune checkpoint inhibitor (e.g., PD-1 inhibitor, PD-L1 inhibitor, CTLA-4 inhibitor). In some embodiments, the kit may include a composition comprising one or more of the bacterial strains described herein.

In some embodiments, the kits may be for screening bacteria or substances derived from bacteria, for example of activation of CD8+ IFN-producing T cells. In some embodiments, the kits include cells, such as cells of a cell line. In some embodiments, the cells are intestinal epithelial cells, peripheral blood mononuclear cells.

In some embodiments, the kit or device further includes a support member. In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e g., 24-, 48-, 96-, 384- or greater well plates, may be used for high throughput detection assays.

In the kit or detecting device, one or more of the binding agents may be immobilized on a support member, which can be a membrane, a bead, a slide, or a multi-well plate. Selection of an appropriate support member for the immunoassay will depend on various factor such as the number of samples and method of detecting the signal released from label conjugated to the second agent.

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of immune system activation, selecting a treatment, and/or diagnostic purposes. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like.

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Table 1 below provides sequence identifier numbers (SEQ ID NOs) used in the compositions of the experiments disclosed herein. The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

Strains and species with highest homology

| Strain # | SEQ ID NO | Strain ID | Species with highest homology | NCBI accession # of 165 locus | SEQ ID of NCBI 165 locus |
|---|---|---|---|---|---|
| 1 | 1 | 265 | *Phascolarctobacterium faecium* | LN998073 | 27 |
| 2 | 2 | 1A6 | *Fusobacterium ulcerans* | KR822463 | 28 |
| 3 | 3 | 1811 | *Bacteroides dorei* | CP011531 | |
| 4 | 4 | 261 | *Bacteroides uniformis* | N8112945 | 30 |
| 5 | 5 | 281 | *Subdoligranulum* sp. | KM098109 | 31 |
| 6 | 6 | 2A6 | *Paraprevoteila xyfaniphila* | N8113078 | 32 |
| 7 | 7 | 2F11 | *Parabacteroides johnsonii* | NR041464 | 33 |
| 8 | 8 | 1E7 | *Alistipes* sp. | LT223566 | 34 |
| 9 | 9 | 1H9 | *Parabacteroides gorcionii* | INR112835 | 35 |
| 10 | 10 | 1C1 | *Eubacterium limosurn* | N8113248 | 36 |
| 11 | 11 | 269 | *Parabacteroides distasonis* | NR041342 | 37 |

The nucleic acid sequences of the 16S rDNA, or portion thereof, for the bacterial strains described herein are provided below:

strain 1 2G5_*Phascolarctobacterium faecium*_LN998073

SEQ ID NO: 1

GAC-

GAACGCTGGCGGCGTGCCTAACACATGCAAGTCGAACGGAGAATTTTATT

TCGGTAGAATTCTTAGTGGCGAACGGGTGAGTAACGCGTAGGCAACCTAC

CCTTTAGACGGGGACAACATTCCGAAAGGAGTGCTAATACCGGATGTGAT

CATCTTGCCGCATGGCAGGATGAAGAAAGATGGCCTCTACAAGTAAGCTA

TCGCTAAAGGATGGGCCTGCGTCTGATTAGCTAGTTGGTAGTGTAACGGA

CTACCAAGGCGATGATCAGTAGCCGGTCTGAGAGGATGAACGGCCACATT

GGGACTGAGACACGGCCCAAACTCCTACGGGAGGCAGCAGTGGGGAATCT

TCCGCAATGGACGAAAGTCTGACGGAGCAACGCCGCGTGAGTGATGAAGG

ATTTCGGTCTGTAAAGCTCTGTTGTTTATGACGAACGTGCAGTGTGTGAA

CAATGCATTGCAATGACGGTAGTAAACGAGGAAGCCACGGCTAACTACGT

GCCAGCAGCCGCGGTAATACGTAGGTGGCGAGCGTTGTCCGGAATTATTG

GGCGTAAAGAGCATGTAGGCGGCTTAATAAGTCGAGCGTGAAAATGCGGG

GCTCAACCCCGTATGGCGCTGGAAACTGTTAGGCTTGAGTGCAGGAGAGG

AAAGGGGAATTCCCAGTGTAGCGGTGAAATGCGTAGATATTGGGAGGAAC

ACCAGTGGCGAAGGCGCCTTTCTGGACTGTGTCTGACGCTGAGATGCGAA

AGCCAGGGTAGCGAACGGGATTAGATACCCCGGTAGTCCTGGCCGTAAAC

GATGGGTACTAGGTGTAGGAGGTATCGACCCCTTCTGTGCCGGAGTTAAC

GCAATAAGTACCCCGCCTGGGGAGTACGGCCGCAAGGTTGAAACTCAAAG

GAATTGACGGGGGCCCGCACAAGCGGTGGAGTATGTGGTTTAATTCGACG

CAACGCGAAGAACCTTACCAAGGCTTGACATTGATTGAACGCTCTAGAGA

TAGAGATTTCCCTTCGGGGACAAGAAAACAGGTGGTGCATGGCTGTCGTC

AGCTCGTGTCGTGAGATGTTGGGTTAAGTCCCGCAACGAGCGCAACCCCT

ATCCTATGTTACCAGCAAGTAAAGTTGGGGACTCATGGAGACTGCCAGG

GACAACCTGGAGGAAGGCGGGGATGACGTCAAGTCATCATGCCCCTTATG

TCTTGGGCTACACACGTACTACAATGGTCGGAAACAGAGGGAAGCGAAGC

CGCGAGGCAGAGCAAACCCCAGAAACCCGATCTCAGTTCGGATCGCAGGC

TGCAACCCGCCTGCGTGAAGTCGGAATCGCTAGTAATCGCAGGTCAGCAT

ACTGCGGTGAATACGTTCCCGGGCCTTGTACACACCGCCCGTCACACCAC

GAAAGTTGGTAACACCCGAAGCCGGTGAGGTAACCTA strain 2 1A6_*Fusobacterium ulcerans*_KR822463

SEQ ID NO: 2

GATGAACGCT-

GACAGAATGCTTAACACATGCAAGTCTACTTGATCCTTCGGGTGAAGGTG

GCGGACGGGTGAGTAACGCGTAAAGAACTTGCCTTACAGACTGGGACAAC

ATTTGGAAACGAATGCTAATACCGGATATTATGATTGGGTCGCATGATCT

GATTATGAAAGCTATATGCGCTGTGAGAGAGCTTTGCGTCCCATTAGTTA

GTTGGTGAGGTAACGGCTCACCAAGACGATGATGGGTAGCCGGCCTGAGA

-continued

GGGTGAACGGCCACAAGGGGACTGAGACACGGCCCTTACTCCTACGGGAG

GCAGCAGTGGGGAATATTGGACAATGGACCAAAAGTCTGATCCAGCAATT

CTGTGTGCACGAAGAAGTTTTTCGGAATGTAAAGTGCTTTCAGTTGGGAA

GAAGTCAGTGACGGTACCAACAGAAGAAGCGACGGCTAAATACGTGCCAG

CAGCCGCGGTAATACGTATGTCGCAAGCGTTATCCGGATTTATTGGGCGT

AAAGCGCGTCTAGGCGGCTTAGTAAGTCTGATGTGAAAATGCGGGGCTCA

ACCCCGTATTGCGTTGGAAACTGCTAAACTAGAGTACTGGAGAGGTAGGC

GGAACTACAAGTGTAGAGGTGAAATTCGTAGATATTTGTAGGAATGCCGA

TGGGGAAGCCAGCCTACTGGACAGATACTGACGCTAAAGCGCGAAAGCGT

GGGTAGCAAACAGGATTAGATACCCTGGTAGTCCACGCCGTAAACGATGA

TTACTAGGTGTTGGGGGTCGAACCTCAGCGCCCAAGCTAACGCGATAAGT

AATCCGCCTGGGGAGTACGTACGCAAGTATGAAACTCAAAGGAATTGACG

GGGACCCGCACAAGCGGTGGAGCATGTGGTTTAATTCGACGCAACGCGAG

GAACCTTACCAGCGTTTGACATCCCAAGAAGTTAACAGAGATGTTTTCGT

GCCTCTTCGGAGGAACTTGGTGACAGGTGGTGCATGGCTGTCGTCAGCTC

GTGTCGTGAGATGTTGGGTTAAGTCCCGCAACGAGCGCAACCCCTTTCGT

ATGTTACCATCATTAAGTTGGGGACTCATGCGAGACTGCCTGCGATGAGC

AGGAGGAAGGTGGGGATGACGTCAAGTCATCATGCCCCTTATACGCTGGG

CTACACACGTGCTACAATGGGTAGTACAGAGAGCTGCAAACCTGCGAGGG

TAAGCTAATCTCATAAAACTATTCTTAGTTCGGATTGTACTCTGCAACTC

GAGTACATGAAGTTGGAATCGCTAGTAATCGCAAATCAGCTATGTTGCGG

TGAATACGTTCTCGGGTCTTGTACACACCGCCCGTCACACCACGAGAGTT

GGTTGCACCTGAAGTAACAGGCCTAACCGTAA strain 3 1B11_*Bacteroides dorei*_CP011531

SEQ ID NO: 3

AGTTTGNNNTATGGCTCAGGATGAACGCTAGCTACAGGCTTAACACATGC

AAGTCGAGGGGCAGCATGGTCTTAGCTTGCTAAGGCTGATGGCGACCGGC

GCACGGGTGAGTAACACGTATCCAACCTGCCGTCTACTCTTGGCCAGCCT

TCTGAAAGGAAGATTAATCCAGGATGGGATCATGAGTTCACATGTCCGCA

TGATTAAAGGTATTTTCCGGTAGACGATGGGGATGCGTTCCATTAGATAG

TAGGCGGGGTAACGGCCCACCTAGTCAACGATGGATAGGGGTTCTGAGAG

GAAGGTCCCCCACATTGGAACTGAGACACGGTCCAAACTCCTACGGGAGG

CAGCAGTGAGGAATATTGGTCAATGGGCGATGGCCTGAACCAGCCAAGTA

GCGTGAAGGATGACTGCCCTATGGGTTGTAAACTTCTTTTATAAAGGAAT

AAAGTCGGGTATGCATACCCGTTTGCATGTACTTTATGAATAAGGATCGG

CTAACTCCGTGCCAGCAGCCGCGGTAATACGGAGGATCCGAGCGTTATCC

GGATTTATTGGGTTTAAAGGGAGCGTAGATGGATGTTTAAGTCAGTTGTG

AAAGTTTGCGGCTCAACCGTAAAATTGCAGTTGATACTGGATGTCTTGAG

TGCAGTTGAGGCAGGCGGAATTCGTGGTGTAGCGGTGAAATGCTTAGATA

TCACGAAGAACTCCGATTGCGAAGGCAGCCTGCTAAGCTGCAACTGACAT

TGAGGCTCGAAAGTGTGGGTATCAAACAGGATTAGATACCCTGGTAGTCC

-continued

ACACGGTAAACGATGAATACTCGCTGTTTGCGATATACGGCAAGCGGCCA

AGCGAAAGCGTTAAGTATTCCACCTGGGGAGTACGCCGGCAACGGTGAAA

CTCAAAGGAATTGACGGGGGCCCGCACAAGCGGAGGAACATGTGGTTTAA

TTCGATGATACGCGAGGAACCTTACCCGGGCTTAAATTGCACTCGAATGA

TCCGGAAACGGTTCAGCTAGCAATAGCGAGTGTGAAGGTGCTGCATGGTT

GTCGTCAGCTCGTGCCGTGAGGTGTCGGCTTAAGTGCCATAACGAGCGCA

ACCCTTGTTGTCAGTTACTAACAGGTGATGCTGAGGACTCTGACAAGACT

GCCATCGTAAGATGTGAGGAAGGTGGGGATGACGTCAAATCAGCACGGCC

CTTACGTCCGGGGCTACACACGTGTTACAATGGGGGGTACAGAGGGCCGC

TACCACGCGAGTGGATGCCAATCCCTAAAACCCCTCTCAGTTCGGACTGG

AGTCTGCAACCCGACTCCACGAAGCTGGATTCGCTAGTAATCGCGCATCA

GCCACGGCGCGGTGAATACGTTCCCGGGCCTTGTACACACCGCCCGTCAA

GCCATGGGAGCCGGGGGTACCTGAAGTGCGTAACCGCGAGGAT strain 4 2G1_*Bacteroides uniformis*_NR_112945

SEQ ID NO: 4

GATGAACGC-

TAGCTACAGGCTTAACACATGCAAGTCGAGGGGCAGCATGAACTTAGCTT

GCTAAGTTTGATGGCGACCGGCGCACGGGTGAGTAACACGTATCCAACCT

GCCGATGACTCGGGGATAGCCTTTCGAAAGAAAGATTAATACCCGATGGC

ATAGTTCTTCCGCATGGTAGAACTATTAAAGAATTTCGGTCATCGATGGG

GATGCGTTCCATTAGGTTGTTGGCGGGGTAACGGCCCACCAAGCCTTCGA

TGGATAGGGGTTCTGAGAGGAAGGTCCCCCACATTGGAACTGAGACACGG

TCCAAACTCCTACGGGAGGCAGCAGTGAGGAATATTGGTCAATGGACGAG

AGTCTGAACCAGCCAAGTAGCGTGAAGGATGACTGCCCTATGGGTTGTAA

ACTTCTTTTATACGGGAATAAAGTGAGGCACGTGTGCCTTTTTGTATGTA

CCGTATGAATAAGGATCGGCTAACTCCGTGCCAGCAGCCGCGGTAATACG

GAGGATCCGAGCGTTATCCGGATTTATTGGGTTTAAAGGGAGCGTAGGCG

GACGCTTAAGTCAGTTGTGAAAGTTTGCGGCTCAACCGTAAAATTGCAGT

TGATACTGGGTGTCTTGAGTACAGTAGAGGCAGGCGGAATTCGTGGTGTA

GCGGTGAAATGCTTAGATATCACGAAGAACTCCGATTGCGAAGGCAGCCT

GCTGGACTGTAACTGACGCTGATGCTCGAAAGTGTGGGTATCAAACAGGA

TTAGATACCCTGGTAGTCCACACCAGTAAACGATGAATACTCGCTGTTTG

CGATATACAGTAAGCGGCCAAGCGAAAGCGTTAAGTATTCCACCTGGGGA

GTACGCCGGCAACGGTGAAACTCAAAGGAATTGACGGGGGCCCGCACAAG

CGGAGGAACATGTGGTTTAATTCGATGATACGCGAGGAACCTTACCCGGG

CTTGAATTGCAACTGAATGATGTGGAGACATGTCAGCCGCAAGGCAGTTG

TGAAGGTGCTGCATGGTTGTCGTCAGCTCGTGCCGTGAGGTGTCGGCTTA

AGTGCCATAACGAGCGCAACCCTTATCGATAGTTACCATCAGGTGATGCT

GGGGACTCTGTCGAGACTGCCGTCGTAAGATGTGAGGAAGGTGGGGATGA

CGTCAAATCAGCACGGCCCTTACGTCCGGGGCTACACACGTGTTACAATG

GGGGGTACAGAAGGCAGCTACACGGCGACGTGATGCTAATCCCGAAAGCC

TCTCTCAGTTCGGATTGGAGTCTGCAACCCGACTCCATGAAGCTGGATTC

-continued

GCTAGTAATCGCGCATCAGCCACGGCGCGGTGAATACGTTCCCGGGCCTT

GTACACACCGCCCGTCAAGCCATGAAAGCCGGGGGTACCTGAAGTGCGTA

ACCGCAAGGAG strain 5 2B1_*Subdoligranulum* sp. 4_3_54A2FAA_NZ-ACWW00000000

SEQ ID NO: 5

GACGAACGCTG-

GCGGCGCGCCTAACACATGCAAGTCGAACGGAGCTGTTTTCTCTGAAGTT

TTCGGATGGAAGAGAGTTCAGCTTAGTGGCGAACGGGTGAGTAACACGTG

AGCAACCTGCCTTTCAGTGGGGGACAACATTTGGAAACGAATGCTAATAC

CGCATAAGACCACAGTGTCGCATGGCACAGGGGTCAAAGGATTTATCCGC

TGAAAGATGGGCTCGCGTCCGATTAGCTAGATGGTGAGGTAACGGCCCAC

CATGGCGACGATCGGTAGCCGGACTGAGAGGTTGAACGGCCACATTGGGA

CTGAGACACGGCCCAGACTCCTACGGGAGGCAGCAGTGGGGAATATTGCA

CAATGGGGGAAACCCTGATGCAGCGACGCCGCGTGGAGGAAGAAGGTCTT

CGGATTGTAAACTCCTGTCCCAGGGGACGATAATGACGGTACCCTGGGAG

GAAGCACCGGCTAACTACGTGCCAGCAGCCGCGGTAAAACGTAGGGTGCA

AGCGTTGTCCGGAATTACTGGGTGTAAAGGGAGCGCAGGCGGATTGGCAA

GTTGGGAGTGAAATCTATGGGCTCAACCCATAAATTGCTTTCAAAACTGT

CAGTCTTGAGTGGTGTAGAGGTAGGCGGAATTCCCGGTGTAGCGGTGGAA

TGCGTAGATATCGGGAGGAACACCAGTGGCGAAGGCGGCCTACTGGGCAC

TAACTGACGCTGAGGCTCGAAAGCATGGGTAGCAAACAGGATTAGATACC

CTGGTAGTCCATGCCGTAAACGATGATTACTAGGTGTGGGAGGATTGACC

CCTTCCGTGCCGCAGTTAACACAATAAGTAATCCACCTGGGGAGTACGAC

CGCAAGGTTGAAACTCAAAGGAATTGACGGGGGCCCGCACAAGCAGTGGA

GTATGTGGTTTAATTCGAAGCAACGCGAAGAACCTTACCAGGTCTTGACA

TCGGATGCATACCTAAGAGATTAGGGAAGTCCTTCGGGACATCCAGACAG

GTGGTGCATGGTTGTCGTCAGCTCGTGTCGTGAGATGTTGGGTTAAGTCC

CGCAACGAGCGCAACCCTTATCGTTAGTTACTACGCAAGAGGACTCTAGC

GAGACTGCCGTTGACAAAACGGAGGAAGGTGGGGATGACGTCAAATCATC

ATGCCCTTTATGACCTGGGCTACACACGTACTACAATGGCTATTAACAGA

GAGAAGCGATACCGCGAGGTGGAGCAAACCTCACAAAAATAGTCTCAGTT

CGGATCGCAGGCTGCAACCCGCCTGCGTGAAGCCGGAATTGCTAGTAATC

GCGGATCAGCATGCCGCGGTGAATACGTTCCCGGGCCTTGTACACACCGC

CCGTCACACCATGAGAGCCGGGGGGACCCGAAGTCGGTAGTCTAACCGC strain 6 2A6_*Paraprevotella xylaniphila*_AB331897

SEQ ID NO: 6

GATGAACGC-

TAGCTACAGGCTTAACACATGCAAGTCGAGGGGCAGCATGAACTTAGCTT

GCTAAGTTTGATGGCGACCGGCGCACGGGTGAGTAACGCGTATCCAACCT

GCCCTTTACCCGGGGATAGCCTTCTGAAAAGGAAGTTTAATACCCGATGA

ATTCGTTTAGTCGCATGGCTNGATGAATAAAGATTAATTGGTAAAGGATG

GGGATGCGTCCCATTAGCTTGTTGGCGGGGTAACGGCCCACCAAGGCGAC

-continued

GATGGGTAGGGGTTCTGAGAGGAAGGTCCCCCACATTGGAACTGAGACAC
GGTCCAAACTCCTACGGGAGGCAGCAGTGAGGAATATTGGTCAATGGGCG
CGAGCCTGAACCAGCCAAGTAGCGTGGAGGACGACGGCCCTACGGGTTGT
AAACTCCTTTTATAAGGGGATAAAGTTGGCCATGTATGGCCATTTGCAGG
TACCTTATGAATAAGCATCGGCTAATTCCGTGCCAGCAGCCGCGGTAATA
CGGAAGATGCGAGCGTTATCCGGATTTATTGGGTTTAAAGGGAGCGTAGG
CGGGCTGTCAAGTCAGCGGTCAAATGGCGCGGCTCAACCGCGTTCCGCCG
TTGAAACTGGCAGCCTTGAGTATGCACAGGGTACATGGAATTCGTGGTGT
AGCGGTGAAATGCTTAGATATCACGAGGAACTCCGATCGCGCAGGCATTG
TACCGGGGCATTACTGACGCTGAGGCTCGAAGGTGCGGGTATCAAACAGG
ATTAGATACCCTGGTAGTCCGCACAGTAAACGATGAATGCCCGCTGTCGG
CGACATAGTGTCGGCGGCCAAGCGAAAGCGTTAAGCATTCCACCTGGGGA
GTACGCCGGCAACGGTGAAACTCAAAGGAATTGACGGGGGCCCGCACAAG
CGGAGGAACATGTGGTTTAATTCGATGATACGCGAGGAACCTTACCCGGG
CTTGAATCGCAGGTGCATGGGCCGGAGACGGCCCTTTCCTTCGGGACTCC
TGCGAAGGTGCTGCATGGTTGTCGTCAGCTCGTGCCGTGAGGTGTCGGCT
TAAGTGCCATAACGAGCGCAACCCCCTCCCCAGTTGCCACCGGGTAATG
CCGGGCACTTTGGGGACACTGCCACCGCAAGGTGCGAGGAAGGTGGGGAT
GACGTCAAATCAGCACGGCCCTTACGTCCGGGGCGACACACGTGTTACAA
TGGGGGGTACAGAGGGCCGCTGCCCGGTGACGGTTGGCCAATCCCTAAAA
CCCCTCTCAGTTCGGACTGGAGTCTGCAACCCGACTCCACGAAGCTGGAT
TCGCTAGTAATCGCGCATCAGCCATGGCGCGGTGAATACGTTCCCGGGCC
TTGTACACACCGCCCGTCAAGCCATGAAAGCCGGGGGTGCCTGAAGTCCG
TNNCCGCGA strain 7 2F11_*Parabacteroides johnsonii*_AB261128
SEQ ID NO: 7

GATGAACGC-
TAGCGACAGGCTTAACACATGCAAGTCGAGGGGCAGCATGGTAAGTAGCA
ATACTTATTGATGGCGACCGGCGCACGGGTGAGTAACGCGTATGCAACTT
ACCTATCAGAGGGGGATAGCCCGGCGAAAGTCGGATTAATACTCCATAAA
ACAGGGGTTCCGCATGGGACTATTTGTTAAAGATTCATCGCTGATAGATA
GGCATGCGTTCCATTAGGCAGTTGGCGGGGTAACGGCCCACCAAACCGAC
GATGGATAGGGGTTCTGAGAGGAAGGTCCCCCACATTGGTACTGAGACAC
GGACCAAACTCCTACGGGAGGCAGCAGTGAGGAATATTGGTCAATGGCCG
AGAGGCTGAACCAGCCAAGTCGCGTGAAGGATGAAGGATCTATGGTTTGT
AAACTTCTTTTATAGGGGAATAAAGTGTGGGACGTGTTCCATTTTGTATG
TACCCTATGAATAAGCATCGGCTAACTCCGTGCCAGCAGCCGCGGTAATA
CGGAGGATGCGAGCGTTATCCGGATTTATTGGGTTTAAAGGGTGCGTAGG
TGGTAATTTAAGTCAGCGGTGAAAGTTTGTGGCTCAACCATAAAATTGCC
GTTGAAACTGGGTTACTTGAGTGTGTTTGAGGTAGGCGGAATGCGTGGTG
TAGCGGTGAAATGCATAGATATCACGCAGAACTCCAATTGCGAAGGCAGC

-continued

TTACTAAACCATAACTGACACTGAAGCACGAAAGCGTGGGTATCAAACAG
GATTAGATACCCTGGTAGTCCACGCAGTAAACGATGATTACTAGGAGTTT
GCGATACACAGTAAGCTCTACAGCGAAAGCGTTAAGTAATCCACCTGGGG
AGTACGCCGGCAACGGTGAAACTCAAAGGAATTGACGGGGGCCCGCACAA
GCGGAGGAACATGTGGTTTAATTCGATGATACGCGAGGAACCTTACCCGG
GTTTGAACGTAGTCAGACCGACCTTGAAAGAGGTTTTCTAGCAATAGCTG
ATTACGAGGTGCTGCATGGTTGTCGTCAGCTCGTGCCGTGAGGTGTCGGC
TTAAGTGCCATAACGAGCGCAACCCTTATCACTAGTTACTAACAGGTTAA
GCTGAGGACTCTGGTGAGACTGCCAGCGTAAGCTGTGAGGAAGGTGGGGA
TGACGTCAAATCAGCACGGCCCTTACATCCGGGGCGACACACGTGTTACA
ATGGCATGGACAAAGGGCAGCTACCTGGCGACAGGATGCTAATCTCTAAA
CCATGTCTCAGTTCGGATCGGAGTCTGCAACTCGACTCCGTGAAGCTGGA
TTCGCTAGTAATCGCGCATCAGCCATGGCGCGGTGAATACGTTCCCGGGC
CTTGTACACACCGCCCGTCAAGCCATGGGAGCCGGGGGTACCTGAAGTCC
GTAACCGCAA strain 8 1E7_*Alistipes* sp. JC136_NZ-CAEG00000000
SEQ ID NO: 8

GATGAACGC-
TAGCGGCAGGCCTAACACATGCAAGTCGAGGGGCAGCGGGATTGAAGCTT
GCTTCAGTTGCCGGCGACCGGCGCACGGGTGCGTAACGCGTATGCAACCT
ACCCATAACAGGGGGATAACACTGAGAAATCGGTACTAATATCCCATAAC
ATCAAGAGGGGCATCCCTTTTGGTTGAAAACTCCGGTGGTTATGGATGGG
CATGCGTTGTATTAGCTAGTTGGTGAGGTAACGGCTCACCAAGGCGACGA
TACATAGGGGGACTGAGAGGTTAACCCCCCACATTGGTACTGAGACACGG
ACCAAACTCCTACGGGAGGCAGCAGTGAGGAATATTGGTCAATGGACGCA
AGTCTGAACCAGCCATGCCGCGTGCAGGATGACGGCTCTATGAGTTGTAA
ACTGCTTTTGTACGAGGGTAAACCCGGATACGTGTATCCGGCTGAAAGTA
TCGTACGAATAAGGATCGGCTAACTCCGTGCCAGCAGCCGCGGTAATACG
GAGGATTCAAGCGTTATCCGGATTTATTGGGTTTAAAGGGTGCGTAGGCG
GTTTGATAAGTTAGAGGTGAAATACCGGTGCTTAACACCGGAACTGCCTC
TAATACTGTTGAGCTAGAGAGTAGTTGCGGTAGGCGGAATGTATGGTGTA
GCGGTGAAATGCTTAGAGATCATACAGAACACCGATTGCNGAAGGCAGCT
TACCAAACTATATCTGACGTTNGAGGCACGAAAGCGTGGGGGAGCAAACA
GGATTAGATACCCTGGTAGTCCACGCAGTAAACGATGATAACTCGCTGTC
GGCGATACACAGTCGGTGGCTAAGCGAAAGCGATAAGTTATCCACCTGGG
GAGTACGTTCGCAAGAATGAAACTCAAAGGAATTGACGGGGGCCCGCACA
AGCGGAGGAACATGTGGTTTAATTCGATGATACGCGAGGAACCTTACCCG
GGCTTGAAAGTTACTGACGATTCTGGAAACAGGATTTCCCTTCGGGGCAG
GAAACTAGGTGCTGCATGGTTGTCGTCAGCTCGTGCCGTGAGGTGTCGGG
TTAAGTCCCATAACGAGCGCAACCCCTACCGTTAGTTGCCATCAGGTCAA
GCTGGGCACTCTGGCGGGACTGCCGGTGTAAGCCGAGAGGAAGGTGGGGA
TGACGTCAAATCAGCACGGCCCTTACGTCCGGGGCTACACACGTGTTACA

-continued

ATGGTAGGTACAGAGGGCAGCTACCCAGTGATGGGATGCGAATCTCGAAA GCCTATCTCAGTTCGGATTGGAGGCTGAAACCCGCCTCCATGAAGTTGGA TTCGCTAGTAATCGCGCATCAGCCATGGCGCGGTGAATACGTTCCCGGGC CTTGTACACACCGCCCGTCAAGCCATGGAAGCTGGGGGTGCCTGAAGTTC GTGAC strain 9 1H9_*Parabacteroides gordonii*_AB470343
SEQ ID NO: 9

GATGAACGC-
TAGCGACAGGCTTAACACATGCAAGTCGAGGGGCAGCAGGAAGTAGCAAT ACTTTGCTGGCGACCGGCGCACGGGTGAGTAACGCGTATGCAACCTACCT ATCAGAGGGGGATAACCCGGCGAAAGTCGGACTAATACCGCATAAAACAG GGGTCCCGCATGGGAATATTTGTTAAAGATTTATTGCTGATAGATGGGCA TGCGTTCCATTAGATAGTTGGTGAGGTAACGGCTCACCAAGTCTTCGATG GATAGGGGTTCTGAGAGGAAGGTCCCCCACACTGGTACTGAGACACGGAC CAGACTCCTACGGGAGGCAGCAGTGAGGAATATTGGTCAATGGGCGAGAG CCTGAACCAGCCAAGTCGCGTGAAGGATGAAGGATCTATGGTTCGTAAAC TTCTTTTATAGGGGAATAAAGTGCAGGACGTGTCCTGTTTTGTATGTACC CTATGAATAAGGATCGGCTAACTCCGTGCCAGCAGCCGCGGTAATACGGA GGATCCGAGCGTTATCCGGATTTATTGGGTTTAAAGGGTGCGTAGGTGGC TTTTTAAGTCAGCGGTGAAAGTTTGTGGCTCAACCATAAAATTGCCGTTG AAACTGGAGGGCTTGAGTATATTTGAGGTAGGCGGAATGCGTGGTGTAGC GGTGAAATGCATAGATATCACGCAGAACTCCAATTGCGAAGGCAGCTTAC TAAACTATAACTGACACTGAAGCACGAAAGCGTGGGGATCAAACAGGATT AGATACCCTGGTAGTCCACGCAGTAAACGATGATTACTAGGAGTTTGCGA TACACAGTAAGCTCTACAGCGAAAGCGTTAAGTAATCCACCTGGGGAGTA CGCCGGCAACGGTGAAACTCAAAGGAATTGACGGGGGCCCGCACAAGCGG AGGAACATGTGGTTTAATTCGATGATACGCGAGGAACCTTACCCGGGTTT GAACGTAAGTTGACCGGAGTGGAAACACTCTTTCTAGCAATAGCAATTTA CGAGGTGCTGCATGGTTGTCGTCAGCTCGTGCCGTGAGGTGTCGGCTTAA GTGCCATAACGAGCGCAACCCTTATCTTTAGTTACTAACAGGTCGAGCTG AGGACTCTAAAGAGACTGCCAGCGTAAGCTGTGAGGAAGGTGGGGATGAC GTCAAATCAGCACGGCCCTTACATCCGGGGCGACACACGTGTTACAATGG TGGGGACAAAGGGCAGCTACCTGGCGACAGGATGCTAATCTCCAAACCCC ATCTCAGTTCGGATCGAAGTCTGCAACCCGACTTCGTGAAGCTGGATTCG CTAGTAATCGCGCATCAGCCATGGCGCGGTGAATACGTTCCCGGGCCTTG TACACACCGCCCGTCAAGCCATGGGAGTTGGGGGTACCTAAAGTCCGTNA CCGCAAG strain 10 1C1_*Eubacterium limosum*_AB595134
SEQ ID NO: 10

GAC-
GAACGCTGGCGGTATGCTTAACACATGCAAGTCGAACGAGAAGGTTTTGA TGGATCCTTCGGGTGACATTAGAACTGGAAAGTGGCGAACGGGTGAGTAA

-continued

CGCGTGGGTAACCTGCCCTATGGAAAGGAATAGCCTCGGGAAACTGGGAG TAAAGCCTTATATTATGGTTTTGTCGCATGGCAAGATCATGAAAACTCCG GTGCCATAGGATGGACCCGCGTCCCATTAGCTAGTTGGTGAGATAACAGC CCACCAAGGCGACGATGGGTAACCGGTCTGAGAGGGCGAACGGTCACACT GGAACTGAGACACGGTCCAGACTCCTACGGGAGGCAGCAGTGGGGAATAT TGCGCAATGGGGGCAACCCTGACGCAGCAATACCGCGTGAGTGAAGAAGG TTTTCGGATCGTAAAGCTCTGTTATTGGGGAAGAAGAATGACGGTACCCA ATGAGGAAGTCCCGGCTAACTACGTGCCAGCAGCCGCGGTAATACGTAGG GGACAAGCGTTGTCCGGAATGACTGGGCGTAAAGGGCGCGTAGGCGGTCT ATTAAGTCTGATGTGAAAGGTACCGGCTCAACCGGTGAAGTGCATTGGAA ACTGGTAGACTTGAGTATTGGAGAGGCAAGTGGAATTCCTAGTGTAGCGG TGAAATGCGTAGATATTAGGAGGAACACCAGTGGCGAAGGCGGCTTGCTG GACAAATACTGACGCTGAGGTGCGAAAGCGTGGGGAGCGAACAGGATTAG ATACCCTGGTAGTCCACGCCGTAAACGATGAATGCTAGGTGTTGGGGAAA CTCAGTGCCGCAGTTAACACAATAAGCATTCCGCCTGGGGAGTACGACCG CAAGGTTGAAACTCAAAGGAATTGACGGGGACCCGCACAAGCAGCGGAGC ATGTGGTTTAATTCGAAGCAACGCGAAGAACCTTACCAGGTCTTGACATC CTCTGACGAGCCTAGAGATAGGAAGTTTCCTTCGGGAACAGAGAGACAGG TGGTGCATGGTTGTCGTCAGCTCGTGTCGTGAGATGTTGGGTTAAGTCCC GCAACGAGCGCAACCCCTGCCTTTAGTTGCCAGCATTAAGTTGGGCACTC TAGAGGGACTGCCGTAGACAATACGGAGGAAGGTGGGGACGACGTCAAAT CATCATGCCCCTTATGACCTGGGCTACACACGTGCTACAATGGTCTGAAC AGAGGGCCGCGAAGCCGCGAGGTGAAGCAAATCCCTTAAAACAGATCCCA GTTCGGATTGCAGGCTGCAACTCGCCTGCATGAAGTTGGAGTTGCTAGTA ATCGCGGATCAGAATGCCGCGGTGAATGCGTTCCCGGGTCTTGTACACAC CGCCCGTCACACCACGAGAGTTGGCAACACCCGAAGCCTGTGAGAGAACC GTAAGGACTCAGCAGT strain 11 2G9_*Parabacteroidesdistasonis*_HE974920
SEQ ID NO: 11

GATGAACGC-
TAGCGACAGGCTTAACACATGCAAGTCGAGGGGCAGCACAGGTAGCAATA CCGGGTGGCGACCGGCGCACGGGTGAGTAACGCGTATGCAACTTGCCTAT CAGAGGGGGATAACCCGGCGAAAGTCGGACTAATACCGCATGAAGCAGGG GCCCCGCATGGGGATATTTGCTAAAGATTCATCGCTGATAGATAGGCATG CGTTCCATTAGGCAGTTGGCGGGGTAACGGCCCACCAAACCGACGATGGA TAGGGGTTCTGAGAGGAAGGTCCCCCACATTGGTACTGAGACACGGACCA AACTCCTACGGGAGGCAGCAGTGAGGAATATTGGTCAATGGCCGAGAGGC TGAACCAGCCAAGTCGCGTGAGGGATGAAGGTTCTATGGATCGTAAACCT CTTTTATAAGGGAATAAAGTGCGGGACGTGTCCCGTTTTGTATGTACCTT ATGAATAAGGATCGGCTAACTCCGTGCCAGCAGCCGCGGTAATACGGAGG ATCCGAGCGTTATCCGGATTTATTGGGTTTAAAGGGTGCGTAGGCGGCCT

-continued

TTTAAGTCAGCGGTGAAAGTCTGTGGCTCAACCATAGAATTGCCGTTGAA

ACTGGGGGGCTTGAGTATGTTTGAGGCAGGCGGAATGCGTGGTGTAGCGG

TGAAATGCATAGATATCACGCAGAACCCCGATTGCGAAGGCAGCCTGCCA

AGCCATTACTGACGCTGATGCACGAAAGCGTGGGGATCAAACAGGATTAG

ATACCCTGGTAGTCCACGCAGTAAACGATGATCACTAGCTGTTTGCGATA

CACTGTAAGCGGCACAGCGAAAGCGTTAAGTGATCCACCTGGGGAGTACG

CCGGCAACGGTGAAACTCAAAGGAATTGACGGGGGCCCGCACAAGCGGAG

GAACATGTGGTTTAATTCGATGATACGCGAGGAACCTTACCCGGGTTTGA

ACGCATTCGGACCGAGGTGGAAACACCTTTTCTAGCAATAGCCGTTTGCG

AGGTGCTGCATGGTTGTCGTCAGCTCGTGCCGTGAGGTGTCGGCTTAAGT

GCCATAACGAGCGCAACCCTTGCCACTAGTTACTAACAGGTAAAGCTGAG

GACTCTGGTGGGACTGCCAGCGTAAGCTGCGAGGAAGGCGGGGATGACGT

CAAATCAGCACGGCCCTTACATCCGGGGCGACACACGTGTTACAATGGCG

TGGACAAAGGGAAGCCACCTGGCGACAGGGAGCGAATCCCCAAACCACGT

CTCAGTTCGGATCGGAGTCTGCAACCCGACTCCGTGAAGCTGGATTCGCT

AGTAATCGCGCATCAGCCATGGCGCGGTGAATACGTTCCCGGGCCTTGTA

CACACCGCCCGTCAAGCCATGGGAGCCNGGGGTACCTGAAGTCCGTAACC

GCGA

SEQ ID NO:27 16S RNA sequence corresponding to LN998073

SEQ ID NO:28 16S RNA sequence corresponding to KR822463

SEQ ID NO:30 16S RNA sequence corresponding to NR112945

SEQ ID NO:31 16S RNA sequence corresponding to KM098109

SEQ ID NO:32 16S RNA sequence corresponding to NR113078

SEQ ID NO:33 16S RNA sequence corresponding to NR041464

SEQ ID NO:34 16S RNA sequence corresponding to LT223566

SEQ ID NO:35 16S RNA sequence corresponding to NR112835

SEQ ID NO:36 16S RNA sequence corresponding to NR113248

SEQ ID NO:37 16S RNA sequence corresponding to NR041342

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of “including,” “comprising,” or “having,” “containing,” “involving,” and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Identification of a CD8+ T-Cell Inducing Bacterial Cocktail

Figure 2:
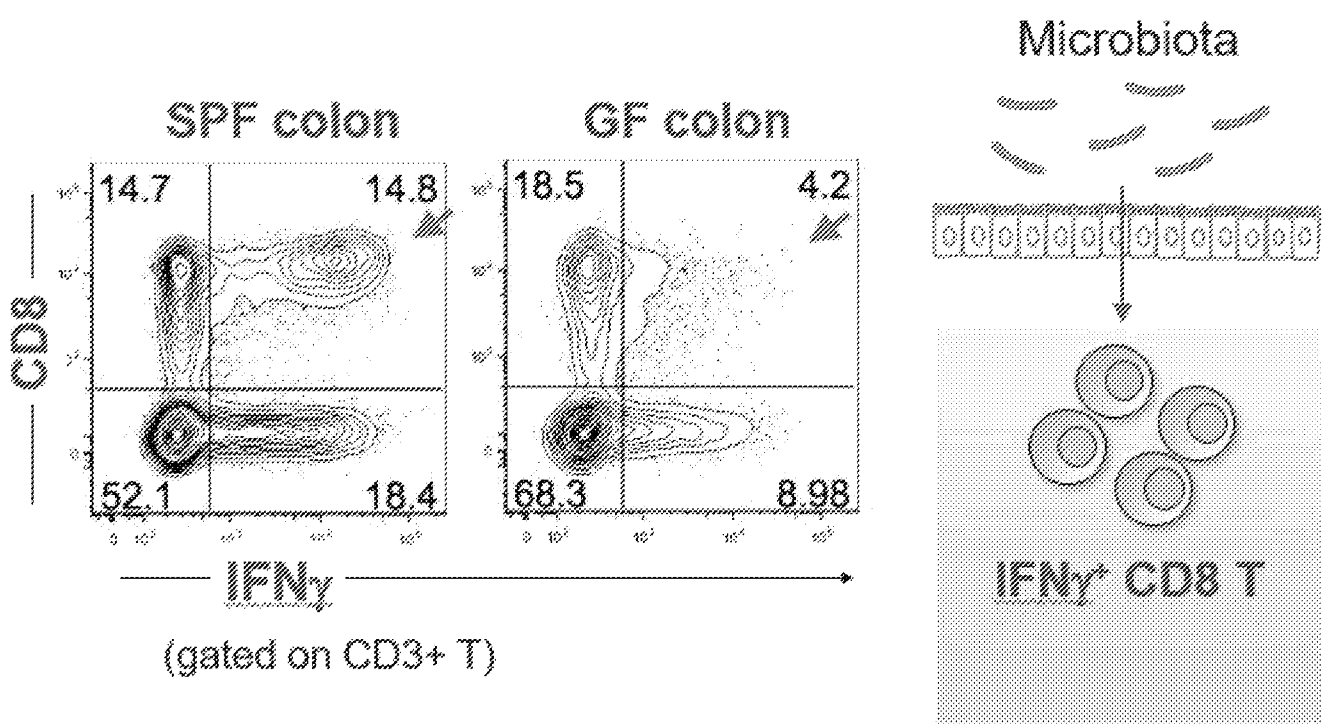
FIG. 2 shows data of experiments with lymphocytes that were isolated from colon mucosal lamina propria of SPF and germ-free (GF) mice. CD3 and IFN were stained with antibodies and analyzed by flow cytometry. The expression of CD8 and IFN by the gated CD3 positive cells is shown for representative mice.

FIG. 1 shows that IFN-gamma expressing CD8 T cells were found to be present in various organs. This population usually constitute 15% of the CD8 T cells in lymphoid and non-lymphoid organs, whereas it is more than 50% in the intestinal lamina propria. This frequency was found to be markedly decreased in the colon and small intestine of germ-free mice (FIG. 2), suggesting that the microbiota plays a role in the accumulation of IFN-+CD8+ T cells in the intestine.

Figure 3:
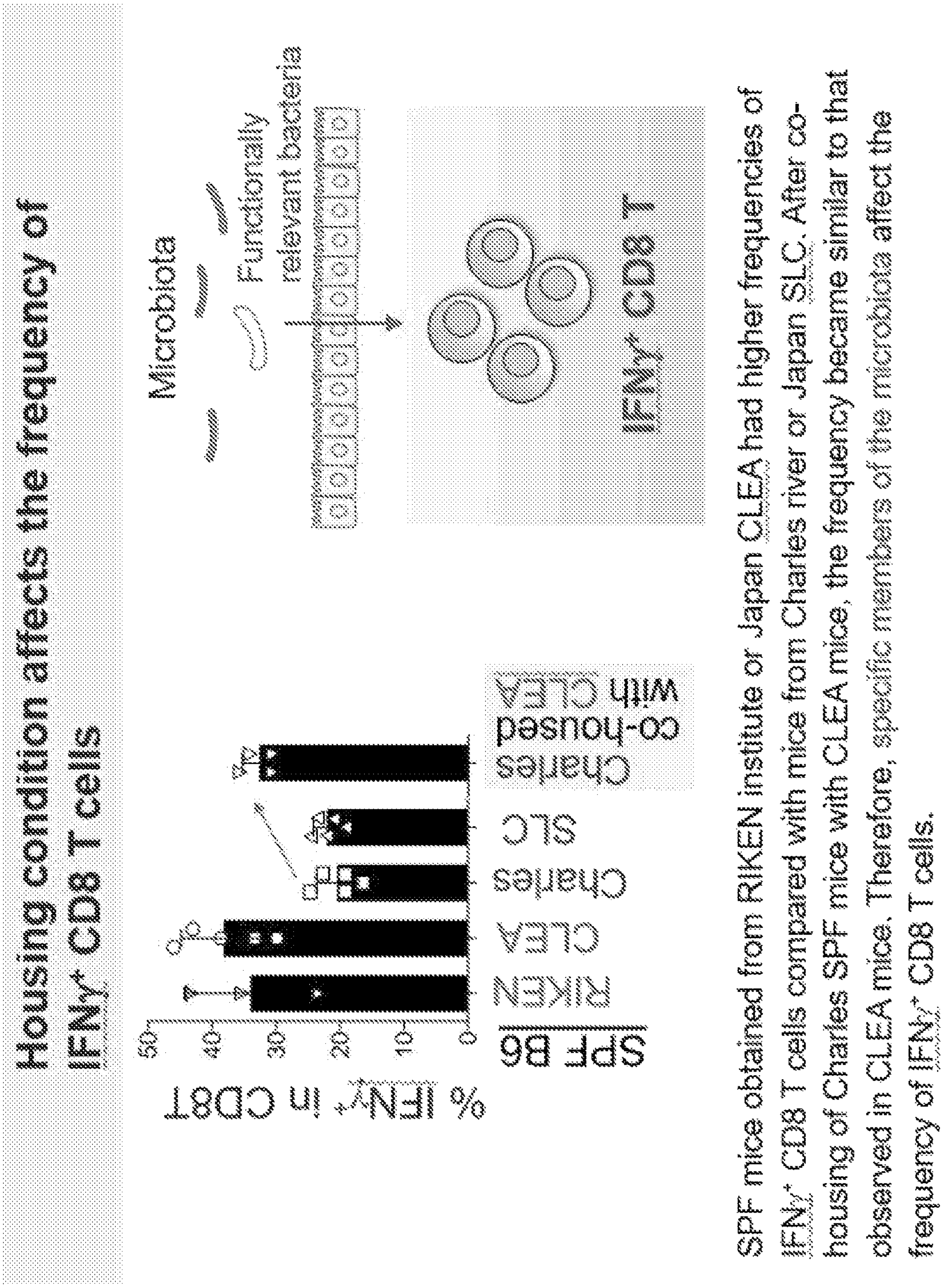
FIG. 3 shows the percentage of IFN-positive CD8 T cells in SPF mice obtained from each of the different laboratory animal facilities, indicating that the housing condition affects the frequency of IFN-positive CD8 T cells.

FIG. 3 shows that the frequency of IFN+CD8+ T-cells differed between SPF C57BL/6 mice purchased from Charles River Laboratories Inc. and Japan SLC Inc. as compared to SPF C57BL/6 mice purchased from CLEA Japan Inc. and mice bred in RIKEN. When SPF C578L/6 mice from Charles River Laboratories Inc. were co-housed together with CLEA mice in the same cage, an increase of IFN+CD8+ T-cells was observed in mice delivered from Charles River Laboratories Inc. (FIG. 3). This finding strongly supports a hypothesis that there are specific microbial species in the mouse microbiota which induce and accumulate IFN+CD8+ T cells in the intestine.

Figure 4:
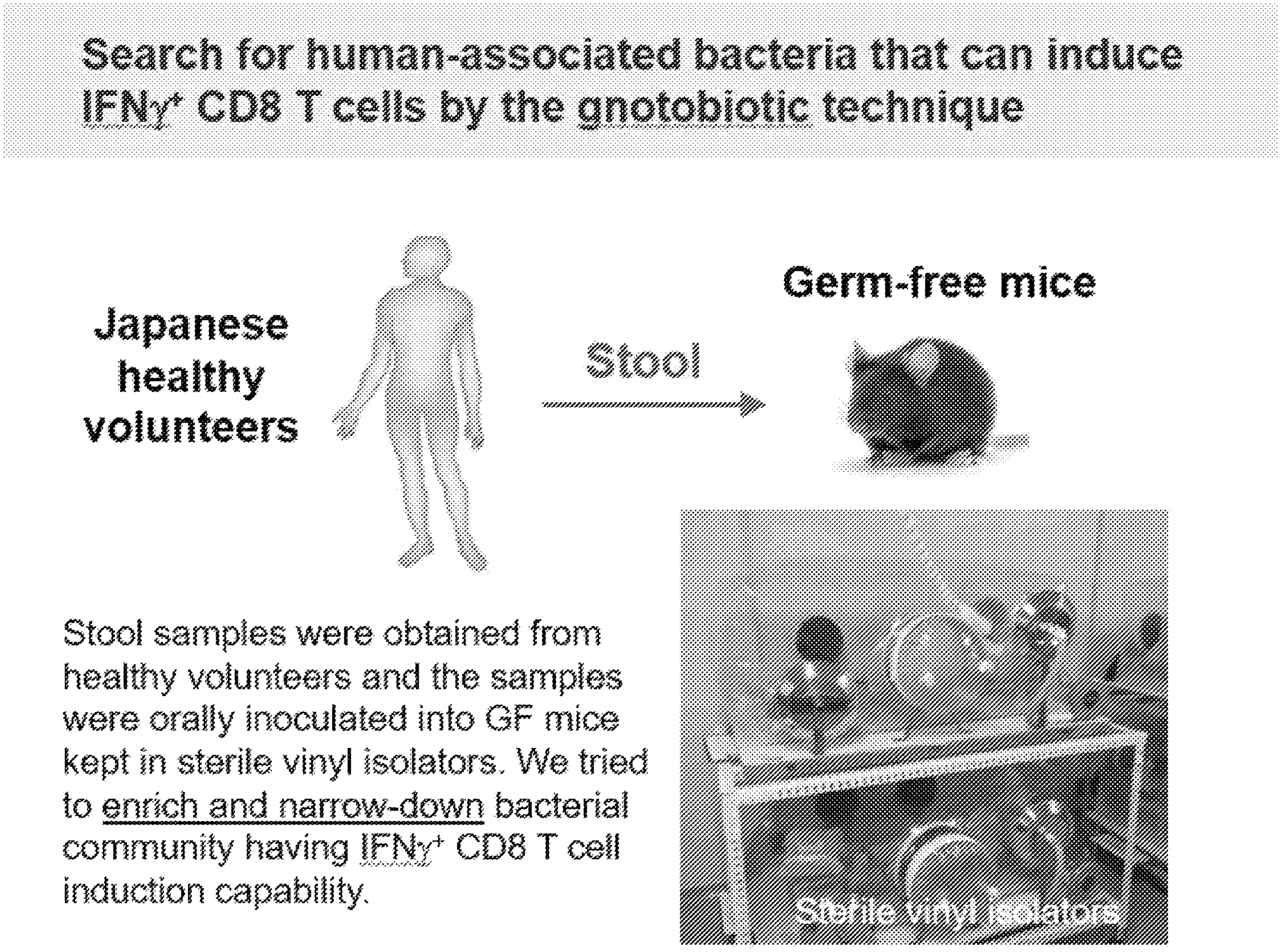
FIG. 4 shows a schematic of a process used to identify human associated bacteria that can induce IFN-positive CD8 T cells.
Figure 5:
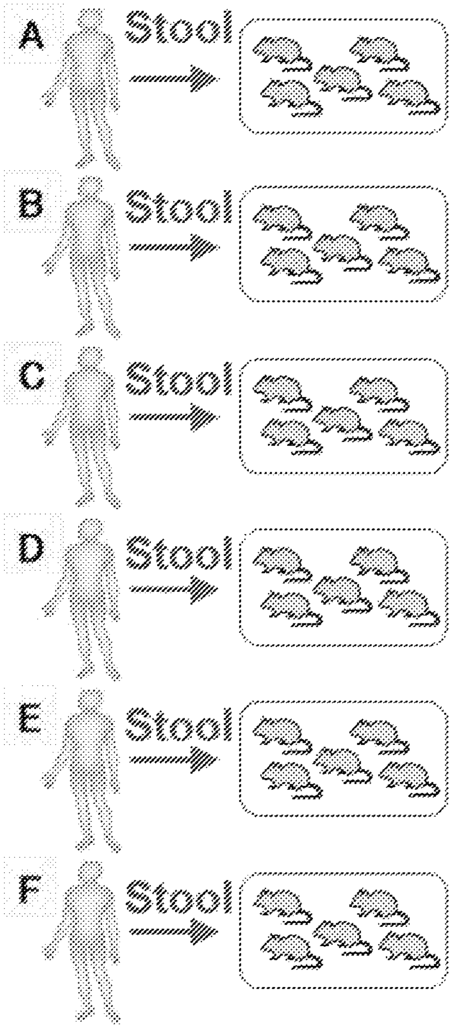
FIG. 5 shows a schematic in which stool samples were obtained from six healthy volunteers. Samples were inoculated into germ-free mice. After 3 weeks, colonic IFN-positive CD8 T cells were assessed.

Next, it was investigated whether the human gut microbiota contained microbes which were able to induce IFN+ CD8+ T cells (FIG. 4). Stool samples were collected from six healthy human volunteers (A~F) (FIG. 5). The samples were individually administered orally into germ free C517BL/6 mice kept in sterile isolators (five or six mice per group). Four weeks after oral inoculation of stool samples, mice were sacrificed, and small intestine and colons were harvested and investigated for IFN+CD8+ T-cells by FACS.

Figure 6:
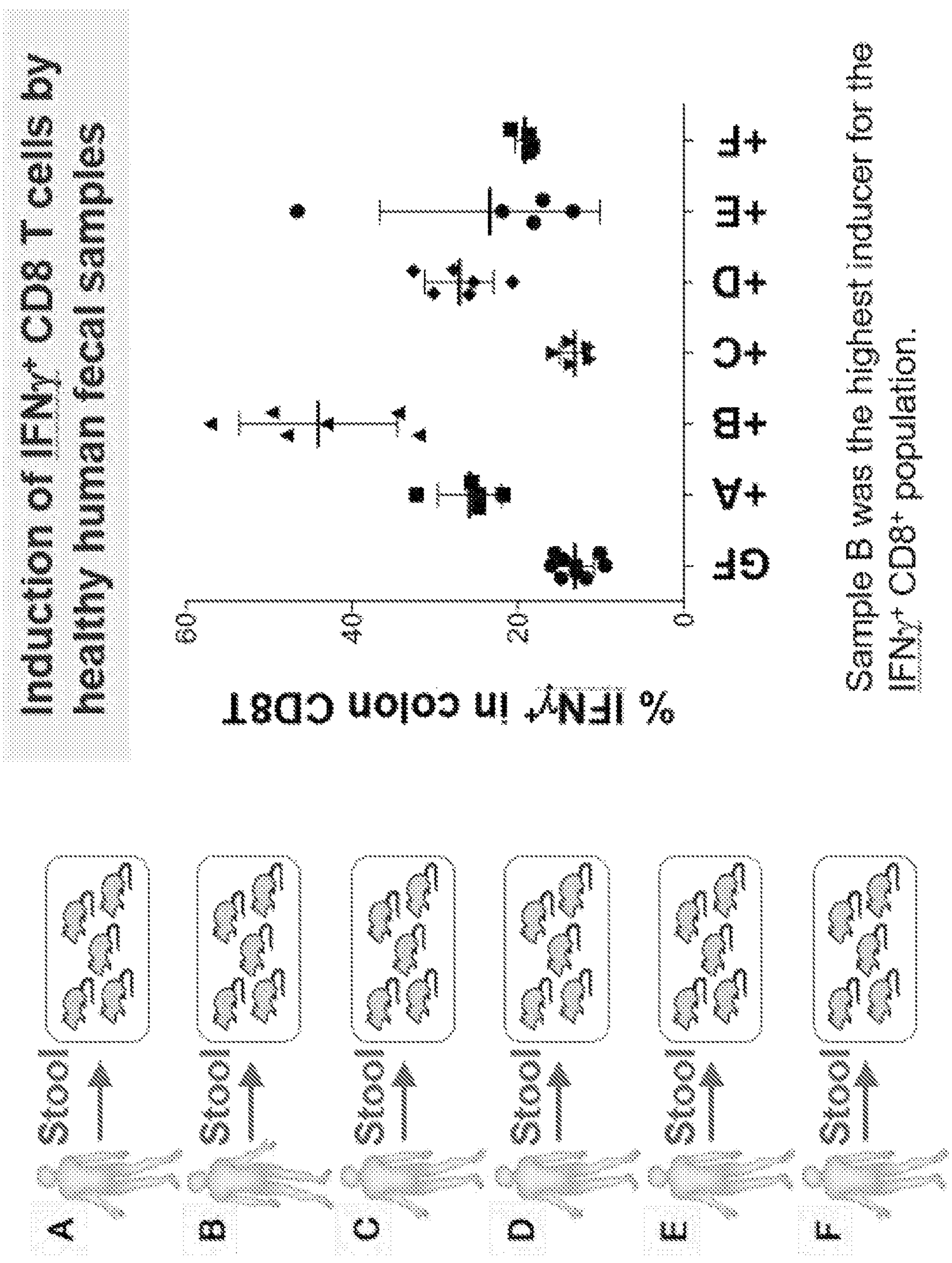
FIG. 6 shows a data from an experiment in which stool samples were obtained from six healthy volunteers. Samples were inoculated into germ-free mice, and the percentage of IFN-positive CD8 T cells induced by healthy human fecal samples was assessed.
Figure 7:
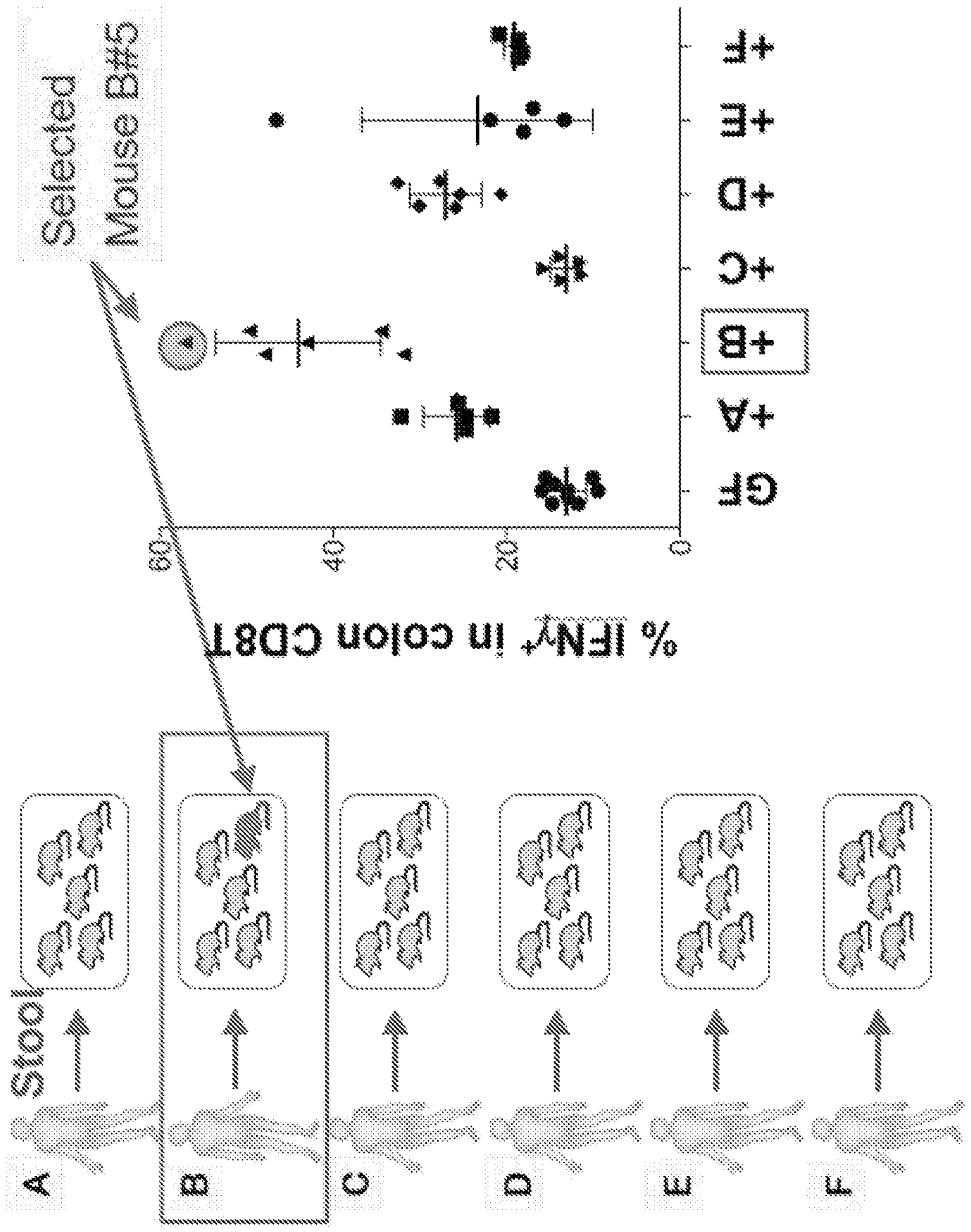
FIG. 7 shows a data from an experiment in which stool samples were obtained from six healthy volunteers. Samples were inoculated into germ-free mice, and the percentage of IFN-positive CD8 T cells induced by healthy human fetal samples was assessed. Mouse B #5 was found to have the highest induction of IFN-positive CD8 T cells and was selected for further analysis.
Figure 8:
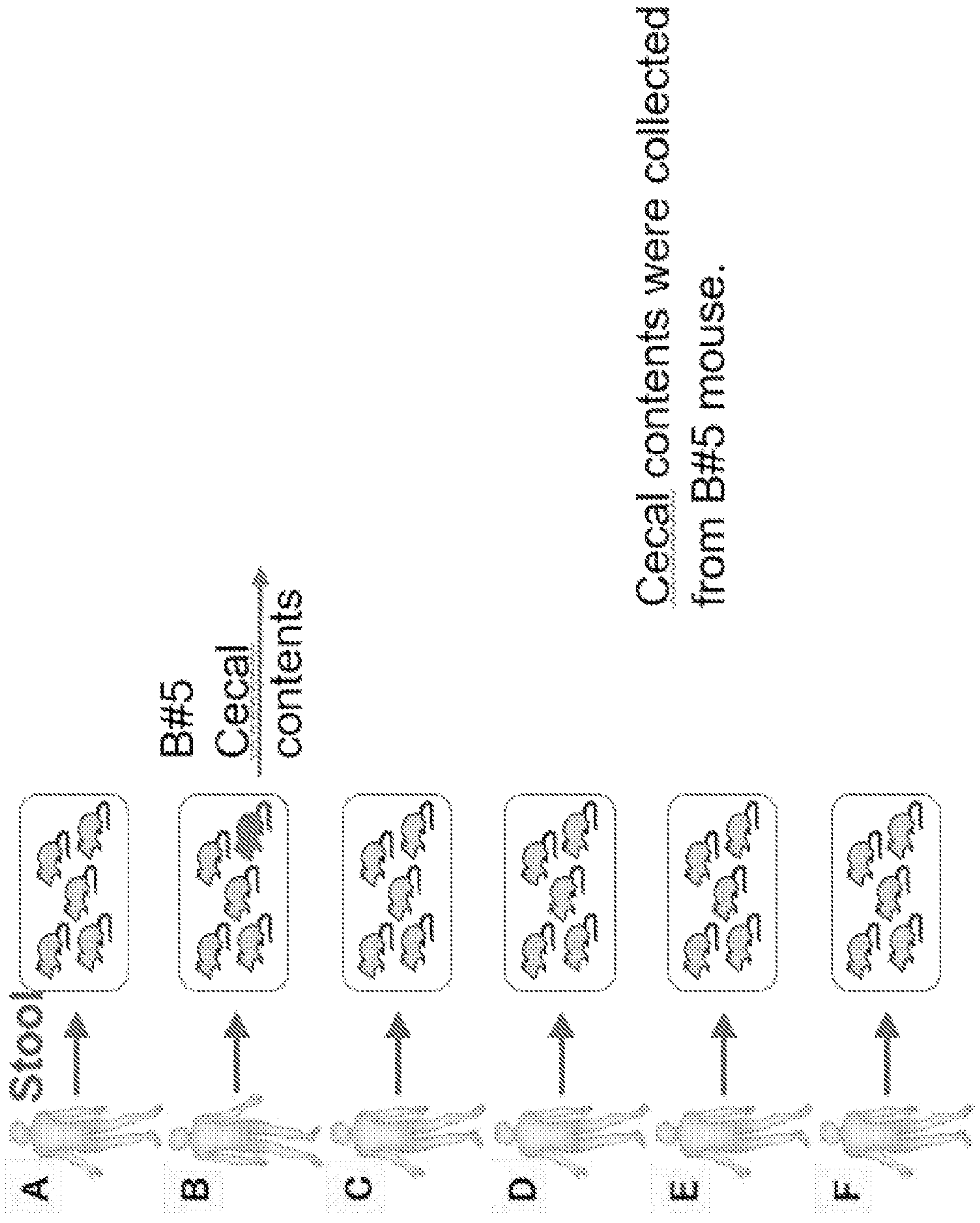
FIG. 8 shows a schematic in which the cecal contents of mouse B #5 were collected.
Figure 9:
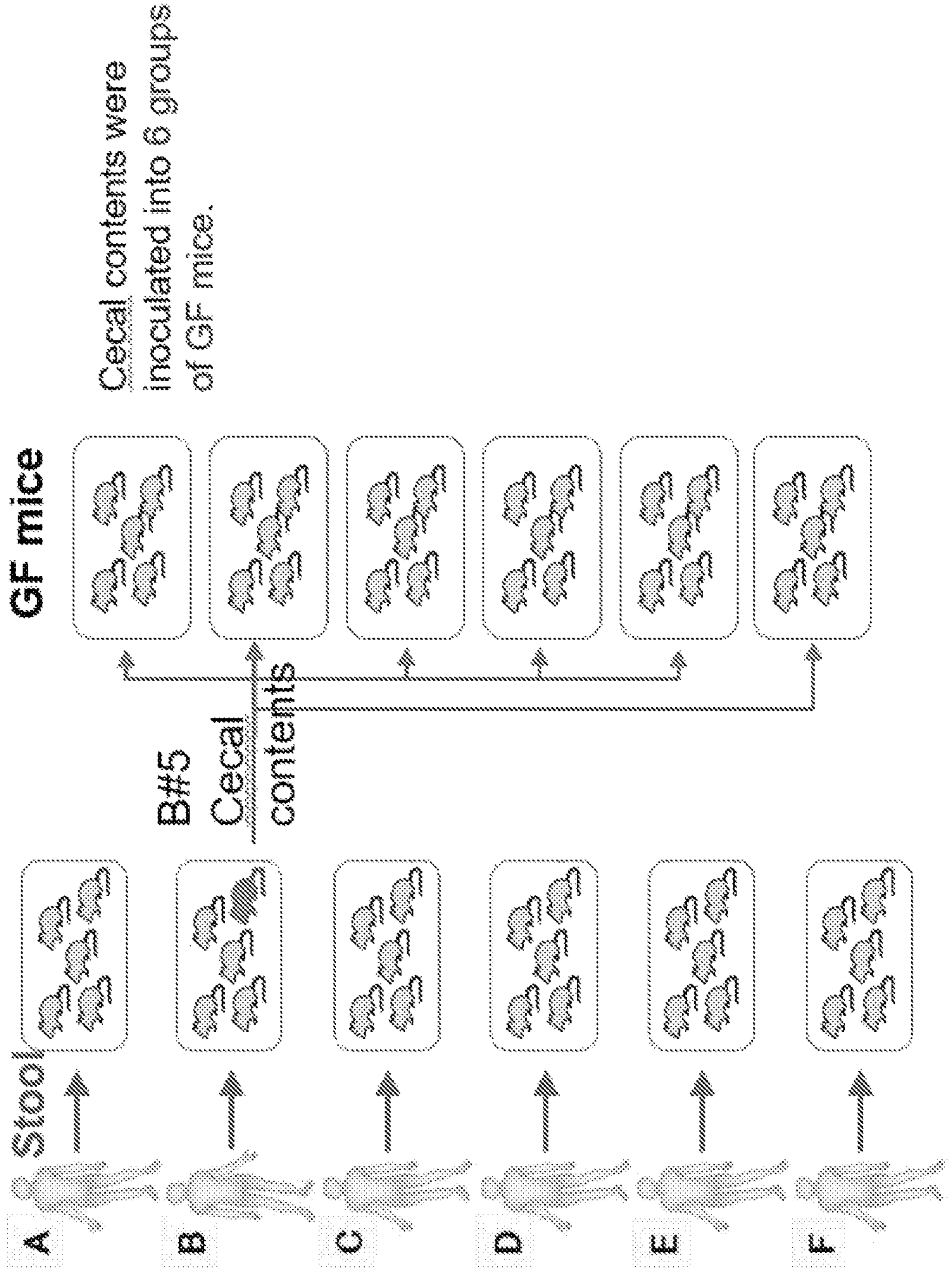
FIG. 9 shows a schematic in which the cecal contents of mouse B #5 were used to inoculate six groups of germ-free mice.
Figure 10:
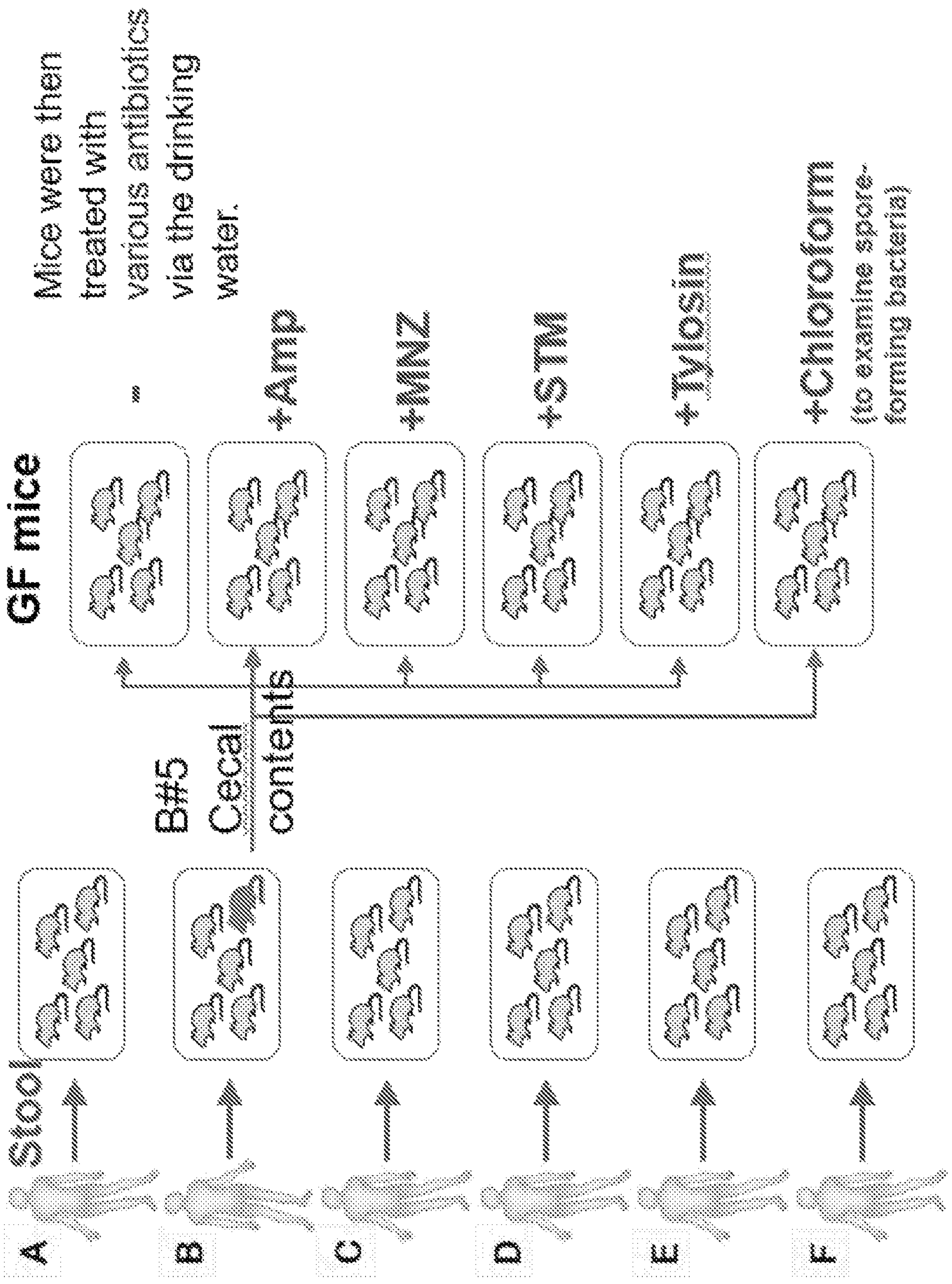
FIG. 10 shows a schematic in which the cecal contents of mouse B #5 were used to inoculate six groups of germ-free mice. The groups of mice received the indicated antibiotics, chloroform or nothing (control "–") in the drinking water. Amp, ampicillin; MNZ, metronidazole, STM, streptomycin.
Figure 11:
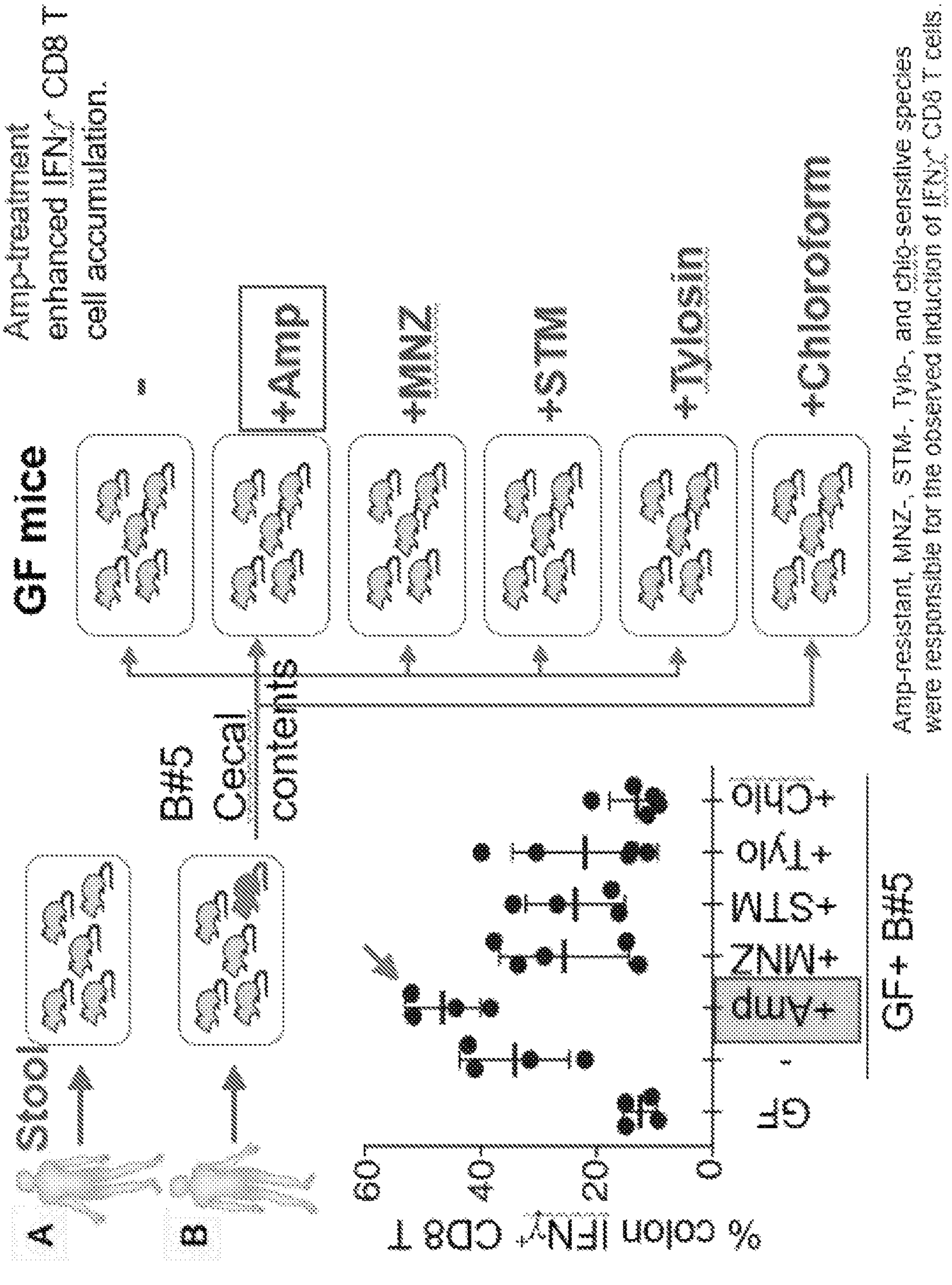
FIG. 11 shows data of an experiment in which the cecal contents of mouse B #5 were used to inoculate six groups of germ-free mice. The groups of mice received the indicated antibiotics, chloroform or nothing (control "–") in the drinking water. The mice were assessed for the percentage of colonic IFN-positive CD8 T cells by flow cytometric analysis. Amp, ampicillin; MNZ, metronidazole; STM, streptomycin.
Figure 21:
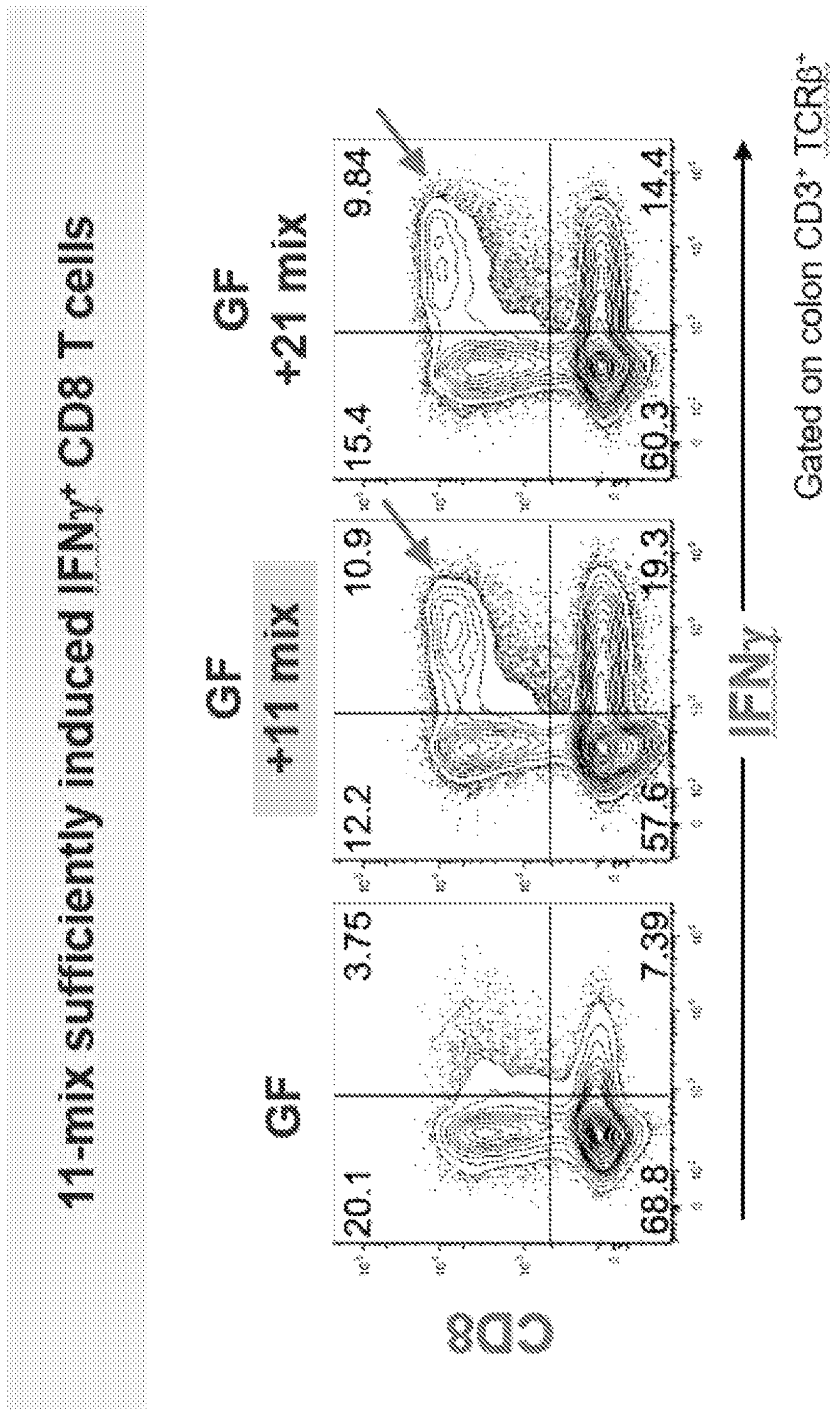
FIG. 21 shows data on the mixture of the 21 strains or 11 strains (11 strain mixture ("11-mix" or "11 mix") corresponds to strains #1-11; See Table 1), which were orally administered to germ free mice. Inoculation with the mixture of 11 isolated bacterial strains was sufficient to induce IFN-positive CD8 T cells, CD3, TCR, CD8 and IFN were stained with antibodies and analyzed by flow cytometry. Expression of CD8 and IFN by the gated CD3 and TCR positive cells is shown for representative mice.

As shown in FIG. 6, colonic IFN+CD8+ T-cells were most remarkably induced in mice inoculated with a stool sample collected from donor B. Among mice inoculated with the donor B stool sample, we selected a mouse that exhibited the highest frequency of IFN+CD8+ T cells (called ‘mouse B #5’ hereafter; FIG. 7). In order to concentrate microbes responsible for IFN+CD8+ T cell induction, cecal contents were collected from the mouse B #5 and inoculated into further germ-free mice (FIGS. 8 and 9). The mice were then orally administrated drinking water with or without Ampicillin, Metronidazole, Streptomycin or Tylosin (five mice per group) (FIG. 10). Alternatively, cecal contents of mouse B #5 were treated with 3% chloroform and orally inoculated into another five germ-free mice ('B #5+Chrolo'). FIG. 11 shows that Ampicillin treatment enhanced induction of colonic lamina propria IFN+CD8+ T-cells by the mouse B #5 microbiota, whereas other antibiotic treatment or chloroform treatment reduced the induction capability of IFN+ CD8+ T-Cells by the: mouse. B #5 microbiota.

mix) (FIG. 21). Identification of the bacterial species with the highest homology to each of the strains in the 11 mix is provided in Table 1.

Example 1A: Further Characterization of the Mixture of 11 Strains

The strains of Table 1 where characterized further by resequencing of the 16S sequences and by whole genome sequencing. The results of the further characterization are found in Table 2.

TABLE 2

Further characterization of the 11-mix (the mixture of 11 strains)

| Strain # | SEQ ID NO | Strain ID | species with highest homology based on original 16S analysis | NCBI accession ID | species with highest homology based on 16S resequencing | 16S Identity (%) of re-sequencing | species with highest homology based on whole genome sequencing (WGS) | WGS Identity (%) | WGS Coverage (%) | Alternative species with high(est) homology |
|---|---|---|---|---|---|---|---|---|---|---|
| 2 | 2 | 1A6 | *Fusobacterium ulcerans* | KR822463 | *Fusobacterium varium* | 99 | *Fusobacterium ulcerans* | 93.2 | 78.6 | *Fusobacterium* sp. |
| 7 | 7 | 2F11 | *Parabacteroides johnsonii* | NR041464 | *Parabacteroides johnsonii* | 99 | *Parabacteroides johnsonii* | 99.9 | 90.5 | |
| 6 | 6 | 2A6 | *Paraprevotella xylaniphila* | NR113078 | *Paraprevotella xylaniphila* | 99 | *Paraprevotella xylaniphila* | 98.9 | 92.1 | |
| 11 | 11 | 2G9 | *Parabacteroides distasonis* | NR041342 | *Parabacteroides distasonis* | 99 | *Parabacteroides* sp. CAG:2 | 99.4 | 95.4 | |
| 8 | 8 | 1E7 | *Alistipes* sp. | LT223566 | *Alistipes senegalensis* | 99 | *Alistipes senegalensis* | 98.7 | 72.2 | *Alistipes timonensis* |
| 10 | 10 | 1C1 | *Eubacterium limosum* | NR113248 | *Eubacterium limosum* | 99 | *Eubacterium limosum* | 95 | 81 | |
| 3 | 3 | 1B11 | *Bacteroides dorei* | CP011531 | *Bacteroides dorei* | 99 | *Bacteroides dorei* | 99.3 | 79.5 | *Bacteroides fluxus* |
| 9 | 9 | 1H9 | *Parabacteroides gordonii* | NR112835 | *Parabacteroides gordonii* | 97 | *Parabacteroides* sp. HGS0025 | 90 | 50 | |
| 5 | 5 | 2B1 | *Subdolinogranulum* sp. | KM098109 | *Gemminger formicilis* | 99 | *Ruminococcaceae bacterium* cv2 | 99.2 | 73.9 | *Rutheni-bacterium lactatiformans* |
| 4 | 4 | 2G1 | *Bacteroides uniformis* | NR112945 | *Bacteroides uniformis* | 99 | *Bacteroides* sp. D20 | 98.5 | 81 | *Bacterium* IAFR67 |
| 1 | 1 | 2G5 | *Phascolarcto-bacterium faecium* | LN998073 | *Phascolarcto-bacterium faecium* | 99 | *Phascolarcto-bacterium* sp. CAG:207 | 99.2 | 87 | |

Figure 12:
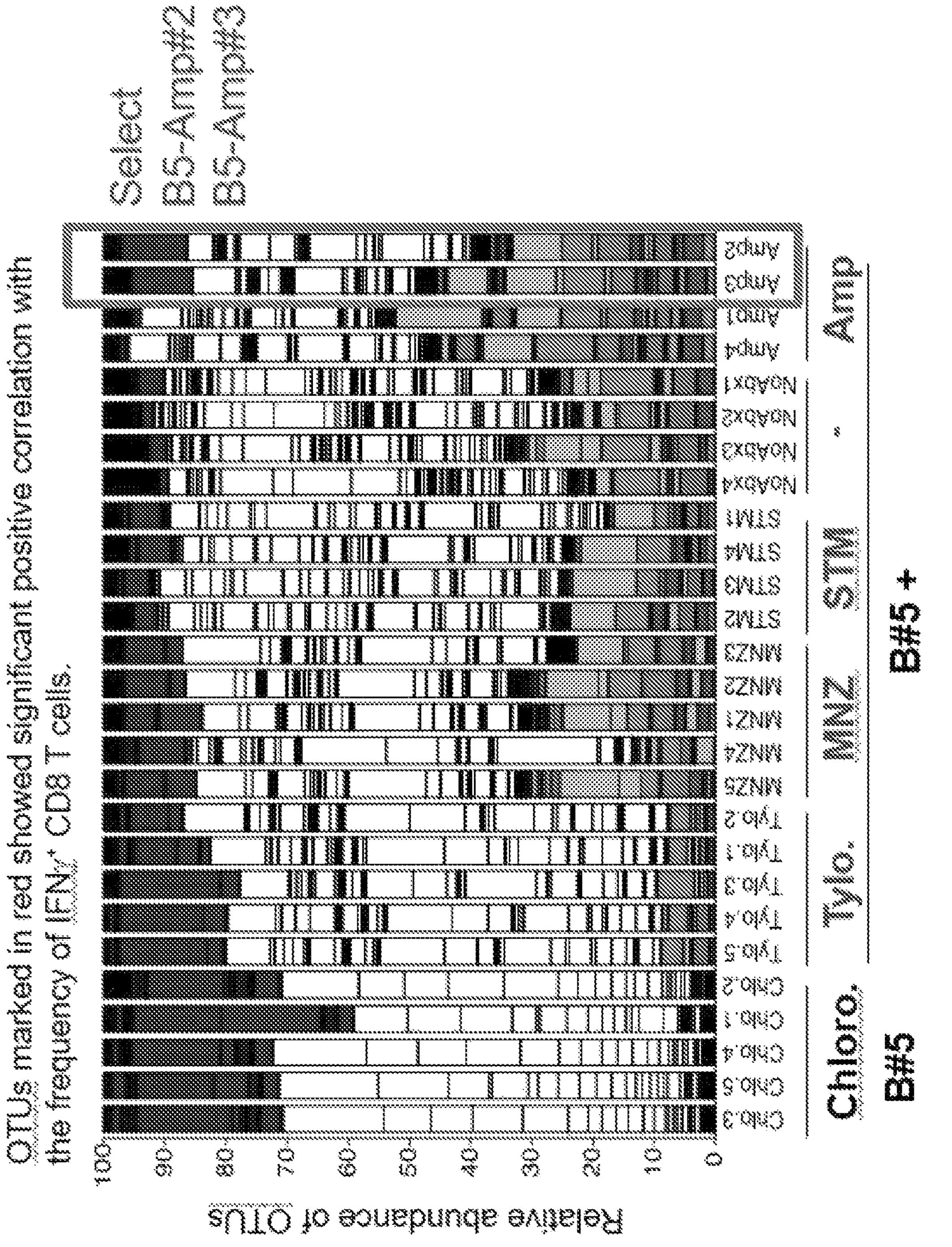
FIG. 12 shows 16S rRNA gene sequence data of the cecal microbiota of the mice prepared in FIG. 11, which were comprehensively analyzed using a next generation sequencer. The y-axis shows the relative abundance of the operational taxonomic units (OTUs). The OTUs corresponding to the isolated strains from the B #5-AMP #2 and B #5-AMP #3 mice are indicated in a box and were selected for further analysis. Amp, ampicillin; MNZ, metronidazole; STM, streptomycin; Chloro, chloroform; Tylo, tylosin.
Figure 13:
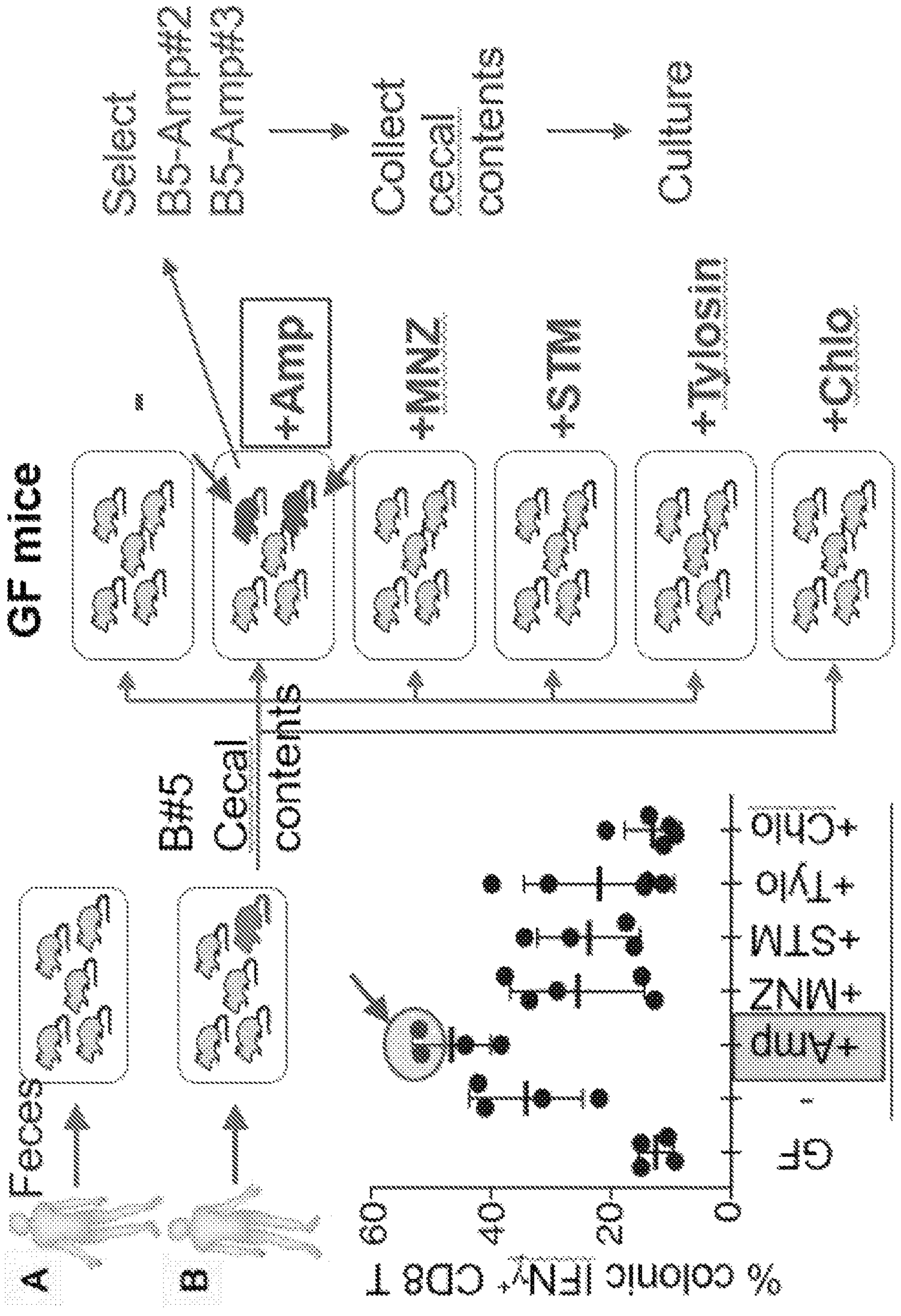
FIG. 13 shows a schematic in which the percentage of colonic IFN-positive CD8 T cells were assessed in each of the groups of mice that had beer inoculated with cecal contents from mouse B #5. Mouse B5-Amp #2 and mouse B #5-Amp #3 were found to have the highest induction of IFN-positive CD8 T cells, and cecal contents were collected and cultured from these mice. Amp, ampicillin; MNZ, metronidazole; STM, streptomycin; Chlo, chloroform; Tylo, tylosin.
Figure 14:
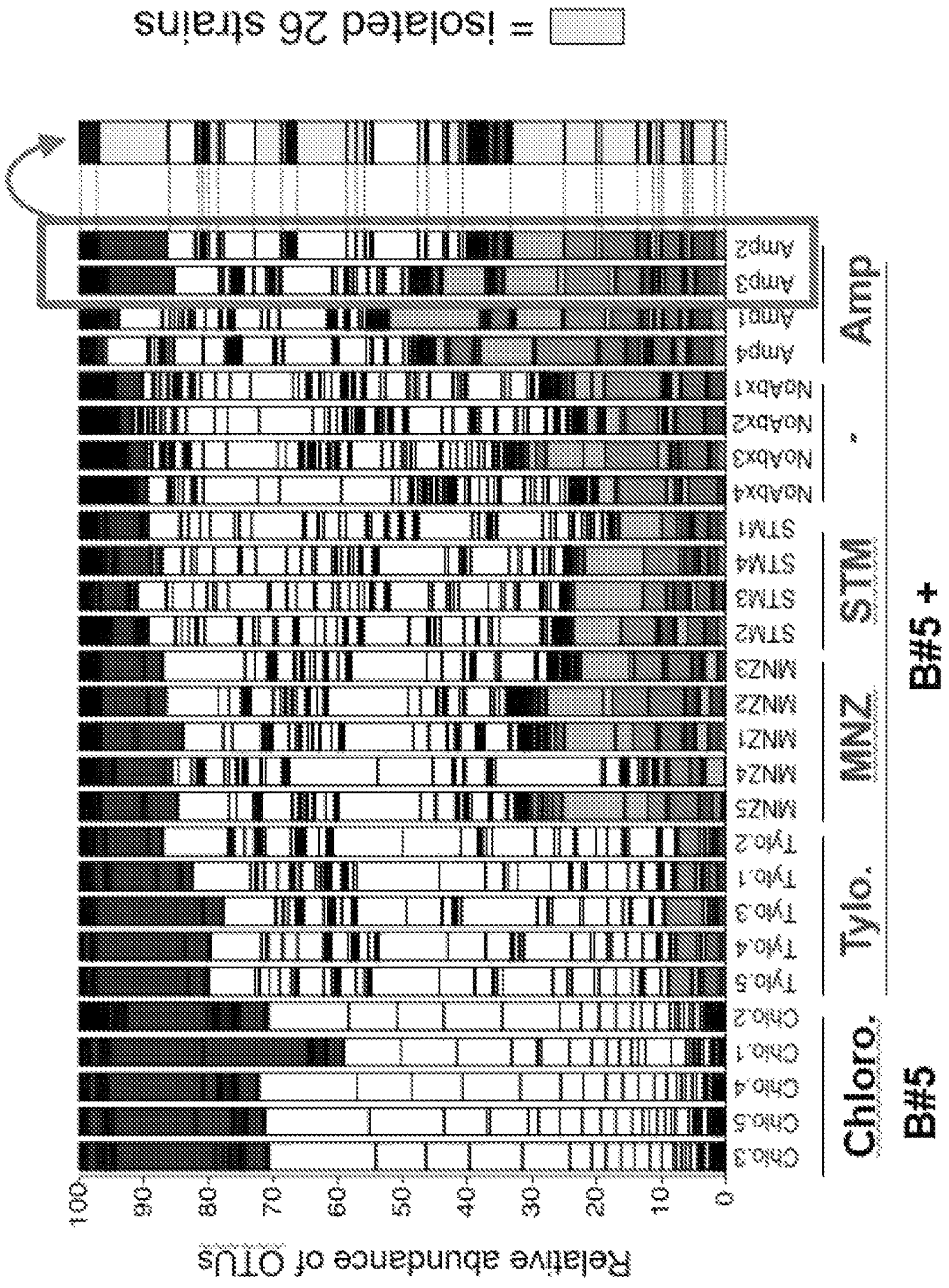
FIG. 14 shows 16S rRNA gene sequence data of 26 isolated strains from the B π5-AMP #2 and B #5-AMP #3 mice. The OTUs of the 26 strains broadly cover the bacterial species colonized in the B #5-AMP #2 and B #5-AMP #3 mice. Amp, ampicillin; MNZ, metronidazole; STM, streptomycin; Chloro, chloroform; Tylo, tylosin.
Figure 17:
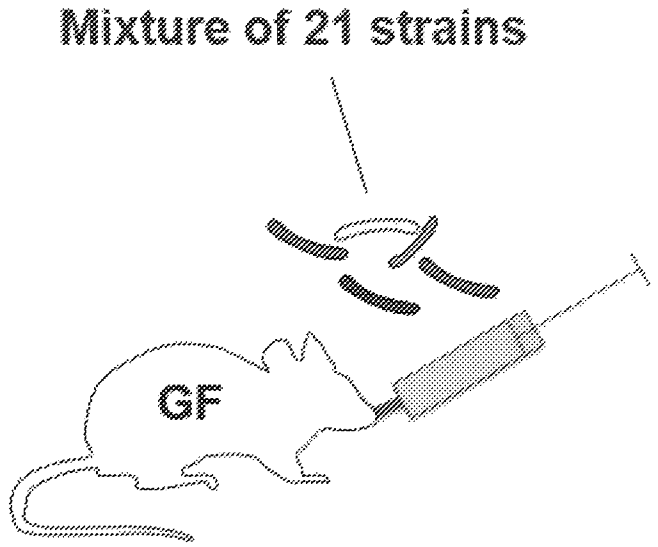
FIG. 17 shows a schematic of a germ-free mouse orally inoculated with a bacterial mixture of the 21 isolated bacterial strains shown in FIG. 16.
Figure 18:
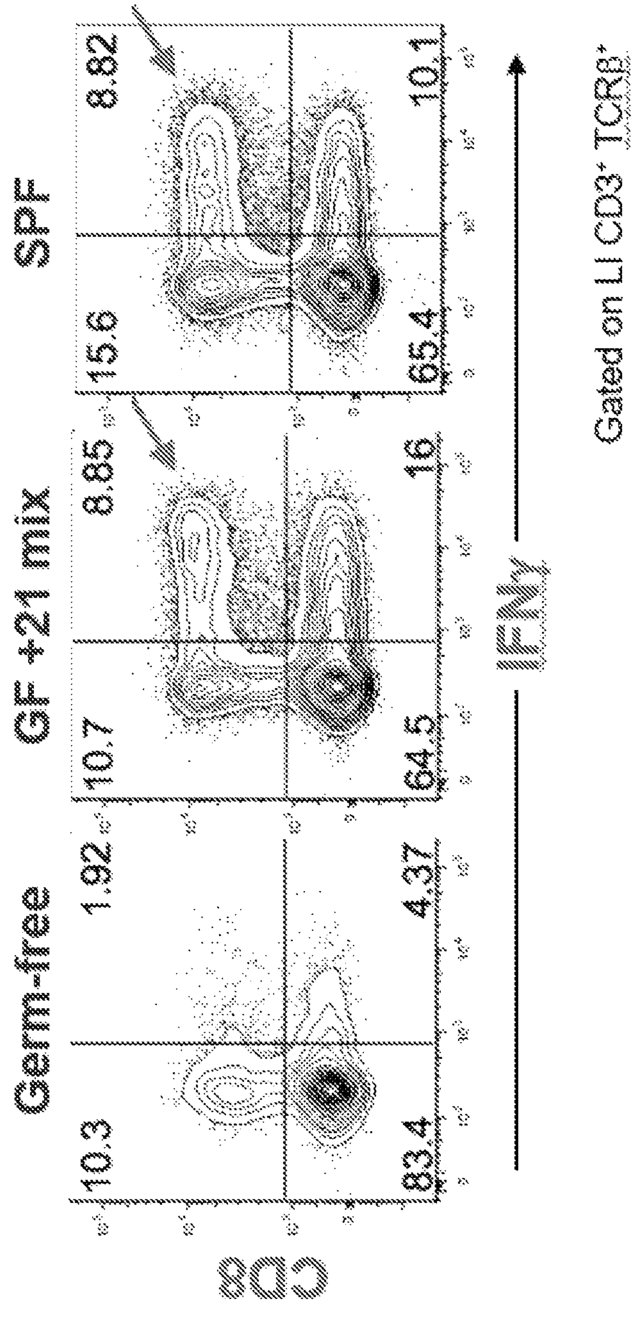
FIG. 18 shows data on the mixture of 21 isolated strains which was orally administered to germ free mice. As compared to germ-free mice, inoculation with the mixture of 21 isolated bacterial strains resulted in an induction of colonic IFN-positive CD8 T cells, CD3, CD8, TOR and IFN were stained with antibodies and analyzed by flow cytometry. Expression of CD8 and IFN by the gated CD3 and TCR positive cells is shown for representative mice.
Figure 19:
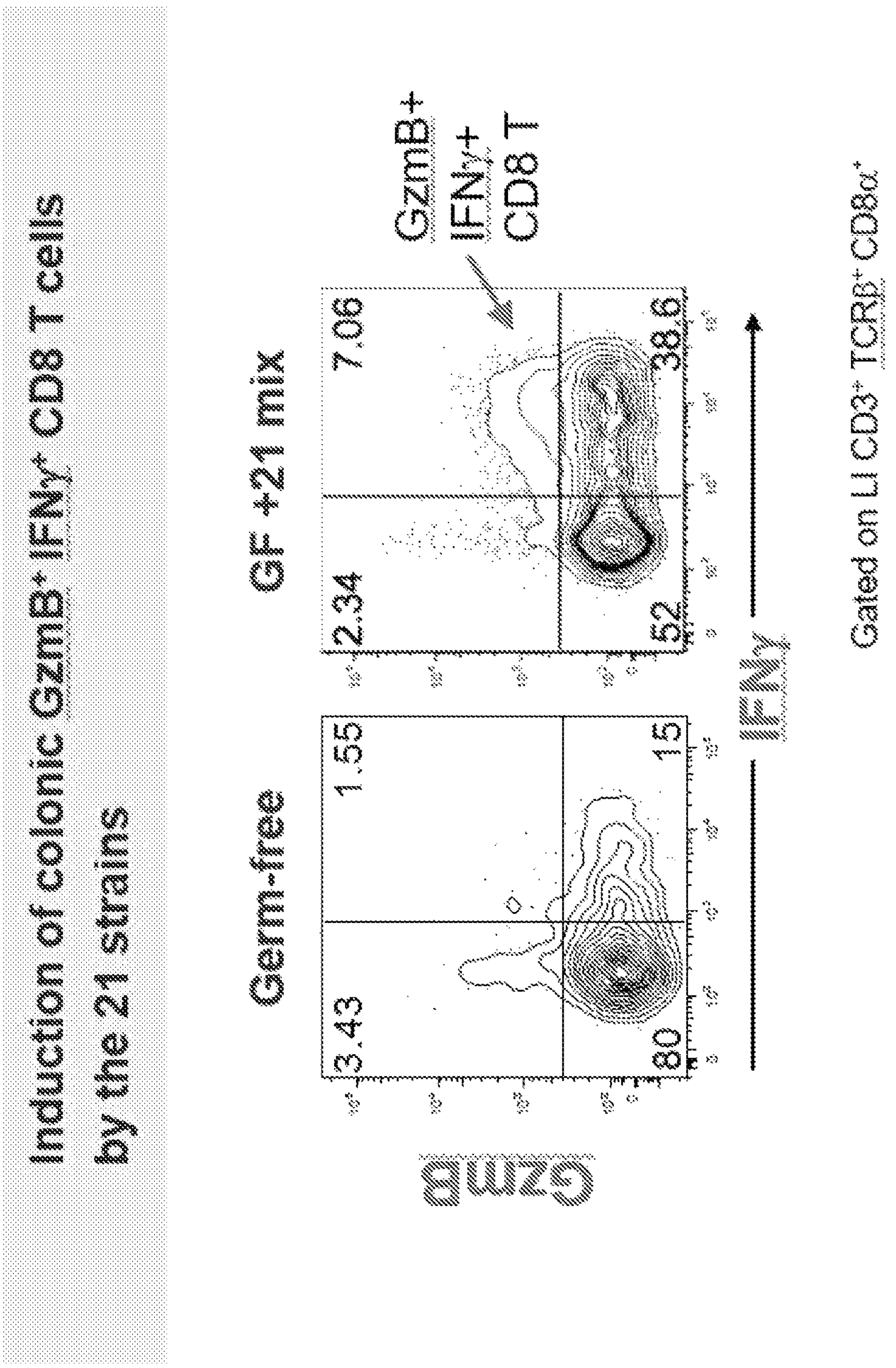
FIG. 19 shows data on the mixture of 21 isolated bacterial strains which was orally administered to germ free mice. As compared to germ-free mice, inoculation with the mixture of 21 isolated bacterial strains resulted in an induction of GzmB positive IFN-positive CD8 T cells. CD3, TCR, CD8, CD103, IFN and GzmB were stained with antibodies and analyzed by flow cytometry. Expression of GzmB by the gated CD8 T cells is shown for representative mice.

FIG. 12 shows the operational taxonomic unit (OTU) analysis of intestinal contents of mice inoculated with mouse B #5 microbiota and treated with/without antibiotics or chloroform. Cecal contents were collected from two B #5+AMP mice that exhibited the highest frequency of IFN+ CD8+ T cells (mouse B #5+-AMP-2 and mouse B #5+-AMP-3) and cultured in an anaerobic chamber (FIG. 13). 304 colonies were picked and sequencing of the 16S rRNA gene revealed that 26 strains were isolated (FIGS. 14 and 15). Twenty-one strains were selected from the 26 strains, excluding 5 strains which were included in the microbiota of B #5+Chrolo mice (therefore predicted to be unnecessary for induction of IFN+CD8+ T-cells) (FIG. 15). The mixture of 21 strains was orally inoculated into germ free mice and strong induction of IFN+CD8+ T-cells was observed. (FIGS. 17 and 18). IFN+CD8+ T cells induced by the 21 strains also expressed Granzyme B as well (FIG. 19). A mixture of 11 strains with the highest correlation with IFN+CD8+ T-cells was inoculated into GF mice as well. The mixture of 11 strains (11 mix) was orally a strong induction of IFN+CD8+ T-cells, even when compared to the 21 strains mixture (21

Figure 23:
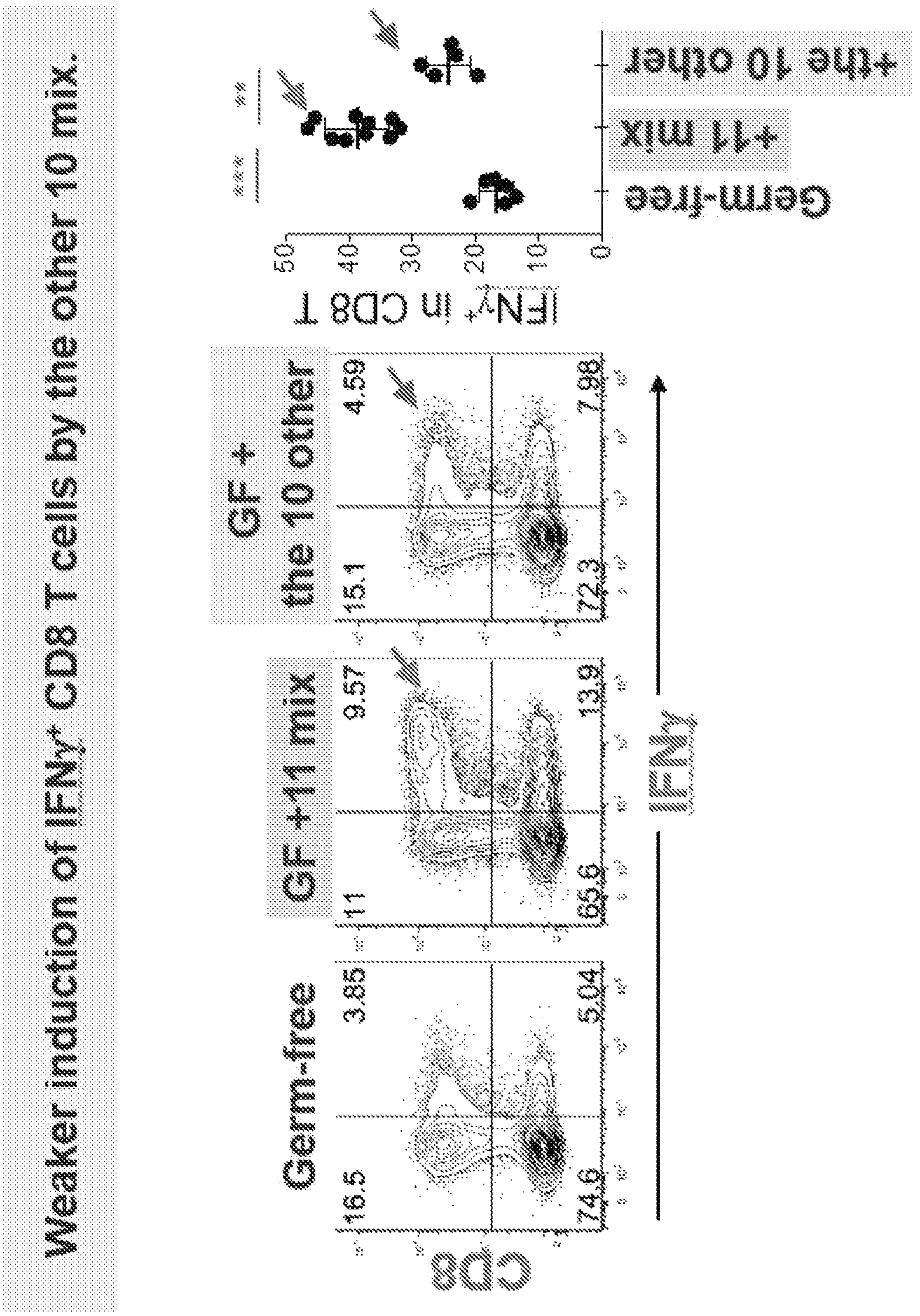
FIG. 23 shows data on the mixture of the 11 isolated strains ("11 mix") or the other 10 isolated strains that had been excluded, shown in FIG. 22 ("the other 10 mix", "the 10 other"). Inoculation with the mixture of 10 isolated bacterial strains resulted in lower levels of IFN-positive CD8 T cells, as compared to mice that had been inoculated with the mixture of 11 isolated bacterial strains. CD3, TCR, CD8 and IFN were stained with antibodies and analyzed by flow cytometry. Expression of CD8 and IFN by the gated CD3 and TCR positive cells is shown for representative mice.
Figure 24:
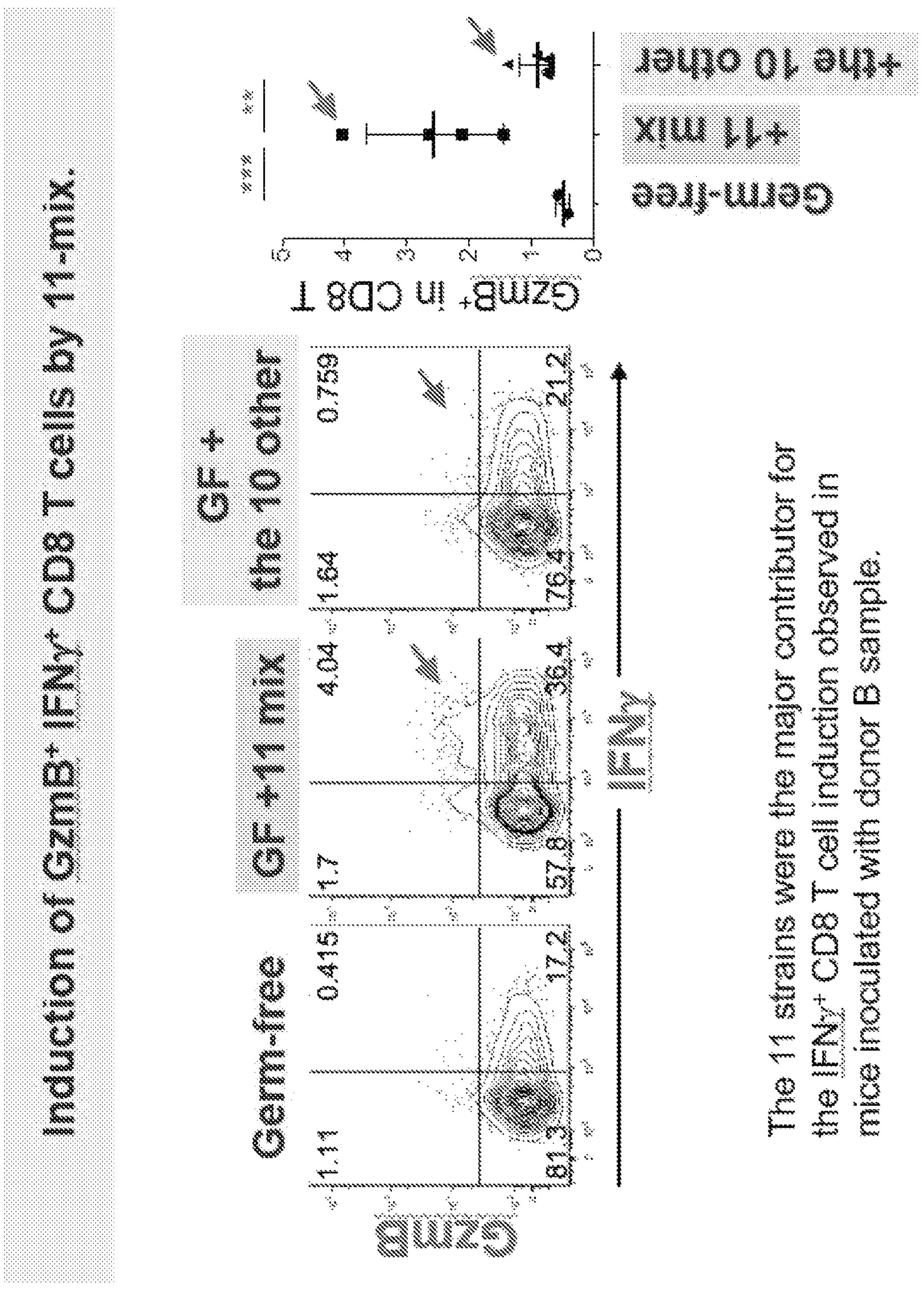
FIG. 24 shows data on the mixture of 11 isolated strains ("11 mix") or the other 10 isolated strains that had been excluded, shown in FIG. 22 ("the other 10 mix", "the 10 other"). Inoculation with the mixture of the other 10 isolated bacterial strains resulted in lower levels of GzmB-positive IFN-positive CD8 T cells, as compared to mice that had been inoculated with the mixture of 11 isolated bacterial strains. Expression of GzmB by the gated CD8 T cells is shown for representative mice.
Figure 25:
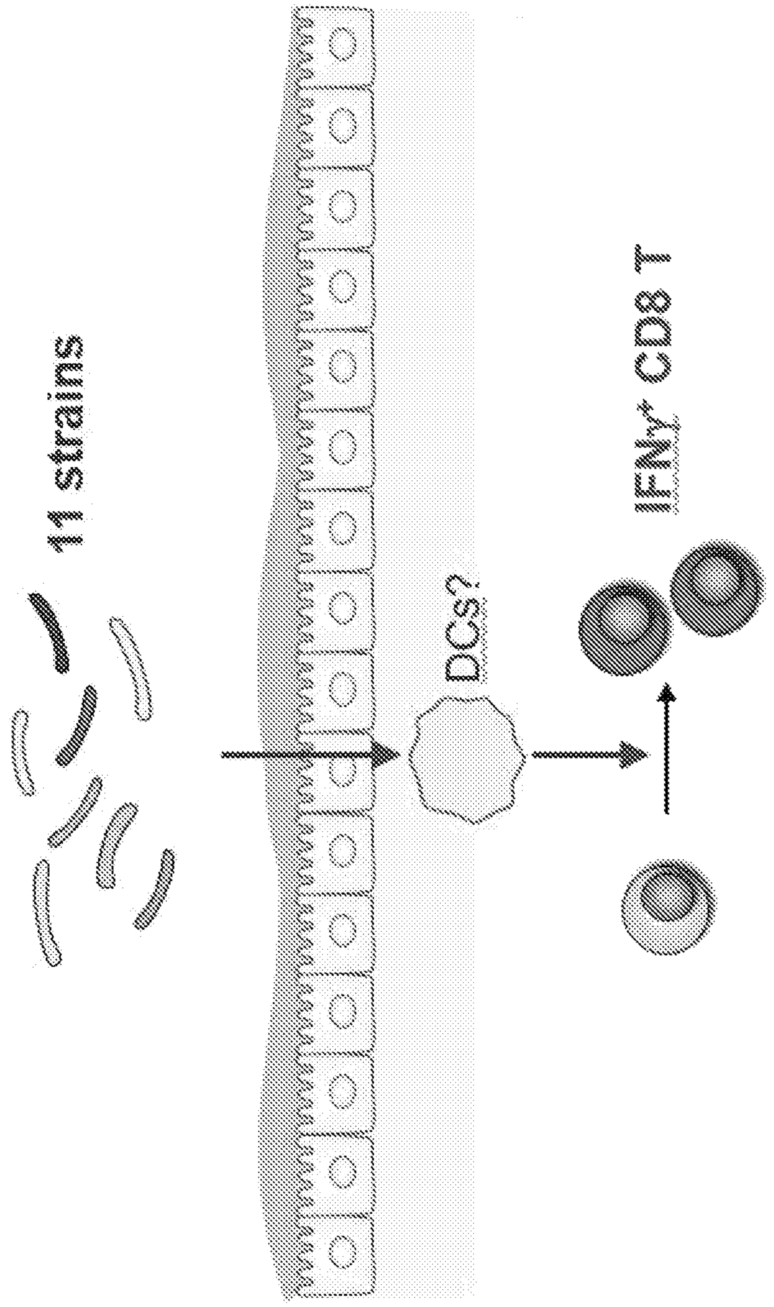
FIG. 25 shows a schematic of a non-limiting model in which the mixture of 11 isolated bacterial strains may induce IFN-positive CD8 T cells through activation of dendritic cell populations.

Example 2: Further Characterization of a CD8+ T-Cell Inducing Bacterial Cocktail Twenty six strains isolated from cecal contents of B #5+AMP mice that exhibited high frequencies of IFNγ+ CD8+ T cells are shown in FIG. 15. Among the 26 strains, 11 strains ("11 mix") were positively correlated with the frequency of IFNγ+CD8+ T cells. Therefore, these 11 strains were selected for further experiments, and the mixture of 11 strains ("11-mix") was inoculated into germ-tree mice (see also Table 2). Colonization with the 11-mix resulted in a strong induction of colonic IFNγ+CD8+ T cells, whereas the other 10 strains ("10-mix") weakly induced IFNγ+CD8+ T cells and GzmB+CD8+ T cells compared to the levels induced by the 11-mix (FIGS. 22-24)

A phylogenetic comparison using 16S rRNA gene sequences showed that the 11 strain mixture (also referred to as "the 11 mix") consists of 7 strains falling within Bacteroidales ("7 strains") and 4 strains of non-Bacteroidales: 2 Clostridiales, 1 Fusobacterials and 1 Selenomonadales ("4 strains") (See FIG. 29).

Figure 30:
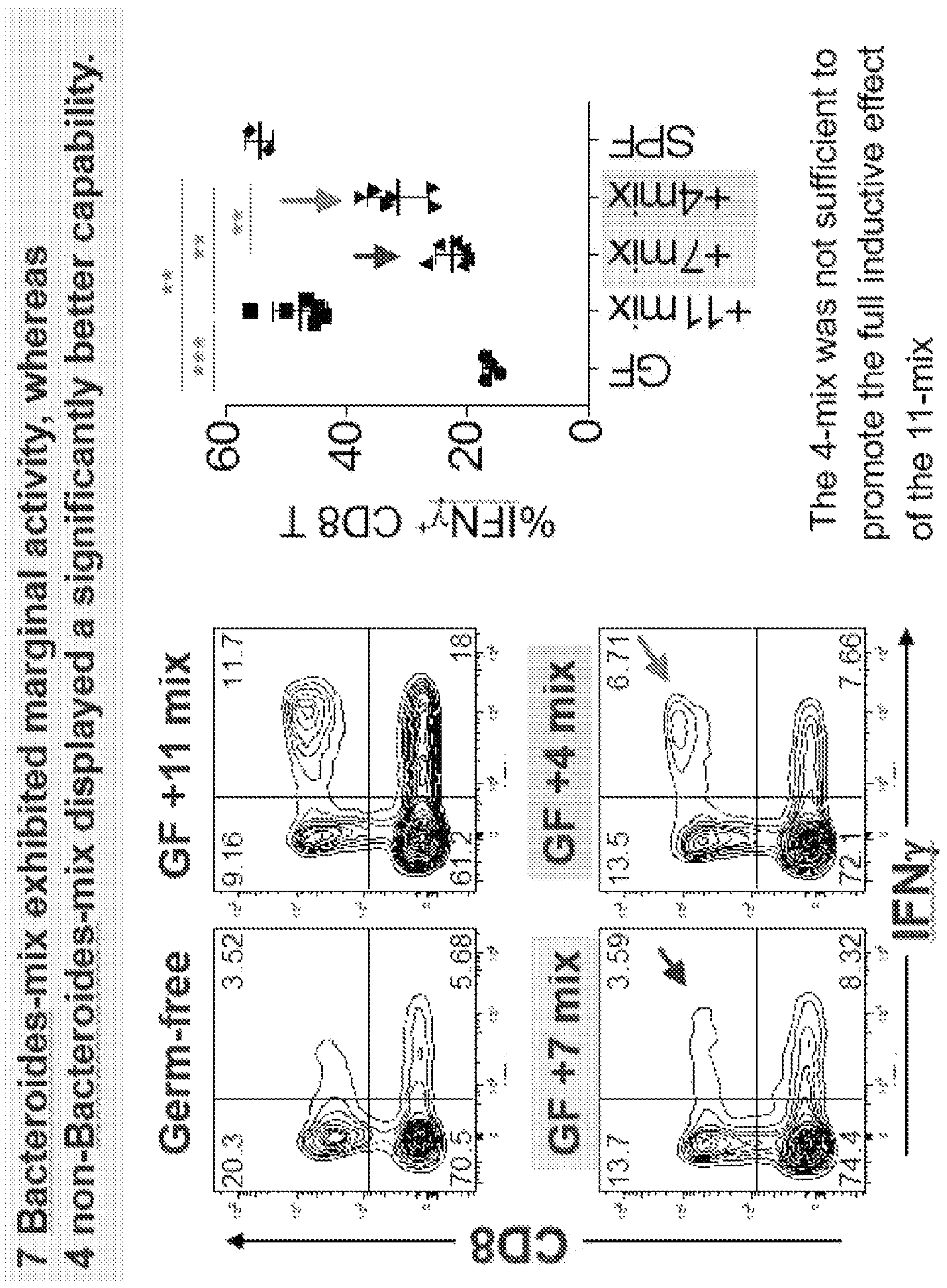
FIG. 30 shows data relating to Example 2. The mixtures of the 11 strains ("11 mix"), 7 Bacteroides strains ("7 mix") or 4 non-Bacteroides strains ("4 mix") indicated in FIG. 29, were orally administered to germ free mice. CD3, TCR, CD8 and IFN were stained with antibodies and analyzed by flow cytometry. The expression of CD8 and IFN by the gated CD3 and TCR positive cells of representative mice is show in right panel, as indicated by the percentage of IFN+ cells in CD8T cells.
Figure 31:
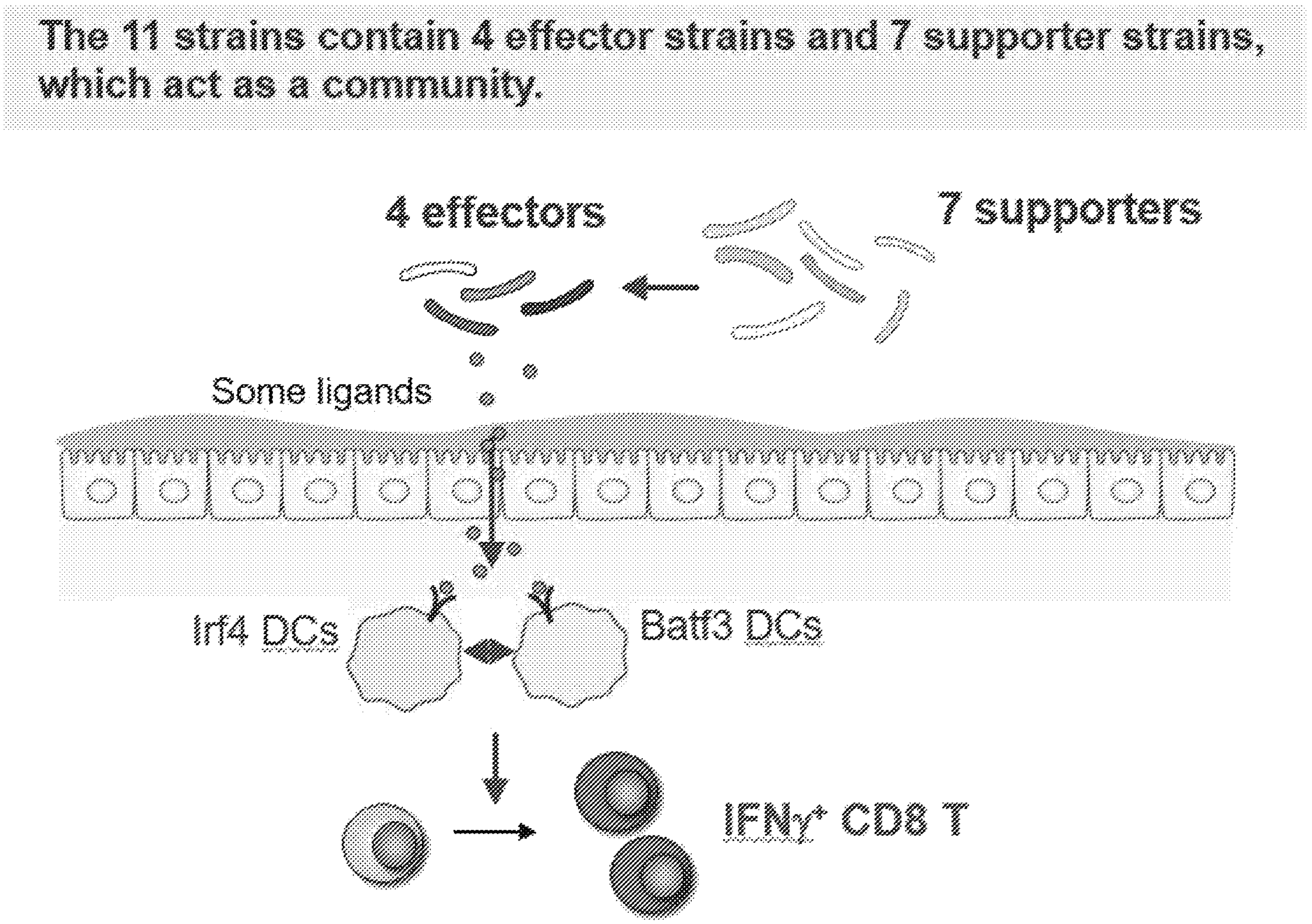
FIG. 31 shows a schematic of a non-limiting model in which the mixture of 11 isolated bacterial strains contains 4 effector strains and 7 supporter strains, which act together, and produce ligands that induce IFN-positive CD8 T cells through activation of Batf3-dependent and Irf4-dependent dendritic cell populations.

Inoculation with the mixture of 4 non-Bacteroidales strains ("4-mix") resulted in a strong accumulation of colonic IFNγ+CD8+ T cells, comparable to the level of colonic IFNγ+CD8+ T cells observed in mice colonized with the 11 mix. In contrast, colonization with 7 Bacteroidales strains ("7-mix") weakly induced IFNγ+CD8+ T cells (FIG. 30). The 11-mix is more effective than either the 7-mix or the 4-mix.

Identification of the bacterial specks with the highest homology to each of the strains in the 4 mix is provided in Table 3, below.

TABLE 3

| Mixture of 4 strains | | | | | |
|---|---|---|---|---|---|
| Strain # | SEQ ID NO | Strain ID | Species with highest homology | NCBI accession # of 16S locus | SEQ ID of NCBI 165 locus |
| 1 | 1 | 2G5 | *Phascolarctobacterium faecium* | LN998073 | 27 |
| 2 | 2 | 1A6 | *Fusobacterium ulcerans* | KR822463 | 28 |
| 5 | 5 | 2B1 | *Subtioligranulum* sp. | KM098109 | 31 |
| 10 | 10 | 1C1 | *Eubacterium limosurn* | NR113248 | 36 |

Example 3: Anti-Cancer Characteristics of CD8+ T-Cell Inducing Bacterial Cocktails in Combination with an Anti-PD1 Antibody To investigate whether colonization with the 11-mix in combination with immune checkpoint inhibitor anti-PD1 could enhance anticancer immune responses, a MC38 colon cancer cell line was subcutaneously injected into mice.

Figure 37:
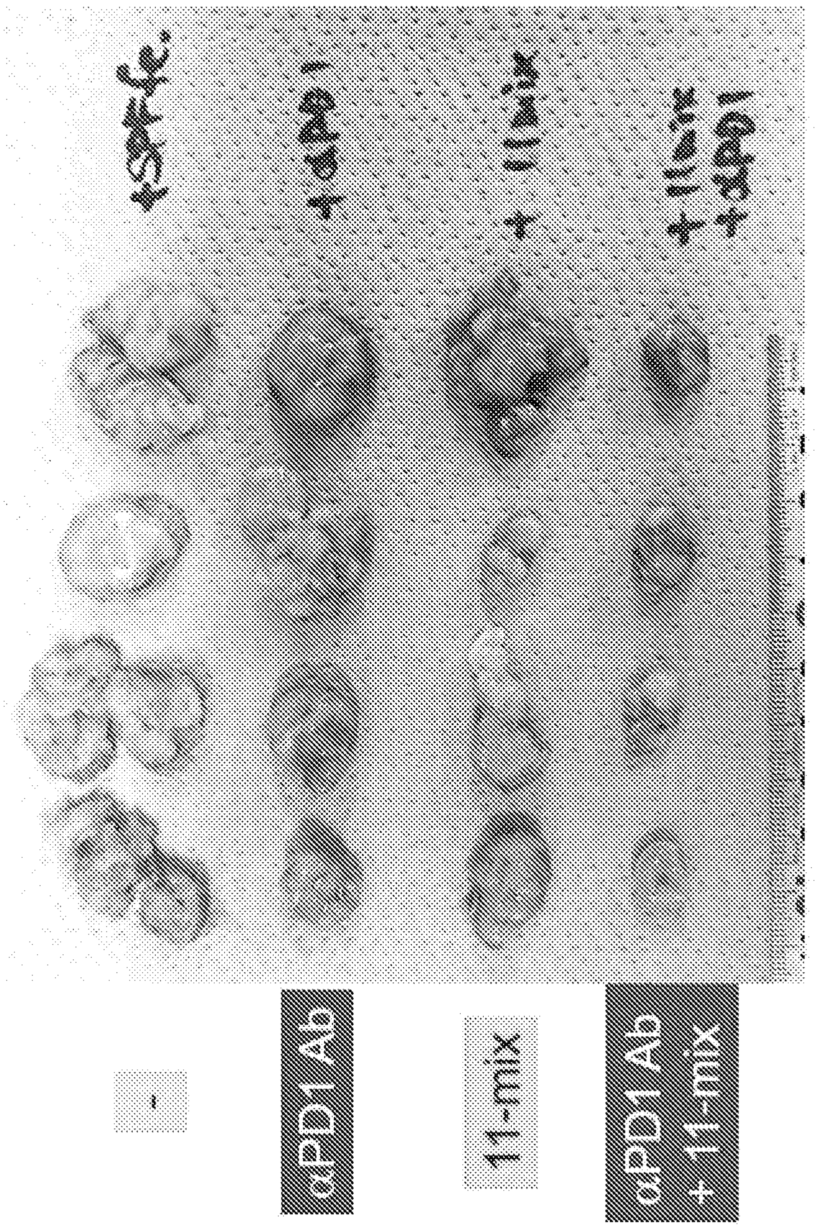
FIG. 37 shows photographs of the tumors isolated from mice described in FIG. 36.

Mice were administered an anti-PD1 antibody (arrows on the timelines in FIG. 36) and/or the 11-mix (arrows with asterisk on the timelines in FIG. 36). The 11-mix was administered to the indicated groups of mice by gavage. Mice that received the combination of the anti-PD1 antibody and the 11-mix had reduced tumor volume (FIGS. 36 and 37) compared to the other groups of mice.

Figure 38:
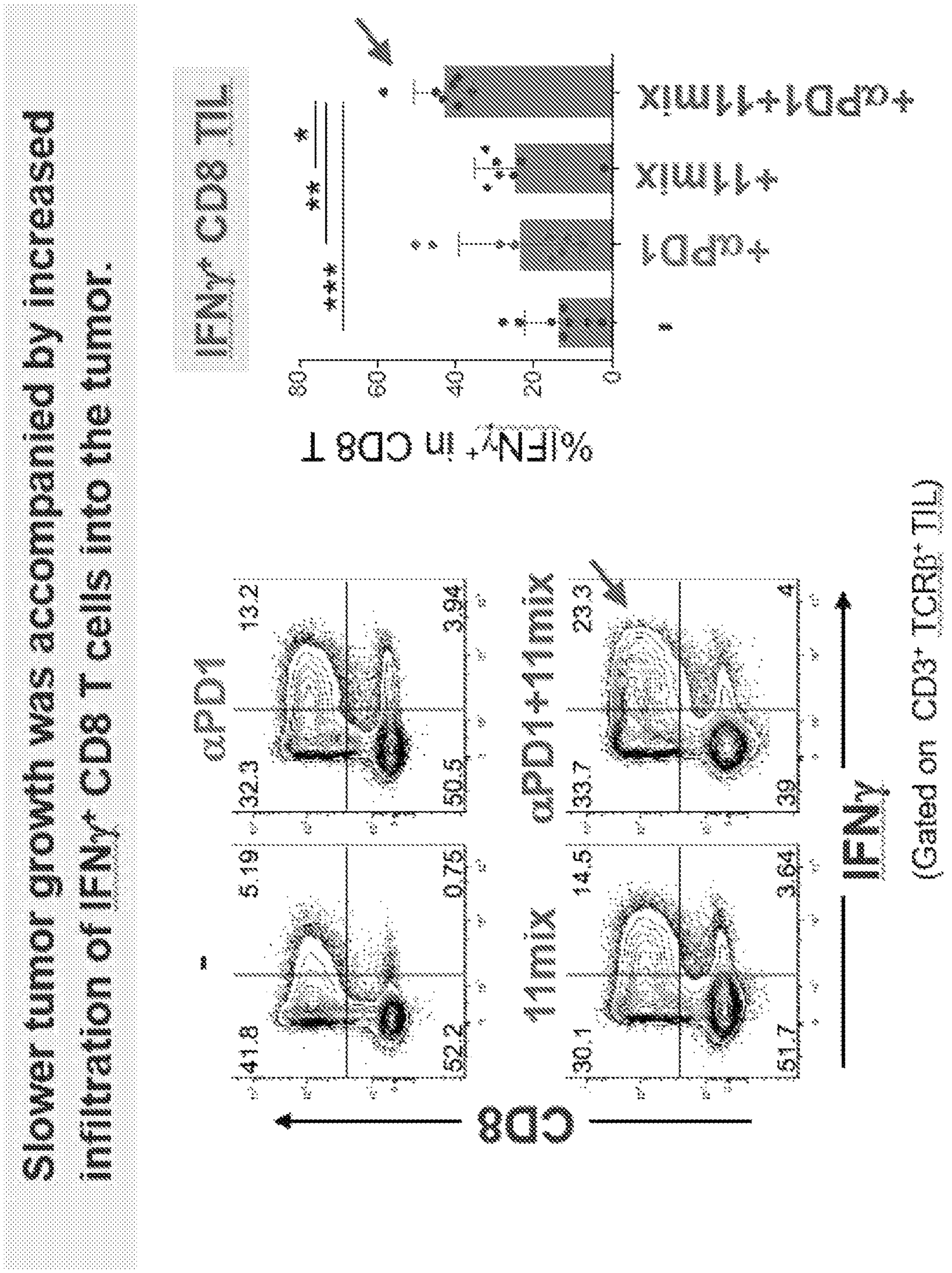
FIG. 38 shows show data on lymphocytes isolated from tumor cells described in Example 4. CD3, TCR, CD8 and IFN were stained with antibodies and analyzed by flow cytometry. Expression of CD8 and IFN by the gated CD3 and TCR positive cells is shown for representative mice (left panel). Summarized data of the percentages of IFN+ cells in in CD8T cells (right panel). *, , and * indicate increasing amounts of statistical significance.
Figure 39:
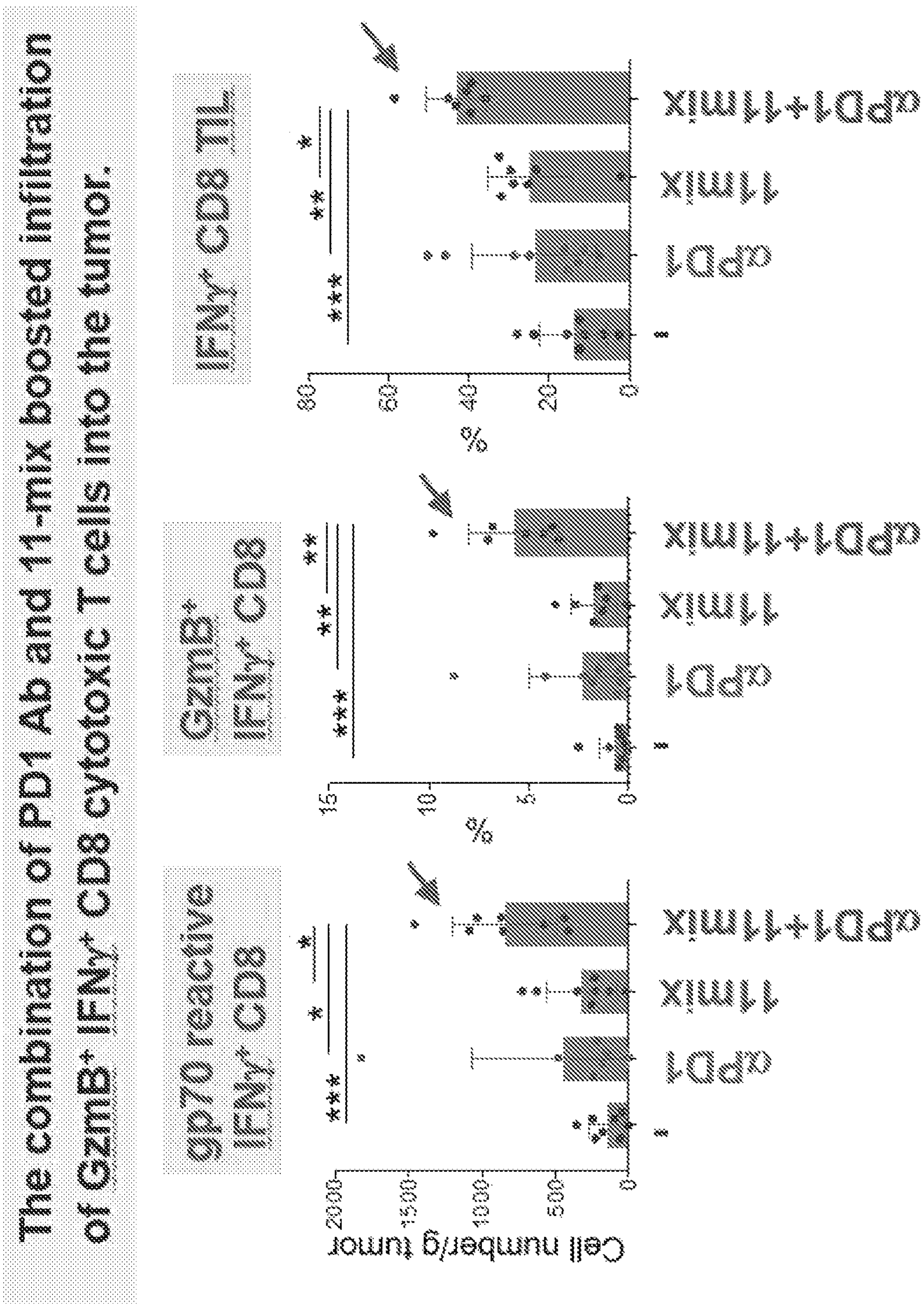
FIG. 39 shows data on lymphocytes isolated from tumor cells described in Example 4. The number of gp70-reactive IFN+ cells in CD8 T cells, GzmB+ IFN+ cells in CD8 T cells, and percentage of IFN+ CD8 T cells was assessed by flow cytometry analysis. *, , and * indicate increasing amounts of statistical significance.

Infiltrating lymphocytes from the groups of mice were also analyzed. It was found that mice that received the combination of the anti-PD1 antibody and the 11-mix had increased levels of infiltrating IFN+CD8+ T cells and increased levels of gp70-reactive IFN+CD8+ T cells and GzmB+IFN+CD8+ T cells (FIGS. 38 and 39).

Example 4: Anti-Cancer Characteristics of CD8+ T-Cell Inducing Bacterial Cocktail in Combination with CTLA-4 Immune Checkpoint Inhibitor To investigate whether colonization with the 11-mix in combination with immune checkpoint inhibitor anti-PD1 antibody could enhance anticancer immune responses, a MC38 colon cancer cell line was subcutaneously injected into mice.

Figure 40:
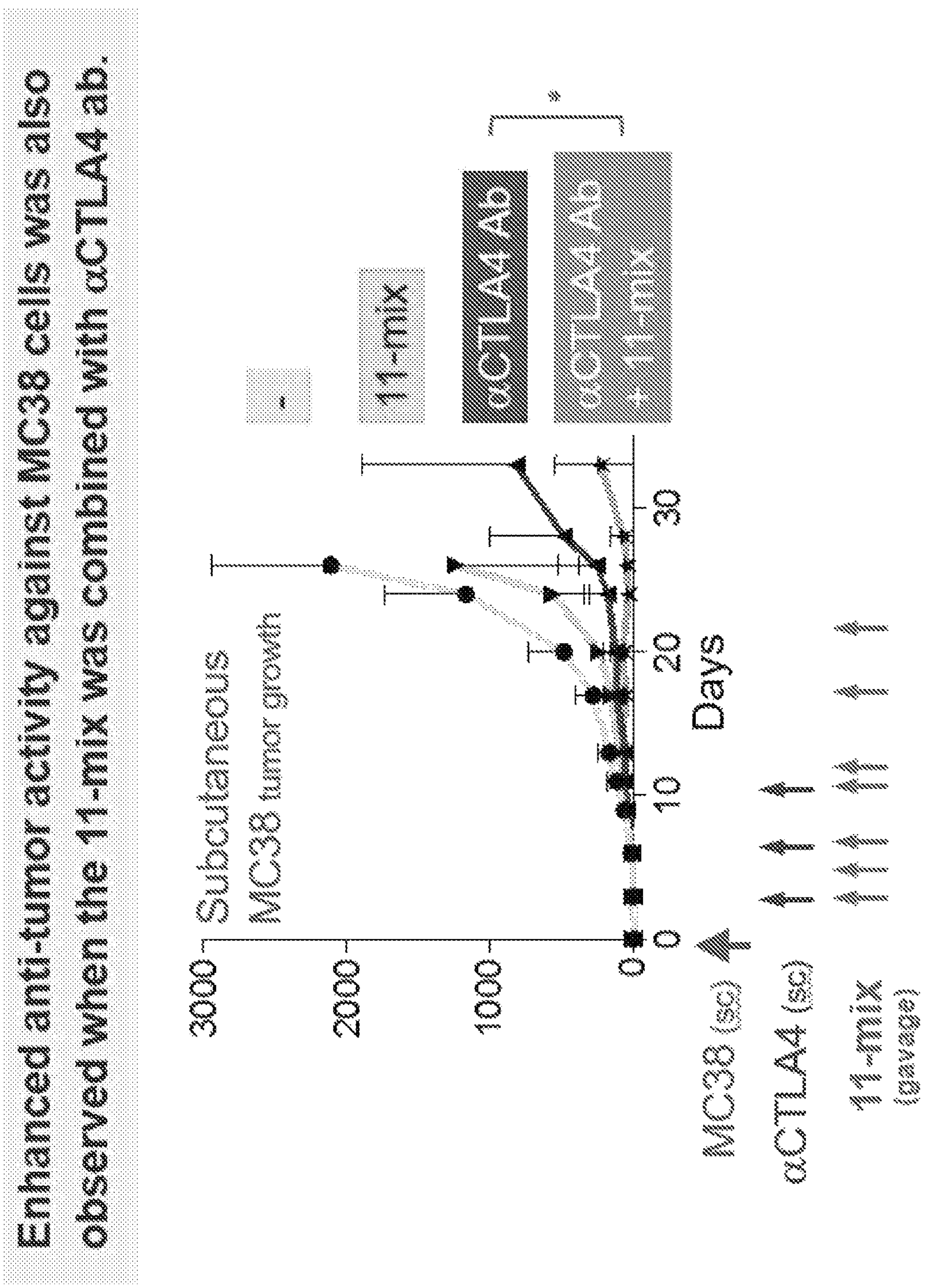
FIG. 40 shows data on experiments with MC38 tumor model described in Example 4. Mice were administered anti-CTLA4 antibody ("+αCTLA4 Ab") on the indicated days. Mice were gavaged with the mixture of 11 isolated bacterial strains on the indicated days ("11-mix"). Tumor volume was measured. * indicates statistical significance.

Mice were administered an anti-CTLA4 antibody (arrows on the timelines in FIG. 40) and/or the 11-mix (arrows with asterisk on the timelines in FIG. 40). The 11-mix was administered to the indicated groups of mice by gavage. Mice that received the combination of the anti-CTLA4 antibody and the 11-mix had reduced tumor volume (FIG. 40) compared to the other groups of mice.

Figure 41:
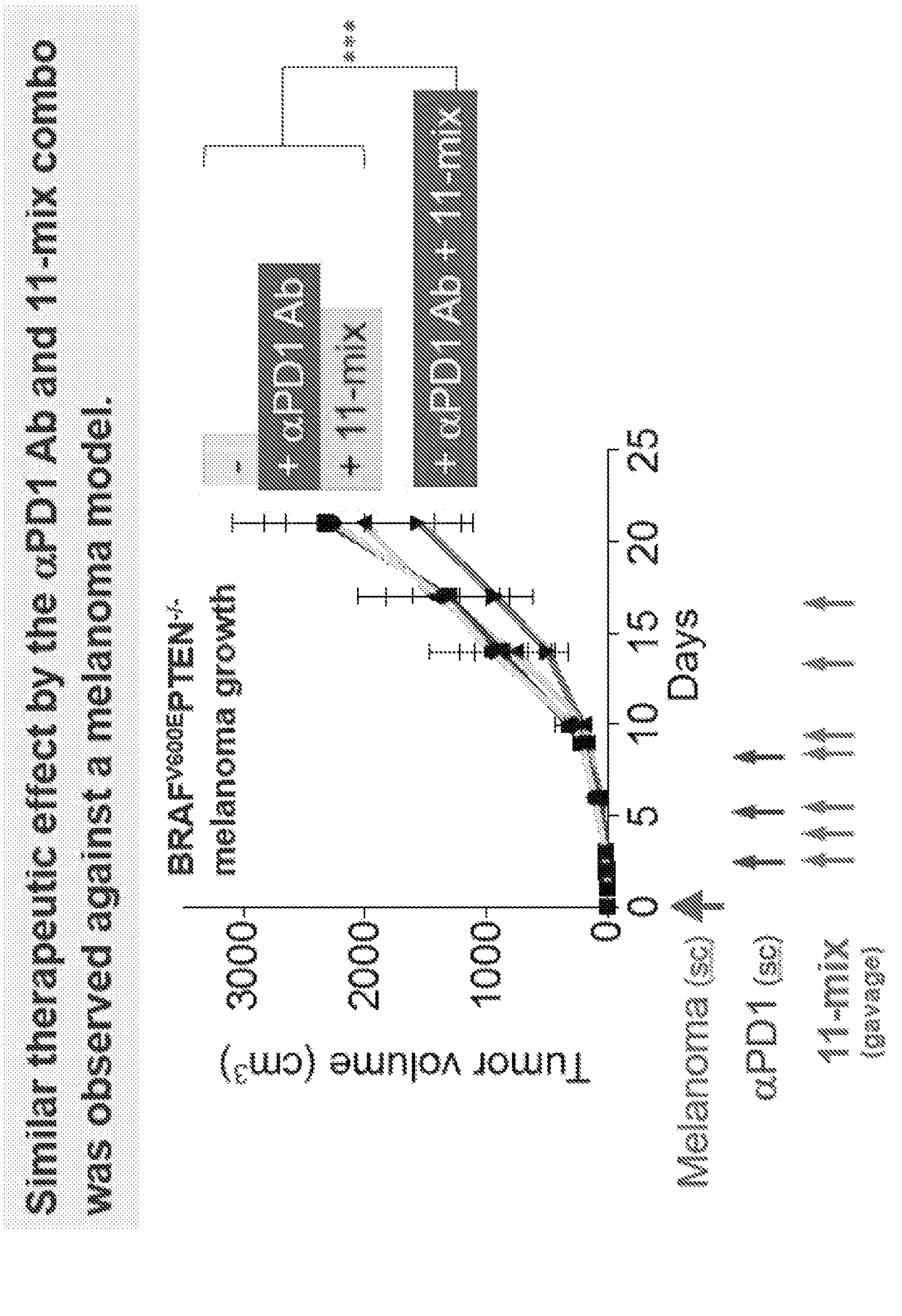
FIG. 41 shows data on experiments using the Braf Pten melanoma model described in Example 5. Mice were administered anti-PD1 antibody ("+αPD1 Ab") on the indicated days. Mice were gavaged with the mixture of 11 isolated bacterial strains on the indicated days ("11-mix"). Tumor volume was measured. *** indicates statistical significance.
Figure 42:
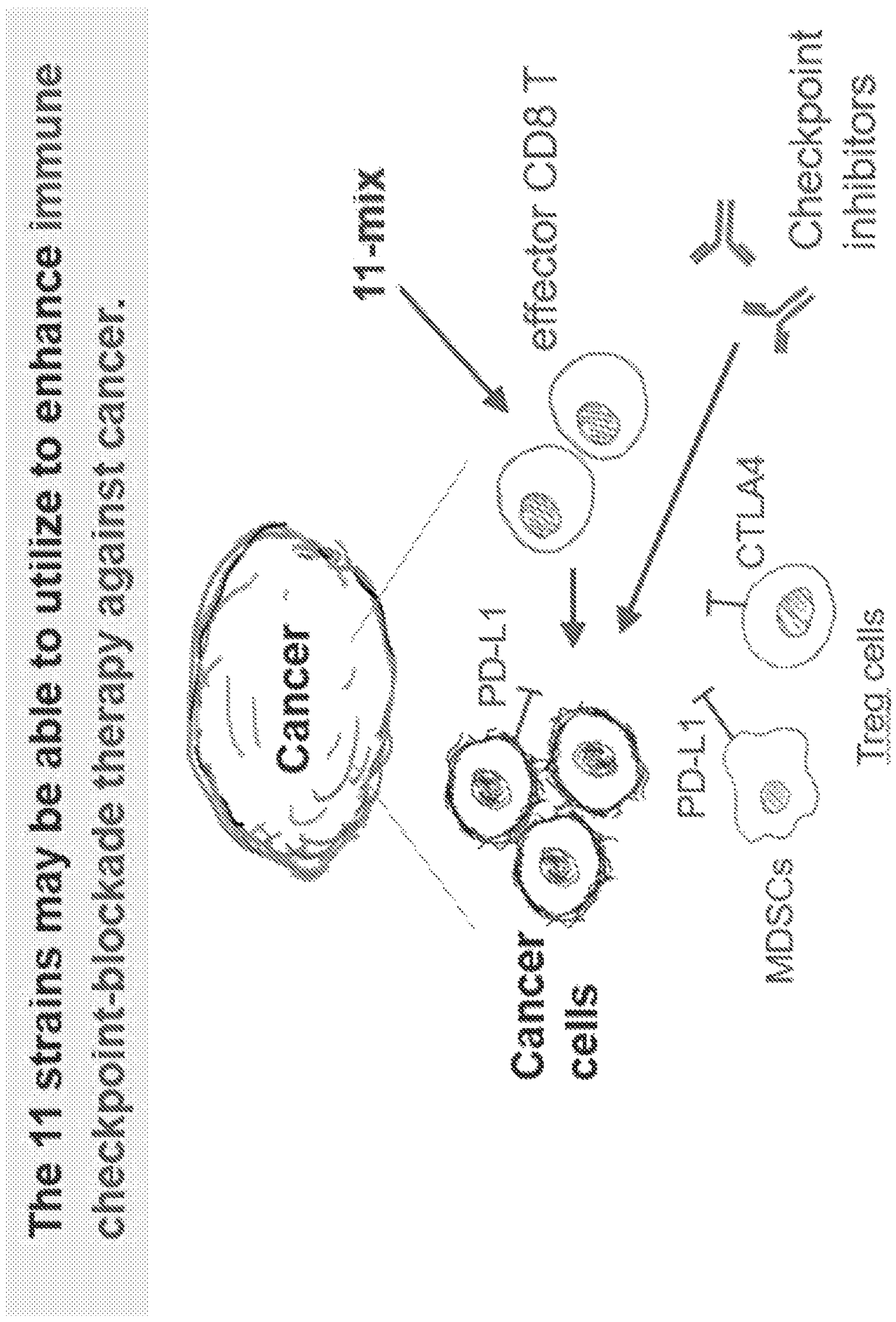
FIG. 42 shows a schematic of a non-limiting model schematic model in which the mixture of 11 isolated bacterial strains ("11-mix") and checkpoint inhibitors may be used for the treatment of cancer.

Example 5: Cancer Characteristics of CD8+ T-Cell Inducing Bacterial Cocktail Combination with an Anti-PD1 Antibody in a Melanoma Model A melanoma engraftment mouse model was used to evaluate the efficacy of the 11-mix in combination with a PD-1 antibody in the treatment of melanoma. Mice were engrafted with Braf Pten melanoma cells. Mice were administered an anti-PD1 antibody (arrows on the timelines in FIG. 41) and/or the 11-mix (arrows with asterisk on the timelines in FIG. 41). The 11-mix was administered to the indicated groups of mice by gavage. Mice that received the combination of the anti-PD1 antibody and the 11-mix had reduced tumor volume (FIG. 41), as compared to the other groups of mice.

These results show that treatment with 11-mix in combination with the anti-PD1 antibody systemically activates CD8 T cells in the melanoma.

Example 6: The Role of Transcription Factors BATF3 and Irf4

Figure 26:
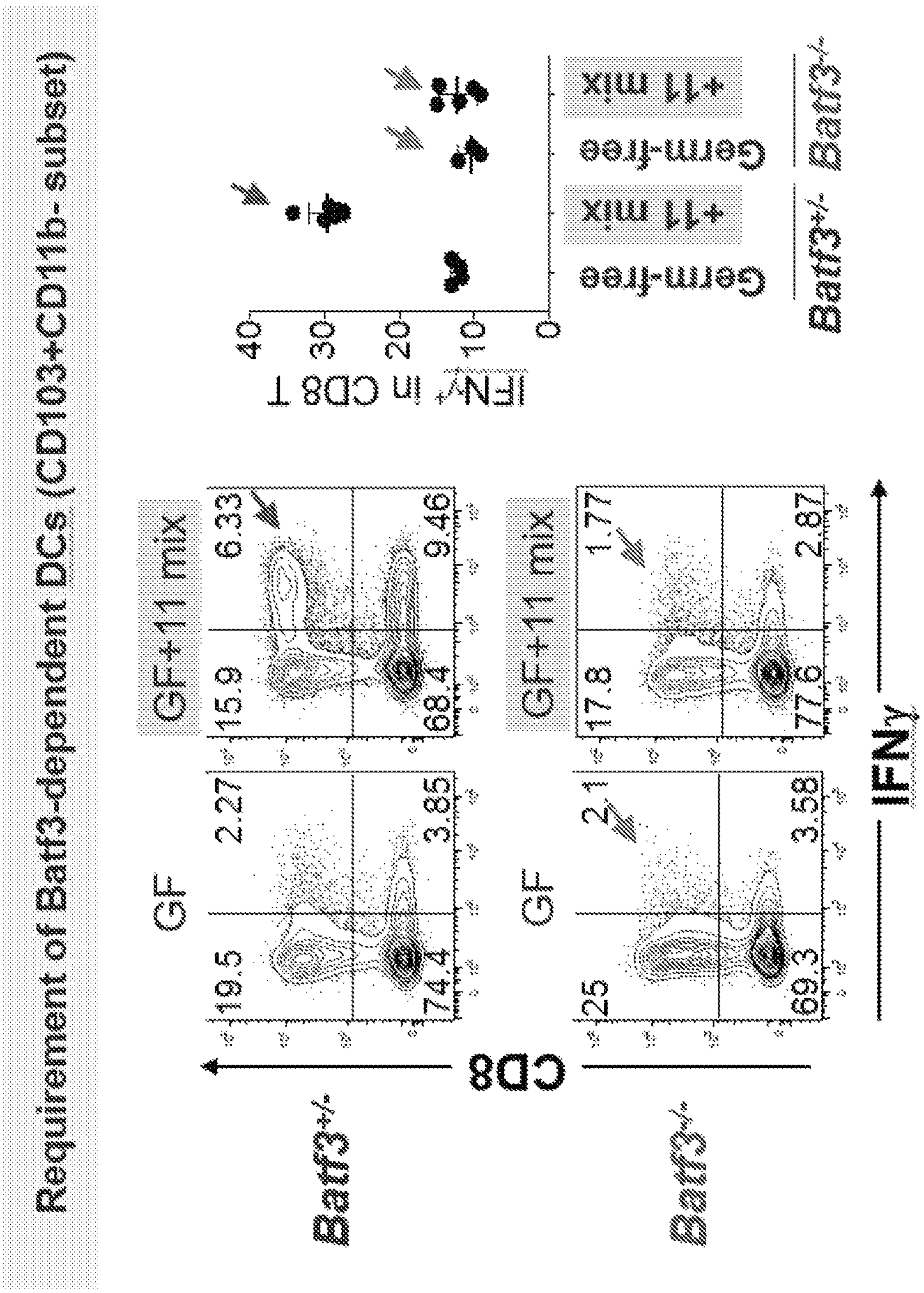
FIG. 26 shows the results from the experiments of Example 6. The experiments show that Batf3 is required for the 11-mix to induce CD8-T cells, as evidenced by the flow cytometry and the percentage of IFN+ in the CD8+ population of cells isolated from the indicated mice.
Figures 43A, 43B, 43C, 43D, 43E:
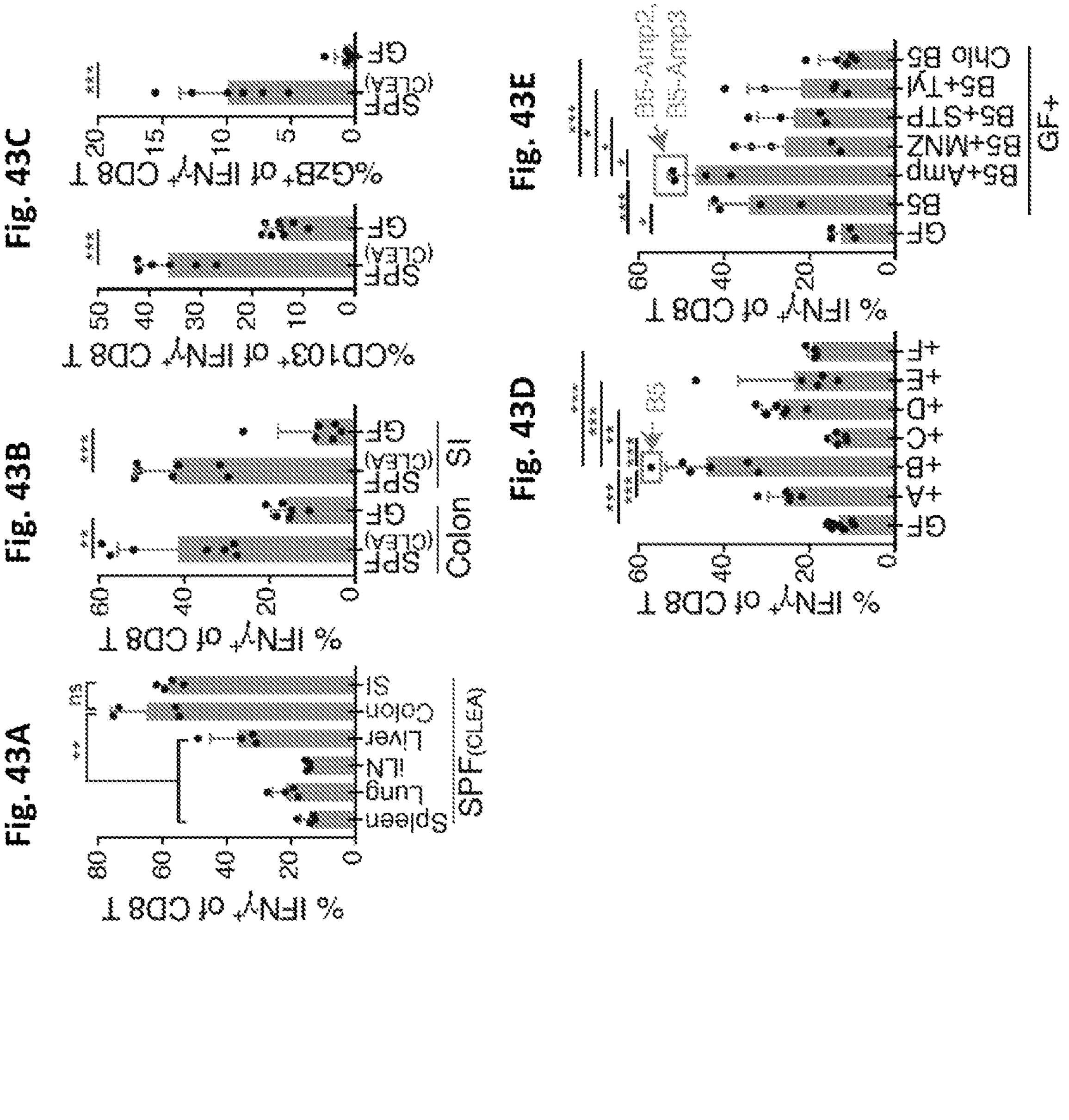
FIGS. 43A-43M show isolation and identification of 11 bacterial strains from healthy human microbiota that induce IFN+CD8 T cells.

The 11-mix was administered to mice that have the BATF3 transcription factor and mice that do not have the BATF3 transcription factor. Mice that do not have the transcription factor BATF3 are not susceptible to CD8 T cell induction by the 11-mix (FIG. 26). It is likely that CD103-CD11b dendritic cells are required for stimulation of IFN-gamma producing CD8 and Th1 cells. The induction of Th17 cells by the 11-mix cocktail is independent of BAFT3 status. (FIG. 43C). FIGS. 43 and 44 show the results from the experiments of Example 8. The experiments show that BATF3 is required for the 11-mix to induce CD8-T cells. BATF3 is not required to induce Th17.

Figure 27:
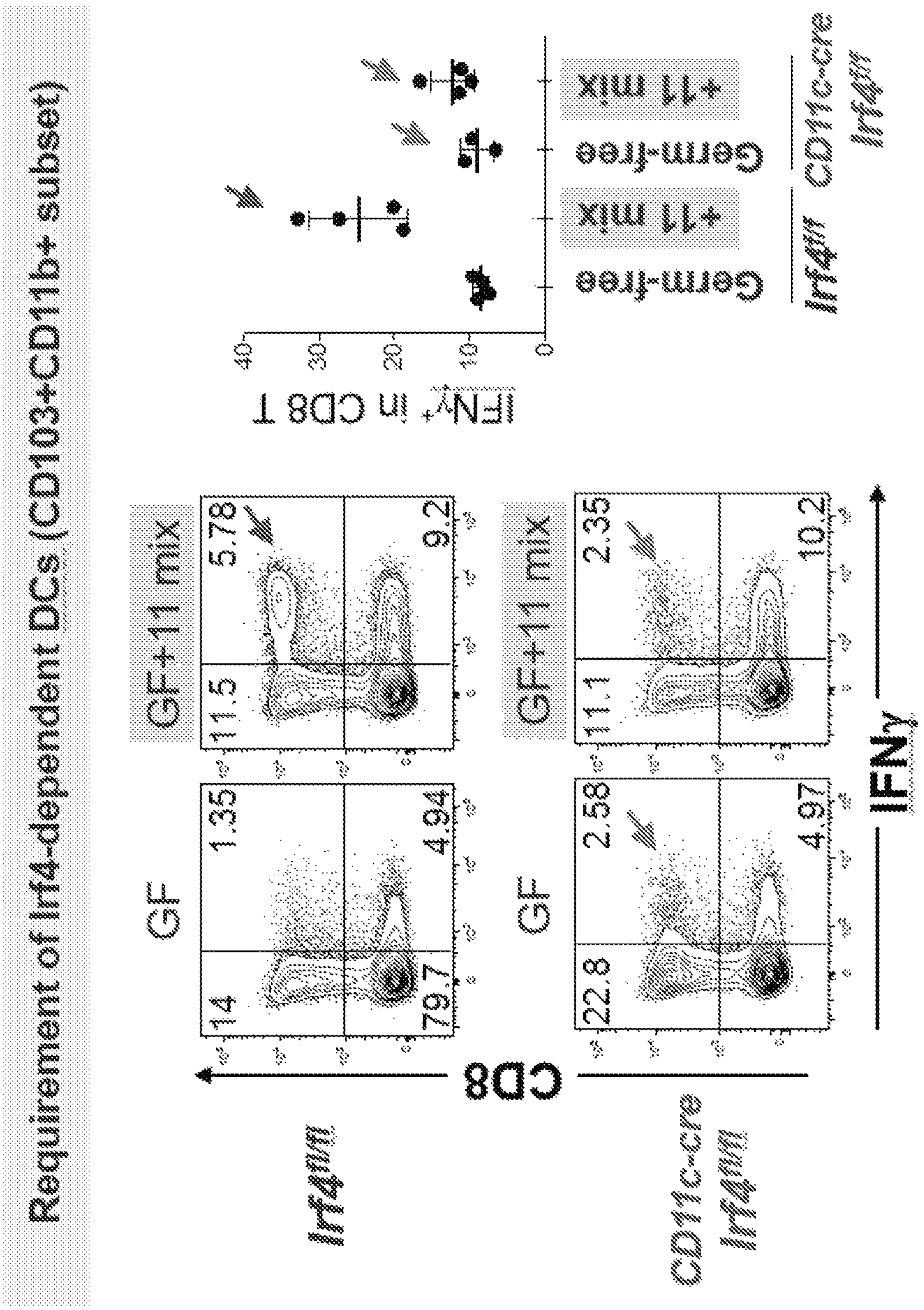
FIG. 27 shows the results from the experiments of Example 6. The experiments show that Irf4 is required for the 11-mix to induce CD8-T cells, as evidenced by the flow cytometry and the percentage of IFN+ in the CD8+ population of cells isolated from the indicated mice.

The 11-mix was also administered to mice that have the Irf4 transcription factor and mice that do not have the Irf4 transcription factor. Mice that do not have the transcription factor Irf4 are not susceptible to CD8 T cell induction by the 11-mix (FIG. 27). The experiments show that Irf4 is required for the 11-mix to induce CD8-T cells.

Figure 28:
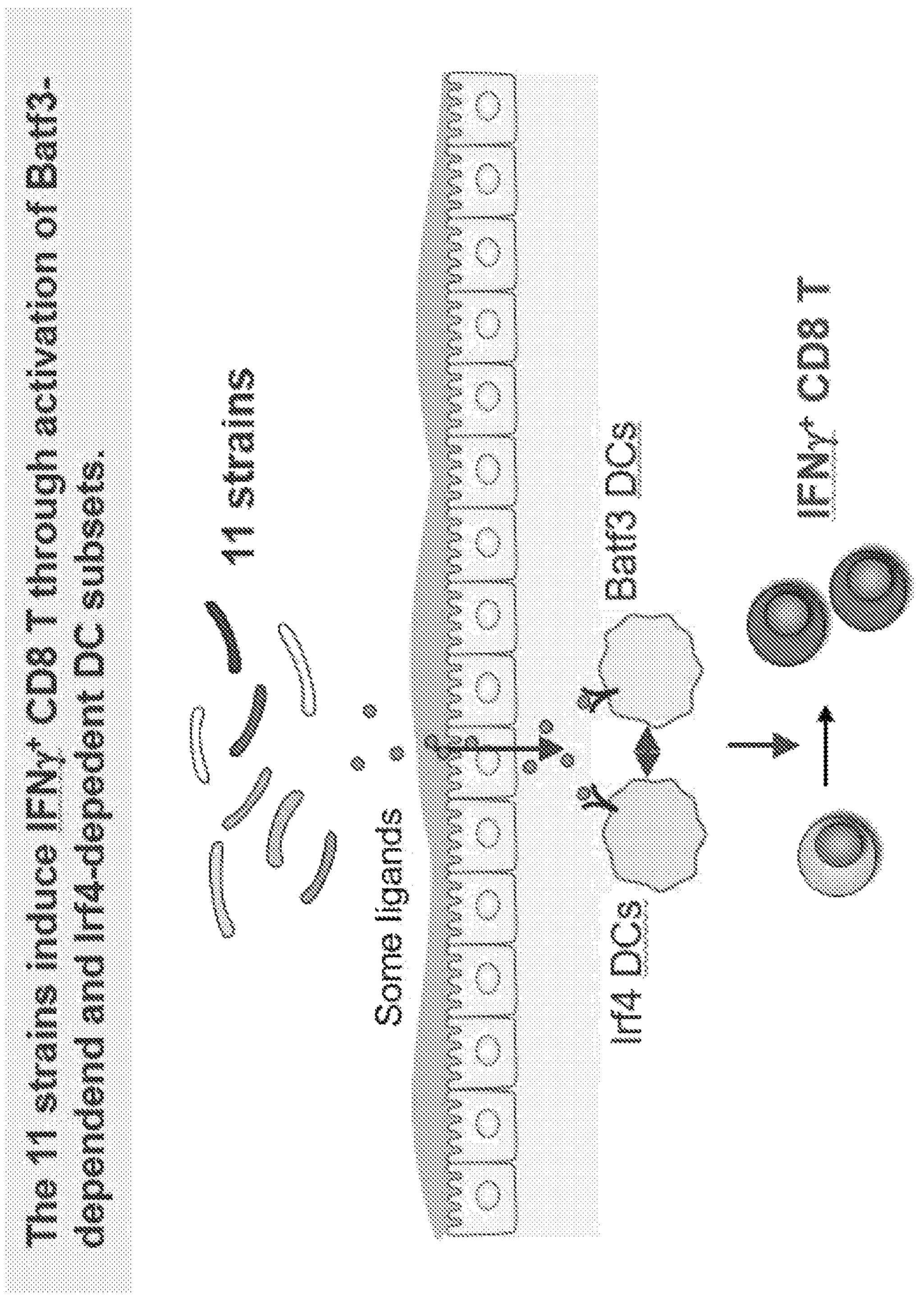
FIG. 28 shows a schematic of a non-limiting model in which ligands from the mixture of 11 isolated bacterial strains induce IFN-positive CD8 T cells through activation of Batf3-dependent and Irf4-dependent dendritic cell populations.

These results suggest that the mixture of 11 isolated bacterial stains, or ligands from the mixture, induces IFN+ CD8+ T cells through BATF3-dependent dendritic cells and/or Irf4-dependent dendritic cells (FIG. 28).

Example 7: Treatment of Listeria Infected Mice

Figure 34:
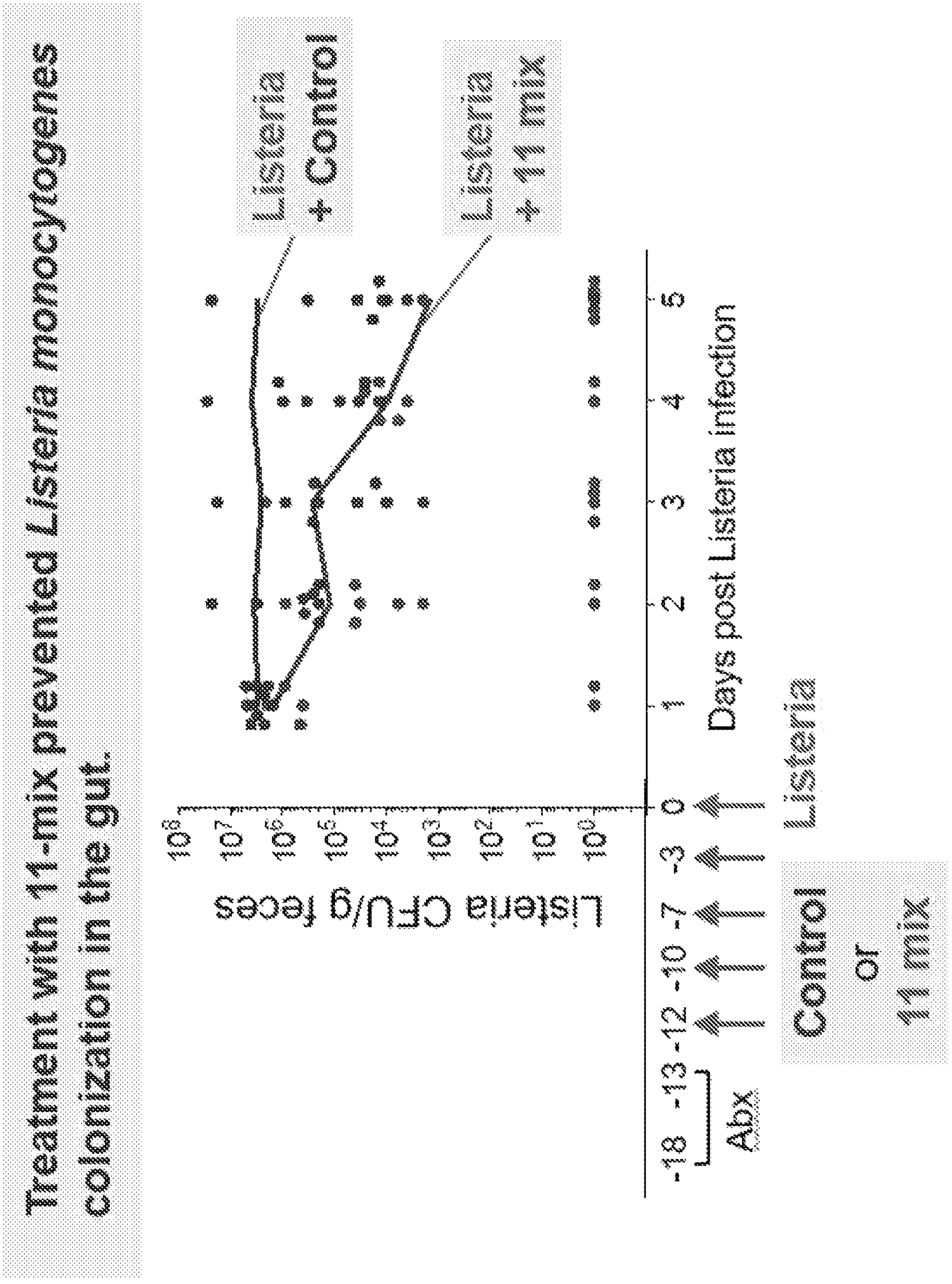
FIG. 34 shows the results from the experiments of Example 7. The experiments show that the 11-mix is effective in clearing Listeria from infected mice, as evidenced in a decrease in the amount of Listeria CFUs in the feces.
Figure 35:
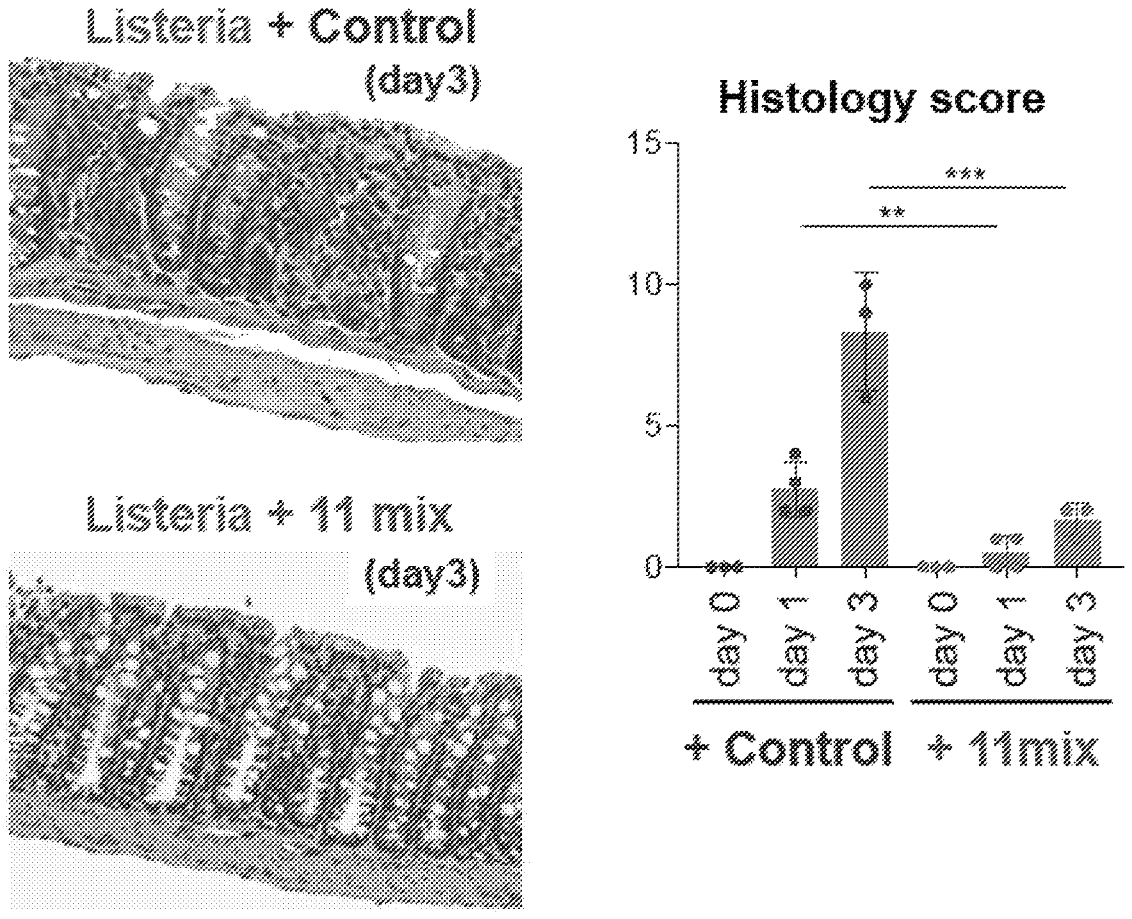
FIG. 35 shows the results from the experiments of Example 7. The experiments show that inoculation with the mixture of 11 isolated bacterial strains prevented intestinal pathology in Listeria infected mice.

Since IFNg+CD8+ T cells have been reported to play critical roles in controlling intracellular pathogens, it was evaluated whether oral supplementation with the 11 strain mixture in a multiple dosing regimen could augment host protective immunity against Listeria monocytogenes infection. SPF mice were treated with AVMN (ampicillin, vancomycin, metronidazole, neomycin) for 5 days via the drinking water. After one day washout of antibiotics, multiple oral administrations of the 11-mix (4 times) were performed. To reconstitute complex microbiota, fecal microbiota from SPF mice were introduced together with the first administration of 11-mix. The mice were then orally infected with Listeria monocytogenes on day 0. Fecal Listeria CFU and body weight of mice were determined. Treatment with 11-mix significantly reduced Listeria monocytogenes colonization of the gut lumen (FIG. 34).

Intestines from Listeria infected mice were also evaluated by histology. Treatment with 11-mix significantly reduced intestinal pathology and histology score of Listeria monocytogenes infected mice (FIG. 34).

Thus, administration of the 11 strain-mixture can provide protective immunity against an intracellular, infectious pathogen.

Example 8: Abundance of Bacterial Strains in Healthy Human Microbiota

Figure 32:
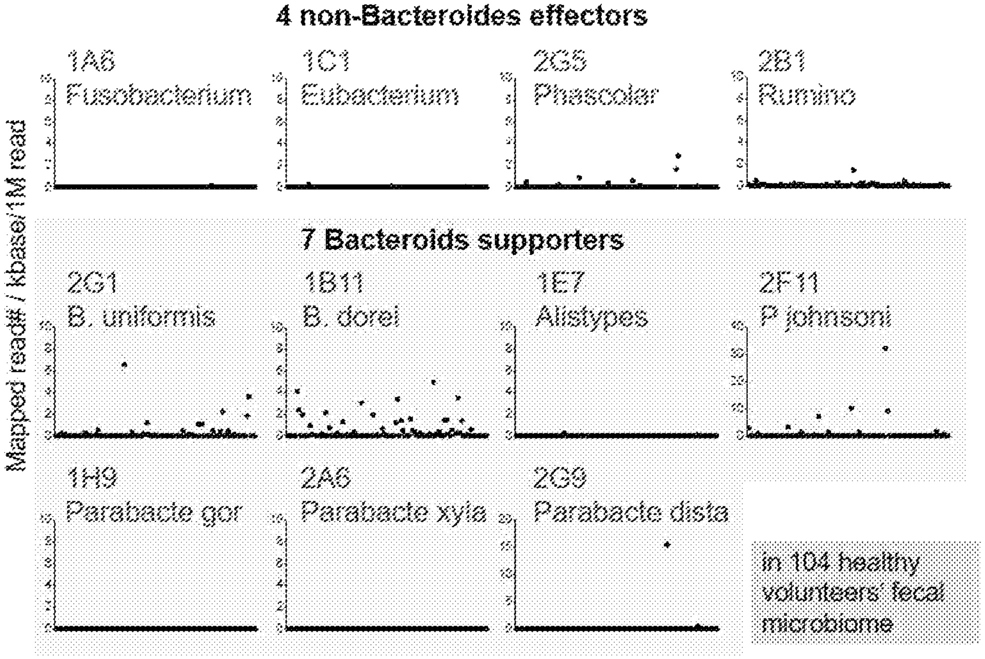
FIG. 32 presents plots showing the abundance of each of the indicated bacterial strains in the fecal microbiota of 104 human volunteers. Abundance is shown as the number of mapped reads/kbase/1M read for each of the bacterial strains.

The fecal microbiota from 104 healthy volunteers was analyzed to determine the abundance of each of the bacterial strains of the 11 mixture. Briefly, fecal samples were processed and sequenced. As shown in FIG. 32, many of the 11 bacterial strains were found to be rare or of very low abundance in the human microbiome samples. In particular, two effector strains, *Fusobacterium ulcerans* and *Eubacterium limosum* were found to have low abundance, even in the sample from the donor from which these strains were isolated.

Example 9: Further Analysis of the Mixture of 11 Bacterial Strains

Figure 33:
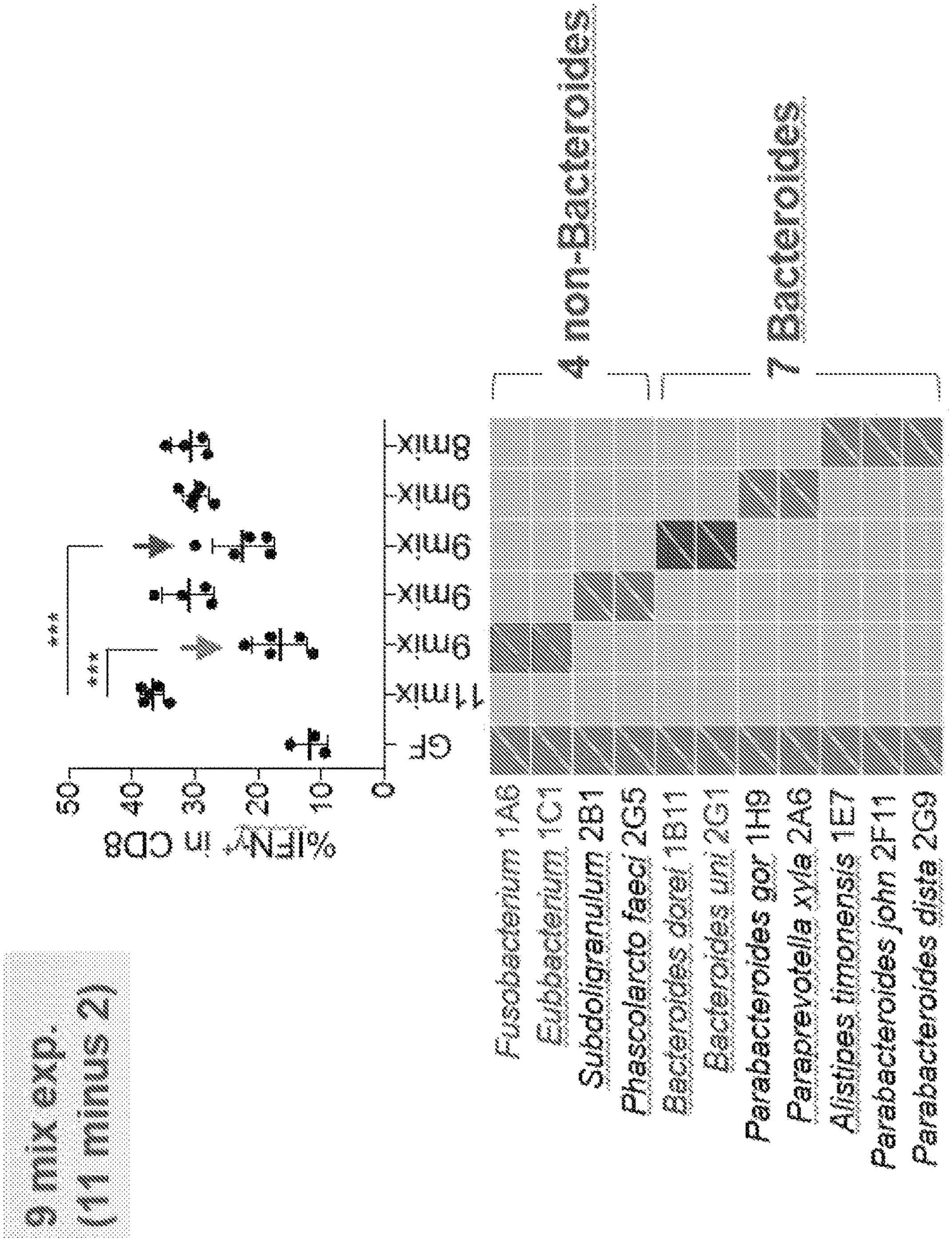
FIG. 33 shows data of experiments with the indicated purified bacterial mixtures, which were orally administered to germ free mice. Lymphocytes were isolated from the lamina propria of the large intestine and stimulated with PMA/ionomycin for 3.5 hours. CD8 and IFN were stained with antibodies and analyzed by flow cytometry. The graph presents a summary of the data of the percentages of IFN positive cells within CD8+ cell population. Each symbol represents an individual mouse. *** denotes statistical significance. The bacterial strains present in each of the purified bacterial mixtures are shown below. A diagonal slash indicates strains of the 11 isolated bacterial strains ("11 mix") that are absent from the respective mixtures of 9 strains ("9 mix") or 8 strains ("8 mix").

The mixture of 11 bacterial strains was further analyzed to determine whether specific strains were important components for the induction of IFN producing CD8+ T cells. As shown in FIG. 33, several bacterial mixtures containing 8 or 9 strains from the 11 strain mixture were prepared.

Briefly, bacterial mixtures that lacked *Fusobacterium ulcerans* and *Eubacterium limosum* were found to induce reduced levels of IFN producing CD8+ T cells compared to the 11 strain mixture (FIG. 33). Additionally, bacterial mixtures that lacked *Bacteroides dorei* and *Bacteroides uniformis* were found to induce reduced levels of IFN producing CD8+ T cells compared to the 11 strain mixture (FIG. 33).

Example 10: A Defined Consortium of Human Gut Commensals Induces CD8 T Cells and Modulates Host Microbial and Cancer Immunity There is a growing appreciation for the importance of the gut microbiota as a therapeutic target in various diseases, including infection and cancer[1-3]. However, there are only a handful of known commensal strains (either single species or defined communities) that can potentially be utilized to manipulate specific host physiological functions, such as the immune response[4-7]. In this study, we rationally isolated a consortium of commensal bacteria from healthy human donor faeces that was capable of robustly inducing interferon-(IFNγ)-producing CD8 T cells in the intestine and enhancing anti-microbial and anti-tumour immunity. IFN+CD8 T cells were highly abundant in the intestines of specific pathogen-free (SPF) mice but were greatly diminished in germ-free (GF) mice. To identify and isolate human-associated IFN+CD8 T cell-inducing bacteria, GF mice were colonised with faecal microbiota from healthy human volunteers. Individual stool samples showed considerable variability in their ability to induce colonic IFN+CD8 T cells. Focusing or the sample that elicited the greatest induction, we performed a series of rigorous selection steps to narrow the candidate effector bacteria down to 11 strains without sacrificing IFN+CD8 T cell-induction potency. These 11 strains act cooperatively to mediate colonic IFN+CD8 T cell induction through the activation of Batf3-dependent and IRF4-dependent dendritic cell subsets without causing inflammation. Repetitive administration of the 11-strain mixture to SPF mice enhanced both host resistance against Listens monocytogenes infection and therapeutic efficacy in syngeneic tumour models when given in conjunction with PD-1 or CTLA4 monoclonal antibody (mAb) immune checkpoint inhibitors. The 11 strains primarily represent rare, low-abundance components of the human microbiome, and thus have great potential as broadly effective biotherapeutics.

Figure 47A:
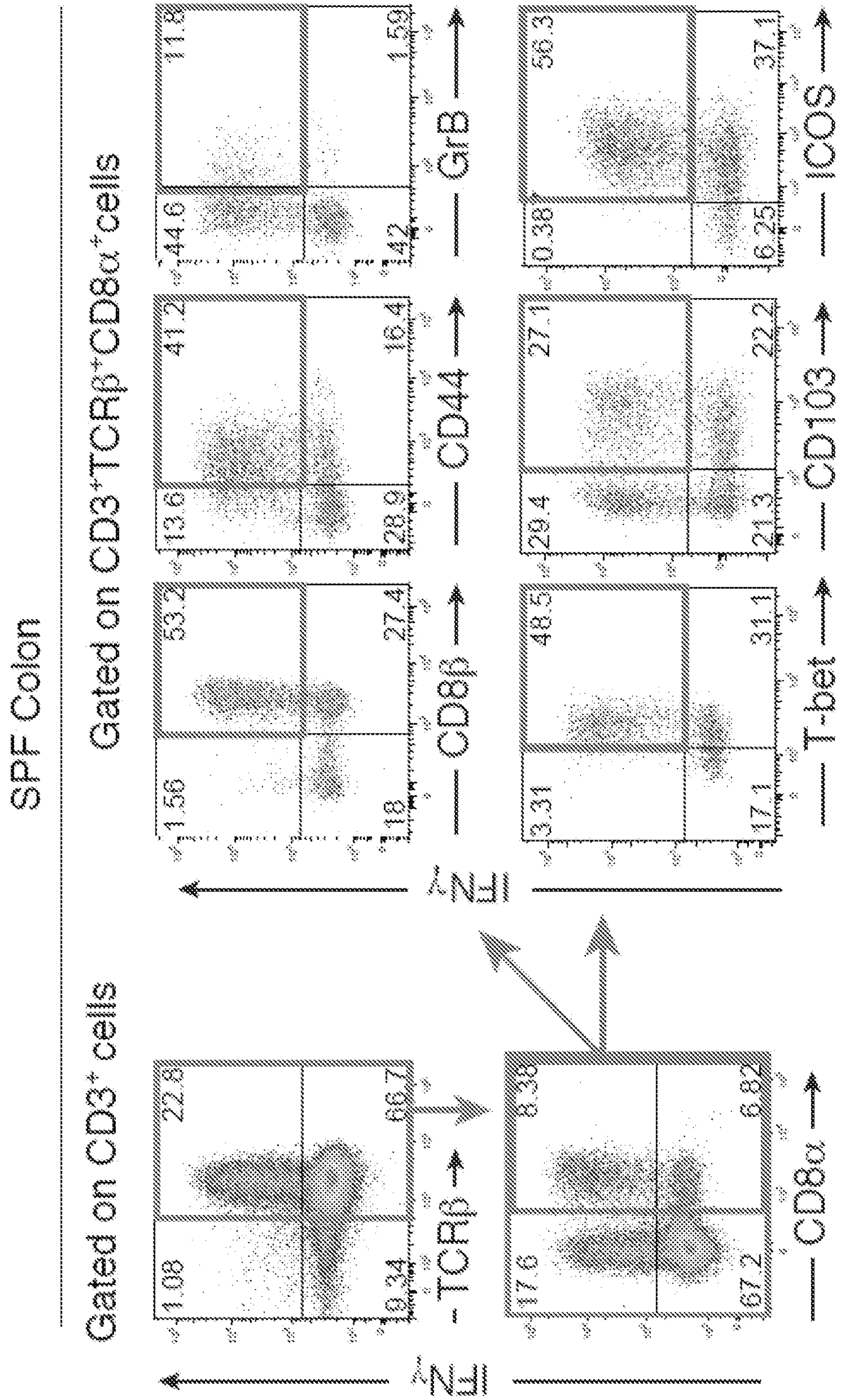
FIGS. 47A-47E show characterization of intestinal IFN+ CD8 T cell populations in GF and SPF mice.
Figures 47B, 47C, 47D, 47E:
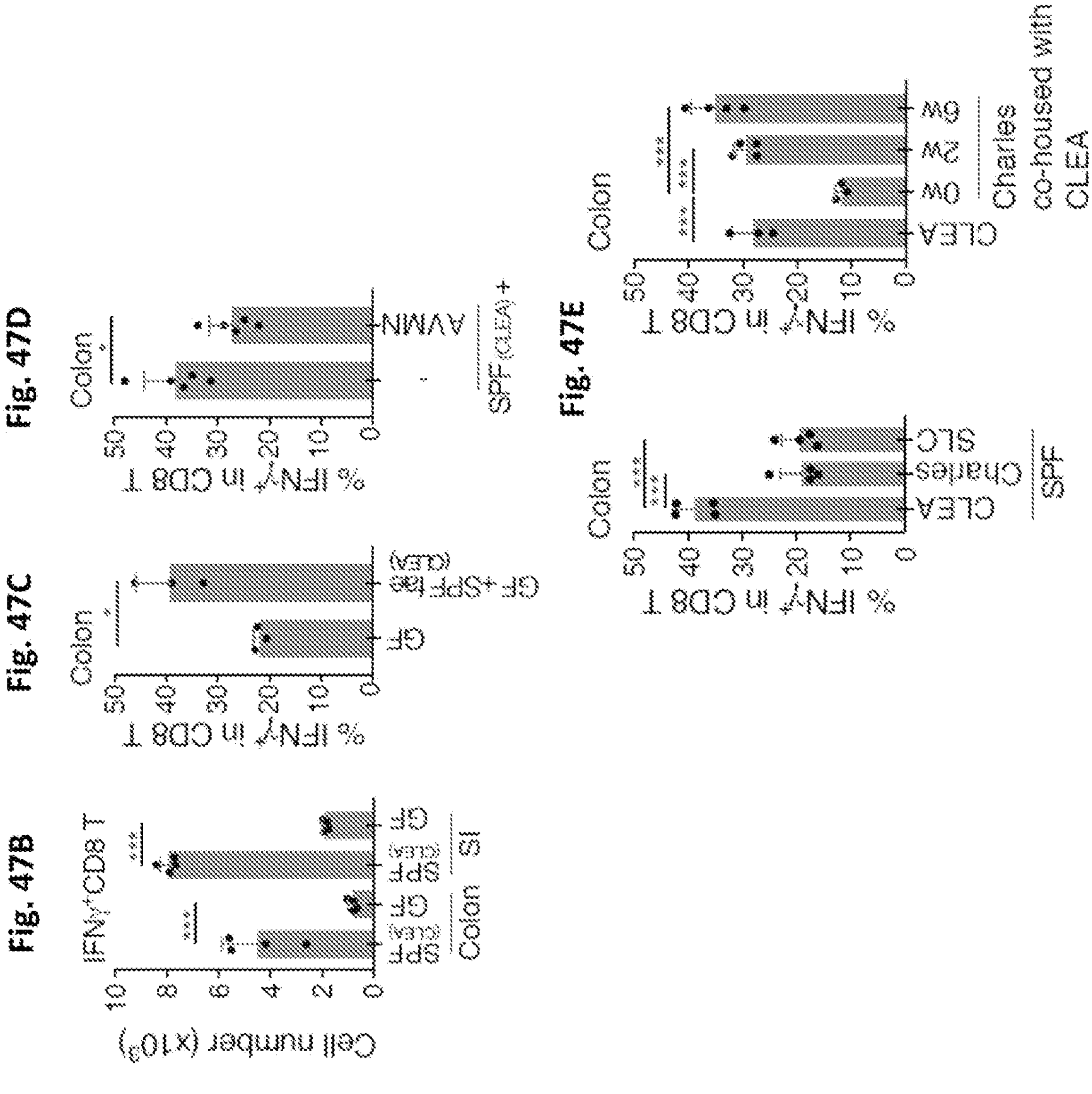

IFN-expressing CD8 T cells were constitutively present at high frequencies in the colonic and small intestinal (SI) lamina propria (LP) as compared to other organs in SPF mice (C57BL/6 obtained from CLEA Japan) (FIG. 43A), reminiscent of the preferential localization of T helper 17 ($T_H17$) and regulatory T ($T_{reg}$) cells to the gut[4,8,9]. A large proportion of colonic LP IFN+CD8 T cells expressed the -T cell receptor (TCR), CD8/, CD44, and T-bet (FIG. 47A), indicating they were primarily activated/memory cells differentiated from conventional CD8 T cells. Many of the IFN+CD8 T cells expressed inducible T cell costimulator (ICOS) and the -chain (CD103) of integrin E7 (FIG. 47A), both markers of tissue-resident memory T ($T_{RM}$) cells[10-12]. A subset of IFN+CD8 T cells also expressed granzyme B (GrB) (FIG. 47A). The frequency and number of both colonic and SI LP IFN+CD8 T cells were markedly decreased in GF as compared to SPF mice (FIG. 43B and FIG. 47B), suggesting that the microbiota plays a critical role in IFN+CD8 T cell accumulation. This microbiota dependence was also clearly observed in the CD103+ and GrB+ cell fractions of IFN+CD8 T cells (FIG. 43C). Oral administration of faecal suspensions from SPF mice ameliorated the deficit in colonic IFN+CD8 T cells in GF mice (FIG. 47C). Conversely, treatment of adult SPF mice with an antibiotic cocktail of ampicillin, vancomycin, metronidazole, and neomycin (AVMN) markedly reduced IFN+CD8 T cell frequency (FIG. 47D). Furthermore, this subpopulation in SPF mice varied with housing conditions (high in mice obtained from CLEA; low in those from SLC and Charles), and co-housing of mice with high versus low frequencies for 2 weeks resulted in all mice ultimately displaying a high-frequency phenotype (FIG. 47E). Collectively, these results suggest that the frequency of IFN+CD8 T cells is plastic, with specific members of the microbiota promoting their accumulation in the intestine in an inducible and reversible manner.

Figures 43F, 43G:
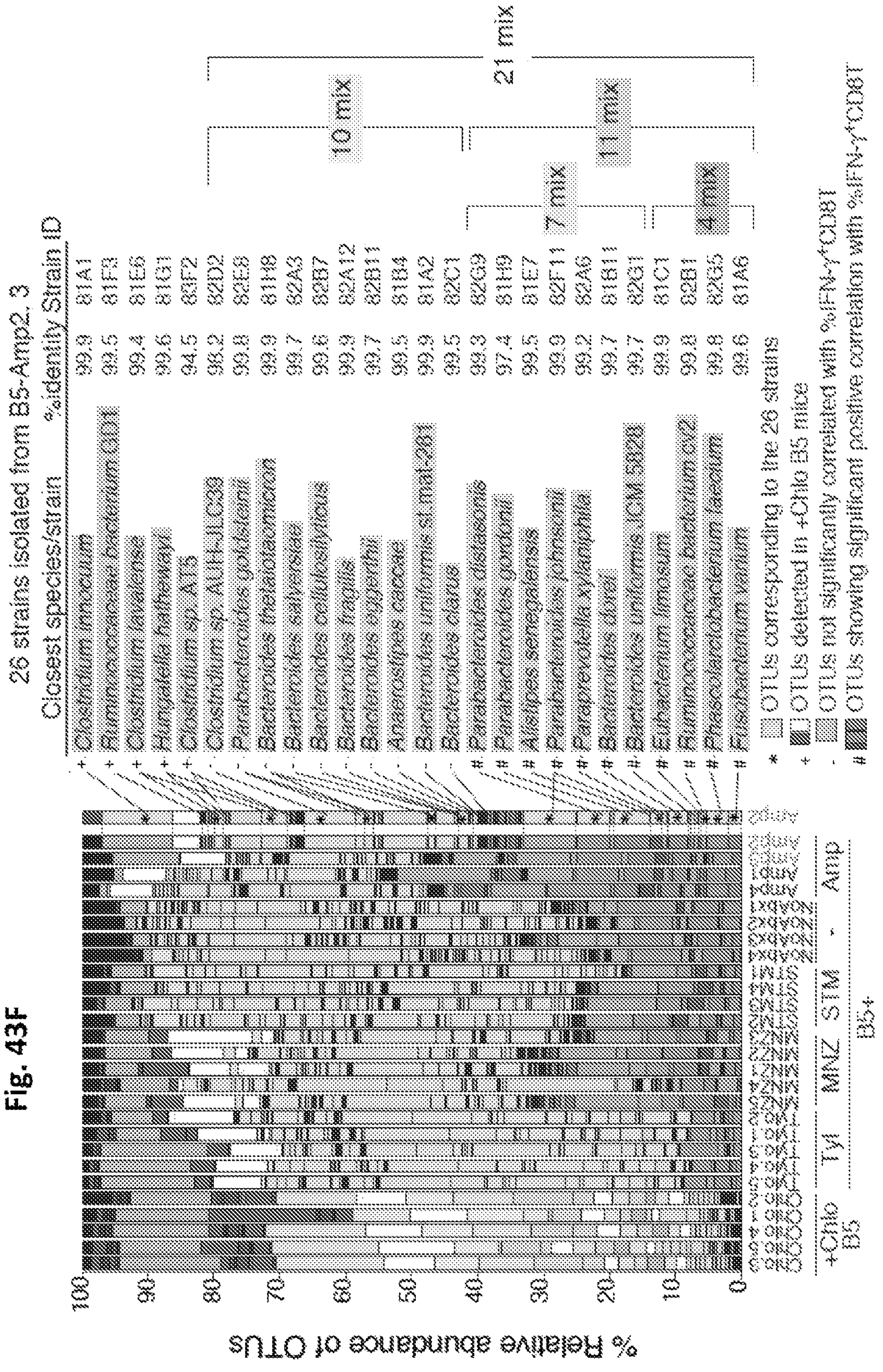
Figure 48:
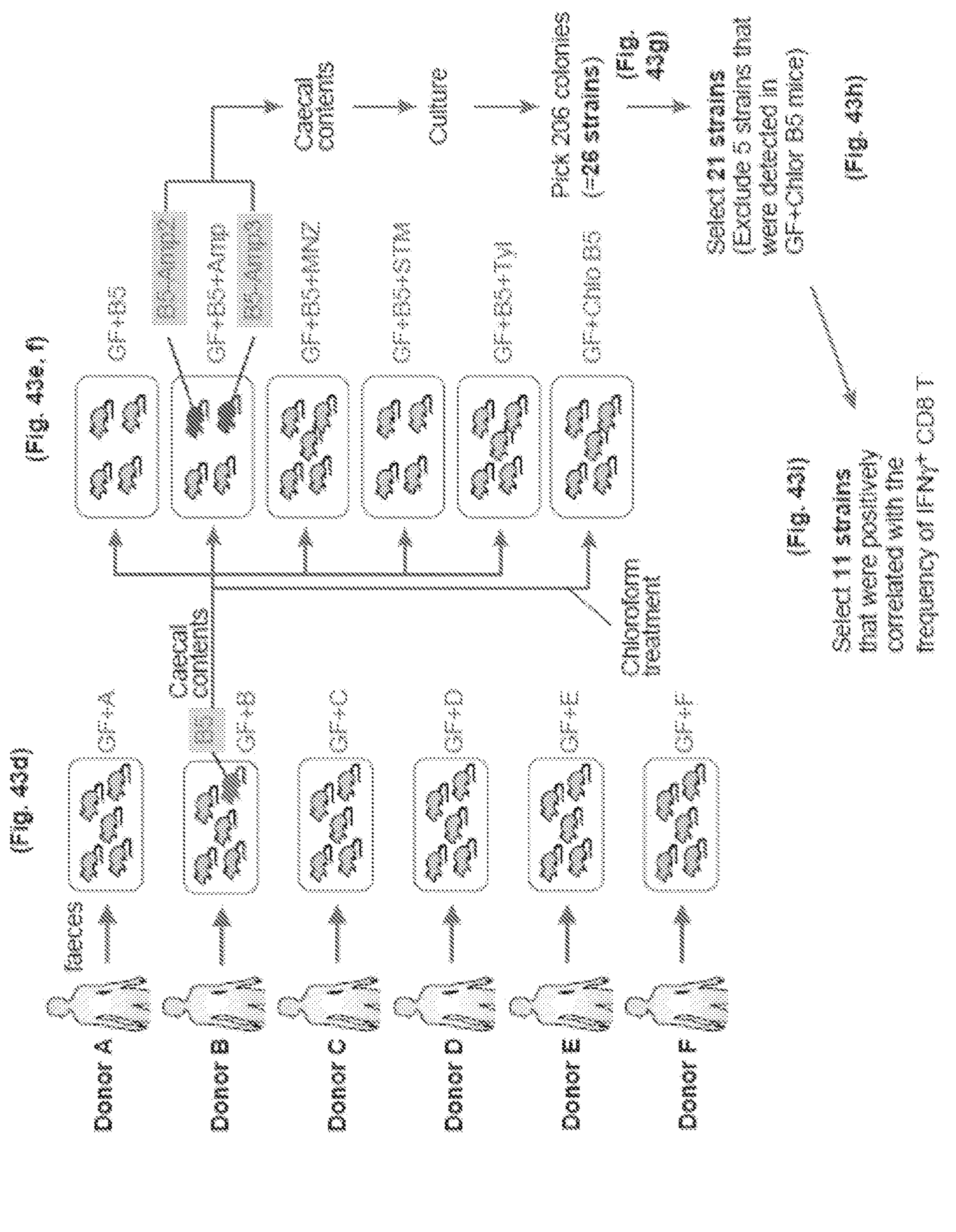
FIG. 48 shows a schematic representation of the strategy for isolating IFN+CD8+ T cell-inducing bacteria from healthy human gut microbiota.
Figure 49A:
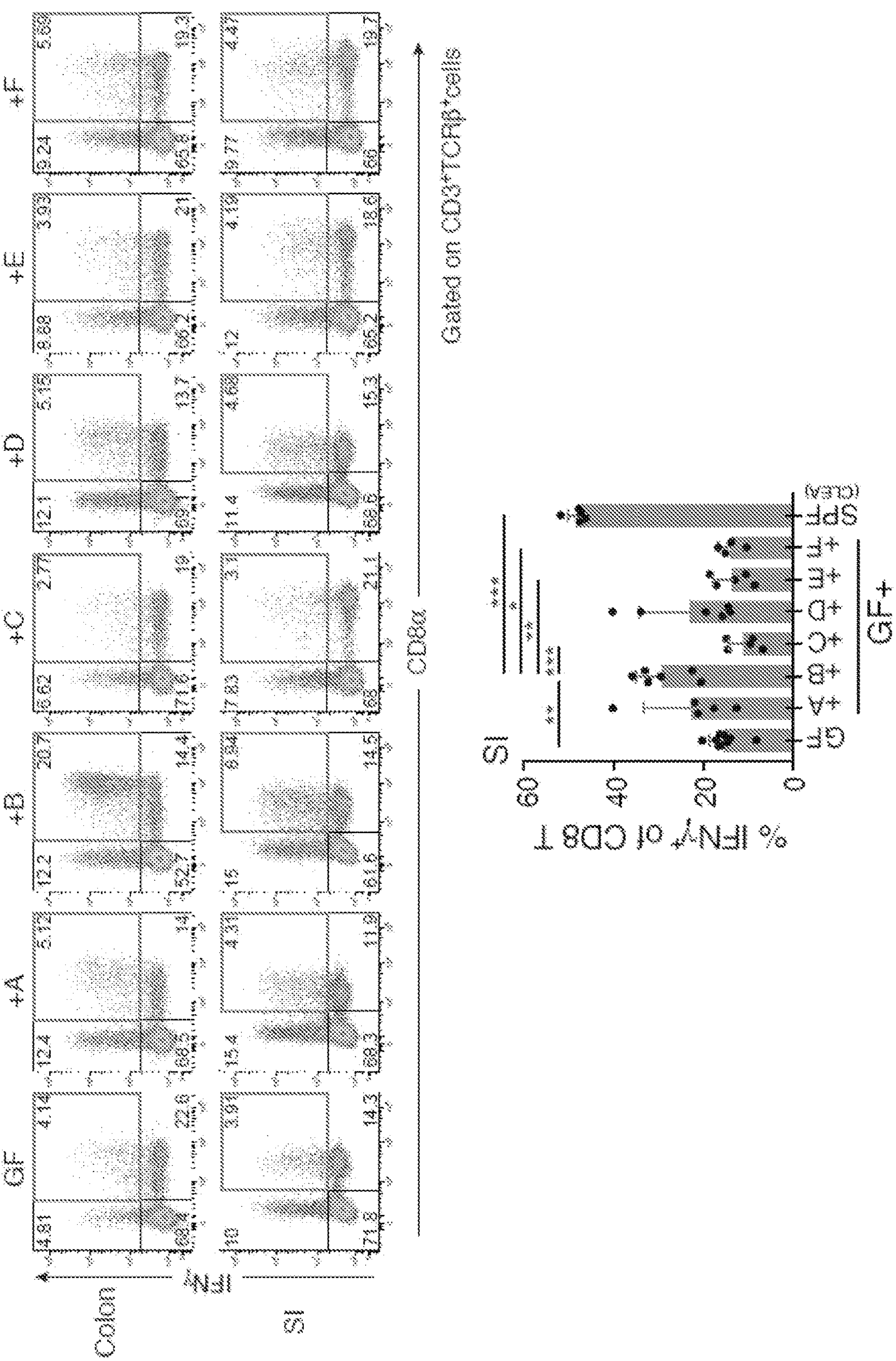
Figure 49B:
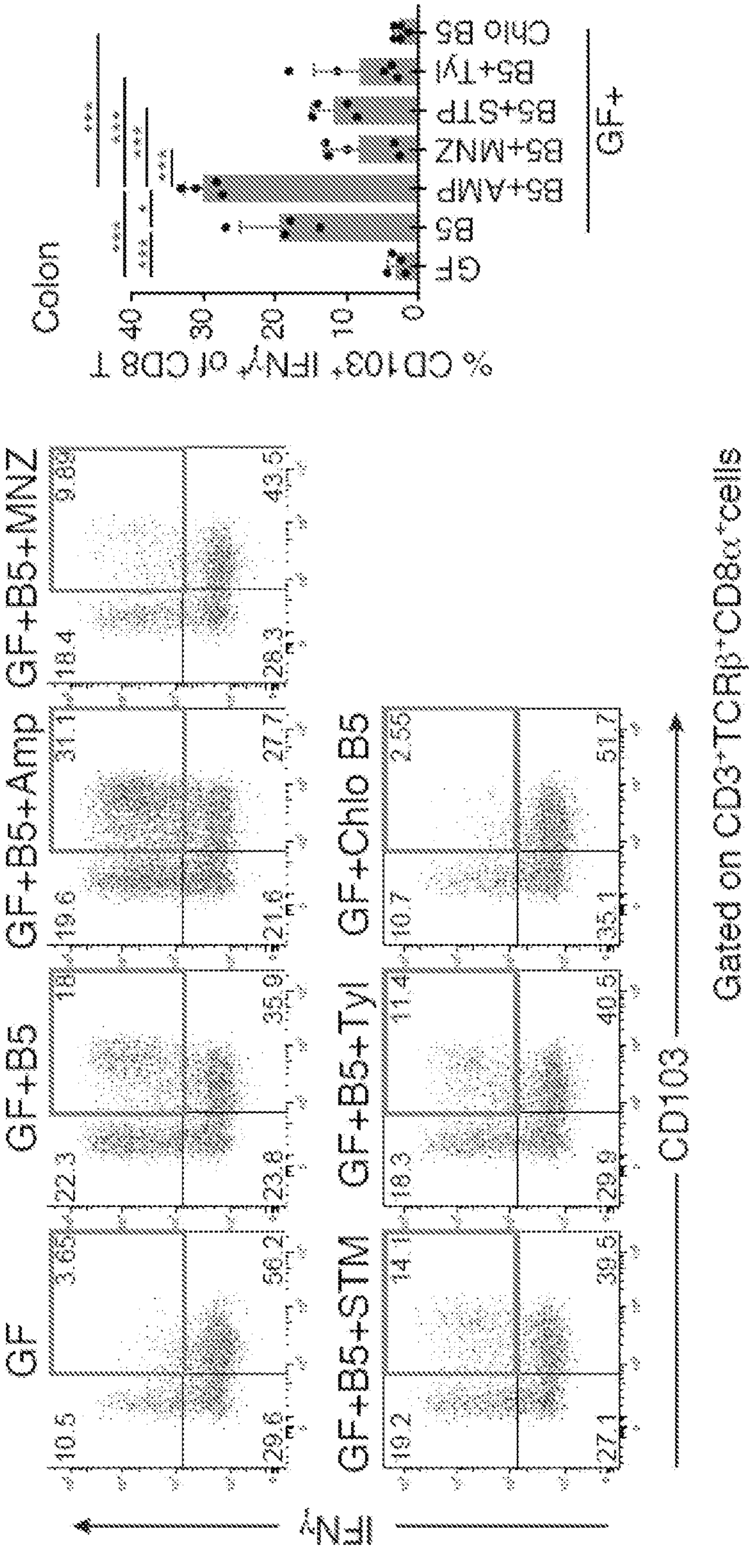
FIG. 49B shows representative flow cytometry plots (left) showing the frequency of IFN+ CD103+ cells among the colonic LP CD3+TCR+CD8+ parent population in GF mice orally inoculated with caecal contents from mouse B5 and treated with the indicated antibiotics (B5+Abx), untreated (B5), or GF mice inoculated with chloroform-treated caecal contents from mouse B5 (Chlo B5). The bar graph (FIG. 49B, right) summarizes the frequency of IFN+CD103+ cells among the colonic lamina propria CD3+TCR+CD8+ parent population of cells in each group of mice. Each symbol represents an individual animal (n=4-9), and the height of the bars indicates the mean. Error bars, s50]

From a translational perspective we mined the human, rather than the murine, faecal microbiota for bacterial strains that could induce the accumulation of IFN+CD8 T cells in the intestine (experimental procedure outlined in FIG. 48). Faecal samples were obtained from six healthy Japanese volunteers (Donors A to F) and were each orally administered to GF mice housed in separate gnotobiotic isolators. The extent of colonic IFN+CD8+ T cell induction varied greatly between samples (FIG. 43D). Faeces from Donor B elicited the strongest induction, to a degree comparable to that observed in SPF mice (compare FIGS. 43B and 43D). The induction was more pronounced in the colon than in the SI (FIG. 49A), potentially due to preferential colonic colonization. We then selected the mouse that exhibited the strongest IFN+CD8 T cell induction ("mouse B5") (FIG. 43D), suspended its caeeal contents in broth media, and gavaged this suspension into GF mice (GF+B5 mice). Next, the mice were treated with either ampicillin (Amp), metronidazole (MNZ), streptomycin (STM), tylosin (Tyl), or a vehicle control via the drinking water. Chloroform (Chlo)-treated caecal contents of mouse B5 were inoculated into an additional group of GF mice (GF+Chlo B5 mice) to examine the effects of spore-forming commensal bacteria[8]. As expected, colonization with the caecal microbiota from mouse B5 resulted in a significant increase in frequency of colonic IFN+CD8 T cells as compared to GF controls (FIG. 43E). Treatment with MNZ, STM, or Tyl, however, resulted in a substantial decrease in IFN+CD8 T cell induction relative to the untreated group, and Chlo treatment abrogated it altogether (FIG. 43E). In contrast, Amp treatment enhanced the induction of IFN+CD8 T cells (FIG. 43E). This trend was mirrored by the CD103+IFN+CD8 subpopulation, representing IFN+ $T_{RM}$ cells (FIG. 49B). We followed up on the two Amp-treated mice that exhibited the strongest IFNγ+CD8 T cell induction (denoted B5-Amp2 and B5-Amp3) and cultured their caecal contents in vitro in a variety of media under anaerobic conditions (FIG. 43E). We picked 206 distinct colonies and analysed them by 16S ribosomal RNA (rRNA) gene sequencing to elaborate a consortium of 26 unique strains (FIG. 43G).

Figures 43H, 43I, 43J, 43K, 43L, 43M:
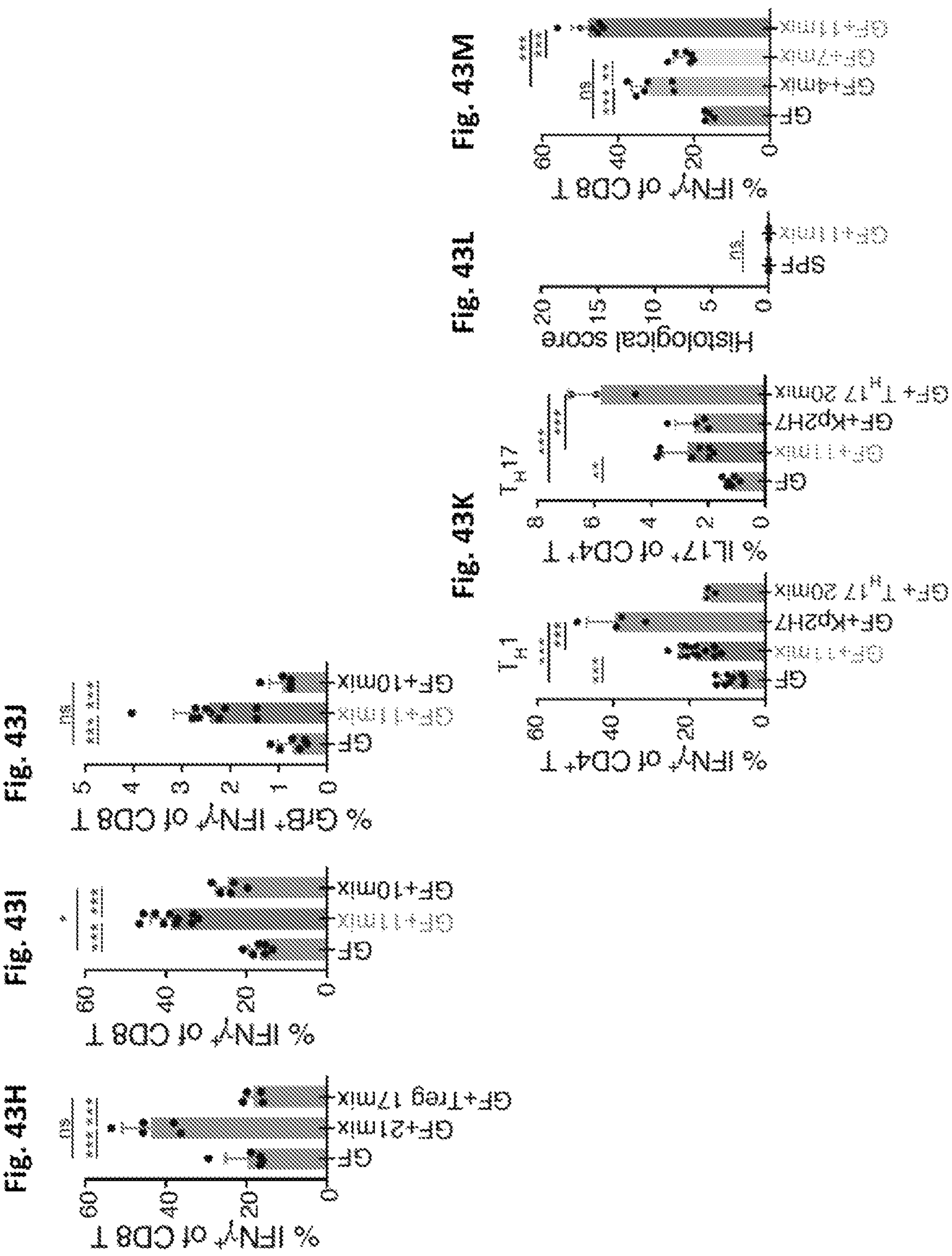
Figure 50:
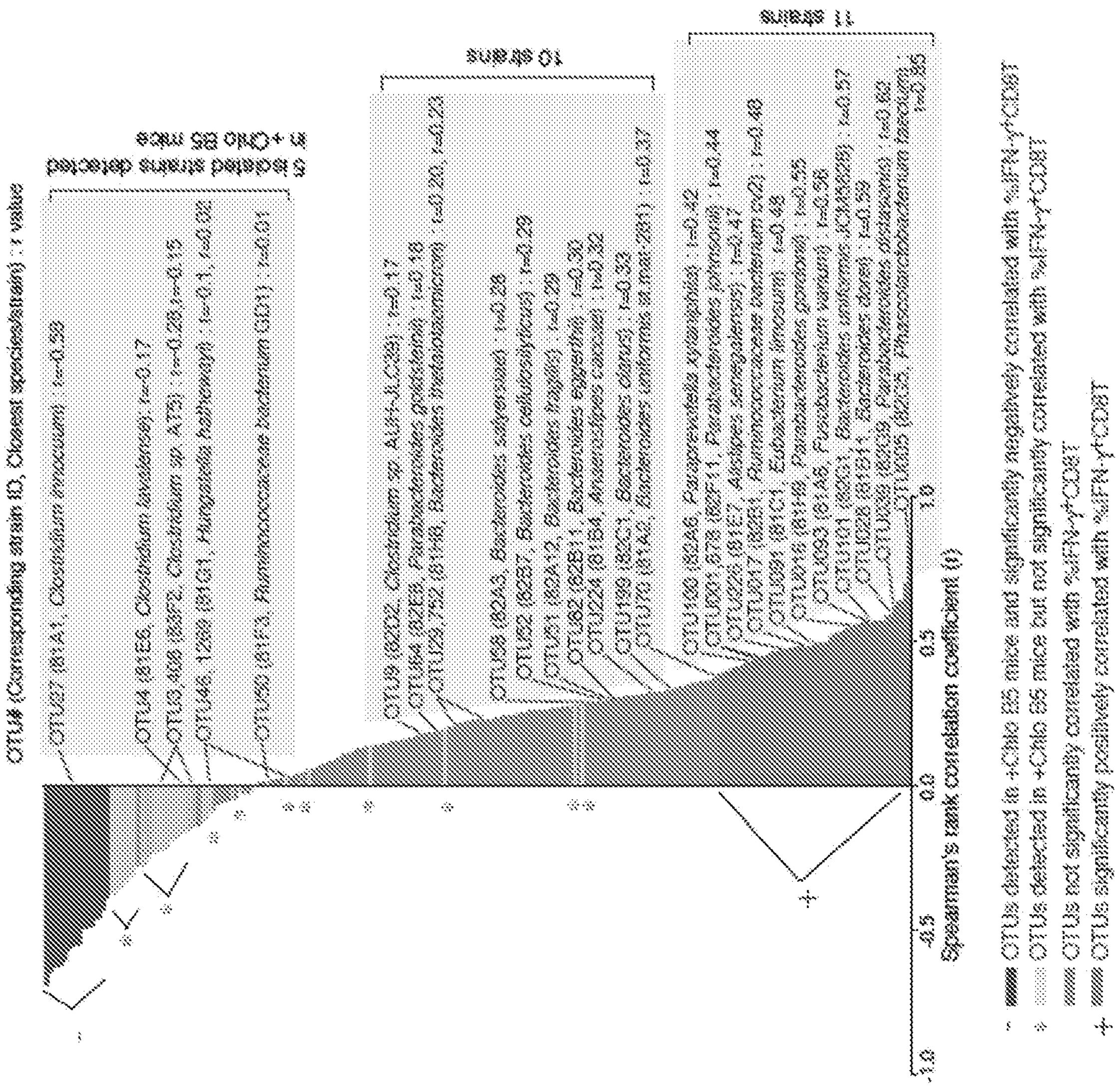
FIG. 50 shows a Spearman's correlation between OTUs and IFN+CD8 T cells. The Spearman's correlation coefficient (r) between the number of reads of individual bacterial OTUs (among 3000 reads) detected in mice shown in FIG. 43F and the percentage of IFN+ among the colonic CD3+TCR+CD8+ parent population of cells shown in FIG. 43E was calculated using GraphPad PrismR with a P value for the correlation between the two variables. OTUs that were significantly positively correlated and significantly negatively correlated with the frequency of colonic IFN+ CD8+ T cells (P<0.05) are indicated with an "+" and "−", respectively. OTUs that were detected in +Chlo B5 mice are indicated with a "−" or "*". OTUs showing no significant correlation (P>0.05) are shown in grey. The closest species/strain to the indicated OTUs and individual r values for each OTU are also shown.
Figure 51A:
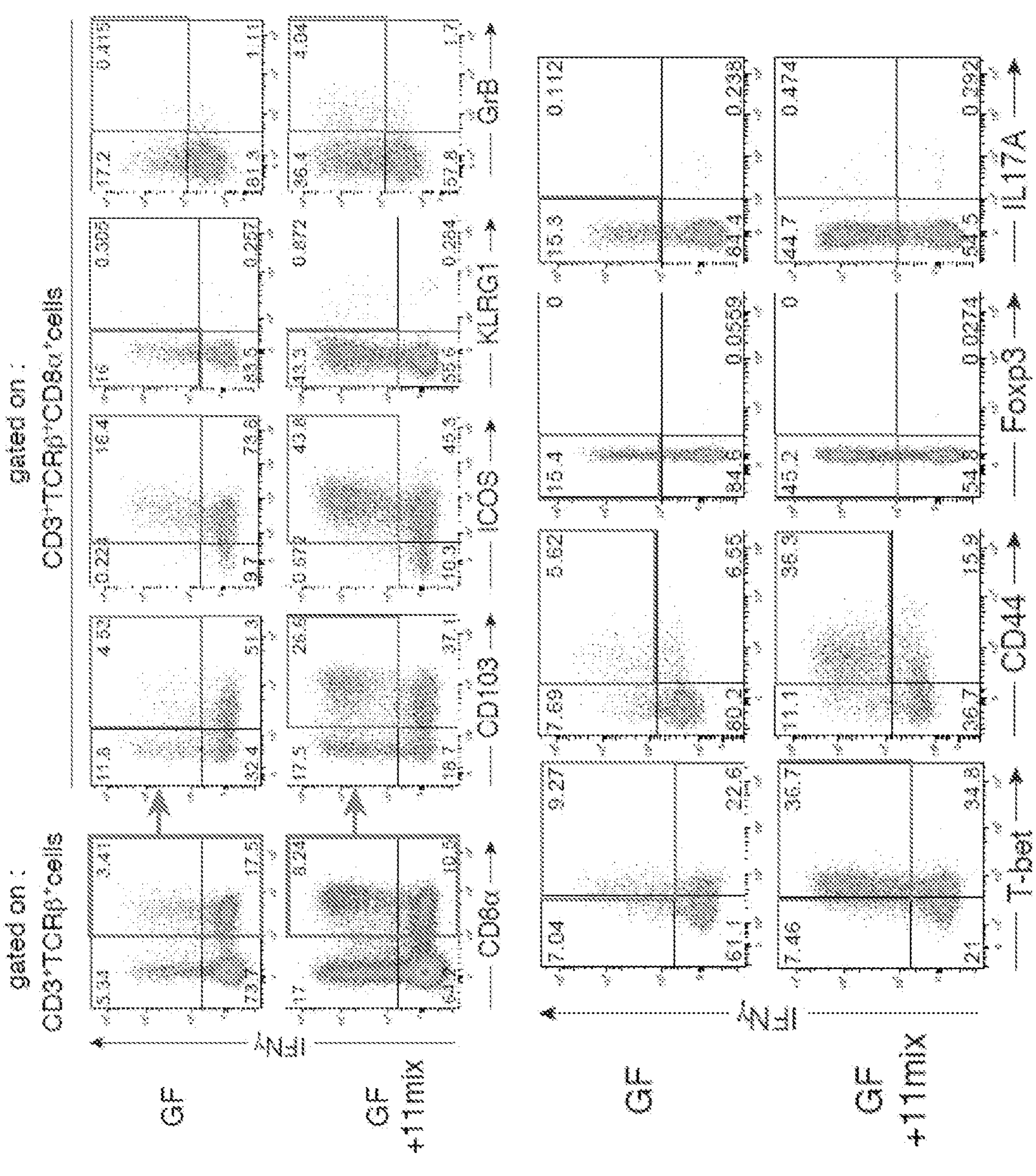
FIGS. 51A and 51B show the phenotype of IFN+CD8 T cells induced by the mixture of 11 bacterial strains.
Figure 51B:
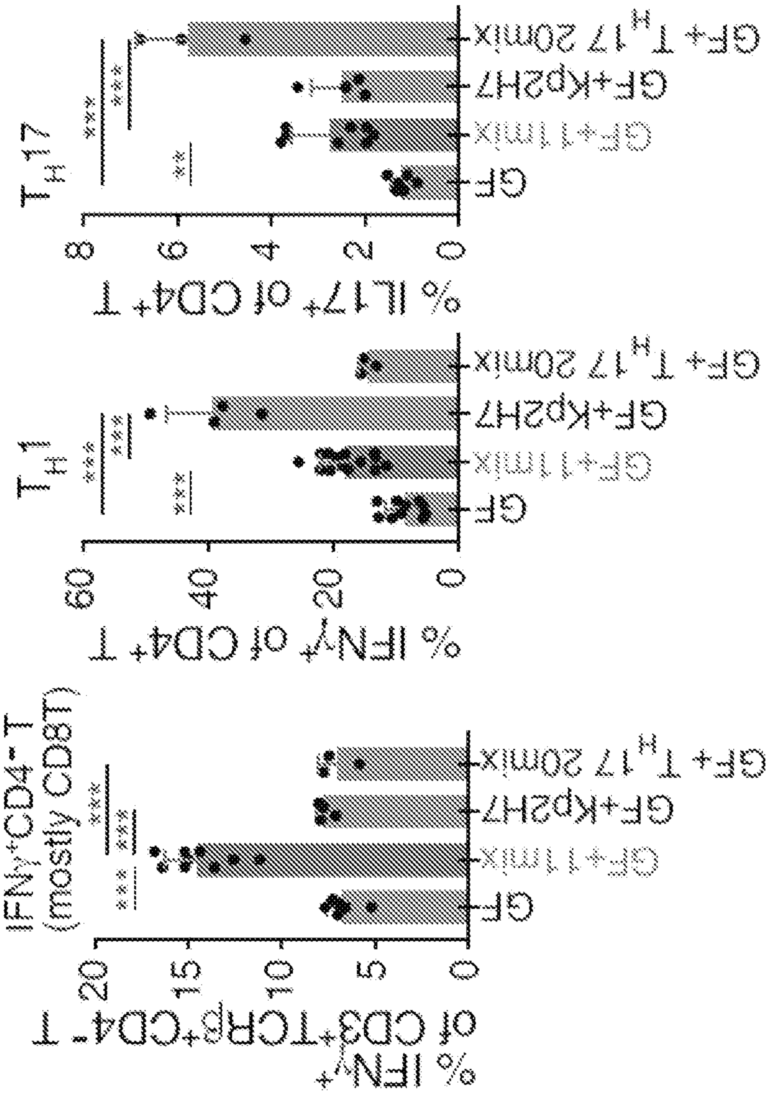
Figure 52A:
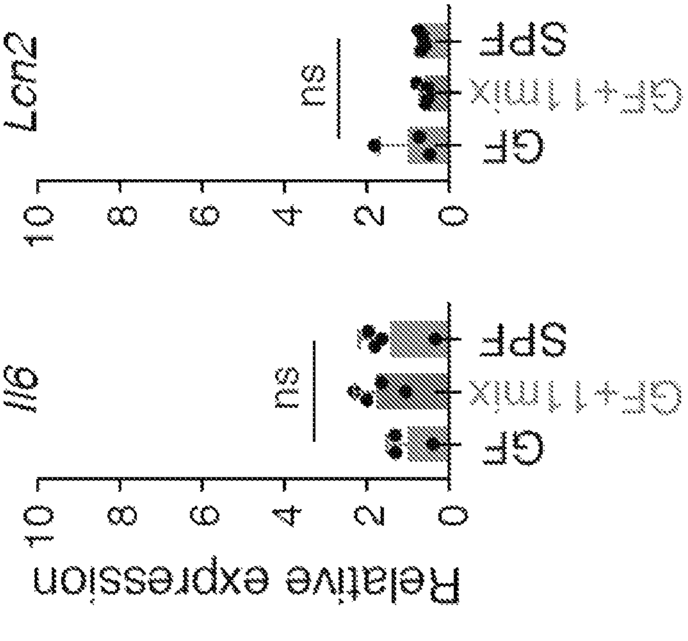
FIGS. 52A-52C show data relating to immunomodulation by the mixture of 11 bacterial strains without causing inflammation.
Figure 52B:
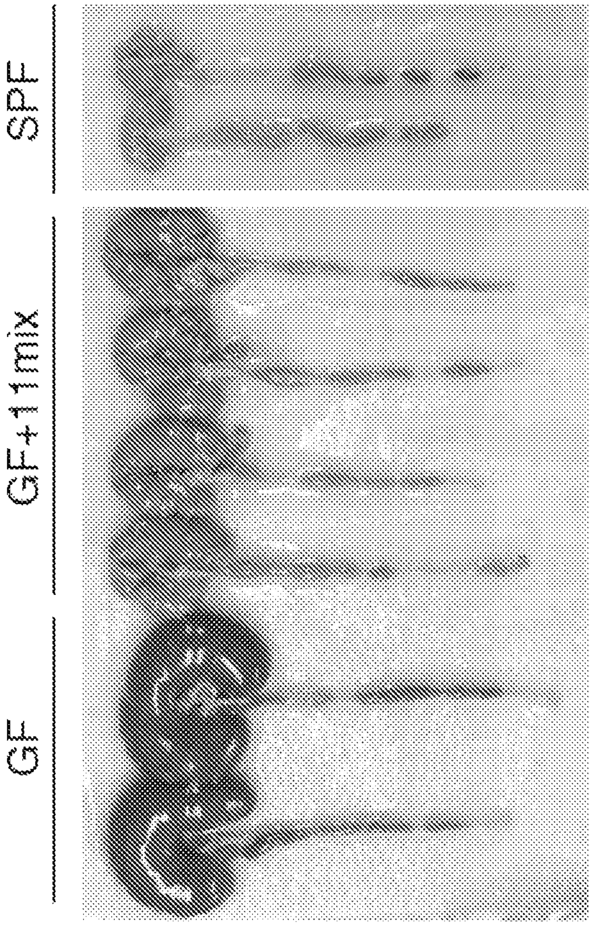
Figure 52C:
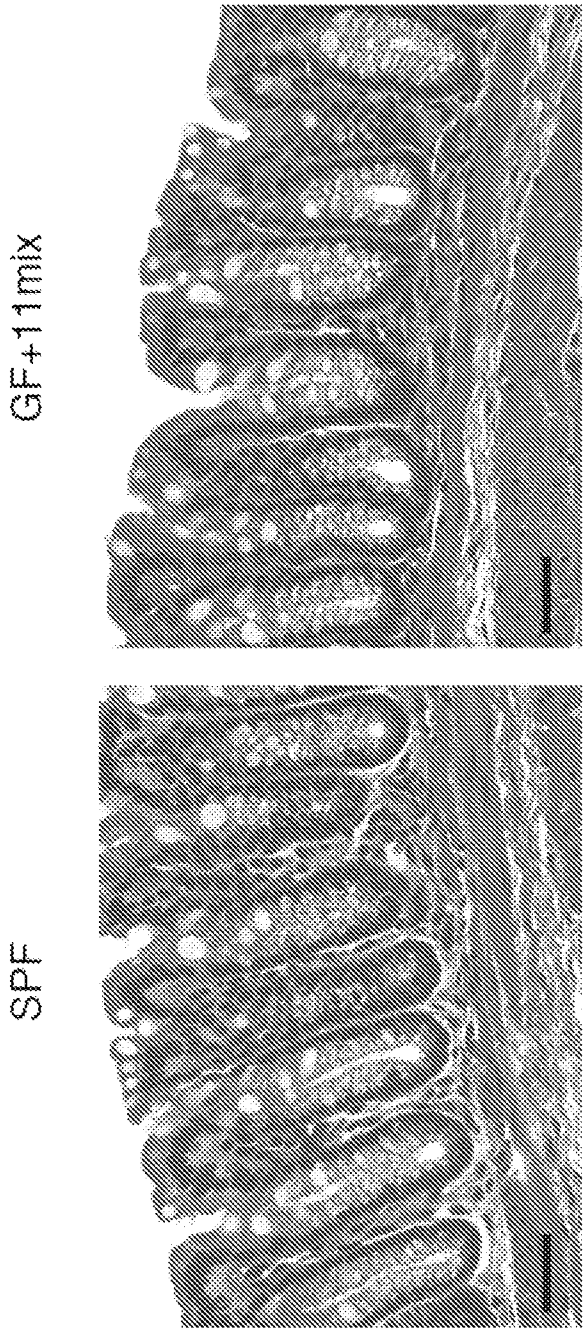

In addition, we examined the caecal microbiota composition of all mice from the antibiotic experiment by 16S rRNA gene sequencing. The relative abundance of each operational taxonomic unit (OTU) was determined in every sample by subjecting 3000 quality filter-passed reads to OTU analysis with a similarity threshold of 97%, revealing that the 26 isolated strains together roughly recapitulate the microbiota of mice B5-Amp2 and B5-Amp3 (FIGS. 43F and 43G). To identify functionally relevant isolates, we excluded five strains detected in the microbiome of GF+Chlo B5 mice (indicated with "+" in FIGS. 43F and 43G) and selected the remaining 21 for further analysis (FIG. 43G). To ascertain whether the 21 strains had IFN+CD8 T cell-inducing capacity, they were cultured individually and introduced as a mixture (21-mix) into GF mice (GF+21-mix mice). For comparison, we also analysed mice colonised with a mixture of 17 $T_{reg}$ cell-inducing *Clostridia* strains (GF+Treg 17mix) that were previously isolated from a human faecal sample[8]. We observed a very strong induction of IFN+CD8 T cells in the colonic LP of GF<21-mix mice, with a magnitude comparable to that in SPF mice (compute FIGS. 43B and 43H). GF+Treg 17mix mice showed no induction above the GF baseline (FIG. 43H). We then performed a Spearman's rank correlation test comparing the relative abundances of the 21 strains with IFN+CD8 T cell frequency using data from the aforementioned antibiotic experiment. Among the 21 strains, 11 were positively associated with IFN+CD8 T cell frequency (indicated with a "#" in FIGS. 43F and 43G) and 10 showed no significant association (indicated with a "–" in FIGS. 43F and 43G) (see, also FIG. 50). To hone in on the effector microbes, we compared the efficacy of the 11 versus 10 strains in inducing colonic IFN+CD8 T cells. GF+11-mix mice exhibited a robust induction, to the same extent as did GF+21 mix mice (compare FIGS. 43H and 43I). IFN+CD8 T cells induced by the 11-mix were largely positive for T-bet and CD44, and included subsets of GrB+ cells and KLRG1−ICOS+CD103+ cells (FIG. 43J and FIG. 51A). The induction of IFN+CD8 T cells in GF+10-mix mice was significantly lower than that observed in GF+11-mix mice (FIG. 43I), and that of GrB+IFN+CD8 T cells was non-existent (FIG. 43J). The inductive ability of the 11-mix was not confined to CD8 T cells, but extended to CD4 T cells as well. Indeed, a significant increase in the frequencies of colonic $T_H17$ cells and $T_H1$ cells was observed after colonization with the 11-mix. However, these responses were significantly weaker than those induced by the 20 reported $T_H17$ cell-inducing human associated strains ($T_H17$ 20mix, ref.[9]), and by a repotted $T_H1$ cell-inducing *Klebsiella pneumoniae* strain (Kp2H7, ref.[13]), respectively (FIG. 43K and FIG. 51). Importantly, the induction of IFN+CD8 T cells by the 11-mix was not inflammatory in origin, as there were no gross, histological, or transcriptional signs of colonic inflammation in GF+11-mix mice (FIG. 43L and FIGS. 52A-52C). Taken together, these data suggest that the 11 strains were major contributors to the IFN+CD8 T cell induction observed in mice inoculated with Donor B faeces and have non-inflammatory immunomodulatory activity that is relatively specific to CD8 T cells.

Figure 54:
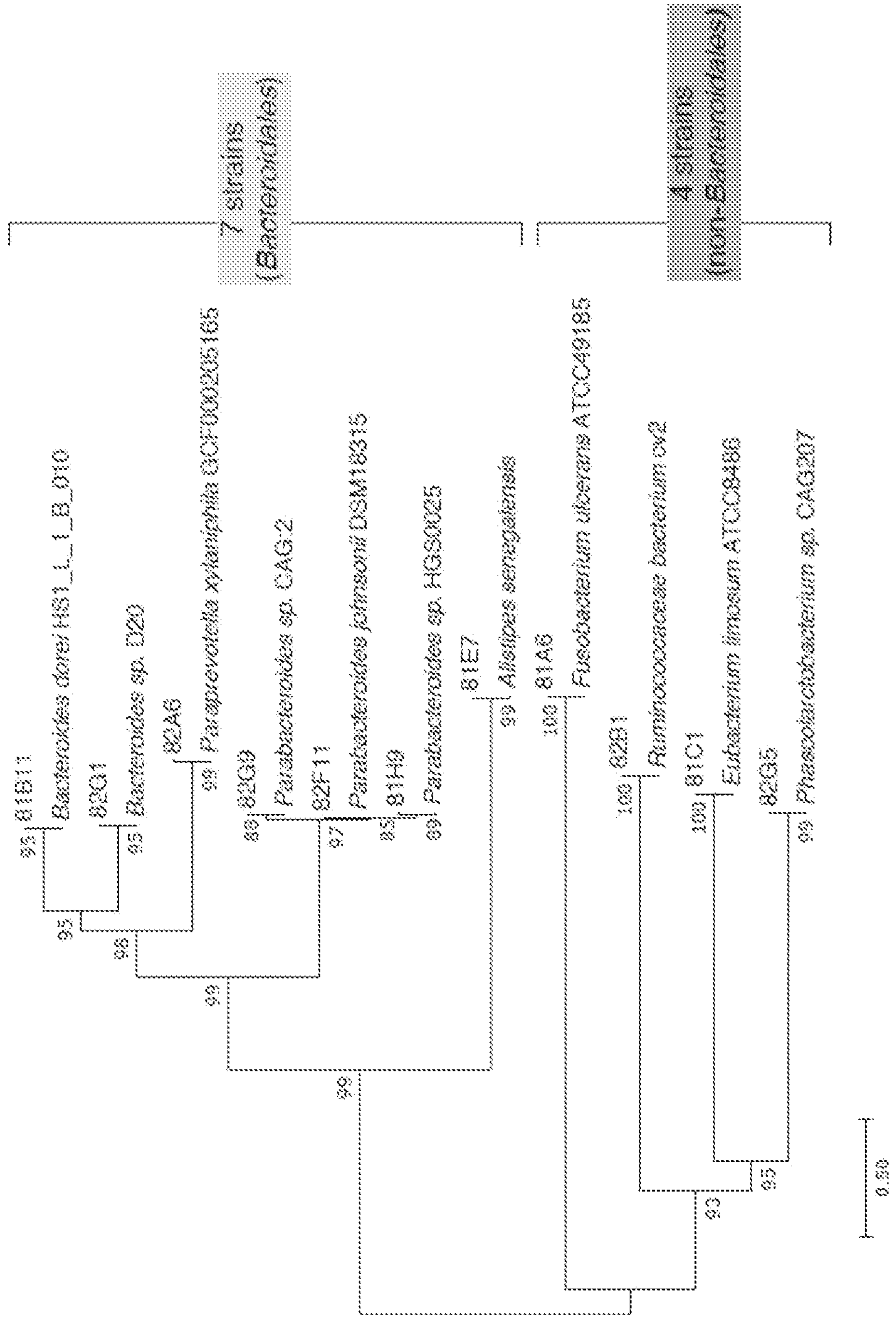
FIG 54 shows the phylogenetic distribution of the 11 isolated strains. The phylogenetic tree was constructed by comparing 37-42 ribosomal protein gene sequences concatenated together using the MEGA v5.0 package and the neighbour-joining method with a bootstrap of 500 replicates. Whole-genome phylogenetic analysis of the 11 strains was performed based on the Mash distances.

To fully characterize each of the 11 strains, we sequenced their genomes using a MiSeq Illumina platform, attaining between 100- and 200-fold coverage per strain (FIG. 53). No prominent virulence factors or toxins were identified (data not shown). Although tetracycline-resistance and beta-lactamase genes were present in most of the genomes, multidrug-resistant strains were not identified (data not shown). A phylogenetic comparison revealed that the 11 strains comprised 7 Bacteroidales and 4 non-Bacteroidales species (FIG. 43G, FIG. 53, and FIG. 54). When inoculated into GF mice, the 7 Bacteroidales-mix (7-mix) failed to induce IFN+CD8 T cells, whereas the 4 non-Bacteroidales-mix (4-mix) displayed a significantly better induction capacity compared to the 7-mix. However, the 4-mix alone was not sufficient to achieve the full inductive effect of the 11-mix (FIG. 43M). These results suggest that the 11 strains act as a community wherein the 4 non-Bacteroidales species act as effector elements and the 7 Bacteroidales play a supporting role.

Figures 44A, 44B, 44C, 44D, 44E, 44F:
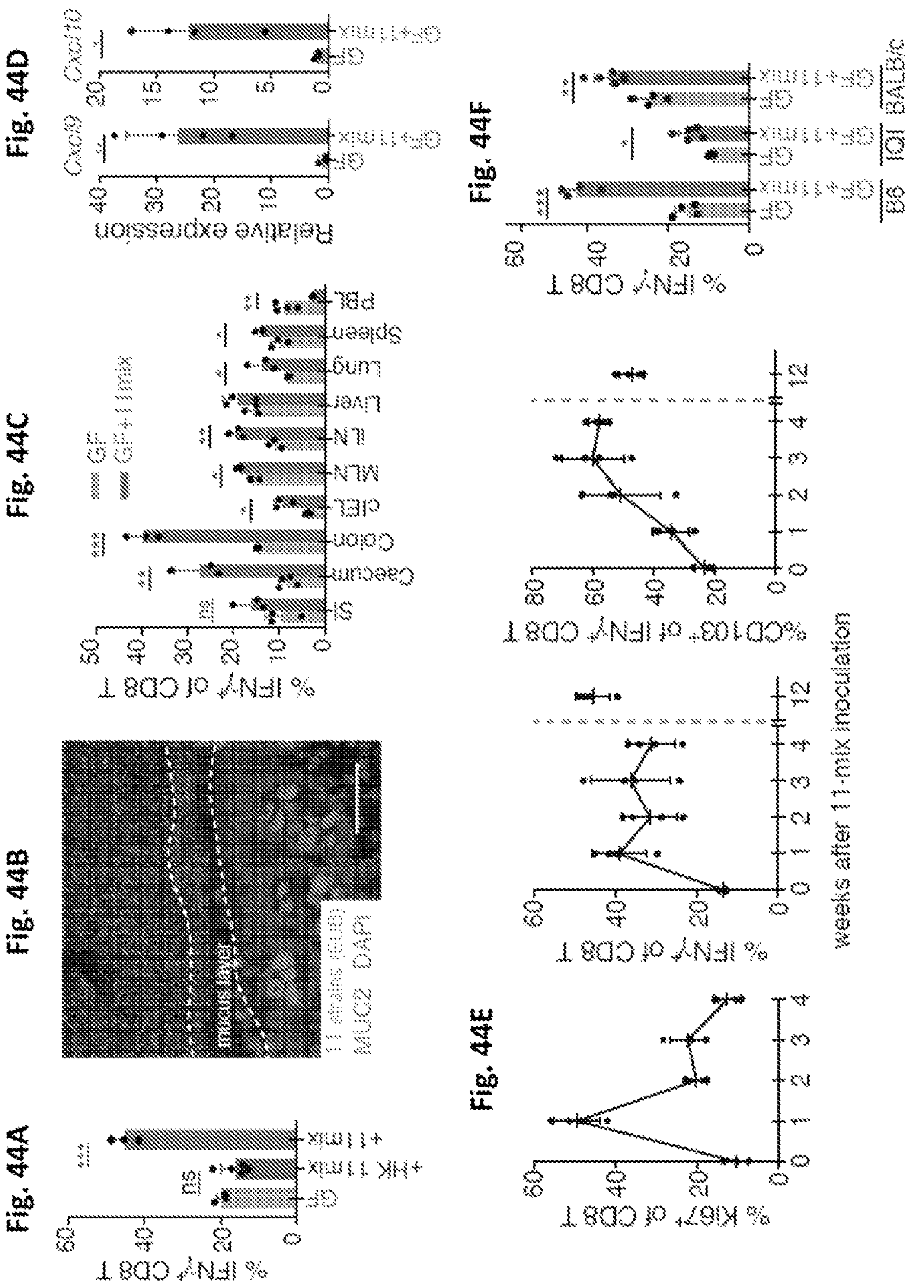
FIGS. 44A-44K show data relating to DC-mediated IFN+ CD8 T cell induction by the mixture of 11 bacterial strains (11-mix).
Figure 44G:
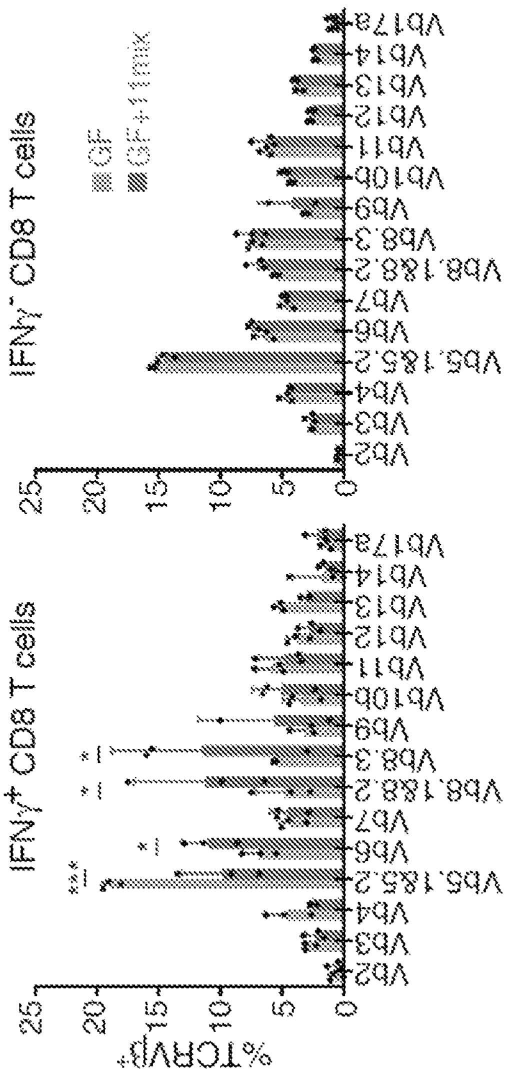
Figure 55A:
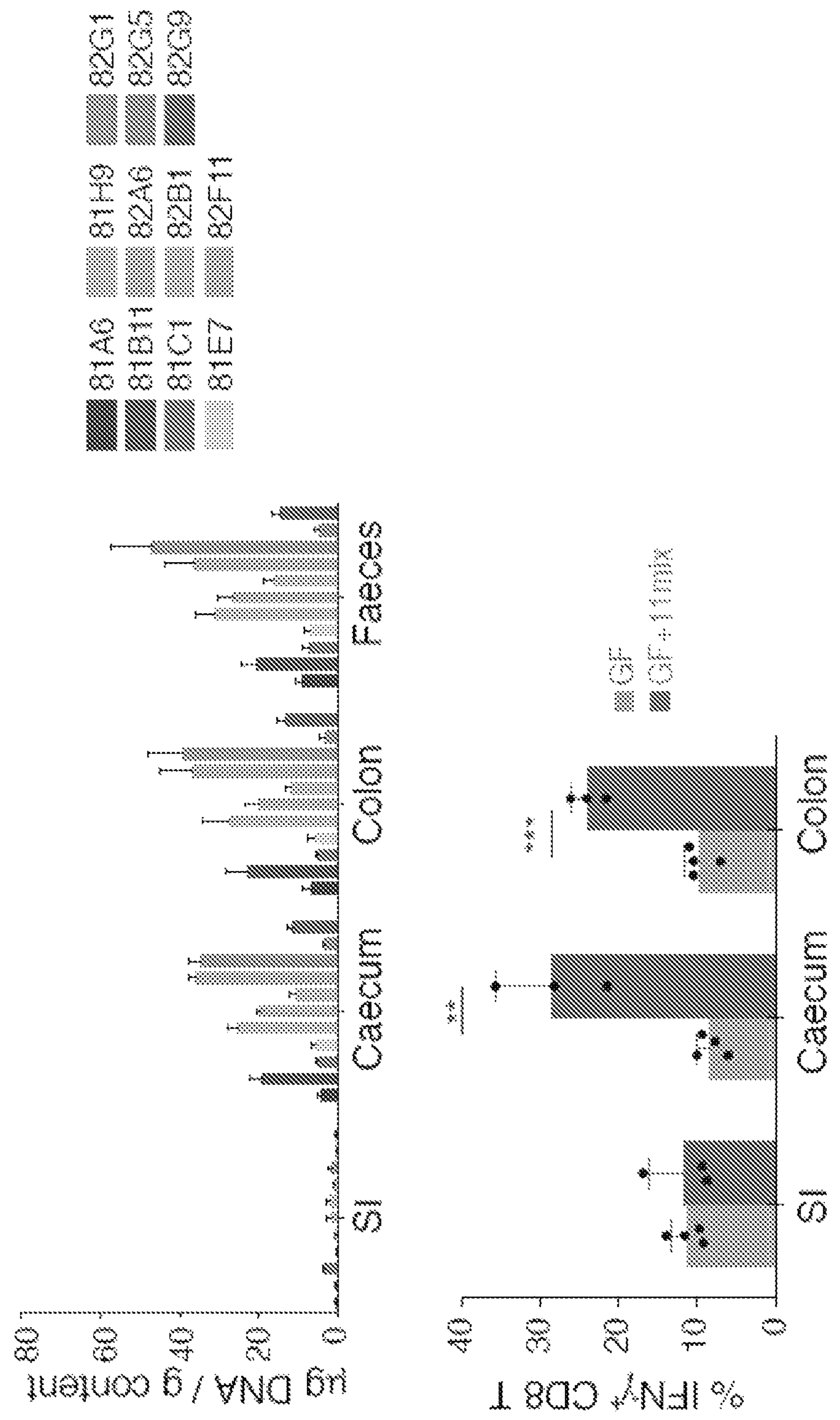
FIGS. 55A and 55B show colonic colonization and induction of IFN-stimulated genes in colonic epithelial cells by the mixture of 11 bacterial strains.
Figure 55B:
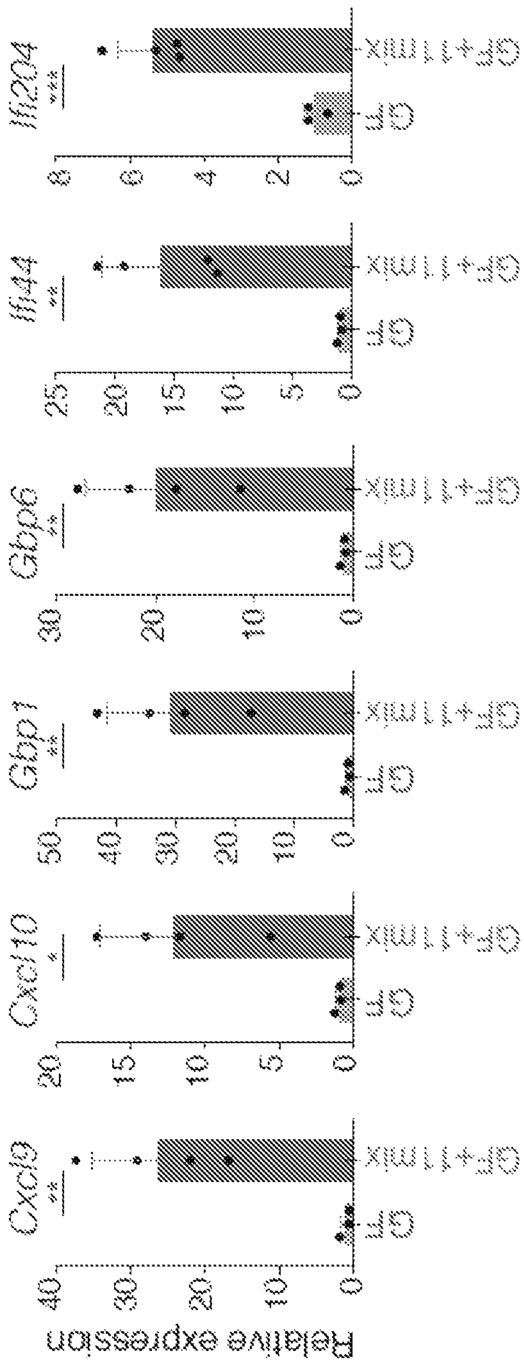

We next sought to gain insight into the mechanism by which the consortium of 11 strains induces colonic IFN+CD8 T cells. Treating GF mice with heat-killed 11-mix via the drinking water for four weeks failed to induce IFN+CD8 T cells (FIG. 44A), indicating that bacterial viability is required for immunomodulation. Fluorescence in situ hybridization performed on colonic samples from GF+11-mix mice highlighted the strains' ability to enter the mucus layer, though no invasion into the epithelial layer was detected (FIG. 44B). This implies that active colonization, likely of the mucus layer, is necessary for IFN+CD8 T cell induction. The 11 strains mainly colonised the caecum and colon, which was reflected by a prominent induction of IFN+CD8 T cells at these sites (FIG. 44C and FIG. 55). Nevertheless, the immunomodulatory phenotype extended beyond the intestine, as an increase in IFN+CD8 T cell frequency was also observed in several additional organs, including the inguinal lymph nodes, lungs, and spleen, although the magnitude in each was much smaller than that in the colon (FIG. 44C). Notably, the IFN-+CD8 T cell frequency in the peripheral blood was reduced after 11-mix administration (FIG. 44C). Therefore, the effect of the 11-mix is systemic as it affects the overall tissue distribution of IFN-+CD8 T cells. Colonic epithelial cells (ECs) upregulated expression of Cxcl9 and Cxcl10 chemokine transcripts along with those encoding other IFN-inducible genes as early as 1 week post-inoculation of the 11-mix (FIG. 44D and FIG. 55B), which likely contributed to the recruitment and accumulation of IFN+CD8 T cells in the colon[10]. Time course analyses of IFN+CD8 T cell accumulation as well as expression of CD103 and the proliferation marker Ki67 in GF+11-mix mice revealed that expansion of CD8 T cells (Ki67-positive) occurred within a one-week timeframe and was accompanied by a dramatic increase in IFN+CD8 T cell frequency (FIG. 44E). The accumulated IFN+CD8 T cells at 1-week post-colonization were primarily CD103, though the CD103+ $T_{RM}$ subset gradually increased in frequency thereafter and persisted stably for at least 12 weeks (FIG. 44E), suggesting a stepwise differentiation pattern. The baseline level and induction magnitude of IFN+CD8 T cells varied substantially depending on genetic background, with the greatest induction occurring in C57BL/6 mice (FIG. 44F). Furthermore. IFN+CD8 T cell TCR Vβ usage differed significantly between GF+11-mix and GF mice: the GF+11-mix group showed a relative enrichment for Vβ6+ and Vβ8+ subsets, at the expense of the Vβ5+ subset (FIG. 44G). In contrast, there was no difference in IFN-negative CD8 T cell TCR V composition between GF and GF+11-mix mice (FIG. 44G). Taken together, these data suggest that the accumulation of IFN+CD8 T cells is likely due to the cumulative effects of colonic homing, cellular expansion, and TCR-mediated differentiation.

Figure 44H:
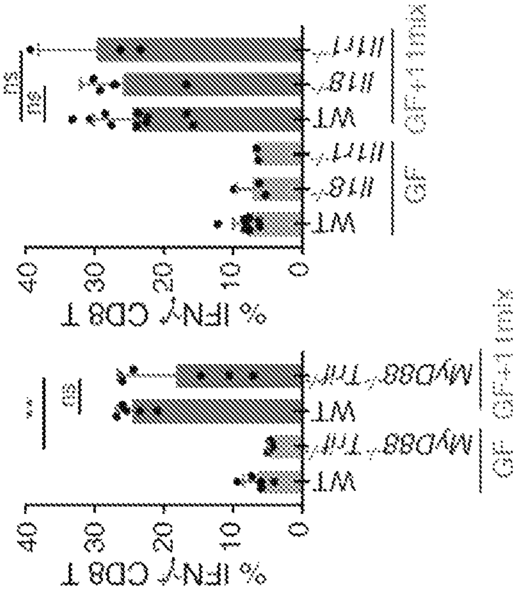
Figures 44I, 44J, 44K:
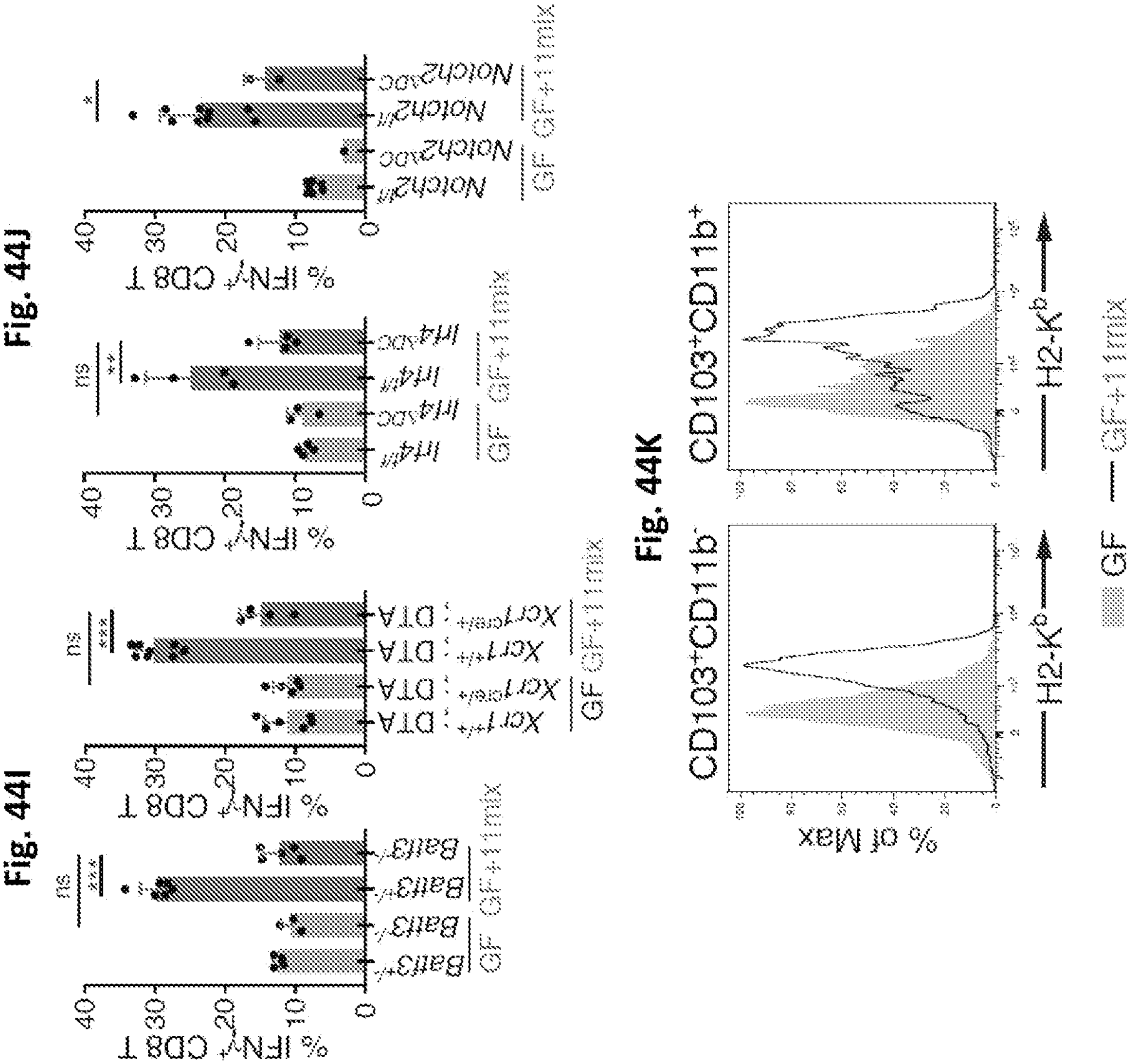

We next examined the contribution of major innate signalling pathways said dendritic cells (DCs). Neither Myd88$^{-/-}$Trif$^{-/-}$, Il1br$^{-/-}$, nor Il18$^{-/-}$GF+11-mix mice showed any difference in IFN+CD8 T cell inductive capacity its compared to wild-type (WT) controls (FIG. 44H). In contrast, the 11-mix treatment failed to induce colonic IFN+CD8 T cells in Batf3$^{-/-}$ mice and XcrI$^{+/cre}$×R26: lacZbpA$^{flor}$DTA mice (FIG. 44I), both of which lack the intestinal CD11b-CD103+ DC subset crucial for antigen cross-presentation to CD8 T cells[14-16]. Interestingly, the induction was also abrogated in CD11c-Cre×Irf4$^{fl/fl}$ (Irf4$^{DC}$) mice and CD11c-Cre×Notch2$^{fl/fl}$ (Notch2$^{DC}$) mice (FIG. 44J), which have defective CD11b+CD103+ DC subsets[16,17]. Colonization with the 11-mix enhanced expression of MHC class I (H2-K$^b$) in both CD11b−CD103+ and CD11b+CD103+ colonic LP DC populations (FIG. 44K). These results are consistent with the hypothesis that the 11 strains localize to the colonic mucus layer and produce Toll-like receptor-independent ligands that activate CD11b−CD103+ and CD11b+CD103+ LP DCs to induce IFN+CD8 T cell accumulation.

Figure 56A:
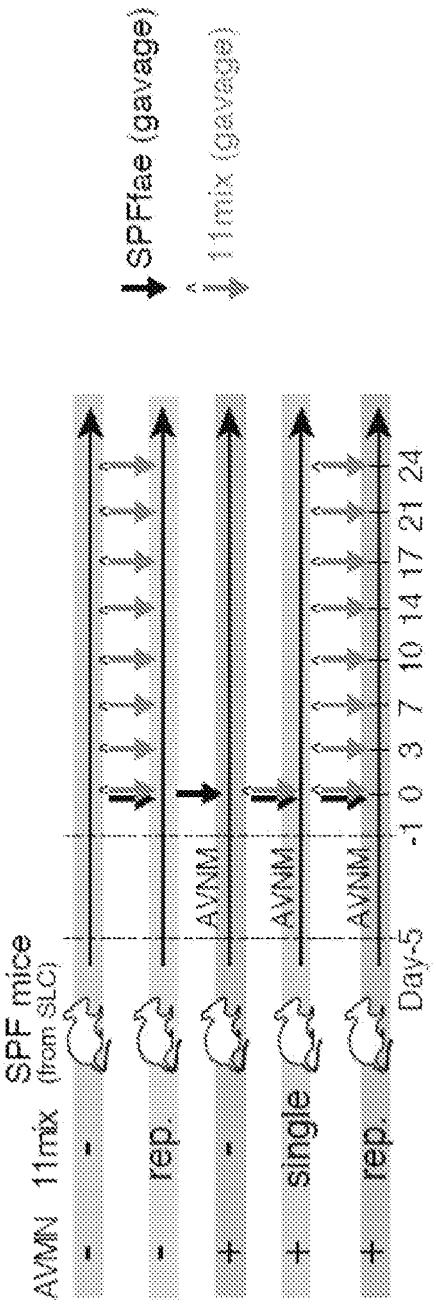
FIGS. 56A and 56B show induction of IFN+CD8 T cell induction by the mixture of 11 bacterial strains in the context of a complex microbiota.
Figure 56B:
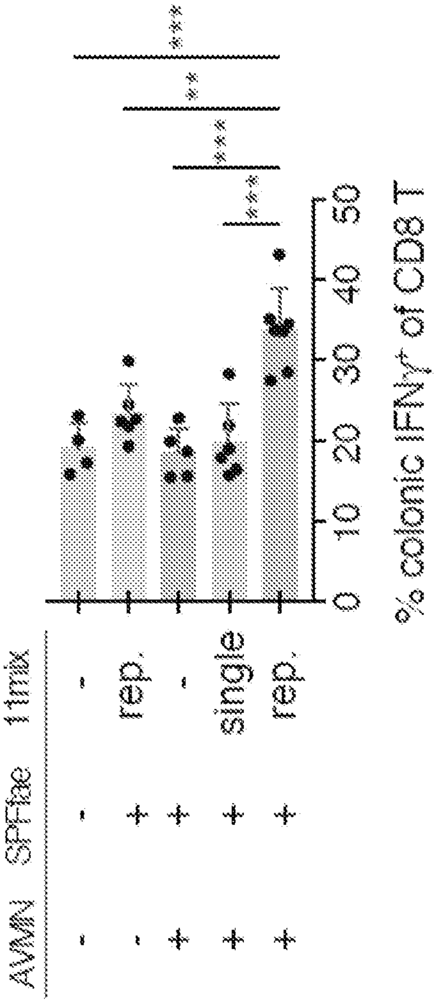

We next examined whether the 11-mix was capable of augmenting IFN+CD8 T cell accumulation in the context of a complex microbiota. In SPF mice with a fully intact gut microbiota, the 11 strains failed to induce IFN+CD8 T cells even after repetitive oral gavage (FIGS. 56A and 56B). To open up niches in the intestinal environment, SPF mice were treated with AVMN or a vehicle control for 4 days via the drinking water and then recolonised with a complex SPF faecal (SPFfae) microbiota supplemented or without the 11-mix. One experimental group received only the initial 11-mix gavage, while another received subsequent repetitive oral gavage several times per week for three weeks (FIGS. 56A and 56B). The latter combination treatment (first with AVMN, then with repetitive administration of the 11-mix) resulted in a significant increase in the frequency of colonic IFN+CD8 T cells, as compared to the other groups (FIGS. 56A and 56B).

Figures 45A, 45B, 45C:
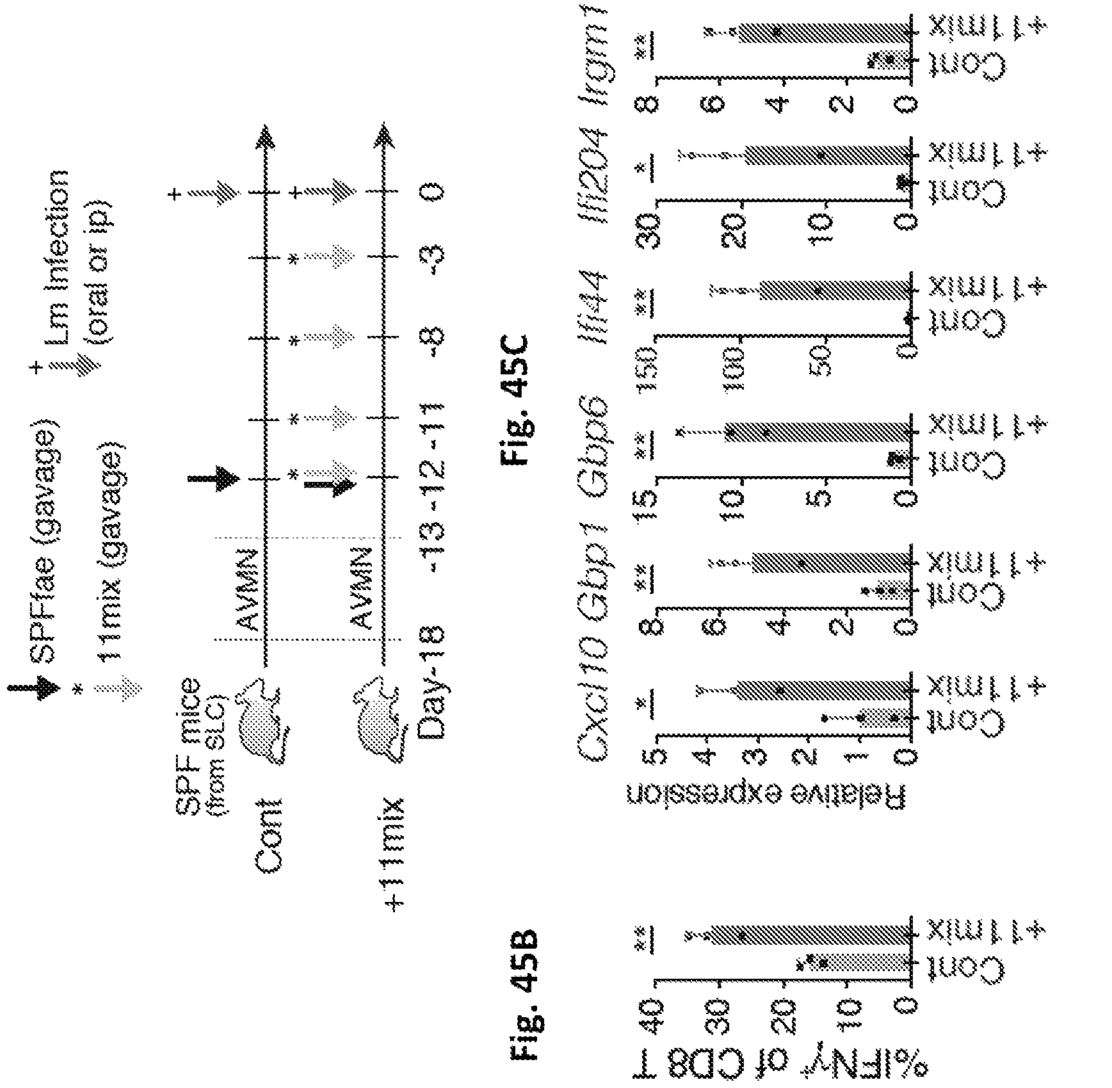
FIGS. 45A-45H show the mixture of 11 bacterial strains enhances the immune response against Listeria monocytogenes (Lm) infection.
Figure 45E:
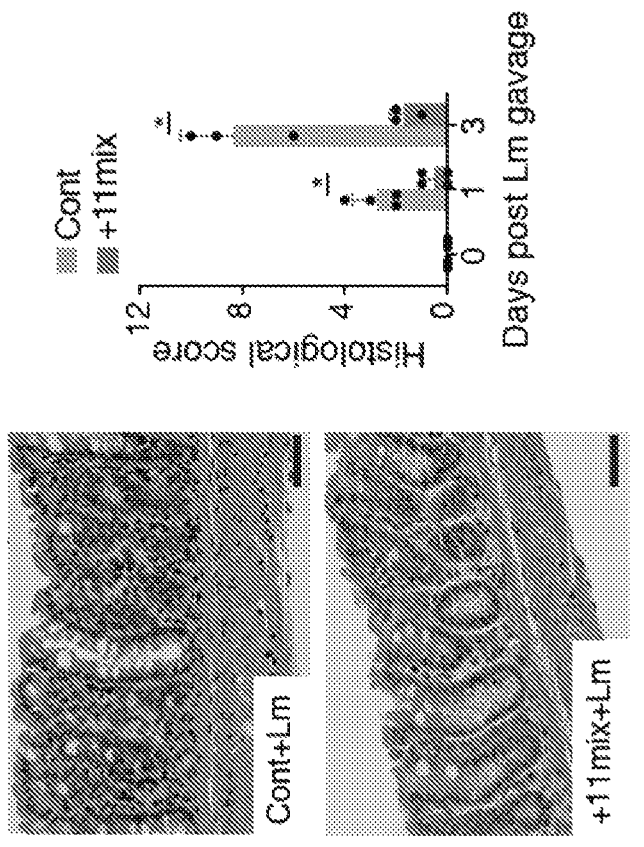
Figure 45D:
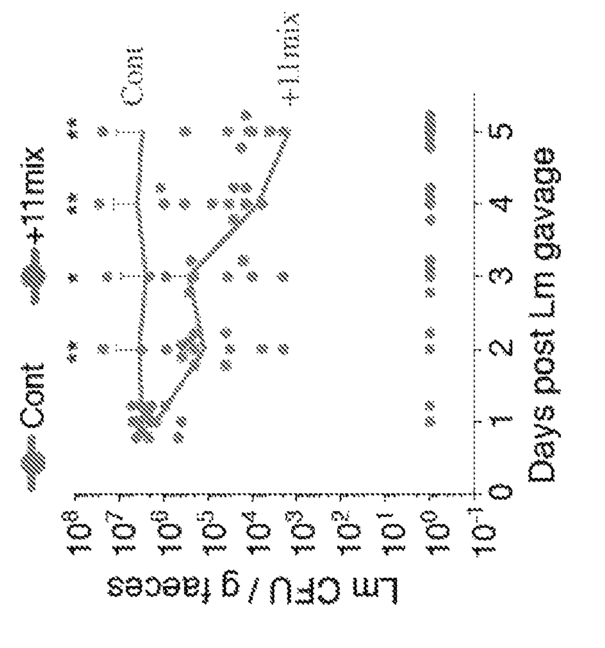
Figures 45F, 45G, 45H:
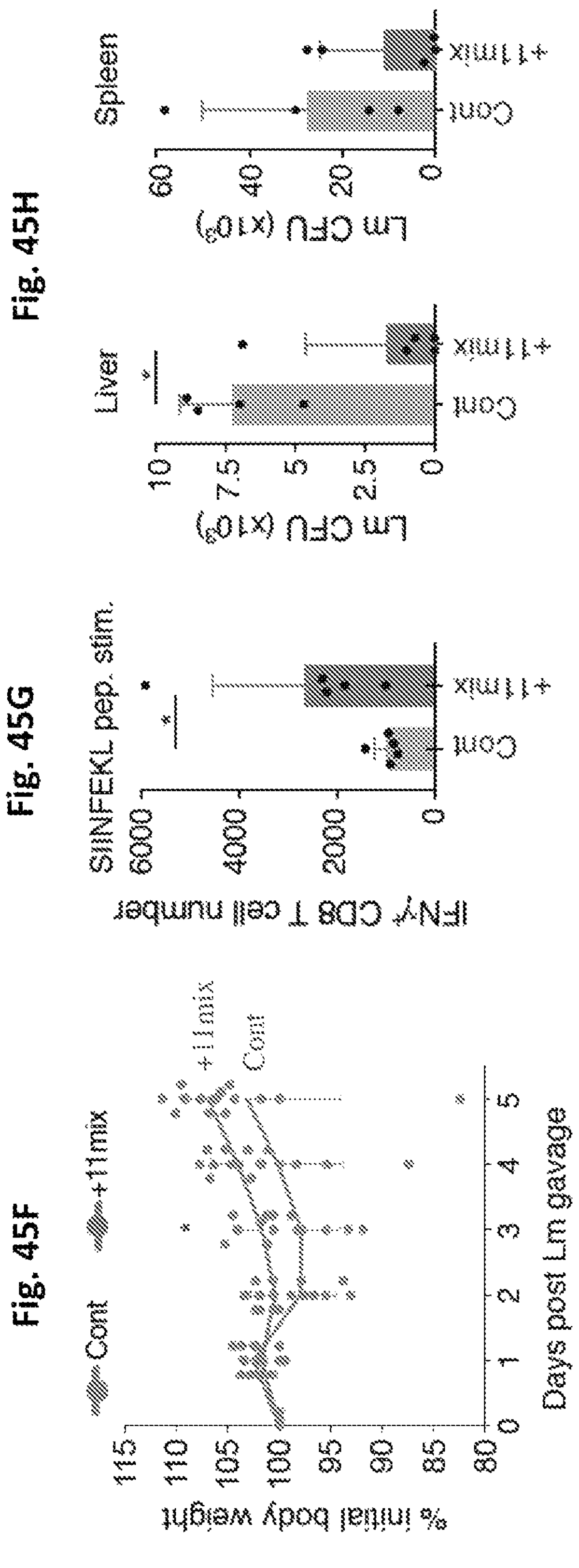

Since IFN+CD8 T cells are known to promote the clearance of intracellular pathogens[12,18], we next tested whether oral administration of the 11 strains could augment host protective immunity against Listeria monocytogenes (Lm) infection. SPF mice were pre-treated with AVMN and gavaged once with SPFfae, followed by repetitive gavage with the 11-mix (FIG. 45A). This led to the expected increase in frequency of colonic IFN+CD8 T cells (FIG. 45B) and an upregulation of IFN-regulated antimicrobial genes in colonic ECs, such as those encoding guanylate-binding proteins (GBPs), interferon-induced proteins (IFIs), Cxcl10, and autophagy-related Irgm1 (FIG. 45C). The mice were then orally infected with Lm. Pre-treatment with the 11-mix significantly facilitated Lm clearance, as evidenced by a rapid decrease in faecal Lm colony-forming units (CPU) (FIG. 45D), markedly better colon histology scores (FIG. 45E), and reduced weight loss (FIG. 45F) as compared to untreated controls. Treatment with the 11-mix enhanced ovalbumin (OVA)-specific CD8 T cell proliferation in response to OVA-expressing Lm (Lm-OVA, ref.[19]) infection (FIG. 45G). If was also effective in protecting mice from systemic infection after intraperitoneal injection of Lm, as reflected by enhanced clearance from the liver and spleen (FIG. 45H).

Figure 46A:
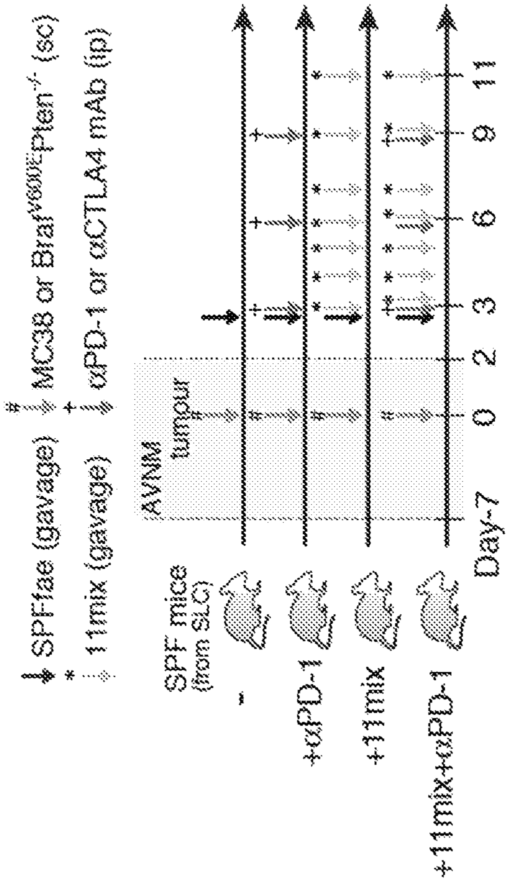
FIGS. 46A-46J show administration of the mixture of 11 bacterial strains suppresses tumour growth.
Figure 46B:
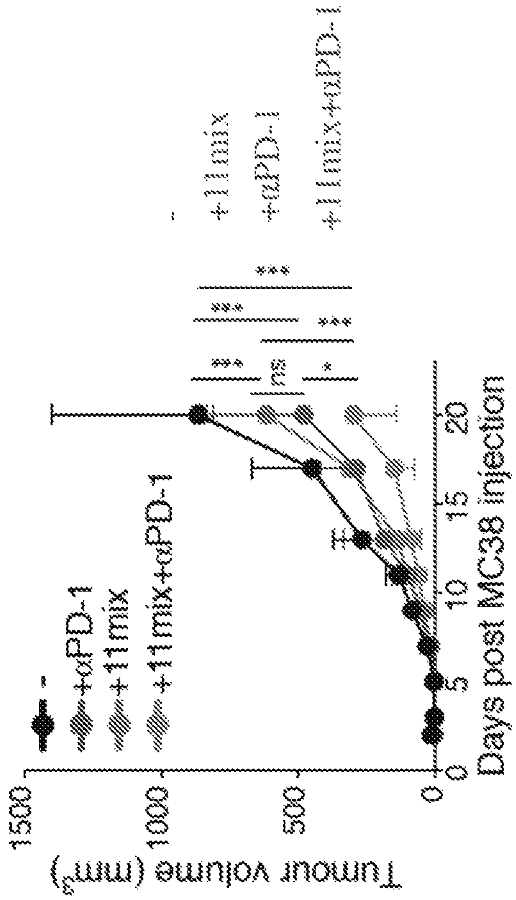
Figures 46C, 46D, 46E, 46F, 46G, 46H:
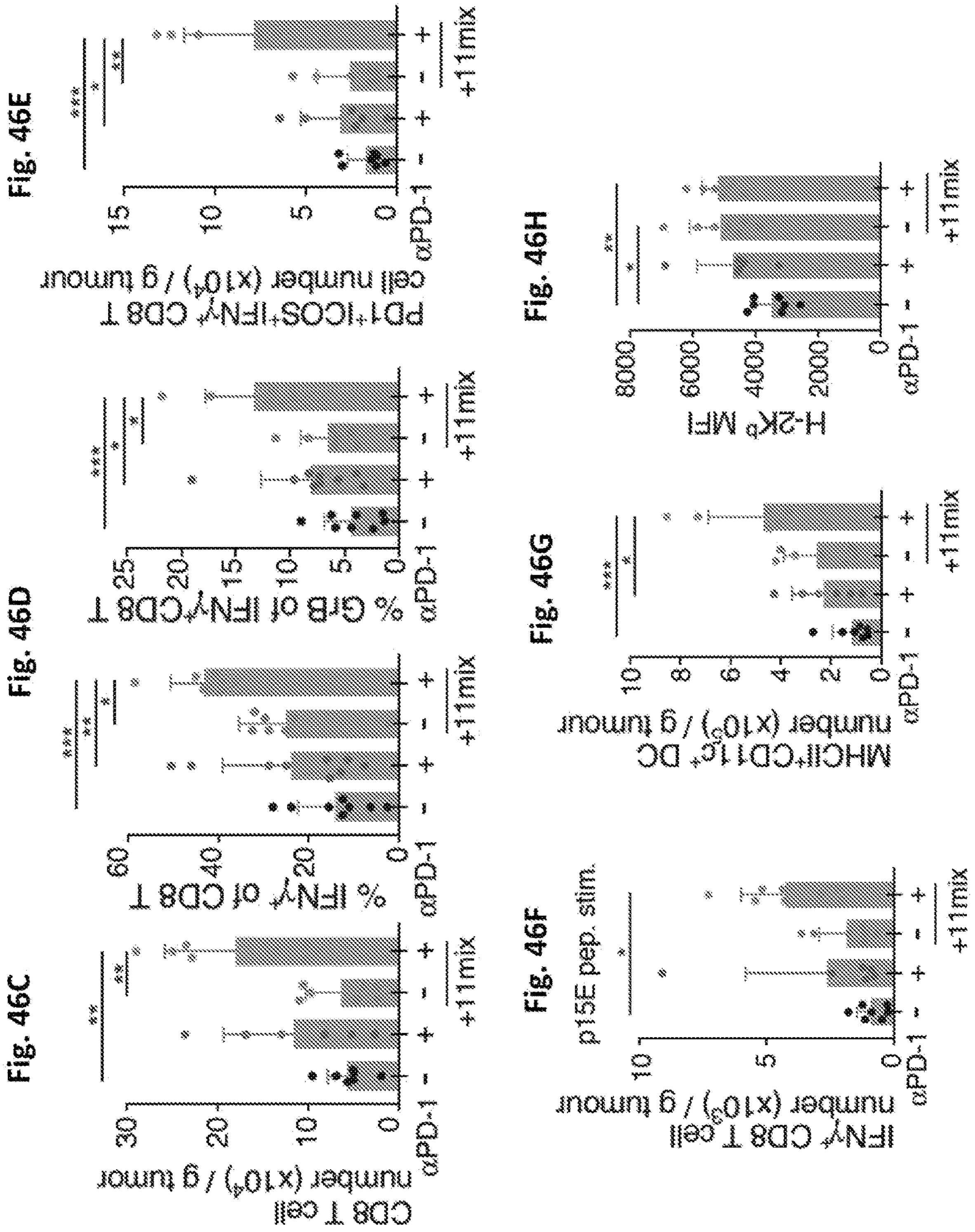
Figure 46I:
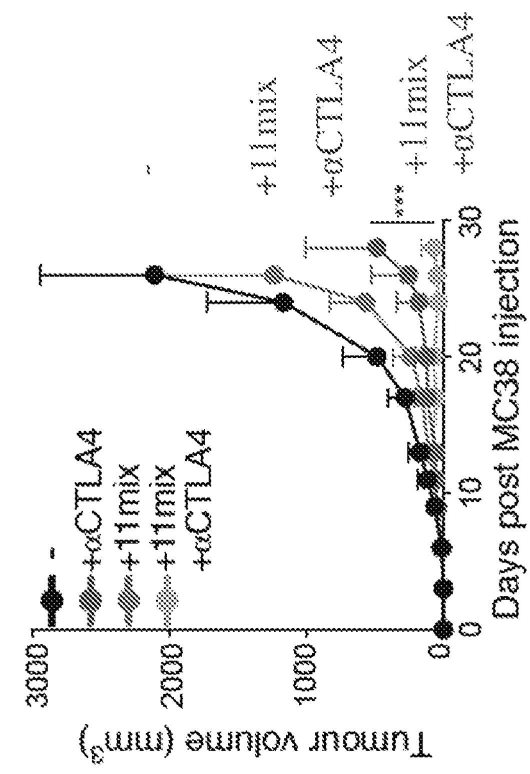
Figure 46J:
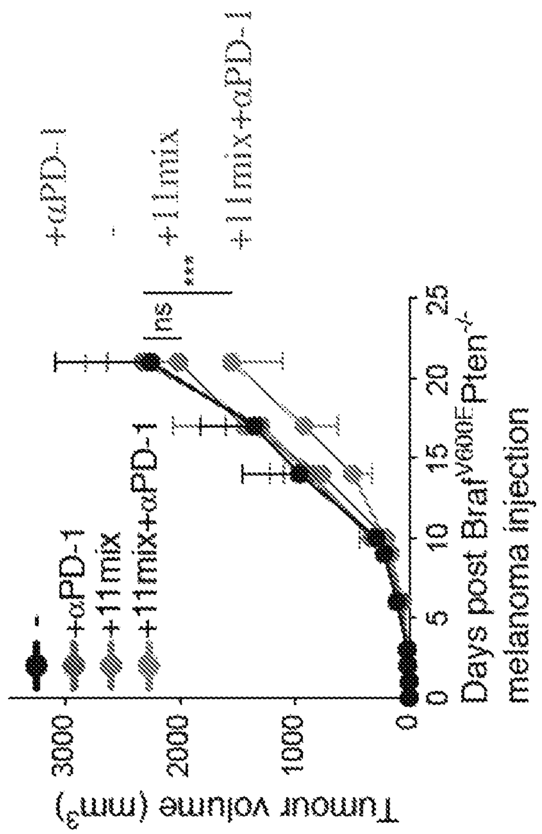
Figure 57A:
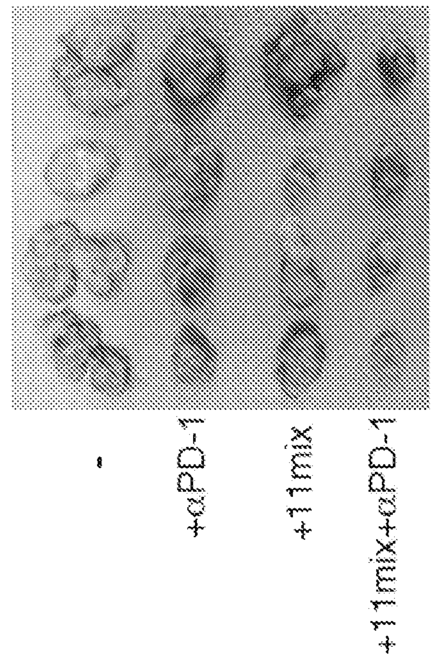
FIGS. 57A-57B shows to the efficacy of the mixture of 11 bacterial strains in enhancing treatment of MC38 tumours. SPF mice were subjected to treatment with AVMN (ampicillin, vancomycin, metronidazole, neomycin) (from day −7 to day 2) followed by subcutaneous implantation of MC38 adenocarcinoma cells (day 0). Abx-treated mice were reconstituted with SPF faecal microbiota on day 3. For the groups that received the mixture of 11 bacterial strains, the initial administration of the 11-mix was done simultaneously with SPF faecal microbiota on day 3, followed by repeated gavage 2-3 times per week until the end of the experiment. The anti-PD-1 antibody (αPD-1) or anti-CTLA4 antibody (αCTLA4) was injected intraperitoneally every third day between days 3 and 9.
Figure 57B:
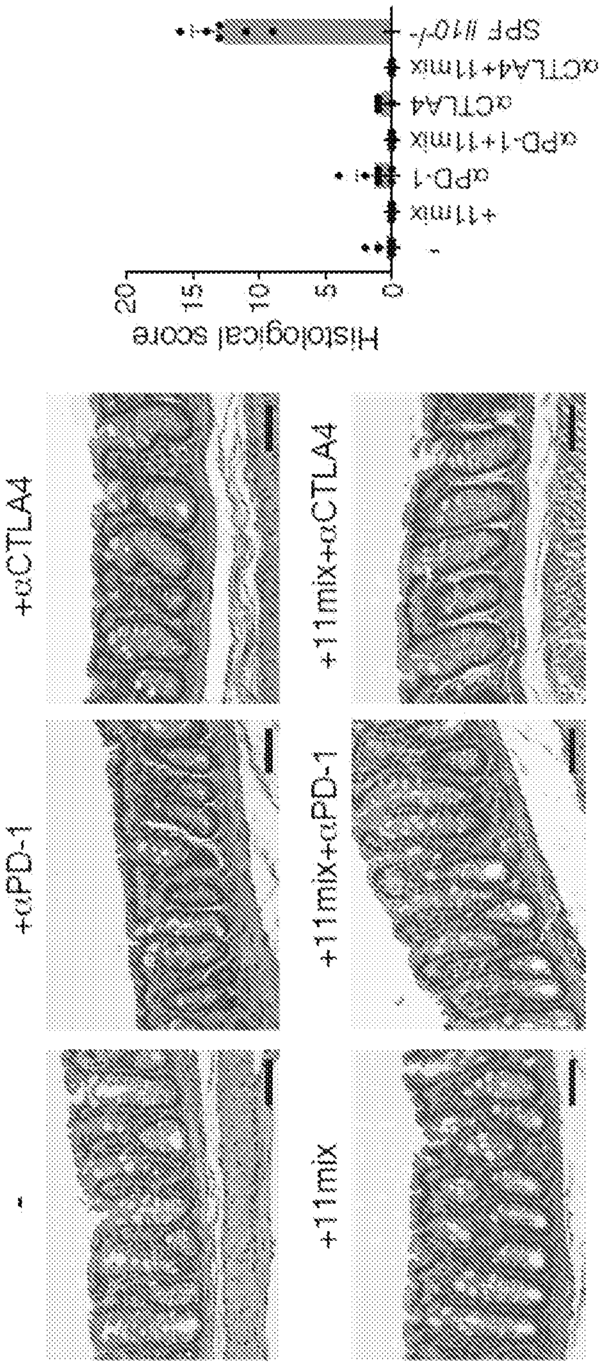

In addition to fending off intracellular pathogens, IFN+CD8 T cells also play a critical role in anti-tumour immunity and mediate immune checkpoint inhibitor (ICI) therapies like mAbs targeting PD-1, PD-L1, and CTLA-4 (refs[3,20-22]). We thus examined whether colonization with the 11 strains could enhance the therapeutic efficacy of ICIs in murine cancer models. SPF mice were treated with AVMN and subcutaneously engrafted with MC38 adenocarcinoma cells, followed by microbiota reconstitution with SPFfae either with or without repetitive dosing of the 11-mix. Tumour growth was then tracked in the presence or absence of intraperitoneal PD-1 mAb administration (FIG. 46A). Consistent with previous reports[22,23], PD-1 mAb monotherapy significantly suppressed tumour growth (FIG. 46B). Notably, repetitive dosing of the 11-mix alone controlled tumour growth to the same extent as PD-1 mAb therapy, and the combination of PD-1 and 11-mix treatment was significantly more effective than either monotherapy (FIG. 46B, FIG. 57A, and FIG. 57B). In keeping with these observations, the combination therapy increased the number of tumour-infiltrating CD8 T lymphocytes (TILs) (FIG. 46C), many of which were IFN+ with a comparatively large GrB+ subpopulation (FIG. 46D). IFN+CD8 TILs were mostly PD-1+ and ICOS+ (FIG. 46E) and included a subset specific for the MC38 tumour-associated antigen p15E (ref.[24]) (FIG. 46F). Additionally, combination therapy resulted in an increase in number of tumour-infiltrating CD11c+MHC class II+ DCs (FIG. 46G), which exhibited heightened expression of MHC class I (FIG. 46H). To test the generalizability of our findings, we next probed the ability of the 11-mix to modulate the efficacy of CTLA-4 mAb ICI treatment in the MC38 cancer model. Combination therapy of the 11-mix and CTLA-4 mAb significantly enhanced the host anti-tumour response (FIG. 46I). Importantly, there was no histological evidence of colitis in any of the experimental groups, a frequently observed adverse effect of ICI therapies[3,25] (FIG. 57B). In addition to entrancing treatment efficacy in the highly immunogenic MC38 tumour model, the combination of PD-1 mAb and the 11-mix was also effective against the less immunogenic BRAF$^{V600E}$PTEN$^{-/-}$ melanoma although, unlike in the MC38 case, neither PD-1 nor 11-mix monotherapy slowed tumour growth (FIG. 46J). Collectively, these results suggest that the 11 strains modulate anti-tumour immunity and have the capability to enhance ICI therapies.

Figure 58A:
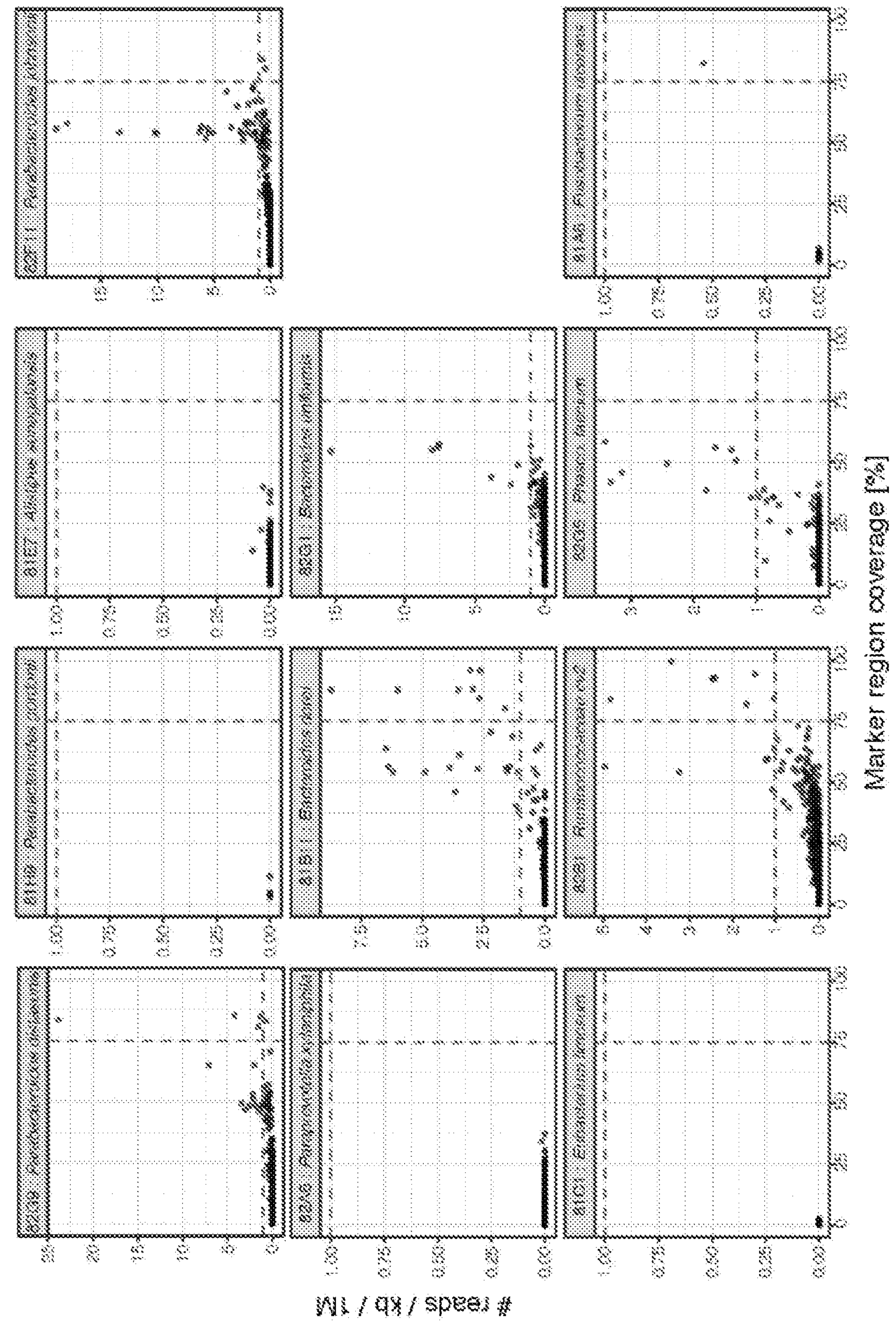
FIGS. 58A and 58B show the level of abundance of the 11 strains in the human gut microbiome. Draft genomes of the 11 strains were split into 1 kilobase pair (kbp) regions and mapped against NCBI RefSeq (~85 k genomes) to identify regions with no or weak similarity to known isolates (Identity <80%, Coverage <85%). Of these, consecutive regions with a minimum 5 kbp were defined as marker regions that are unique to each strain. Gut metagenome samples with at least 1M quality controlled reads across various datasets (HMP1-2[32], LLDeep[33], MetaHIT[34,34], 500FG[36], HMP2[27] (only first time point used), and healthy Japanese adults[39] ("Japanese")) were mapped to 1 kbp regions in all strains (filtered by 95% mapping identity). The mapped read counts were normalized to reads per kbp per million (RPKM).
Figure 58B:
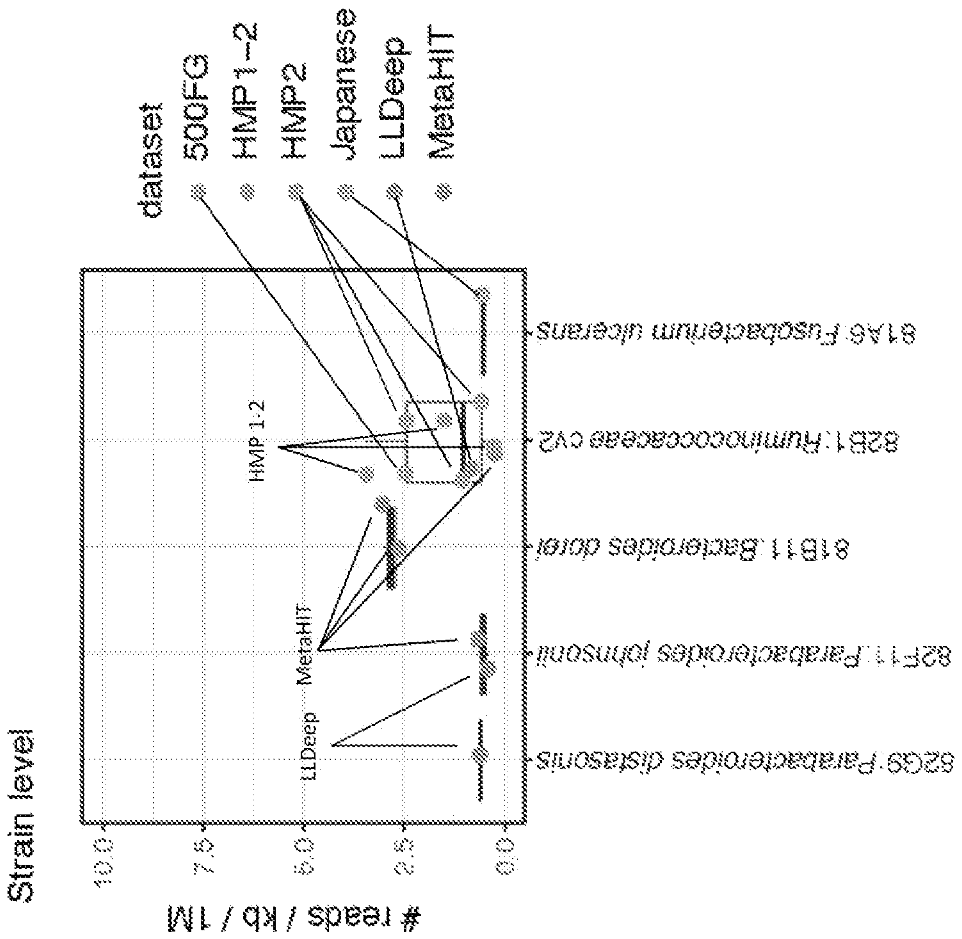

Finally, to evaluate the abundance of the 11 strains in the average human gut microbiome, we mined 3039 samples from metagenomic datasets, including JPGM, HMP1-2, LLDeep, MetaHIT, 500FG, and HMP2. We found that most of the 11 strains are generally rare, low-abundance components of the human microbiota (FIGS. 58A-60). At strain-level resolution, 5 of the 11 were detected in very few individuals (15 out of the 3039 evaluated samples) (FIG. 58B). Even at the species level, bacteria corresponding to Fusobacterium ulcerans (strain 1A6), Eubacterium limosum (strain 1C1), Parabacteroides gordonii (strain 81H9), and

Figure 59:
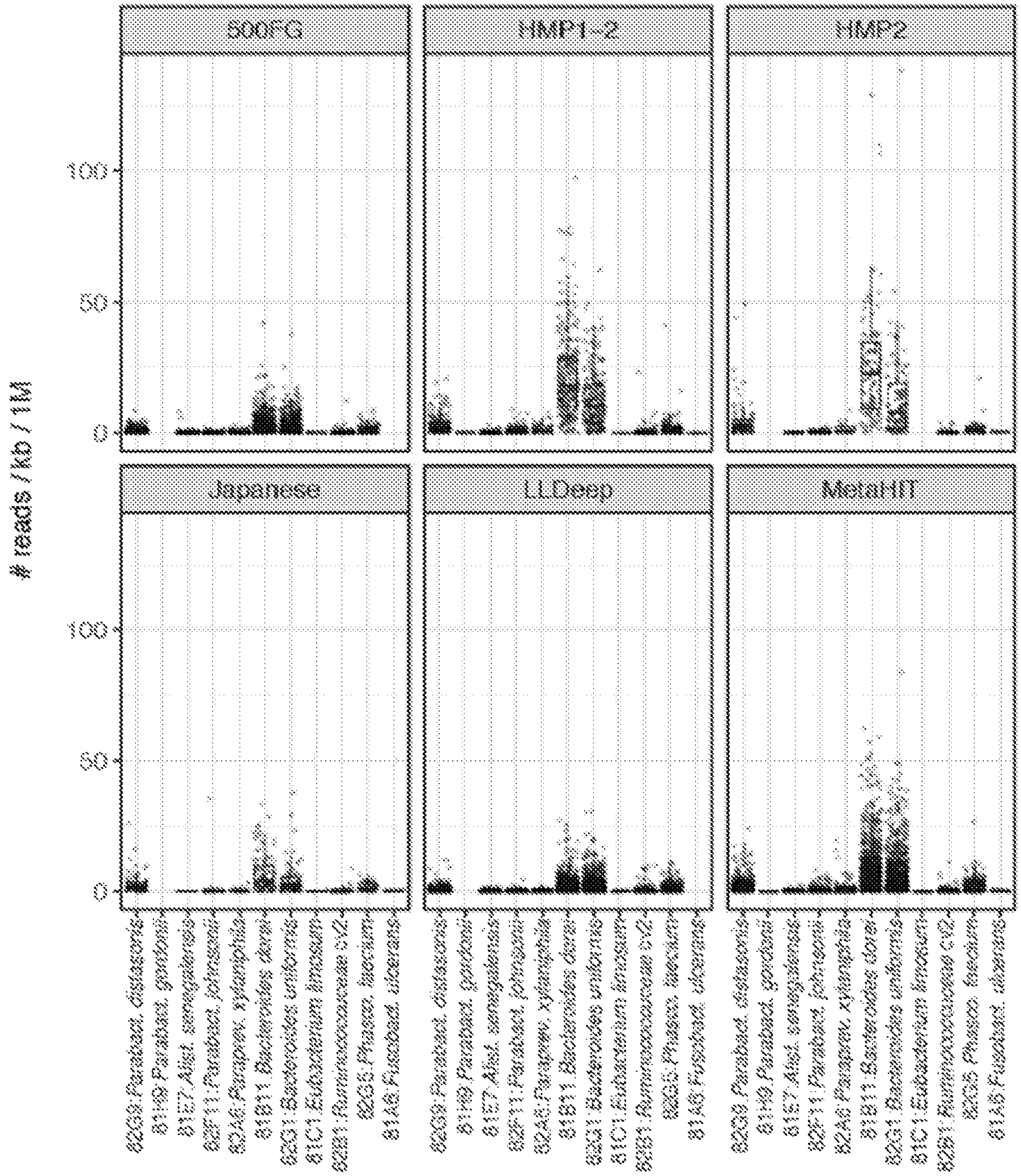
FIG. 59 shows the species level abundance of the 11 strains in the human gut microbiome. The abundance at a species level was calculated as a median abundance across all 1 kbp regions in a genome using 3039 metagenome samples with at least 1M quality controlled reads (mapped reads were filtered at 95% mapping identity). The mapped read counts were normalized to reads per kilobase per million (RPKM). The abundance of the 11 strains is shown for each of the datasets used.
Figures 60A, 60B:
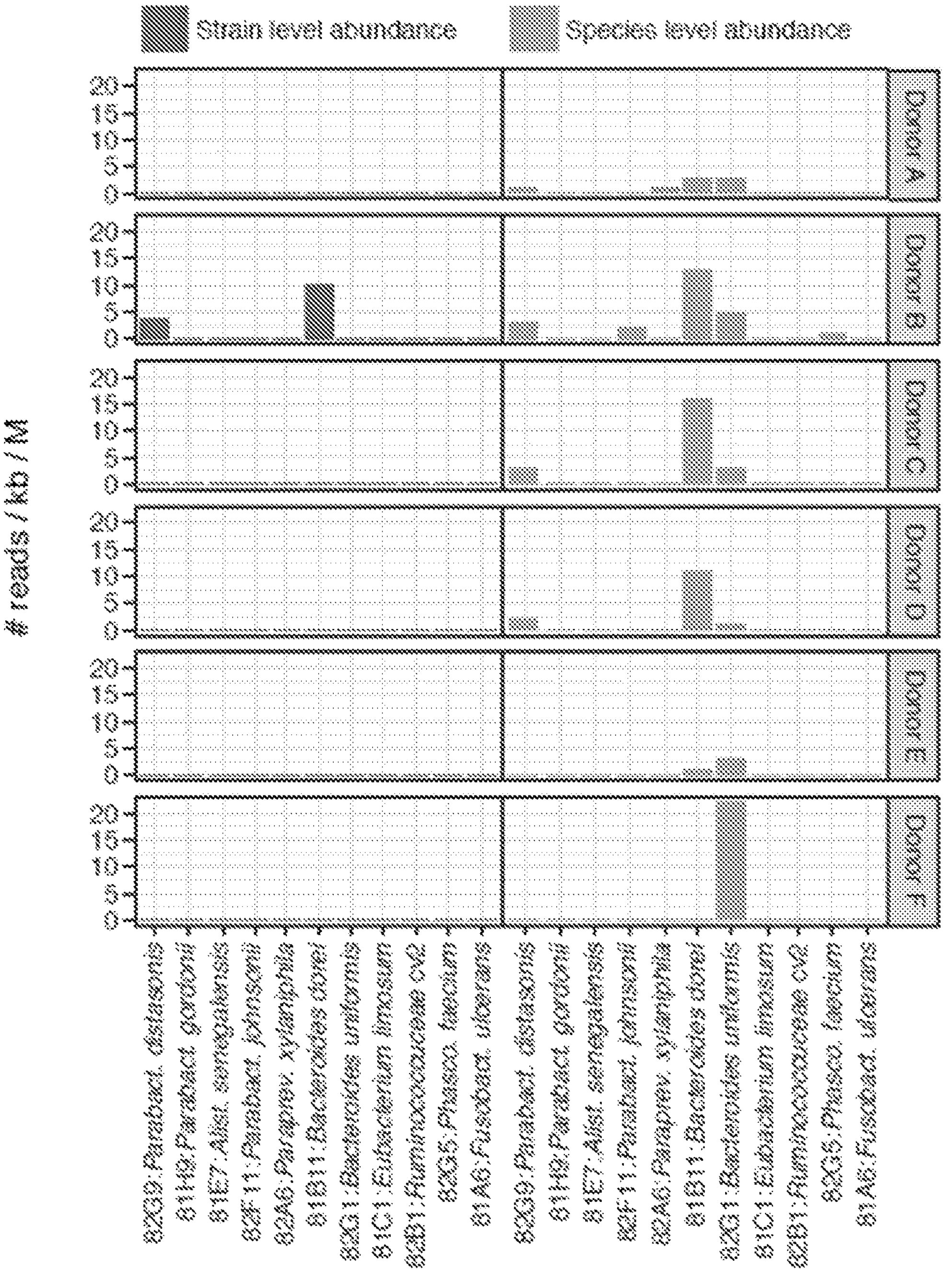
FIGS. 60A and 60B show the abundance of the 11 strains in the faecal microbiome of healthy human donors.

*Alistipes senegalensis* (strain 81E7) were particularly rare in the human gut microbiome across all cohorts (FIG. 59). Similarly, most of the strains were below the detection limit even in the microbiome of Donor B, from which they were isolated (FIG. 60).

In this study, we have identified 11 healthy human-associated bacterial strains that act together to induce intestinal IFN+CD8 T cells with a $T_{RM}$ phenotype via activation of DCs. IFNγ released by these cells can promote an anti-pathogenic environment in the gut by upregulating a number of IFN-induced antimicrobial genes and chemokines, likely conferring resistance to the intracellular pathogen Lm in this fashion. Moreover, the 11-strain consortium was effective in inhibiting tumour growth in syngeneic cancer models in conjunction with ICIs. These findings are consistent with previous reports demonstrating the important role of IFN+CD8 T cells and DCs in tumour immunity[3,14,20-22]. More research will be needed to elucidate the molecular mechanism by which the 11 strains effect the observed immunomodulation. One possibility is TCR cross-reactivity between bacterial and tumour antigens, though this is less likely given that the immunomodulatory response was seen in two distinct cancer models. It is also possible that DCs activated in the colon may migrate into the tumour to stimulate CD8 T cells. Alternatively, bacterial products released by the 11 strains may directly and/or indirectly stimulate DCs and CD8 T cells within the tumour microenvironment to support the development of tumour specific CD8 T cells.

Several reports have demonstrated that the composition of the gut microbiome influences response to ICIs in humans and mice, suggesting that its manipulation holds immense therapeutic potential[3,21,28-30]. However, the specific microbiota members associated with enhanced clinical response vary substantially between studies. Cross-referencing human gut microbiome datasets, we found that most of the 11 strains are rare, low-abundance components of the human microbiota. Although further investigation is required to assess whether the IFNγ+CD8 T cell-inducing strains identified in this study are functionally related to these correlated with improved ICI efficacy in recent reports[28-30], our findings provide an example of rare species that can induce IFN+CD8 T cells and enhance infection and cancer treatment with a potentially large effect size[31]. The contribution of such species may be underestimated by traditional, sequence-oriented microbiome analysis. Our isolated strains have great biotherapeutic potential and could be broadly applicable to enhancing the treatment of cancer and infectious disease, as they are severely underrepresented in the gut microbiota of most individuals.

Example 11

Figures 61A, 61B, 61C, 61D:
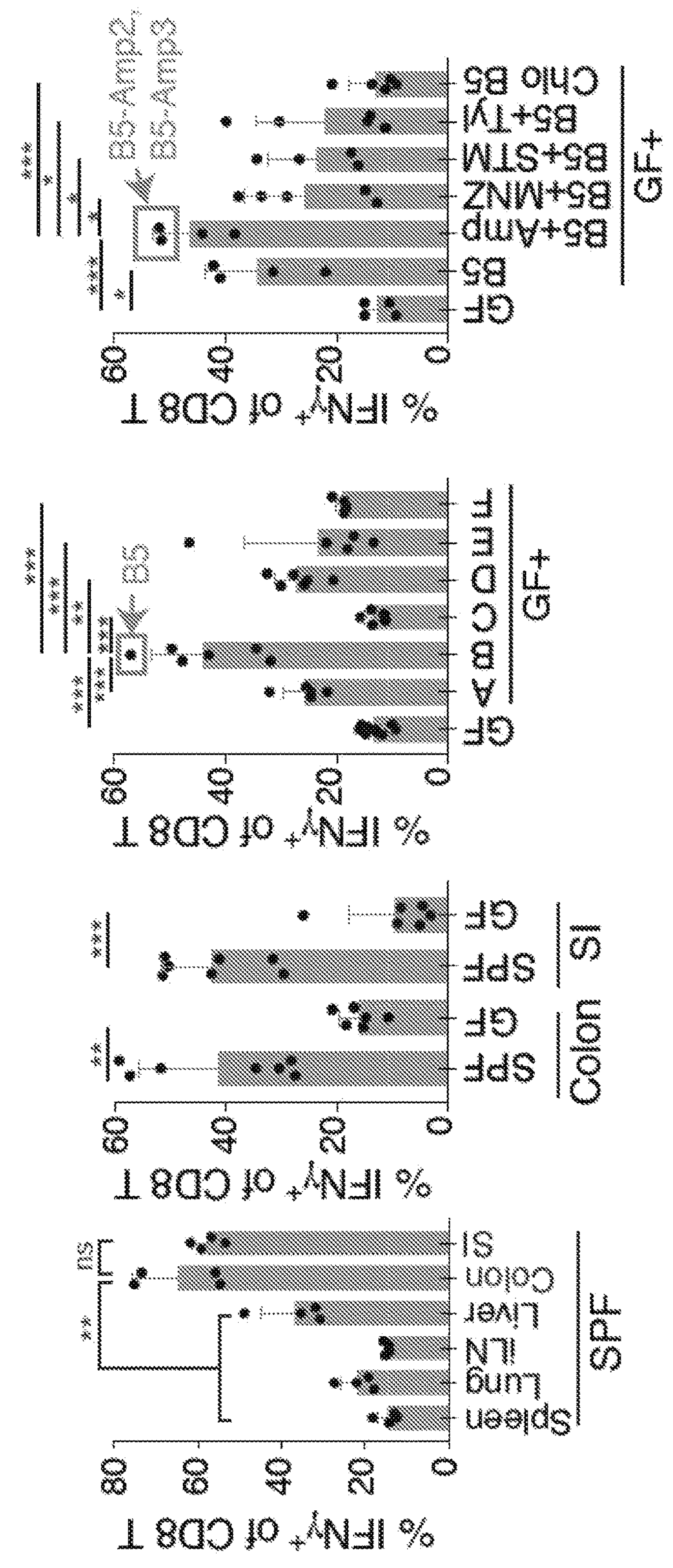
FIGS. 61A-61I show the isolation and identification of 11 IFNγ+CD8 T cell inducing bacterial strains from the microbiome of healthy human donors.
Figure 65B:
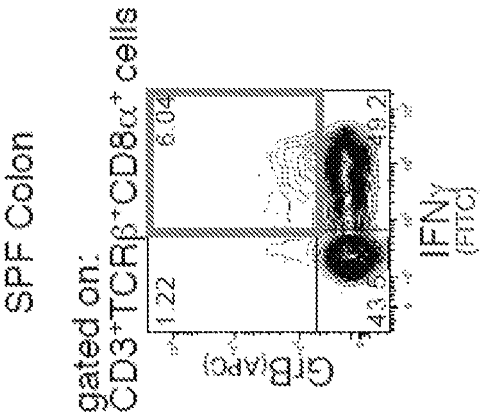
FIGS. 65A-65F show the characterization of the intestinal IFNγ+CD8 T cell population in GF and SPF mice.
Figure 65A:
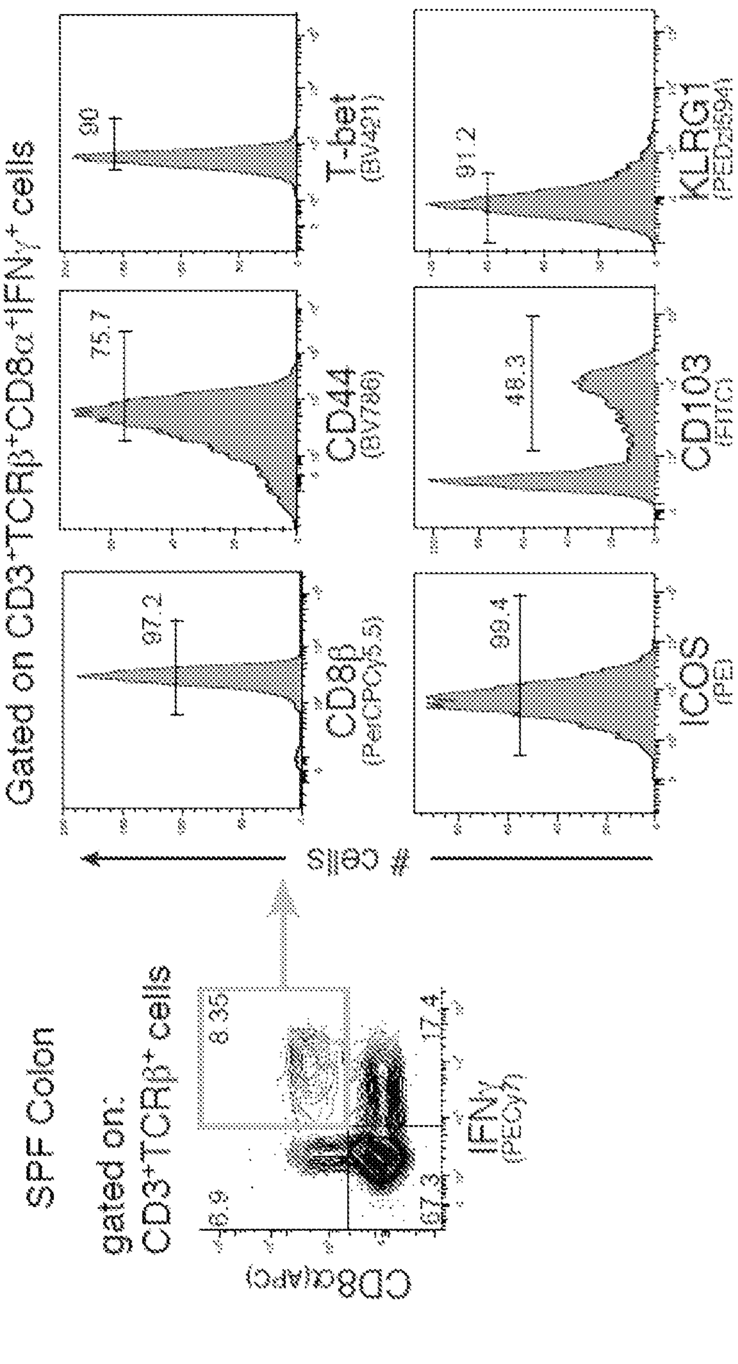
Figures 65C, 65D, 65E, 65F:
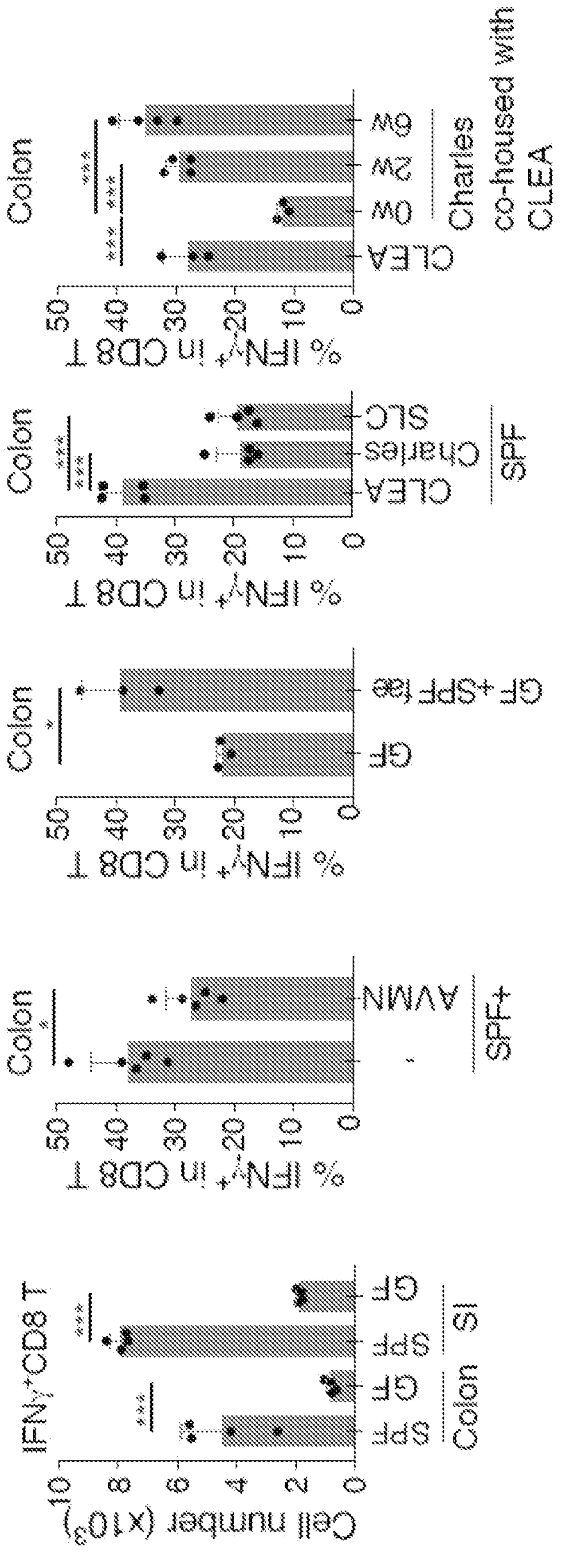

IFNγ-expressing CD8 T cells were constitutively present at high frequencies in the colonic and small intestinal (SI) lamina propria (LP) as compared to other organs in SPF mice (FIG. 61A), reminiscent of the preferential localization of T helper 17 (TH17) and regulatory T (Treg) cells to the gut[4,8,9]. A large proportion of colonic LP IFNγ+CD8 T cells expressed the αβ-T cell receptor (TCR), CD8α/β, CD44, T-bet, and inducible T cell costimulator (ICOS) (FIG. 65A), indicating they were primarily activated/memory cells differentiated from conventional CD8 T cells. The IFNγ+CD8 T cells contained subsets expressing CD103, a marker of tissue-resident memory T (TRM) cells[10,12], and granzyme B (GrB), a key effector molecule of cytotoxic T cells (FIGS. 65A, 65B). The frequency and number of both colonic and SI LP IFNγ+CD8 T cells were markedly decreased in GF as compared to SPF mice (FIG. 61B and FIG. 65C). Similarly, treatment of adult SPF mice with an antibiotic cocktail significantly reduced IFNγ+CD8 T cell frequency (FIG. 65D). Conversely, oral administration of faecal suspensions from SPF mice (SPFfae) ameliorated the deficit in GF mice (FIG. 65E). Furthermore, the relative abundance of this cell population in SPF mice varied with housing conditions, and co-housing for 2 weeks resulted in all mice ultimately displaying a high-frequency phenotype (FIG. 65F). Collectively, these results suggested that the frequency of IFNγ+CD8 T cells is plastic, with specific members of the microbiota promoting their intestinal accumulation in an inducible and reversible manner.

Figure 66:
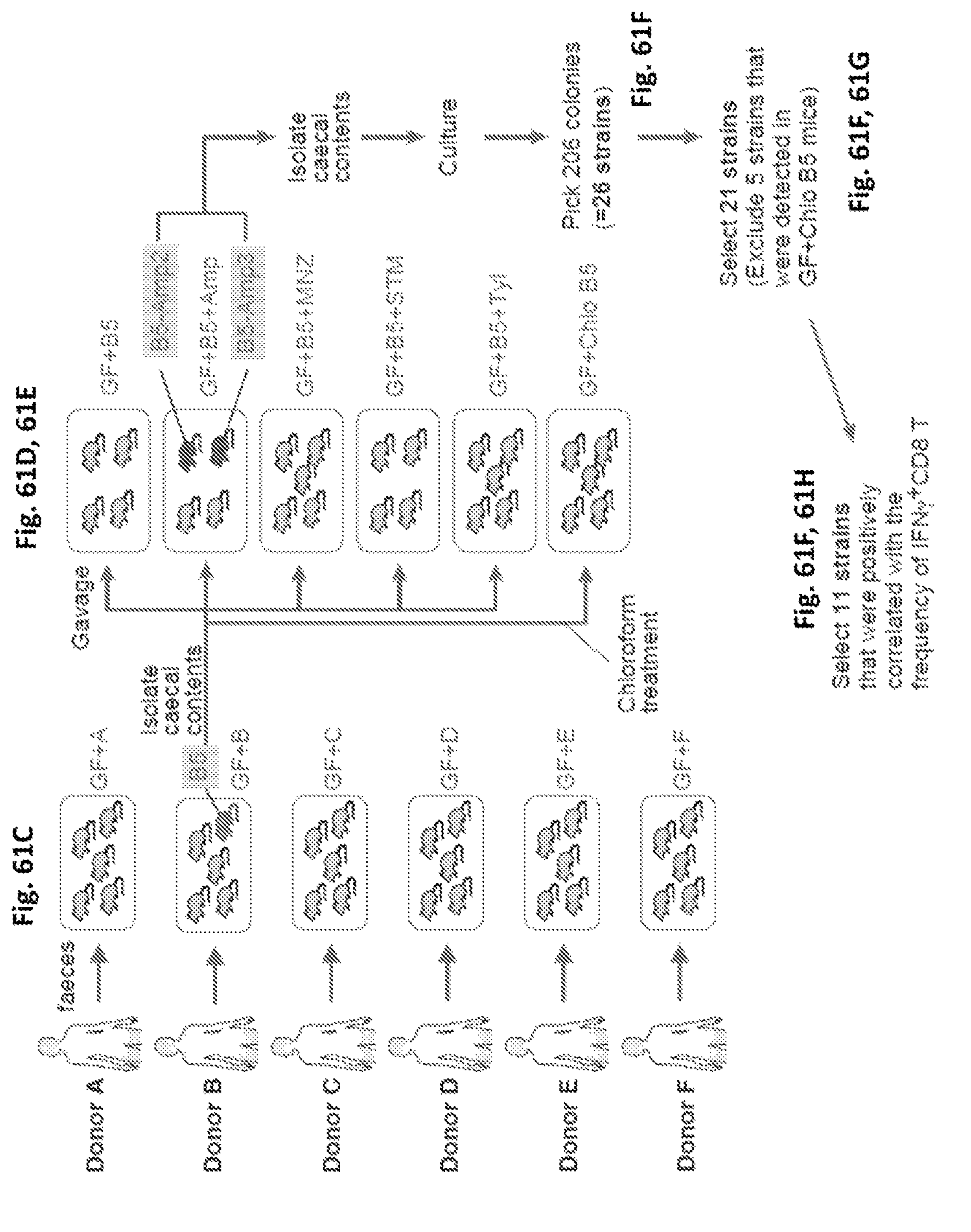
FIG. 66 shows a schematic representation of the strategy for isolating IFNγ+ CD8 T cell-inducing bacteria from the gut microbiota of healthy human donors.
Figure 67A:
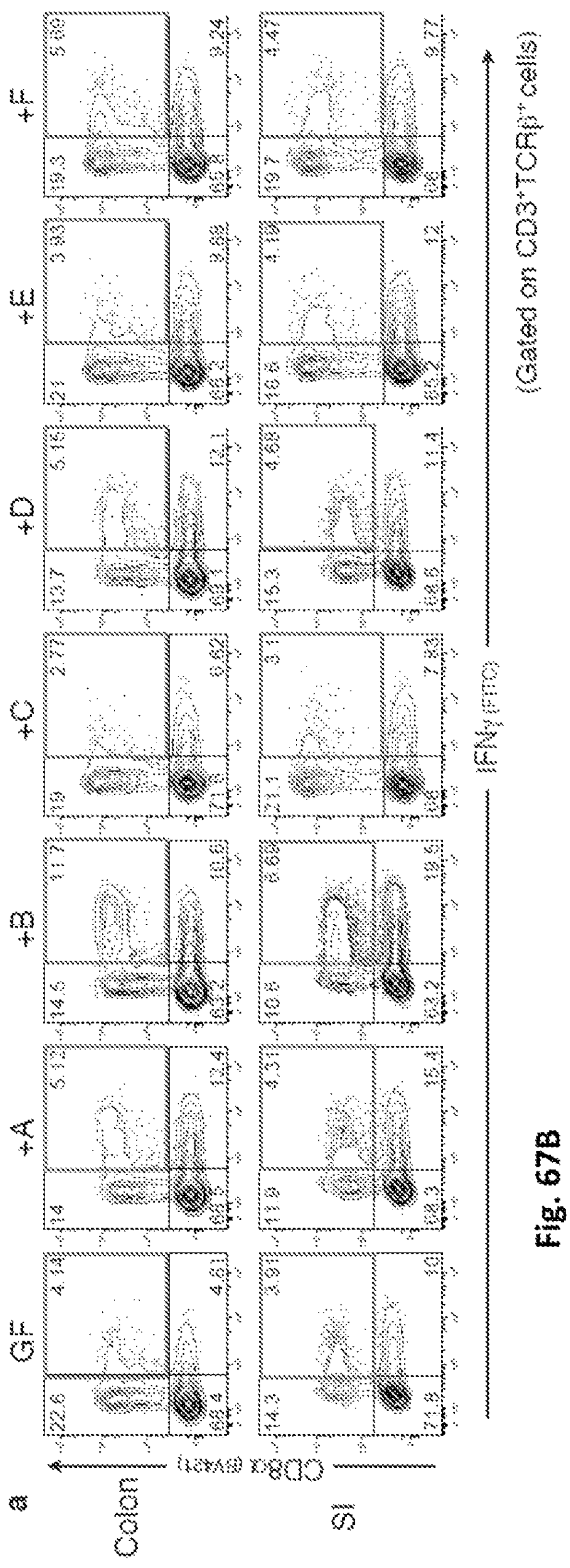
FIGS. 67A and 67B show induction of IFNγ+CD8+ T cells by gut microbiota from various healthy human donors (A-F).
Figure 67B:
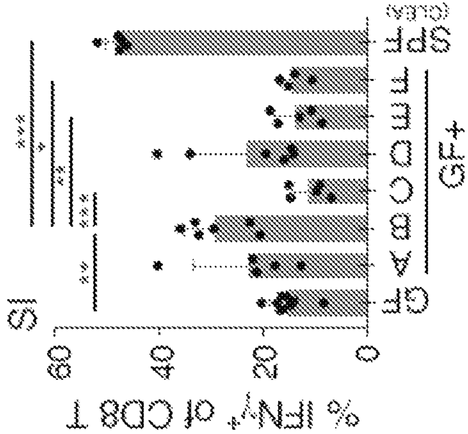

From a translational perspective the human, rather than the murine, faecal microbiota was mined for bacterial strains that could induce the accumulation of IFNγ+CD8 T cells in the intestine (outlined in FIG. 66). Faecal samples were obtained from six healthy volunteers (Donors A to F) and were each orally administered to GF mice housed in separate gnotobiotic isolators. The extent of colonic IFNγ+CD8 T cell induction varied greatly between samples (FIG. 61C and FIG. 67). Faeces from Donor B elicited the strongest induction, to a degree comparable to that observed in SPF mice (compare FIGS. 61B and 61C). Then the mouse that exhibited the strongest induction ("mouse B5") (FIG. 61C) was selected and gavaged a suspension of its caecal contents into GF mice (GF+B5 mice). These mice were treated with either ampicillin (Amp), metronidazole (MNZ), streptomycin (STM), tylosin (Tyl), or a vehicle control via the drinking water. Chloroform-treated caecal contents of mouse B5 were inoculated into an additional group of GF mice (GF+Chlo B5 mice) to examine the effects of spore-forming commensal bacteria[3]. As expected, GF+B5 mice showed a significant increase in frequency of colonic IFNγ+CD8 T cells (FIG. 65D). Treatment with MNZ, STM, or Tyl, however, resulted in a substantial decrease, and chloroform treatment abrogated induction altogether (FIG. 65D). In contrast, Amp treatment enhanced the observed induction (FIG. 65D). The two Amp-treated mice exhibiting the strongest IFNγ+CD8 T cell induction (denoted B5-Amp2 and B5-Amp3) were selected for further analysis and their caecal contents were cultured in vitro in a variety of media. 206 distinct colonies were picked and analysed by 16S ribosomal RNA (rRNA) gene sequencing to elaborate a consortium of 26 unique strains (FIG. 61F).

Figures 61E, 61F:
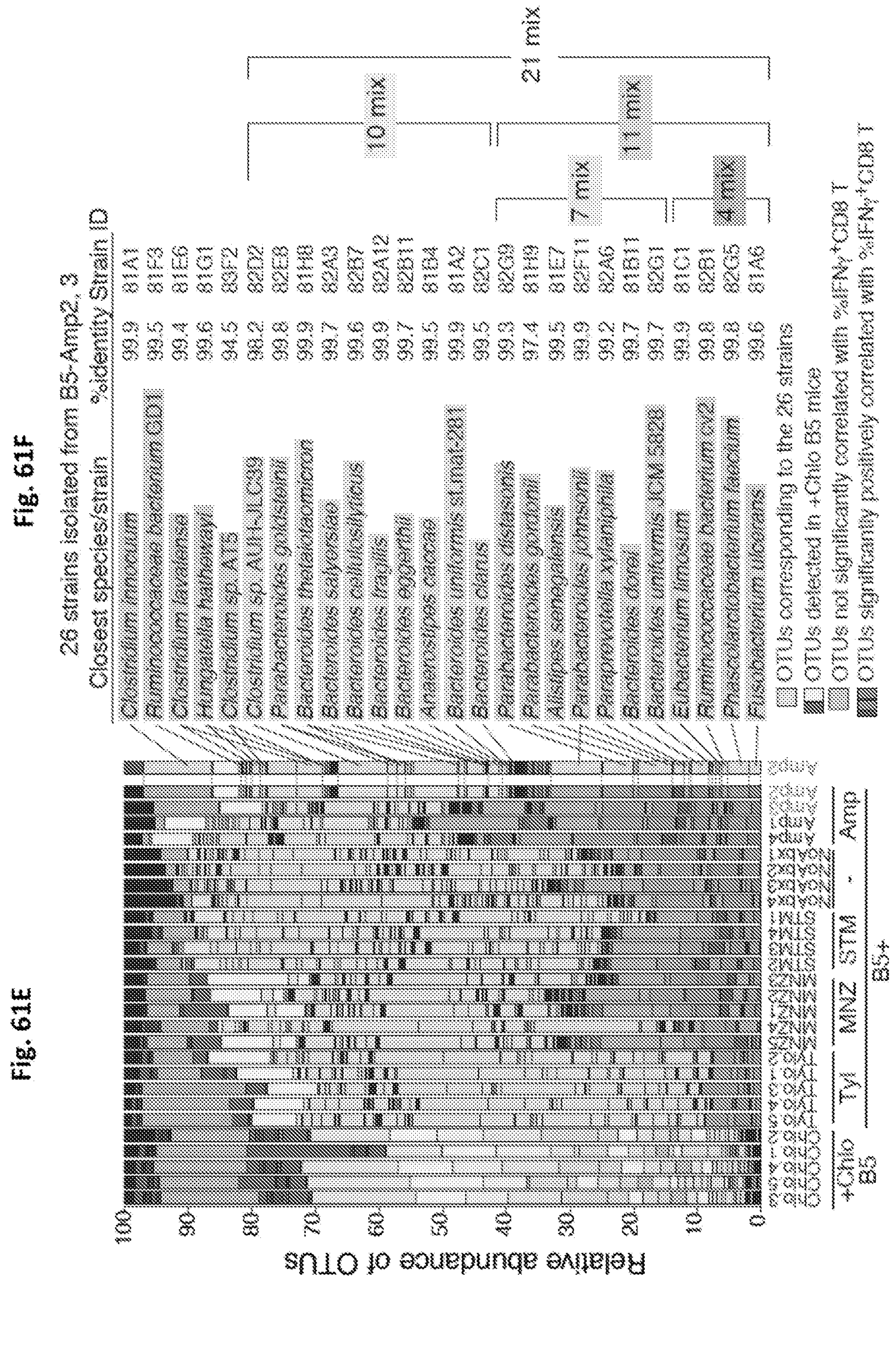
Figure 61J:
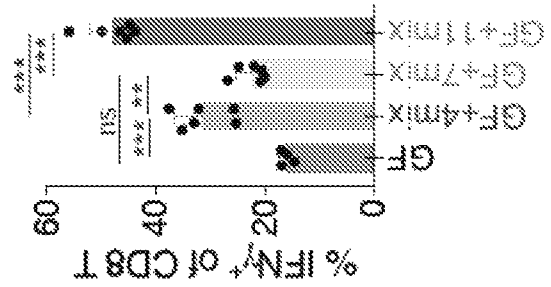
Figure 61I:
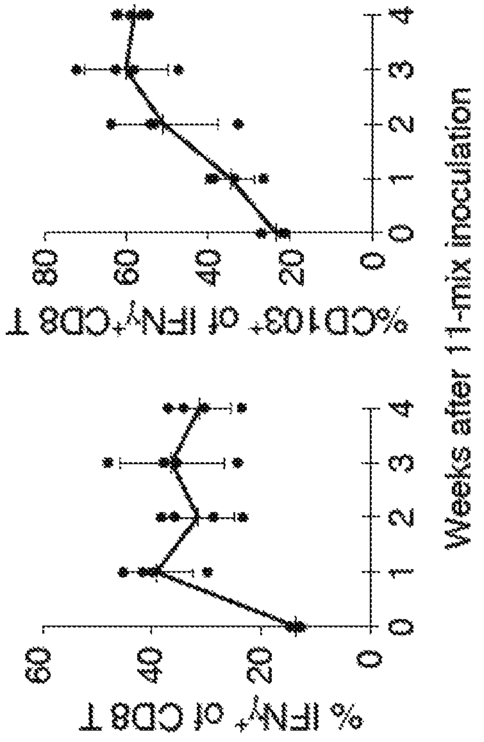
Figure 61H:
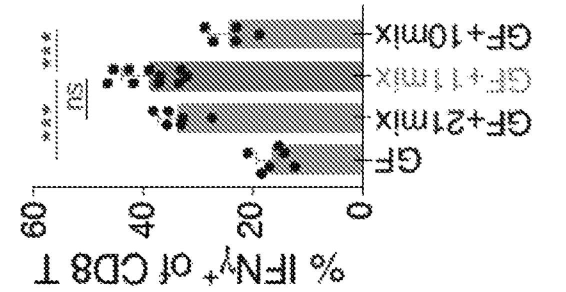
Figure 61G:
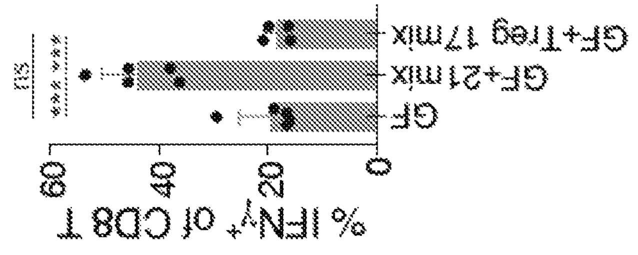
Figure 68:
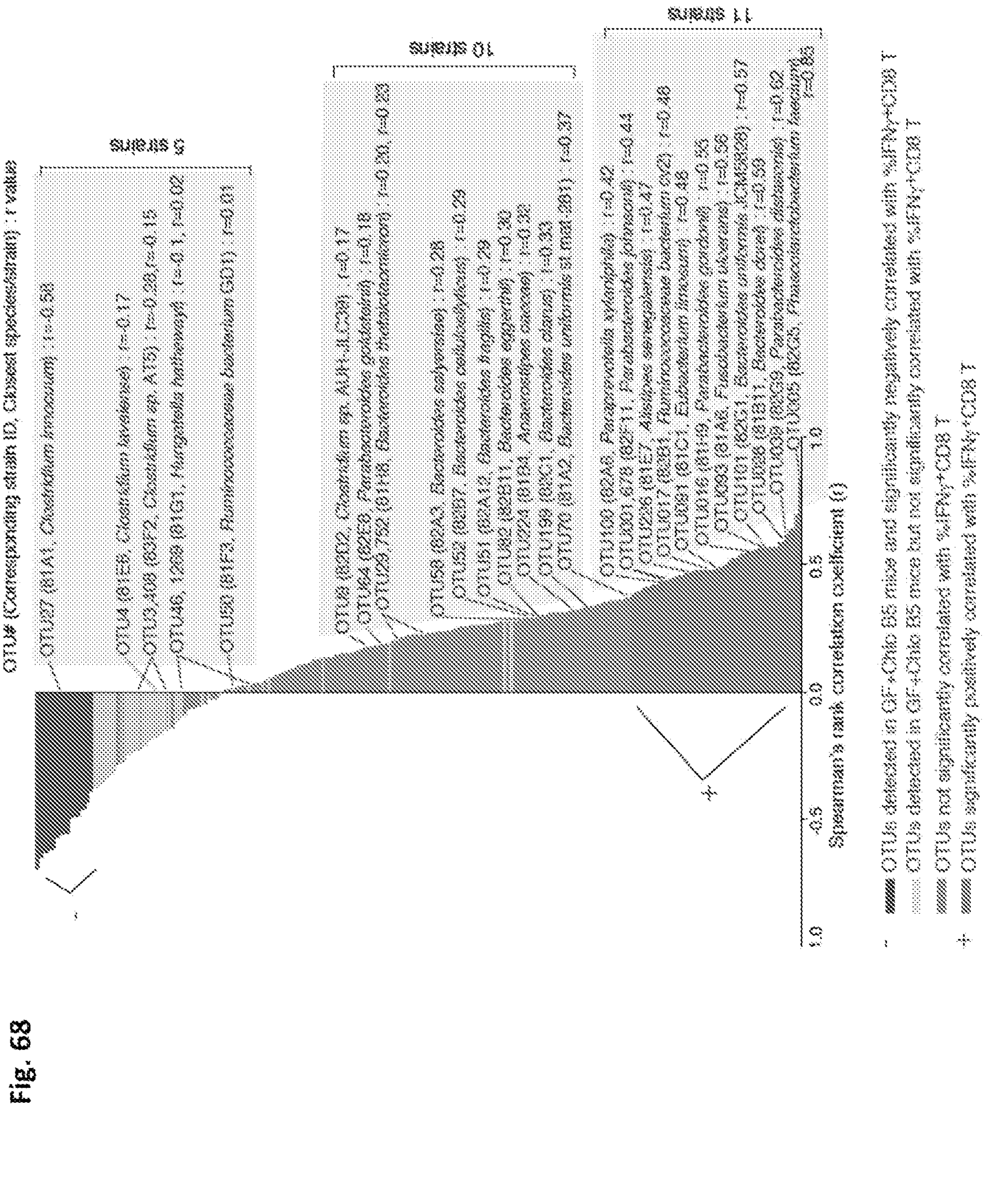
FIG. 68 shows the Spearman's correlation between OTU relative abundance and IFNγ+CD8 T cell frequency. The Spearman's correlation coefficient (r) and p-value for the relationship between the number of individual bacterial OTUs (among 3000 reads) detected in mice (shown in FIG. 61E) and the percentage of IFNγ+ cells among the colonic CD8 T cell population (shown in FIG. 61D) were calculated using GraphPad PrismR. OTUs significantly positively and significantly negatively correlated with the frequency of colonic IFNγ+CD8 T cells (P<0.05) are shown with and "+" and "−", respectively. OTUs detected in GF+Chlo B5 mice are indicated with "−" and "+", respectively. The closest species/strain and individual r value for each OTU are shown.
Figures 69A, 69B:
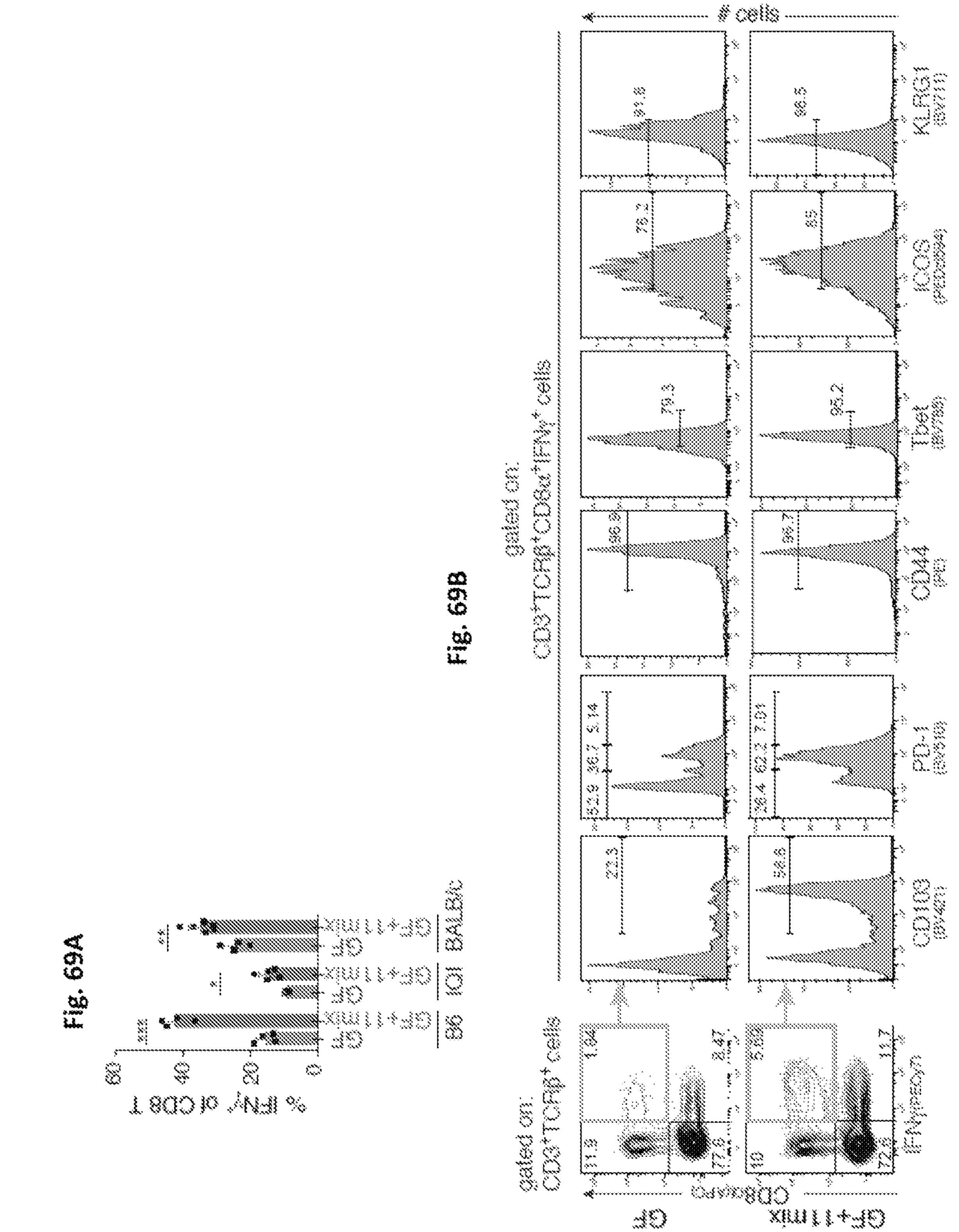
FIGS. 69A-69D show characterization of IFNγ+CD8 T cells induced by the mixture of 11 bacterial strains.
Figure 69C:
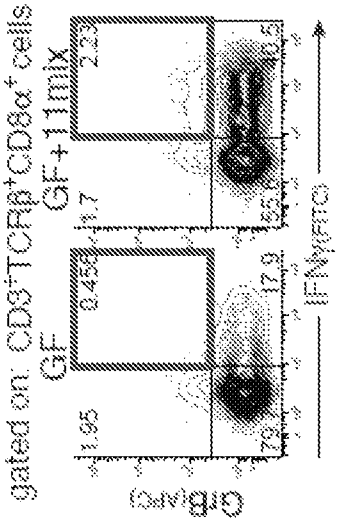
Figure 69D:
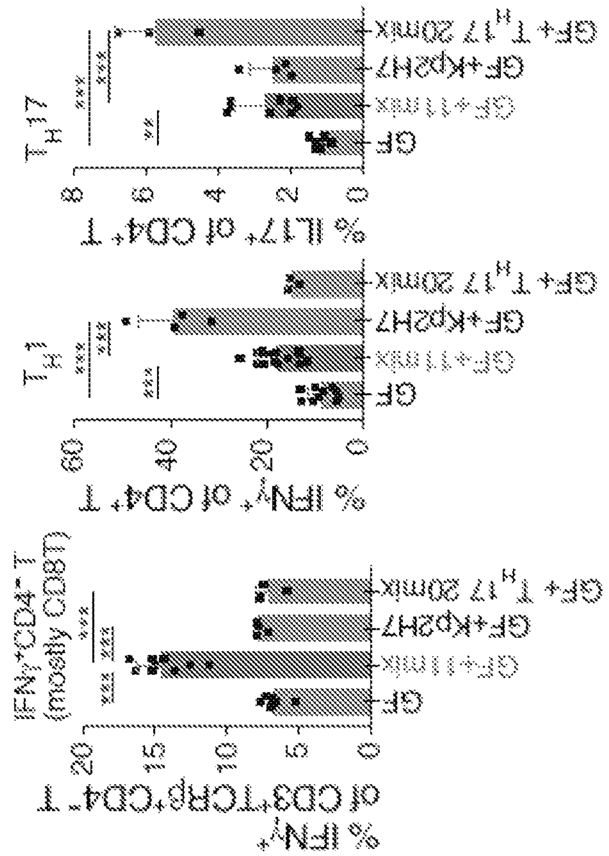
Figure 70B:
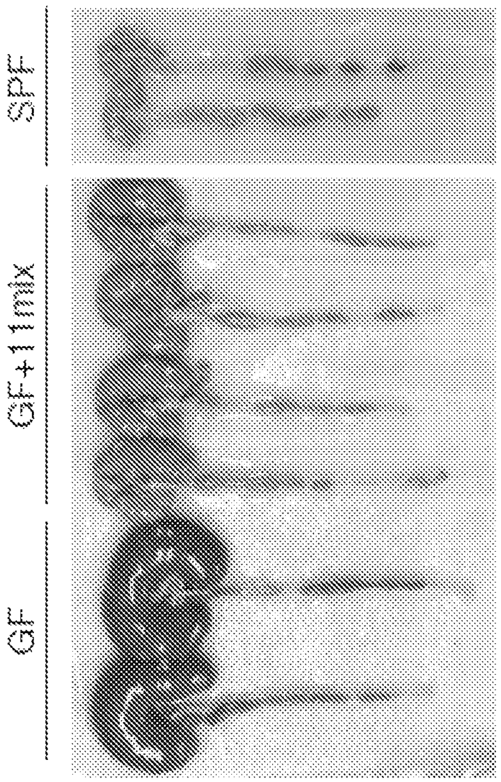
FIGS. 70A-70E show non-inflammatory immunomodulation by the mixture of 11 bacterial strains.
Figure 70A:
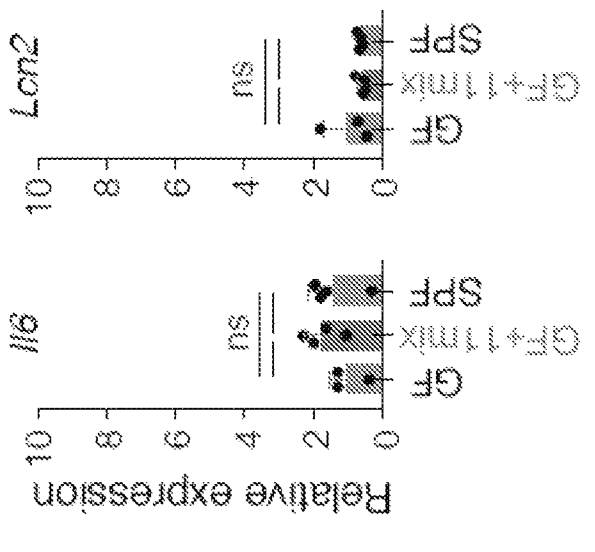
Figures 70C, 70D, 70E:
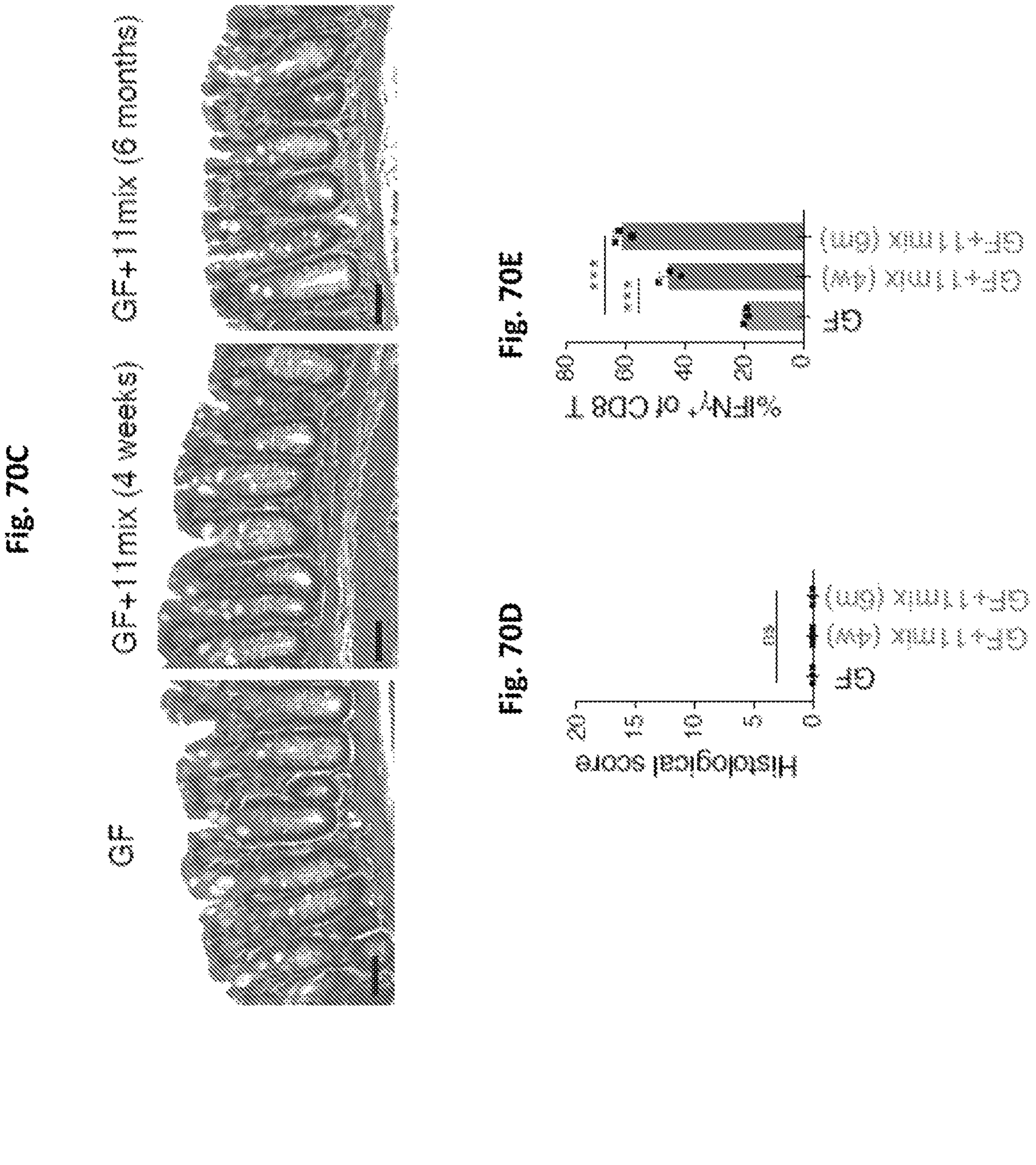

Analysis of caecal microbiota composition revealed that the 26 isolated strains together roughly recapitulated the microbiota of mice B5-Amp2 and B5-Amp3 (FIGS. 61E, 61F). From these 26 strains, five strains detected in the microbiome of GF+Chlo B5 mice (FIGS. 61E, 61F) were excluded and the remaining 21 were selected for further analysis (FIG. 61F). The 21 strains were cultured individually and introduced as a mixture (21-mix) into GF mice (GF+21-mix mice). For comparison, mice colonized with a mixture of 17 Treg cell-inducing *Clostridia* strains (GF+Treg 17-mix) that were previously isolated from a human faecal sample were analyzed[8]. A very strong induction of IFNγ+CD8 T cells was observed in the colonic LP of GF+21-mix mice, with a magnitude comparable to that in SPF mice (compare FIGS. 61B, 61G), whereas GF+Treg 17-mix mice showed no induction above the GF baseline (FIG. 61G). A Spearman's rank correlation test was performed comparing the relative abundances of the 21 strains with IFNγ+CD8 T cell frequency. Among the 21 strains, 11 were positively associated with IFNγ+CD8 T cell frequency (FIGS. 61E and 61F) and 10 showed no significant association (FIGS. 61E and 61F) (see also FIG. 68). The efficacy of the 11 strains was compared versus the efficacy of the 10 strains in inducing colonic IFNγ+CD8 T cells. GF+11-mix mice exhibited a robust induction, to the same extent as did GF+21-mix mice, whereas GF+10-mix mice did not (FIG. 61H). The 11-mix-mediated increase in IFNγ+CD8 T cells was observed in mice of various genetic backgrounds, although the baseline and induction magnitude varied substantially between groups (FIG. 69A). IFNγ+*CD8 T cells induced by the 11-mix were largely PD-$1^{intermediate}$, CD44+, T-bet+, ICOS+, and KLRG1+, and a small subset was GrB+ (FIGS. 69B and 69C). Time course analysis of GF+11-mix mice revealed that the dramatic increase in IFNγ+CD8 T cells occurred within a one-week timeframe (FIG. 61I). These incipient IFNγ+CD8 T cells were primarily CD103−, though the CD $103+_{TRM}$ phenotype subset gradually increased in frequency thereafter (FIG. 61I and FIG. 69B), suggesting a stepwise differentiation pattern. Importantly, IFNγ+CD8 T cells persisted stably for 6 months, and neither gross, histological, nor transcriptional signs of colonic inflammation were observed in GF+11-mix mice (FIG. 70). The inductive ability of the 11-mix was not confined to CD8 T cells, but extended to CD4 T cells as well. Indeed, a significant increase in the frequencies of colonic TH17 and TH1 cells was observed, although these responses were significantly weaker than those induced by 20 reported TH17 cell-inducing strains (TH17 20-mix",) and by a reported TH1 cell-inducing *Klebsiella pneumoniae* strain (Kp2H7[13]), respectively (FIG. 69). These data suggested that the 11 strains have non-inflammatory immunomodulatory activity that is relatively specific to CD8 T cells.

Figure 72:
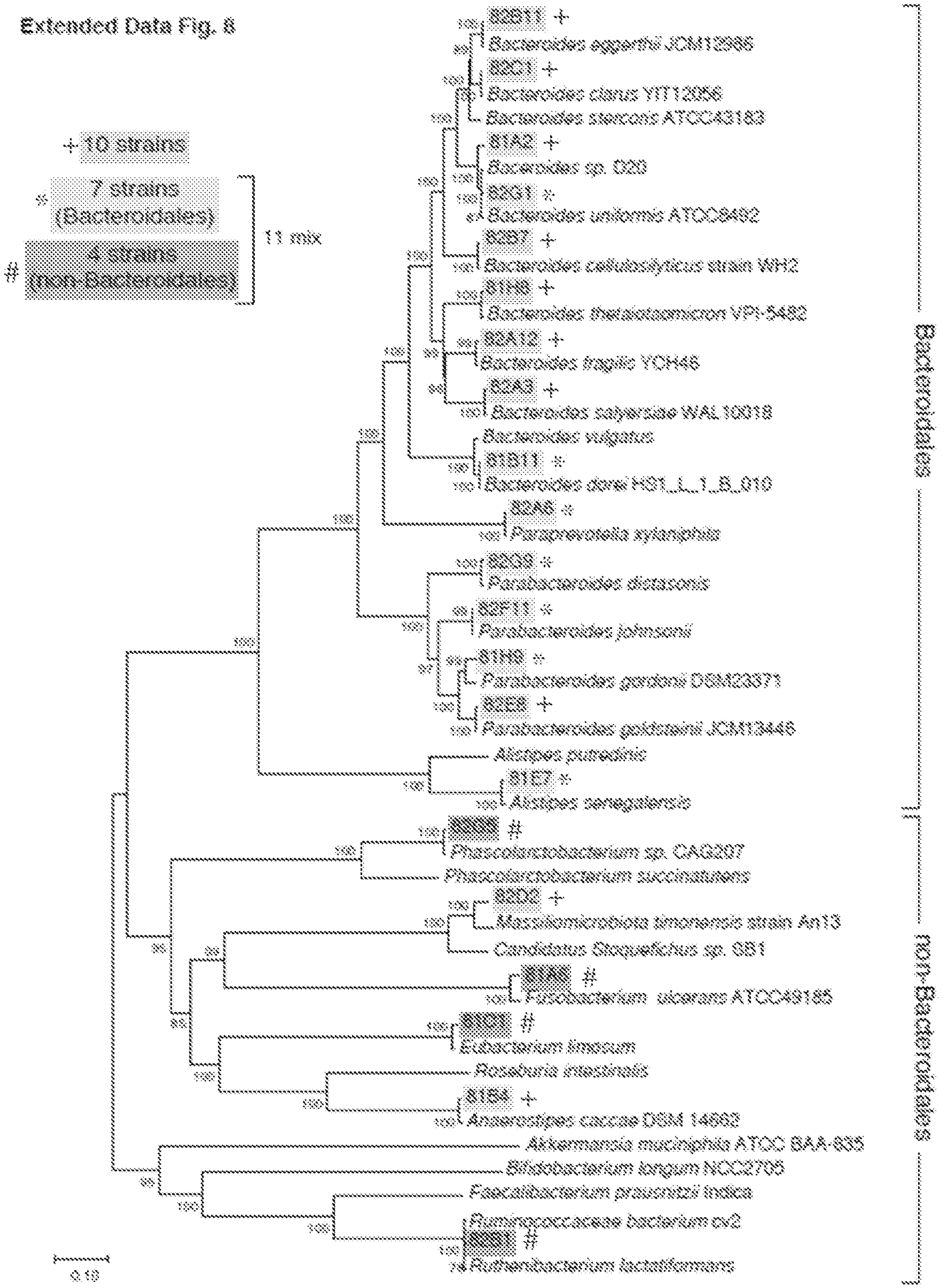
FIG. 72 shows the phylogenetic distribution of the 11 isolated strains. A phylogenetic tree was constructed by comparing 40 concatenated ribosomal gene sequences of each isolate using the MEGA v7.0 package and the neighbor-joining method with a bootstrap of 1000 replicates.

A phylogenetic comparison revealed that the 11 strains comprised 7 Bacteroidales and 4 non-Bacteroidales species (FIGS. 61F, 71, and 72). When inoculated into GF mice, the 7 Bacteroidales-mix (7-mix) failed to induce IFNγ+CD8 T cells, whereas the 4 non-Bacteroidales-mix (4-mix) displayed a significantly better induction capacity. However, the 4 mix alone was not sufficient to achieve the full inductive effect of the 11-mix (FIG. 61J). These results suggested that the 11 strains act as a consortium wherein the 4 non-Bacteroidales species act as effector elements, and the 7 Bacteroidales play a supporting role.

Figures 62A, 62B, 62C, 62D, 62E:
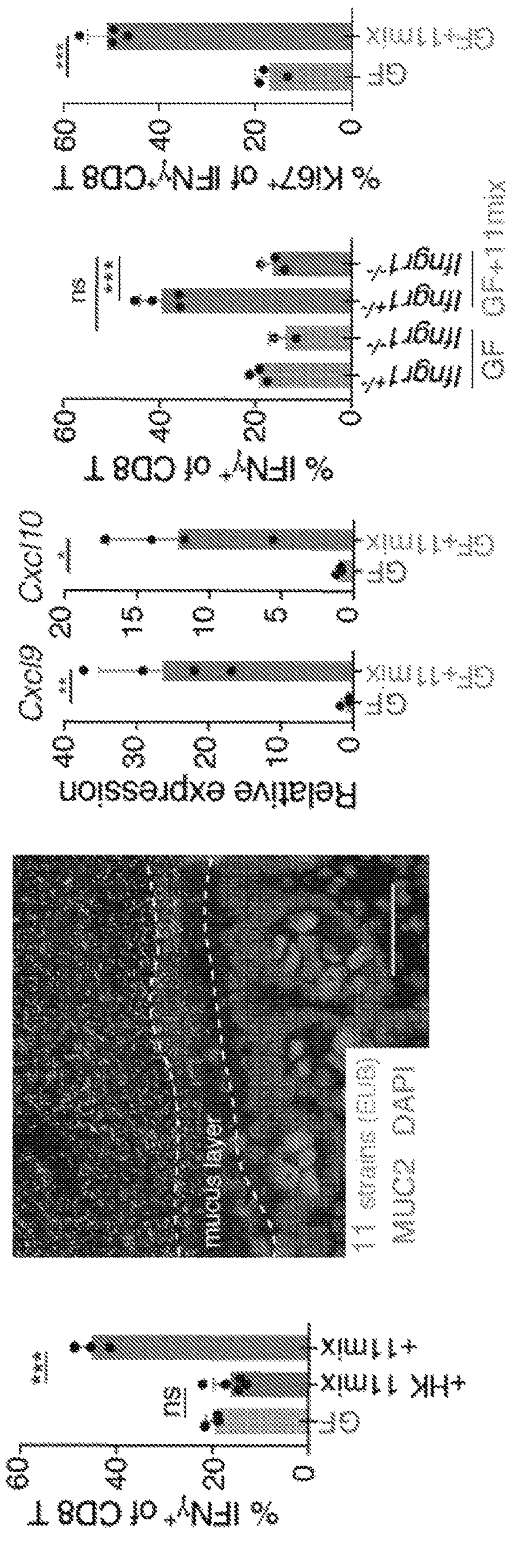
FIGS. 62A-62L show DC-mediated IFNγ+CD8 T cell induction by the 11 strains.
Figure 62F:
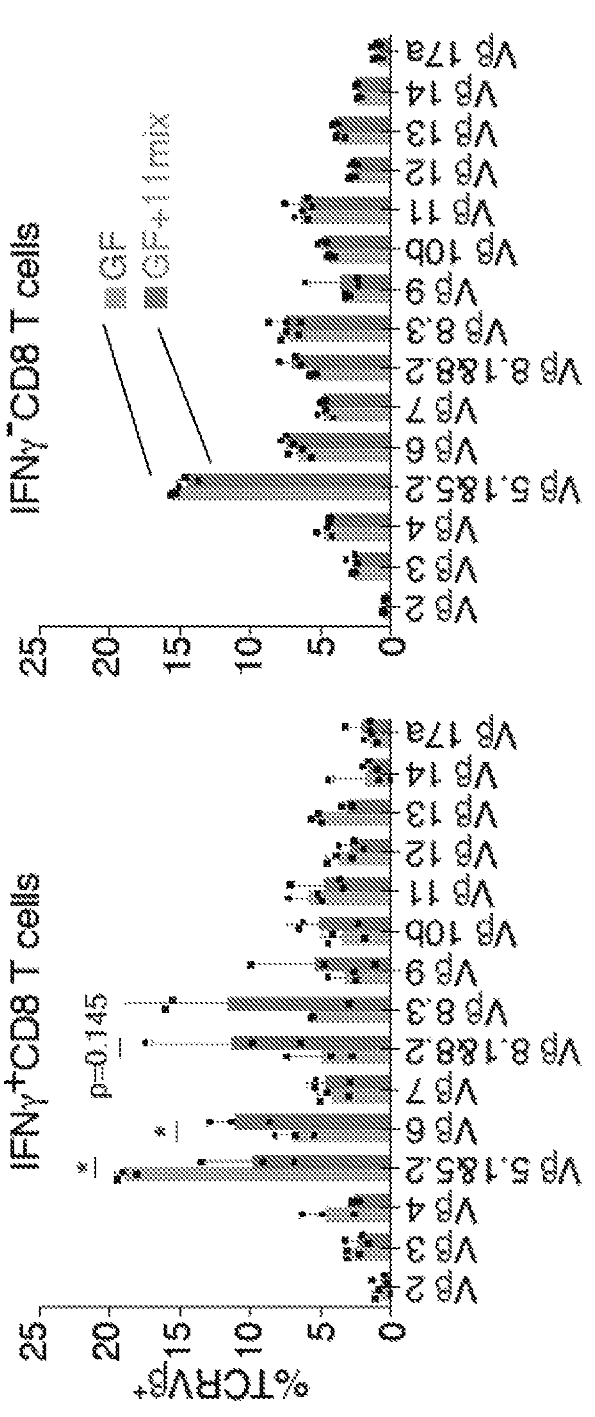
Figure 62G:
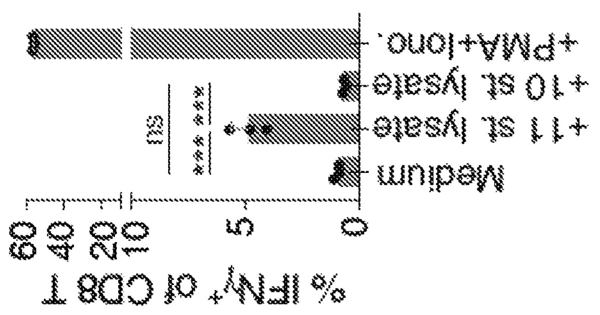

The mechanisms underlying 11-mix-mediated IFNγ+CD8 T cell accumulation in the colon were further elucidated. No accumulation was observed after treating GF mice with heat-killed 11-mix (FIG. 62A), and fluorescence in situ hybridization (FISH) highlighted the strains' ability to enter the colonic mucus layer, though no invasion into the epithelium was detected (FIG. 62B). Colonization with live 11-mix unregulated the expression of chemokines Cxcl9 and Cxcl10 as well as other IFN-inducible genes in colonic epithelial cells (ECs) (FIGS. 62C and 73A), and gnotobiotic IfngrI−/− mice displayed markedly suppressed IFNγ+CD8 T cell induction (FIG. 62D). These results suggested that active colonization near ECs might establish an IFNγ mediated feed-forward loop that plays a role in the recruitment and accumulation of IFNα+CD8 T cells. Furthermore, approximately half of the IFNγ+CD8 T cells were undergoing active proliferation one week post colonization, as evidenced by their Ki67 expression (FIG. 62E), suggesting that cellular expansion is at least partially responsible for the observed accumulation. Additionally, IFNγ+CD8 T cell TCR Vβ usage differed significantly between GF+11-mix and GF mice: the GF+11-mix group showed a relative enrichment for the Vβ6+ and Vβ8+ subsets, at the expense of Vβ5+ subset (2-way ANOVA interaction p-value=0.0001) (FIG. 62F). In contrast, there was no difference in IFNγnegative CD8 T cell TCR Vβ composition between GF and GF+11-mix mice (p-value=0.31) (FIG. 62F). The antigen specificity of the induced colonic IFNγ+CD8 T cells was also probed, and it was found that a substantial fraction of the cells recognized bacterial antigens derived from the 11 strains (FIG. 62G). Taken together, these data suggested that the accumulation of IFNγ+CD8 T cells is likely due to the cumulative effects of colonic recruitment, cellular expansion, and bacterial antigen-mediated differentiation.

Figures 62H, 62I:
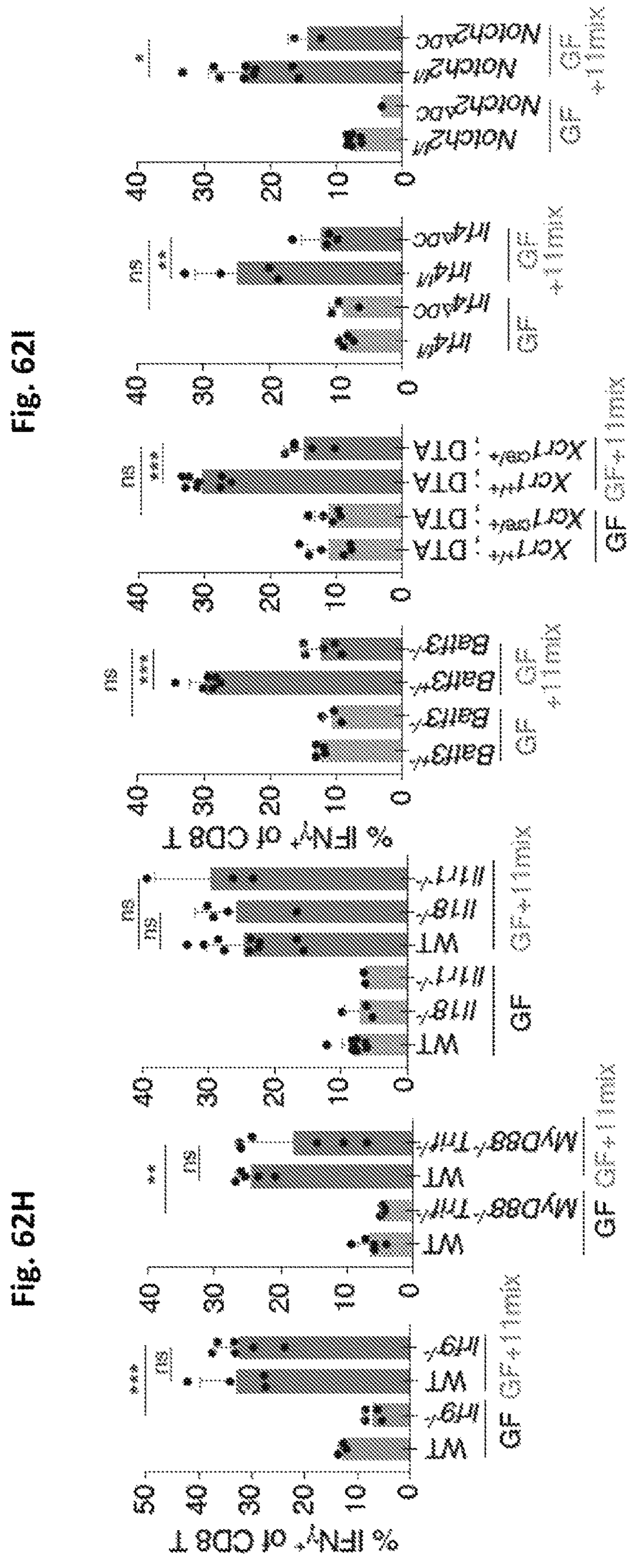
Figures 62J, 62K, 62L:
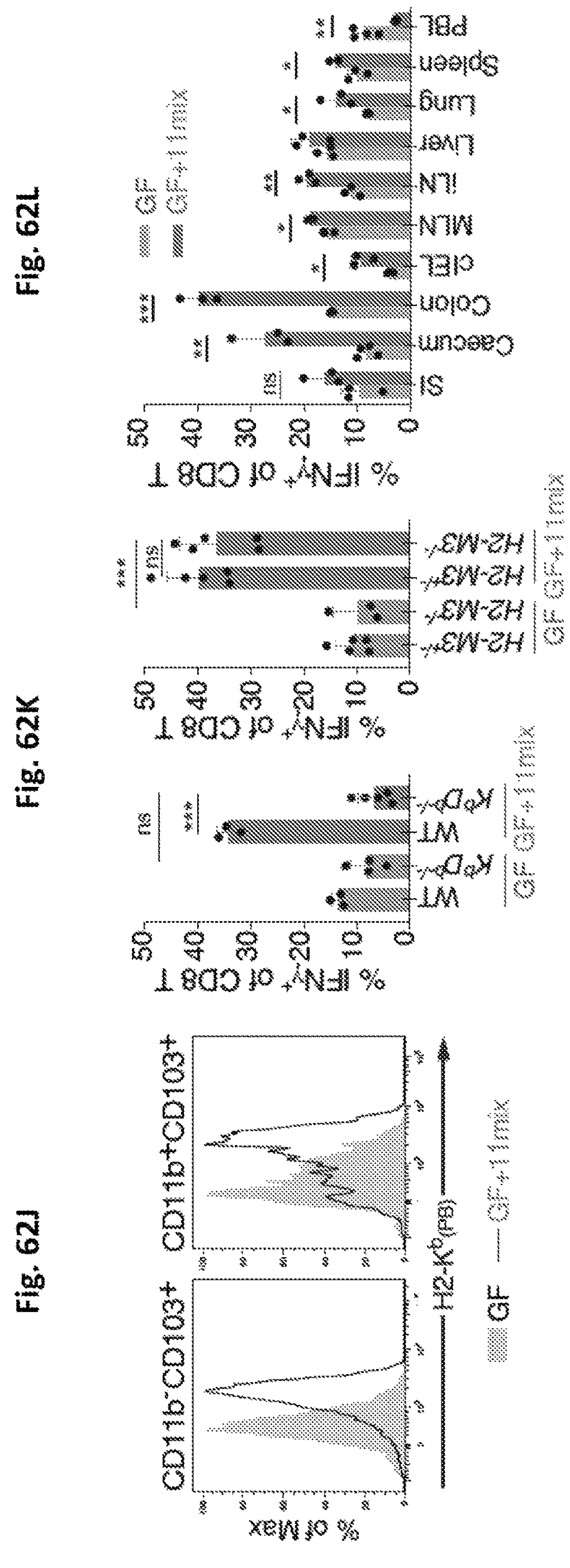

The contributions of major innate signalling pathways and dendritic cells (DCs) was next examined. Neither $Irf9^{-/-}$ (type I IFN signalling-deficient), $Myd^{-/-}Trif^{-/-}$ (Toll-like receptor signalling-deficient), $I11br^{-/-}$, nor $I118^{-/-}$ GF+11-mix mice showed any difference in IFNγ+CD8 T cell inductive capacity as compared to wild-type (WT) controls (FIG. 62H). In contrast, the 11-mix treatment failed to induce colonic IFNγ+CD8 T cells in Ratf3−/− mice and $Xcrl^{+/cre}$xR26:lacZbp$A^{fk12}$DTA mice (FIG. 62I), both of which lack the intestinal CD11b-CD103+ DC subset[14-16]. Induction was also abrogated in CD11c-CrexIrf$4^{fl/fl}$ (Irf4γDC) mice and CD11c-CrexNotch$2^{DC}$ (Notch2γDC) mice (FIG. 62I), which have defective CD11b+CD103+ DC subsets[16,17]. Colonization with the 11-mix enhanced expression of MHC class I (H2-$K^b$) in both CD11b+CD103+ and CD11b+CD103+ colonic LP DC populations in WT mice (FIG. 62J). Additionally, IFNγ+CD8 T cell accumulation was dramatically impaired in MHC class Ia-deficient ($K^bD^{b-/-}$), but not MHC class Ib-deficient (H2-$M3^{-/-}$), mice (FIG. 62K). These results were consistent with the hypothesis that the 11 strains activate signalling independent of major innate immune pathways, which conditions CD103+ LP DCs to induce IFNγ+CD8 T cell accumulation in a classical MHC class Ia-dependent manner.

Figure 73A:
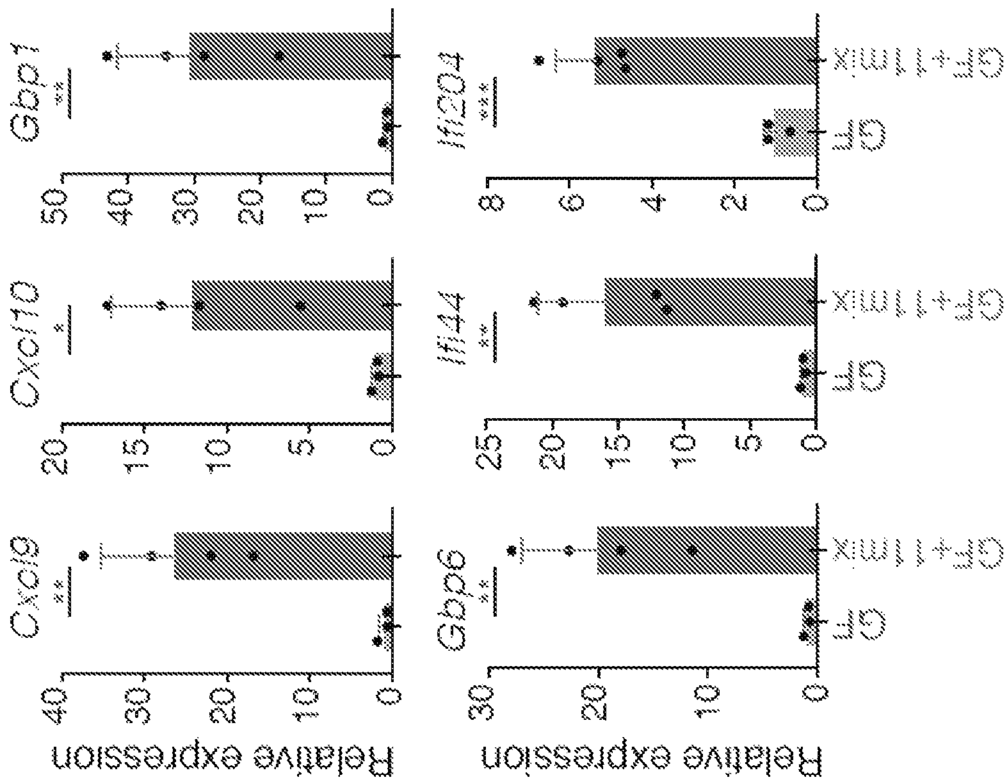
FIGS. 73A-73C show induction of IFN-stimulated genes in colonic epithelial cells (ECs) following colonic colonization with the mixture of 11 bacterial strains.
Figure 73B:
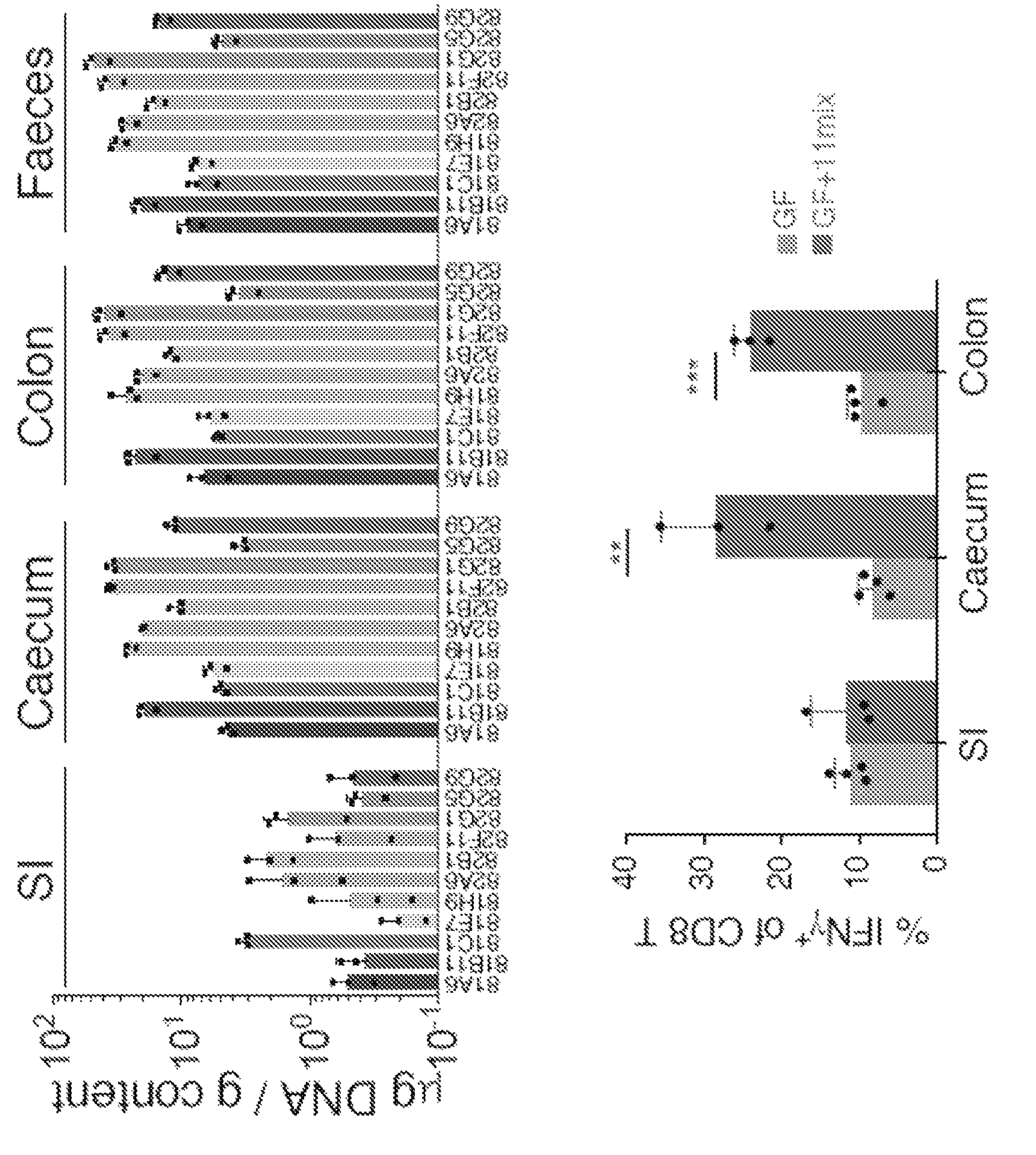
Figure 73C:
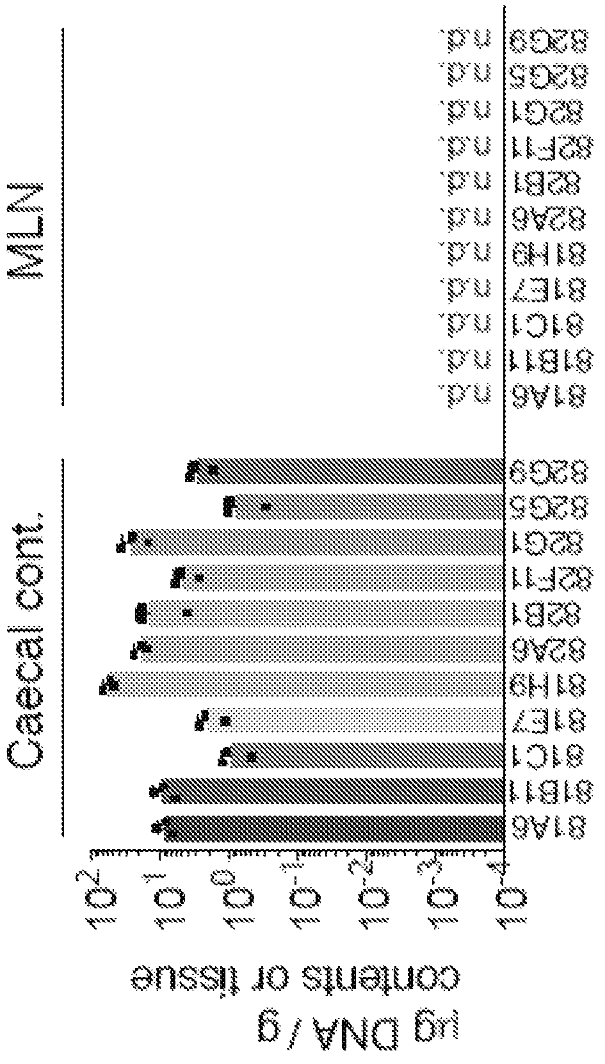
Figure 74A:
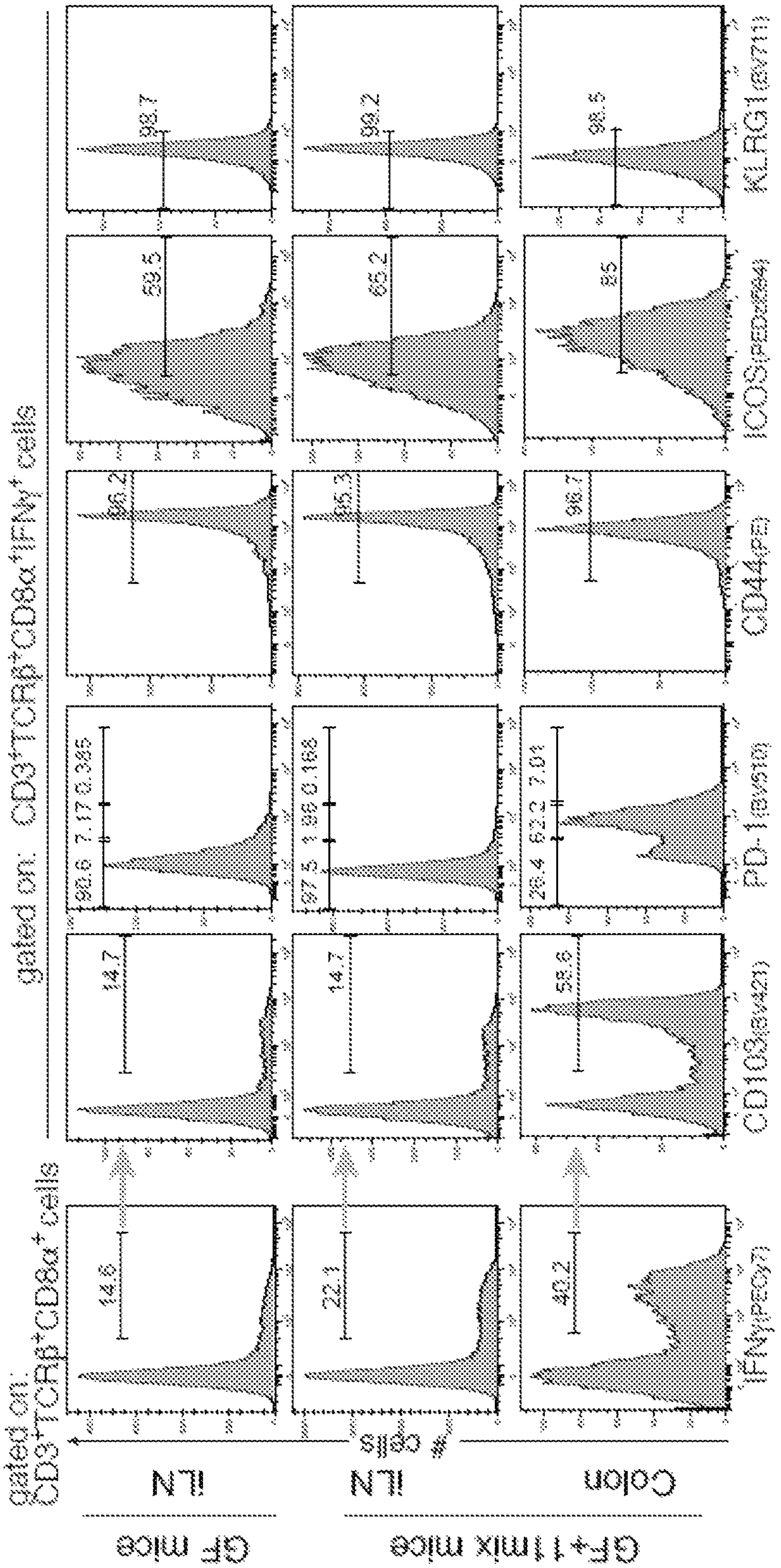
Figure 74B:
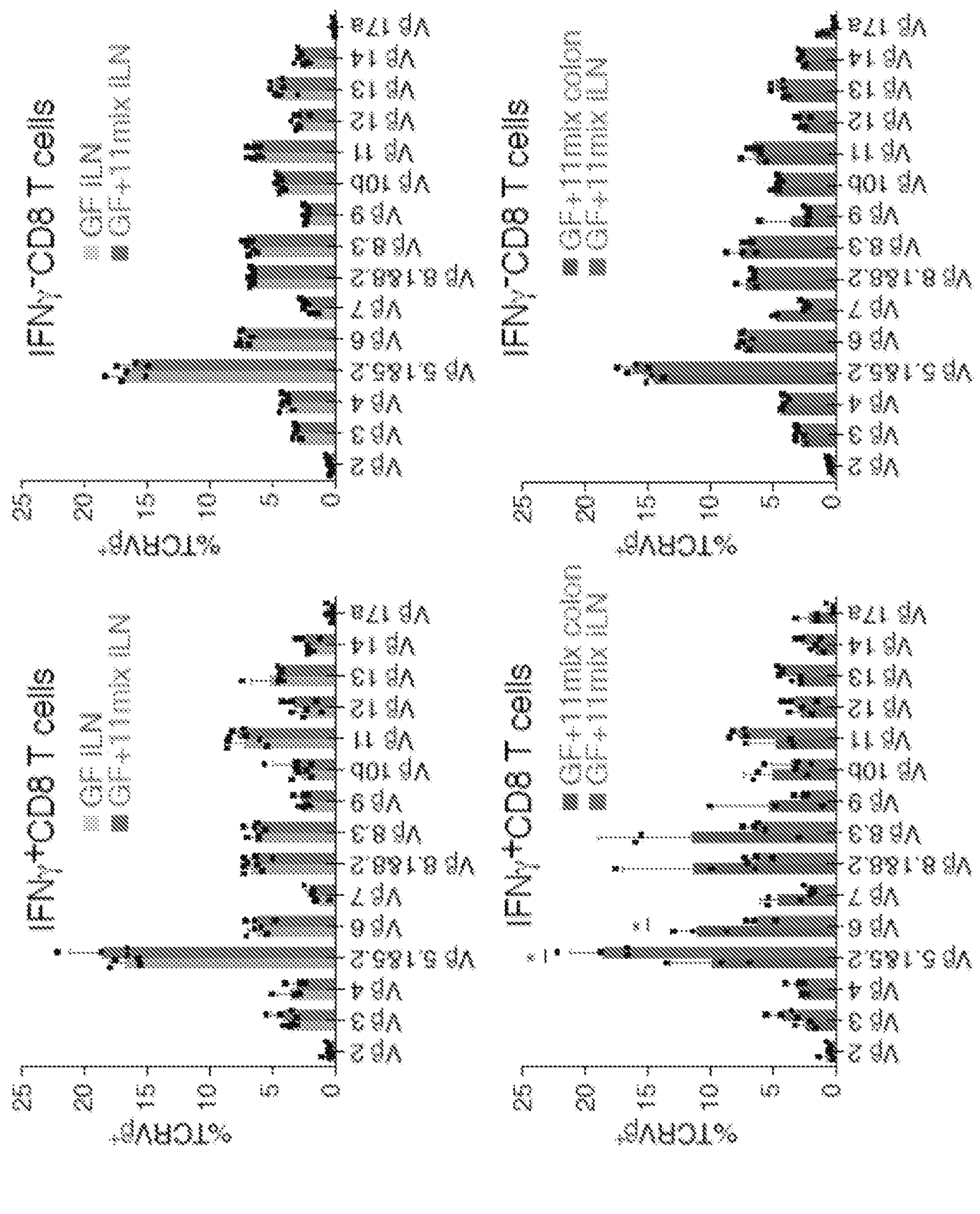
FIG. 74B, top row, shows the frequencies of Vβ gene usage among IFNγ+CD8 T cells (left panel) and IFNγ+CD8 T cells (right panel) from the iLNs of GF mice or GF mice colonized with the mixture of 11 bacterial strains. For each gene, the left column corresponds to GF mice and the right column corresponds to GF mice colonized with the mixture of 11 bacterial strains.
Figure 75A:
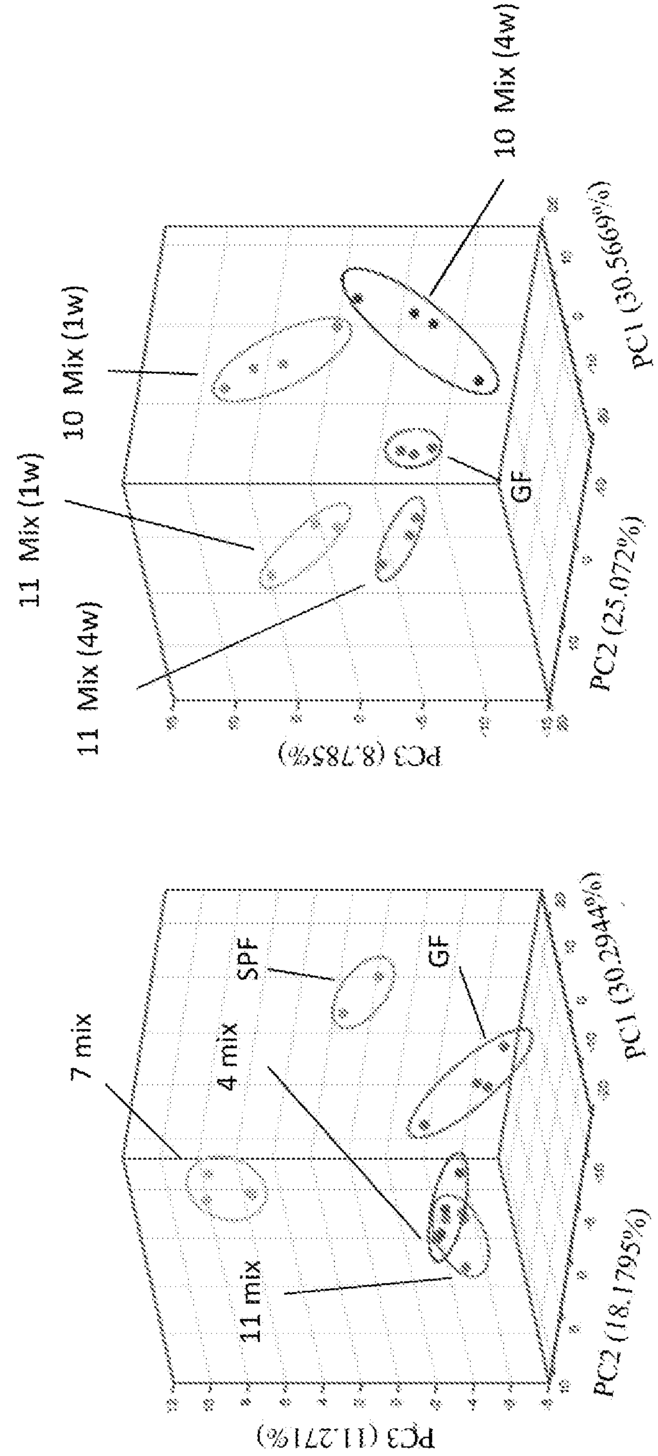
FIGS. 75A-75D show metabolomic analysis of mice colonized with the mixture of 11 bacterial strains.
Figure 75B:
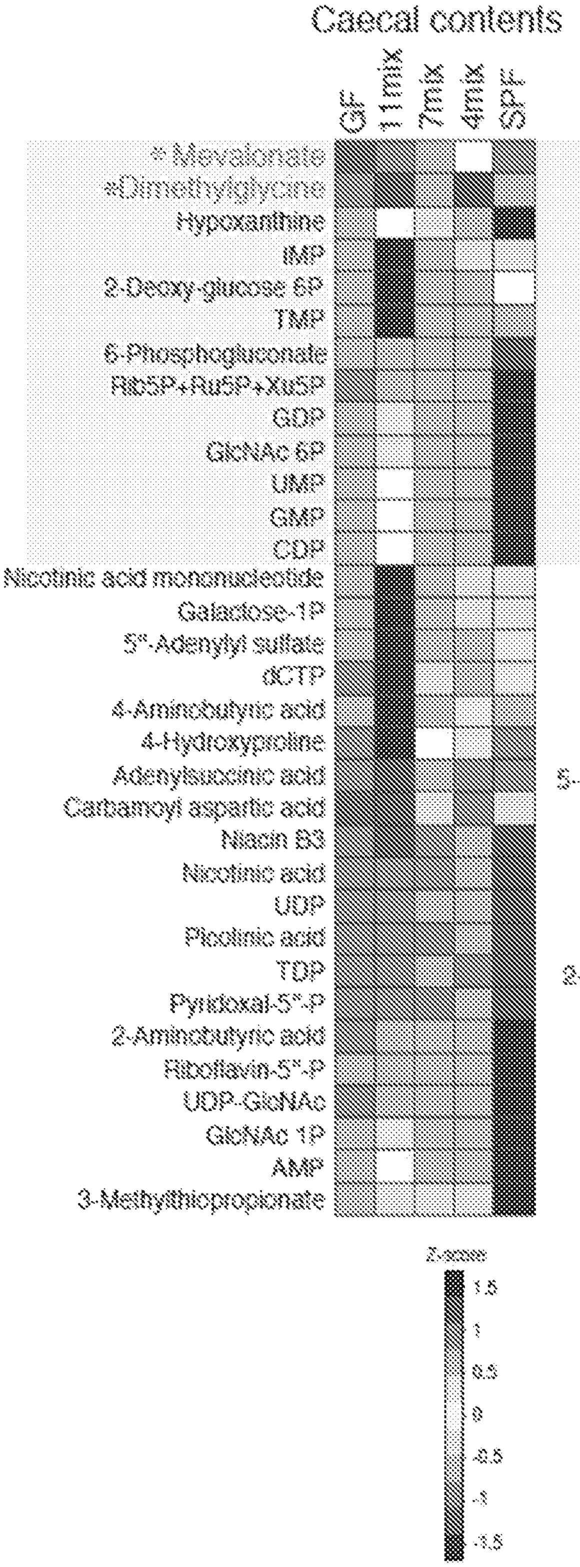
Figure 75C:
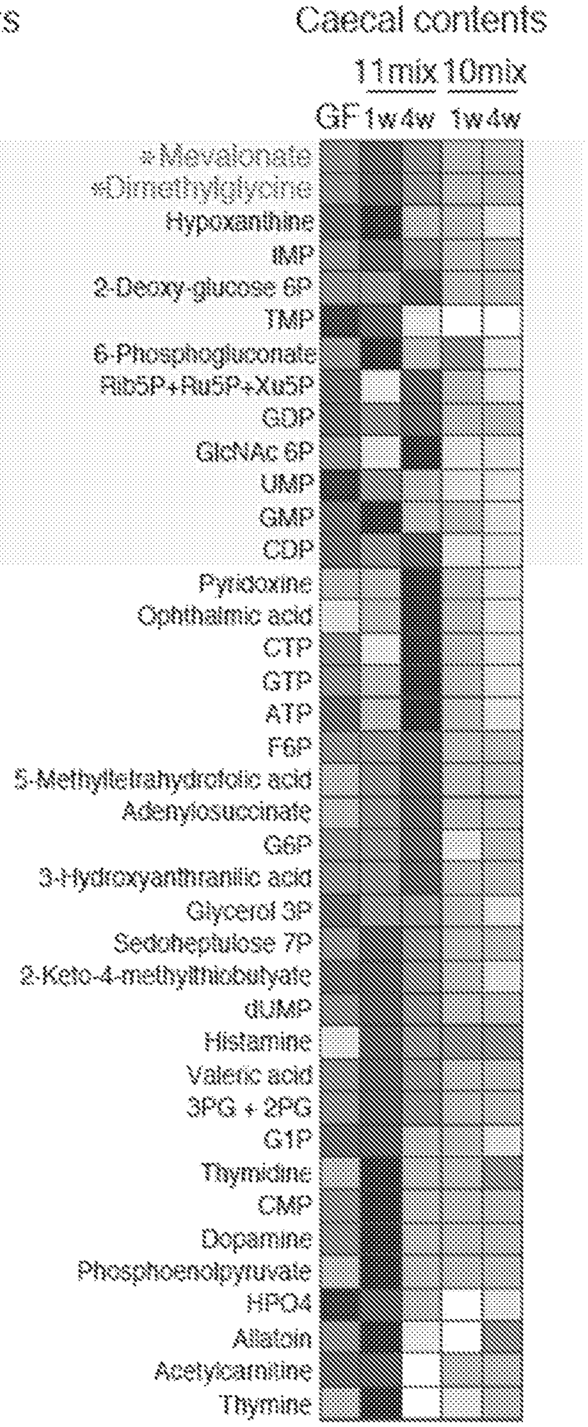
Figure 75D:
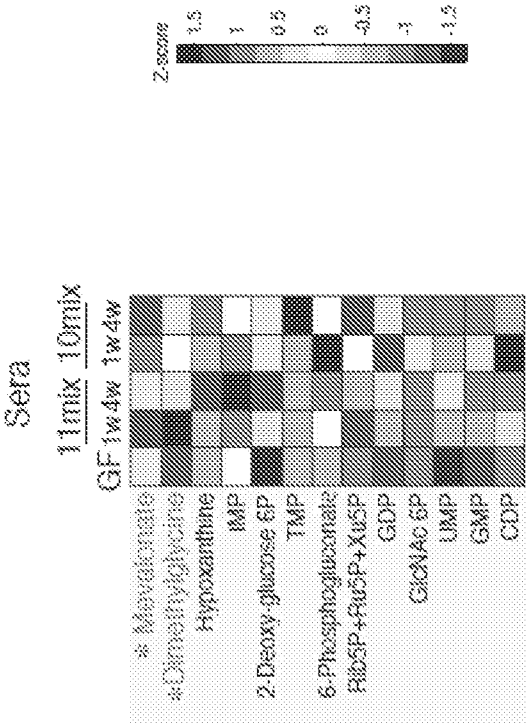

The systemic effects of 11-mix colonization were examined. All strains preferentially localized to the caecum and colon, which was reflected by a prominent induction of IFNγ+CD8 T cells at these sites (FIGS. 62L, 73B). Nevertheless, the immunomodulatory phenotype extended well beyond the intestine, as an increase in IFNγ+CD8 T cell frequency was observed in several additional organs (FIG. 62L). The systemic effects of the 11-mix were likely due neither to bacterial dissemination (FIG. 73C) nor to systemic circulation of gut-origin IFNγ+CD8 T cells, as the colonic and systemic subsets were phenotypically distinct (FIG. 74). It is hypothesized that the systemic effects may be due to circulating metabolites induced by the 11 strains. Indeed, examination of caecal contents from GF, GF+4-mix, GF+7-mix, GF+11-mix, and GF+10-mix revealed differences in the overall metabolomic profile of each group, though GF+11-mix and GF+4-mix mice clustered more tightly than other groups, consistent with their immunomodulatory phenotype (FIG. 75A). Several molecules, such as mevalonate and dimethylglycine, were elevated in both the caecal contents and the sera of GF+11-mix mice (FIGS. 75B-75D), suggesting a potential mechanistic role.

Figure 76A:
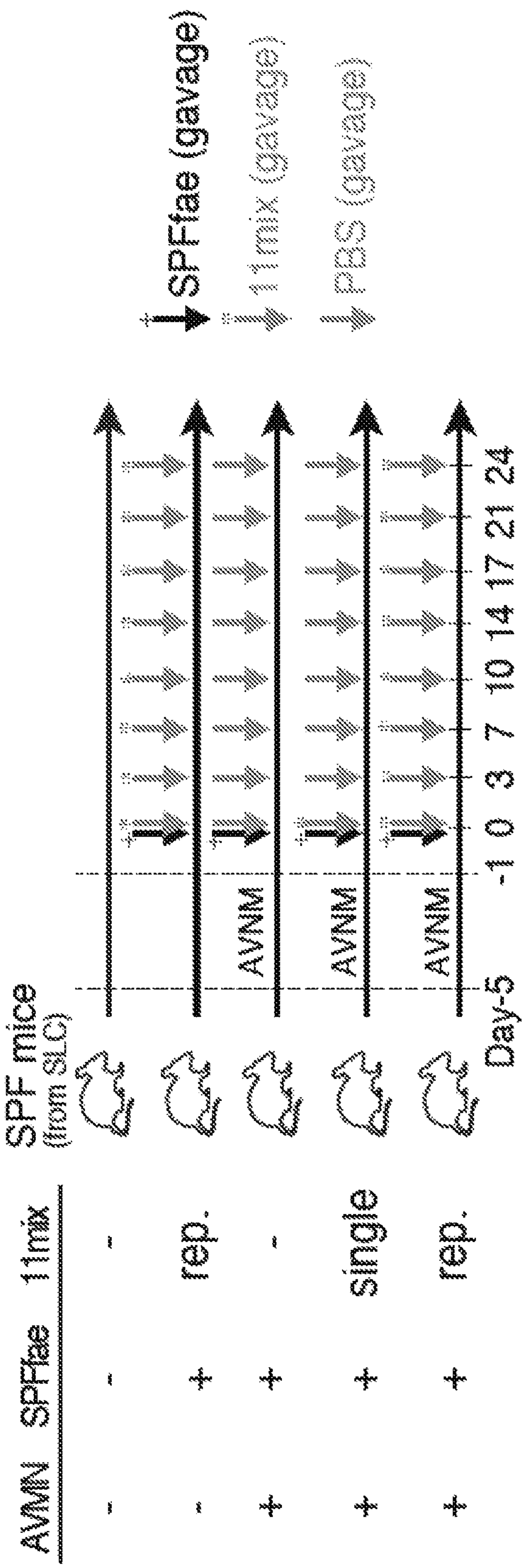
FIGS. 76A-76C show IFNγ+CD8 T cell induction following colonization with the mixture of 11 bacterial strains in the context of a complex microbiota.
Figure 76B:
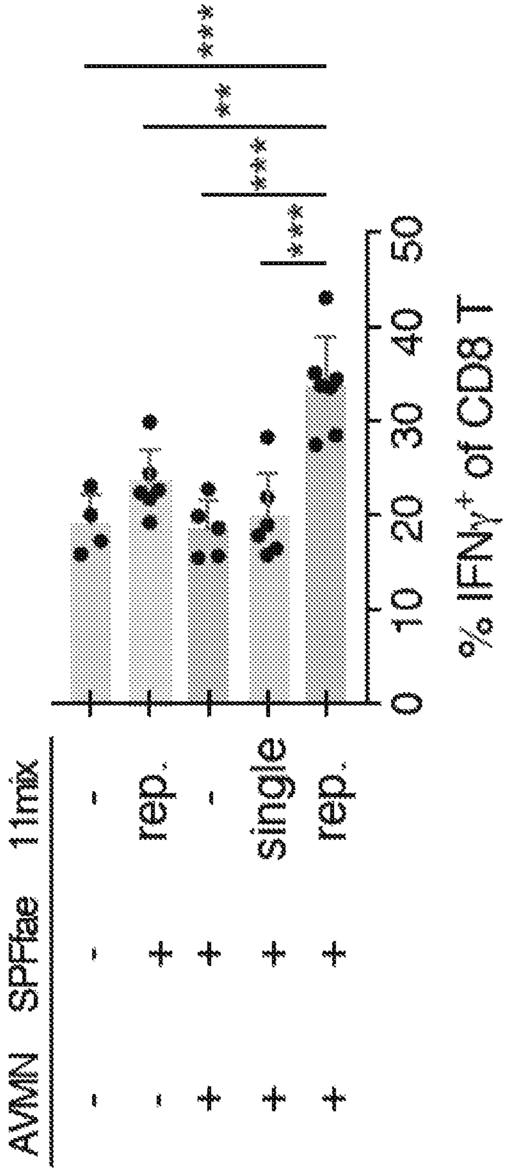
Figure 76C:
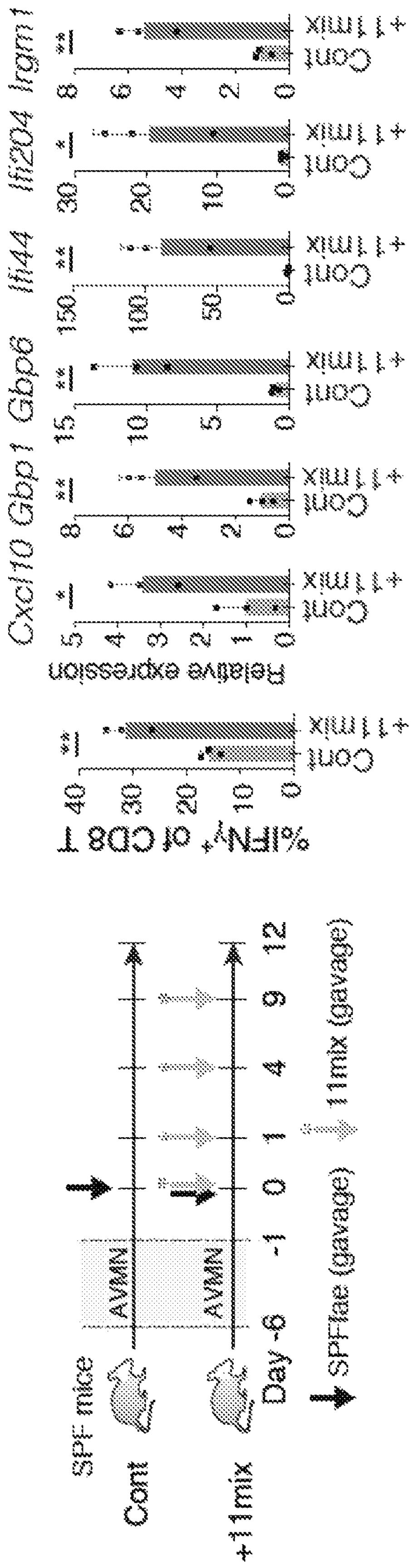
Figure 77:
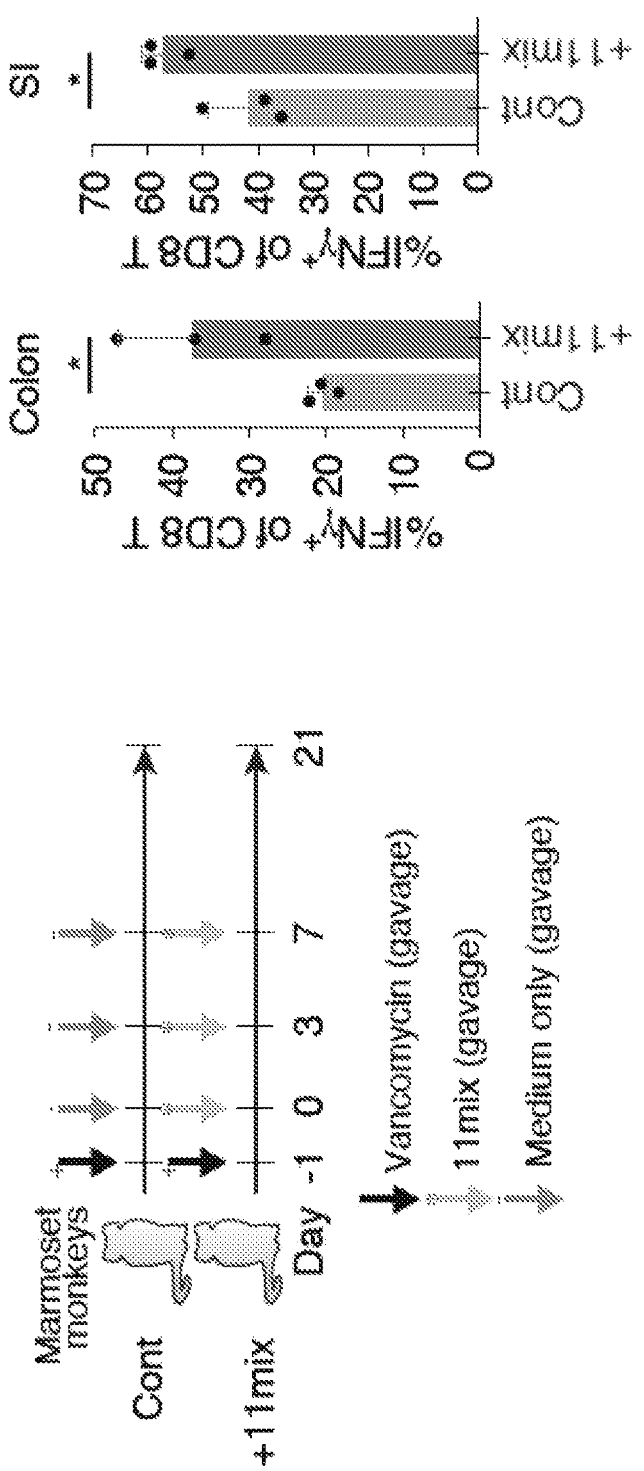
FIG. 77 shows induction of IFNγ+CD8 T cells in common marmoset monkeys following colonization with the mixture of 11 bacterial strains. As shown in the schematic of the experimental design, conventional common marmoset monkeys were treated with vancomycin (50 mg/head), then orally administered the mixture of 11 bacterial strains or medium only (control) at the indicated time points. The percentage of IFNγ+ cells among colonic and SI LP CD8 T cells are shown for control monkeys ("Cont") and monkeys that were colonized with the mixture of 11 bacterial strains. Each circle represents an individual animal and the height of each bar indicates the mean. Error bars, s.d. *P<0.05.

With the goal of clinical translation, the 11 strains' genomes were examined and no prominent virulence factors or toxins were found (Table 4). Although tetracycline-resistance and β-lactamase genes were present in most of the genomes, no strains were multidrug-resistant (Tables 5 and 6). The effects of the 11-mix in the context of a complex microbiota were also examined. In SPF mice, the 11 strains failed to induce IFNγ+CD8 T cells even after repetitive oral gavage (FIG. 76). In contrast, antibiotic pre-treatment coupled with repetitive 11-mix gavage resulted in a significant induction of colonic IFNγ+CD8 T cells and an upregulation of IFN-inducible genes in colonic ECs (FIG. 76). To further probe clinical translatability, vancomycin-treated marmoset monkeys were gavaged with the 11-mix, and significant increases in IFNγ+CD8 T cell frequency were observed in the colonic and SI LP (FIG. 77), suggesting that these strains are therapeutically applicable across vastly different species.

Figure 86A:
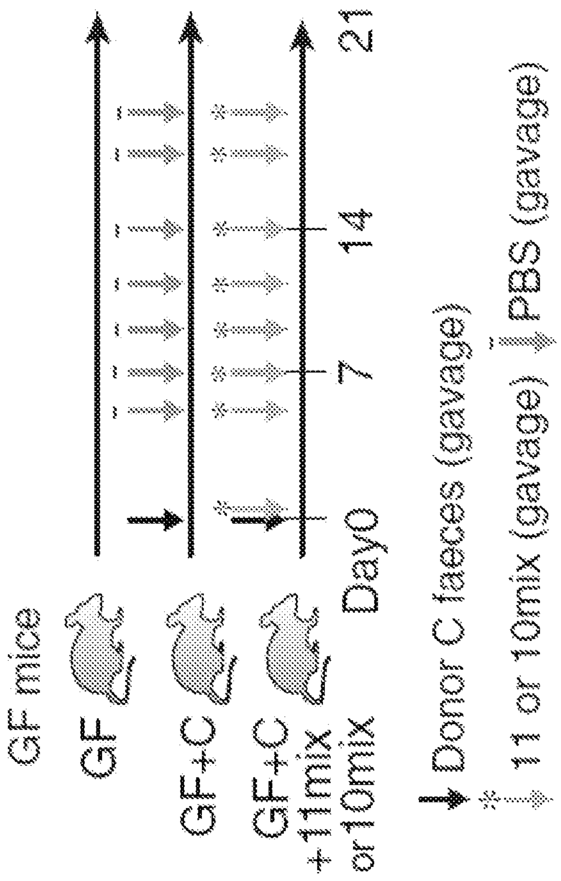
FIGS. 86A-86C show the efficacy of colonization with the 11 mix bacterial strains in enhancing treatment of MC38 tumours.
Figure 86B:
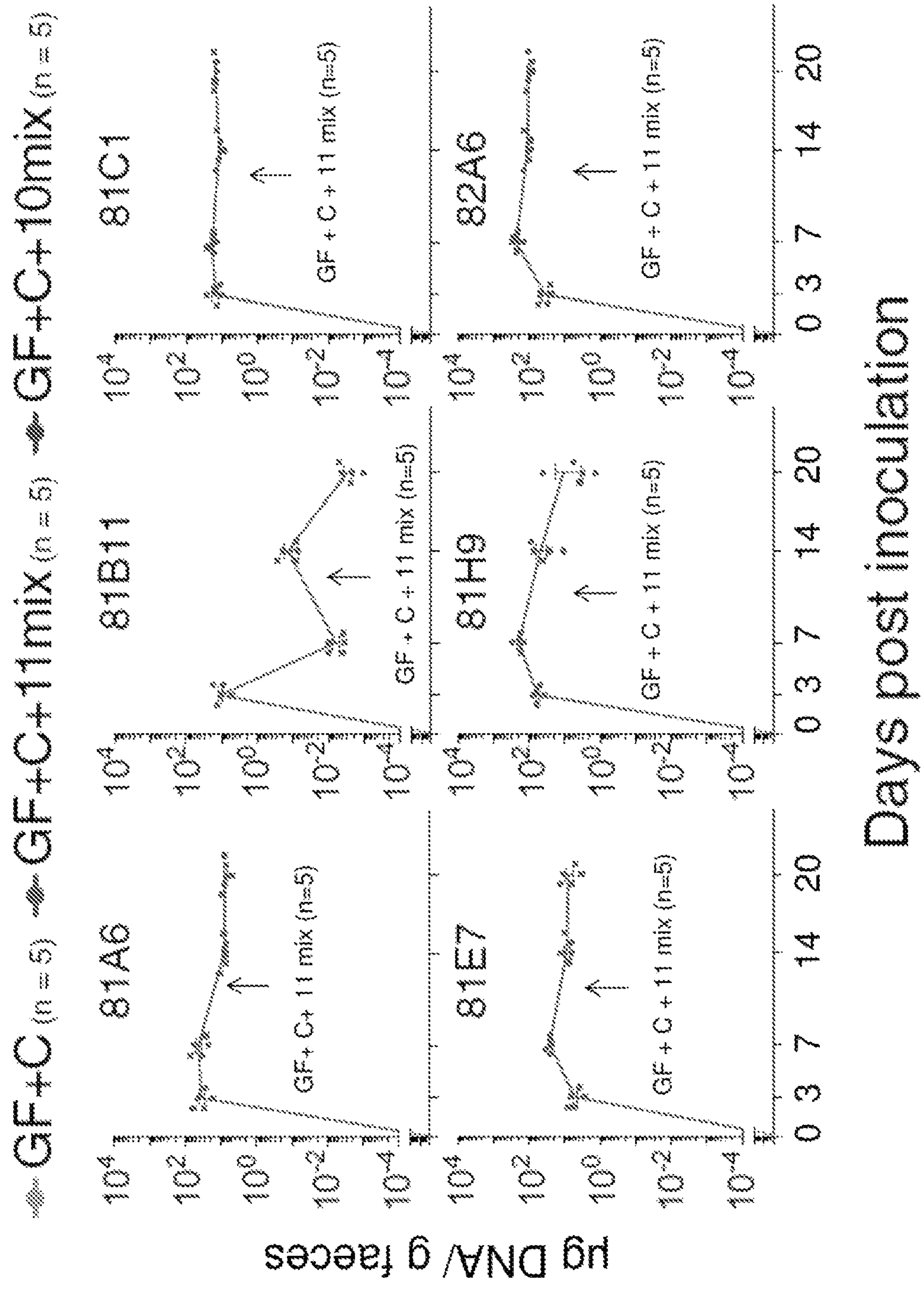
Figure 86B:
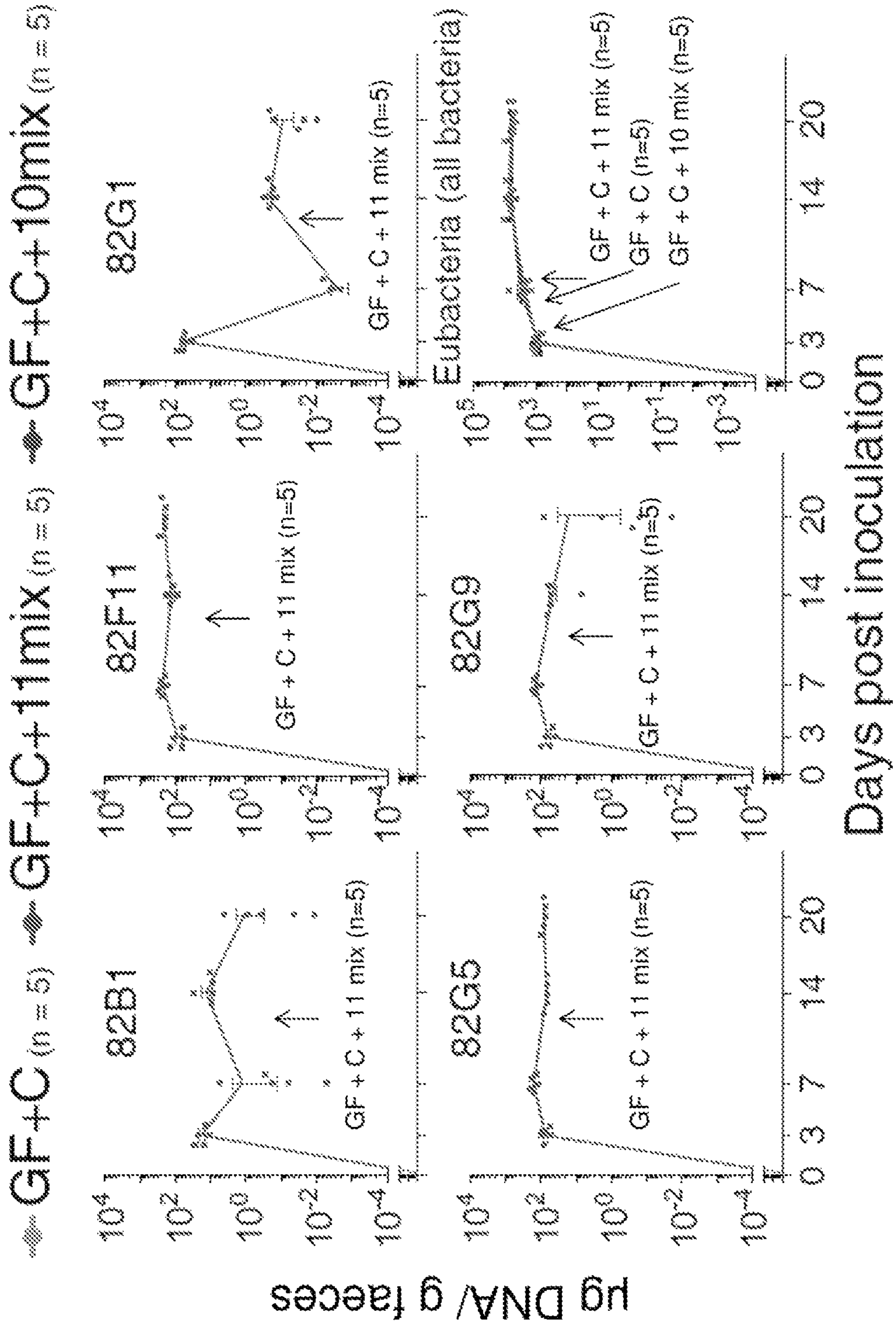
Figure 86C:
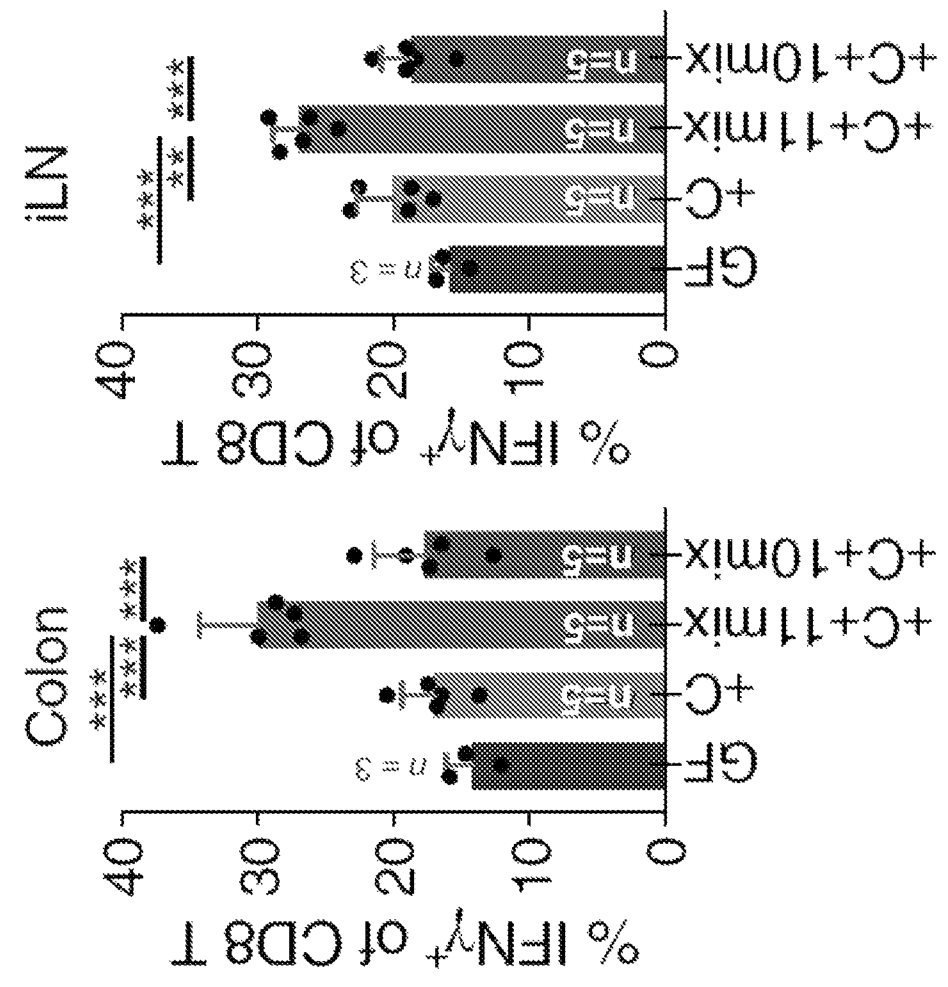

To further evaluate the effects of the 11-mix in the context of a complex microbiota, germ free mice were colonized with faecal microbiota samples from donor C or left uncolonized (FIG. 86A). The mice were then gavaged repeatedly with PBS (control) or a bacterial composition (11-mix or 10-mix) and assessed for colonization with each of the bacterial strains of the composition. Each of the bacterial strains was detected, indicating colonization (FIG. 86B). On day 21 post inoculation, the percentage IFN+CD8+ T-cells were quantified in the colonic lamina propria and iLNs. As shown in FIG. 86C, administration of the 11-mix resulted in the induction of IFN+CD8+ T-cells eyen in complex microbiota-colonized mice.

TABLE 4

Putative toxins and virulence factors found in the genomes of the 11 strains

| Strain | Gene No. | query length (aa) | Annotation | Subject length (aa) | Identity |
|---|---|---|---|---|---|
| 81A6 | prokka_H81A6_03151 | 374 | >VFG005042(gi:70725395) (capG) capsular polysaccharide synthesis enzyme CapG [Capsule (CVF110)] [*Staphylococcus haemolyticus* JCSC1435] | 374 | 275/374 |
| 81B11 | prokka_H81B11_00727_UDP-glucose_6-dehydrogenase | 416 | >VFG005992(gi:116516033) (cps2K) UDP-glucose 6-dehydrogenase, putative [Capsule (CVF186)] [*Streptococcus pneumoniae* D39] | 412 | 311/412 |
| | prokka_H81B11_00020_Enolase | 426 | >VFG018662(gi:157151177) (eno) *enolase* [*Streptococcal enolase* (CVF153)] [*Streptococcus gordonii* str. Challis substr. CH1] | 434 | 306/420 |
| 81C1 | prokka_H81C1_04327_UDP-glucose_6-dehydrogenase | 409 | >VFG005992(gi:116516033) (cps2K) UDP-glucose 6-dehydrogenase, putative [Capsule (CVF186)] [*Streptococcus pneumoniae* D39] | 412 | 299/411 |
| | prokka_H81C1_03122 | 375 | >VFG005042(gi:70725395) (capG) capsular polysaccharide synthesis enzyme CapG [Capsule (CVF110)] [*Staphylococcus haemolyticus* JCSC1435] | 374 | 269/375 |
| | prolool_H81C1_03120_UDP-glucose_4-epimerase | 341 | >2267_VFDB_setB_pro.fas (cps4J) capsular polysaccharide biosynthesis protein Cps4J [Capsule (VF0144)] [*Streptococcus pneumoniae* TIGR4] | 351 | 243/341 |
| | prokka_H81C1_02417_60_kDa_chaperonin | 542 | >VFG012095(gi:126697767) (groEL) 60 kDa chaperonin [GroEL(Hsp60) (A1317)] [*Clostridium difficile* 630] | 542 | 383/526 |
| 81E7 | prokka_H81E7_02411_UDP-glucose_6-dehydrogenase | 415 | >VFG005992(gi:116516033) (cps2K) UDP-glucose 6-dehydrogenase, putative [Capsule (CVF186)] [*Streptococcus pneumoniae* D39] | 412 | 317/411 |
| | prokka_H81E7_01858_Elongation_factor_Tu | 395 | >VFG016490(gi:42560712) (tuf) translation elongation factor Tu [EF-Tu (CVF587)] [*Mycoplasma mycoides* subsp. *mycoides* SC str. PG1] | 395 | 282/395 |
| | prokka_H81E7_00350_Enolase | 433 | >VFG018662(gi:157151177) (eno) *enolase* [*Streptococcal enolase* (CVF153)] [*Streptococcus gordonii* str. Challis substr. CH1] | 434 | 306/425 |
| 81H9 | prokka_H81H9_02198_putative_deoxyribonuclease_RhsA | 100 | >VFG041187(gi:269139783) (evpJ) type VI secretion system protein EvpJ [EVP (*E. tarda* virulent protein) (SS189)] [*Edwardsiella tarda* EIB202] | 100 | 76/98 |
| | prokka_H81H9_04311 | 380 | >2269_VFDB_setB_pro.fas (cps4L) UDP-N-acetylglucosamine 2-epimerase [Capsule (VF0144)] [*Streptococcus pneumoniae* TIGR4] | 394 | 277/377 |
| | prokka_H81H9_03469_Enolase | 428 | >VFG018662(gi:157151177] (eno) *enolase* [*Streptococcal enolase* (CVF153)] [*Streptococcus gordonii* str. Challis substr. CH1] | 434 | 306/420 |
| | prokka_H81H9_04273_Glucose-1-phosphate_thymidylyltransferase_1 | 291 | >VFG007660(gi:37678485) (rmlA) O-glucose-1-phosphate thymidylyltransferase [Capsular polysaccharide (CVF282)] [*Vibrio vulnificus* YJ016] | 295 | 208/291 |
| | prokka_H81H9_01526_Elongation_factor_Tu | 395 | >VFG016490(gi:42560712) (tuf) translation elongation factor Tu [EF-Tu (CVF587)] [*Mycoplasma mycoides* subsp. *mycoides* SC str. PG1] | 395 | 281/393 |
| 82A6 | prokka_H82A6_02973_UDP-glucose_6-dehydrogenase | 84 | >VFG005992(gi:116516033) (cps2K) UDP-glucose 6-dehydrogenase, putative [Capsule (CVF186)] [*Streptococcus pneumoniae* D39] | 412 | 67/84 |
| | prokka_H82A6_02867_UDP-glucose_6-dehydrogenase | 84 | >VFG005992(gi:116516033) (cps2K) UDP-glucose 6-dehydrogenase, putative [Capsule (CVF186)] [*Streptococcus pneumoniae* D39] | 412 | 66/84 |
| | prokka_H82A6_00216_Enolase | 426 | >VFG018662(gi:157151177) (eno) *enolase* [*Streptococcal enolase* (CVF153)] [*Streptococcus gordonii* str. Challis substr. CH1] | 434 | 307/420 |
| 82B1 | prokka_H82B1_01560 | 379 | >2269_VFDB_setB_pro.fas (cps4L) UDP-N-acetylglucosamine 2-epimerase [Capsule (VF0144)] [*Streptococcus pneumoniae* TIGR4] | 394 | 283/377 |
| | prokka_H82B1_00238_Elongation_factor_Tu | 400 | >VFG016490(gi:42560712) (tuf) translation elongation factor Tu [EF-Tu (CVF587)] [*Mycoplasma mycoides* subsp. *mycoides* SC str. PG1] | 395 | 298/400 |
| | prokka_H82B1_01368_60_kDa_chaperonin | 547 | >VFG012103(gi:125975373) (groEL) chaperonin GroEL [GroEL (CVF403)] [*Clostridium thermocellum* ATCC 27405] | 541 | 386/526 |
| 82F11 | prokka_H82F11_02264_UDP-glucose_6-dehydrogenase | 415 | >VFG005992(gi:116516033) (cps2K) UDP-glucose 6-dehydrogenase, putative [Capsule (CVF186)] [*Streptococcus pneumoniae* D39] | 412 | 310/411 |
| | prokka_H82F11_03138_Enolase | 426 | >VFG018662(gi:157151177) (eno) *enolase* [*Streptococcal enolase* (CVF153)] [*Streptococcus gordonii* str. Challis substr. CH1] | 434 | 307/420 |
| | prokka_H82F11_01792_Enolase | 427 | >VFG018662(gi:157151177) (eno) *enolase* [*Streptococcal enolase* (CVF153)] [*Streptococcus gordonii* str. Challis substr. CH1] | 434 | 303/420 |
| | prokka_H82F11_00551_Elongation_factor_Tu | 395 | >VFG016490(gi:42560712) (tuf) translation elongation factor Tu [EF-Tu (CVF587)] [*Mycoplasma mycoides* subsp. *mycoides* SC str. PG1] | 395 | 280/394 |
| 82G1 | prokka_H82G1_01690 | 393 | >2269_VFDB_setB_pro.fas (cps4L) UDP-N-acetylglucosamine 2-epimerase [Capsule (VF0144)] [*Streptococcus pneumoniae* TIGR4] | 394 | 312/393 |
| | prokka_H82G1_01137_Enolase | 429 | >VFG018662(gi:157151177) (eno) *enolase* [*Streptococcal enolase* (CVF153)] [*Streptococcus gordonii* str. Challis substr. CH1] | 434 | 307/420 |
| 82G5 | prokka_H82G5_01198_Elongation_factor_Tu | 395 | >VFG016490(gi:42560712) (tuf) translation elongation factor Tu [EF-Tu (CVF587)] [*Mycoplasma mycoides* subsp. *mycoides* SC str. PG1] | 395 | 291/395 |
| | prokka_H82G5_01223_Elongation_factor_Tu | 395 | >VFG016490(gi:42560712) (tuf) translation elongation factor Tu [EF-Tu (CVF587)] [*Mycoplasma mycoides* subsp. *mycoides* SC str. PG1] | 395 | 291/395 |
| | prokka_H82G5_02288_60_kDa_chaperonin | 543 | >VFG012103(gi:125975373) (groEL) chaperonin GroEL [GroEL (CVF403)] [*Clostridium thermocellum* ATCC 27405] | 541 | 389/527 |

TABLE 4-continued

Putative toxins and virulence factors found in the genomes of the 11 strains

| Strain | Gene No. | query length (aa) | Annotation | Subject length (aa) | Identity |
|---|---|---|---|---|---|
| 82G9 | prokka_H82G9_02380_hypothetical_protein | 100 | >VFG041187(gi:269139783) (evpJ) type VI secretion system protein EvpJ [EVP (*E. tarda* virulent protein) (SS189)] [*Edwardsiella tarda* EIB202] | 100 | 78/98 |
| | prokka_H82G9_04389_UDP-glucose_6-dehydrogenase | 219 | >VFG005992(gi:116516033) (cps2K) UDP-glucose 6-dehydrogenase, putative [Capsule (CVF186)] [*Streptococcus pneumoniae* D39] | 412 | 162/219 |
| | prokka_H82G9_03293_Catalase | 488 | >VFG037035(gi:254805741) (katA) catalase [Catalase (CVF760)] [*Neisseria meningitidis* alpha 14] | 504 | 350/478 |
| | prokka_H82G9_00955_Elongation_factor_Tu | 395 | >VFG016490(gi:42560712) (tuf) translation elongation factor Tu [EF-Tu (CVF587)] [*Mycoplasma mycoides* subsp. *mycoides* SC str. PG1] | 395 | 281/394 |
| | prokka_H82G9_01993_Glucose-1-phosphate_thymidylyltransferase_1 | 291 | >VFG007660(gi:37678485) (rmlA) D-glucose-1-phosphate thymidylyltransferase [Capsular polysaccharide (CVF282)] [*Vibrio vulnificus* YJ016] | 295 | 207/291 |
| | prokka_H82G9_04317_Enolase | 426 | >VFG018662(gi:157151177) (eno) *enolase* [*Streptococcal enolase* (CVF153)] [*Streptococcus gordonii* str. Challis substr. CH1] | 434 | 303/420 |

TABLE 5

Putative antibiotic resistance genes in the genomes of the 11 strains
BLASTP result (database = Antibiotic Resistance Genes Database)

| Strain | Gene No. | Query length (aa) | Annotation | Subject length (aa) | Identity | Identity % | Coverage % |
|---|---|---|---|---|---|---|---|
| 81A6 | No hit found | — | — | — | — | — | — |
| 81B11 | prokka_H81B11_04637_putative_MFS-type transporter | 405 | >ZP_03302371 hypothetical protein BACDOR_03769 [*Bacteroides dorei* DSM 17855]. | 405 | 405/405 | 100% | 100% |
| | prokka_H81B11_04640_rRNA_adenine_N-6-methyltransferase | 244 | >ZP_03015699 hypothetical protein BACINT_03296[*Bacteroides intestinalis* DSM 17393]. | 244 | 243/244 | 99% | 100% |
| 81C1 | prokka_H81C1_03772_Tetracycline_resistance protein TetO | 639 | >ABV82122 Tet32 [*Streptococcus salivarius*]. | 639 | 639/639 | 100% | 100% |
| 81E7 | No hit found | — | — | — | — | — | — |
| 81H9 | prokka_H81H9_05320_Tetracycline_resistance protein TetM from | 432 | >ZP_04557016 tetracycline resistance protein tetQ [*Bacteroides* sp. D4], | 657 | 431/432 | 99% | 100% |
| | prokka_H81H9_05320_Tetracycline_resistance protein TetM from | 432 | >BAD46890 tetracycline resistant protein TetQ [*Bacteroides fragilis* YCH46]. | 657 | 431/432 | 99% | 100% |
| | prokka_H81H9_02310_Extended-spectrum beta-lactamase PER-1 | 321 | >AAL79549 class A beta-lactamase CFXA3 precursor [*Capnocytophaga ochracea*]. | 321 | 319/321 | 99% | 99% |
| | prokka_H81H9_05282_rRNA_adenine_N-6-methyltransferase | 258 | >AAA27431 clindamycin resistance determinant (ermFS) [*Bacteroides fragilis*]. | 266 | 225/228 | 98% | 87% |
| 82A6v | prokka_H82A6_02186_Tetracycline_resistance protein TetM from | 641 | >AAS83507 TetQ [*Bacteroides fragilis*]. | 641 | 641/641 | 100% | 100% |
| 82B1 | prokka_H82B1_02950_Tetracycline_resistance protein TetO | 639 | >AAT27386 tetracycline resistance protein [*Clostridiaceae bacterium* K10]. | 639 | 639/639 | 100% | 100% |
| 82F11 | prokka_H82F11_03404_Tetracycline_resistance protein TetM from | 641 | >Q00937 RecName: Full = Tetracycline resistance protein tetQ; AltName: Full = TetA(Q)1. | 641 | 641/641 | 100% | 100% |
| 82G1 | prokka_H82G1_03948_Tetracycline_resistance protein TetM from | 641 | >AAS83507 TetQ [*Bacteroides fragilis*]. | 641 | 641/641 | 100% | 100% |
| | prokka_H82G1_01501 Extended-spectrum beta-lactamase PER-1 | 296 | >AAA66962 beta-lactamase [*Bacteroides uniformis*]. | 296 | 295/296 | 99% | 100% |
| | prokka_H82G1_01465 Extended-spectrum beta-lactamase PER-1 | 321 | >AAL79549 class A beta-lactamase CFXA3 precursor [*Capnocytophaga ochracea*]. | 321 | 319/321 | 99% | 99% |
| | prokka_H82G1_04416_rRNA_adenine_N-6-methyltransferase | 165 | >CAA60706 ermF [*Bacteroides* sp.]. | 266 | 133/133 | 100% | 81% |
| 82G5 | No hit found | — | — | — | — | — | — |
| 82G9 | prokka_H82G9_00897_Extended-spectrum beta-lactamase PER-1 | 321 | >AAD23513 class A beta-lactamase CFXA2 precursor [*Prevotella intermedia*]. | 321 | 321/321 | 100% | 100% |
| | prokka_H82G9_02188_Tetracycline_resistance_protein_TetM_from | 641 | >Q00937 RecName: Full = Tetracycline resistance protein tetQ; AltName: Full = TetA(Q)1. | 641 | 641/641 | 100% | 100% |

TABLE 6

In vitro antibiotic sensitivity of the 11 strains

| Strain ID | Top Hit species in reference database | Medium | Inoculum | Ampicillin | Vancomycin | Streptomycin | Metronidazole | Tylosin |
|---|---|---|---|---|---|---|---|---|
| 82G5 | *Phascolarctobacterium faecium* | R-Cl + ss | Broth culture method | 0.25 | >128 | 32 | 0.5 | >128 |
| 81A6 | *Fusobacterium ulcerans* | BHK | Colony suspension | 1 | >128 | >128 | ≤0.125 | 128 |
| 81B11 | *Bacteroides dorei* | BHK | Colony suspension | >128 | 32 | >128 | 1 | 8 |
| 82G1 | *Bacteroides uniformis* | BHK | Colony suspension | >128 | 32 | >128 | 1 | 0.25 |
| 82B1 | *Ruminococcaceae bacterium* cv2 | PYG | Broth culture method | 1 | 0.5 | 8 | 1 | 4 |
| 82A6 | *Paraprevotella xylaniphila* | BHK | Colony suspension | 4 | 8 | >128 | 1 | 2 |
| 82F11 | *Parabacteroides johnsonii* | BHK | Colony suspension | 32 | 32 | >128 | 2 | 0.25 |
| 81E7 | *Alistipes senegalensis* | BHK | Colony suspension | 64 | 64 | >128 | 0.25 | ≤0.125 |
| 81H9 | *Parabacteroides gordonii* | BHK | Colony suspension | >128 | 32 | >128 | 4 | 8 |
| 81C1 | *Eubacterium limosum* | BHK | Colony suspension | ≤0.125 | 1 | >128 | ≤0.125 | ≤0.125 |
| 82G9 | *Parabacteroides distasonis* | BHK | Colony suspension | >128 | 128 | >128 | 2 | 2 |
| | *Bacterides fragilis* ATCC25285 | BHK | Colony suspension | 32 | 32 | >128 | 8 | 2 |

Figures 63A, 63B, 63C, 63D:
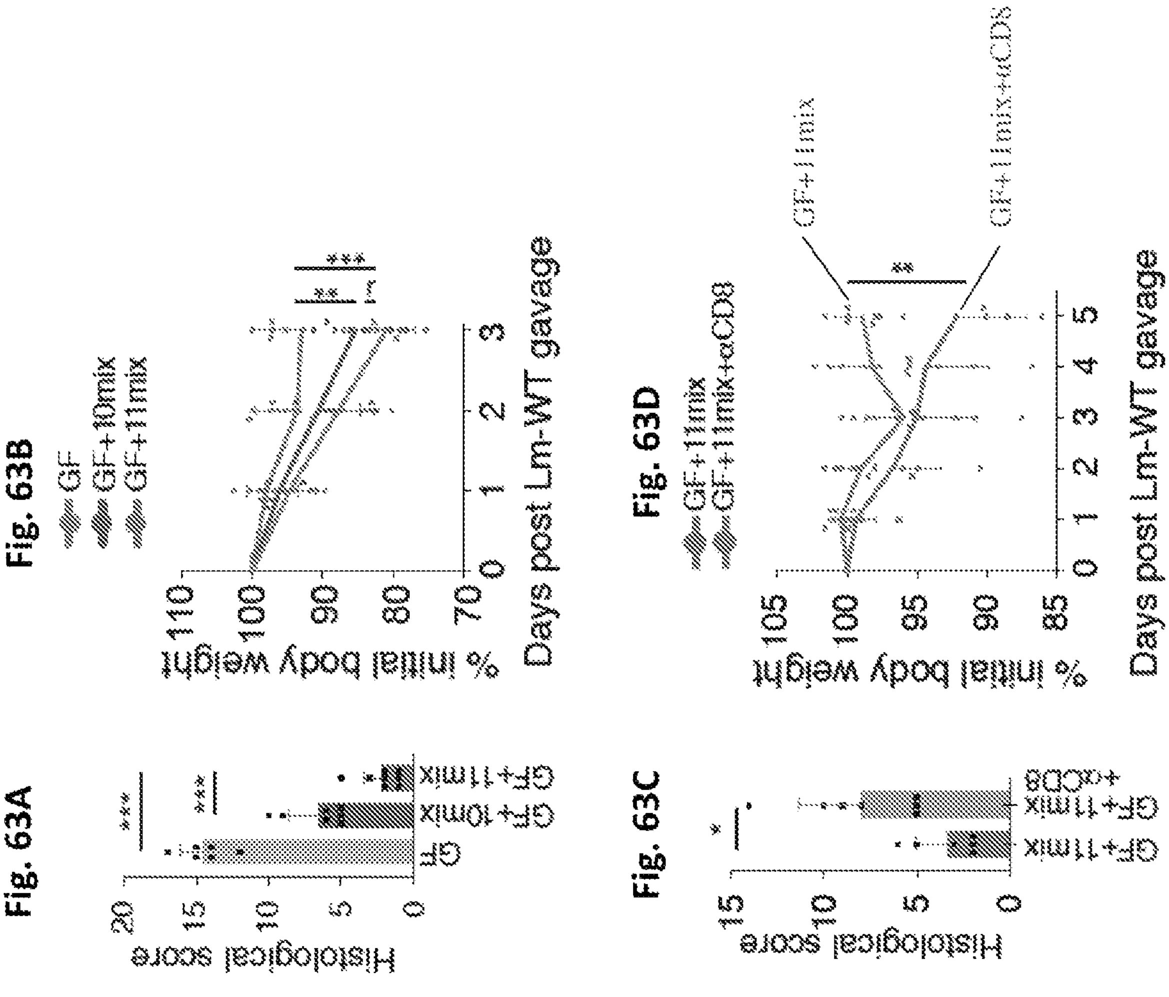
FIGS. 63A-63J show enhancement of host immune responses against Listeria monocytogenes infection mediated by colonization with the mixture of 11 bacterial strains. For FIGS. 63A-63D, the C57BL/6 GF mice were colonized with the mixture of 11 bacterial strains or the mixture of 10 bacterial strains, or left uncolonized as a control. Then, the mice were orally infected with Lm-WT (FIG. 78A shows the experimental design).
Figures 63E, 63F, 63G:
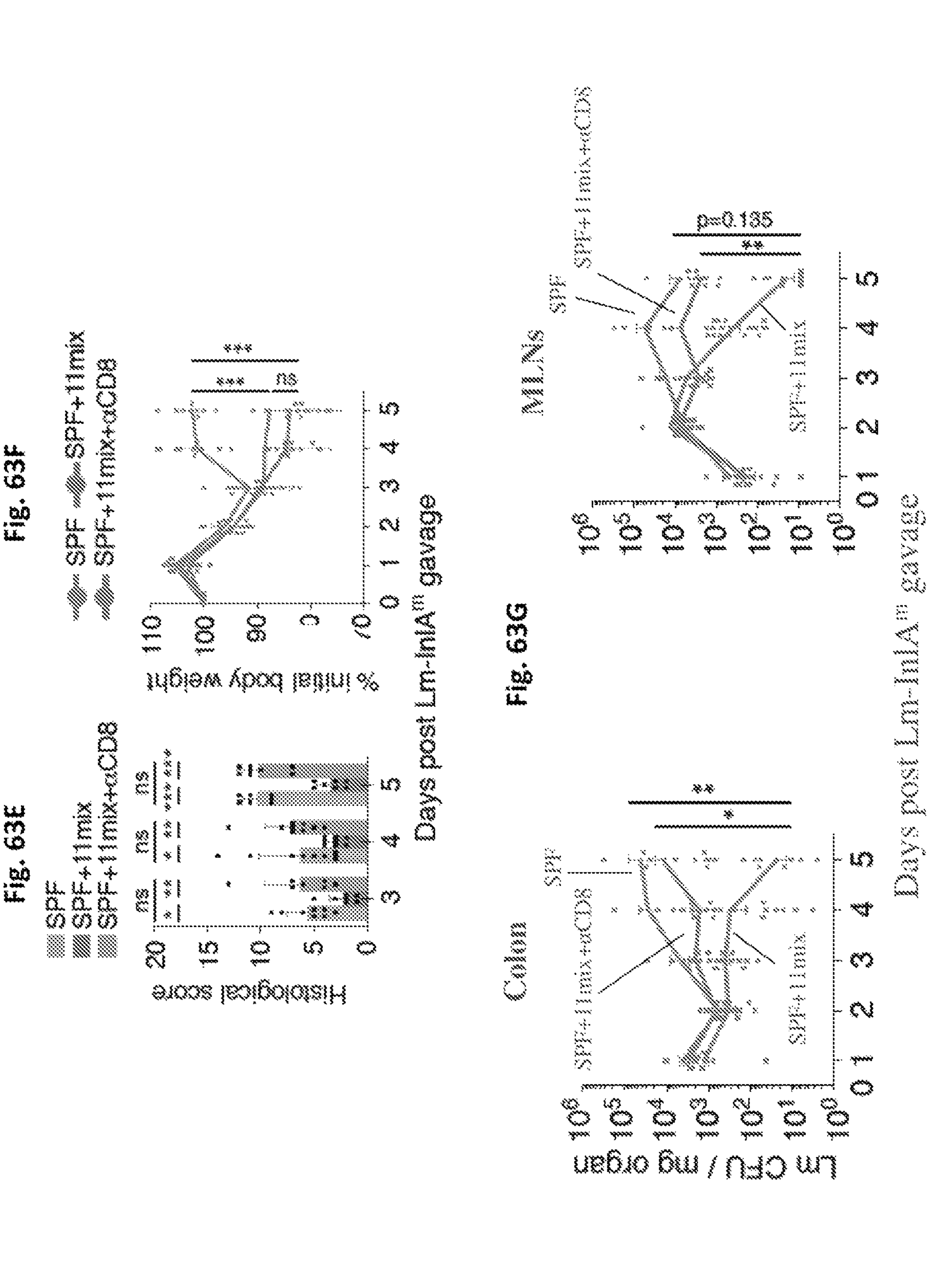
Figure 63J:
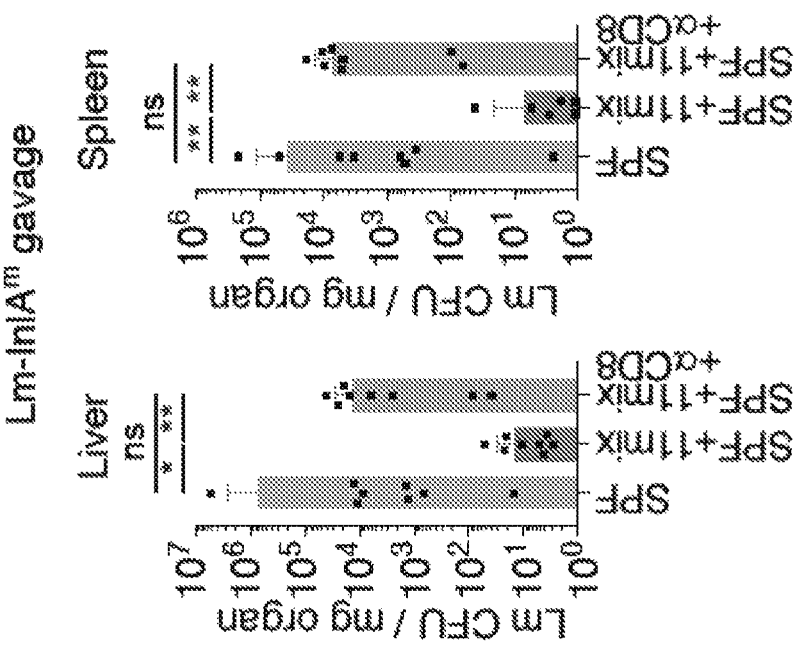
Figure 63I:
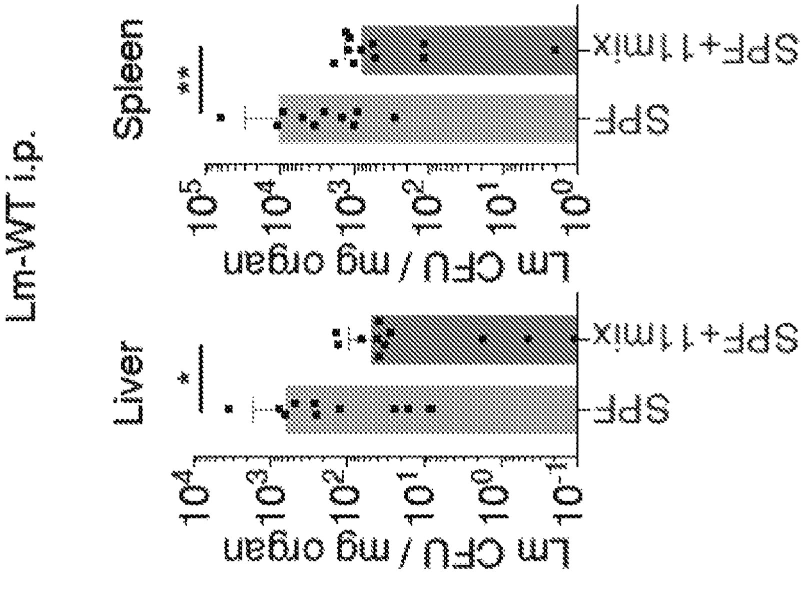
Figure 63H:
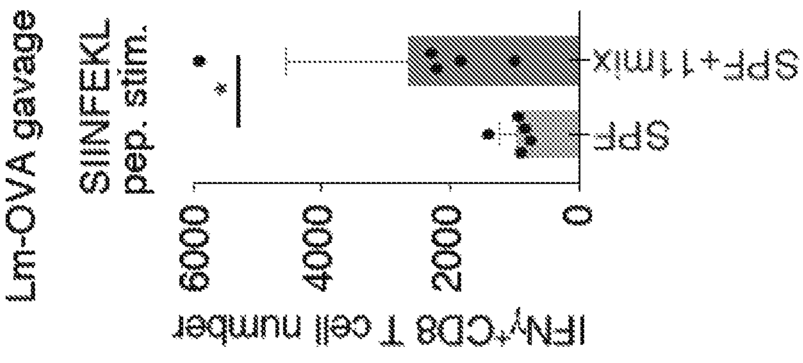
Figure 78B:
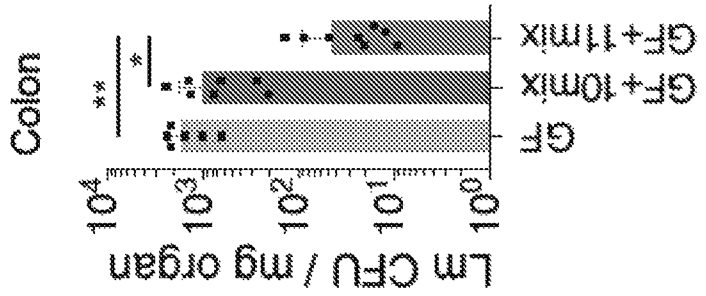
FIGS. 78A-78I show enhancement of host protection against Listeria monocytogenes (Lm) infection following administration of the mixture of 11 bacterial strains.
Figure 78A:
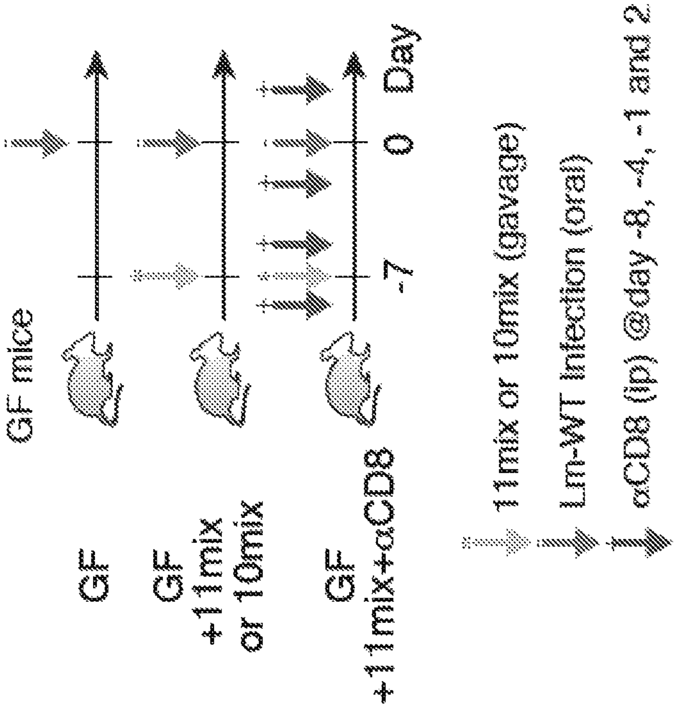
Figure 78C:
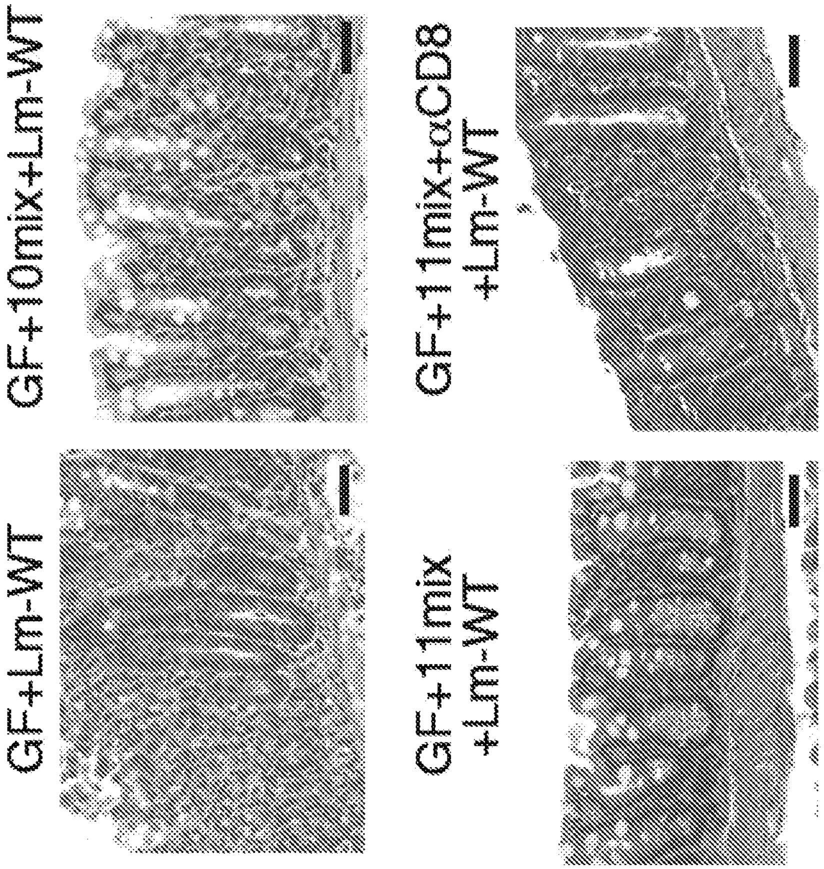
Figure 78D:
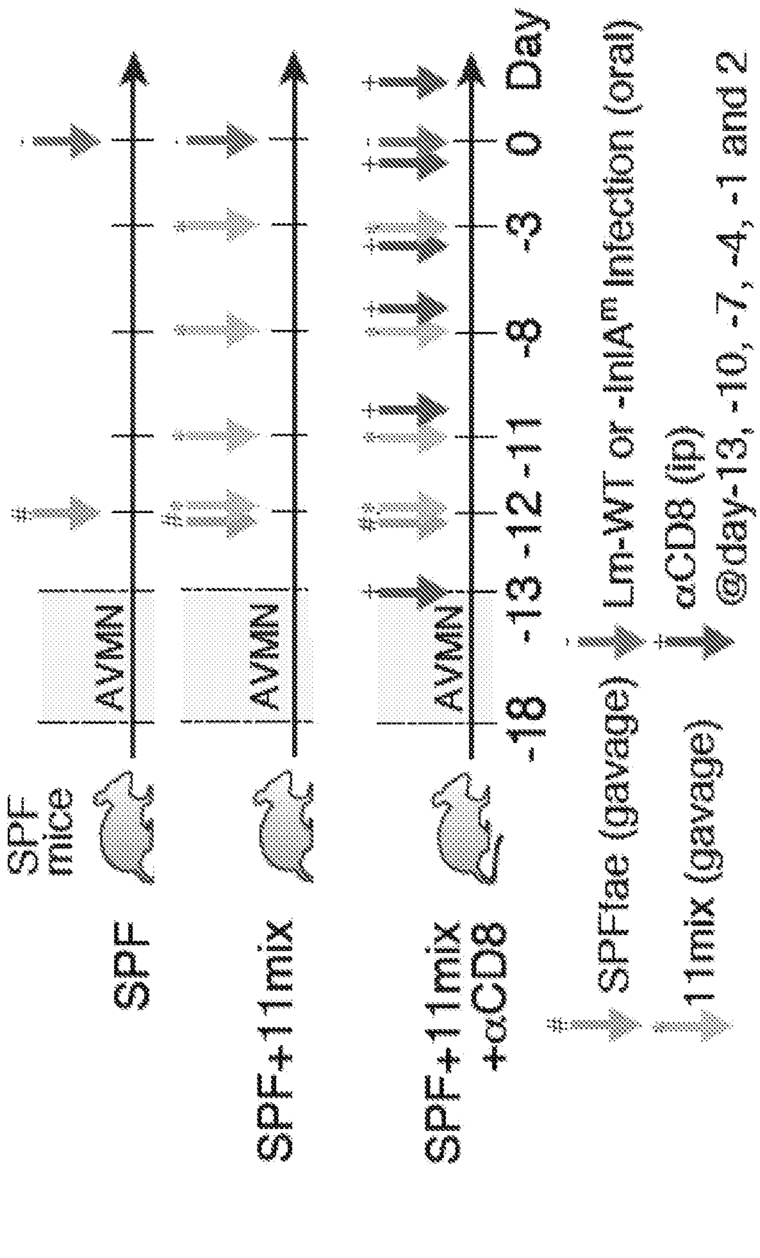
Figure 78E:
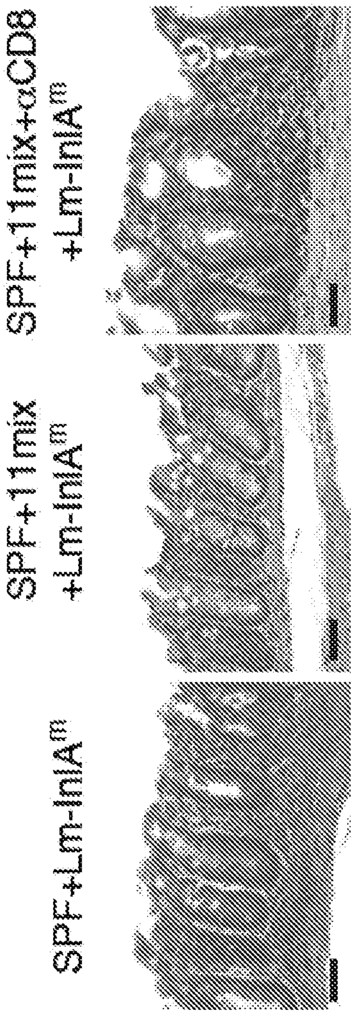
Figure 78F:
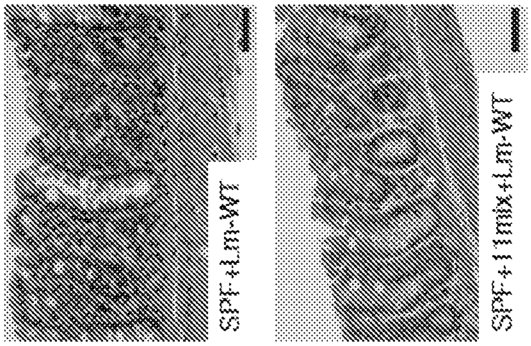
Figure 78G:
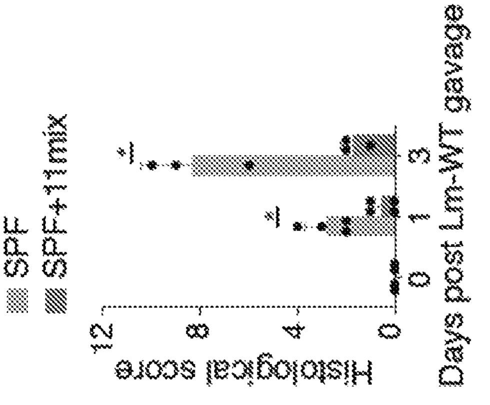
Figure 78H:
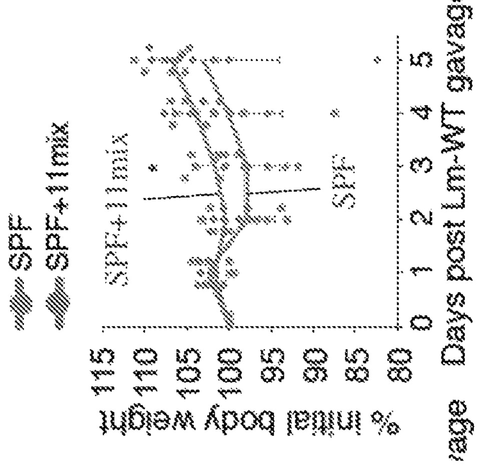
Figure 78I:
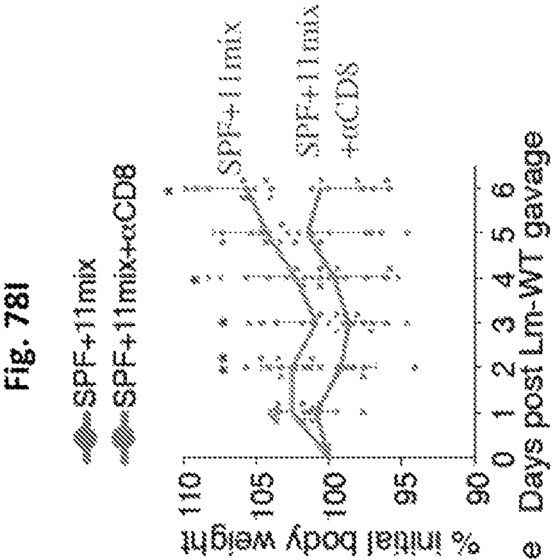
Figure 85:
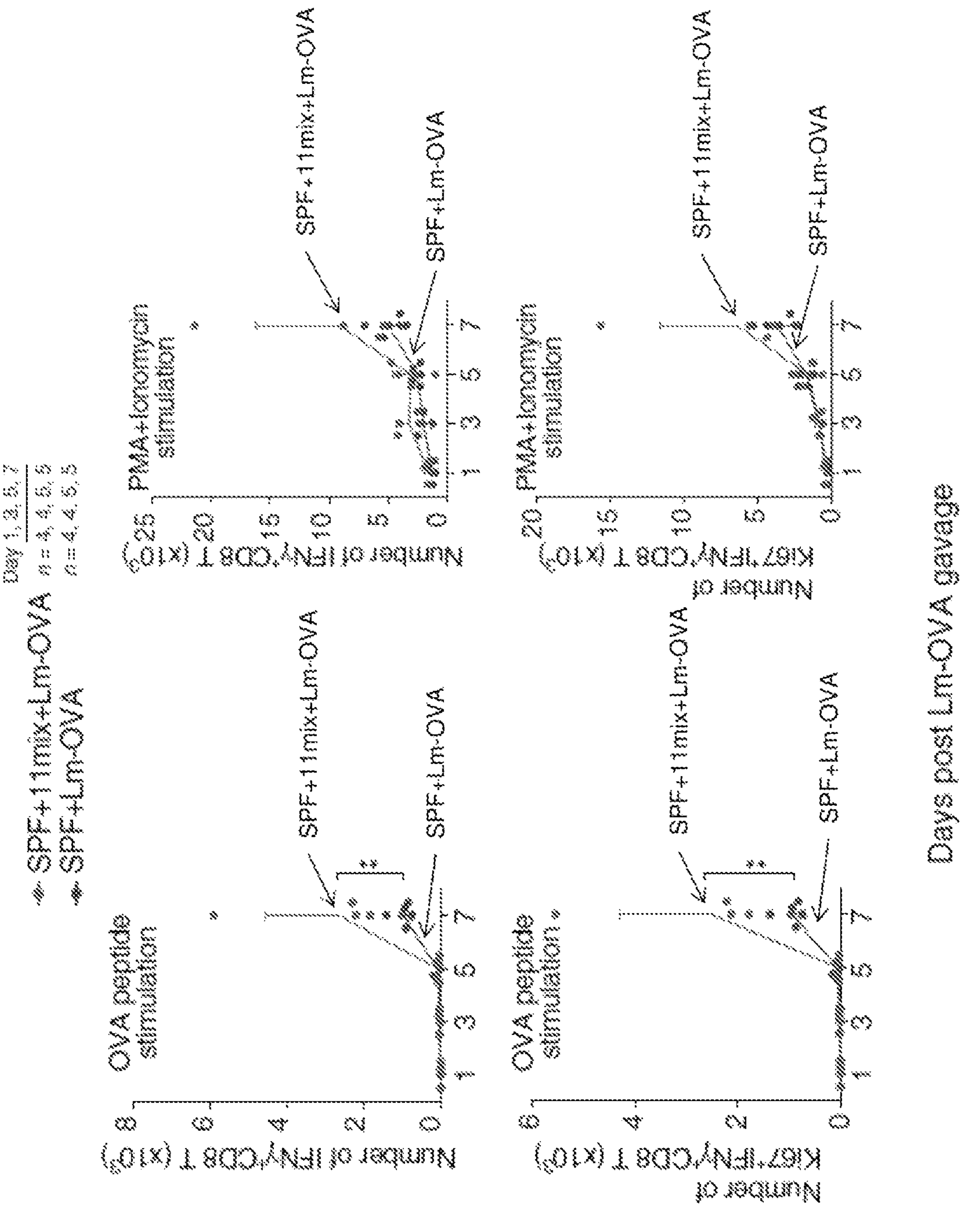
FIG. 85 shows that the 11-mix elicits induction of colonic IFNγ+CD8 T cells. C57BL/6 specific pathogen free (SPF) mice were treated with AVMN (ampicillin, vancomycin, metronidazole, neomycin), as shown in FIG. 78D, then reconstituted with a fecal suspension from untreated SPF mice (SPFae) by oral gavage. In the 11 mix treatment group (+11 mix), initial administration of the 11 mix was simultaneous with SPFae, followed by repetitive oral gavage of the 11 mix alone at days 1, 3, 5, and 7. Mice were then orally treated with Listeria monocytogenes-ovalbumin ((Lm)-OVA). The number of ovalbumin (OVA) peptide SIINFEKL-specific or general (determined by PMA+ ionomycin stimulation) colonic IFNγ+CD8 T cells induced after (Lm)-OVA infection were assessed, as measured by flow cytometry at the indicated time points. The mean of each group is represented by a line. Each circle represents an individual animal, and the number of mice per time point is indicated. Error bars, s.d. **P<0.01; *P<0.05.

Since IFNγ+CD8 T cells are known to promote the clearance intracellular pathogens[12,18], the 11 strains were tested to determine if they could augment host protective immunity against orally-administered. Listeria monocytogenes (Lm). GF+11-mix mice exhibited enhanced Lm clearance, as evidenced by markedly improved colon histology scores, reduced weight loss, and a decrease in colon tissue Lm colony-forming units (CFU) as compared to GF+10-mix mice (FIGS. 61A, 61B, and 78A-78C). Anti-CD8 mAb-mediated CD8 T cell depletion significantly diminished the protective effects of the 11-mix (FIGS. 61C, 61D, and 78C). These trends were replicated under SPF conditions, in infection models using an invasive mutant (Lm-InlA[10,18]) or a WT strain (FIGS. 63E-63G and 78D-I). Moreover, in an ovalbumin-expressing Lm (Lm-OVA[19]) infection model, treatment with the 11-mix enhanced OVA-specific CD8 T cell proliferation (FIGS. 63H, 85). Colonization with the 11-mix also protected mice from systemic infection after intraperitoneal injection of WT Lm or oral gavage with invasive Lm-InlA$^{m}$ (FIGS. 63I and 63J).

Figures 64A, 64B, 64C:
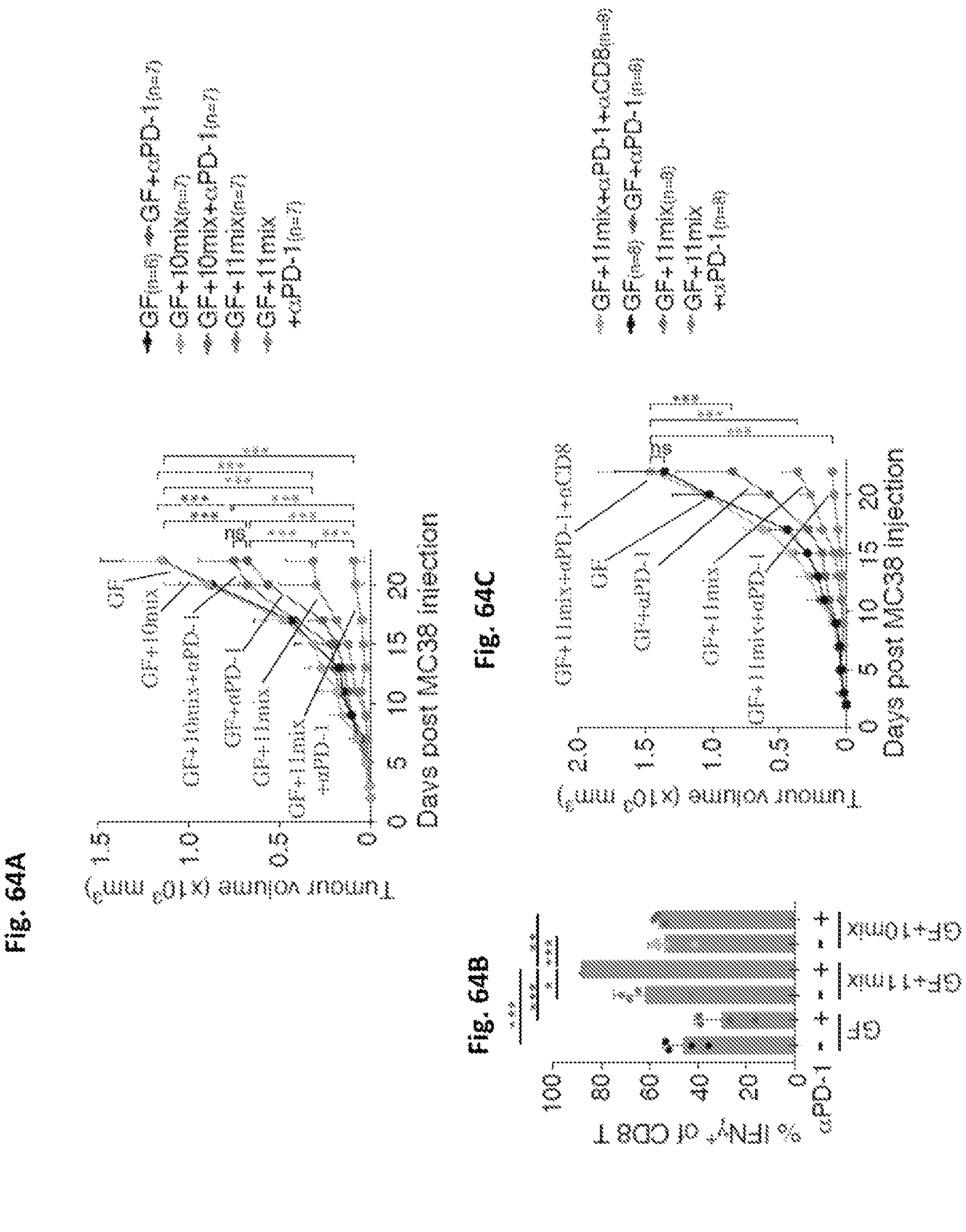
FIGS. 64A-64K show that colonization with the mixture of 11 bacterial strains suppresses tumour growth and enhances immune checkpoint inhibitor (ICI) treatment efficacy. As shown in the experimental design in FIG. 79D, for FIGS. 64A-64C, C57BL/6 GF mice were colonized with the mixture of 11 bacterial strains (11-mix) or mixture of 10 bacterial strains (10-mix) on day −7, or left uncolonized. The mice were subjected to subcutaneous implantation of MC38 adenocarcinoma cells on day 0. Anti-PD-1 mAb (αPD-1) was injected intraperitoneally every third day between days 3 and 9. For the depletion of CD8 T cells, anti-CD8 mAb (αCD8) was administered intraperitoneally 1 day before the administration of mixture of 11 bacterial strains, and every 3 to 4 days thereafter.
Figures 64D, 64E, 64F, 64G:
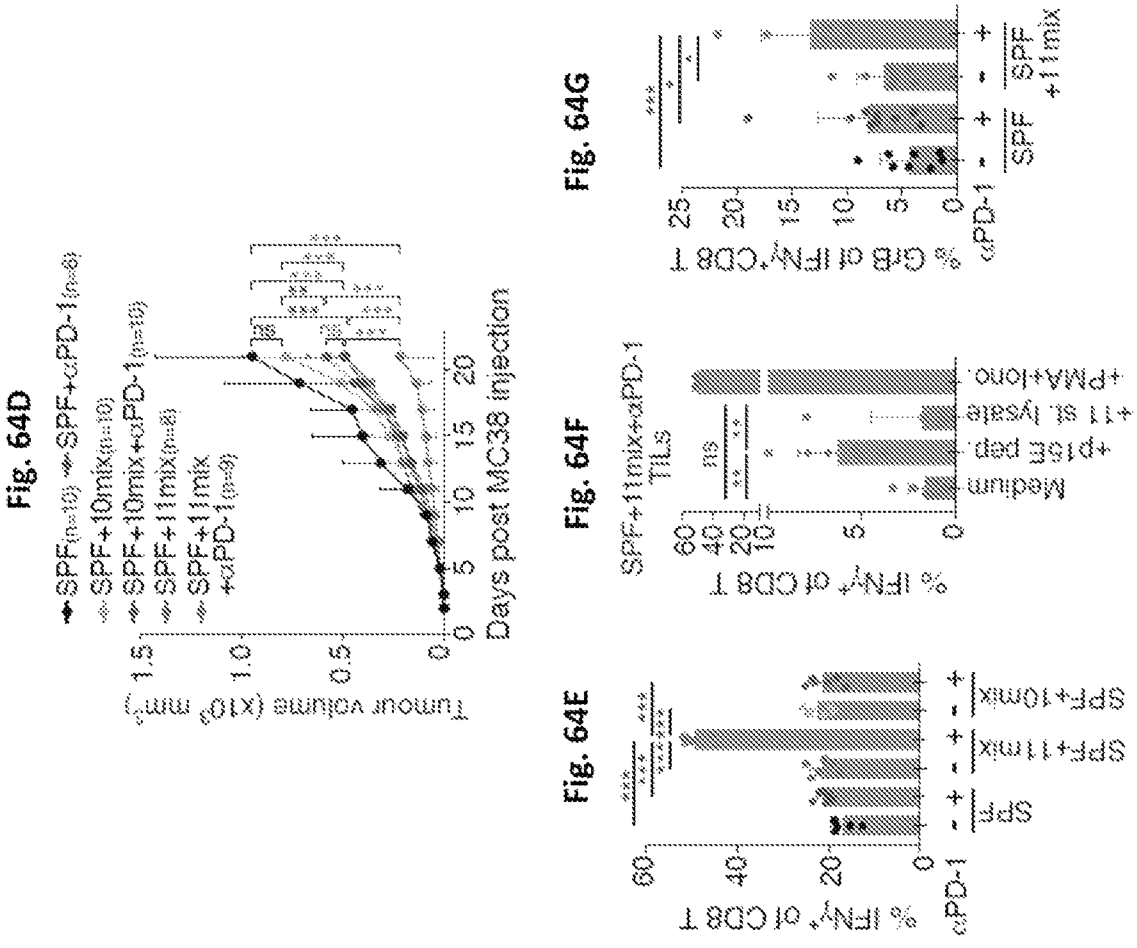
Figure 64H:
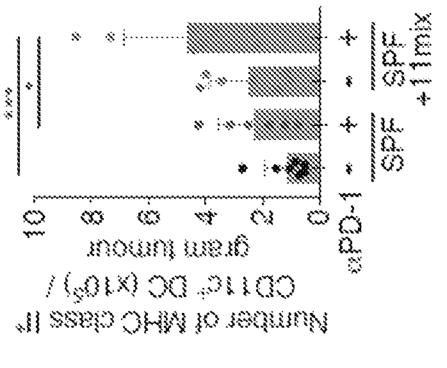
Figure 64I:
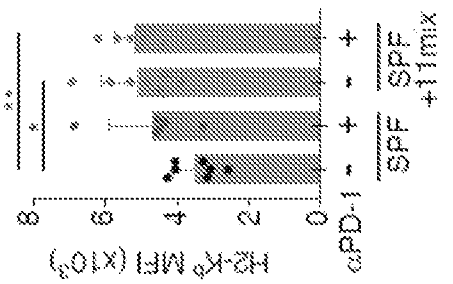
Figure 64J:
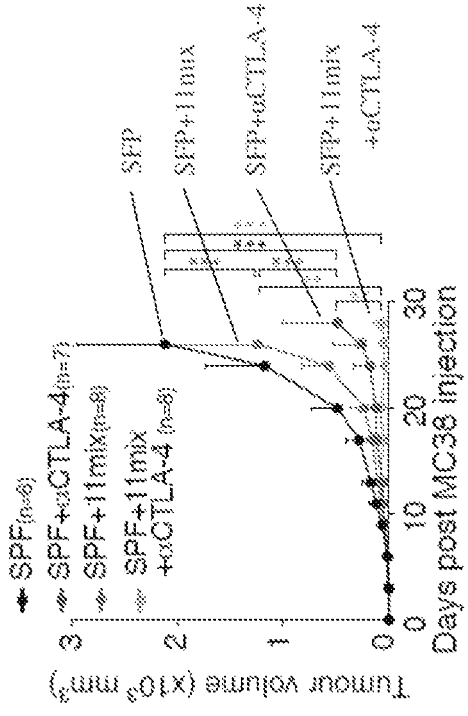
Figure 64K:
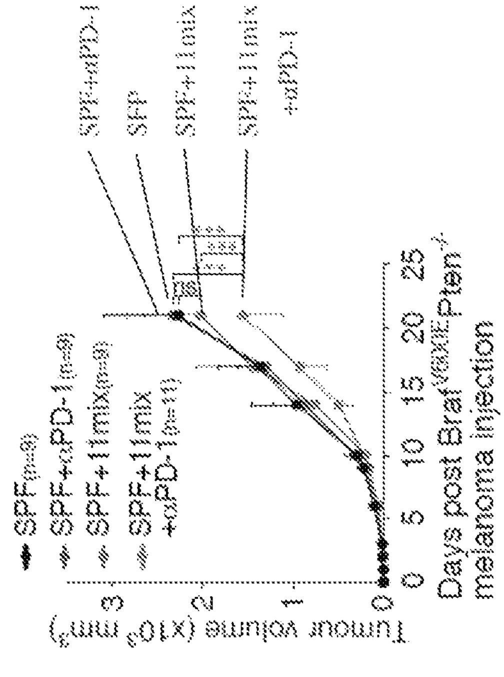
Figure 79A:
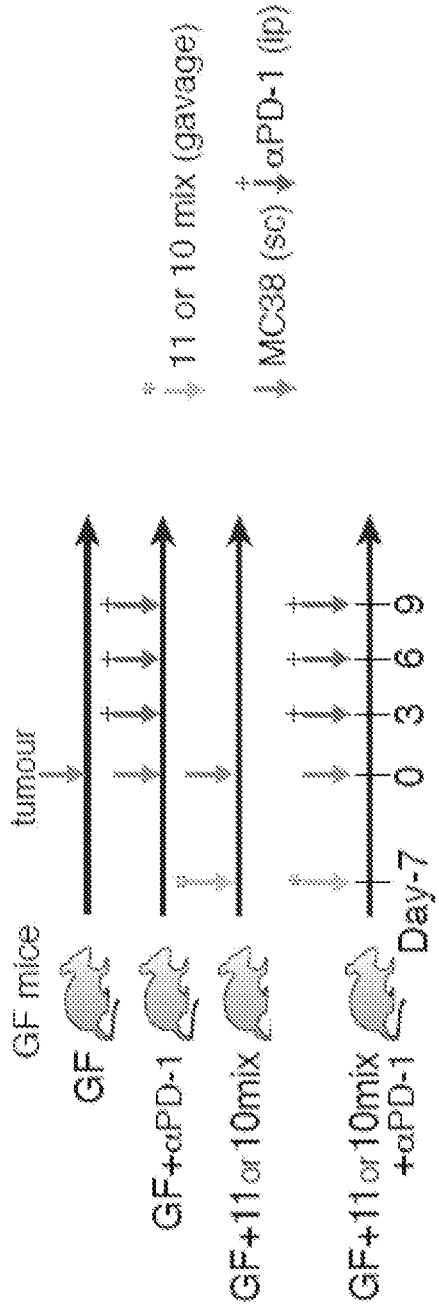
FIGS. 79A-79C show characterization of IFNγ+CD8 TILs induced by colonization with the mixture of 11 bacterial strains.
Figure 79B:
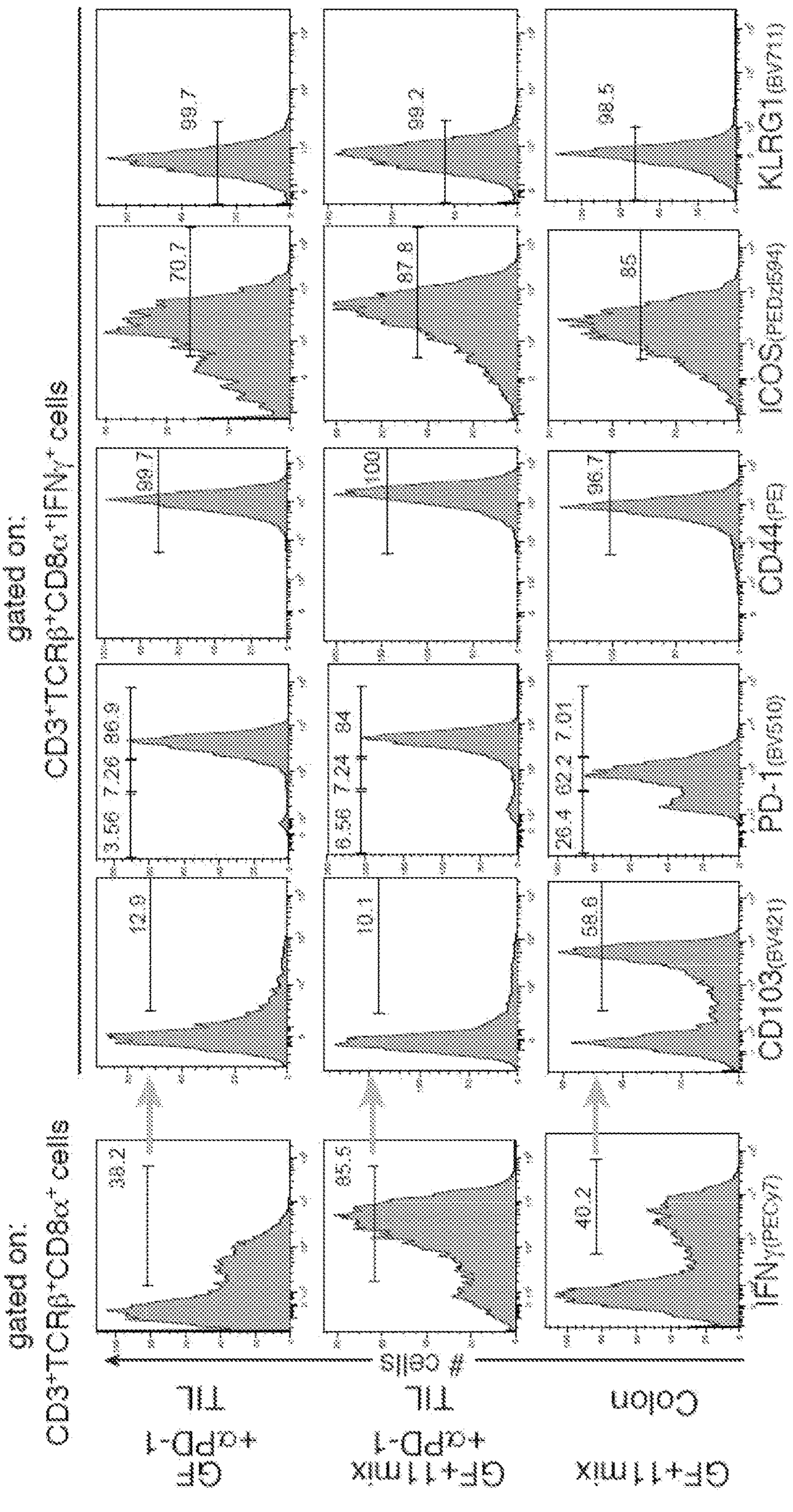
Figure 79C:
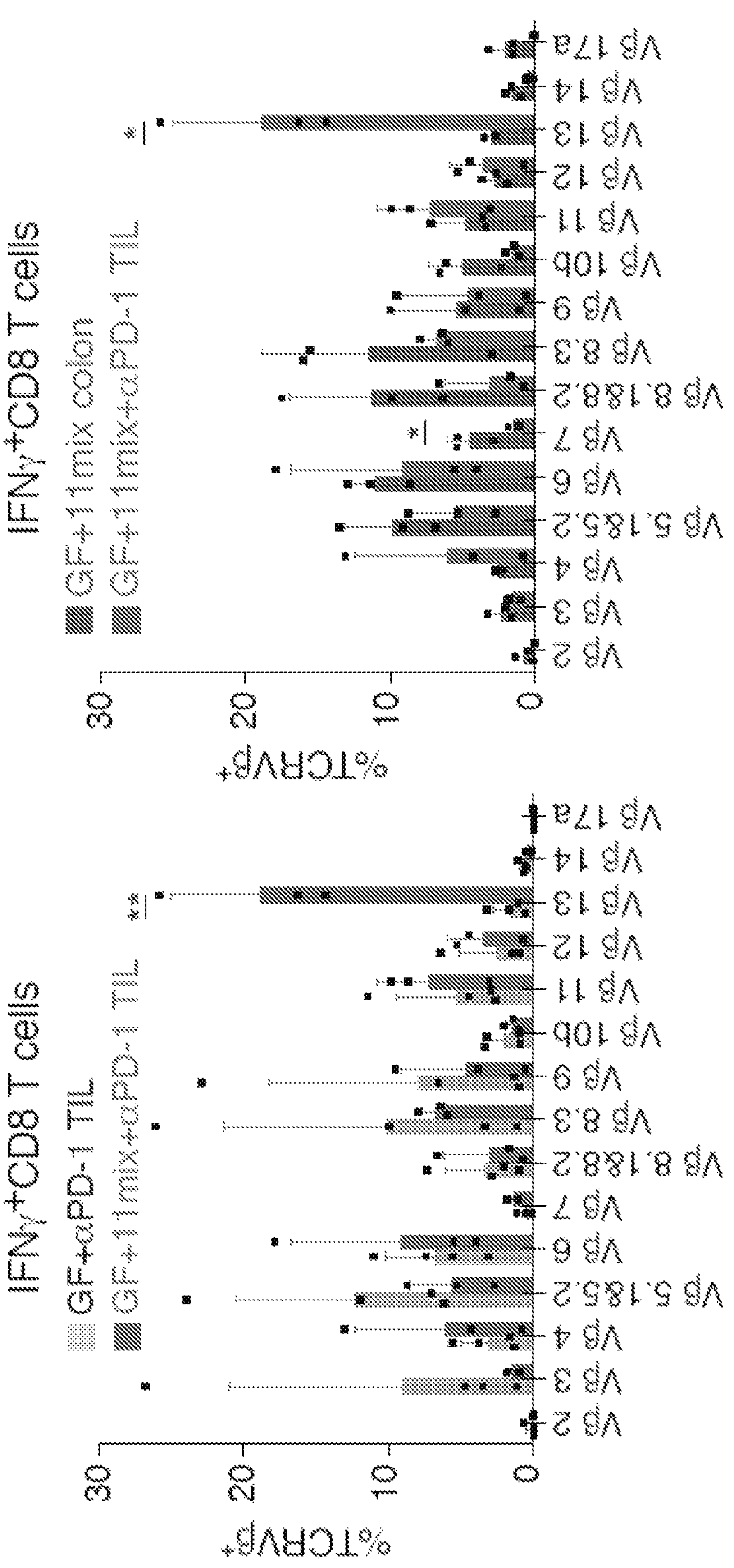
Figure 80A:
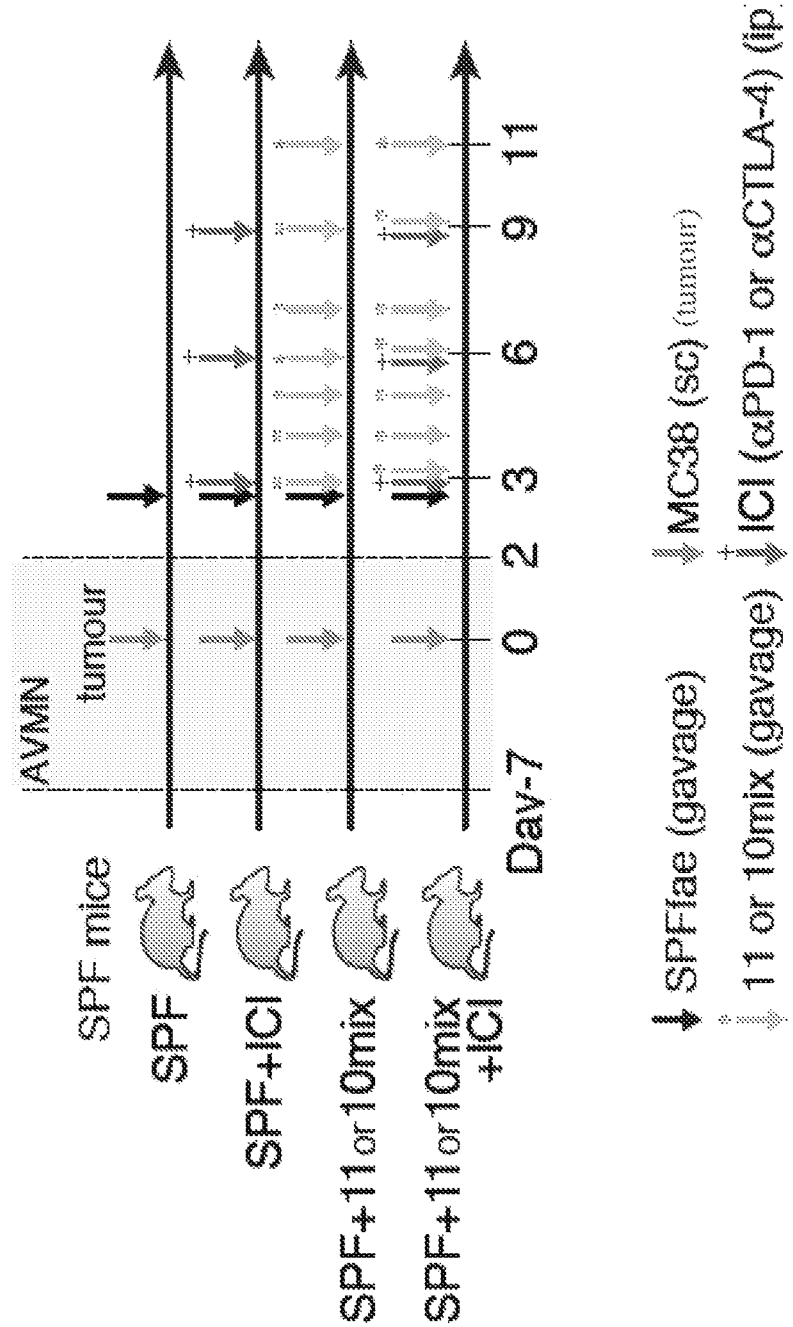
FIGS. 80A-80C show the efficacy of colonization with the mixture of 11 bacterial strains in enhancing treatment of MC38 tumours.
Figure 80B:
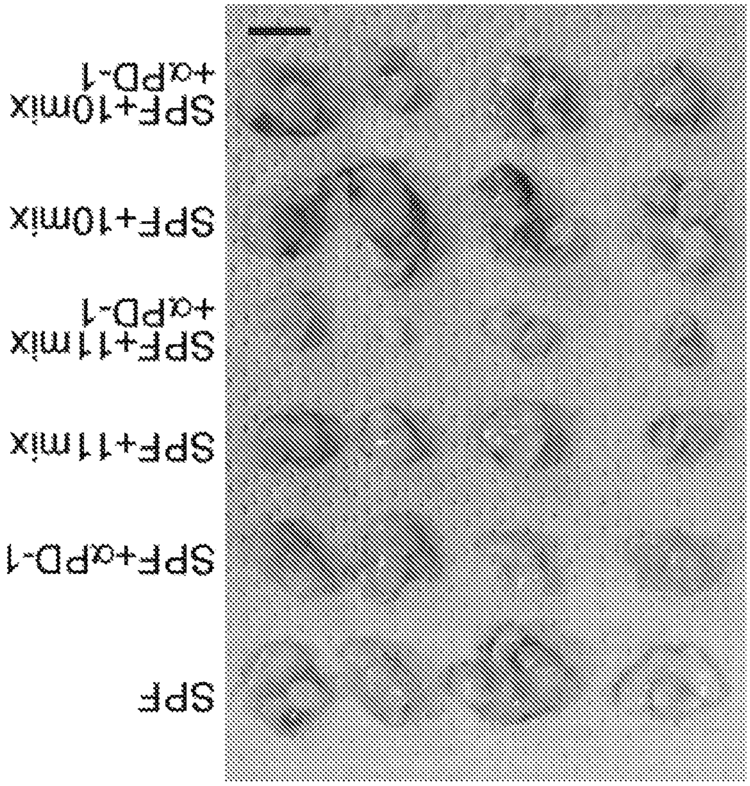
Figure 80C:
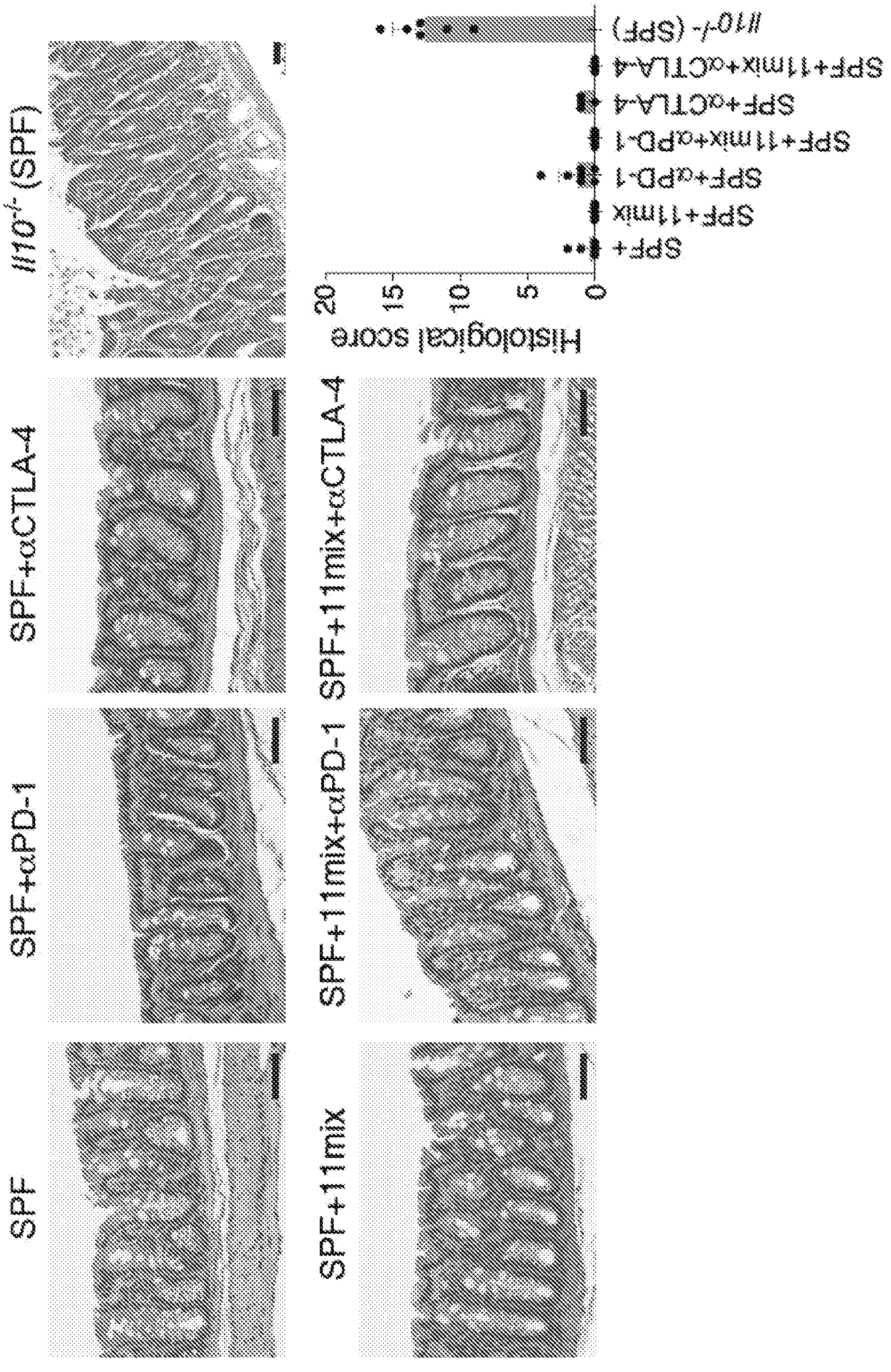
Figure 84A:
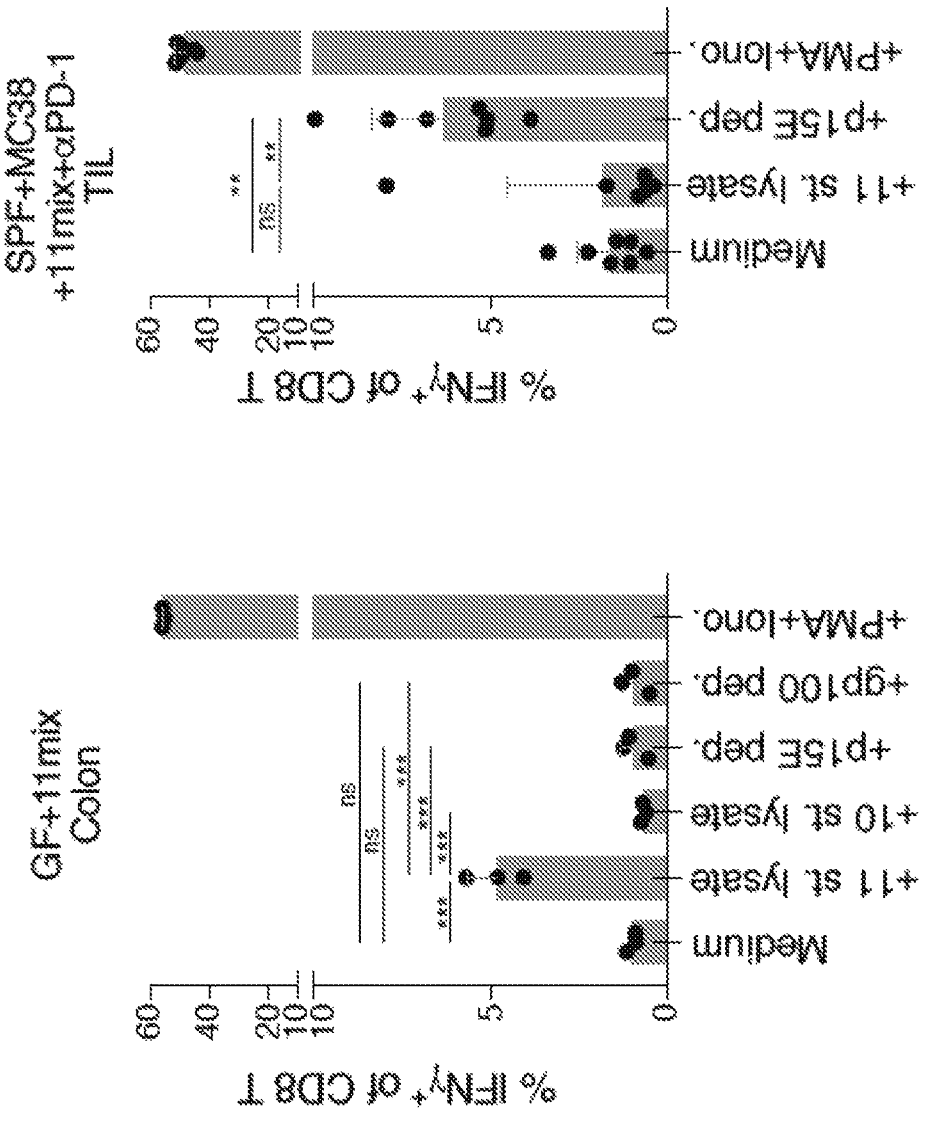
FIGS. 84A and 84B show that antigen-specificity and TCR Vβ usage of IFNγ+CD8 T cells induced by the mixture of 11 bacterial strains differed by anatomical location.
Figure 84B:
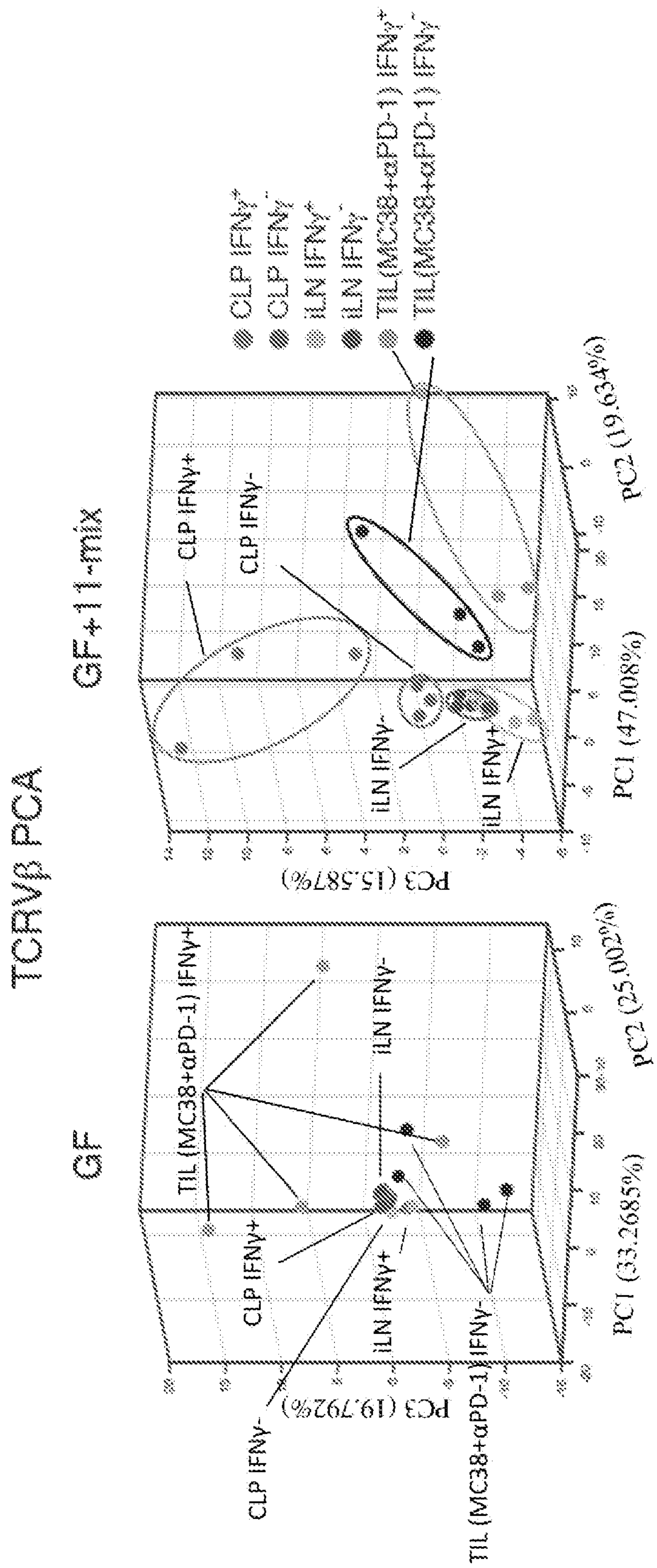

IFNγ+CD8 T cells also play a critical role in anti-tumour immunity and mediate immune checkpoint inhibitor (ICI) therapies[1,20-22], so it was also examined whether colonization with the 11 strains could enhance ICI therapeutic efficacy. GF, GF+11-mix, and GF+10-mix mice were subcutaneously engrafted with MC38 adenocarcinoma cells, and tumour growth was monitored with or without intraperitoneal ant-PD-1 mAb administration (FIG. 79A). Anti-PD-1 mAb treatment was strikingly more efficacious in GF+11-mix than in GF+10-mix or GF mice (FIG. 64A). This therapeutic efficacy was accompanied by an increase in frequency of IFNγ+CD8 tumour-infiltrating lymphocytes (TILs) (FIG. 64B), and antibody-mediated CD8 T cell depletion significantly diminished the protective effects (FIG. 64C). IFNγ+CD8 TILs in GF+11-mix+PD-1 mAb mice were primarily PD-1$^{high}$, CD103−, and relatively enriched for the Vβ13+ subset, and thus are phenotypically distinct from the IFNγ+CD8 T cells induced in the colon (2-way AVOVA interaction p-value=0.0001) (FIGS. 79 and 84B). Interestingly, 11-mix colonization significantly suppressed tumour growth even in the absence of PD-1 mAb treatment (FIG. 64A). Collectively, these results suggested that the 11 strains are sufficient and specific in enhancing both spontaneous and ICI-mediated anti-tumor immunity in a CD8 T cell-dependent manner. The 11-mix was also effective in the more clinically-relevant setting of complex-microbiota colonized mice (FIGS. 64D, 64E, 80A and 80B). A subset of the IFNγ+CD8 TILs expressed TCRs specific for the MC38 tumour-associated antigen p15E[29], though none were specific to 11-mix antigens (FIG. 64F). Additionally, combination therapy resulted in an increase in both frequency of GrB+IFNγ+CD8 T cells and in MHC class I-expression by tumour-infiltrating DCs (FIGS. 64G-64I). Supplementation with the 11-mix was similarly effective when combined with anti-CTLA-4 mAb in the MC38 model (FIG. 64J) and with anti-PD-1 mAb in the less immunogenic BRAF$^{V600E}$PTEN$^{-/-}$ melanoma model[24,25] (FIG. 64K). Importantly, there was no histological evidence of colitis in the 11-mix treatment groups, a frequently observed adverse effect of ICI therapy[1,36] (FIG. 80C). Collectively, these results suggested that the 11 strains modulate anti-tumour immunity and have the capacity to simultaneously enhance ICI therapies and negate their colitogenic side effects.

Figure 81A:
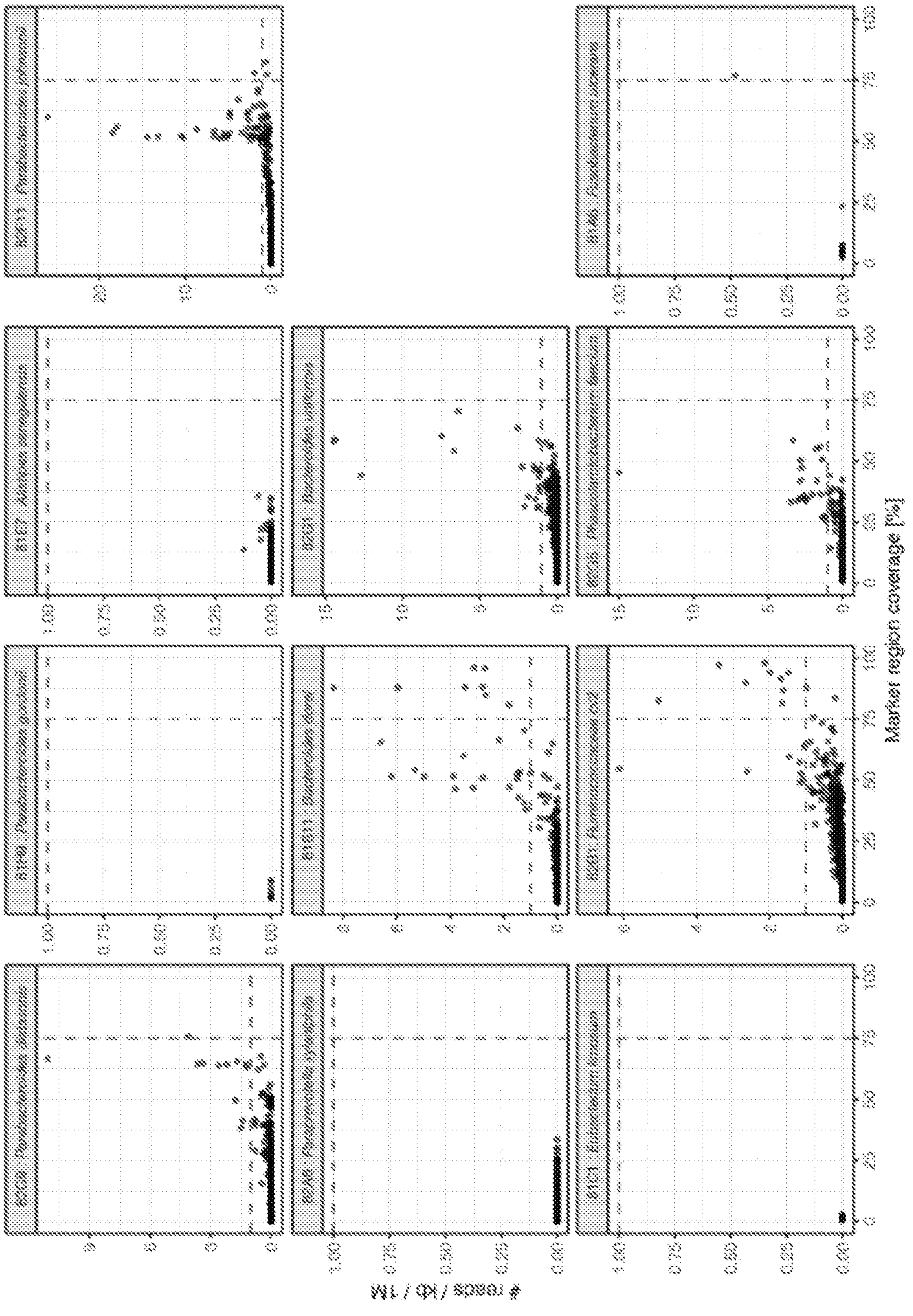
FIGS. 81A-81B shows the strain-level abundance of the 11 isolates in the human gut microbiome. Draft genomes of the 11 strains were split into 1 kilobase pair (kbp) regions and mapped against NCBI RefSeq (~85 k gnomes) to identify regions with no or weak similarity to known isolates (Identity <80%, Coverage <85%). Of these, consecutive regions with minimum 5 kbp were defined as marker regions that are unique to each strain. 3327 gut metagenome samples with at least 1M quality controlled reads across various datasets (HMP1-2, LLDeep, MetHIT, 500FG, HMP2 (only the first time point was used), healthy Japanese adults, and three microbiome in cancer immunotherapy studies were mapped to 1 kbp regions in all strains (filtered by 95% mapping identity). The mapped read counts were normalized to reads per kbp per million (RPKM).
Figure 81B:
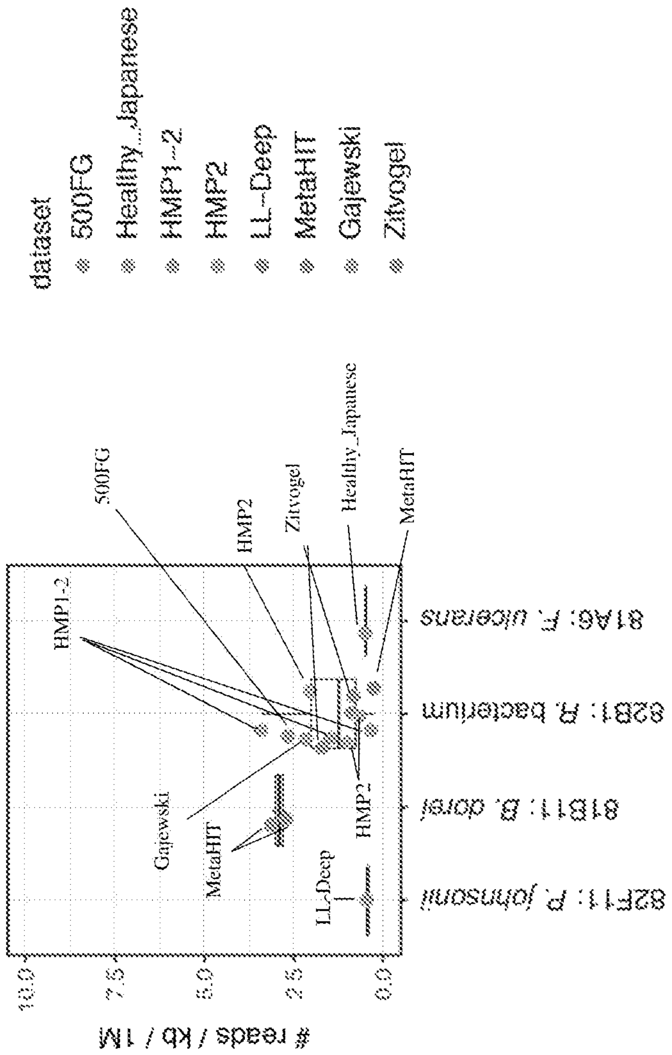
Figure 82:
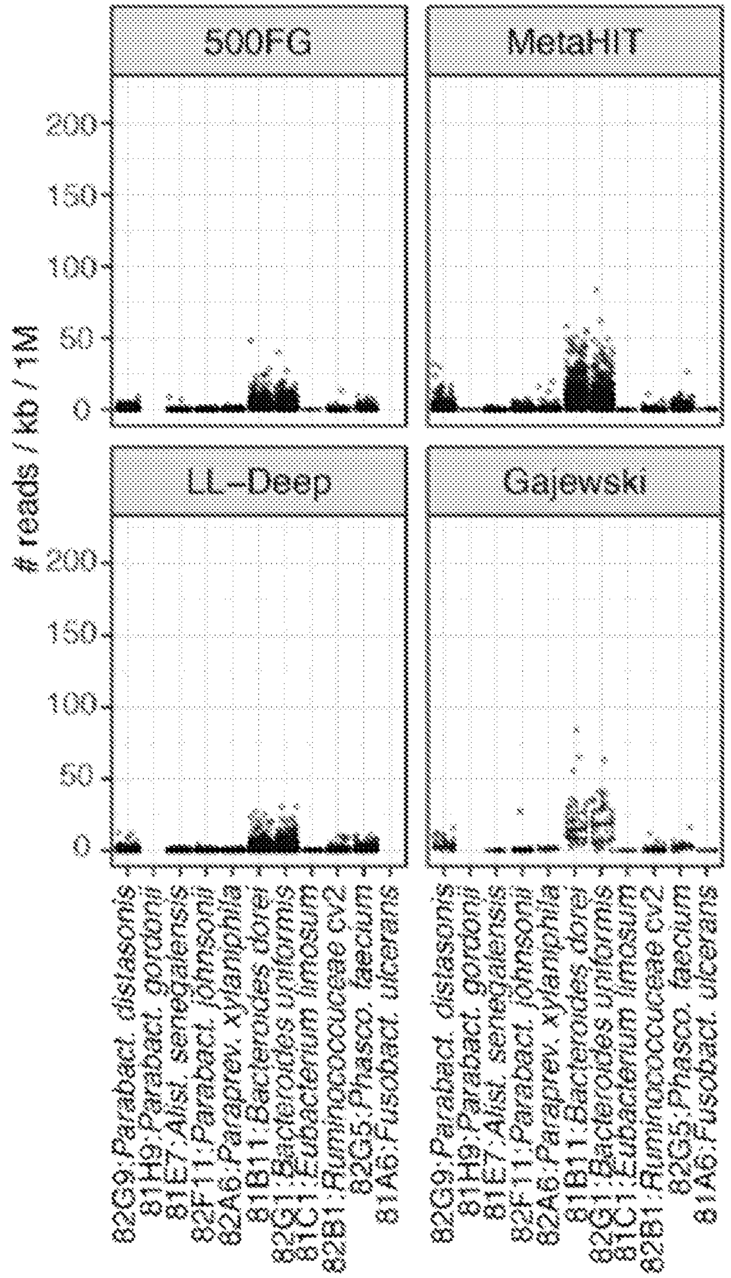
FIG. 82 shows species-level abundance of 11 isolates in the human gut microbiome. The abundance at the species level was calculated as the median abundance across all 1 kbp regions in a genome using 3327 metagenome samples with at least 1M quality controlled ready's (mapped reads were filtered at 95% mapping identity). The mapped read counts were normalized to reads per RPKM.
Figures 83A, 83B:
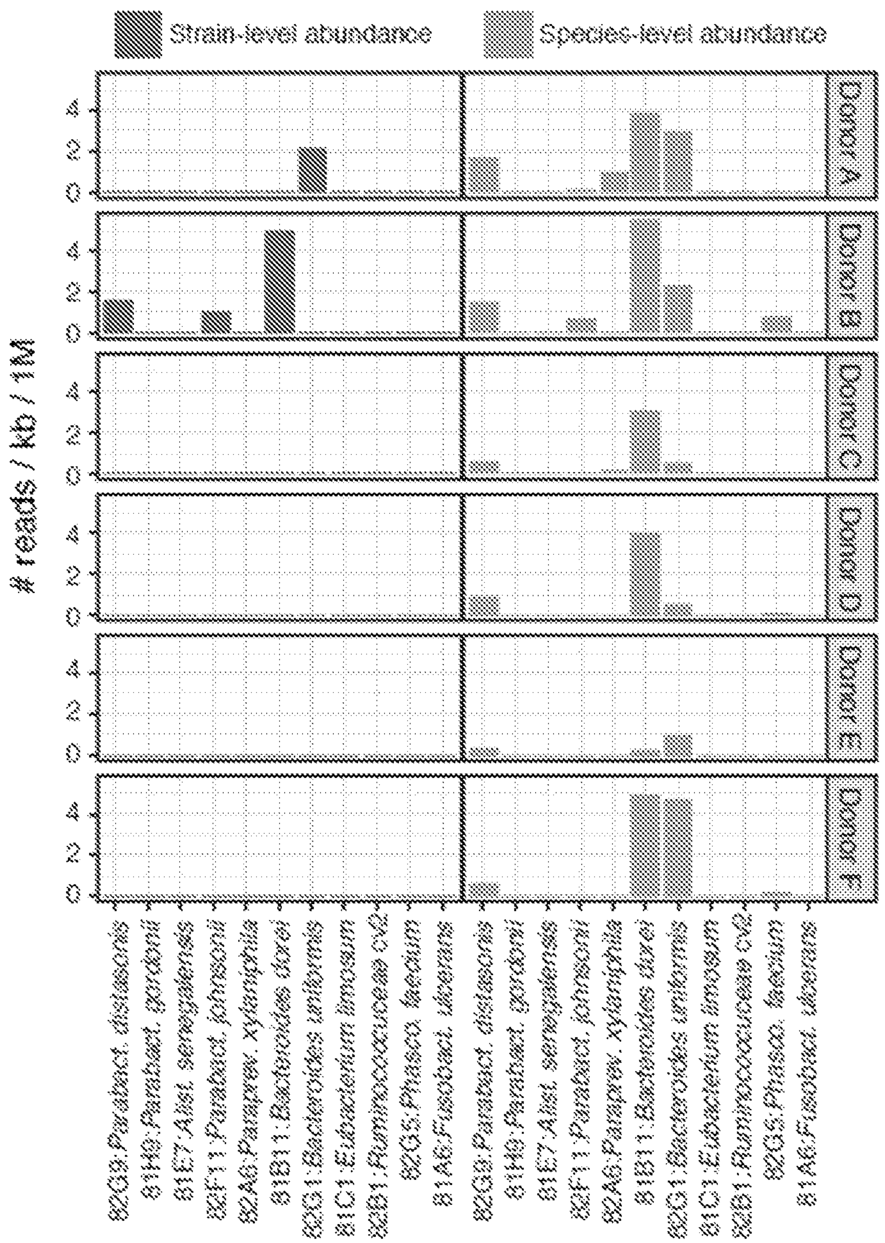
FIGS. 83A-83B shows the abundance of the 11 strains in the faecal microbiome of healthy human donors.

Finally, the abundance of the 11 strains in the human gut microbiome was evaluated using several metagenomic datasets. Most of the 11 strains were found to be are generally rare, low-abundance components of the human microbiota at both strain- and species-level resolution (FIGS. 81-83). Most of the strains were scarce even in the microbiome of Donor B, from which they were isolated (FIG. 83). Similar low-abundance trends were observed in both responder and non-responder melanoma patients treated with ICIs in the reported datasets[27,29] (FIGS. 81 and 82).

In this study, 11 healthy human-associated bacterial strains were identified that act together to induce IFNγ+CD8 T cells, confer resistance to the intracellular pathogen Lm, and are effective in inhibiting tumour growth in conjunction with ICIs. More research will be needed to elucidate the cellular and molecular mechanism by which the 11 strains effect the observed local and systemic immunomodulation. Several reports have demonstrated that the composition of the gut microbiota influences response to ICIs in both humans and mice, suggesting that its manipulation holds immense therapeutic potential[3,21,27,29]. However, the specific microbiota members associated with enhanced clinical response vary substantially between studies. The isolated strains in this study have great biotherapeutic potential and could be broadly applicable to enhancing the treatment of cancer and infectious disease, as they are severely underrepresented in the gut microbiota of most individuals.

Discussion

The gut microbiota is an attractive therapeutic target for the. treatment: and/or prevention of infectious and inflammatory disease, and also for boosting the efficacy of cancer immunotherapy. In this context, bacterial strains that can potently affect the development and function of intestinal CD4 T cells, including SFB (a $T_H$17-inducer)[9,42], Clostridia ($T_{reg}$-inducers)[8,43], and Klebsiella spp. ($T_H$1-inducers)[13]

were previously identified and isolated using gnotobiotic animal models. In contrast, the relationship between the microbiota and intestinal CD8 T cells remains poorly characterized and largely unknown. In this study, a consortium of 11 bacterial strains from the healthy human gut that act together to induce the accumulation of IFNγ+CD8 T cells in the colon and also at distal sites were rationally isolated. This 11-strain mixture was able to enhance both host resistance against Listeria infection and therapeutic efficacy of PD-1 and CTLA-4 monoclonal antibody therapies against cancer.

Possible Mechanisms of 11-Mix-Mediated Colonic (Local) IFN+CD8 T-Cell Induction.

The 11 strain-driven colonic IFN+CD8 T cell accumulation is likely mediated through complex multi-cellular and molecular pathways. Supporting this notion, 11-mix-induced colonic IFN+CD8 T cells constituted a highly heterogeneous population characterized by distinct expression levels of CD103, GrB, and PD-1, as well as distinct TCR V usage and antigen specificity. In particular, colonic IFN+ CD8 T cells induced by the 11-mix contained both CD103+ and CD103− subpopulations (FIGS. 61I and 69B). CD103 is the -chain of integrin E7 and a marker of tissue-resident memory T ($T_{RM}$) cells[10-12]. Earlier studies have shown that CD8 T cells upregulate CD103 upon chronic TCR stimulation, particularly in the presence of transforming growth factor-β (TGF)[10]Therefore, the CD103+IFN+CD8 T cell subset might be induced by an active and sustained response to bacteria or bacteria-derived antigens in the TGF-rich gut microenvironment[44]. Consistent with the hypothesis of sustained TCR activation-mediated differentiation, IFN+CD8 T cells in GF+11-mix mice expressed intermediate levels of PD-1 (FIG. 69B), though expression was lower than that by TILs isolated from MC38 tumours (FIG. 79B). As PD-1 expression is known to be induced and maintained by chronic TCR signaling[45-47], it is likely that the observed IFN+CD8 T cell accumulation is at least in part mediated by sustained TCR stimulation. Additionally, examination of TCR V usage revealed that IFN+CD8 T cell TCR composition differed significantly between GF+11-mix and GF mice: the GF+11-mix group showed a relative enrichment for the V6+ and V8+ subsets (FIG. 62F). Furthermore, investigation of antigen specificity revealed that a substantial fraction of colonic IFN+CD8 T cells in GF+11-mix mice recognized 11 strain-derived antigen(s) (FIG. 62G). Finally, the accumulation of IFN+CD8 T cells was dramatically impaired in CD103+ dendritic (DC)-deficient ($Batf3^{-/-}$, XCR-DTA, $Irf4^{DC}$, $Notch2^{DC}$) and MHC class Ia-deficient ($KbDb^{-/-}$) mice (FIGS. 62I and 62K). Taken together, these data indicated that the 11-mix-mediated IFN+CD8 T cell induction can at least in part be attributed to TCR-driven de novo differentiation.

In addition to differentiation, colonic recruitment and maintenance are likely mechanisms by which the observed IFN+CD8 T cell induction is affected. Transcriptomic analysis of colonic epithelial cells (ECs) revealed significant upregulation of Cxcl9 and Cxcl10 chemokine transcripts, along with those encoding other IFN-inducible genes, as early as one week post-inoculation of the 11-mix (FIGS. 62C and 73A). These chemokines are ligands for CXCR3 and are reported to be the key molecules that facilitate effector CD8 T cell reruitment[48-50]; therefore, they likely to contribute to IFN+CD8 T cell recruitment to the colon. Consistent with this notion, the IFN+CD8 T cell frequency in the peripheral blood was reduced after 11-mix administration (FIG. 62L). It is noteworthy that Cxcl9 and Cxcl10 are both IFN-inducible genes[31], and that $IFNR1^{-/-}$ mice showed significantly reduced colonic IFN+CD8 T cell induction (FIG. 62D). These results suggest that 11-mix colonization establishes a feed-forward IFN loop, leading to a robust and sustained accumulation of IFN+CD8 T cells. Moreover, approximately half of the colonic IFN+CD8 T cells were positive for proliferation marker Ki67 at one week post-colonization (FIG. 62E), indicating that they were undergoing active proliferation. Therefore, cellular expansion is also at least partially responsible for the observed accumulation. Taking all of this data into account, the accumulation of IFN+CD8 T cells is likely due to the cumulative effects of colonic recruitment, cellular expansion, and bacterial antigen-mediated differentiation.

Our data additionally suggest that bacterial localization and metabolic output may also be relevant to the aforementioned cellular mechanisms. Investigation of the bacterial spatial distribution in the colon by FISH revealed that the 11 strains can enter and colonize the mucus layer (FIG. 62B). Since localization across different niches in the gut has been known to influence bacterial effects on the immune system[9, 52], the fact that the 11 strains colonize the mucus layer (i.e., near the epithelium) may be mechanisically related to the observed CD8 T cell activation. Additionally, since heat-killed bacteria had no effect (FIG. 62A), and since the immunomodulation occurred independently of major innate immune signalling, such as those involving TLRs, IL-1, IL-18 and type I IFN (FIG. 62H), it was hypothesized that metabolites, rather than microorganism-associated molecular patterns, may be responsible for the IFN+CD8 T cell induction. Based on phenotypic data, it is likely that the effector metabolite(s) is produced most efficiently by the 11-strain consortium, and to a lesser extent by the 4-mix (FIG. 61J). Consistent with this hypothesis, GF+11-mix and GF+4-mix mice showed similar caecal metabolomic profiles, and several metabolites were found to be elevated specifically in GF+11-mix mice or in both GF+11-mix and GF+4-mix mice (FIG. 75A). For example, the level of mevalonate mirrored the extent of colonic IFN+CD8 T cell induction across groups and was elevated in the serum of GF+11-mix mice (FIGS. 75B-D), immediately suggesting a potential mechanistic role at both the local and systemic levels (see below). Interestingly, the mevalonate pathway has been reported to affect T cell function and differentiation: the sterol branch of mevalonate metabolism provides precursors for cholesterol biosynthesis, thus affecting T cell proliferation and function, while the non-sterol branch is involved in protein prenylation, controlling T cell migration and signaling[53,54]. Mevalonate derivatives can also act as T cell extrinsic cues and potent T cell agonists[53,54]. Dimethylglycine is another metabolite that was elevated in the caecal contents of both GF+11-mix and GP+4-mix mice and tended to be increased in the serum of GF+11-mix mice, and thus may contribute to the induction of local and systemic IFN+CD8 T cells. Dimethylglycine is a key intermediate of choline metabolism and is purported to be effective in enhancing neurological functions and managing autism[55]. It has also been shown to enhance T cell-mediated immune response.

In summary, without being bound by a particular mechanism, in the current model, the 11 strains localize near the colonic epithelium and produce certain immunostimulatory ligands (possibly metabolites) and antigens, which could contact ECs, CD103+DCs, and/or CD8 T cells to activate MyD88- and type I IFN-independent but IFNR-dependent signaling pathways. This, in turn, could lead to elevated chemokine expression and MHC class I upregulation, among other things, resulting in the recruitment, proliferation, and differentiation of 11-strain antigen-specific and -nonspecific IFN+CD8 T cells. Narrowing down these non-mutually exclusive hypotheses to determine the actual 11-strain-mediated immunomodulatory mechanism of action will require substantial work in the future, and could enhance both our understanding of basic immunobiology and the effectiveness of current therapeutics.

Possible Mechanisms of 11-Mix-Mediated Systemic Immunomodulation.

The CD8 T cell accumulation observed at organs other than the intestine in GF+11-mix mice could theoretically result from a number of mechanisms, including systemic circulation of: 1) gut-induced CD8 T cells, 2) bacteria, bacterial antigen, or bacteria-loaded DCs, or 3) metabolites (induced or produced by the 11 strains) and/or cytokines. It is unlikely that CD8 T cells of gut origin migrate out of the intestine, circulate systemically, and modulate the immune response against subcutaneous tumours and splenic or hepatic Listeria monocytogenes infection, as the IFN+CD8 T cells that accumulated in the colon, tumour, and at distal organs were phenotypically distinct. Indeed, the CD103+ subpopulation was exclusively induced in the intestine (FIGS. 74A and 79B), and it is unlikely that these $T_{RM}$ phenotype cells leave their site of induction. Moreover, the expression level of PD-1 was significantly different (FIGS. 74A and 79B), and there was no overlap in V usage between colonic, systemic, and tumour IFN+CD8 T cells (2-way ANOVA interaction p-value <0.0001) (FIG. 84B). Additionally, 11 strain-specific, Listeria (Lm-OVA)-specific, and tumour-specific T cells were differentially detected at distinct anatomical sites (FIGS. 62G, 63H, 64F, and 84A). That is, a substantial fraction of the accumulated colonic IFN+ CD8 T cells was specific for 11-strain-derived bacterial antigens, while no response was observed against MC38-derived p15E tumor antigen[57] or melanoma-derived glycoprotein 100 (gp100) antigen[58-60]. Conversely, IFN+CD8 TILs from MC38 tumours mounted a response to p15E antigen, but not to the heat-killed 11 strains (FIGS. 64F and 84A). Although the possible systemic circulation of gut-origin IFN+CD8 T cells (in particular, the CD103-negative non-$T_{RM}$ subpopulation) cannot be excluded, it is highly likely that the IFN+CD8 T cells accumulated in the colon, tumour, and distal organs are induced locally and independently of one another. Systemic circulation of bacterial antigens or bacteria-loaded DCs is also unlikely because we detected neither bacterial translocation (FIG. 73C) nor overlap in TCR V usage or antigen specificity at different anatomical sites (FIG. 84). The simplest and most likely explanation is that the accumulation of IFN+CD8 T cells in organs distal to the intestine is due to the general proliferation and activation of CD8 T cells that do not necessarily recognize 11-strain-derived antigen. Since there were elevated levels of known immunomodulatory metabolites, such as mevalonate and dimethylglycine, in the sera of GF+11-mix mice (FIG. 75D), systemic immune activation across different tissues may be mediated by circulating metabolites rather than by specific bacterial antigen-driven CD8 T cell de novo differentiation or by cross-reactivity between bacteria-specific TCRs and tumour antigens. Nevertheless, further investigation is required to establish the definitive mechanism(s) of the observed systemic and local induction of IFN+CD8 T cells.

Towards Clinical Application

The 11 strains conferred resistance to intracellular pathogenic infections such as L. monocytogenes. In particular, 11 strain colonization protected against bacterial invasion as well as systemic dissemination (FIGS. 63 and 78). The clinical benefits endowed by the 11-mix are mediated not just by intestinal luminal competition, but at least in part by CD8 T cells, as antibody-mediated depletion of CD8 T cells in GF+11-mix mice significantly diminished protection (FIGS. 63 and 78). IFN released by CD8 T cells may promote an anti-pathogenic environment in the gut by upregulating a number of IFN-induced antimicrobial genes and chemokines (FIGS. 73A and 76C), thereby conferring resistance to invading pathogens like Lm. Since the 11 strains are capable of inducing $T_H1$ and $T_H17$ cells (FIG. 69D), the enhancement of anti-microbial immunity might also be due in part to these effector CD4 T cells. Intestinal barrier dysfunction and bacterial translocation are well known to cause and perpetuate inflammation in various diseases[61-63]; as such, supplementation with the 11 strains might aid in the prevention and management of such conditions.

In addition to defending against pathogens, the 11-strain consortium was effective in inhibiting tumour growth in syngeneic cancer models in conjunction with ICIs (FIG. 64). The recent development of ICI therapies like anti-PD-1, anti-PD-L1, and antiCTLA-4 mAbs represents a significant advance in cancer treatment. However, patients' responses to ICIs are heterogeneous and not always durable[64,65], so there is an urgent need to understand and enhance their efficacy. In this context, several reports have demonstrated that the composition of the gut microbiome influences response to ICIs in humans and mice, suggesting that its manipulation could be therapeutically viable[3,66]. Favorable microbiome signatures have been associated with enhanced CD8 T cell and IFN responses[3,21,66-68]. However, the specific microbiota members associated with such responses vary substantially between studies: one implicates *Akkermansia* spp.[29], another, *Faecalibacterium* spp.[27], and yet another, *Bifidobacterium* spp.[28], as important effectors. One reason for this variability could be that several bacterial consortia may be able to induce IFN+CD8 T cells and regulate anti-tumour immunity like the 11-mix. Further investigation is required to assess the functional similarity between the 11 strains and those associated with improved clinical outcomes in cancer patients treated with ICIs. Another possible reason for the variability could be that bona fide effector species represent minor members of the microbiota, and that the previously reported species play a supporting role for the effectors (akin to the 7-mix supporting the effector 4-mix in our model). The contribution of such minor species is likely underestimated by traditional, sequence-oriented microbiome analysis. In fact, the 11 strains primarily represent rare, low-abundance components of the human microbiota. Mining the metagenomic datasets HMP1-2, LLDeep, MetaHIT, 500FG, HMP2, and JPGM, which included 3327 samples from individuals in Europe, the United States, China, and Japan, revealed that most of the 11 strains are generally rare, low-abundance components of the human microbiota. At strain-level resolution, 4 of the 11 were detected in very few individuals (16 out of the 3327 evaluated samples) (FIG. 81). Even at the species level, *Fusobacterium ulcerans* (strain 81A6), *Eubacterium limosum* (strain 81C1), *Parabacteroides gordonii* (strain 81H9), and *Alistipes senegalensis* (strain 81E7) were particularly rare across all cohorts (FIG. 82). Most of the strains were scarce even in the microbiome of Donor B, from which they were isolated (FIG. 83). Similar results were also obtained from a dataset of melanoma patients treated with ICIs[27-29], and as such the 11 strains lacked enough power to stratify individuals into responder vs. non-responder groups (FIGS. 81 and 82). The data demonstrate that preferentially enriching certain low-abundance members of the intestinal microbiota can have profound immunological effects in the context of infectious disease treatment and cancer immunotherapy. The current data could form the basis of a clinical drug development program in which the 11 strains are uniquely positioned to be used as powerful biotherapeutics, as they are safe (seeing as they were isolated from healthy microbiota, do not have prominent toxins, and are not multi-drug resistant) and potentially broadly applicable (as they are effective in both mice and marmosets, and are not detectable in most individuals' microbiota).

These findings are consistent with previous reports demonstrating the important roles of CD8 T cells, IFN, and CD103+ DCs in anti-tumour responses[20,22,50]. The precise mechanism by which the 11 strains support anti-tumour immunity requires further investigation. Given that the effect was observed in at least two different tumour models and that there was no cross-reactivity between TCRs recognizing 11 strain-derived antigens and those recognizing tumour antigens, the improved anti-tumour immunity is likely occurring in an antigen-independent fashion. As described above, one hypothesis is that bacterial products released by the 11 strains may directly and/or indirectly stimulate DCs within the tumour microenvironment or in the draining LNs to support printing of tumour-specific CD8 T cells.

Methods

Mice

SPF or GF C57BL/6, BALB/c, and IQI mice were purchased from Sankyo Laboratories Japan, SLC Japan, CLEA Japan, and Charles River Japan. GF and gnotobiotic mice were bred and maintained within the gnotobiotic facility of Keio University or RIKEN, Ifngr1$^{-/-}$, Batf3$^{-/-}$, I118$^{-/-}$, I11r1$^{-/-}$, Cd11c-Cre×Irf4$^{fl/fl}$, CD11c-Cre×Ntoch2$^{DC}$, and I110$^{-/-}$ mice were purchased from the Jackson Laboratories. Myd88$^{-/-}$Trif$^{-/-}$ mice were purchased from Oriental Bio Service. Xcrl$^{+/cre}$×R26:lacZbpA$^{flor}$DTA mice were generated as previously described[15]. Irf9$^{-/-}$ and H2-M3$^{-/-}$ mice (RBRC00916, 10034) was provided by the RIKEN BRC through the National Bio-Resource Project of the MEXT/AMED, Japan. K$^{b}$D$^{b-/-}$ mice were purchased from MMRKC. GF rederivation was performed at the gnotobiotic facilities of RIKEN and Keio University. All animal experiments were approved by the Keio University Institutional Animal Care and Use Committee, and the RIKEN Yokohama Institute. Unless otherwise noted, all SPF mice were C57BL/6 mice obtained from CLEA Japan.

Human Faecal Samples, Bacterial Culture, and the Generation of Gnotobiotic Animals Human faecal samples were collected at the RIKEN institute and Keio University according to the study protocol approved by the institutional review board. Informed consent was obtained from each subject. Faecal samples and mouse B5 caecal contents were suspended in equal volume (w/v) of PBS containing 20% glycerol/PBS, snap-frozen in liquid nitrogen, and stored at −80° C. until use. The frozen stocks were thawed, suspended in TS broth, filtered through a 100 m cell strainer, and orally inoculated into GF mice (approximately 5-60 mg/250 μL, per mouse). After 24 hours of inoculation, some mice were treated with ampicillin (1 g/L), metronidazole (1 g/L), tylosin (0.5 g/L) or streptomycin (0.5 g/L) via the drinking water. For chloroform treatment of B5 caecal contents, the caecal content suspension was mixed with chloroform (final concentration 3%) and incubated in a shaking water bath for 60 min followed by evaporation of chloroform via bubbling with $N_2$ gas for 30 min. To isolate IFN+CD5 T cell-inducing bacterial strains, caecal contents from GF+B5-Amp2 and GF+B5-Amp3 mice were serially dilated with PBS and seeded onto non-selective and selective agar plates (GAM, CM0151, and BBE). After culture under anaerobic conditions (80% $N_2$, 10% $H_2$, 10% $CO_2$) in an anaerobic chamber (Coy Laboratory Products) at 37° C. for 2 to 4 days, individual colonies were picked, and the 16S rRNA gene region was amplified with universal primers (27F: 5'-AGRGTTTGATYMTGGCTCAG-3' (SEQ ID NO:12), 1492R: 5'-GGYTACCTTGTTACGACTT-3' (SEQ ID NO:13)) and sequenced. Individual isolates in the culture collection were grouped as "strains" if their 16S rRNA gene sequences had 100% identity. The resulting strain sequences were compared to those in the RDP database and to OTUs observed in caecal samples from GF+B5−Amp2 and GF+B5−Amp3 to determine closely related species or strains and their corresponding OTUs. To prepare a bacterial mixture, bacterial strains were individually grown in GAM, CM0149, or EG both to confluence and equal volumes of media were mixed. For culture of strain 82G5, succinate was added to EG or CM0149 (final concentration 100 mM). The mixture of isolates was orally administered to GF mice (approximately 1-2×$10^8$ CFU of each strain in 250 μL medium per mouse). All mice receiving a given mixture of bacterial strains were maintained in a single gnotobiotic isolator. For administration of heat-killed bacteria, 11 strains cultured individually for 3 days were mixed, washed with autoclaved water, heat-killed at 121° C. for 30 min, and given to GF mice via the drinking water (2-10×$10^7$ equivalent CFU of each strain per 1 mL) for 4 weeks. C57BL/6 GF mice (6-12 weeks old) were used and analysed 3-4 weeks after bacterial colonization unless otherwise indicated.

16S rRNA Gene Pyrosequencing

Frozen caecal contents and faecal pellets from mice were thawed and suspended in 850 L TE10 (10 mM Tris-HCl, 10 mM EDTA) buffer containing RNase A (final concentration of 100 μg/mL, Invitrogen) and lysozyme (final 3.0 mg/mL, Sigma). The suspension was incubated for 1 h at 37° C. with gentle mixing. Purified achromopeptidase (Wako) was added to a final concentration of 2,000 unit/mL, and the sample was further incubated for 30 min at 37° C. Then, sodium dodecyl sulfate (final concentration 1%) and proteinase K (final concentration 1 mg/mL, Nacalai) were added to the suspension and the mixture was incubated for 1 h at 55° C. High-molecular mass DNA was extracted with phenol:chloroform:isoamyl alcohol (25:24:1), precipitated with isopropanol, washed with 70% ethanol, and resuspended in 200 L of TE PCR was performed using 27Fmod 5'-AGRGTTTGATYMTGGCTCAG-3' (SEQ ID NO:14) and 338R 5'-TGCTGCCTCCCGTAGGAGT-3' (SEQ ID NO:15) to the V1-V2 region of the 16S rRNA gene. Amplicons generated from each sample (~330 bp) were subsequently purified using AMPure XP (Beckman Coulter). DNA was quantified using a Quant-iT Picogreen dsDNA assay kit (Invitrogen) and a TBS-380 Mini-Fluorometer (Turner Biosystems). The 16S metagenomic sequencing was performed according to the Illumina protocol. Two paired-end reads were merged using the fastq-join program based on overlapping sequences. Reads with an average quality value of <25 and inexact matches to both universal primer were filtered off. Filter-passed reads were used for further analysis after trimming off both primer sequences. For each sample, 3000 quality filter-passed reads were rearranged in descending order according to the quality value and then clustered into operational taxonomic units (OTUs) with a 97% pairwise-identity cutoff using the UCLUST program (Edgar 2010) version 5.2.32 (www.drive5.com/). Taxonomic assignments of each OTU were made by similarity searching against the Ribosomal Database Project (RDP) and the National Center for Biotechnology Information genome database using the GLSEARCH program.

Bacterial Genome Sequencing

The genomic DNA of the 11 strains was extracted by a method similar to that described above as a part of the 16S rRNA gene pyrosequencing. The genome sequences were determined by using a whole-genome shotgun strategy with the Illumina MiSeq sequencer. The genomic DNA was sheared by sonication to obtain DNA fragments. Template DNA was prepared according to each supplier's protocol. Sequences concatenated with genes encoding 40 ribosomal proteins/large subunits L1, L2, L3, L4, L5, L6, L7/L12, L9, L10, L11, L13, L14, L15, L16, L17, L18, L19, L20, L21, L22, L23, L24, L27, L28, L29, L32 and L35, and small subunits S5, S6, S7, S8, S9, S10, S11, S12, S13, S15, S16, S19 and S20) predicted from the genomes of each strain were used to construct a phylogenetic tree. The sequences of other bacterial species used for the tree construction were obtained from the ribosomal multi-locus sequencing typing (MLST) database. The calculation was performed using the MESA v5.0 package and the neighbor-joining method with a bootstrap of 1,000 replicates.

Isolation and Flow Cytometric Analysis of Intestinal Lymphocytes, DCs, and ECs

For analysis of intestinal lymphocytes, DCs, and ECs, intestines were opened longitudinally and washed with PBS to remove luminal contents. All samples were incubated in 20 mL of Hanks' balanced salt solution (HBSS) containing 5 mM EDTA for 20 min at 37° C. in a shaking water bath to remove ECs. After vigorous vortexing, colonic ECs released into suspension were centrifuged, immediately frozen in liquid nitrogen, and stored at −80° C. until further analysis. An aliquot of ECs was subjected to PERCOLLR gradient separation to isolate colonic intraepithelial lymphocytes (cIELs). After removal of the ECs, the muscle layer and adipose tissue were removed manually using forceps. The remaining LP layer was cut into small pieces and incubated in 10 mL of RPMI1640 containing 4% fetal bovine serum, 0.5 mg/mL collagenase D (Roche), 0.5 mg/mL dispase (Gibco), and 40 μg/mL DNase I (Roche) for 45 min at 37° C. in a shaking water bath. The digested tissues were washed with 10 mL of HBSS containing 5 mM EDTA, resuspended in 5 mL of 40% PERCOLLRIGE Healthcare), and underlaid with 2.5 mL of 80% Percoll in a 15 mL Falcon tube. PERCOLLR gradient separation was performed by centrifugation at 900 g for 30 min at 25° C. The fraction containing lymphocytes and antigen presenting cells was collected from the interface of the two layers and washed with RPMI1640 containing 10% FBS. For DC staining, the cells were labeled with Ghost Dye 780 (Tonbo Biosciences) and then stained with anti-I-A/I-E (FITC, Biolegend), CD11c (APC, Biolegend), CD103 (PE/Cγ7, Biolegend), CD11b (BV605, Biolegend) and H-2Kb (PacificBlue, Biolegend). For cytokine detection, the cells were stimulated with 50 ng/mL PMA and 750 ng/mL ionomycin (both firm Sigma) in the presence of GOLGISTOPR (BD Biosciences) at 37° C. for 3.5 h. After labeling with Ghost Dye 780, the cells were permeabilized and stained with anti-CD3 (BV605 or BV650; Biolegend), CD4 (BV510 or FITC; Biolegend), CD8γ (APC, BV421 or PE/Cy7; Biolegend), TCRβ (PerCP-Cy5.5 or BV711; Biolegend), CD8γ (PerCP-Cy5.5), CD103 (BV421 or FITC), GranzymeB (APC or PacificBlue; Biolegend), ICOS (PE/Dazzle594, PE or FITC; Biolegend), CD44 (PE or BV786; Biolegend), KLRG1 (BV711 or PE/Dazzle594; Biolegend), PD-1 (BV510; Biolegend), IFNγ (PE/Cy7 or FITC; Biolegend), IL-17A (PE: BD Bioscience), T-bet (PE/Cy7, BV421 or BY785; Biolegend) and Ki67 (AF488; Biolegend) using the Foxp3/Transcription Factor Staining Buffer Kit (eBiosciences) as per the manufacture's instructions. For analysis of TCRVβ repertoire of CD8 T cells, lymphocytes were stained using the Anti-Mouse TCRVβ Screening Panel (BD Bioscience). All data were collected on a BD LSR-Fortessa or FACSAria IIIu (BD Biosciences) instrument and analysed with Flowjo software (TreeStar). CD8 T cells were defined as the CD8γ-TCRβ-CD3+ population within the live cell gate. For assessment of the IFNγ responses against bacterial lysate, the 11 strains were cultured individually for 3 days, washed with PBS, heat-killed at 70° C. for 30 min, and used at a final concentration of 1-2×106 CFU/mL of each strain. PERCOLLR-enriched colonic LP cells, which include T cells and antigen-presenting cells, isolated from GF+11-mix mice were stimulated ex vivo with bacterial lysate for 18 h, then GOLGISTOPR was added and the suspension was incubated for an additional 3.5 h.

Colonization of SPF Mice with the 11-Mix

SPF C57BL/6 mice (6-7-weeks old) from SLC Japan (which display a relatively low-frequency IFNγ+CD8 T cell phenotype, see FIG. 65F) were treated or not with AVMN [ampicillin (1 g/L), vancomycin (500 mg/L), metronidazole (1 g/L) and neomycin (1 g/L)] for 5-9 days via the drinking water. After a one-day washout of antibiotics, a faecal suspension from untreated SPF mice (SLC Japan, approximately 1 mg per mouse) was orally introduced along with or without the initial 11-mix by gavage. For repetitive administration, oral gavage of the 11-mix was performed 2 or 3 times per week. For each inoculation, the 11 strains were grown for 2 or 3 days in GAM, CM0149, EG broth and approximately 1-2×$10^8$ CFU of each strain were used to inoculate each mouse. Faeces or caecal contents were collected and DNA was extracted as a part of the aforementioned 16S rRNA gene pyrosequencing. Confirmation of colonization was achieved by qPCR with the following specific primers for each strain:

```
81A6
(5'-TGCACTGTTGGATTTTCTAAAAAGG-3' (SEQ ID NO: 16),
5'-ACTTTGGGCATGCTAAACCA-3' (SEQ ID NO: 17));

81B11
(5'-GCATATATCTTGACTGAGCCGA-3' (SEQ ID NO: 18),
5'-TTCCCCCGATGAATAAAGCGT-3' (SEQ ID NO: 19));

81C1
(5'-CCGCACAAGAGAAATAAACGCCA-3', (SEQ ID NO: 20)
5'-TGGCAAATTCAAAGGTGAGCGAA-3' (SEQ ID NO: 21)),

81E7
(5'-GGGAATAAAGCTGTTCCGATATGC-3' (SEQ ID NO: 22),
5'-TCATGCAACATTCTTTCGTTGG-3' (SEQ ID NO: 23)),

81H9
(5'-TTCACCTTCTACGGCTACTACTACG-3' (SEQ ID NO: 24),
5'-ACATAACGATCAAGGGTGCTGAAG-3' (SEQ ID NO: 25)),

82A6
(5'-GCTCTTTTTAGCCTGTATCCGGT-3' (SEQ ID NO: 26),
5'-ATACGATACGAACGACCAACCT-3' (SEQ ID NO: 38)),

82B1
(5'-CTTCGTTGTTCTTGAACTTCTCGCC-3' (SEQ ID NO: 39),
5'-CAGACATTTCCGAAAACCTCCAG-3' (SEQ ID NO: 40)),

82F11
(5'-GCACAGATTCTACACTCCCCT-3' (SEQ ID NO: 41),
5'-AGCAACGAAACAACCTGTGA-3' (SEQ ID NO: 42)),
```

-continued

```
82G1
(5'-GAGGAAGTGAACCTTGGGTGTG-3' (SEQ ID NO: 43),
5'-AAAAAGTGGACATGATAAAGCGGAT-3' (SEQ ID NO: 44)),

82G5
(5'-AGGATCCCTTCGCTGTAGTAAAAGA-3' (SEQ ID NO: 45),
5'-ACAATCCGGTCTGATGATCAATG-3' (SEQ ID NO: 46)),

82G9
(5'-GCCCGCCTCAACTTAGAATCAC-3' (SEQ ID NO: 47),
5'-TCTATGTGTTTCCGGTTTGTTACG-3' (SEQ ID NO: 48)).
```

For detection of bacteria in the MLNs, the organs were homogenized and total DNA was isolated according to the faecal DNA isolation protocol, followed by qPCR using the specific primers described above. We confirmed the detection of bacterial DNA with this method by analyzing MLNs from mice infected with the invasive Listeria monocytogenes strain (Lm-In1A$^{m}$).

qPCR Analysis

Total RNA was isolated from colonic ECs and DCs using TRIzol reagent (Invitrogen) as per the manufacturer's instructions. For real-time qPCR analysis, cDNA was synthesized using SuperScript VILO Master Mix (Thermo Fisher), and qPCR was performed using the Thunderbird SYBR qPCR Mix (TOYOBO) on a LightCycler 480 (Roche). The following primer pairs were used:

```
Actb,
                              (SEQ ID NO: 49)
5'-TTGCTGACAGGATGCAGAAG-3'
and
                              (SEQ ID NO: 50)
5'-ATCCACATCTGCTGGAAGGTG-3';

Gbp1,
                              (SEQ ID NO: 51)
5'-ATGGGCCACGTCTAAAAAGC-3'
and
                              (SEQ ID NO: 52)
5'-TTTGCACTGCTGCTGAGTTC-3';

Gbp6,
                              (SEQ ID NO: 54)
5'-AATGCCTTGAAGCTGATCCC-3'
and
                              (SEQ ID NO: 55)
5'-GTTCTTTGTCATGCGTTGGC-3';

Ifi44,
                              (SEQ ID NO: 56)
5'-AGACAAGAGGCATTGCTGTG-3'
and
                              (SEQ ID NO: 57)
5'-AGCAGAACTCGTGTTTGCTG-3';

Ifi204,
                              (SEQ ID NO: 58)
5'-AAGCAAGGGGGACATTTGTG-3'
and
                              (SEQ ID NO: 59)
5'-TGGTTCACACCTGACATTGG-3';

Cxcl9,
                              (SEQ ID NO: 60)
5'-CGAGGCACGATCCACTACAA-3'
and
                              (SEQ ID NO: 61)
5'-CCGGATCTAGGCAGGTTTGA-3';
```

-continued

```
Cxcl10,
                              (SEQ ID NO: 62)
5'-TCCTGCCCACGTGTTGAGAT-3'
and
                              (SEQ ID NO: 63)
5'-TGCGTGGCTTCACTCCAGTT-3';

Irgm1,
                              (SEQ ID NO: 64)
5'-TTCCAGGAAGGCCACTAACATC-3'
and
                              (SEQ ID NO: 65)
5'-AGCCTGTTTGGTATGACGTG-3';

Il6,
                              (SEQ ID NO: 66)
5'-CTGCAAGAGACTTCCATCCAGTT-3'
and
                              (SEQ ID NO: 67)
5'-AAGTAGGGAAGGCCGTGGTT-3';

Lcn2,
                              (SEQ ID NO: 68)
5'-AATGTCACCTCCATCCTGGTC-3'
and
                              (SEQ ID NO: 69)
5'-GTGGCCACTTGCACATTGTA-3'.
```

Listeria Monocytogenes (Lm) Infection

SPF C57BL/6 mice (6-7 weeks old) from SLC Japan were treated with AVNM through the drinking water, then reconstituted with SPFfae at day-13. For the 11-mix treatment group, an initial oral administration of the 11-mix was done in conjunction with SPFfae, followed by repetitive oral gavage of the 11-mix alone at day-13, -12, -8, and -3. For the oral infection group, mice were orally gavaged with approximately $5\times10^{9}$ CFU of Lm-WT (strain EGD) or Lm-OVA, or $1\times10^{11}$ CFU of Lm-InlA[33] on day 0. For quantitation of bacterial titers, colons, MLNs, spleens, liver, or faeces were homogenized in PBS, plated on CHROMagar Listeria (CHROMagar) for 2 days at 37° C., and colonies with white halos were counted at the indicated times after infection. For systemic infection, Lm strain EGD ($1\times10^{6}$ CFU) was injected intraperitoneally at day 0. To quantify the bacterial titers, livers or spleens were homogenized in PBS and plated on LB agar kw 2 days at 37° C. For the Lm-OVA (Nanjing Sungyee Biotech)-specific IFN response of CD8 T cells, colonic LP cells containing lymphocytes and antigen presenting cells were isolated and OVA-specific IFN-CD8 T cells were detected by stimulation with 5 g/mL OVA-derived peptide SIINFEKL (MBL) in the presence of GOLGISTOP (BD Biosciences) at 37° C. for 5 h. For GF mice-based studies, C57BL/6 GF mice were colonized with 11- or 10-mix, or left untreated, on day -7. Then, the mice were orally infected with $1\times10^{6}$ CFU of Lm-WT (strain EGD). For depletion of CD8 T cells, 200 μg of CD8γ mAb (Clone 2.43, BioXCell) was administered intraperitoneally 1 day before administration of 11-mix, and every 3 to 4 days thereafter.

Subcutaneous Tumour Model

The MC38 adenocarcinoma cell line was a gift from the Surgery Branch, National Cancer Institute, National Institutes of Health (Bethesda, Md., USA). BRAF$^{v600E}$PTEN$^{-/-}$ melanoma cells were isolated and cultured at Keio University from a tumour induced in BRaf$^{CA}$ Pten$^{ioxP}$ Tyr::CreER$^{T2}$ mice (ref. 27, purchased from Jackson laboratory) by the treatment with 4-OH-tamoxifen on the mice's clean-shaven back skin. SPF C57BL/6 mice (6-7 weeks old, from SLC Japan) were treated with AVNM trough the drinking water (from day ~7 to day 2), and $3\times10^5$ MC38 adenocarcinoma cells or $7\times10^5$ $BRAP^{v600E}PTEN^{-/-}$ melanoma cells were subcutaneously implanted on day 0. The mice were reconstituted with a faecal SPF microbiota on day 3. For the 11-mix treatment groups, the initial dosing of 11-mix was done together with the SPF microbiota on day 3, followed by repetitive dosing 2 or 3 times per week until the end of the experiment. Mice were injected intraperitoneally with 200 g anti-PD1 mAb (Clone J43, BioXCell) or anti-CTLA4 mAb (Clone 9H10, BioXCell) every 3 days staring from day 3 to 9. Tumour size was measured 2 or 3 times per week and the volume was determined as length$\times$width$^2\times$0.5. Mice were sacrificed either at indicated time points or when their tumours reached an endpoint volume of 2000 $mm^3$ and the tumour weight was determined. For GF mouse-based studies, C57BL/6 GF mice were colonized with 11- or 10-mix, or left untreated, and were subjected to subcutaneous implantation of $3\times10^5$ MC38 adenocarcinoma cells on day 0. Anti-PD-1 mAb injection and tumour measurement were performed as described above in the SPF mouse-based study section. For depletion of CD8 T cells, 200 μg of CD8γ mAb (Clone 2.43, BioXCell) was administered intraperitoneally 1 day before administration of 11-mix, and every 3 to 4 days thereafter. For isolation of TILs and myeloid cells, tumours were cut into small pieces and incubated in 10 mL of RPMI1640 containing 4% fetal bovine serum, 0.5 mg/mL collagenase D (Roche), 0.5 mg/mL dispase (Gibco), and 40 μg/mL DNase I (Roche) for 45 min at 37° C. in a shaking water bath. The digested tumour cells were resuspended with 10 mL of HBSS containing 5 mM EDTA and passed through a 100 m cell strainer. Cell suspensions corresponding to 0.5 g of the total tumour weight were used for 40-80% Percoll gradient separation described above. Lymphocytes and myeloid cells were collected from the interface of the Percoll gradient and washed with RPMI1640 containing 10% FBS and stimulated with 50 ng/mL PMA and 750 ng/mL ionomycin (both from Sigma) in the presence of Golgistop (BD Biosciences) at 37° C. for 4.5 h. For the p15E peptide-specific IFN response of CD8 T cells, the cells were stimulated with 5 g/mL p.5E peptide KSPWFTTL (SEQ ID NO:69) (MBL) or bacterial lysate (1-$2\times10^6$ CFU/mL of each strain, prepared as described above) for 18 h, the GOLGISTOPR was added and the suspension was incubated for an additional 3.5 h in the presence Golgistop (BD Biosciences) at 37° C. for 5 h. Staining and FACS analysis were performed as described above.

Histological Analysis

For fluorescence in situ hybridization staining (FISH), colon tissue was fixed with methanol-Carnoy's solution and embedded in paraffin[32]. The sections were treated with 0.1 M HCl and hybridized with the 5' Alexa 488-labeled EUB338 (5'-GCTGCCTCCCGTAGGAGT-3' (SEQ ID NO:29)) probe in hybridization buffer [0.9 M NaCl, 0.02 M Tris-HCl (pH 7.6), 0.01% sodium dodecyl sulfate] at 50° C. overnight. Then slides were incubated with FISH washing buffer [0.45 M NaCl, 0.02 M Tris-HCl (pH 7.6), 0.01% sodium dodecyl sulfide] preheated to 50° C. for 10 min and washed three times in PBS. For mucus visualization, sections were incubated with blocking buffer (1% BSA, 2% FBS, 0.05% Tween20 in PBS) at room temperature for 60 min and stained with a rabbit anti-Muc2 antibody (1:1000, Santa Cruz Biotechnology) for 120 min, followed by Alexa 546-labeled goat anti-rabbit IgG (1:500, Life Technologies) in blocking buffer for 60 min. All sections were counterstained with 4,6-diamidino-2-phenylindole (DAPI, Dojind, 1:5000), mounted with Fluoromount/Plus (Diagnostics BioSystems) and visualized using a TCS SP5 confocal microscope.

To evaluate the development and severity of colitis, colons were fixed with 4% paraformaldehyde, embedded in paraffin, sectioned, and stained with hematoxylin and eosin. The degree of colitis was graded according to the following criteria: inflammatory cell infiltration (score, 0-4), mucosa thickening (score, 0-4), goblet cell depletion (score, 0-4), crypt abscess (score, 0-4) and destruction of architecture (score, 0-4). The final histological score was defined as the sum of the scores of these parameters.

Metagenome Sequencing of Faecal Microbiota from Healthy Volunteers (A-F)

Faecal DNA from donors A-F was isolated as described above. Whole-genome shotgun libraries were prepared using the TruSeq DNA PCR-Free Sample Preparation kit (Illumina). 300 bp at each end of the libraries was sequenced on a MiSeq instrument with the MiSeq Reagent kit v3 (600 cycles, Illumina).

Abundance Profiling Across Metagenomic Datasets

Draft genomes of the 11 strains were split into 1 kilobase pair (kbp) regions and mapped against NCBI RefSeq (~85 k genomes) to identify regions with no or weak similarity to known isolates (Identity <80%, Coverage <85%). Of these, consecutive regions of at minimum 5 kbp were defined as marker regions unique to each strain. Gut metagenome samples with at least 1M quality-controlled reads across various datasets [HMP1-2[33], LLDeep[34], MetalHIT[35,36], 500FG[37], HMP2 (first time point only)[38], and JPGM[39]] were mapped to the 1 kbp regions in all strains (filtered by 95% mapping identity). The mapped read counts were normalized to reads per kbp per million (RPKM). A strain was deemed detected if at least 95% of the 1 kbp regions within the marker region were detected, and the abundance was calculated as median abundance across all marker regions in the genome. Species level abundance was calculated as median abundance across all 1 kbp regions in the genome.

Sample Preparation for Metabolome Analysis

Metabolite extraction from serum and caecal contents for metabolome analyses was performed as described previously[33]. Briefly, frozen caecal contents together with internal standard (IS) compounds (see below) were homogenized in ice-cold methanol (500 μL) using a manual homogenizer (Finger Masher (AM79330), Sarstedt) followed by the addition of an equal volume of chloroform and 0.4 times the volume of ultrapure water (LC/MS grade, Wako). 40 μL of serum spiked with the ISs were added with ice-cold methanol (400 μL) followed by the addition of an equal volume of chloroform and 120 μL of ultrapure water. These suspensions were then centrifuged at 15,000 g for 15 min at 4° C. After centrifugation, the aqueous phase was ultrafiltered using an ultrafiltration tube (Ultrafree MC-PLHCC, Human Metabolome Technologies). The filtrate was concentrated with a vacuum concentrator (SpeedVac, Thermo). The concentrated filtrate was dissolved in ultrapure water and used for LC-MS/MS and IC-MS analyses.

Qualification and Quantification of Metabolites by Internal and External Standards We used both IS (added to the samples before extraction) and external standard (ES) compounds to determine the m/z value and the specific retention time for all metabolites examined. The detailed methods are as follows. Internal standard (IS) compounds: we used 2-morpholinoethanesulfonic acid (MES) and L-methionine sulfone as ISs for anionic and cationic metabolites, respectively. These compounds are not present in the samples analyzed; thus, they serve as ideal standards. Loss of endogenous metabolites during sample preparation was corrected by calculating the recovery rate (%) for each sample measurement. ES compounds: before sample analysis, we measured the mixture of authentic compounds of target metabolites in ultrapure water to determine both the m/z value and the retention time of all metabolites examined.

Ion Chromatography-Tandem Mass Spectrometry for Anionic Metabolites

Anionic metabolites were measured using an orbitrap-type MS (Q-Exactive focus, Thermo Fisher Scientific, San Jose, Calif.), connected to a high performance ion-chromatography system (ICS-5000+, Thermo Fisher Scientific) that enables us to perform highly selective and sensitive metabolite quantification owing to the IC-separation and Fourier Transfer MS principle[34].

The IC was equipped with an anion electrolytic suppressor (Thermo Scientific Dionex AERS 500) to convert the potassium hydroxide gradient into pure water before the sample enters the mass spectrometer. The separation was performed using a Thermo Scientific Dionex IonPar AS11-HC, 4-μm particle size column. IC flow rate was 0.25 mL/min supplemented post-column with 0.18 mL/min makeup flow of MeOH. The potassium hydroxide gradient conditions for IC separation are as follows: from 1 mM to 100 mM (0-40 min), 100 mM (40-50 min), and 1 mM (50.1-60 min), at a column temperature of 30° C. The Q Exactive focus mass spectrometer was operated under an ESI negative mode for all detections. Full mass scan (m/z 70-900) was used at a resolution of 70,000. The automatic gain control (AGC) target was set at $3\times10^6$ ions, and maximarn ion injection time (IT) was 100 ms. Source ionization parameters were optimized with the spray voltage at 3 kV and other parameters were as follows: transfer temperature was 320° C., S-Lens level was 50, heater temperature was 300° C., Sheath gas was 36, and Aux gas was 10.

Liquid Chromatography-Tandem Mass Spectrometry for Amino Acid Measurement

The amounts of various cationic metabolites were quantified using liquid chromatography-tandem mass spectrometry (LC-MS/MS)[35]. Briefly, a triple-quadrupole mass spectrometer equipped with an electrospray ionization (ESI) ion source (LCMS-8060, Shimadzu Corporation) was used in the positive and negative-ESI and multiple reaction monitoring (MRM) modes. The samples were resolved on the Discovery HS F5-3 column (2.1 mmI.D.×150 mmL, 3 μm particle, Sigma-Aldrich), using a step gradient with mobile phase A (0.1% formate) and mobile phase B (0.1% acetonitrile) at ratios of 100:0 (0-5 min), 75:25 (5-11 min), 65:35 (11-15 min), 5:95 (15-20 min) and 100:0 (20-25 min), at a flow rate of 0.25 mL/min and a column temperature of 40° C.

Colonization of Common Marmoset Monkeys with the 11-Mix

Marmoset experiments were approved by the Institutional Animal Care and Use Committee of the Central Institute for Experimental Animals (CIEA) and were performed at CIEA. Six male common marmosets (8 months old) were purchased from CLEA Japan and intragastrically gavaged with a single dose of 2 mL of vancomycin (25 mg/mL). Each of the 11 strains was cultured in 10 mL media for 2 or 3 days, as described above. Then, all confluent cultures were collected, centrifuged at 6000 g for 5 min, and resuspended in 10 mL of PBS. Three marmosets were intragastrically gavaged with 2 mL of the mixture of 11 strains 24 hours after vancomycin treatment. The 11-mix was repeatedly inoculated on day 3 and 7, and colonization was confirmed by qPCR of faecal DNA. Three weeks after the first 11-mix inoculation, marmosets were sacrificed, and large and small intestines were collected to quantify IFNγ+CD8 T cells. Isolation of lymphocytes and flow cytometric analysis were performed as in the mouse experiments, using anti-CD3 BV605 (BV605, clone SP34-2), CD8 (PE, clone 6F10) and IFNγ (FITC, clone B27) (Biolegend).

Statistical Analysis

All statistical analyses were performed using GraphPad PrismR software (GraphPad Software, Inc.) with two-tailed unpaired Student's t-test (parametric) or Mann-Whitney test (nonparametric), one-way analysis of variance (ANOVA) followed by Tukey's post hoc test (3 or more groups, parametric), and two-way ANOVA with Tukey's test (time course experiments with 3 or more groups).

REFERENCES

1. Mimee, M., Citorik, R. J. & Lu, T. K. Microbiome therapeutics—Advances and challenges. Advanced drug delivery reviews 105, 44-54, doi:10.1016/j.addr.2016.04.032 (2016).
2. Kim, S., Covington, A. & Pamer, E. G. The intestinal microbiota: Antibiotics, colonization resistance, and enteric pathogens. Immunological reviews 279, 90-105, doi:10.1111/imr.12563 (2017).
3. Bliati, A. P., Redinbo, M. R. &l Bultman, S. J. The role of the microbiome in cancer development and therapy. CA: a cancer journal for clinicians 67, 326-344, doi:10.3322/caac.21398 (2017).
4. Honda, K. & Littman, D. R. The microbiota in adaptive immune homeostasis and disease. Nature 535, 75-84, doi:10.1038/nature18848 (2016).
5. El Hage, R., Hernandez-Sanabria, E. & Van de Wiele, T. Emerging Trends in "Smart Probiotics": Functional Consideration for the Development of Novel Health and industrial Applications. Frontiers in microbiology 8, 1889, doi:10.3389/fmicb.2017.01889 (2017).
6. O'Toole, P. W., Marchesi, J. R. & Hill, C. Next-generation probiotics: the spectrum from probiotics to live biotherapeutics. Nat Microbial 2, 17057, doi:10.1038/nmicrobiol.2017.57 (2017).
7. Blander, J. M., Longman, R. S., Iliev, I. D., Sonnenberg, G. F. & Artis, D. Regulation of inflammation by microbiota interactions with the host. Nat Immunol 18, 851-860, doi:10.1038/ni.3780 (2017).
8. Atarashi, K. et al. Treg induction by a rationally selected mixture of Clostridia strains from the human microbiota. Nature. 500, 232-236, doi:10.1038/nature12331 (2013).
9. Atarashi, K. et al. Th17 Cell Induction by Adhesion of Microbes to Intestinal Epithelial Cells. Cell 163, 367-380, doi:10.1016/j.cell.2015.08.058 (2015).
10. Mackay, L. K. et al. The developmental pathway for CD103(+)CD8+ tissue-resident memory T cells of skin. Nat Immunol 14, 1294-1301, doi:10.1038/ni.2744 (2013).
11. Iijima, N. & Iwasaki, A. Tissue instruction for migration and retention of TRM cells. Trends in immunology 36, 556-564, doi:10.1.016/j.it.2015.07.002 (2015).
12. Park, C. O. & Kupper, T. S. The emerging role of resident memory T cells in protective immunity and inflammatory disease. Nat Med 21, 688-697, doi:10.1038/nm.3883 (2015).
13. Atarashi, K. et al. Ectopic colonization of oral bacteria in the intestine drives TH1 cell induction and inflammation. Science 358, 359-365, doi:10.1126/science.aan4526 (2017).

14. Hildner, K. et al. Batf3 deficiency reveals a critical role for CD8alpha+ dendritic cells in cytotoxic T cell immunity. Science 322, 1097-1100, doi:10.1126/science.1164206 (2008).
5. Ohta, T. et al. Crucial roles of XCR1-expressing dendritic cells and the XCR1-XCL1 chemokine axis in intestinal immune homeostasis. Scientific reports 6, 23505, doi: 10.1038/srep23505 (2016).
16. Joeris, T., Muller-Luda, K., Agace, W. W. & Mowat, A. M. Diversity and functions of intestinal mononuclear phagocytes. Mucosal Immunol 10, 845-864, doi:10.1038/mi.2017.22 (2017).
17. Satpadhy, A. T. et al. Notch2-dependent classical dendritic cells orchestrate intestinal immunity to attaching-and-effacing bacterial pathogens, Nat Immunol 14, 937-948, doi:10.1038/ni.2679 (2013).
18. Sheridan, B. S. et al. Oral infection drives a distinct population of intestinal resident memory CD8(+) T cells with enhanced protective function. Immunity 40, 747-757, doi:10.1016/j.immuni.2014.03:007 (2014).
19. Foulds, K. E. et al. Cutting edge: CD4 and CD8 T cells are intrinsically different in their proliferative responses. J Immunol 168, 1528-1532 (2002).
20. Gao, J. et al. Loss of IFN-gamma Pathway Genes in Tumor Cells as a Mechanism of Resistance to Anti-CTLA-4 Therapy. Cell 167, 397-404 e399, doi:10.1016/j.cell.2016.08.069 (2016).
21. Spranger, S., Sivan, A., Corrales, L. & Gajewski, T. F. Tumor and Host Factors Controlling Antitumor Immunity and Efficacy of Cancer Immunotherapy. Adv Immunol 130, 75-93, doi:10.1016/bs.ai.2015.12.003 (2016).
22. Wei, S. C. et al. Distinct Cellular Mechanisms Underlie Anti-CTLA-4 and Anti-PD-1 Checkpoint Blockade. Cell 170, 1120-1133 e1117, doi:10.1016/j.cell.2017.07.024 (2017).
23. Juneja, V. R. et at. PD-L1 on tumor cells is sufficient for immune evasion in immunogenic tumors and inhibits CD8 T cell cytotoxicity. J Exp Med 214, 895-904, doi: 10.1084/jem.20160801 (2017).
24. Yang, J. C. & Perry-Lalley, D. The envelope protein of an endogenous murine retrovirus is a tumor-associated T-cell antigen for multiple marine tumors. J Immunother 23, 177-183 (2000).
25. Dubin, K. et al. Intestinal microbiome analyses identify melanoma patients at risk for checkpoint-blockade-induced colitis. Nat Commun 7, 10391, doi:10.1038/ncomms10391 (2016).
26. Cooper, Z. A. et al. Response to BRAF inhibition in melanoma is enhanced when combined with immune checkpoint blockade. Cancer Immunol Res 2, 643-654, doi:10:1158/2326-6066.CIR-13-0215 (2014).
27. Dankort, D. et al. Braf(V600E) cooperates with Pten loss to induce metastatic melanoma. Nat Genet 41, 544-552, doi:10.1038/ng.356 (2009).
28. Gopalakrishnan, V. et al. Gut microbiome modulates response to anti-PD-1 immunotherapy in melanoma patients. Science 359, 97-103, doi:10.1126/science.aan4236 (2018).
29. Matson, V. et al. The commensal microbiome is associated with anti-PD-1 efficacy in metastatic melanoma patients. Science 359, 104-108, doi:10.1126/science.aao3290 (2018).
30. Routy, B. et al. Gut microbiome influences efficacy of PD-1-based immunotherapy against epithelial tumors. Science 359, 91-97, doi:10.1126/science/aan3706 (2018).
31. Debelius, J. et al. Tiny microbes, enormous impacts: what matters in gut microbiome studies? Genome biology 17, 217, doi:10.1186/s13059-016-1086-x (2016).
32. Johansson, M. E. et al. The inner of the two Muc2 mucin-dependent mucus layers in colon is devoid of bacteria. Proceedings of the National Academy of Sciences of the United States of America 105, 15064-15069, doi:10.1073/pnas.0803124105 (2008).
33. Lloyd-Price, J. et al. Strains, functions and dynamics in the expanded Human Microbiome Project. Nature 550, 61-66, doi:10.1038/nature23389 (2017).
34. Zhernakova, A. et al. Population-based metagenomics analysis reveals markers for gut microbiome composition and diversity. Science 352, 565-569, doi:10.1126/science.aad3369 (2016).
35. Qin, J. et al. A human gut microbial gene catalogue established by metagenomic sequencing. Nature 464, 59-65, doi:10.1038/nature08821 (2010).
36. Li, J. et al. An integrated catalog of reference genes in the human gut microbiome. Nat Biotechnol 32, 834-841, doi:10.1038/nbt.2942 (2014).
37. Schirmer, M. et al. Linking the Human Gut Microbiome to Inflammatory Cytokine Production Capacity. Cell 167, 1897, doi:10.1016/j.cell.2016.11.046 (2016).
38. Integrative, H. M. P. R. N. C. The Integrative Human Microbiome Project: dynamic analysis of microbiome-host omics profiles during periods of human health and disease. Cell host & microbe 16, 276-289, doi:10.1016/j.chom.2014.08.014 (2014).
39. Nishijima. S. et al. The gut microbiome of healthy Japanese and its microbial and functional uniqueness. DNA research: an international journal for rapid publication of reports on genes and genomes 23, 125-133, doi:10.1093/dnares/dsw002 (2016).

Example 12

Clinical data suggests the gut microbiome influences response to checkpoint inhibitor therapy however the precise identity and mode of action of commensals associated with clinical response has not been elucidated. We report the generation of a consortium of human gut derived commensals capable of inducing CD8 T cells and augmenting anti-cancer immunity.

The microbiota of healthy humans was used to inoculate germ-free mice and assess the level of CD8 T cell induction. Human derived commensals were isolated from inoculated mice exhibiting high levels of CD8 T cell induction and sequenced. Consortia consisting of isolated human commensals were tested for the ability to induce. CD8 T cells in germ-free and SPF mice. A minimal consortium capable of inducing CD8 T cells was administered with checkpoint inhibitor antibodies to tumor-bearing mice to assess anti-cancer activity and the level of accumulation of tumor infiltrating lymphocytes.

Interferon-gamma producing CD8 T cells are abundant in the intestines of SPF bat not germ-free mice. A consortium of human-derived commensals dubbed VE800 (also referred to herein as "11-mix") which robustly induces CD8 T cells in germ-free mice was identified. VE800 administration promotes activation of intestinal dendritic cells and stimulation of interferon-gamma producing CD8 T cells is dependent on the transcription factor BATF3. Comparative gene pathway analysis revealed several of the VE800 strains are related to strains associated with favorable clinical response in metastatic melanoma patients treated with immunotherapy. Administration of the VE800 cocktail with anti- CTLA4 antibodies enhanced anti-tumor activity and survival in the MC38 tumor model. VE800 also enhanced the anti-tumor activity of anti-PD1 in the MC38 and B-raf Pten melanoma tumor models. VE800 treatment alone is sufficient to enhance the level of tumor infiltrating CD8 T cells in the MC38 model to a level comparable to anti-PD1 antibodies alone however the combination of VE800 and anti-PD1 antibodies promoted the highest level of tumor infiltrating CD8 T cells in the MC38 model as well as in the more aggressive B-raf Pten model. VE800 administration promoted enhanced accumulation of interferon-gamma producing CD8 T cells in the spleens of tumor-bearing mice indicating the consortium promotes systemic cellular immune cell activation.

A rationally-designed consortium of human gut-derived commensals induces CD8 T cells in vivo and potentiates anti-cancer immunity when administered with checkpoint inhibitors. Given the consortium can be produced via cGMP manufacturing and administered orally on a repeated basis. VE800 constitutes a safe agent for alteration of the microbiome of cancer patients to enhance anti-cancer immunity.

The invention claimed is:

1. A composition comprising:

(i) a purified bacterial mixture comprising two or more bacterial strains of species selected from *Fusobacterium ulcerans* and *Eubacterium limosum*, or *Bacteroides dorei* and *Bacteroides uniformis*, wherein the bacterial strains are lyophilized; and (ii) one or more metabolites selected from the group consisting of mevalonate, dimethylglycine, hypoxanthine, IMP (inosine monophosphate), 2-deoxy-glucose 6-phosphate, TMP (trimethylpentane), 6PG (6-phosphogluconic acid), Rib5P (ribose 5-phosphate), Ru5P (ribulose 5-phosphate), Xu5p (xylulose 5-phosphate), GDP (guanosine 5'-diphosphate), GlcNAc 6P (N-acetylglucosamine-6-phosphate), UMP (uridine monophosphate), GMP (guanosine monophosphate), and CDP (cytidine diphosphate).

2. The composition of claim 1, wherein (i) the purified bacterial mixture comprises *Fusobacterium ulcerans* and *Eubacterium limosum* and further comprises one or more bacterial strains of species selected from the group consisting of *Parabacteroides gordonii, Paraprevotella xylaniphila, Alistipes* sp., *Parabacteroides johnsonii, Parabacteroides distasonis, Bacteroides dorei*, and *Bacteroides uniformis*; or (ii) the purified bacterial mixture comprises *Bacteroides dorei* and *Bacteroides uniformis* and further comprises one or more bacterial strains of species selected from the group consisting of *Phascolarctobacterium faecium, Subdoligranulum* sp., *Parabacteroides gordonii, Paraprevotella xylaniphila, Alistipes* sp., *Parabacteroides johnsonii, Parabacteroides distasonis, Fusobacterium ulcerans* and *Eubacterium limosum.*

3. The composition of claim 1, wherein (a) the purified bacterial mixture comprises *Fusobacterium ulcerans, Eubacterium limosum, Bacteroides dorei, Bacteroides uniformis, Parabacteroides gordonii, Paraprevotella xylaniphila, Alistipes* sp., *Parabacteroides johnsonii*, and *Parabacteroides distasonis;*

(b) the purified bacterial mixture comprises *Fusobacterium ulcerans, Eubacterium limosum, Phascolarctobacterium faecium, Subdoligranulum* sp., *Bacteroides dorei, Bacteroides uniformis, Alistipes* sp., *Parabacteroides johnsonii*, and *Parabacteroides distasonis;*

(c) the purified bacterial mixture comprises *Fusobacterium ulcerans, Eubacterium limosum, Phascolarctobacterium faecium, Subdoligranulum* sp., *Bacteroides dorei, Bacteroides uniformis, Parabacteroides gordonii*, and *Paraprevotella xylaniphila;*

(d) wherein the purified bacterial mixture comprises *Subdoligranulum* sp., *Phascolarctobacterium faecium, Bacteroides dorei, Bacteroides uniformis, Parabacteroides gordonii, Paraprevotella xylaniphila, Alistipes* sp., *Parabacteroides johnsonii*, and *Parabacteroides distasonis*, or (e) the purified bacterial mixture comprises *Fusobacterium ulcerans, Eubacterium limosum, Subdoligranulum* sp., *Phascolarctobacterium faecium, Parabacteroides gordonii, Paraprevotella xylaniphila, Alistipes* sp., *Parabacteroides johnsonii*, and *Parabacteroides distasonis.*

4. A composition comprising:

(i) a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterium limosum*, and *Parabacteroides distasonis*, wherein the bacterial strains are lyophilized; and (ii) one or more metabolites selected from the group consisting of mevalonate, dimethylglycine, hypoxanthine, IMP (inosine monophosphate), 2-deoxy-glucose 6-phosphate, TMP (trimethylpentane), 6PG (6-phosphogluconic acid), Rib5P (ribose 5-phosphate), Ru5P (ribulose 5-phosphate), Xu5p (xylulose 5-phosphate), GDP (guanosine 5'-diphosphate), GlcNAc 6P (N-acetylglucosamine-6-phosphate), UMP (uridine monophosphate), GMP (guanosine monophosphate), and CDP (cytidine diphosphate).

5. A composition comprising:

(i) a purified bacterial mixture comprising two or more bacterial strains comprising 16S rDNA sequences of at least 95% sequence identity to SEQ ID NO:2 and SEQ ID NO:10, or SEQ ID NO:3 and SEQ ID NO:4, wherein the bacterial strains are lyophilized; and (ii) one or more metabolites selected from the group consisting of mevalonate, dimethylglycine, hypoxanthine, IMP (inosine monophosphate), 2-deoxy-glucose 6-phosphate, TMP (trimethylpentane), 6PG (6-phosphogluconic acid), Rib5P (ribose 5-phosphate), Ru5P (ribulose 5-phosphate), Xu5p (xylulose 5-phosphate), GDP (guanosine 5'-diphosphate), GlcNAc 6P (N-acetylglucosamine-6-phosphate), UMP (uridine monophosphate), GMP (guanosine monophosphate), and CDP (cytidine diphosphate).

6. The composition of claim 5, wherein (i) the purified bacterial mixture comprises bacterial strains comprising 16S rDNA sequences of at least 95% sequence identity to SEQ ID NO:2 and SEQ ID NO:10, and further comprises one or more bacterial strains comprising 16S rDNA sequences of at least 95% sequence identity to 16S rDNA sequences selected from the group consisting of SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11; or (ii) the purified bacterial mixture comprises bacterial strains comprising 16S rDNA sequences of at least 95% sequence identity to SEQ ID NO:3 and SEQ ID NO:4, and further comprises one or more bacterial strains comprising 16S rDNA sequences of at least 95% sequence identity to 16S rDNA sequences selected from the group consisting of SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11.

7. The composition of claim 1, wherein (a) the purified bacterial mixture comprises bacterial strains comprising 16S rDNA sequences of at least 95% sequence identity to SEQ ID NO:1, SEQ ID NO:3, SEQ ID NO:4, SEQ ID NO:5, SEQ ID NO:6, SEQ ID NO:7, SEQ ID NO:8, SEQ ID NO:9, and SEQ ID NO:11;

(b) the purified bacterial mixture comprises bacterial strains comprising 16S rDNA sequences of at least 95% sequence identity to SEQ ID NO:1, SEQ ID NO:2, SEQ ID NO:5, SEQ ID NO:6, SEQ ID NO:7, SEQ ID NO:8, SEQ ID NO:9, SEQ ID NO:10, and SEQ ID NO:11;

(c) the purified bacterial mixture comprises bacterial strains comprising 16S rDNA sequences of at least 95% sequence identity to SEQ ID NO:2, SEQ ID NO:3, SEQ ID NO:4, SEQ ID NO:6, SEQ ID NO:7, SEQ ID NO:8, SEQ ID NO:9, SEQ ID NO:10, and SEQ ID NO:11;

(d) the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:7, SEQ ID NO:8, SEQ ID NO:10, and SEQ ID NO:11; or (e) the purified bacterial mixture comprises bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:9, and SEQ ID NO:10.

8. A composition comprising:

(i) a purified bacterial mixture comprising one or more bacterial strains comprising 16S rDNA sequences of at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, wherein the bacterial strains are lyophilized; and (ii) one or more metabolites selected from the group consisting of mevalonate, dimethylglycine, hypoxanthine, IMP (inosine monophosphate), 2-deoxy-glucose 6-phosphate, TMP (trimethylpentane), 6PG (6-phosphogluconic acid), Rib5P (ribose 5-phosphate), Ru5P (ribulose 5-phosphate), Xu5p (xylulose 5-phosphate), GDP (guanosine 5'-diphosphate), GlcNAc 6P (N-acetylglucosamine-6-phosphate), UMP (uridine monophosphate), GMP (guanosine monophosphate), and CDP (cytidine diphosphate).

9. The composition of claim 1, wherein one or more of the bacterial strains is a spore-former, optionally wherein one or more of the bacterial strains is in spore form.

10. The composition of claim 1, wherein the composition is a pharmaceutical composition; and optionally wherein the pharmaceutical composition is formulated for oral administration or rectal administration.

11. The pharmaceutical composition of claim 10, wherein the pharmaceutical composition is formulated for delivery to the intestine, optionally wherein the pharmaceutical composition is formulated for delivery to the colon; and/or the pharmaceutical composition further comprises a pH sensitive composition comprising one or more enteric polymers.

12. The pharmaceutical composition of claim 10, wherein one or more of the bacterial strains is in the form of a capsule.

13. The composition of claim 1, wherein the composition further comprises one or more anticancer agents; one or more cytokines; one or more costimulatory agents; one or more vaccines; and/or one or more anti-inflammatory agents.

14. The composition of claim 13, wherein (i) the anticancer agent is a chemotherapy agent, optionally a cancer immunotherapy agent, optionally a PD-1 inhibitor, PD-L-1 inhibitor, or CTLA-4 inhibitor;

(ii) the cytokine is IL-2, IL-15, or IL-21;

(iii) the costimulatory agent is a CD-28 antibody, OX-40 antibody, 4-1BB antibody, CD40 antibody, ICOS/CD278, CD28-type molecule, CD27/TNFRSF7, CD30/TNFRSF8, or GITR/CD357;

(iv) the vaccine is a dendritic cell vaccine; and/or (vii) the anti-inflammatory agent is an NSAID.

15. A method for activating the immune system or activating CD8+IFN-gamma producing T-cells, the method comprising administering to a subject the composition of claim 1.

16. A method for inducing the proliferation and/or accumulation of CD8+ T cells in the intestine, the method comprising administering to a subject the composition of claim 1, wherein the administration results in the induction of proliferation and/or accumulation of CD8+ T cells in the intestine of the subject.

17. The composition of claim 1, wherein the one or more metabolites are mevalonate and/or dimethylglycine.

* * * * *

SEQUENCE LISTING

```
<160> NUMBER OF SEQ ID NOS: 69

<210> SEQ ID NO 1
<211> LENGTH: 1440
<212> TYPE: DNA
<213> ORGANISM: Phascolarctobacterium faecium

<400> SEQUENCE: 1

gacgaacgct ggcggcgtgc ctaacacatg caagtcgaac ggagaatttt atttcggtag     60

aattcttagt ggcgaacggg tgagtaacgc gtaggcaacc taccctttag acggggacaa    120

cattccgaaa ggagtgctaa taccggatgt gatcatcttg ccgcatggca ggatgaagaa    180

agatggcctc tacaagtaag ctatcgctaa aggatgggcc tgcgtctgat tagctagttg    240

gtagtgtaac ggactaccaa ggcgatgatc agtagccggt ctgagaggat gaacggccac    300

attgggactg agacacggcc caaactccta cgggaggcag cagtggggaa tcttccgcaa    360

tggacgaaag tctgacggag caacgccgcg tgagtgatga aggatttcgg tctgtaaagc    420

tctgttgttt atgacgaacg tgcagtgtgt gaacaatgca ttgcaatgac ggtagtaaac    480

gaggaagcca cggctaacta cgtgccagca gccgcggtaa tacgtaggtg gcgagcgttg    540

tccggaatta ttgggcgtaa agagcatgta ggcggcttaa taagtcgagc gtgaaaatgc    600

ggggctcaac cccgtatggc gctggaaact gttaggcttg agtgcaggag aggaaagggg    660

aattcccagt gtagcggtga aatgcgtaga tattgggagg aacaccagtg gcgaaggcgc    720

ctttctggac tgtgtctgac gctgagatgc gaaagccagg gtagcgaacg ggattagata    780

ccccggtagt cctggccgta aacgatgggt actaggtgta ggaggtatcg accccttctg    840

tgccggagtt aacgcaataa gtaccccgcc tggggagtac ggccgcaagg ttgaaactca    900

aaggaattga cgggggcccg cacaagcggt ggagtatgtg gtttaattcg acgcaacgcg    960

aagaacctta ccaaggcttg acattgattg aacgctctag agatagagat ttcccttcgg   1020

ggacaagaaa acaggtggtg catggctgtc gtcagctcgt gtcgtgagat gttgggttaa   1080

gtcccgcaac gagcgcaacc cctatcctat gttaccagca agtaaagttg gggactcatg   1140

ggagactgcc agggacaacc tggaggaagg cggggatgac gtcaagtcat catgcccctt   1200

atgtcttggg ctacacacgt actacaatgg tcggaaacag agggaagcga agccgcgagg   1260

cagagcaaac cccagaaacc cgatctcagt tcggatcgca ggctgcaacc cgcctgcgtg   1320

aagtcggaat cgctagtaat cgcaggtcag catactgcgg tgaatacgtt cccgggcctt   1380

gtacacaccg cccgtcacac cacgaaagtt ggtaacaccc gaagccggtg aggtaaccta   1440


<210> SEQ ID NO 2
<211> LENGTH: 1392
<212> TYPE: DNA
<213> ORGANISM: Fusobacterium ulcerans

<400> SEQUENCE: 2
```

```
gatgaacgct gacagaatgc ttaacacatg caagtctact tgatccttcg ggtgaaggtg      60

gcggacgggt gagtaacgcg taaagaactt gccttacaga ctgggacaac atttggaaac     120

gaatgctaat accggatatt atgattgggt cgcatgatct gattatgaaa gctatatgcg     180

ctgtgagaga gctttgcgtc ccattagtta gttggtgagg taacggctca ccaagacgat     240

gatgggtagc cggcctgaga gggtgaacgg ccacaagggg actgagacac ggcccttact     300

cctacgggag gcagcagtgg ggaatattgg acaatggacc aaaagtctga tccagcaatt     360

ctgtgtgcac gaagaagttt ttcggaatgt aaagtgcttt cagttgggaa gaagtcagtg     420

acggtaccaa cagaagaagc gacggctaaa tacgtgccag cagccgcggt aatacgtatg     480

tcgcaagcgt tatccggatt tattgggcgt aaagcgcgtc taggcggctt agtaagtctg     540

atgtgaaaat gcggggctca accccgtatt gcgttggaaa ctgctaaact agagtactgg     600

agaggtaggc ggaactacaa gtgtagaggt gaaattcgta gatatttgta ggaatgccga     660

tggggaagcc agcctactgg acagatactg acgctaaagc gcgaaagcgt gggtagcaaa     720

caggattaga taccctggta gtccacgccg taaacgatga ttactaggtg ttggggggtcg    780

aacctcagcg cccaagctaa cgcgataagt aatccgcctg gggagtacgt acgcaagtat     840

gaaactcaaa ggaattgacg ggacccgca caagcggtgg agcatgtggt ttaattcgac      900

gcaacgcgag gaaccttacc agcgtttgac atcccaagaa gttaacagag atgttttcgt     960

gcctcttcgg aggaacttgg tgacaggtgg tgcatggctg tcgtcagctc gtgtcgtgag    1020

atgttgggtt aagtcccgca acgagcgcaa ccccttttcgt atgttaccat cattaagttg   1080

gggactcatg cgagactgcc tgcgatgagc aggaggaagg tggggatgac gtcaagtcat    1140

catgcccctt atacgctggg ctacacacgt gctacaatgg gtagtacaga gagctgcaaa    1200

cctgcgaggg taagctaatc tcataaaact attcttagtt cggattgtac tctgcaactc    1260

gagtacatga agttggaatc gctagtaatc gcaaatcagc tatgttgcgg tgaatacgtt    1320

ctcgggtctt gtacacaccg cccgtcacac cacgagagtt ggttgcacct gaagtaacag    1380

gcctaaccgt aa                                                        1392


<210> SEQ ID NO 3
<211> LENGTH: 1443
<212> TYPE: DNA
<213> ORGANISM: Bacteroides dorei
<220> FEATURE:
<221> NAME/KEY: misc_feature
<222> LOCATION: (7)..(9)
<223> OTHER INFORMATION: n is a, c, g, or t

<400> SEQUENCE: 3

agtttgnnnt atggctcagg atgaacgcta gctacaggct taacacatgc aagtcgaggg      60

gcagcatggt cttagcttgc taaggctgat ggcgaccggc gcacgggtga gtaacacgta     120

tccaacctgc cgtctactct tggccagcct tctgaaagga agattaatcc aggatgggat     180

catgagttca catgtccgca tgattaaagg tattttccgg tagacgatgg ggatgcgttc     240

cattagatag taggcggggt aacggcccac ctagtcaacg atggataggg gttctgagag     300

gaaggtcccc cacattggaa ctgagacacg gtccaaactc ctacgggagg cagcagtgag     360

gaatattggt caatgggcga tggcctgaac cagccaagta gcgtgaagga tgactgccct     420

atgggttgta aacttctttt ataaaggaat aaagtcgggt atgcataccc gtttgcatgt     480

actttatgaa taaggatcgg ctaactccgt gccagcagcc gcggtaatac ggaggatccg     540
```

-continued agcgttatcc ggatttattg ggtttaaagg gagcgtagat ggatgtttaa gtcagttgtg 600
aaagtttgcg gctcaaccgt aaaattgcag ttgatactgg atgtcttgag tgcagttgag 660
gcaggcggaa ttcgtggtgt agcggtgaaa tgcttagata tcacgaagaa ctccgattgc 720
gaaggcagcc tgctaagctg caactgacat tgaggctcga aagtgtgggt atcaaacagg 780
attagatacc ctggtagtcc acacggtaaa cgatgaatac tcgctgtttg cgatatacgg 840
caagcggcca agcgaaagcg ttaagtattc cacctgggga gtacgccggc aacggtgaaa 900
ctcaaaggaa ttgacggggg cccgcacaag cggaggaaca tgtggtttaa ttcgatgata 960
cgcgaggaac cttacccggg cttaaattgc actcgaatga tccggaaacg gttcagctag 1020
caatagcgag tgtgaaggtg ctgcatggtt gtcgtcagct cgtgccgtga ggtgtcggct 1080
taagtgccat aacgagcgca acccttgttg tcagttacta acaggtgatg ctgaggactc 1140
tgacaagact gccatcgtaa gatgtgagga aggtggggat gacgtcaaat cagcacggcc 1200
cttacgtccg ggctacacac cgtgttacaa tgggggtac agagggccgc taccacgcga 1260
gtggatgcca atccctaaaa cccctctcag ttcggactgg agtctgcaac ccgactccac 1320
gaagctggat tcgctagtaa tcgcgcatca gccacggcgc ggtgaatacg ttcccgggcc 1380
ttgtacacac cgcccgtcaa gccatgggag ccgggggtac ctgaagtgcg taaccgcgag 1440
gat 1443

<210> SEQ ID NO 4
<211> LENGTH: 1420
<212> TYPE: DNA
<213> ORGANISM: Bacteroides uniformis

<400> SEQUENCE: 4
gatgaacgct agctacaggc ttaacacatg caagtcgagg ggcagcatga acttagcttg 60
ctaagtttga tggcgaccgg cgcacgggtg agtaacacgt atccaacctg ccgatgactc 120
ggggatagcc tttcgaaaga aagattaata cccgatggca tagttcttcc gcatggtaga 180
actattaaag aatttcggtc atcgatgggg atgcgttcca ttaggttgtt ggcggggtaa 240
cggcccacca agccttcgat ggataggggt tctgagagga aggtccccca cattggaact 300
gagacacggt ccaaactcct acgggaggca gcagtgagga atattggtca atggacgaga 360
gtctgaacca gccaagtagc gtgaaggatg actgccctat gggttgtaaa cttcttttat 420
acgggaataa agtgaggcac gtgtgccttt ttgtatgtac cgtatgaata aggatcggct 480
aactccgtgc cagcagccgc ggtaatacgg aggatccgag cgttatccgg atttattggg 540
tttaaaggga gcgtaggcgg acgcttaagt cagttgtgaa agtttgcggc tcaaccgtaa 600
aattgcagtt gatactgggt gtcttgagta cagtagaggc aggcggaatt cgtggtgtag 660
cggtgaaatg cttagatatc acgaagaact ccgattgcga aggcagcctg ctggactgta 720
actgacgctg atgctcgaaa gtgtgggtat caaacaggat tagataccct ggtagtccac 780
accagtaaac gatgaatact cgctgtttgc gatatacagt aagcggccaa gcgaaagcgt 840
taagtattcc acctggggag tacgccggca acggtgaaac tcaaaggaat tgacgggggc 900
ccgcacaagc ggaggaacat gtggtttaat tcgatgatac gcgaggaacc ttacccgggc 960
ttgaattgca actgaatgat gtggagacat gtcagccgca aggcagttgt gaaggtgctg 1020
catggttgtc gtcagctcgt gccgtgaggt gtcggcttaa gtgccataac gagcgcaacc 1080
cttatcgata gttaccatca ggtgatgctg gggactctgt cgagactgcc gtcgtaagat 1140
gtgaggaagg tggggatgac gtcaaatcag cacggccctt acgtccgggg ctacacacgt 1200

| | | |
|---|---|---|
| gttacaatgg ggggtacaga aggcagctac acggcgacgt gatgctaatc ccgaaagcct | 1260 | |
| ctctcagttc ggattggagt ctgcaacccg actccatgaa gctggattcg ctagtaatcg | 1320 | |
| cgcatcagcc acggcgcggt gaatacgttc ccgggccttg tacacaccgc ccgtcaagcc | 1380 | |
| atgaaagccg ggggtacctg aagtgcgtaa ccgcaaggag | 1420 | |

<210> SEQ ID NO 5
<211> LENGTH: 1410
<212> TYPE: DNA
<213> ORGANISM: Subdoligranulum sp. 4_3_54A2FAA

<400> SEQUENCE: 5

| | |
|---|---|
| gacgaacgct ggcggcgcgc ctaacacatg caagtcgaac ggagctgttt tctctgaagt | 60 |
| tttcggatgg aagagagttc agcttagtgg cgaacgggtg agtaacacgt gagcaacctg | 120 |
| cctttcagtg ggggacaaca tttggaaacg aatgctaata ccgcataaga ccacagtgtc | 180 |
| gcatggcaca ggggtcaaag gatttatccg ctgaaagatg ggctcgcgtc cgattagcta | 240 |
| gatggtgagg taacggccca ccatggcgac gatcggtagc cggactgaga ggttgaacgg | 300 |
| ccacattggg actgagacac ggcccagact cctacgggag gcagcagtgg ggaatattgc | 360 |
| acaatggggg aaaccctgat gcagcgacgc cgcgtggagg aagaaggtct tcggattgta | 420 |
| aactcctgtc ccaggggacg ataatgacgg taccctggga ggaagcaccg gctaactacg | 480 |
| tgccagcagc cgcggtaaaa cgtagggtgc aagcgttgtc cggaattact gggtgtaaag | 540 |
| ggagcgcagg cggattggca agttgggagt gaaatctatg ggctcaaccc ataaattgct | 600 |
| ttcaaaactg tcagtcttga gtggtgtaga ggtaggcgga attcccggtg tagcggtgga | 660 |
| atgcgtagat atcgggagga acaccagtgg cgaaggcggc ctactgggca ctaactgacg | 720 |
| ctgaggctcg aaagcatggg tagcaaacag gattagatac cctggtagtc catgccgtaa | 780 |
| acgatgatta ctaggtgtgg gaggattgac cccttccgtg ccgcagttaa cacaataagt | 840 |
| aatccacctg gggagtacga ccgcaaggtt gaaactcaaa ggaattgacg ggggcccgca | 900 |
| caagcagtgg agtatgtggt ttaattcgaa gcaacgcgaa gaaccttacc aggtcttgac | 960 |
| atcggatgca tacctaagag attagggaag tccttcggga catccagaca ggtggtgcat | 1020 |
| ggttgtcgtc agctcgtgtc gtgagatgtt gggttaagtc ccgcaacgag cgcaaccctt | 1080 |
| atcgttagtt actacgcaag aggactctag cgagactgcc gttgacaaaa cggaggaagg | 1140 |
| tggggatgac gtcaaatcat catgcccttt atgacctggg ctacacacgt actacaatgg | 1200 |
| ctattaacag agagaagcga taccgcgagg tggagcaaac ctcacaaaaa tagtctcagt | 1260 |
| tcggatcgca ggctgcaacc cgcctgcgtg aagccggaat tgctagtaat cgcggatcag | 1320 |
| catgccgcgg tgaatacgtt cccgggcctt gtacacaccg cccgtcacac catgagagcc | 1380 |
| gggggaccc gaagtcggta gtctaaccgc | 1410 |

<210> SEQ ID NO 6
<211> LENGTH: 1418
<212> TYPE: DNA
<213> ORGANISM: Paraprevotella xylaniphila
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (1411)..(1412)
<223> OTHER INFORMATION: n is a, c, g, or t

<400> SEQUENCE: 6

```
gatgaacgct agctacaggc ttaacacatg caagtcgagg ggcagcatga acttagcttg     60
ctaagtttga tggcgaccgg cgcacgggtg agtaacgcgt atccaacctg ccctttaccc    120
ggggatagcc ttctgaaaag gaagtttaat acccgatgaa ttcgtttagt cgcatggctn    180
gatgaataaa gattaattgg taaaggatgg ggatgcgtcc cattagcttg ttggcggggt    240
aacggcccac caaggcgacg atgggtaggg gttctgagag gaaggtcccc cacattggaa    300
ctgagacacg gtccaaactc ctacgggagg cagcagtgag gaatattggt caatgggcgc    360
gagcctgaac cagccaagta gcgtggagga cgacggccct acgggttgta aactcctttt    420
ataaggggat aaagttggcc atgtatggcc atttgcaggt accttatgaa taagcatcgg    480
ctaattccgt gccagcagcc gcggtaatac ggaagatgcg agcgttatcc ggatttattg    540
ggtttaaagg gagcgtaggc gggctgtcaa gtcagcggtc aaatggcgcg gctcaaccgc    600
gttccgccgt tgaaactggc agccttgagt atgcacaggg tacatggaat tcgtggtgta    660
gcggtgaaat gcttagatat cacgaggaac tccgatcgcg caggcattgt accggggcat    720
tactgacgct gaggctcgaa ggtgcgggta tcaaacagga ttagataccc tggtagtccg    780
cacagtaaac gatgaatgcc cgctgtcggc gacatagtgt cggcggccaa gcgaaagcgt    840
taagcattcc acctggggag tacgccggca acggtgaaac tcaaaggaat tgacgggggc    900
ccgcacaagc ggaggaacat gtggtttaat tcgatgatac gcgaggaacc ttacccgggc    960
ttgaatcgca ggtgcatggg ccggagacgg ccctttcctt cgggactcct gcgaaggtgc   1020
tgcatggttg tcgtcagctc gtgccgtgag gtgtcggctt aagtgccata acgagcgcaa   1080
ccccctccc cagttgccac cggtaatgc cgggcacttt ggggacactg ccaccgcaag   1140
gtgcgaggaa ggtggggatg acgtcaaatc agcacggccc ttacgtccgg ggcgacacac   1200
gtgttacaat gggggtaca gagggccgct gcccggtgac ggttggccaa tccctaaaac   1260
ccctctcagt tcggactgga gtctgcaacc cgactccacg aagctggatt cgctagtaat   1320
cgcgcatcag ccatggcgcg gtgaatacgt tcccgggcct tgtacacacc gcccgtcaag   1380
ccatgaaagc cgggggtgcc tgaagtccgt nnccgcga                            1418
```

<210> SEQ ID NO 7
<211> LENGTH: 1419
<212> TYPE: DNA
<213> ORGANISM: Parabacteroides johnsonii

<400> SEQUENCE: 7

```
gatgaacgct agcgacaggc ttaacacatg caagtcgagg ggcagcatgg taagtagcaa     60
tacttattga tggcgaccgg cgcacgggtg agtaacgcgt atgcaactta cctatcagag    120
ggggatagcc cggcgaaagt cggattaata ctccataaaa caggggttcc gcatgggact    180
atttgttaaa gattcatcgc tgatagatag gcatgcgttc cattaggcag ttggcggggt    240
aacggcccac caaaccgacg atggataggg gttctgagag gaaggtcccc cacattggta    300
ctgagacacg gaccaaactc ctacgggagg cagcagtgag gaatattggt caatggccga    360
gaggctgaac cagccaagtc gcgtgaagga tgaaggatct atggtttgta aacttctttt    420
ataggggaat aaagtgtggg acgtgttcca ttttgtatgt accctatgaa taagcatcgg    480
ctaactccgt gccagcagcc gcggtaatac ggaggatgcg agcgttatcc ggatttattg    540
ggtttaaagg gtgcgtaggt ggtaatttaa gtcagcggtg aaagtttgtg gctcaaccat    600
aaaattgccg ttgaaactgg gttacttgag tgtgtttgag gtaggcggaa tgcgtggtgt    660
```

-continued

```
agcggtgaaa tgcatagata tcacgcagaa ctccaattgc gaaggcagct tactaaacca    720

taactgacac tgaagcacga aagcgtgggt atcaaacagg attagatacc ctggtagtcc    780

acgcagtaaa cgatgattac taggagtttg cgatacacag taagctctac agcgaaagcg    840

ttaagtaatc cacctgggga gtacgccggc aacggtgaaa ctcaaaggaa ttgacggggg    900

cccgcacaag cggaggaaca tgtggtttaa ttcgatgata cgcgaggaac cttacccggg    960

tttgaacgta gtcagaccga ccttgaaaga ggttttctag caatagctga ttacgaggtg   1020

ctgcatggtt gtcgtcagct cgtgccgtga ggtgtcggct taagtgccat aacgagcgca   1080

acccttatca ctagttacta acaggttaag ctgaggactc tggtgagact gccagcgtaa   1140

gctgtgagga aggtggggat gacgtcaaat cagcacggcc cttacatccg ggcgacaca    1200

cgtgttacaa tggcatggac aaagggcagc tacctggcga caggatgcta atctctaaac   1260

catgtctcag ttcggatcgg agtctgcaac tcgactccgt gaagctggat tcgctagtaa   1320

tcgcgcatca gccatggcgc ggtgaatacg ttcccgggcc ttgtacacac cgcccgtcaa   1380

gccatgggag ccgggggtac ctgaagtccg taaccgcaa                          1419


<210> SEQ ID NO 8
<211> LENGTH: 1414
<212> TYPE: DNA
<213> ORGANISM: Alistipes sp. JC136
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t

<400> SEQUENCE: 8

gatgaacgct agcggcaggc ctaacacatg caagtcgagg ggcagcggga ttgaagcttg     60

cttcagttgc cggcgaccgg cgcacgggtg cgtaacgcgt atgcaaccta cccataacag    120

ggggataaca ctgagaaatc ggtactaata tcccataaca tcaagagggg catccctttt    180

ggttgaaaac tccggtggtt atggatgggc atgcgttgta ttagctagtt ggtgaggtaa    240

cggctcacca aggcgacgat acataggggg actgagaggt taacccccca cattggtact    300

gagacacgga ccaaactcct acgggaggca gcagtgagga atattggtca atggacgcaa    360

gtctgaacca gccatgccgc gtgcaggatg acggctctat gagttgtaaa ctgcttttgt    420

acgagggtaa acccggatac gtgtatccgg ctgaaagtat cgtacgaata aggatcggct    480

aactccgtgc cagcagccgc ggtaatacgg aggattcaag cgttatccgg atttattggg    540

tttaaagggt gcgtaggcgg tttgataagt tagaggtgaa ataccggtgc ttaacaccgg    600

aactgcctct aatactgttg agctagagag tagttgcggt aggcggaatg tatggtgtag    660

cggtgaaatg cttagagatc atacagaaca ccgattgcng aaggcagctt accaaactat    720

atctgacgtt ngaggcacga aagcgtgggg gagcaaacag gattagatac cctggtagtc    780

cacgcagtaa acgatgataa ctcgctgtcg gcgatacaca gtcggtggct aagcgaaagc    840

gataagttat ccacctgggg agtacgttcg caagaatgaa actcaaagga attgacgggg    900

gcccgcacaa gcggaggaac atgtggttta attcgatgat acgcgaggaa ccttacccgg    960

gcttgaaagt tactgacgat tctggaaaca ggatttccct tcggggcagg aaactaggtg   1020

ctgcatggtt gtcgtcagct cgtgccgtga ggtgtcgggt taagtcccat aacgagcgca   1080
```

acccctaccg ttagttgcca tcaggtcaag ctgggcactc tggcgggact gccggtgtaa 1140
gccgagagga aggtggggat gacgtcaaat cagcacggcc cttacgtccg ggctacacac 1200
cgtgttacaa tggtaggtac agagggcagc tacccagtga tgggatgcga atctcgaaag 1260
cctatctcag ttcggattgg aggctgaaac ccgcctccat gaagttggat tcgctagtaa 1320
tcgcgcatca gccatggcgc ggtgaatacg ttcccgggcc ttgtacacac cgcccgtcaa 1380
gccatggaag ctgggggtgc ctgaagttcg tgac 1414

<210> SEQ ID NO 9
<211> LENGTH: 1416
<212> TYPE: DNA
<213> ORGANISM: Parabacteroides gordonii
<220> FEATURE:
<221> NAME/KEY: misc_feature
<222> LOCATION: (1408)..(1408)
<223> OTHER INFORMATION: n is a, c, g, or t

<400> SEQUENCE: 9
gatgaacgct agcgacaggc ttaacacatg caagtcgagg ggcagcagga agtagcaata 60
ctttgctggc gaccggcgca cgggtgagta acgcgtatgc aacctaccta tcagaggggg 120
ataacccggc gaaagtcgga ctaataccgc ataaaacagg ggtcccgcat gggaatattt 180
gttaaagatt tattgctgat agatgggcat gcgttccatt agatagttgg tgaggtaacg 240
gctcaccaag tcttcgatgg ataggggttc tgagaggaag gtcccccaca ctggtactga 300
gacacggacc agactcctac gggaggcagc agtgaggaat attggtcaat gggcgagagc 360
ctgaaccagc caagtcgcgt gaaggatgaa ggatctatgg ttcgtaaact tcttttatag 420
gggaataaag tgcaggacgt gtcctgtttt gtatgtaccc tatgaataag gatcggctaa 480
ctccgtgcca gcagccgcgg taatacggag gatccgagcg ttatccggat ttattgggtt 540
taaagggtgc gtaggtggct ttttaagtca gcggtgaaag tttgtggctc aaccataaaa 600
ttgccgttga aactggaggg cttgagtata tttgaggtag gcggaatgcg tggtgtagcg 660
gtgaaatgca tagatatcac gcagaactcc aattgcgaag gcagcttact aaactataac 720
tgacactgaa gcacgaaagc gtggggatca aacaggatta gataccctgg tagtccacgc 780
agtaaacgat gattactagg agtttgcgat acacagtaag ctctacagcg aaagcgttaa 840
gtaatccacc tggggagtac gccggcaacg gtgaaactca aaggaattga cgggggcccg 900
cacaagcgga ggaacatgtg gtttaattcg atgatacgcg aggaacctta cccgggtttg 960
aacgtaagtt gaccggagtg gaaacactct ttctagcaat agcaatttac gaggtgctgc 1020
atggttgtcg tcagctcgtg ccgtgaggtg tcggcttaag tgccataacg agcgcaaccc 1080
ttatctttag ttactaacag gtcgagctga ggactctaaa gagactgcca gcgtaagctg 1140
tgaggaaggt ggggatgacg tcaaatcagc acggccctta catccggggc gacacacgtg 1200
ttacaatggt ggggacaaag ggcagctacc tggcgacagg atgctaatct ccaaacccca 1260
tctcagttcg gatcgaagtc tgcaacccga cttcgtgaag ctggattcgc tagtaatcgc 1320
gcatcagcca tggcgcggtg aatacgttcc cgggccttgt acacaccgcc cgtcaagcca 1380
tgggagttgg gggtacctaa agtccgtnac cgcaag 1416

<210> SEQ ID NO 10
<211> LENGTH: 1419
<212> TYPE: DNA
<213> ORGANISM: Eubacterium limosum

<400> SEQUENCE: 10
gacgaacgct ggcggtatgc ttaacacatg caagtcgaac gagaaggttt tgatggatcc 60
ttcgggtgac attagaactg gaaagtggcg aacgggtgag taacgcgtgg gtaacctgcc 120
ctatggaaag gaatagcctc gggaaactgg gagtaaagcc ttatattatg gttttgtcgc 180
atggcaagat catgaaaact ccggtgccat aggatggacc cgcgtcccat tagctagttg 240
gtgagataac agcccaccaa ggcgacgatg ggtaaccggt ctgagagggc gaacggtcac 300
actggaactg agacacggtc cagactccta cgggaggcag cagtggggaa tattgcgcaa 360
tgggggcaac cctgacgcag caataccgcg tgagtgaaga aggttttcgg atcgtaaagc 420
tctgttattg gggaagaaga atgacggtac ccaatgagga agtcccggct aactacgtgc 480
cagcagccgc ggtaatacgt aggggacaag cgttgtccgg aatgactggg cgtaaagggc 540
gcgtaggcgg tctattaagt ctgatgtgaa aggtaccggc tcaaccggtg aagtgcattg 600
gaaactggta gacttgagta ttggagaggc aagtggaatt cctagtgtag cggtgaaatg 660
cgtagatatt aggaggaaca ccagtggcga aggcggcttg ctggacaaat actgacgctg 720
aggtgcgaaa gcgtggggag cgaacaggat tagataccct ggtagtccac gccgtaaacg 780
atgaatgcta ggtgttgggg aaactcagtg ccgcagttaa cacaataagc attccgcctg 840
gggagtacga ccgcaaggtt gaaactcaaa ggaattgacg gggacccgca caagcagcgg 900
agcatgtggt ttaattcgaa gcaacgcgaa gaaccttacc aggtcttgac atcctctgac 960
gagcctagag ataggaagtt tccttcggga acagagagac aggtggtgca tggttgtcgt 1020
cagctcgtgt cgtgagatgt tgggttaagt cccgcaacga gcgcaacccc tgcctttagt 1080
tgccagcatt aagttgggca ctctagaggg actgccgtag acaatacgga ggaaggtggg 1140
gacgacgtca aatcatcatg ccccttatga cctgggctac acacgtgcta caatggtctg 1200
aacagagggc cgcgaagccg cgaggtgaag caaatccctt aaaacagatc ccagttcgga 1260
ttgcaggctg caactcgcct gcatgaagtt ggagttgcta gtaatcgcgg atcagaatgc 1320
cgcggtgaat gcgttcccgg gtcttgtaca caccgcccgt cacaccacga gagttggcaa 1380
cacccgaagc ctgtgagaga accgtaagga ctcagcagt 1419

<210> SEQ ID NO 11
<211> LENGTH: 1413
<212> TYPE: DNA
<213> ORGANISM: Parabacteroides distasonis
<220> FEATURE:
<221> NAME/KEY: misc_feature
<222> LOCATION: (1387)..(1387)
<223> OTHER INFORMATION: n is a, c, g, or t

<400> SEQUENCE: 11
gatgaacgct agcgacaggc ttaacacatg caagtcgagg ggcagcacag gtagcaatac 60
cgggtggcga ccggcgcacg ggtgagtaac gcgtatgcaa cttgcctatc agagggggat 120
aacccggcga aagtcggact aataccgcat gaagcagggg ccccgcatgg ggatatttgc 180
taaagattca tcgctgatag ataggcatgc gttccattag gcagttggcg gggtaacggc 240
ccaccaaacc gacgatggat aggggttctg agaggaaggt cccccacatt ggtactgaga 300
cacggaccaa actcctacgg gaggcagcag tgaggaatat tggtcaatgg ccgagaggct 360
gaaccagcca agtcgcgtga gggatgaagg ttctatggat cgtaaacctc ttttataagg 420
gaataaagtg cgggacgtgt cccgttttgt atgtacctta tgaataagga tcggctaact 480
ccgtgccagc agccgcggta atacggagga tccgagcgtt atccggattt attgggttta 540

-continued

```
aagggtgcgt aggcggcctt ttaagtcagc ggtgaaagtc tgtggctcaa ccatagaatt    600

gccgttgaaa ctgggggct tgagtatgtt tgaggcaggc ggaatgcgtg gtgtagcggt    660

gaaatgcata gatatcacgc agaaccccga ttgcgaaggc agcctgccaa gccattactg    720

acgctgatgc acgaaagcgt ggggatcaaa caggattaga taccctggta gtccacgcag    780

taaacgatga tcactagctg tttgcgatac actgtaagcg gcacagcgaa agcgttaagt    840

gatccacctg ggagtacgc cggcaacggt gaaactcaaa ggaattgacg ggggcccgca    900

caagcggagg aacatgtggt ttaattcgat gatacgcgag gaaccttacc cgggtttgaa    960

cgcattcgga ccgaggtgga aacacctttt ctagcaatag ccgtttgcga ggtgctgcat   1020

ggttgtcgtc agctcgtgcc gtgaggtgtc ggcttaagtg ccataacgag cgcaaccctt   1080

gccactagtt actaacaggt aaagctgagg actctggtgg gactgccagc gtaagctgcg   1140

aggaaggcgg ggatgacgtc aaatcagcac ggcccttaca tccggggcga cacacgtgtt   1200

acaatggcgt ggacaaaggg aagccacctg gcgacaggga gcgaatcccc aaaccacgtc   1260

tcagttcgga tcggagtctg caacccgact ccgtgaagct ggattcgcta gtaatcgcgc   1320

atcagccatg gcgcggtgaa tacgttcccg ggccttgtac acaccgcccg tcaagccatg   1380

ggagccnggg gtacctgaag tccgtaaccg cga                                1413
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12

agrgtttgat ymtggctcag                                                 20


<210> SEQ ID NO 13
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 13

ggytaccttg ttacgactt                                                  19


<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14

agrgtttgat ymtggctcag                                                 20


<210> SEQ ID NO 15
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 15

tgctgcctcc cgtaggagt                                                  19
```

<210> SEQ ID NO 16
<211> LENGTH: 25
<212> TYPE: DNA
<213> ORGANISM: Fusobacterium ulcerans
<220> FEATURE:
<223> OTHER INFORMATION: Synthetic polynucleotide

<400> SEQUENCE: 16
tgcactgttg gattttctaa aaagg 25

<210> SEQ ID NO 17
<211> LENGTH: 20
<212> TYPE: DNA
<213> ORGANISM: Fusobacterium ulcerans
<220> FEATURE:
<223> OTHER INFORMATION: Synthetic polynucleotide

<400> SEQUENCE: 17
actttgggca tgctaaacca 20

<210> SEQ ID NO 18
<211> LENGTH: 22
<212> TYPE: DNA
<213> ORGANISM: Bacteroides dorei
<220> FEATURE:
<223> OTHER INFORMATION: Synthetic polynucleotide

<400> SEQUENCE: 18
gcatatatct tgactgagcc ga 22

<210> SEQ ID NO 19
<211> LENGTH: 21
<212> TYPE: DNA
<213> ORGANISM: Bacteroides dorei
<220> FEATURE:
<223> OTHER INFORMATION: Synthetic polynucleotide

<400> SEQUENCE: 19
ttcccccgat gaataaagcg t 21

<210> SEQ ID NO 20
<211> LENGTH: 23
<212> TYPE: DNA
<213> ORGANISM: Eubacterium limosum
<220> FEATURE:
<223> OTHER INFORMATION: Synthetic polynucleotide

<400> SEQUENCE: 20
ccgcacaaga gaaataaacg cca 23

<210> SEQ ID NO 21
<211> LENGTH: 23
<212> TYPE: DNA
<213> ORGANISM: Eubacterium limosum
<220> FEATURE:
<223> OTHER INFORMATION: Synthetic polynucleotide

<400> SEQUENCE: 21
tggcaaattc aaaggtgagc gaa 23

<210> SEQ ID NO 22
<211> LENGTH: 24
<212> TYPE: DNA
<213> ORGANISM: Alistipes senegalensis
<220> FEATURE:
<223> OTHER INFORMATION: Synthetic polynucleotide

```
<400> SEQUENCE: 22

gggaataaag ctgttccgat atgc                                              24


<210> SEQ ID NO 23
<211> LENGTH: 22
<212> TYPE: DNA
<213> ORGANISM: Alistipes senegalensis
<220> FEATURE:
<223> OTHER INFORMATION: Synthetic polynucleotide

<400> SEQUENCE: 23

tcatgcaaca ttctttcgtt gg                                                22


<210> SEQ ID NO 24
<211> LENGTH: 25
<212> TYPE: DNA
<213> ORGANISM: Parabacteroides gordonii
<220> FEATURE:
<223> OTHER INFORMATION: Synthetic polynucleotide

<400> SEQUENCE: 24

ttcaccttct acggctacta ctacg                                             25


<210> SEQ ID NO 25
<211> LENGTH: 24
<212> TYPE: DNA
<213> ORGANISM: Parabacteroides gordonii
<220> FEATURE:
<223> OTHER INFORMATION: Synthetic polynucleotide

<400> SEQUENCE: 25

acataacgat caagggtgct gaag                                              24


<210> SEQ ID NO 26
<211> LENGTH: 23
<212> TYPE: DNA
<213> ORGANISM: Paraprevotella xylaniphila
<220> FEATURE:
<223> OTHER INFORMATION: Synthetic polynucleotide

<400> SEQUENCE: 26

gctcttttta gcctgtatcc ggt                                               23


<210> SEQ ID NO 27
<211> LENGTH: 1522
<212> TYPE: DNA
<213> ORGANISM: Phascolarctobacterium faecium

<400> SEQUENCE: 27

agagtttgat cctggctcag gacgaacgct ggcggcgtgc ctaacacatg caagtcgaac      60

ggagaatttt atttcggtag aattcttagt ggcgaacggg tgagtaacgc gtaggcaacc     120

tgccctttag acggggacaa cattccgaaa ggagtgctaa taccggatgt gatcatcgtg     180

ccgcatggca ggatgaagaa agatggcctc tacaagtaag ctatcgctaa aggatgggcc     240

tgcgtctgat tagctagttg gtagtgtaac ggactaccaa ggcgatgatc agtagccggt     300

ctgagaggat gaacggccac attgggactg agacacggcc caaactccta cgggaggcag     360

cagtggggaa tcttccgcaa tggacgaaag tctgacggag caacgccgcg tgagtgatga     420

aggatttcgg tctgtaaagc tctgttgttt atgacgaacg tgcagtgtgt gaacaatgca     480

ttgcaatgac ggtagtaaac gaggaagcca cggctaacta cgtgccagca gccgcggtaa     540

tacgtaggtg gcgagcgttg tccggaatta ttgggcgtaa agagcatgta ggcggcttaa     600
```

```
taagtcgagc gtgaaaatgc ggggctcaac cccgtatggc gctggaaact gttaggcttg    660
agtgcaggag aggaaagggg aattcccagt gtagcggtga aatgcgtaga tattgggagg    720
aacaccagtg gcgaaggcgc ctttctggac tgtgtctgac gctgagatgc gaaagccagg    780
gtagcgaacg ggattagata ccccggtagt cctggccgta aacgatgggt actaggtgta    840
ggaggtatcg accccttctg tgccggagtt aacgcaataa gtaccccgcc tggggagtac    900
ggccgcaagg ttgaaactca aaggaattga cgggggcccg cacaagcggt ggagtatgtg    960
gtttaattcg acgcaacgcg aagaacctta ccaaggcttg acattgattg aacgctctag   1020
agatagagct ttcccttcgg ggacaagaaa acaggtggtg catggctgtc gtcagctcgt   1080
gtcgtgagat gttgggttaa gtcccgcaac gagcgcaacc cctatcctat gttaccagca   1140
agtaaagttg ggactcatgg ggagactgcc agggacaacc tggaggaagg cggggatgac   1200
gtcaagtcat catgcccctt atgtcttggg ctacacacgt actacaatgg tcggaaacag   1260
agggaagcga agccgcgagg cagagcaaac cccagaaacc cgatctcagt tcggatcgca   1320
ggctgcaacc cgcctgcgtg aagtcggaat cgctagtaat cgcaggtcag catactgcgg   1380
tgaatacgtt cccgggcctt gtacacaccg cccgtcacac cacgaaagtt ggtaacaccc   1440
gaagccggtg aggtaaccta ttaggagcca gccgtctaag gtggggccga tgattggggt   1500
gaagtcgtaa caaggtagcc gt                                            1522
```

```
<210> SEQ ID NO 28
<211> LENGTH: 1431
<212> TYPE: DNA
<213> ORGANISM: Fusobacterium ulcerans

<400> SEQUENCE: 28
```

```
tgctcaggat gaacgctgac agaatgctta acacatgcaa gtctacttga tccttcgggt     60
gaaggtggcg gacgggtgag taacgcgtaa agaacttgcc ttacagactg ggacaacatt    120
tggaaacgaa tgctaatacc ggatattatg attgggtcgc atgatctgat tatgaaagct    180
atatgcgctg tgagagagct ttgcgtccca ttagttagtt ggtgaggtaa cggctcacca    240
agacgatgat gggtagccgg cctgagaggg tgaacggcca caaggggact gagacacggc    300
ccttactcct acgggaggca gcagtgggga atattggaca atggaccaaa agtctgatcc    360
agcaattctg tgtgcacgat gaagtttttc ggaatgtaaa gtgctttcag ttgggaagaa    420
gtcagtgacg gtaccaacag aagaagcgac ggctaaatac gtgccagcag ccgcggtaat    480
acgtatgtcg caagcgttat ccggatttat tgggcgtaaa gcgcgtctag gcggcttagt    540
aagtctgatg tgaaaatgcg gggctcaacc ccgtattgcg ttggaaactg ctaaactaga    600
gtactggaga ggtaggcgga actacaagtg tagaggtgaa attcgtagat atttgtagga    660
atgccgatgg ggaagccagc ctactggaca gatactgacg ctaaagcgcg aaagcgtggg    720
tagcaaacag gattagatac cctggtagtc cacgccgtaa acgatgatta ctaggtgttg    780
ggggtcgaac ctcagcgccc aagctaacgc gataagtaat ccgcctgggg agtacgtacg    840
caagtatgaa actcaaagga attgacgggg acccgcacaa gcggtggagc atgtggttta    900
attcgacgca acgcgaggaa ccttaccagc gtttgacatc ccaagaagtt aacagagatg    960
ttttcgtgcc tcttcggagg aacttggtga caggtggtgc atggctgtcg tcagctcgtg   1020
tcgtgagatg ttgggttaag tcccgcaacg agcgcaaccc ctttcgtatg ttaccatcat   1080
taagttgggg actcatgcga gactgcctgc gatgagcagg aggaaggtgg ggatgacgtc   1140
```

-continued

```
aagtcatcat gccccttata cgctgggcta cacacgtgct acaatgggta gtacagagag   1200

ctgcaaacct gcgagggtaa gctaatctca taaaactatt cttagttcgg attgtactct   1260

gcaactcgag tacatgaagt tggaatcgct agtaatcgca aatcagctat gttgcggtga   1320

atacgttctc gggtcttgta cacaccgccc gtcacaccac gagagttggt tgcacctgaa   1380

gtaacaggcc taaccgtaag gagggatgtt ccgagggtgt gattagcgat t            1431
```

<210> SEQ ID NO 29
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 29

```
gctgcctccc gtaggagt                                                   18
```

<210> SEQ ID NO 30
<211> LENGTH: 1477
<212> TYPE: DNA
<213> ORGANISM: Bacteroides uniformis
<220> FEATURE:
<223> OTHER INFORMATION: Synthetic polynucleotide

<400> SEQUENCE: 30

```
ctggctcagg atgaacgcta gctacaggct taacacatgc aagtcgaggg gcagcatgaa     60

cttagcttgc taagtttgat ggcgaccggc gcacgggtga gtaacacgta tccaacctgc    120

cgatgactcg ggatagcct ttcgaaagaa agattaatac ccgatggcat agttcttccg    180

catggtagaa ctattaaaga atttcggtca tcgatgggga tgcgttccat taggttgttg    240

gcggggtaac ggcccaccaa gccttcgatg gataggggtt ctgagaggaa ggtcccccac    300

attggaactg agacacggtc caaactccta cgggaggcag cagtgaggaa tattggtcaa    360

tggacgagag tctgaaccag ccaagtagcg tgaaggatga ctgccctatg ggttgtaaac    420

ttcttttata cgggaataaa gtgaggcacg tgtgcctttt tgtatgtacc gtatgaataa    480

ggatcggcta actccgtgcc agcagccgcg gtaatacgga ggatccgagc gttatccgga    540

tttattgggt ttaaagggag cgtaggcgga cgcttaagtc agttgtgaaa gtttgcggct    600

caaccgtaaa attgcagttg atactgggtg tcttgagtac agtagaggca ggcggaattc    660

gtggtgtagc ggtgaaatgc ttagatatca cgaagaactc cgattgcgaa ggcagcttgc    720

tggactgtaa ctgacgctga tgctcgaaag tgtgggtatc aaacaggatt agataccctg    780

gtagtccaca cagtaaacga tgaatactcg ctgtttgcga tatacagtaa gcggccaagc    840

gaaagcgtta agtattccac ctggggagta cgccggcaac ggtgaaactc aaaggaattg    900

acgggggccc gcacaagcgg aggaacatgt ggtttaattc gatgatacgc gaggaacctt    960

acccgggctt gaattgcaac tgaatgatgt ggagacatgt cagccgcaag gcagttgtga   1020

aggtgctgca tggttgtcgt cagctcgtgc cgtgaggtgt cggcttaagt gccataacga   1080

gcgcaaccct tatcgatagt taccatcagg ttatgctggg gactctgtcg agactgccgt   1140

cgtaagatgt gaggaaggtg gggatgacgt caaatcagca cggcccttac gtccggggct   1200

acacacgtgt tacaatgggg ggtacagaag gcagctacac ggcgacgtga tgctaatccc   1260

taaagcctct ctcagttcgg attggagtct gcaacccgac tccatgaagc tggattcgct   1320

agtaatcgcg catcagccac ggcgcggtga atacgttccc gggccttgta cacaccgccc   1380

gtcaagccat gaaagccggg ggtacctgaa gtgcgtaacc gcaaggagcg ccctagggta   1440
```

```
aaactggtga ttggggctaa gtcgtaacaa ggtaacc                               1477
```

<210> SEQ ID NO 31
<211> LENGTH: 1519
<212> TYPE: DNA
<213> ORGANISM: Ruthenibacterium lactatiformans
<220> FEATURE:
<223> OTHER INFORMATION: Synthetic polynucleotide

<400> SEQUENCE: 31

```
agagtttgat cctggctcag gacgaacgct ggcggcgcgc ctaacacatg caagtcgaac     60
ggagctgttt tctctgaagt tttcggatgg aagagagttc agcttagtgg cgaacgggtg    120
agtaacacgt gagcaacctg cctttcagtg ggggacaaca tttggaaacg aatgctaata    180
ccgcataaga ccacagtgtc gcatggcaca ggggtcaaag gatttatccg ctgaaagatg    240
ggctcgcgtc cgattagcta gatggtgagg taacggccca ccatggcgac gatcggtagc    300
cggactgaga ggttgaacgg ccacattggg actgagacac ggcccagact cctacgggag    360
gcagcagtgg ggaatattgc acaatggggg aaaccctgat gcagcgacgc cgcgtggagg    420
aagaaggtct tcggattgta aactcctgtc ccaggggacg ataatgacgg taccctggga    480
ggaagcaccg gctaactacg tgccagcagc cgcggtaaaa cgtagggtgc aagcgttgtc    540
cggaattact gggtgtaaag ggagcgcagg cggattggca agttgggagt gaaatctatg    600
ggctcaaccc ataaattgct ttcaaaactg tcagtcttga gtggtgtaga ggtaggcgga    660
attcccggtg tagcggtgga atgcgtagat atcgggagga acaccagtgg cgaaggcggc    720
ctactgggca ctaactgacg ctgaggctcg aaagcatggg tagcaaacag gattagatac    780
cctggtagtc catgccgtaa acgatgatta ctaggtgtgg gaggattgac cccttccgtg    840
ccgcagttaa cacaataagt aatccacctg gggagtacga ccgcaaggtt gaaactcaaa    900
ggaattgacg ggggcccgca caagcagtgg agtatgtggt ttaattcgaa gcaacgcgaa    960
gaaccttacc aggtcttgac atcggatgca tacctaagag attagggaag tccttcggga   1020
catccagaca ggtggtgcat ggttgtcgtc agctcgtgtc gtgagatgtt gggttaagtc   1080
ccgcaacgag cgcaaccctt atcgttagtt actacgcaag aggactctag cgagactgcc   1140
gttgacaaaa cggaggaagg tggggatgac gtcaaatcat catgcccttt atgacctggg   1200
ctacacacgt actacaatgg ctattaacag agagaagcga taccgcgagg tggagcaaac   1260
ctcacaaaaa tagtctcagt tcggatcgca ggctgcaacc cgcctgcgtg aagccggaat   1320
tgctagtaat cgcggatcag catgccgcgg tgaatacgtt cccgggcctt gtacacaccg   1380
cccgtcacac catgagagcc gggggaccc gaagtcggta gtctaaccgt aaggaggacg   1440
ccgccgaagg taaaactggt gattggggtg aagtcgtaac aaggtagccg tatcggaagg   1500
tgcggctgga tcacctcct                                                  1519
```

<210> SEQ ID NO 32
<211> LENGTH: 1488
<212> TYPE: DNA
<213> ORGANISM: Paraprevotella xylaniphila
<220> FEATURE:
<223> OTHER INFORMATION: Synthetic polynucleotide

<400> SEQUENCE: 32

```
agagtttgat cctggctcag gatgaacgct agctacaggc ttaacacatg caagtcgagg     60
ggcagcatga acttagcttg ctaagtttga tggcgaccgg cgcacgggtg agtaacgcgt    120
```

-continued

```
atccaacctg ccctttacgc ggggatagcc ttctgaaagg aagtttaata cccgatgaat    180

tcgtttagtc gcatggcttg atgaataaag atttatcagt aaaggatggg gatgcgtccc    240

attagcttgt tggcggggta acggcccacc aaggcgacga tgggtagggg ttctgagagg    300

aaggtccccc acattggaac tgagacacgg tccaaactcc tacgggaggc agcagtgagg    360

aatattggtc aatgggcgcg agcctgaacc agccaagtag cgtggaggac gacggcccta    420

cgggttgtaa actcctttta taaggggata aagttggcca tgtatggcca tttgcaggta    480

ccttatgaat aagcatcggc taattccgtg ccagcagccg cggtaatacg gaagatgcga    540

gcgttatccg gatttattgg gtttaaaggg agcgtaggcg ggcagtcaag tcagcggtca    600

aatggcgcgg ctcaaccgcg ttccgccgtt gaaactggca gccttgagta tgcacagggt    660

acatggaatt cgtggtgtag cggtgaaatg cttagatatc acgaggaact ccgatcgcgc    720

aggcattgta ccggggcatt actgacgctg aggctcgaag gtgcgggtat caaacaggat    780

tagataccct ggtagtccgc acagtaaacg atgaatgccc gctgtcggcg acatagtgtc    840

ggcggccaag cgaaagcgtt aagcattcca cctggggagt acgccggcaa cggtgaaact    900

caaaggaatt gacgggggcc cgcacaagcg gaggaacatg tggtttaatt cgatgatacg    960

cgaggaacct tacccgggct tgaatcgcag gtgcatgggc cggagacggc cctttccttc   1020

gggactcctg cgaaggtgct gcatggttgt cgtcagctcg tgccgtgagg tgtcggctta   1080

agtgccataa cgagcgcaac ccccctcccc agttgccatc gggtaatgcc gggcactttg   1140

gggacactgc caccgcaagg tgcgaggaag gtggggatga cgtcaaatca gcacggccct   1200

tacgtccggg gcgacacacg tgttacaatg gggggtacag agggccgctg cccggtgacg   1260

gttggccaat ccctaaagcc cctctcagtt cggactggag tctgcaaccc gactccacga   1320

agctggattc gctagtaatc gcgcatcagc catggcgcgg tgaatacgtt cccgggcctt   1380

gtacacaccg cccgtcaagc catgaaagcc gggggtgcct gaagtccgtg accgcgaggg   1440

tcggcctagg gtaaaaccgg tgattggggc taagtcgtaa caaggtaa                1488

<210> SEQ ID NO 33
<211> LENGTH: 1492
<212> TYPE: DNA
<213> ORGANISM: Parabacteroides johnsonii
<220> FEATURE:
<223> OTHER INFORMATION: Synthetic polynucleotide

<400> SEQUENCE: 33

agagtttgat cctggctcag gatgaacgct agcgacaggc ttaacacatg caagtcgagg     60

ggcagcatgg taagtagcaa tacttattga tggcgaccgg cgcacgggtg agtaacgcgt    120

atgcaactta cctatcagag gggatagcc cggcgaaagt cggattaata ctccataaaa    180

caggggttcc gcatgggact atttgttaaa gattcatcgc tgatagatag gcatgcgttc    240

cattaggcag ttggcggggt aacggcccac caaaccgacg atggataggg gttctgagag    300

gaaggtcccc cacattggta ctgagacacg gaccaaactc ctacgggagg cagcagtgag    360

gaatattggt caatggccga gaggctgaac cagccaagtc gcgtgaagga tgaaggatct    420

atggtttgta aacttctttt ataggggaat aaagtgtggg acgtgttcca ttttgtatgt    480

accctatgaa taagcatcgg ctaactccgt gccagcagcc gcggtaatac ggaggatgcg    540

agcgttatcc ggatttattg ggtttaaagg gtgcgtaggt ggtaatttaa gtcagcggtg    600

aaagtttgtg gctcaaccat aaaattgccg ttgaaactgg gttacttgag tgtgtttgag    660

gtaggcggaa tgcgtggtgt agcggtgaaa tgcatagata tcacgcagaa ctccaattgc    720
```

-continued

```
gaaggcagct tactaaacca taactgacac tgaagcacga aagcgtgggt atcaaacagg    780

attagatacc ctggtagtcc acgcagtaaa cgatgattac taggagtttg cgatacacag    840

taagctctac agcgaaagcg ttaagtaatc cacctgggga gtacgccggc aacggtgaaa    900

ctcaaaggaa ttgacggggg cccgcacaag cggaggaaca tgtggtttaa ttcgatgata    960

cgcgaggaac cttacccggg tttgaacgta gtcagaccga ccttgaaaga ggtcttctag   1020

caatagctga ttacgaggtg ctgcatggtt gtcgtcagct cgtgccgtga ggtgtcggct   1080

taagtgccat aacgagcgca acccttatca ctagttacta acaggtcaag ctgaggactc   1140

tggtgagact gccagcgtaa gctgtgagga aggtggggat gacgtcaaat cagcacggcc   1200

cttacatccg gggcgacaca cgtgttacaa tggcatggac aaagggcagc tacctggcga   1260

caggatgcta atctctaaac catgtctcag ttcggatcgg agtctgcaac tcgactccgt   1320

gaagctggat tcgctagtaa tcgcgcatca gccatggcgc ggtgaatacg ttcccgggcc   1380

ttgtacacac cgcccgtcaa gccatgggag ccgggggtac ctgaagtccg taaccgcaag   1440

gatcggccta gggtaaaact ggtgactggg gctaagtcgt aacaaggtaa cc            1492
```

<210> SEQ ID NO 34
<211> LENGTH: 1491
<212> TYPE: DNA
<213> ORGANISM: Alistipes sp.
<220> FEATURE:
<223> OTHER INFORMATION: Synthetic polynucleotide

<400> SEQUENCE: 34

```
agagtttgat cctggctcag gatgaacgct agcggcaggc ctaacacatg caagtcgagg     60

ggcagcggga ttgaagcttg cttcaatcgc cggcgaccgg cgcacgggtg cgtaacgcgt    120

atgcaaccta cccagaacag gggataaca ctgagaaatt ggtactaata tcccataaca    180

tcataagggg catccctttt ggttgaaaac tccggtggtt ctggatgggc atgcgttgta    240

ttagctggtt ggtgaggtaa cggctcacca aggcaacgat acatagggg actgagaggt    300

taaccccca cattggtact gagacacgga ccaaactcct acgggaggca gcagtgagga    360

atattggtca atggacgcaa gtctgaacca gccatgccgc gtgcaggaag acggctctat    420

gagttgtaaa ctgcttttgt actagggtaa actcagatac gcgtatctga ctgaaagtat    480

agtacgaata aggaccggct aactccgtgc cagcagccgc ggtaatacgg agggtccaag    540

cgttatccgg atttattggg tttaaagggt gcgtaggcgg ttagataagt tagaggtgaa    600

ataccggtgc ttaacaccgg aactgcctct aatactgttt agctagagaa tagttgcggt    660

aggsggaatg tatggtgtag cggtgaaatg cttagagatc atacagaaca ccgattgcga    720

aggcagctta ccaagctatt tctgacgttg aggcacgaaa gcgtggggag caaacaggat    780

tagataccct ggtagtccac gcagtaaacg atgataactc gctgtcggcg atacacagtc    840

ggcggctaag cgaaagcgat aagttatcca cctggggagt acgttcgcaa gaatgaaact    900

caaaggaatt gacgggggcc cgcacaagcg gaggaacatg tggtttaatt cgatgatacg    960

cgaggaacct tacccgggct tgaaagttac tgacgattct ggaaacagga tttcccttcg   1020

gggcaggaaa ctaggtgctg catggttgtc gtcagctcgt gccgtgaggt gtcgggttaa   1080

gtcccataac gagcgcaacc cctaccgtta gttgccatca ggtcaagctg ggcactctga   1140

cgggactgcc ggtgtaagcc gagaggaagg tggggatgac gtcaaatcag cacggccctt   1200

acgtccgggg ctacacacgt gttacaatgg taggtacaga gggcagctac cctgcgaagg   1260
```

gatgcgaatc tcgaaagcct atctcagttc ggatcggagg ctgaaacccg cctccgtgaa 1320
gttggattcg ctagtaatcg cgcatcagcc atggcgcggt gaatacgttc ccgggccttg 1380
tacacaccgc ccgtcaagcc atggaagctg gggtgcctg aagttcgtga ccgcaaggag 1440
cgacctaggg caaaaccggt gactggggct aagtcgtaac aaggtagccg t 1491

<210> SEQ ID NO 35
<211> LENGTH: 1485
<212> TYPE: DNA
<213> ORGANISM: Parabacteroides gordonii
<220> FEATURE:
<223> OTHER INFORMATION: Synthetic polynucleotide

<400> SEQUENCE: 35
agagtttgat cctggctcag gatgaacgct agcgacaggc ttaacacatg caagtcgagg 60
ggcagcagga agtagcaata ctttgctggc gaccggcgca cgggtgagta acgcgtatgc 120
aacctaccta tcagaggggg ataacccggc gaaagtcgga ctaataccgc ataaaacagg 180
ggtcccgcat gggaatattt gttaaagatt aattgctgat agatgggcat gcgttccatt 240
agatagttgg taaggtaacg gcttaccaag tctgcgatgg atagggggttc tgagaggaag 300 gtcccccaca ctggtactga gacacggacc agactcctac gggaggcagc agtgaggaat 360
attggtcaat gggcgagagc ctgaaccagc caagtcgcgt gaaggatgaa ggatctatgg 420
ttcgtaaact tcttttataa gggaataaag tgcggacgtg tcctgttttg tatgtacctt 480
atgaataagg atcggctaac tccgtgccag cagccgcggt aatacggagg atccgagcgt 540
tatccggatt tattgggttt aaagggtgcg taggtggttt attaagtcag cggtgaaagt 600
ttgtggctca accataaaat tgccgttgaa actggttaac ttgagtatat ttgaggtagg 660
cggaatgcgt ggtgtagcgg tgaaatgcat agatatcacg cagaactcca attgcgaagg 720
cagcttacta aactataact gacactgaag cacgaaagcg tggggatcaa acaggattag 780
ataccctggt agtccacgca gtaaacgatg attactagga gtttgcgata cacagtaagc 840
tctacagcga aagcgttaag taatccacct ggggagtacg ccggcaacgg tgaaactcaa 900
aggaattgac gggggcccgc acaagcggag gaacatgtgg tttaattcga tgatacgcga 960
ggaaccttac ccgggtttga acgcattgga cagtccttga aagaggatct ctagcaatag 1020
ccatttgcga ggtgctgcat ggttgtcgtc agctcgtgcc gtgaggtgtc ggcttaagtg 1080
ccataacgag cgcaaccctt atctttagtt actaacaggt ctgctgagga ctctaaagag 1140
actgccagcg taagctgtga ggaaggtggg gatgacgtca aatcagcacg gcccttacat 1200
ccggggcgac acacgtgtta caatggtggg gacaaagggc agctacacag cgatgtgatg 1260
ctaatctcca aaccccatct cagttcggat cgaagtctgc aacccgactt cgtgaagctg 1320
gattcgctag taatcgcgca tcagccatgg cgcggtgaat acgttcccgg gccttgtaca 1380
caccgcccgt caagccatgg gagttggggg tacctaaagt ccgtaaccgc aaggatcggc 1440
ctaggtaaaa ccgatgactg gggctaagtc gtaaccaagg taacc 1485

<210> SEQ ID NO 36
<211> LENGTH: 1484
<212> TYPE: DNA
<213> ORGANISM: Eubacterium limosum
<220> FEATURE:
<223> OTHER INFORMATION: Synthetic polynucleotide

<400> SEQUENCE: 36
agagtttgat cctggctcag gacgaacgct ggcggtatgc ttaacacatg caagtcgaac 60
gagaaggttt tgatggatcc ttcgggtgac attagaactg gaaagtggcg aacgggtgag 120
taacgcgtgg gtaacctgcc ctatggaaag gaatagcctc gggaaactgg gagtaaagcc 180
ttatattatg gttttgtcgc atggcaagat catgaaaact ccggtgccat aggatggacc 240
cgcgtcccat tagctagttg gtgagataac agcccaccaa ggcgacgatg ggtaaccggt 300
ctgagagggc gaacggtcac actggaactg agacacggtc cagactccta cgggaggcag 360
cagtggggaa tattgcgcaa tgggggcaac cctgacgcag caataccgcg tgagtgaaga 420
aggttttcgg atcgtaaagc tctgttattg gggaagaaga atgacggtac ccaatgagga 480
agtcccggct aactacgtgc cagcagccgc ggtaatacgt aggggacaag cgttgtccgg 540
aatgactggg cgtaaagggc gcgtaggcgg tctattaagt ctgatgtgaa aggtaccggc 600
tcaaccggtg aagtgcattg gaaactggta gacttgagta ttggagaggc aagtggaatt 660
cctagtgtag cggtgaaatg cgtagatatt aggaggaaca ccagtggcga aggcggcttg 720
ctggacaaat actgacgctg aggtgcgaaa gcgtggggag cgaacaggat tagataccct 780
ggtagtccac gccgtaaacg atgaatgcta ggtgttgggg aaactcagtg ccgcagttaa 840
cacaataagc attccgcctg gggagtacga ccgcaaggtt gaaactcaaa ggaattgacg 900
gggacccgca caagcagcgg agcatgtggt ttaattcgaa gcaacgcgaa gaaccttacc 960
aggtcttgac atcctctgac gagcctagag ataggaagtt tccttcggga acagagagac 1020
aggtggtgca tggttgtcgt cagctcgtgt cgtgagatgt tgggttaagt cccgcaacga 1080
gcgcaacccc tgcctttagt tgccagcatt aagttgggca ctctagaggg actgccgtag 1140
acaatacgga ggaaggtggg gacgacgtca aatcatcatg ccccttatga cctgggctac 1200
acacgtgcta caatggtctg aacagagggc cgcgaagccg cgaggtgaag caaatccctt 1260
aaaacagatc ccagttcgga ttgcaggctg caactcgcct gcatgaagtt ggagttgcta 1320
gtaatcgcgg atcagaatgc cgcggtgaat gcgttcccgg gtcttgtaca caccgcccgt 1380
cacaccacga gagttggcaa cacccgaagc ctgtgagaga accgcaagga ctcagcagtc 1440
gaaggtgggg ctagtaattg gggtgaagtc gtaacaaggt aacc 1484

<210> SEQ ID NO 37
<211> LENGTH: 1488
<212> TYPE: DNA
<213> ORGANISM: Parabacteroides distasonis
<220> FEATURE:
<223> OTHER INFORMATION: Synthetic polynucleotide

<400> SEQUENCE: 37
agagtttgat cctggctcag gatgaacgct agcgacaggc ttaacacatg caagtcgagg 60
ggcagcgggg tgtagcaata caccgccggc gaccggcgca cgggtgagta acgcgtatgc 120
aacttgccta tcagaggggg ataacccggc gaaagtcgga ctaataccgc atgaagcagg 180
gatcccgcat gggaatattt gctaaagatt catcgctgat agataggcat gcgttccatt 240
aggcagttgg cggggtaacg gcccaccaaa ccgacgatgg atagggggttc tgagaggaag 300 gtcccccaca ttggtactga gacacggacc aaactcctac gggaggcagc agtgaggaat 360
attggtcaat gggcgtaagc ctgaaccagc caagtcgcgt gagggatgaa ggttctatgg 420
atcgtaaacc tcttttataa gggaataaag tgcgggacgt gtcccgtttt gtatgtacct 480
tatgaataag gatcggctaa ctccgtgcca gcagccgcgg taatacggag gatccgagcg 540
ttatccggat ttattgggtt taaagggtgc gtaggcggcc ttttaagtca gcggtgaaag 600

```
tctgtggctc aaccatagaa ttgccgttga aactgggggg cttgagtatg tttgaggcag    660

gcggaatgcg tggtgtagcg gtgaaatgca tagatatcac gcagaacccc gattgcgaag    720

gcagcctgcc aagccattac tgacgctgat gcacgaaagc gtggggatca aacaggatta    780

gataccctgg tagtccacgc agtaaacgat gatcactagc tgtttgcgat acactgtaag    840

cggcacagcg aaagcgttaa gtgatccacc tggggagtac gccggcaacg gtgaaactca    900

aaggaattga cgggggcccg cacaagcgga ggaacatgtg gtttaattcg atgatacgcg    960

aggaacctta cccgggtttg aacgcattcg gaccgaggtg gaaacacctt ttctagcaat   1020

agccgtttgc gaggtgctgc atggttgtcg tcagctcgtg ccgtgaggtg tcggcttaag   1080

tgccataacg agcgcaaccc ttgccactag ttactaacag gttaggctga ggactctggt   1140

gggactgcca gcgtaagctg cgaggaaggc ggggatgacg tcaaatcagc acggccctta   1200

catccggggc gacacacgtg ttacaatggc gtggacaaag ggaggccacc tggcgacagg   1260

gagcgaatcc ccaaaccacg tctcagttcg gatcggagtc tgcaacccga ctccgtgaag   1320

ctggattcgc tagtaatcgc gcatcagcca tggcgcggtg aatacgttcc cgggccttgt   1380

acacaccgcc cgtcaagcca tgggagccgg gggtacctga agtccgtaac cgaaaggatc   1440

ggcctagggt aaaactggtg actggggcta agtcgtaaca aggtaacc                1488


<210> SEQ ID NO 38
<211> LENGTH: 22
<212> TYPE: DNA
<213> ORGANISM: Paraprevotella xylaniphila
<220> FEATURE:
<223> OTHER INFORMATION: Synthetic polynucleotide

<400> SEQUENCE: 38

atacgatacg aacgaccaac ct                                              22


<210> SEQ ID NO 39
<211> LENGTH: 25
<212> TYPE: DNA
<213> ORGANISM: Ruminococcaceae bacterium cv2
<220> FEATURE:
<223> OTHER INFORMATION: Synthetic polynucleotide

<400> SEQUENCE: 39

cttcgttgtt cttgaacttc tcgcc                                           25


<210> SEQ ID NO 40
<211> LENGTH: 23
<212> TYPE: DNA
<213> ORGANISM: Ruminococcaceae bacterium cv2
<220> FEATURE:
<223> OTHER INFORMATION: Synthetic polynucleotide

<400> SEQUENCE: 40

cagacatttc cgaaaacctc cag                                             23


<210> SEQ ID NO 41
<211> LENGTH: 21
<212> TYPE: DNA
<213> ORGANISM: Parabacteroides johnsonii
<220> FEATURE:
<223> OTHER INFORMATION: Synthetic polynucleotide

<400> SEQUENCE: 41

gcacagattc tacactcccc t                                               21
```

<210> SEQ ID NO 42
<211> LENGTH: 20
<212> TYPE: DNA
<213> ORGANISM: Parabacteroides johnsonii
<220> FEATURE:
<223> OTHER INFORMATION: Synthetic polynucleotide

<400> SEQUENCE: 42
agcaacgaaa caacctgtga 20

<210> SEQ ID NO 43
<211> LENGTH: 22
<212> TYPE: DNA
<213> ORGANISM: Bacteroides uniformis
<220> FEATURE:
<223> OTHER INFORMATION: Synthetic polynucleotide

<400> SEQUENCE: 43
gaggaagtga accttgggtg tg 22

<210> SEQ ID NO 44
<211> LENGTH: 25
<212> TYPE: DNA
<213> ORGANISM: Bacteroides uniformis
<220> FEATURE:
<223> OTHER INFORMATION: Synthetic polynucleotide

<400> SEQUENCE: 44
aaaaagtgga catgataaag cggat 25

<210> SEQ ID NO 45
<211> LENGTH: 25
<212> TYPE: DNA
<213> ORGANISM: Phascolarctobacterium faecium
<220> FEATURE:
<223> OTHER INFORMATION: Synthetic polynucleotide

<400> SEQUENCE: 45
aggatccctt cgctgtagta aaaga 25

<210> SEQ ID NO 46
<211> LENGTH: 23
<212> TYPE: DNA
<213> ORGANISM: Phascolarctobacterium faecium
<220> FEATURE:
<223> OTHER INFORMATION: Synthetic polynucleotide

<400> SEQUENCE: 46
acaatccggt ctgatgatca atg 23

<210> SEQ ID NO 47
<211> LENGTH: 22
<212> TYPE: DNA
<213> ORGANISM: Parabacteroides distasonis
<220> FEATURE:
<223> OTHER INFORMATION: Synthetic polynucleotide

<400> SEQUENCE: 47
gcccgcctca acttagaatc ac 22

<210> SEQ ID NO 48
<211> LENGTH: 24
<212> TYPE: DNA
<213> ORGANISM: Parabacteroides distasonis
<220> FEATURE:
<223> OTHER INFORMATION: Synthetic polynucleotide

<400> SEQUENCE: 48
tctatgtgtt tccggtttgt tacg 24

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
ttgctgacag gatgcagaag 20

<210> SEQ ID NO 50
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 50
atccacatct gctggaaggt g 21

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
atgggccacg tctaaaaagc 20

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
tttgcactgc tgctgagttc 20

<210> SEQ ID NO 53
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 53

Lys Ser Pro Trp Phe Thr Thr Leu
1 5

<210> SEQ ID NO 54
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 54
aatgccttga agctgatccc 20

<210> SEQ ID NO 55

<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 55
gttctttgtc atgcgttggc 20

<210> SEQ ID NO 56
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 56
agacaagagg cattgctgtg 20

<210> SEQ ID NO 57
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 57
agcagaactc gtgtttgctg 20

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58
aagcaagggg gacatttgtg 20

<210> SEQ ID NO 59
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 59
tggttcacac ctgacattgg 20

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
cgaggcacga tccactacaa 20

<210> SEQ ID NO 61
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 61
ccggatctag gcaggtttga 20

<210> SEQ ID NO 62
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 62
tcctgcccac gtgttgagat 20

<210> SEQ ID NO 63
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 63
tgcgtggctt cactccagtt 20

<210> SEQ ID NO 64
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 64
ttccaggaag gccactaaca tc 22

<210> SEQ ID NO 65
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 65
agcctgtttg gtatgacgtg 20

<210> SEQ ID NO 66
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 66
ctgcaagaga cttccatcca gtt 23

<210> SEQ ID NO 67
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 67
aagtagggaa ggccgtggtt 20

<210> SEQ ID NO 68
<211> LENGTH: 21
<212> TYPE: DNA

```
<213> ORGANISM: Artificial Sequence
<220> FEATURE:
<223> OTHER INFORMATION: Synthetic polynucleotide

<400> SEQUENCE: 68

aatgtcacct ccatcctggt c                                               21


<210> SEQ ID NO 69
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 69

gtggccactt gcacattgta                                                 20
```